(12) United States Patent
Machacek et al.

(10) Patent No.: US 9,242,984 B2
(45) Date of Patent: Jan. 26, 2016

(54) PYRAZOLYL DERIVATIVES AS SYK INHIBITORS

(71) Applicants: Merck Sharp & Dohme Corp., Rahway, NJ (US); Merck Canada Inc., Kirkland, Quebec (CA)

(72) Inventors: Michelle R. Machacek, Brookline, MA (US); Michael D. Altman, Needham, MA (US); Eric T. Romeo, Allston, MA (US); Dilrukshi Vitharana, Somerville, MA (US); Brandon Cash, Framingham, MA (US); Tony Siu, Brookline, MA (US); Hua Zhou, Acton, MA (US); Matthew Christopher, Brookline, MA (US); Solomon D. Kattar, Arlington, MA (US); Andrew M. Haidle, Cambridge, MA (US); Kaleen Konrad Childers, Medfield, MA (US); Matthew L. Maddess, Boston, MA (US); Michael H. Reutershan, Brookline, MA (US); Yves Ducharme, Brookline, MA (US); David J. Guerin, Natick, MA (US); Kerrie Spencer, Woonsocket, RI (US); Christian Beaulieu, Laval (CA); Vouy Linh Truong, Pierrefonds (CA); Daniel Guay, Lachine (CA); Alan B. Northrup, Reading, MA (US); Brandon M. Taoka, Hoboken, NJ (US); Jongwon Lim, Lexington, MA (US); Christian Fischer, Natick, MA (US); John W. Butcher, Berlin, MA (US); Ryan D. Otte, Natick, MA (US); Binyuan Sun, Needham Heights, MA (US); John Michael Ellis, Needham, MA (US)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 0 days.

(21) Appl. No.: 14/409,133

(22) PCT Filed: Jun. 18, 2013

(86) PCT No.: PCT/US2013/046219
§ 371 (c)(1),
(2) Date: Dec. 18, 2014

(87) PCT Pub. No.: WO2013/192125
PCT Pub. Date: Dec. 27, 2013

(65) Prior Publication Data
US 2015/0191461 A1    Jul. 9, 2015

Related U.S. Application Data

(60) Provisional application No. 61/662,203, filed on Jun. 20, 2012.

(51) Int. Cl.
| | |
|---|---|
| C07D 401/00 | (2006.01) |
| A61K 31/00 | (2006.01) |
| C07D 471/04 | (2006.01) |
| C07D 403/12 | (2006.01) |
| C07D 401/14 | (2006.01) |
| C07D 405/14 | (2006.01) |
| C07D 413/14 | (2006.01) |
| C07D 403/14 | (2006.01) |
| C07D 409/14 | (2006.01) |

(52) U.S. Cl.
CPC ............ *C07D 471/04* (2013.01); *C07D 401/14* (2013.01); *C07D 403/12* (2013.01); *C07D 403/14* (2013.01); *C07D 405/14* (2013.01); *C07D 409/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 5,064,963 | A | 11/1991 | Dean |
| 5,710,129 | A | 1/1998 | Lynch et al. |
| 6,248,790 | B1 | 6/2001 | Uckun et al. |
| 6,589,950 | B1 | 7/2003 | Collingwood et al. |
| 6,770,643 | B2 | 8/2004 | Cox et al. |
| 6,897,207 | B2 | 5/2005 | Cox et al. |
| 6,897,208 | B2 | 5/2005 | Edwards et al. |
| 6,911,443 | B2 | 6/2005 | Yura et al. |
| 7,060,827 | B2 | 6/2006 | Singh et al. |
| 7,122,542 | B2 | 10/2006 | Singh et al. |
| 7,227,020 | B2 | 6/2007 | Cox et al. |
| 7,259,154 | B2 | 8/2007 | Cox et al. |
| 8,551,984 | B2 | 10/2013 | Altman et al. |

(Continued)

FOREIGN PATENT DOCUMENTS

| | | |
|---|---|---|
| JP | 2004203748 | 12/2002 |
| WO | 0160816 A1 | 8/2001 |

(Continued)

OTHER PUBLICATIONS

Written Opinion of the International Searching Authority, PCT/US2013/46219, Nov. 1, 2013, 4 pages.

(Continued)

*Primary Examiner* — Heidi Reese
(74) *Attorney, Agent, or Firm* — Eric A. Meade; Catherine D. Fitch

(57) ABSTRACT

The present invention provides novel pyrazole derivatives of formula I which are potent inhibitors of spleen tyrosine kinase, and are useful in the treatment and prevention of diseases mediated by said enzyme, such as asthma, COPD, rheumatoid arthritis, and cancer.

21 Claims, No Drawings

(56) References Cited

U.S. PATENT DOCUMENTS

| | | |
|---|---|---|
| 8,735,417 B2 | 5/2014 | Altman et al. |
| 8,759,366 B2 | 6/2014 | Childers et al. |
| 8,796,310 B2 | 8/2014 | Romeo et al. |
| 2004/0029902 A1 | 2/2004 | Singh et al. |
| 2004/0054179 A1 | 3/2004 | Yura et al. |
| 2006/0135543 A1 | 6/2006 | Singh et al. |
| 2006/0178407 A1 | 8/2006 | Argade et al. |
| 2006/0205731 A1 | 9/2006 | Kodama et al. |
| 2006/0211657 A1 | 9/2006 | Singh et al. |
| 2006/0234483 A1 | 10/2006 | Arak et al. |
| 2006/0247262 A1 | 11/2006 | Baenteli et al. |
| 2007/0004626 A1 | 1/2007 | Masuda et al. |
| 2007/0129362 A1 | 6/2007 | Bhamidipati et al. |
| 2007/0197782 A1 | 8/2007 | Clough et al. |
| 2010/0216764 A1 | 8/2010 | Kim et al. |
| 2014/0100250 A1 | 4/2014 | Altman et al. |
| 2014/0148474 A1 | 5/2014 | Altman et al. |
| 2014/0249130 A1 | 9/2014 | Deschenes et al. |
| 2015/0148327 A1 | 5/2015 | Haidle et al. |

FOREIGN PATENT DOCUMENTS

| | | | |
|---|---|---|---|
| WO | WO 03026664 A1 * | 4/2003 | |
| WO | WO03057659 A1 | 7/2003 | |
| WO | WO03078404 A1 | 9/2003 | |
| WO | 2004058722 A1 | 7/2004 | |
| WO | WO2004080463 A1 | 9/2004 | |
| WO | WO2005013996 A2 | 2/2005 | |
| WO | WO2005026158 A1 | 3/2005 | |
| WO | WO2005033103 A1 | 4/2005 | |
| WO | WO2006004865 A1 | 1/2006 | |
| WO | WO2006028833 A1 | 3/2006 | |
| WO | WO2006050480 A2 | 5/2006 | |
| WO | WO2006068770 A1 | 6/2006 | |
| WO | WO2006078846 A1 | 7/2006 | |
| WO | WO2006093247 A1 | 9/2006 | |
| WO | WO2006129100 A1 | 12/2006 | |
| WO | WO2006133426 A2 | 12/2006 | |
| WO | WO2006135915 A2 | 12/2006 | |
| WO | WO2007009681 A1 | 1/2007 | |
| WO | WO2007009773 A1 | 1/2007 | |
| WO | WO2007028445 A1 | 3/2007 | |
| WO | WO2007042298 A1 | 4/2007 | |
| WO | WO2007042299 A1 | 4/2007 | |
| WO | WO2007070872 A1 | 6/2007 | |
| WO | WO2007085540 A1 | 8/2007 | |
| WO | WO2007107469 A1 | 9/2007 | |
| WO | WO2007120980 A2 | 10/2007 | |
| WO | WO2009031011 A2 | 3/2009 | |
| WO | WO2009084695 A1 | 7/2009 | |
| WO | WO2009097287 A1 | 8/2009 | |
| WO | WO2009102468 A1 | 8/2009 | |
| WO | WO2009131687 A2 | 10/2009 | |
| WO | WO2009136995 A2 | 11/2009 | |
| WO | WO2009145856 A1 | 12/2009 | |
| WO | WO2010027500 A1 | 3/2010 | |
| WO | WO2010068257 A1 | 6/2010 | |
| WO | WO2010068258 A1 | 6/2010 | |
| WO | WO2010129802 A1 | 11/2010 | |
| WO | WO2013192088 A1 | 12/2013 | |
| WO | WO2013192128 A1 | 12/2013 | |
| WO | WO2014031438 A2 | 2/2014 | |

OTHER PUBLICATIONS

Extended European Search Report for PCT/US2013/046219, Issued Nov. 12, 2015.

* cited by examiner

PYRAZOLYL DERIVATIVES AS SYK INHIBITORS

CROSS REFERENCE TO RELATED APPLICATIONS

This application is a U.S. National Phase application under 35 U.S.C. §371 of PCT Application No. PCT/US2013/046219, filed Jun. 18, 2013, which claims priority under 35 U.S.C. §119(e) from U.S. Provisional Application No. 61/662,203, filed Jun. 20, 2012.

BACKGROUND OF THE INVENTION

Spleen Tyrosine Kinase (Syk) is a protein tyrosine kinase which has been described as a key mediator of immunoreceptor signaling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}R1$ and or $Fc_{epsilon}R1$ receptors, and is positioned early in the signaling cascade. In mast cells, for example, the early sequence of $Fc_{epsilon}R1$ signaling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al., 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterized by inflammation of articular joints leading to debilitating destruction of bone and cartilage. Recent clinical studies with Rituximab, which causes a reversible B cell depletion, (J. C. W. Edwards et al., 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterized by a block in B cell development (M. Turner et al., 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

U.S. Pat. No. 7,803,801 discloses Syk inhibitors having the formula:

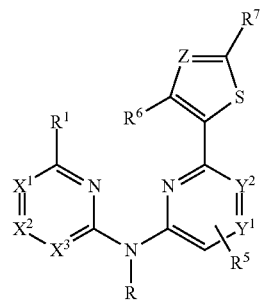

wherein the variables are as defined therein.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of Syk as well as pharmaceutical compositions containing them. As Syk inhibitors compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

The present invention provides compounds of formula I:

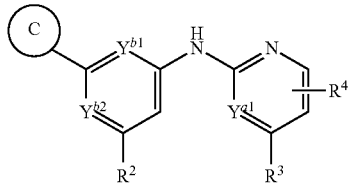

or a pharmaceutically acceptable salt thereof, wherein:

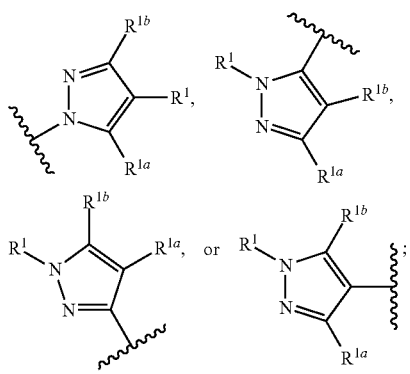 is:

ring a is

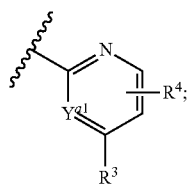

ring b is

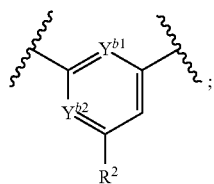

$Y^{a1}$ is independently CH or N;
$Y^{b1}$ and $Y^{b2}$ are independently CH or N, such that $Y^{a1}$ and $Y^{b1}$ are not both simultaneously C or N;
$R^{1a}$ and $R^{1b}$ are independently: H, halogen, $C_1$-$C_3$-alkyl, or $C_1$-$C_3$-fluoroalkyl;
$R^1$ is:
H;
halogen;
$C_1$-$C_6$-alkyl, optionally with one to four substituents selected from: CN, OH, oxo, $NH_2$, $CF_3$, $C_1$-$C_3$-alkyl, and $C_1$-$C_3$-alkoxyl;
$(CR^aR^b)_nCO_2R^c$;
$(CR^aR^b)_nCONR^dR^e$;
$(CHR^a)_nNHCONR^dR^e$;
$(CHR^a)_nNHCO_2R^c$;
$(CHR^a)_nNHCOR^c$;
$(CHR^a)_nCONHSO_2R^d$;
$(CHR^a)_nSO_2R^d$;
$(CHR^a)_nSO_2NR^dR^e$;
$(CHR^a)_nNHSO_2R^d$;
$(CR^aR^b)_n$-heterocyclyl; wherein heterocyclyl is as defined below;
$(CHR^a)_p$—C(O)-heterocyclyl; wherein heterocyclyl is as defined below;
$(CR^aR^b)_n$-carbocyclyl; wherein carbocyclyl is as defined below;
$CR^a(carbocyclyl)_2$; wherein carbocyclyl is as defined below;
$(CR^aR^b)_n$-aryl; wherein aryl is as defined below;
$(CR^aR^b)_n$—O-carbocyclyl; wherein carbocyclyl is as defined below;
$(CR^aR^b)_n$—O-aryl; wherein aryl is as defined below;
or optionally, $R^1$ and $R^{1a}$, $R^1$ and $R^{1b}$, $R^{1a}$ and $R^{1b}$, when present on adjacent pyrazolyl ring atoms, taken together can form a 5- or 6-membered ring with the atoms to which they are attached; the ring may contain one or two heteroatoms selected from N, O, or S including the nitrogens of the pyrazole ring to which the ring is fused and the ring may be saturated, unsaturated or aromatic and may be optionally substituted with one to three substituents selected from: $C_1$-$C_3$-alkoxyl and $C_1$-$C_3$-alkyl;

Heterocyclyl is a 4-, 5-, 6-, or 7-membered monocyclic ring or 8-, 9-, 10-membered bicyclic ring, or 13- or 14-membered tricyclic ring; the monocyclic, bicyclic or tricyclic ring can be saturated, unsaturated or aromatic, containing one to four heteroatoms selected from O, N. or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, $C_{3-6}$cycloalkyl, $(CR^aR^b)_nCO_2R^c$, $(CR^aR^b)_nCONR^dR^e$, $(CHR^a)_nNHCONR^dR^e$, $(CHR^a)NHCO_2R^c$, and $(CHR^a)_p$—C(O)-heterocyclyl; or alternatively 2 substituents geminally substituted on a common ring carbon atom of said heterocyclyl may together with the common ring carbon atom form a $C_{3-6}$ spirocyclic ring;

Carbocyclyl is a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated and that ring being isolated or fused to one or two such rings or to a benzene ring; the carbocyclyl may optionally be substituted with one to four substituents selected from hydroxyl, $C_1$-$C_3$-alkyl, $C_1$-$C_3$-alkoxyl, $(CR^aR^b)_nO_2R^c$, $(CR^aR^b)_nCONR^dR^e$, and a spiro-linked —$OCH_2CH_2O$—;

Aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, $(CR^aR^b)_nO_2R^c$, and $(CR^aR^b)_n CONR^dR^e$;

$R^2$ is H, halogen, $C_1$-$C_3$-alkyl, $C_1$-$C_3$-haloalkyl, $C_3$-$C_7$-cycloalkyl, heterocyclyl, $NR^dR^e$, $CONR^dR^e$, $NHCONR^dR^e$, or $NO_2$;

$R^3$ is H or $C_1$-$C_4$-alkyl, $C_1$-$C_3$-fluoroalkyl, $C_1$-$C_3$-alkoxyl, optionally substituted with one to three substituents selected from hydroxyl; —O—$(CH_2)_2$—O—$Si(CH_3)_3$; $C_3$-$C_6$-cycloalkyl and pyridyl;

$R^4$ is H, halogen, or $C_1$-$C_3$-alkyl;

$R^a$ and $R^b$ are independently: H, OH, CN, $NH_2$, cyclopropyl, $C_1$-$C_3$-fluoroalkyl, or $C_1$-$C_3$-alkyl optionally substituted with hydroxyl;

$R^c$ is: H, $C_{1-6}$ alkyl, $C_{3-6}$cycloalkyl, -M-$R^{CH}$, —$(CH_2)_{1-2}$—$R^f$, —$(CH_2)_2$—O—$(CH_2)_2$—$R^f$, —$(CH_2)_2$—$R^g$, —$CHR^hOCO_2R^i$, or —$(CHR^h)_{1-2}OC(O)R^i$;

$R^d$ and $R^e$ are independently: H, $C_1$-$C_3$-alkoxyl or $C_1$-$C_6$-alkyl, optionally substituted with one to four substituents selected from: CN, OH; oxo, $NH_2$, halogen, $CO_2R^c$, $CONH_2$, $C_1$-$C_3$-alkoxyl, $CO_2R^c$, aryl, carbocyclyl, or heterocyclyl, as defined above;

$R^f$ is $CO_2R^{f1}$, CN, $C(O)N(R^{f2})_2$, —$OC(O)R^{f1}$, or $C_{1-2}$alkoxyl;
$R^{f1}$ is $C_{1-4}$alkyl; and
$R^{f2}$ is H or $C_{1-4}$alkyl;
$R^g$ is OH, $C_{1-4}$alkoxyl, $NH_2$, $NH(C_{1-4}$alkyl$)$ or $N(C_{1-4}$alkyl$)_2$;
$R^h$ is H or $C_{1-4}$alkyl;
$R^i$ is $C_{1-6}$alkyl, $C_{3-6}$cycloalkyl, or phenyl;
M is a bond or —$(CH_2)_{1-3}$—;
$R^{CH}$ is (a) aryl, aryl is phenyl or naphthalyl, optionally substituted with one to three groups independently selected from halo, $C_{1-4}$alkyl, or $C_{1-4}$alkoxy; (b) carbocyclyl, carbocyclyl is a 5-, 6- or 7-membered monocyclic carbon ring, that is saturated or partially unsaturated and the carbocyclyl is optionally substituted with one to three substituents independently selected from halo, $C_{1-4}$alkyl, or $C_{1-4}$alkoxy; or (c) a 5- to 6-membered monocyclic heterocyclyl containing one or two heteroatoms independently selected from the group consisting of N and O, and the heterocyclyl is optionally substituted with one or two substituents independently selected from the group consisting of: oxo and $C_{1-3}$ alkyl;
n is 0, 1, 2, 3 or 4; and
p is 0 or 1.

In an embodiment of the compounds of Formula I,
$R^1$ is:
H;
halogen;
$C_1$-$C_6$-alkyl, optionally with one to four substituents selected from: CN, OH, oxo, $NH_2$, $CF_3$, $C_1$-$C_3$-alkyl, and $C_1$-$C_3$-alkoxyl;
$(CR^aR^b)_nCO_2R^c$;
$(CR^aR^b)_nCONR^dR^e$;
$(CHR^a)_nNHCONR^dR^e$;
$(CHR^a)_nCONHSO_2R^d$;
$(CHR^a)_nSO_2R^d$;
$(CHR^a)_nSO_2NR^dR^e$;
$(CR^aR^b)_n$-heterocyclyl; wherein heterocyclyl is as defined below;
$(CHR^a)_p$—C(O)-heterocyclyl; wherein heterocyclyl is as defined below;
$(CR^aR^b)_n$-carbocyclyl; wherein carbocyclyl is as defined above;
$CR^a$(carbocyclyl)$_2$; wherein carbocyclyl is as defined above;
$(CR^aR^b)_n$-aryl; wherein aryl is as defined above;
$(CR^aR^b)_n$—O-carbocyclyl; wherein carbocyclyl is as defined above;
$(CR^aR^b)_n$—O-aryl; wherein aryl is as defined above;
Heterocyclyl is a 4-, 5-, 6-, or 7-membered monocyclic ring or 8-, 9-, 10-membered bicyclic ring, or 13- or 14-membered tricyclic ring; the monocyclic, bicyclic or tricyclic ring can be saturated, unsaturated or aromatic, containing one to four heteroatoms selected from O, N. or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, $(CR^aR^b)_nCO_2R^c$, $(CR^aR^b)_nCONR^dR^e$, $(CHR^a)NHCONR^dR^e$, and $(CHR^a)_p$—C(O)-heterocyclyl;

$R^c$ is: H, $C_{1-6}$ alkyl, -M-$R^{CH}$, —$(CH_2)_{1-2}$—$R^f$, $(CH_2)_2$—O—$(CH_2)_2$—$R^f$, —$(CH_2)_2$—$R^g$, $CHR^hOCO_2R^i$, or —$(CHR^h)_{1-2}OC(O)R^i$;

$R^f$ is $CO_2R^{f1}$, $C(O)N(R^{f2})_2$, —$OC(O)R^{f1}$, or $C_{1-2}$alkoxyl; and all other substituents are as defined above in the first embodiment.

In an embodiment of the compounds of Formula I

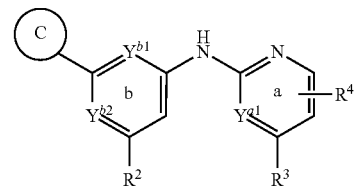

the rings a and b are defined as follows: a) $Y^{a1}$ is N; and $Y^{b1}$ and $Y^{b2}$ are CH; b) $Y^{b1}$ is N; and $Y^{a1}$ and $Y^{b2}$ are CH; c) $Y^{a1}$ and $Y^{b2}$ are N; and $Y^{b1}$ is CH; or d) $Y^{b1}$ and $Y^{b2}$ are N; and $Y^{a1}$ is CH; and all other substituents are as defined in the first embodiment.

In one embodiment of the compounds of Formula Ia

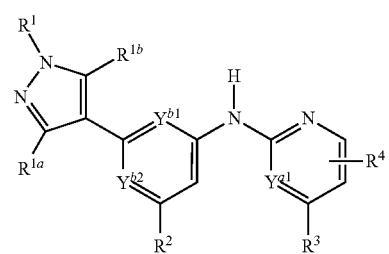

Ia rings a and b are defined as a) $Y^{b1}$ and $Y^{b2}$ are N; and $Y^{a1}$ is CH; or b) $Y^{a1}$ and $Y^{b2}$ are N; and $Y^{b1}$ is CH;
and all other substituents are as defined above.

In another embodiment of the compounds of Formula Ia, the compounds have the formula Ia(i)

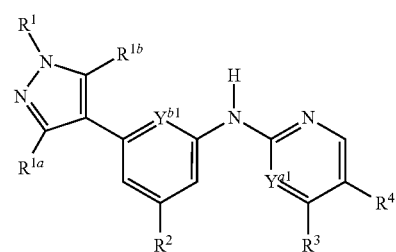

Ia(i)

rings a and b are defined as: a) $Y^{a1}$ are N; and $Y^{b1}$ is CH; or b) $Y^{b1}$ are N; and $Y^{a1}$ is CH; and all other substituents are as defined above.

In an embodiment of the compounds of Formula Ib

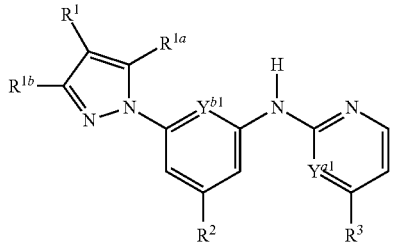

rings a and b are defined as: a) $Y^{a1}$ is N; and $Y^{b1}$ is CH; or b) $Y^{b1}$ is N; and $Y^{a1}$ is CH; and all other substituents are as defined above.

In an embodiment of the compounds of Formula Ic or Id

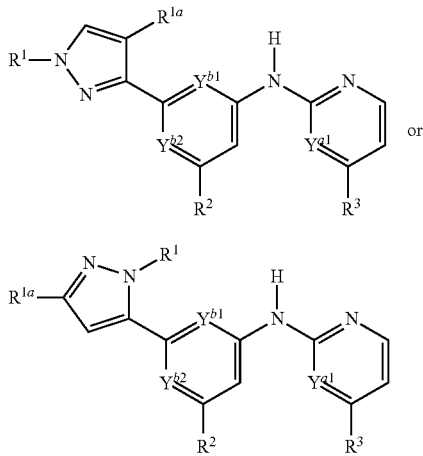

rings a and b are defined as: a) $Y^{a1}$ is N; and $Y^{b1}$ and $Y^{b2}$ are CH; b) $Y^{b1}$ is N; and $Y^{a1}$ and $Y^{b2}$ are CH; or c) $Y^{b1}$ and $Y^{b2}$ are N; and $Y^{a1}$ is CH; and all other substituents are as defined above.

In any one of the above embodiments of the compounds of Formula I, Ia, Ib, Ic and Id, $R^{1a}$ and $R^{1b}$ are independently H, $CH_3$, Cl, F, or $CF_3$. In a second embodiment of the compounds of Formula I, Ia, Ib, Ic and Id, $R^{1a}$ and $R^{1b}$ are both H.

In any one of the above embodiments of the compounds of Formula I, Ia, Ib, Ic and Id, or a pharmaceutically acceptable salt thereof, $R^2$ is H or $CH_3$. In a second embodiment of the compounds of Formula I, Ia, Ib, Ic and Id, $R^2$ is $CH_3$.

In any one of the above embodiments of the compounds of Formula I, Ia, Ib, Ic and Id, or a pharmaceutically acceptable salt thereof, $R^3$ is $CF_3$, $CHF_2$, $CHFCH_3$, $CH_3$, c-propyl, i-propyl, t-butyl, $OCH_3$, $OCH(CH_3)_2$, or $OCH_2CH_2OH$. In a second embodiment of the compounds of Formula I, Ia, Ib, Ic and Id, $R^3$ is $CF_3$.

In any one of the above embodiments of the compounds of Formula I, Ia, Ib, Ic and Id, or a pharmaceutically acceptable salt thereof, $R^4$ is H, Cl or F. In a second embodiment of the compounds of Formula I, Ia, Ib, Ic and Id, $R^4$ is H.

In another embodiment of the compounds of Formula I, Ia, Ib, Ic and Id or a pharmaceutically acceptable salt thereof, wherein: $R^{1a}$ and $R^{1b}$ are independently: H, Cl, F, $CH_3$, or $CF_3$; $R^2$ is H or $CH_3$; $R^3$ is H, Cl, F, $CH_3$, $CH(CH_3)_2$, cyclopropyl, t-butyl, $CHF_2$, or $CF_3$, $CHFCH_3$, $OCH_3$, $OCH(CH_3)_2$, $OCH_2CH_2OH$; $R^4$ is H, Cl or F; and all other substituents are as defined above.

In another embodiment of the compounds of Formula I, Ia, Ib, Ic and Id or a pharmaceutically acceptable salt thereof, wherein: $R^1$ is H; $C_1$-$C_6$-alkyl, optionally substituted with one or more substituent selected from the group consisting of: CN, OH, oxo, $NH_2$, $CF_3$, $C_1$-$C_3$-alkyl, or $C_1$-$C_3$-alkoxyl; $(CR^aR^b)_n CO_2R^c$; $(CR^aR^b)_n CONR^dR^e$; $(CR^aR^b)_n$-heterocyclyl; or $(CR^aR^b)_n$-carbocyclyl. In a second embodiment of the compounds of Formula I, Ia, Ib, Ic and Id, $R^1$ is H; $C_1$-$C_6$-alkyl, optionally substituted with one or more substituent selected from the group consisting of: CN, OH, oxo, $NH_2$, $CF_3$, $CH_3$ or $OCH_3$; $(CR^aR^b)_n CO_2R^c$; $(CR^aR^b)_n CONH_2$, $(CR^aR^b)_n$-heterocyclyl; or $(CR^aR^b)_n$-carbocyclyl, $R^a$ and $R^b$ are independently H, $CH_3$, or OH; $R^c$ is H, or $C_{1-6}$ alkyl; and n is 0, 1, 2, 3 or 4; and all other substituents are as defined above.

In another embodiment of the compounds of Formula I or a pharmaceutically acceptable salt thereof are compound having the formula Ie

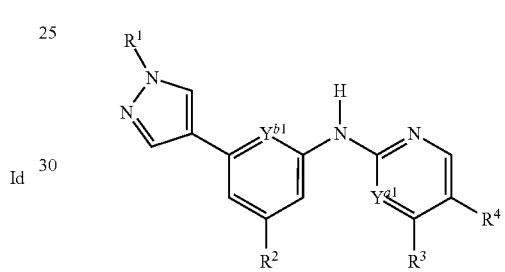

wherein rings a and b are defined as: a) $Y^{a1}$ are N; and $Y^{b1}$ is CH; or b) $Y^{b1}$ are N; and $Y^{a1}$ is CH;

$R^1$ is $(CR^aR^b)_n$-heterocyclyl or $(CR^aR^b)_n$-carbocyclyl;

wherein the heterocyclyl moiety of the $(CR^aR^b)_n$-heterocyclyl is 5- or 6-membered monocyclic ring contain 1 to 2 heteroatoms selected from O, N or S; and wherein the heterocyclyl moiety is unsubstituted or substituted with 1-4 substituents selected from the group consisting of oxo, hydroxyl, $C_{1-3}$ alkyl, $CO_2H$, and $CONH_2$; and wherein the carbocyclyl of the $(CR^aR^b)_n$-carbocyclyl is unsubstituted or substituted with 1-4 substituents selected from the group consisting of hydroxyl, $C_{1-3}$ alkyl, $CO_2H$, and $CONH_2$;

$R^2$ is H, methyl, or chloro;

$R^3$ is H, methyl, or $C_{1-3}$fluoroalkyl;

$R^4$ is H or fluoro;

$R^a$ and $R^b$ are independently H, OH, or $C_{1-3}$ alkyl; and n is 0 or 1.

In another embodiment are compounds of the Formula Ie as set forth above, wherein $R^1$ is $(CR^aR^b)_n$-heterocyclyl, wherein the heterocyclyl moiety of the $(CR^aR^b)_n$-heterocyclyl is pyrrolidine, oxazolidine, or piperidine, wherein the pyrrolidine, oxazolidine, or piperidine is unsubstituted or substituted or substituted with 1-4 substituents selected from the group consisting of oxo, hydroxyl, $C_{1-3}$ alkyl, $CO_2H$, and $CONH_2$. In a specific embodiment n is 0.

In another embodiment are compounds of the Formula Ie as set forth above, wherein $R^1$ is $(CR^aR^b)_n$-carbocyclyl, wherein the carbocyclyl moiety of the $(CR^aR^b)_n$-carbocyclyl is a $C_{4-8}$cycloalkyl, wherein the $C_{4-8}$cycloalkyl is unsubstituted or substituted or substituted with 1-4 substituents selected from the group consisting of hydroxyl, $C_{1-3}$ alkyl, $CO_2H$, and $CONH_2$. In a specific embodiment n is 0.

In another embodiment of the compounds of Formula I or a pharmaceutically acceptable salt thereof are compounds having the formula Ie

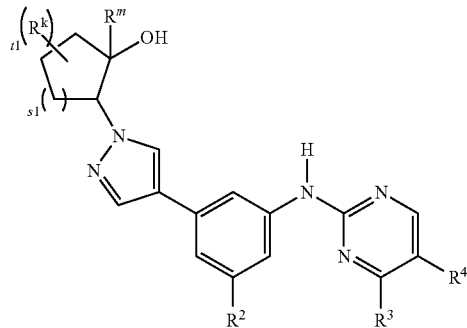

Ie wherein
each $R^k$ is independently $C_{1-3}$ alkyl or OH;
$R^m$ is H or $C_1$-$C_3$-alkyl;
$R^2$ is H or methyl;
$R^3$ is H, methyl, isopropyl, $C_1$-$C_3$-fluoroalkyl, cyclopropyl, or methoxy;
$R^4$ is H or fluoro;
s1 is 1, 2, or 3; and
t1 is 0, 1, 2, or 3

In another embodiment are compounds having the formula Ie or a pharmaceutically acceptable salt thereof,
wherein
the group

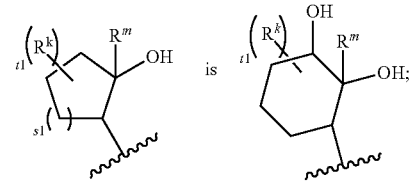

$R^2$ is methyl;
t1 is 0, 1, or 2; and
$R^2$, $R^3$, $R^k$ and $R^m$ are as set forth above.

In another embodiment of the compounds of Formula I or a pharmaceutically acceptable salt thereof are compounds having the formula If

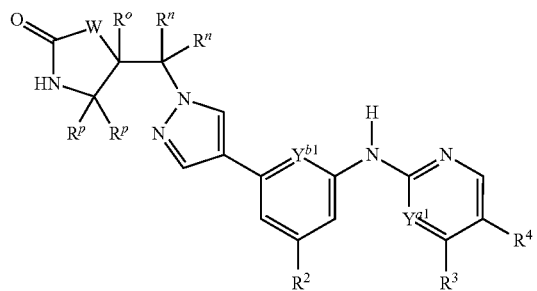

If wherein
(i) $Y^{a1}$ is N and $Y^{b1}$ is CH; or
(ii) $Y^{a1}$ is CH and $Y^{b1}$ is N;
W is O or $CH_2$;
each $R^n$ is independently H or $C_1$-$C_3$-alkyl;
$R^o$ is H, OH, or $C_1$-$C_3$-alkyl;
each $R^p$ is independently H or $C_1$-$C_3$-alkyl; or both $R^p$ together with the carbon atom to which they are attached form a $C_3$-$C_6$-spirocycle;
$R^2$ is H or methyl;
$R^3$ is H, methyl, isopropyl, $C_1$-$C_3$-fluoroalkyl, cyclopropyl, or methoxy; and
$R^4$ is H or fluoro.

In another embodiment are compounds having the formula If or a pharmaceutically acceptable salt thereof, wherein W is O.

In another embodiment are compounds having the formula If or a pharmaceutically acceptable salt thereof, wherein W is $CH_2$.

In another embodiment are compounds having the formula If or a pharmaceutically acceptable salt thereof, wherein
$Y^{a1}$ is N and $Y^{b1}$ is CH;
W is O;
each $R^n$ is independently H or $C_1$-$C_3$-alkyl;
$R^o$ is H or methyl;
each $R^p$ is independently H or methyl; or both $R^p$ together with the carbon atom to which they are attached form a spirocyclopropane;
$R^2$ is methyl;
$R^3$ is H, methyl, or $C_1$-$C_3$-fluoroalkyl; and
$R^4$ is H or fluoro.

In another embodiment of the compounds of Formula I or a pharmaceutically acceptable salt thereof are compounds having the formula If

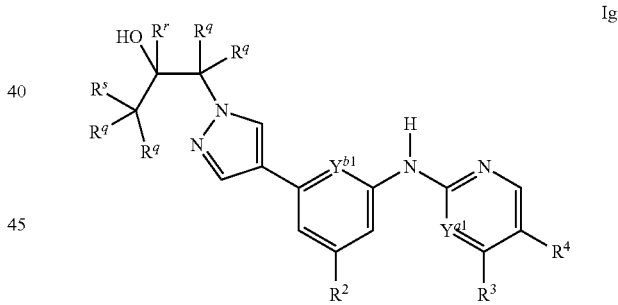

Ig wherein
(i) $Y^{a1}$ is N and $Y^{b1}$ is CH or
(ii) $Y^{a1}$ is CH and $Y^{b1}$ is N;
each $R^q$ is independently H, $C_1$-$C_3$-alkyl, or $C_1$-$C_3$-fluoroalkyl;
$R^q$ is H, $C_1$-$C_3$-alkyl, or $C_1$-$C_3$-fluoroalkyl;
$R^s$ is hydroxyl or CN;
$R^2$ is H or methyl;
$R^3$ is H, methyl, isopropyl, $C_1$-$C_3$-fluoroalkyl, cyclopropyl, or methoxy; and
$R^4$ is H or fluoro.

In another embodiment are compounds having the formula Ig or a pharmaceutically acceptable salt thereof, wherein
$Y^{a1}$ is N and $Y^{b1}$ is CH;
each $R^q$ is independently H or Me;
$R^r$ is H or Me;
$R^s$ is hydroxyl;
$R^2$ is methyl;

$R^3$ is H, methyl, or $C_1$-$C_3$-fluoroalkyl; and
$R^4$ is H or fluoro.

One embodiment of the compounds of Formula I are the compounds of Examples 1.1 to 34.2 (or their pharmaceutically acceptable salts), such as:

N-(3-methyl-5-(pyrazolo[1,5-a]pyridin-3-yl)phenyl)-4-(trifluoromethyl)pyrimidin-2-amine;
3-[4-(3-methyl-5-{[4-(trifluoromethyl)-pyrimidin-2-yl]amino}-phenyl)-1H-pyrazol-1-yl]-propanoic acid;
N-[3-methyl-5-(1-methyl-1H-pyrazol-4-yl)phenyl]-4-(trifluoromethyl)-pyrimidin-2-amine;
tert-butyl 4-[4-(3-methyl-5-{[4-(trifluoromethyl)-pyrimidin-2-yl]amino}-phenyl)-1H-pyrazol-1-yl]-cyclohexanecarboxylate;
N-[3-(1-cyclohex-2-en-1-yl-1H-pyrazol-4-yl)-5-methylphenyl]-4-(trifluoromethyl)-pyrimidin-2-amine;
N-[3-methyl-5-(1H-pyrazol-4-yl)phenyl]-4-(trifluoromethyl)-pyrimidin-2-amine;
N-[3-methyl-5-(1H-pyrazol-3-yl)phenyl]-4-(trifluoromethyl) pyrimidin-2-amine;
N-{3-methyl-5-[1-(1-methylethyl)-1H-pyrazol-5-yl]phenyl}-4-(trifluoromethyl)pyrimidin-2-amine;
N-[3-methyl-5-(1-methyl-1H-pyrazol-5-yl)phenyl]-4-(trifluoromethyl) pyrimidin-2-amine;
N-{3-methyl-5-[1-methyl-3-(trifluoromethyl)-1H-pyrazol-5-yl]phenyl}-4-(trifluoromethyl) pyrimidin-2-amine;
tert-butyl 4-(4-methyl-6-{[4-(trifluoromethyl)pyridin-2-yl]amino}-pyridin-2-yl)-1H-pyrazole-1-carboxylate;
4-methyl-6-(1H-pyrazol-4-yl)-N-[4-(trifluoromethyl)pyridin-2-yl]pyridin-2-amine;
4-methyl-6-(1-methyl-1H-pyrazol-4-yl)-N-[4-(trifluoromethyl)pyridin-2-yl]pyridin-2-amine;
4-methyl-6-[1-(3-methylbutyl)-1H-pyrazol-4-yl]-N-[4-(trifluoromethyl)pyridin-2-yl]pyridin-2-amine;
6-(5,6-dihydro-4H-pyrrolo[1,2-b]pyrazol-3-yl)-4-methyl-N-[4-(trifluoromethyl)pyridin-2-yl]pyridin-2-amine;
ethyl 3-[4-(4-methyl-6-{[4-(trifluoromethyl)pyridin-2-yl]amino}pyridin-2-yl)-1H-pyrazol-1-yl]propanoate;
ethyl 3-(4-{6-[(4-cyclopropylpyridin-2-yl)amino]-4-methylpyridin-2-yl}-1H-pyrazol-1-yl)propanoate;
3-(4-{6-[(4-methylpyridin-2-yl)amino]pyridin-2-yl}-1H-pyrazol-1-yl)propanoic acid;
3-[4-(6-{[4-(trifluoromethyl)pyridin-2-yl]amino}pyridin-2-yl)-1H-pyrazol-1-yl]propanoic acid;
3-(4-{4-methyl-6-[(4-methylpyridin-2-yl)amino]pyridin-2-yl}-1H-pyrazol-1-yl)propanoic acid;
3-[4-(4-methyl-6-{[4-(trifluoromethyl)pyridin-2-yl]amino}pyridin-2-yl)-1H-pyrazol-1-yl]propanoic acid;
3-(4-{6-[(4-cyclopropylpyridin-2-yl)amino]-4-methylpyridin-2-yl}-1H-pyrazol-1-yl)propanoic acid;
ethyl 3-(4-{6-[(4-methylpyridin-2-yl)amino]pyridin-2-yl}-1H-pyrazol-1-yl)propanoate;
ethyl 3-[4-(6-{[4-(trifluoromethyl)pyridin-2-yl]amino}pyridin-2-yl)-1H-pyrazol-1-yl]propanoate;
ethyl 3-(4-{6-[(5-chloro-4-methylpyridin-2-yl)amino]-4-methylpyridin-2-yl}-1H-pyrazol-1-yl)propanoate;
ethyl 3-(4-{4-methyl-6-[(4-methylpyridin-2-yl)amino]pyridin-2-yl}-1H-pyrazol-1-yl)propanoate;
3-(4-{6-[(5-chloro-4-methylpyridin-2-yl)amino]-4-methylpyridin-2-yl}-1H-pyrazol-1-yl)propanoic acid;
5R-{[4-(4-methyl-6-{[4-(trifluoromethyl)pyridin-2-yl]amino}pyridin-2-yl)-1H-pyrazol-1-yl]methyl}-1,3-oxazolidin-2-one;
5S-{[4-(4-methyl-6-{[4-(trifluoromethyl)pyridin-2-yl]amino}pyridin-2-yl)-1H-pyrazol-1-yl]methyl}-1,3-oxazolidin-2-one;
tert-butyl [4-(4-methyl-6-{[4-(trifluoromethyl)pyridin-2-yl]amino}pyridin-2-yl)-1H-pyrazol-1-yl]acetate;
[4-(4-methyl-6-{[4-(trifluoromethyl)pyridin-2-yl]amino}pyridin-2-yl)-1H-pyrazol-1-yl]acetic acid;
4R-{1R-[4-(4-methyl-6-{[4-(trifluoromethyl)pyridin-2-yl]amino}pyridin-2-yl)-1H-pyrazol-1-yl]ethyl}pyrrolidin-2-one;
4R-{1 S-[4-(4-methyl-6-{[4-(trifluoromethyl)pyridin-2-yl]amino}pyridin-2-yl)-1H-pyrazol-1-yl]ethyl}pyrrolidin-2-one;
4S-{1R-[4-(4-methyl-6-{[4-(trifluoromethyl)pyridin-2-yl]amino}pyridin-2-yl)-1H-pyrazol-1-yl]ethyl}pyrrolidin-2-one;
4R-{[4-(6-{[4-(difluoromethyl)pyridin-2-yl]amino}-4-methylpyridin-2-yl)-1H-pyrazol-1-yl]methyl}pyrrolidin-2-one;
4S-{1S-[4-(4-methyl-6-{[4-(trifluoromethyl)pyridin-2-yl]amino}pyridin-2-yl)-1H-pyrazol-1-yl]ethyl}pyrrolidin-2-one;
4S-{[4-(6-{[4-(difluoromethyl)pyridin-2-yl]amino}-4-methylpyridin-2-yl)-1H-pyrazol-1-yl]methyl}pyrrolidin-2-one;
4-{[4-(4-methyl-6-{[4-(trifluoromethyl)pyridin-2-yl]amino}pyridin-2-yl)-1H-pyrazol-1-yl]methyl}pyrrolidin-2-one;
3-[4-(4-methyl-6-{[4-(trifluoromethyl)pyridin-2-yl]amino}pyrimidin-2-yl)-1H-pyrazol-1-yl]propanoic acid;
6-methyl-2-(1H-pyrazol-4-yl)-N-[4-(trifluoro-methyl)pyridin-2-yl]pyrimidin-4-amine;
6-methyl-2-pyrazolo[1,5-a]pyridin-3-yl-N-[4-(trifluoro-methyl)pyridin-2-yl]pyrimidin-4-amine;
N-[2-methyl-6-(1-methyl-1H-pyrazol-4-yl)pyridin-4-yl]-4-(trifluoro-methyl)pyrimidin-2-amine;
N-[2-methyl-6-(1H-pyrazol-4-yl)pyridin-4-yl]-4-(trifluoromethyl)pyrimidin-2-amine;
6-methyl-2-(1-methyl-1H-pyrazol-5-yl)-N-[4-(trifluoro-methyl)pyridin-2-yl]pyrimidin-4-amine;
6-methyl-2-[1-methyl-3-(trifluoromethyl)-1H-pyrazol-5-yl]-N-[4-(trifluoromethyl)pyridin-2-yl]pyrimidin-4-amine;
1H-pyrazol-1-yl)propanoic acid;
ethyl 3-[4-(3-{[4-(trifluoromethyl)pyrimidin-2-yl]amino}phenyl)-1H-pyrazol-1-yl]propanoate;
ethyl 3-(4-{3-[(4-methoxypyrimidin-2-yl)amino]-5-methylphenyl}-1H-pyrazol-1-yl)propanoate;
5R-{[4-(3-methyl-5-{[4-(trifluoromethyl)pyrimidin-2-yl]amino}phenyl)-1H-pyrazol-1-yl]methyl}-1,3-oxazolidin-2-one;
3-[4-(3-{[4-(trifluoromethyl)pyrimidin-2-yl]amino}phenyl)-1H-pyrazol-1-yl]propanoic acid;
3-(4-{3-[(5-fluoro-4-methylpyrimidin-2-yl)amino]-5-methylphenyl}-1H-pyrazol-1-yl)propanamide;
3-(4-{3-[(5-chloro-4-methoxypyrimidin-2-yl)amino]-5-methylphenyl}-1H-pyrazol-1-yl)propanamide;
3-[4-(3-methyl-5-{[4-(1-methylethyl)pyrimidin-2-yl]amino}phenyl)-1H-pyrazol-1-yl]propanamide;
3-[4-(3-{[4-(difluoromethyl)pyrimidin-2-yl]amino}-5-methylphenyl)-1H-pyrazol-1-yl]propanamide;
3-(4-{3-[(4-methylpyrimidin-2-yl)amino]phenyl}-1H-pyrazol-1-yl)propanamide;
3-(4-{3-[(5-fluoro-4-methoxypyrimidin-2-yl)amino]-5-methylphenyl}-1H-pyrazol-1-yl)propanamide;
3-(4-{3-methyl-5-[(4-methylpyrimidin-2-yl)amino]phenyl}-1H-pyrazol-1-yl)propanamide;
3-(4-{3-[(5-chloro-4-methylpyrimidin-2-yl)amino]-5-methylphenyl}-1H-pyrazol-1-yl)propanamide;

3-(4-{3-[(4-cyclopropylpyrimidin-2-yl)amino]-5-methylphenyl}-1H-pyrazol-1-yl)propanamide;
3-[4-(3-{[4-(trifluoromethyl)pyrimidin-2-yl]amino}phenyl)-1H-pyrazol-1-yl]propanamide;
5R or 5 S-[(4-{3-[(4-methylpyrimidin-2-yl)amino]phenyl}-1H-pyrazol-1-yl)methyl]-1,3-oxazolidin-2-one;
5-[(4-{3-[(4-methoxypyrimidin-2-yl)amino]-5-methylphenyl}-1H-pyrazol-1-yl)methyl]-1,3-oxazolidin-2-one;
5-[(4-{3-methyl-5-[(4-methylpyrimidin-2-yl)amino]phenyl}-1H-pyrazol-1-yl)methyl]-1,3-oxazolidin-2-one;
5-[(4-{3-[(4-cyclopropylpyrimidin-2-yl)amino]-5-methylphenyl}-1H-pyrazol-1-yl)methyl]-1,3-oxazolidin-2-one;
5-[(4-{3-[(4-methylpyrimidin-2-yl)amino]phenyl}-1H-pyrazol-1-yl)methyl]-1,3-oxazolidin-2-one;
5-[(4-{3-[(4-methoxypyrimidin-2-yl)amino]-5-methylphenyl}-1H-pyrazol-1-yl)methyl]-1,3-oxazolidin-2-one;
5R or 5 S-[(4-{3-[(5-fluoro-4-methylpyrimidin-2-yl)amino]-5-methylphenyl}-1H-pyrazol-1-yl)methyl]-1,3-oxazolidin-2-one;
5R-[(4-{3-[(5-chloro-4-methoxypyrimidin-2-yl)amino]-5-methylphenyl}-1H-pyrazol-1-yl)methyl]-1,3-oxazolidin-2-one;
5R-{[4-(3-methyl-5-{[4-(1-methylethyl)pyrimidin-2-yl]amino}phenyl)-1H-pyrazol-1-yl]methyl}-1,3-oxazolidin-2-one;
5R-[(4-{3-[(5-fluoro-4-methoxypyrimidin-2-yl)amino]-5-methylphenyl}-1H-pyrazol-1-yl)methyl]-1,3-oxazolidin-2-one;
5R-[(4-{3-[(5-chloro-4-methylpyrimidin-2-yl)amino]-5-methylphenyl}-1H-pyrazol-1-yl)methyl]-1,3-oxazolidin-2-one;
5R-{[4-(3-{[4-(trifluoromethyl)pyrimidin-2-yl]amino}phenyl)-1H-pyrazol-1-yl]methyl}-1,3-oxazolidin-2-one;
5S-[(4-{3-[(5-chloro-4-methoxypyrimidin-2-yl)amino]-5-methylphenyl}-1H-pyrazol-1-yl)methyl]-1,3-oxazolidin-2-one;
5S-{[4-(3-methyl-5-{[4-(1-methylethyl)pyrimidin-2-yl]amino}phenyl)-1H-pyrazol-1-yl]methyl}-1,3-oxazolidin-2-one;
5S-[(4-{3-[(5-fluoro-4-methoxypyrimidin-2-yl)amino]-5-methylphenyl}-1H-pyrazol-1-yl)methyl]-1,3-oxazolidin-2-one;
5R-[(4-{3-methyl-5-[(4-methylpyrimidin-2-yl)amino]phenyl}-1H-pyrazol-1-yl)methyl]-1,3-oxazolidin-2-one;
5S-[(4-{3-[(5-chloro-4-methylpyrimidin-2-yl)amino]-5-methylphenyl}-1H-pyrazol-1-yl)methyl]-1,3-oxazolidin-2-one;
5R or 5S-[(4-{3-[(4-cyclopropylpyrimidin-2-yl)amino]-5-methylphenyl}-1H-pyrazol-1-yl)methyl]-1,3-oxazolidin-2-one;
5S-{[4-(3-{[4-(trifluoromethyl)pyrimidin-2-yl]amino}phenyl)-1H-pyrazol-1-yl]methyl}-1,3-oxazolidin-2-one;
N-(3-methyl-5-pyrazolo[1,5-b]pyridazin-3-ylphenyl)-4-(trifluoromethyl)pyrimidin-2-amine;
N-[3-(6-methoxypyrazolo[1,5-b]pyridazin-3-yl)-5-methylphenyl]-4-(trifluoromethyl)pyrimidin-2-amine;
N-(3-methyl-5-pyrazolo[1,5-a]pyrimidin-3-ylphenyl)-4-(trifluoromethyl)pyrimidin-2-amine;
N-[3-(3,5-dimethyl-1H-pyrazol-4-yl)-5-methylphenyl]-4-(trifluoromethyl)pyrimidin-2-amine;
N-[3-methyl-5-(3-methyl-1H-pyrazol-4-yl)phenyl]-4-(trifluoromethyl)pyrimidin-2-amine;
3-(4-{3-[(4-cyclopropylpyrimidin-2-yl)amino]-5-methylphenyl}-1H-pyrazol-1-yl)propanoic acid;
ethyl 3-(4-{3-[(4-cyclopropylpyrimidin-2-yl)amino]-5-methylphenyl}-1H-pyrazol-1-yl)propanoate;
ethyl 3-(4-{3-methyl-5[(4-methylpyrimidin-2-yl)amino]phenyl}-1H-pyrazol-1-yl)propanoate;
ethyl 3-[4-(3-methyl-5-{[4-(trifluoromethyl)pyrimidin-2-yl]amino}phenyl)-1H-pyrazol-1-yl]propanoate;
3-(4-{3-methyl-5-[(4-methylpyrimidin-2-yl)amino]phenyl}-1H-pyrazol-1-yl)propanoic acid;
5S-{[4-(3-methyl-5-{[4-(trifluoromethyl)pyrimidin-2-yl]amino}phenyl)-1H-pyrazol-1-yl]methyl}-1,3-oxazolidin-2-one;
N-[3-methyl-5-(1-methyl-1H-pyrazol-3-yl)phenyl]-4-(trifluoromethyl)pyrimidin-2-amine;
N-[3-(1H-indazol-3-yl)-5-methylphenyl]-4-(trifluoromethyl)pyrimidin-2-amine;
N-[3-methyl-5-(1-methyl-1H-pyrazol-5-yl)phenyl]-4-(trifluoromethyl)pyrimidin-2-amine;
3-methyl-5-{[4-(3-methyl-5-{[4-(trifluoromethyl)pyrimidin-2-yl]amino}phenyl)-1H-pyrazol-1-yl]methyl}-1,3-oxazolidin-2-one;
(3R)-3-hydroxy-4-[4-(3-methyl-5-{[4-(trifluoromethyl)-pyrimidin-2-yl]amino}phenyl)-1H-pyrazol-1-yl]-butanenitrile;
3-[4-(3-methyl-5-{[4-(trifluoromethyl)-pyrimidin-2-yl]amino}-phenyl)-1H-pyrazol-1-yl]-propanamide;
(2R)-2-methyl-3-[4-(3-methyl-5-{[4-(trifluoromethyl)-pyrimidin-2-yl]-amino}phenyl)-1H-pyrazol-1-yl]-propan-1-ol;
(2S)-2-methyl-3-[4-(3-methyl-5-{[4-(trifluoromethyl)-pyrimidin-2-yl]amino}-phenyl)-1H-pyrazol-1-yl]-propan-1-ol;
1-{3-[4-(3-methyl-5-{[4-(trifluoro-methyl)pyrimidin-2-yl]amino}-phenyl)-1H-pyrazol-1-yl]-propyl}imidazolidin-2-one;
N-(3-{1-[2-(4-acetylpiperazin-1-yl)-2-oxoethyl]-1H-pyrazol-4-yl}-5-methylphenyl)-4-(trifluoromethyl)pyrimidin-2-amine;
N-tert-butyl-2-[4-(3-methyl-5-{[4-(trifluoromethyl)pyrimidin-2-yl]amino}-phenyl)-1H-pyrazol-1-yl]acetamide;
N-{3-[1-(1,4-dioxan-2-ylmethyl)-1H-pyrazol-4-yl]-5-methyl-phenyl}-4-(trifluoro-methyl)pyrimidin-2-amine;
N-(3-methyl-5-{1-[(5-methyl-1,2,4-oxadiazol-3-yl)methyl]-1H-pyrazol-4-yl}phenyl)-4-(trifluoromethyl)pyrimidin-2-amine;
N-(3-{1-[2-(4,4-dimethyl-1,3-oxazolidin-3-yl)-2-oxoethyl]-1H-pyrazol-4-yl}-5-methylphenyl)-4-(trifluoromethyl)pyrimidin-2-amine;
N-(2-methoxy-1,1-dimethylethyl)-2-[4-(3-methyl-5-{[4-(trifluoromethyl)pyrimidin-2-yl]amino}phenyl)-1H-pyrazol-1-yl]acetamide;
N-(3-{1-[2-(3,3-dimethylmorpholin-4-yl)-2-oxoethyl]-1H-pyrazol-4-yl}-5-methylphenyl)-4-(trifluoromethyl)pyrimidin-2-amine;
N-[3-(1-{2-[(3R,5S)-3,5-dimethyl-morpholin-4-yl]-2-oxoethyl}-1H-pyrazol-4-yl)-5-methylphenyl]-4-(trifluoromethyl)-pyrimidin-2-amine;
N-[3-(1-{2-[(3R,5R)-3,5-dimethylmorpholin-4-yl]-2-oxoethyl}-1H-pyrazol-4-yl)-5-methylphenyl]-4-(trifluoromethyl)-pyrimidin-2-amine;
1-{2-[4-(3-methyl-5-{[4-(trifluoromethyl)-pyrimidin-2-yl]-amino}phenyl)-1H-pyrazol-1-yl]ethyl}urea;
3-[4-(3-methyl-5-{[4-(trifluoromethyl)pyrimidin-2-yl]amino}-phenyl)-1H-pyrazol-1-yl]dihydrofuran-2(3H)-one;
N-{3-methyl-5-[1-(oxetan-2-ylmethyl)-1H-pyrazol-4-yl]phenyl}-4-(trifluoromethyl)-pyrimidin-2-amine;

2-{2-[4-(3-methyl-5-{[4-(trifluoromethyl)-pyrimidin-2-yl]-amino}phenyl)-1H-pyrazol-1-yl]ethoxy}ethanol;
N-{3-[1-(3-aminopropyl)-1H-pyrazol-4-yl]-5-methylphenyl}-4-(trifluoromethyl)pyrimidin-2-amine;
N-{3-[1-(cyclopropylmethyl)-1H-pyrazol-4-yl]-5-methylphenyl}-4-(trifluoromethyl)pyrimidin-2-amine;
1-[4-(3-methyl-5-{[4-(trifluoromethyl)pyrimidin-2-yl]amino}phenyl)-1H-pyrazol-1-yl]propan-2-one;
N-{3-[1-(2,2-diethoxyethyl)-1H-pyrazol-4-yl]-5-methylphenyl}-4-(trifluoromethyl)pyrimidin-2-amine;
N-(3-methyl-5-{1-[(5-methyl-1,3,4-oxadiazol-2-yl)methyl]-1H-pyrazol-4-yl}phenyl)-4-(trifluoromethyl)pyrimidin-2-amine;
N-(3-methyl-5-{1-[(3-methylisoxazol-5-yl)methyl]-1H-pyrazol-4-yl}phenyl)-4-(trifluoromethyl)pyrimidin-2-amine;
N-{3-[1-(2-azetidin-1-yl-2-oxoethyl)-1H-pyrazol-4-yl]-5-methylphenyl}-4-(trifluoromethyl)pyrimidin-2-amine;
N-{3-methyl-5-[1-(2-oxo-2-pyrrolidin-1-ylethyl)-1H-pyrazol-4-yl]phenyl}-4-(trifluoromethyl)pyrimidin-2-amine;
methyl 2-[4-(3-methyl-5-{[4-(trifluoromethyl)pyrimidin-2-yl]amino}phenyl)-1H-pyrazol-1-yl]butanoate;
methyl 2-[4-(3-methyl-5-{[4-(trifluoromethyl)pyrimidin-2-yl]amino}phenyl)-1H-pyrazol-1-yl]propanoate;
ethyl 2-[4-(3-methyl-5-{[4-(trifluoromethyl)pyrimidin-2-yl]amino}phenyl)-1H-pyrazol-1-yl]propanoate;
3-[4-(3-methyl-5-{[4-(trifluoromethyl)pyrimidin-2-yl]amino}phenyl)-1H-pyrazol-1-yl]propan-1-ol;
N-{3-methyl-5-[1-(pyridazin-4-ylmethyl)-1H-pyrazol-4-yl]phenyl}-4-(trifluoromethyl)pyrimidin-2-amine;
5-{[4-(3-methyl-5-{[4-(trifluoromethyl)pyrimidin-2-yl]amino}phenyl)-1H-pyrazol-1-yl]methyl}-1,3-oxazolidin-2-one;
2-[4-(3-methyl-5-{[4-(trifluoromethyl)pyrimidin-2-yl]amino}phenyl)-1H-pyrazol-1-yl]butanoic acid;
2-[4-(3-methyl-5-{[4-(trifluoromethyl)pyrimidin-2-yl]amino}phenyl)-1H-pyrazol-1-yl]propanoic acid;
2-[4-(3-methyl-5-{[4-(trifluoromethyl)pyrimidin-2-yl]amino}phenyl)-1H-pyrazol-1-yl]ethanol;
2-[4-(3-methyl-5-{[4-(trifluoromethyl)pyrimidin-2-yl]amino}phenyl)-1H-pyrazol-1-yl]acetamide;
3-[4-(3-{[4-(2-hydroxyethoxy)pyrimidin-2-yl]amino}-5-methylphenyl)-1H-pyrazol-1-yl]propanamide;
1-[4-(3-methyl-5-{[4-(trifluoromethyl)pyrimidin-2-yl]amino}phenyl)-1H-pyrazol-1-yl]methanesulfonamide;
3-(4-{3-[(4-methoxypyrimidin-2-yl)amino]-5-methylphenyl}-1H-pyrazol-1-yl)propanamide;
(2R)-3-[4-(3-methyl-5-{[4-(trifluoromethyl)pyrimidin-2-yl]amino}phenyl)-1H-pyrazol-1-yl]propane-1,2-diol;
(2S)-3-[4-(3-methyl-5-{[4-(trifluoromethyl)pyrimidin-2-yl]amino}phenyl)-1H-pyrazol-1-yl]propane-1,2-diol;
1,1,1-trifluoro-3-[4-(3-methyl-5-{[4-(trifluoromethyl)pyrimidin-2-yl]amino}phenyl)-1H-pyrazol-1-yl]propan-2R-ol;
1,1,1-trifluoro-3-[4-(3-methyl-5-{[4-(trifluoromethyl)pyrimidin-2-yl]amino}phenyl)-1H-pyrazol-1-yl]propan-2S-ol;
3-methyl-5R or 5S-{[4-(3-methyl-5-{[4-(trifluoromethyl)pyrimidin-2-yl]amino}phenyl)-1H-pyrazol-1-yl]methyl}-1,3-oxazolidin-2-one;
(3S)-3-hydroxy-4-[4-(3-methyl-5-{[4-(trifluoromethyl)pyrimidin-2-yl]amino}phenyl)-1H-pyrazol-1-yl]butanenitrile;
N-(3-methyl-5-{1-[2-(methylsulfonyl)ethyl]-1H-pyrazol-4-yl}phenyl)-4-(trifluoromethyl)pyrimidin-2-amine;
methyl 4-[4-(3-methyl-5-{[4-(trifluoromethyl)pyrimidin-2-yl]amino}phenyl)-1H-pyrazol-1-yl]butanoate;
4-[4-(3-methyl-5-{[4-(trifluoromethyl)pyrimidin-2-yl]amino}phenyl)-1H-pyrazol-1-yl]butanoic acid;
4-[4-(3-methyl-5-{[4-(trifluoromethyl)pyrimidin-2-yl]amino}phenyl)-1H-pyrazol-1-yl]-1,2,3,4-tetrahydronaphthalene-1-carboxylic acid;
methyl 4-[4-(3-methyl-5-{[4-(trifluoromethyl)pyrimidin-2-yl]amino}phenyl)-1H-pyrazol-1-yl]-1,2,3,4-tetrahydronaphthalene-1-carboxylate;
4-{1-hydroxy-2-[4-(3-methyl-5-{[4-(trifluoromethyl)pyrimidin-2-yl]amino}phenyl)-1H-pyrazol-1-yl]ethyl}benzoic acid;
methyl 4-{1-hydroxy-2-[4-(3-methyl-5-{[4-(trifluoromethyl)pyrimidin-2-yl]amino}phenyl)-1H-pyrazol-1-yl]ethyl}benzoate;
N-{3-[1-(1,4-dioxaspiro[4.5]dec-8-yl)-1H-pyrazol-4-yl]-5-methylphenyl}-4-(trifluoromethyl)pyrimidin-2-amine;
3-[4-(3-methyl-5-{[4-(trifluoromethyl)pyrimidin-2-yl]amino}phenyl)-1H-pyrazol-1-yl]butanamide;
tert-butyl 4-[4-(3-methyl-5-{[4-(trifluoromethyl)pyrimidin-2-yl]amino}phenyl)-1H-pyrazol-1-yl]piperidine-1-carboxylate;
4-hydroxy-2-[4-(3-methyl-5-{[4-(trifluoromethyl)pyrimidin-2-yl]amino}phenyl)-1H-pyrazol-1-yl]butanoic acid;
6-[1-(methoxyacetyl)-1H-pyrazol-4-yl]-4-methyl-N-[4-(trifluoromethyl)pyridin-2-yl]pyridin-2-amine;
3-[4-(4-methyl-6-{[4-(trifluoro-methyl)pyridin-2-yl]amino}pyridin-2-yl)-1H-pyrazol-1-yl]propan-1-ol;
3-[4-(4-methyl-6-{[4-(trifluoro-methyl)pyridin-2-yl]amino}pyridin-2-yl)-1H-pyrazol-1-yl]propanamide;
2-[4-(4-methyl-6-{[4-(trifluoro-methyl)pyridin-2-yl]amino}pyridin-2-yl)-1H-pyrazol-1-yl]acetamide;
1-{3-[4-(4-methyl-6-{[4-(trifluoro-methyl)pyridin-2-yl]amino}pyridin-2-yl)-1H-pyrazol-1-yl]propyl}imidazolidin-2-one;
6-[1-(1,4-dioxan-2-ylmethyl)-1H-pyrazol-4-yl]-4-methyl-N-[4-(trifluoromethyl)pyridin-2-yl]pyridin-2-amine;
N-(2-methoxy-1,1-dimethylethyl)-2-[4-(4-methyl-6-{[4-(trifluoromethyl)pyridin-2-yl]amino}-pyridin-2-yl)-1H-pyrazol-1-yl]-acetamide;
6-(1-{2-[(3R,5S)-3,5-dimethylmorpholin-4-yl]-2-oxoethyl}-1H-pyrazol-4-yl)-4-methyl-N-[4-(trifluoromethyl)pyridin-2-yl]pyridin-2-amine;
4-methyl-6-[1-(3-morpholin-4-ylpropyl)-1H-pyrazol-4-yl]-N-[4-(trifluoromethyl)pyridin-2-yl]pyridin-2-amine;
4-methyl-6-[1-(oxetan-2-ylmethyl)-1H-pyrazol-4-yl]-N-[4-(trifluoromethyl)-pyridin-2-yl]pyridin-2-amine;
2-{2-[4-(4-methyl-6-{[4-(trifluoromethyl)-pyridin-2-yl]amino}-pyridin-2-yl)-1H-pyrazol-1-yl]-ethoxy}ethanol;
6-[1-(3-aminopropyl)-1H-pyrazol-4-yl]-4-methyl-N-[4-(trifluoromethyl)pyridin-2-yl]pyridin-2-amine;
6-[1-(cyclopropyl-methyl)-1H-pyrazol-4-yl]-4-methyl-N-[4-(trifluoromethyl)pyridin-2-yl]pyridin-2-amine;
6-[1-(2,2-diethoxyethyl)-1H-pyrazol-4-yl]-4-methyl-N-[4-(trifluoromethyl)pyridin-2-yl]pyridin-2-amine;
4-methyl-6-[1-(1-methylethyl)-1H-pyrazol-4-yl]-N-[4-(trifluoromethyl)pyridin-2-yl]pyridin-2-amine;
2-[4-(4-methyl-6-{[4-(trifluoro-methyl)pyridin-2-yl]amino}pyridin-2-yl)-1H-pyrazol-1-yl]ethanol;
4-[4-(4-methyl-6-{[4-(trifluoro-methyl)pyridin-2-yl]amino}pyridin-2-yl)-1H-pyrazol-1-yl]-1,2,3,4-tetrahydro-naphthalene-1-carboxylic acid;
methyl 4-[4-(4-methyl-6-{[4-(trifluoromethyl)pyridin-2-yl]amino}pyridin-2-yl)-1H-pyrazol-1-yl]-1,2,3,4-tetrahydro-naphthalene-1-carboxylate;
4-{1-hydroxy-2-[4-(4-methyl-6-{[4-(trifluoromethyl)pyridin-2-yl]amino}pyridin-2-yl)-1H-pyrazol-1-yl]ethyl}-benzoic acid;

methyl 4-{1-hydroxy-2-[4-(4-methyl-6-{[4-(trifluoromethyl)pyridin-2-yl]amino}pyridin-2-yl)-1H-pyrazol-1-yl]ethyl}-benzoate;

tert-Butyl 4-[4-(4-methyl-6-{[4-(trifluoromethyl)pyridin-2-yl]amino}pyridin-2-yl)-1H-pyrazol-1-yl]piperidine-1-carboxylate;

[4-(4-methyl-6-{[4-(trifluoromethyl)pyridin-2-yl]amino}-pyridin-2-yl)-1H-pyrazol-1-yl]-acetonitrile;

(S) methyl 3-[4-(3-methyl-5-{[4-(trifluoromethyl)pyrimidin-2-yl]amino}phenyl)-1H-pyrazo(-1-yl]-L-alaninate;

2-(4-(3-methyl-5-((4-(trifluoromethyl)pyrimidin-2-yl)amino)phenyl)-1H-pyrazol-1-yl)-1-phenylethanol;

methyl (2S)-2-hydroxy-3-[4-(3-methyl-5-{[4-(trifluoromethyl)-pyrimidin-2-yl]amino}phenyl)-1H-pyrazol-1-yl]propanoate;

methyl (2R)-2-hydroxy-3-[4-(3-methyl-5-{[4-(trifluoromethyl)pyrimidin-2-yl]amino}phenyl)-1H-pyrazol-1-yl]propanoate;

methyl 2-hydroxy-2-methyl-3-[4-(3-methyl-5-{[4-(trifluoromethyl)pyrimidin-2-yl]amino}phenyl)-1H-pyrazol-1-yl]propanoate;

Cis-4-hydroxy-4-{[4-(3-methyl-5-{[4-(trifluoromethyl)pyrimidin-2-yl]amino}phenyl)-1H-pyrazol-1-yl]methyl}cyclohexanecarboxylic acid;

2-hydroxy-2-methyl-3-[4-(3-methyl-5-{[4-(trifluoromethyl)pyrimidin-2-yl]amino}phenyl)-1H-pyrazol-1-yl]propanoic acid;

1-(1-methylethoxy)-3-[4-(3-methyl-5-{[4-(trifluoromethyl)pyrimidin-2-yl]amino}-phenyl)-1H-pyrazol-1-yl]propan-2-ol;

1-[4-(3-methyl-5-{[4-(trifluoromethyl)pyrimidin-2-yl]amino}-phenyl)-1H-pyrazol-1-yl]-3-phenoxypropan-2-ol;

1-[4-(3-methyl-5-{[4-(trifluoromethyl)pyrimidin-2-yl]amino}-phenyl)-1H-pyrazol-1-yl]butan-2-ol;

1-[4-(3-methyl-5-{[4-(trifluoromethyl)pyrimidin-2-yl]amino}-phenyl)-1H-pyrazol-1-yl]-3-morpholin-4-ylpropan-2-ol;

1-(4-methoxy-phenoxy)-3-[4-(3-methyl-5-{[4-(trifluoromethyl)-pyrimidin-2-yl]amino}phenyl)-1H-pyrazol-1-yl]propan-2-ol;

2-methyl-1-[4-(3-methyl-5-{[4-(trifluoromethyl)pyrimidin-2-yl]amino}-phenyl)-1H-pyrazol-1-yl]propan-2-ol;

1-fluoro-3-({3-[1-(3-fluoro-2-hydroxy-propyl)-1H-pyrazol-4-yl]-5-methylphenyl}-[4-(trifluoromethyl)-pyrimidin-2-yl]amino)propan-2-ol;

2-hydroxy-3-[4-(3-methyl-5-{[4-(trifluoromethyl)pyrimidin-2-yl]amino}phenyl)-1H-pyrazol-1-yl]propanoic acid;

3-[4-(3-methyl-5-{[4-(trifluoromethyl)pyrimidin-2-yl]amino}phenyl)-1H-pyrazol-1-yl]propane-1,2-diol;

(2R)-2-hydroxy-3-[4-(3-methyl-5-{[4-(trifluoromethyl)pyrimidin-2-yl]amino}phenyl)-1H-pyrazol-1-yl]propanoic acid;

(2S)-2-hydroxy-3-[4-(3-methyl-5-{[4-(trifluoromethyl)pyrimidin-2-yl]amino}phenyl)-1H-pyrazol-1-yl]propanoic acid;

(2S)-2-hydroxy-N-(2-hydroxyethyl)-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-{[4-(2-hydroxyethoxy)pyrimidin-2-yl]amino}-5-methylphenyl)-1H-pyrazol-1-yl]propanamide;

(2S)-2-hydroxy-3-(4-{3-methyl-5-[(4-methylpyrimidin-2-yl)amino]phenyl}-1H-pyrazol-1-yl)propanamide;

(2S)-2-hydroxy-3-(4-{3-[(4-methoxypyrimidin-2-yl)amino]-5-methylphenyl}-1H-pyrazol-1-yl)propanamide;

(2S)-3-(4-{3[(4-cyclopropylpyrimidin-2-yl)amino]-5-methylphenyl}-1H-pyrazol-1-yl)-2-hydroxypropanamide;

(2S)-2-hydroxy-3-[4-(3-methyl-5-{[4-(1-methylethoxy)pyrimidin-2-yl]amino}phenyl)-1H-pyrazol-1-yl]propanamide;

(2S)-3-(4-{3-[(4-tert-butylpyrimidin-2-yl)amino]-5-methylphenyl}-1H-pyrazol-1-yl)-2-hydroxypropanamide;

(2S)-3-[4-(3-{[4-(1-fluoroethyl)pyrimidin-2-yl]amino}-5-methylphenyl)-1H-pyrazol-1-yl]-2-hydroxypropanamide;

(2S)-2-hydroxy-3-[4-(3-methyl-5-{[4-(1-methylethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]-N-[3-(2-oxopyrrolidin-1-yl)propyl]propanamide;

(2S)-2-hydroxy-N-methyl-3-[4-(3-methyl-5-{[4-(trifluoromethyl)pyrimidin-2-yl]amino}phenyl)-1H-pyrazol-1-yl]propanamide;

(2S)-2-hydroxy-N-(3-methoxypropyl)-3-[4-(3-methyl-5-{[4-(trifluoromethyl)pyrimidin-2-yl]amino}phenyl)-1H-pyrazol-1-yl]propanamide;

(2S)-2-hydroxy-N-(2-methoxyethyl)-3-[4-(3-methyl-5-{[4-(trifluoromethyl)pyrimidin-2-yl]amino}phenyl)-1H-pyrazol-1-yl]propanamide;

4-[4-(4-methyl-6-{[4-(trifluoromethyl)pyridin-2-yl]amino}pyridin-2-yl)-1H-pyrazol-1-yl]-1,2,3,4-tetrahydronaphthalene-1-carboxamide;

(2S)-2-hydroxy-3-[4-(4-methyl-6-{[4-(trifluoromethyl)pyridin-2-yl]amino}pyridin-2-yl)-1H-pyrazol-1-yl]propanamide;

4-{1-hydroxy-2-[4-(4-methyl-6-{[4-(trifluoromethyl)pyridin-2-yl]amino}pyridin-2-yl)-1H-pyrazol-1-yl]ethyl}benzamide;

(R or S)-2-hydroxy-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]-1-alaninamide;

(2R)-2-hydroxy-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

2-hydroxy-3-[4-(3-methyl-5-{[4-(trifluoromethyl)pyrimidin-2-yl]amino}phenyl)-1H-pyrazol-1-yl]butanamide;

2-hydroxy-3-[4-(3-methyl-5-{[4-(trifluoromethyl)pyrimidin-2-yl]amino}phenyl)-1H-pyrazol-1-yl]butanamide;

(R)-2-hydroxy-2-methyl-3-[4-(3-methyl-5-{[4-(trifluoromethyl)pyrimidin-2-yl]amino}phenyl)-1H-pyrazol-1-yl]propanamide;

(2R)-2-hydroxy-3-[4-(3-methyl-5-{[4-(trifluoromethyl)pyrimidin-2-yl]amino}phenyl)-1H-pyrazol-1-yl]propanamide;

(S)-2-hydroxy-2-methyl-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

4-[4-(3-{[4-(2-hydroxyethoxy)pyrimidin-2-yl]amino}-5-methylphenyl)-1H-pyrazol-1-yl]cyclohexanecarboxamide;

4-[4-(3-methyl-5-{[4-(trifluoromethyl)pyrimidin-2-yl]amino}phenyl)-1H-pyrazol-1-yl]cyclohexanecarboxamide;

2,2-dimethyl-4-[4-(3-methyl-5-{[4-(trifluoromethyl)pyrimidin-2-yl]amino}phenyl)-1H-pyrazol-1-yl]cyclohexanecarboxamide;
2-[4-(3-methyl-5-{[4-(trifluoromethyl)pyrimidin-2-yl]amino}phenyl)-1H-pyrazol-1-yl]propanamide;
4-[4-(3-methyl-5-{[4-(trifluoromethyl)pyrimidin-2-yl]amino}phenyl)-1H-pyrazol-1-yl]butanamide;
2-methyl-2-(4-{3-methyl-5-[(4-methylpyrimidin-2-yl)amino]phenyl}-1H-pyrazol-1-yl)propanamide;
2-hydroxy-2-methyl-3-[4-(3-methyl-5-{[4-(trifluoromethyl)pyrimidin-2-yl]amino}phenyl)-1H-pyrazol-1-yl]propanamide;
4-{1-hydroxy-2-[4-(3-methyl-5-{[4-(trifluoromethyl)pyrimidin-2-yl]amino}phenyl)-1H-pyrazol-1-yl]ethyl}benzamide;
(2R)-2-hydroxy-3-[4-(3-methyl-5-{[4-(trifluoromethyl)pyrimidin-2-yl]amino}phenyl)-1H-pyrazol-1-yl]propanamide;
2-hydroxy-2-methyl-3-[4-(3-methyl-5-{[4-(trifluoromethyl)pyrimidin-2-yl]amino}phenyl)-1H-pyrazol-1-yl]propanamide;
2-hydroxy-2-methyl-3-[4-(3-methyl-5-{[4-(trifluoromethyl)pyrimidin-2-yl]amino}phenyl)-1H-pyrazol-1-yl]propanamide;
(2S)-2-hydroxy-3-[4-(3-methyl-5-{[4-(trifluoromethyl)pyrimidin-2-yl]amino}phenyl)-1H-pyrazol-1-yl]propanamide;
4-[4-(3-{[4-(2-hydroxyethoxy)pyrimidin-2-yl]amino}-5-methylphenyl)-1H-pyrazol-1-yl]cyclohexanecarboxamide;
4-[4-(3-methyl-5-{[4-(trifluoromethyl)pyrimidin-2-yl]amino}phenyl)-1H-pyrazol-1-yl]cyclohexanecarboxamide;
2,2-dimethyl-4-[4-(3-methyl-5-{[4-(trifluoromethyl)pyrimidin-2-yl]amino}phenyl)-1H-pyrazol-1-yl]cyclohexanecarboxamide;
2-[4-(3-methyl-5-{[4-(trifluoromethyl)pyrimidin-2-yl]amino}phenyl)-1H-pyrazol-1-yl]propanamide;
4-[4-(3-methyl-5-{[4-(trifluoromethyl)pyrimidin-2-yl]amino}phenyl)-1H-pyrazol-1-yl]butanamide;
2-methyl-2-(4-{3-methyl-5-[(4-methylpyrimidin-2-yl)amino]phenyl}-1H-pyrazol-1-yl)propanamide;
2-hydroxy-2-methyl-3-[4-(3-methyl-5-{[4-(trifluoromethyl)pyrimidin-2-yl]amino}phenyl)-1H-pyrazol-1-yl]propanamide;
4-{1-hydroxy-2-[4-(3-methyl-5-{[4-(trifluoromethyl)pyrimidin-2-yl]amino}phenyl)-1H-pyrazol-1-yl]ethyl}benzamide;
3-methyl-3-[4-(3-methyl-5-{[4-(trifluoromethyl)pyrimidin-2-yl]amino}phenyl)-1H-pyrazol-1-yl]butanenitrile;
2-[4-(3-methyl-5-{[4-(trifluoromethyl)pyrimidin-2-yl]amino}phenyl)-1H-pyrazol-1-yl]-ethanesulfonamide;
3-[4-(3-methyl-5-{[4-(trifluoromethyl)pyrimidin-2-yl]amino}phenyl)-1H-pyrazol-1-yl]cyclohexane-(1R,2S)-diol;
3-[4-(3-methyl-5-{[4-(trifluoromethyl)pyrimidin-2-yl]amino}phenyl)-1H-pyrazol-1-yl]cyclohexane-(1R,2R)-diol;
3-[4-(3-methyl-5-{[4-(trifluoromethyl)pyrimidin-2-yl]amino}phenyl)-1H-pyrazol-1-yl]cyclohexane-(1S,2R)-diol;
3-[4-(3-methyl-5-{[4-(trifluoromethyl)pyrimidin-2-yl]amino}phenyl)-1H-pyrazol-1-yl]cyclohexane-(1S,2S)-diol;
(2R)-3-(4-(3-(4-cyclopropylpyrimidin-2-ylamino)-5-methylphenyl)-1H-pyrazol-1-yl)-2-hydroxypropanoic acid;
(2S)-2-hydroxy-3-(4-{3-[(4-methoxy-pyrimidin-2-yl)amino]-5-methylphenyl}-1H-pyrazol-1-yl)-propanoic acid;
(2S)-2-hydroxy-3-(4-{3-methyl-5-[(4-methylpyrimidin-2-yl)amino]phenyl}-1H-pyrazol-1-yl)-propanoic acid;
(2S)-2-hydroxy-3-(4-{3-[(4-methoxy-pyrimidin-2-yl)-amino]phenyl}-1H-pyrazol-1-yl)-propanoic acid;
(2S)-3-(4-{3-[(4-cyclopropylpyrimidin-2-yl)amino]-5-methyl-phenyl}-1H-pyrazol-1-yl)-2-hydroxy-propanoic acid;
(2S)-3-(4-{3-[(5-chloro-4-methoxy-pyrimidin-2-yl)-amino]-5-methyl-phenyl}-1H-pyrazol-1-yl)-2-hydroxy-propanoic acid;
(2R)-3-(4-{3-[(5-chloro-4-methyl-pyrimidin-2-yl)-amino]-5-methyl-phenyl}-1H-pyrazol-1-yl)-2-hydroxy-propanoic acid;
(2R)-2-hydroxy-3-(4-{3-[(4-methoxy-pyrimidin-2-yl)-amino]-5-methyl-phenyl}-1H-pyrazol-1-yl)propanoic acid;
(2R)-3-(4-{3-[(5-chloro-4-methoxy-pyrimidin-2-yl)-amino]-5-methyl-phenyl}-1H-pyrazol-1-yl)-2-hydroxy-propanoic acid;
(2R)-2-hydroxy-3-(4-{3-methyl-5-[(4-methylpyrimidin-2-yl)amino]phenyl}-1H-pyrazol-1-yl)propanoic acid;
(2R)-2-hydroxy-3-(4-{3-[(4-methoxypyrimidin-2-yl)amino]phenyl}-1H-pyrazol-1-yl)propanoic acid;
(2R)-3-(4-{3-[(4-cyclopropylpyrimidin-2-yl)amino]-5-methylphenyl}-1H-pyrazol-1-yl)-2-hydroxypropanoic acid;
(2R)-3-(4-{3-[(5-fluoro-4-methylpyrimidin-2-yl)amino]-5-methylphenyl}-1H-pyrazol-1-yl)-2-hydroxypropanoic acid;
(2R)-2-hydroxy-3-[4-(3-methyl-5-{[4-(1-methylethoxy)pyrimidin-2-yl]amino}-phenyl)-1H-pyrazol-1-yl]propanoic acid;
(2R)-3-(4-{3-[(5-chloro-4-methoxy-pyrimidin-2-yl)amino]-5-methyl-phenyl}-1H-pyrazol-1-yl)-2-hydroxy-propanoic acid;
(2R)-2-hydroxy-3-[4-(3-methyl-5-{[4-(1-methylethyl)pyrimidin-2-yl]amino}phenyl)-1H-pyrazol-1-yl]propanoic acid;
(2S)-2-hydroxy-3-(4-{4-methyl-6-[(4-methyl-pyridin-2-yl)amino]-pyrimidin-2-yl}-1H-pyrazol-1-yl)propanoic acid;
(2S)-2-hydroxy-3-[4-(6-methyl-4-{[4-(trifluoro-methyl)pyrimidin-2-yl]amino}pyridin-2-yl)-1H-pyrazol-1-yl]propanoic acid;
(2R)-2-hydroxy-3-(4-{4-methyl-6-[(4-methyl-pyridin-2-yl)amino}-pyrimidin-2-yl)-1H-pyrazol-1-yl)propanoic acid;
(2R)-2-hydroxy-3-[4-(6-methyl-4-{[4-(trifluoro-methyl)pyrimidin-2-yl]amino}pyridin-2-yl)-1H-pyrazol-1-yl]propanoic acid;
4-((4-(3-methyl-5-((4-(trifluoromethyl)pyrimidin-2-yl)amino)phenyl)-1H-pyrazol-1-yl)methyl)piperidin-4-ol;
1-{[4-(3-methyl-5-{[4-(trifluoro-methyl)pyrimidin-2-yl]amino}-phenyl)-1H-pyrazol-1-yl]-methyl}-cyclobutanol;
3-methoxy-1-[(4-{3-methyl-5-[(4-methylpyrimidin-2-yl)amino]phenyl}-1H-pyrazol-1-yl)methyl]-cyclobutanol;
tert-Butyl (4-hydroxy-4-{[4-(3-methyl-5-{[4-(trifluoro-methyl)pyrimidin-2-yl]amino}phenyl)-1H-pyrazol-1-yl]methyl}-piperidin-1-yl)acetate;
4-{[4-(3-methyl-5-{[4-(trifluoromethyl)pyrimidin-2-yl]amino}phenyl)-1H-pyrazol-1-yl]methyl}-tetrahydro-2H-pyran-4-ol;
(1R,4S and 1S,4R)-4-hydroxy-2,2-dimethyl-4-{[4-(3-methyl-5-{[4-(trifluoromethyl)pyrimidin-2-yl]amino}phenyl)-1H-pyrazol-1-yl]methyl}-cyclohexanecarboxylic acid;

3-{[4-(3-methyl-5-{[4-(trifluoromethyl)pyrimidin-2-yl]amino}phenyl)-1H-pyrazol-1-yl]methyl}tetrahydro-2H-pyran-3-ol;

Meso (2R,4s,6S)-2,6-dimethyl-4-{[4-(3-methyl-5-{[4-(trifluoro-methyl)pyrimidin-2-yl]amino}phenyl)-1H-pyrazol-1-yl]methyl}-tetrahydro-2H-pyran-4-ol;

2,2-dimethyl-4R-{[4-(3-methyl-5-{[4-(trifluoro-methyl)pyrimidin-2-yl]amino}phenyl)-1H-pyrazol-1-yl]methyl}tetrahydro-2H-pyran-4-ol;

2,2-dimethyl-4S-{[4-(3-methyl-5-{[4-(trifluoromethyl)pyrimidin-2-yl]amino}phenyl)-1H-pyrazol-1-yl]methyl}-tetrahydro-2H-pyran-4-ol;

3R-{[4-(3-methyl-5-{[4-(trifluoromethyl)pyrimidin-2-yl]amino}phenyl)-1H-pyrazol-1-yl]methyl}tetrahydro-2H-pyran-3-ol;

3 S-{[4-(3-methyl-5-{[4-(trifluoromethyl)pyrimidin-2-yl]amino}phenyl)-1H-pyrazol-1-yl]methyl}tetrahydro-2H-pyran-3-ol;

4-[(4-{3-methyl-5-[(4-methylpyrimidin-2-yl)amino]phenyl}-1H-pyrazol-1-yl)methyl]-tetrahydro-2H-pyran-4-ol;

4-{1-[4-(3-methyl-5-{[4-(trifluoromethyl)pyrimidin-2-yl]amino}phenyl)-1H-pyrazol-1-yl]ethyl}-tetrahydro-2H-pyran-4-ol;

(4-hydroxy-4-{[4-(3-methyl-5-{[4-(trifluoromethyl)-pyrimidin-2-yl]amino}-phenyl)-1H-pyrazol-1-yl]methyl}piperidin-1-yl)acetic acid;

N-(3-(1-isopropyl-1H-pyrazol-4-yl)-5-methylphenyl)-4-(trifluoromethyl)-pyrimidin-2-amine;

N-{3-methyl-5-[1-(2-pyrrolidin-2-ylethyl)-1H-pyrazol-4-yl]phenyl}-4-(trifluoromethyl)-pyrimidin-2-amine;

N-{3-methyl-5-[1-(tetrahydrofuran-2-ylmethyl)-1H-pyrazol-4-yl]phenyl}-4-(trifluoromethyl)-pyrimidin-2-amine;

(5R)-[4-(3-methyl-5-{[4-(trifluoromethyl)pyrimidin-2-yl]amino}phenyl)-1H-pyrazol-1-yl]azepan-2-one;

(5S)-[4-(3-methyl-5-{[4-(trifluoromethyl)pyrimidin-2-yl]amino}phenyl)-1H-pyrazol-1-yl]azepan-2-one;

cis-4-[4-(3-methyl-5-{[4-(trifluoromethyl)pyrimidin-2-yl]amino}phenyl)-1H-pyrazol-1-yl]cyclohexanol;

(2S)-3-[4-(3-{[4-(difluoromethyl)pyrimidin-2-yl]amino}-5-methylphenyl)-1H-pyrazol-1-yl]-2-hydroxypropanamide;

4-hydroxy-4-((4-(3-methyl-5-((4-(trifluoromethyl)pyrimidin-2-yl)amino)phenyl)-1H-pyrazol-1-yl)methyl)piperidine-1-carboxamide;

3-(1-(6-((4-(trifluoromethyl)pyridin-2-yl)amino)pyridin-2-yl)-1H-pyrazol-4-yl)propanoic acid;

3-(1-{6-[(4-methylpyridin-2-yl)amino]pyridin-2-yl}-1H-pyrazol-4-yl)propanoic acid;

3-(1-{6-[(4-cyclopropylpyridin-2-yl)amino]-4-methylpyridin-2-yl}-1H-pyrazol-4-yl)propanoic acid;

3-(1-{6-[(5-chloro-4-methylpyridin-2-yl)amino]-4-methylpyridin-2-yl}-1H-pyrazol-4-yl)propanoic acid;

3-(1-(3-methyl-5-((4-(trifluoromethyl)pyrimidin-2-yl)amino)phenyl)-1H-pyrazol-4-yl)propanoic acid;

ethyl 3-[1-(3-methyl-5-{[4-(trifluoromethyl)pyrimidin-2-yl]amino}phenyl)-1H-pyrazol-4-yl]propanoate;

3-(1-{3-[(4-cyclopropylpyrimidin-2-yl)amino]-5-methylphenyl}-1H-pyrazol-4-yl)propanoic acid;

ethyl 3-(1-{3-[(4-cyclopropylpyrimidin-2-yl)amino]-5-methylphenyl}-1H-pyrazol-4-yl)propanoate;

ethyl 3-(1-{3-[(4-methoxypyrimidin-2-yl)amino]-5-methylphenyl}-1H-pyrazol-4-yl)propanoate;

ethyl 3-(1-{3-methyl-5[(4-methylpyrimidin-2-yl)amino]phenyl}-1H-pyrazol-4-yl)propanoate;

4-[4-(3-methyl-5-{[4-(trifluoromethyl)pyrimidin-2-yl]amino}phenyl)-1H-pyrazol-1-yl]-cyclohexanecarboxylic acid;

2,2-dimethyl-4-[4-(3-methyl-5-{[4-(trifluoromethyl)-pyrimidin-2-yl]amino}-phenyl)-1H-pyrazol-1-yl]-cyclohexanecarboxylic acid;

4-{1-[4-(3-methyl-5-{[4-(trifluoromethyl)pyrimidin-2-yl]amino}phenyl)-1H-pyrazol-1-yl]ethyl}benzoic acid;

5-[4-(3-methyl-5-{[4-(trifluoromethyl)pyrimidin-2-yl]amino}phenyl)-1H-pyrazol-1-yl]-5,6,7,8-tetrahydronaphthalene-2-carboxylic acid;

8-[4-(3-methyl-5-{[4-(trifluoromethyl)pyrimidin-2-yl]amino}phenyl)-1H-pyrazol-1-yl]-5,6,7,8-tetrahydronaphthalene-2-carboxylic acid;

4-hydroxy-4-[1-(3-methyl-5-{[4-(trifluoromethyl)-pyrimidin-2-yl]amino}-phenyl)-1H-pyrazol-4-yl]-cyclohexanecarboxylic acid;

4-hydroxy-2,2-dimethyl-4-[1-(3-methyl-5-{[4-(trifluoromethyl)pyrimidin-2-yl]amino}phenyl)-1H-pyrazol-4-yl]-cyclohexanecarboxylic acid;

4-{1-hydroxy-1-[1-(3-methyl-5-{[4-(trifluoromethyl)pyrimidin-2-yl]amino}phenyl)-1H-pyrazol-4-yl]ethyl}-cyclohexanecarboxylic acid;

5-hydroxy-5-[1-(3-methyl-5-{[4-(trifluoromethyl)-pyrimidin-2-yl]amino}-phenyl)-1H-pyrazol-4-yl]-5,6,7,8-tetrahydronaphthalene-2-carboxylic acid;

4-{1-hydroxy-1-[1-(3-methyl-5-{[4-(trifluoromethyl)pyrimidin-2-yl]amino}phenyl)-1H-pyrazol-4-yl]ethyl}benzoic acid;

N-[3-(5-chloro-1H-pyrazol-1-yl)-5-methylphenyl]-4-(trifluoromethyl)pyrimidin-2-amine;

N-[3-(5-fluoro-1H-pyrazol-1-yl)-5-methylphenyl]-4-(trifluoromethyl)pyrimidin-2-amine-methane (1:1);

4-[4-(4-chloro-6-{[4-(trifluoromethyl)pyridin-2-yl]amino}pyridin-2-yl)-1H-pyrazol-1-yl]-cyclohexanecarboxylic acid;

4-[4-(4-cyclopropyl-6-{[4-(trifluoromethyl)pyridin-2-yl]amino}pyridin-2-yl)-1H-pyrazol-1-yl]-cyclohexanecarboxylic acid;

4-[4-(4-amino-6-{[4-(trifluoromethyl)pyridin-2-yl]amino}pyridin-2-yl)-1H-pyrazol-1-yl]-cyclohexanecarboxylic acid; and 4-{4-[4-(acetylamino)-6-{[4-(trifluoromethyl)pyridin-2-yl]amino}pyridin-2-yl]-1H-pyrazol-1-yl}-cyclohexanecarboxylic acid.

An embodiment of the compounds of Formula I, or a pharmaceutically acceptable salt thereof is selected from the group consisting of:

(5R)-5-{[4-(4-methyl-6-{[4-(trifluoromethyl)pyridin-2-yl]amino}pyridin-2-yl)-1H-pyrazol-1-yl]methyl}-1,3-oxazolidin-2-one;

4-methyl-6-(1-piperidin-4-yl-1H-pyrazol-4-yl)-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-pyrazol-1-yl]ethanol;

6-[1-(methoxyacetyl)-1H-pyrazol-4-yl]-4-methyl-N-[4-(trifluoromethyl)pyridin-2-yl]pyridin-2-amine;

(5S)-5-{[4-(4-methyl-6-{[4-(trifluoromethyl)pyridin-2-yl]amino}pyridin-2-yl)-1H-pyrazol-1-yl]methyl}-1,3-oxazolidin-2-one;

[4-(4-methyl-6-{[4-(trifluoromethyl)pyridin-2-yl]amino}pyridin-2-yl)-1H-pyrazol-1-yl]acetonitrile;

4-methyl-6-(1H-pyrazol-4-yl)-N-[4-(trifluoromethyl)pyridin-2-yl]pyridin-2-amine;

3-[4-(4-methyl-6-{[4-(trifluoromethyl)pyridin-2-yl]amino}pyridin-2-yl)-1H-pyrazol-1-yl]propanamide;

(2S)-3-[4-(3-{[4-(1-fluoroethyl)pyrimidin-2-yl]amino}-5-methylphenyl)-1H-pyrazol-1-yl]-2-hydroxypropanamide;

2-hydroxy-2-methyl-3-[4-(3-methyl-5-{[4-(trifluoromethyl)pyrimidin-2-yl]amino}phenyl)-1H-pyrazol-1-yl]propanamide;

(5S)-5-{[4-(3-methyl-5-{[4-(trifluoromethyl)pyrimidin-2-yl]amino}phenyl)-1H-pyrazol-1-yl]methyl}-1,3-oxazolidin-2-one;

3-[4-(3-methyl-5-{[4-(trifluoromethyl)pyrimidin-2-yl]amino}phenyl)-1H-pyrazol-1-yl]butanamide (2R)-2-hydroxy-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

(2R)-3-[4-(3-methyl-5-{[4-(trifluoromethyl)pyrimidin-2-yl]amino}phenyl)-1H-pyrazol-1-yl]propane-1,2-diol;

3-[4-(3-methyl-5-{[4-(trifluoromethyl)pyrimidin-2-yl]amino}phenyl)-1H-pyrazol-1-yl]propane-1,2-diol;

(3S)-3-hydroxy-4-[4-(3-methyl-5-{[4-(trifluoromethyl)pyrimidin-2-yl]amino}phenyl)-1H-pyrazol-1-yl]butanenitrile;

(2R)-2-hydroxy-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]propanamide;

5-[(4-{3-methyl-5-[(4-methylpyrimidin-2-yl)amino]phenyl}-1H-pyrazol-1-yl)methyl]-1,3-oxazolidin-2-one;

(3R)-3-hydroxy-4-[4-(3-methyl-5-{[4-(trifluoromethyl)pyrimidin-2-yl]amino}phenyl)-1H-pyrazol-1-yl]butanenitrile;

(2S)-3-[4-(3-methyl-5-{[4-(trifluoromethyl)pyrimidin-2-yl]amino}phenyl)-1H-pyrazol-1-yl]propane-1,2-diol;

2-hydroxy-3-[4-(3-methyl-5-{[4-(trifluoromethyl)pyrimidin-2-yl]amino}phenyl)-1H-pyrazol-1-yl]butanamide;

2-hydroxy-2-methyl-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]cyclohexane-1,2-diol;

2-[4-(3-methyl-5-{[4-(trifluoromethyl)pyrimidin-2-yl]amino}phenyl)-1H-pyrazol-1-yl]propanamide;

(5R)-5-{[4-(3-methyl-5-{[4-(trifluoromethyl)pyrimidin-2-yl]amino}phenyl)-1H-pyrazol-1-yl]methyl}-1,3-oxazolidin-2-one;

3-[4-(3-{[4-(difluoromethyl)pyrimidin-2-yl]amino}-5-methylphenyl)-1H-pyrazol-1-yl]hexane-2,5-diol;

4-({4-[3-methyl-5-(pyrimidin-2-ylamino)phenyl]-1H-pyrazol-1-yl}methyl)benzamide;

4-({4-[3-methyl-5-(pyrimidin-2-ylamino)phenyl]-1H-pyrazol-1-yl}methyl)phenol;

2,2-dimethyl-4-[4-(3-methyl-5-{[4-(trifluoromethyl)pyrimidin-2-yl]amino}phenyl)-1H-pyrazol-1-yl]cyclohexanecarboxylic acid;

cis-4-[4-(3-{[4-(difluoromethyl)pyrimidin-2-yl]amino}-5-methylphenyl)-1H-pyrazol-1-yl]cyclohexanecarboxylic acid;

trans-4-[4-(3-{[4-(difluoromethyl)pyrimidin-2-yl]amino}-5-methylphenyl)-1H-pyrazol-1-yl]cyclohexanecarboxylic acid;

(R)-5-{[4-(3-{[4-(difluoromethyl)pyrimidin-2-yl]amino}-5-methylphenyl)-1H-pyrazol-1-yl]methyl}-1,3-oxazolidin-2-one;

(S)-5-{[4-(3-{[4-(difluoromethyl)pyrimidin-2-yl]amino}-5-methylphenyl)-1H-pyrazol-1-yl]methyl}-1,3-oxazolidin-2-one;

(R)-5-{[4-(3-{[4-(difluoromethyl)pyrimidin-2-yl]amino}phenyl)-1H-pyrazol-1-yl]methyl}-1,3-oxazolidin-2-one;

(S)-5-{[4-(3-{[4-(difluoromethyl)pyrimidin-2-yl]amino}phenyl)-1H-pyrazol-1-yl]methyl}-1,3-oxazolidin-2-one;

4-{1-[4-(3-{[4-(difluoromethyl)pyrimidin-2-yl]amino}-5-methylphenyl)-1H-pyrazol-1-yl]ethyl}pyrrolidin-2-one;

(R)-3-{[4-(3-{[4-(difluoromethyl)pyrimidin-2-yl]amino}-5-methylphenyl)-1H-pyrazol-1-yl]methyl}pyrrolidine-2,5-dione;

4-{[4-(3-{[4-(difluoromethyl)pyrimidin-2-yl]amino}-5-methylphenyl)-1H-pyrazol-1-yl]methyl}pyridin-2(1H)-one;

(S)-3-{[4-(3-{[4-(difluoromethyl)pyrimidin-2-yl]amino}-5-methylphenyl)-1H-pyrazol-1-yl]methyl}pyrrolidine-2,5-dione;

(R)-5-{[4-(3-{[4-(difluoromethyl)pyrimidin-2-yl]amino}-5-methylphenyl)-1H-pyrazol-1-yl]methyl}-1,3-oxazolidine-2,4-dione;

(S)-5-{[4-(3-{[4-(difluoromethyl)pyrimidin-2-yl]amino}-5-methylphenyl)-1H-pyrazol-1-yl]methyl}-1,3-oxazolidine-2,4-dione;

4-{[4-(3-{[4-(difluoromethyl)pyrimidin-2-yl]amino}-5-methylphenyl)-1H-pyrazol-1-yl]methyl}-5-methylpyrrolidin-2-one;

(R)-4-{[4-(3-{[4-(difluoromethyl)pyrimidin-2-yl]amino}-5-methylphenyl)-1H-pyrazol-1-yl]methyl}-4-methylpyrrolidin-2-one;

(R)-6-{[4-(3-{[4-(difluoromethyl)pyrimidin-2-yl]amino}-5-methylphenyl)-1H-pyrazol-1-yl]methyl}-1,3-oxazinan-2-one;

(S)-4-{[4-(3-{[4-(difluoromethyl)pyrimidin-2-yl]amino}-5-methylphenyl)-1H-pyrazol-1-yl]methyl}-4-methylpyrrolidin-2-one;

(S)-6-{[4-(3-{[4-(difluoromethyl)pyrimidin-2-yl]amino}-5-methylphenyl)-1H-pyrazol-1-yl]methyl}-1,3-oxazinan-2-one;

N-{3-[1-(2-aminoethyl)-1H-pyrazol-4-yl]-5-methylphenyl}-4-(difluoromethyl)pyrimidin-2-amine;

4-(difluoromethyl)-N-(3-methyl-5-{1-[(2S)-morpholin-2-ylmethyl]-1H-pyrazol-4-yl}phenyl)pyrimidin-2-amine;

4-(difluoromethyl)-N-(3-methyl-5-{1-[(2R)-morpholin-2-ylmethyl]-1H-pyrazol-4-yl}phenyl)pyrimidin-2-amine;

N-{3-[1-(2-amino-2-methylpropyl)-1H-pyrazol-4-yl]-5-methylphenyl}-4-(difluoromethyl)pyrimidin-2-amine;

(2S)-2-methyl-3-[4-(3-{[4-(trifluoromethyl)pyrimidin-2-yl]amino}phenyl)-1H-pyrazol-1-yl]propane-1,2-diol;

(2S)-3-[4-(3-{[4-(1-hydroxyethyl)pyrimidin-2-yl]amino}-5-methylphenyl)-1H-pyrazol-1-yl]-2-methylpropane-1,2-diol;

(2S)-3-(4-{3-[(4-methoxypyrimidin-2-yl)amino]-5-methylphenyl}-1H-pyrazol-1-yl)-2-methylpropane-1,2-diol;

(2S)-3-(4-{3-[(5-fluoro-4-methoxypyrimidin-2-yl)amino]-5-methylphenyl}-1H-pyrazol-1-yl)-2-methylpropane-1,2-diol;

(2S)-3-(4-{3-[(4-cyclopropylpyrimidin-2-yl)amino]-5-methylphenyl}-1H-pyrazol-1-yl)-2-methylpropane-1,2-diol;

(2S)-3-[4-(3-fluoro-5-{[4-(trifluoromethyl)pyrimidin-2-yl]amino}phenyl)-1H-pyrazol-1-yl]-2-methylpropane-1,2-diol;

(2S)-3-[4-(3-{[4-(difluoromethyl)pyrimidin-2-yl]amino}phenyl)-1H-pyrazol-1-yl]-2-methylpropane-1,2-diol;

(2S)-3-[4-(3-{[4-(1-hydroxyethyl)pyrimidin-2-yl]amino}phenyl)-1H-pyrazol-1-yl]-2-methylpropane-1,2-diol;

(2S)-3-(4-{3-[(5-fluoro-4-methylpyrimidin-2-yl)amino]-5-methylphenyl}-1H-pyrazol-1-yl)-2-methylpropane-1,2-diol;
(2S)-2-methyl-3-(4-{3-[(4-methylpyrimidin-2-yl)amino]phenyl}-1H-pyrazol-1-yl)propane-1,2-diol;
(2S)-2-methyl-3-[4-(3-methyl-5-{[4-(1-methylethoxy)pyrimidin-2-yl]amino}phenyl)-1H-pyrazol-1-yl]propane-1,2-diol;
(2S)-3-(4-{3-[(5-chloro-4-methylpyrimidin-2-yl)amino]-5-methylphenyl}-1H-pyrazol-1-yl)-2-methylpropane-1,2-diol;
(2S)-3-(4-{3-[(5-chloro-4-methoxypyrimidin-2-yl)amino]-5-methylphenyl}-1H-pyrazol-1-yl)-2-methylpropane-1,2-diol;
(R)-5-{[4-(6-{[4-(difluoromethyl)pyridin-2-yl]amino}-4-methylpyridin-2-yl)-1H-pyrazol-1-yl]methyl}-1,3-oxazolidin-2-one;
(R)-5-{[4-(6-{[4-(difluoromethyl)pyridin-2-yl]amino}pyridin-2-yl)-1H-pyrazol-1-yl]methyl}-1,3-oxazolidin-2-one;
(S)-5-{[4-(6-{[4-(difluoromethyl)pyridin-2-yl]amino}-4-methylpyridin-2-yl)-1H-pyrazol-1-yl]methyl}-1,3-oxazolidin-2-one;
(S)-5-{[4-(6-{[4-(difluoromethyl)pyridin-2-yl]amino}pyridin-2-yl)-1H-pyrazol-1-yl]methyl}-1,3-oxazolidin-2-one;
(R)-5-{[4-(6-{[4-(1,1-difluoroethyl)pyridin-2-yl]amino}-4-methylpyridin-2-yl)-1H-pyrazol-1-yl]methyl}-1,3-oxazolidin-2-one;
(S)-5-{[4-(6-{[4-(1,1-difluoroethyl)pyridin-2-yl]amino}-4-methylpyridin-2-yl)-1H-pyrazol-1-yl]methyl}-1,3-oxazolidin-2-one;
5-{1-[4-(6-{[4-(difluoromethyl)pyridin-2-yl]amino}-4-methylpyridin-2-yl)-1H-pyrazol-1-yl]ethyl}-1,3-oxazolidin-2-one;
(R)-7-{[4-(3-{[4-(difluoromethyl)pyrimidin-2-yl]amino}-5-methylphenyl)-1H-pyrazol-1-yl]methyl}-4-azaspiro[2.4]heptan-5-one;
(S)-7-{[4-(3-{[4-(difluoromethyl)pyrimidin-2-yl]amino}-5-methylphenyl)-1H-pyrazol-1-yl]methyl}-4-azaspiro[2.4]heptan-5-one;
5-{1-[4-(3-{[4-(difluoromethyl)pyrimidin-2-yl]amino}-5-methylphenyl)-1H-pyrazol-1-yl]ethyl}-1,3-oxazolidin-2-one;
(R)-7-{[4-(3-{[4-(difluoromethyl)pyrimidin-2-yl]amino}-5-methylphenyl)-1H-pyrazol-1-yl]methyl}-6-oxa-4-azaspiro[2.4]heptan-5-one;
5-{1-[4-(3-{[4-(difluoromethyl)pyrimidin-2-yl]amino}-5-methylphenyl)-1H-pyrazol-1-yl]ethyl}-1,3-oxazolidin-2-one;
(S)-7-{[4-(3-{[4-(difluoromethyl)pyrimidin-2-yl]amino}-5-methylphenyl)-1H-pyrazol-1-yl]methyl}-6-oxa-4-azaspiro[2.4]heptan-5-one;
5-{[4-(3-{[4-(difluoromethyl)pyrimidin-2-yl]amino}-5-methylphenyl)-1H-pyrazol-1-yl]methyl}pyridin-2(1H)-one;
(4S)-4-{[4-(3-methyl-5-{[4-(trifluoromethyl)pyrimidin-2-yl]amino}phenyl)-1H-pyrazol-1-yl]methyl}-1,3-oxazolidin-2-one;
(4R)-4-{[4-(3-methyl-5-{[4-(trifluoromethyl)pyrimidin-2-yl]amino}phenyl)-1H-pyrazol-1-yl]methyl}-1,3-oxazolidin-2-one;
3-[4-(3-{[4-(difluoromethyl)pyrimidin-2-yl]amino}-5-methylphenyl)-1H-pyrazol-1-yl]butan-2-one;
(R)-4,4-dimethyl-5-{[4-(3-methyl-5-{[4-(trifluoromethyl)pyrimidin-2-yl]amino}phenyl)-1H-pyrazol-1-yl]methyl}-1,3-oxazolidin-2-one;
(S)-4,4-dimethyl-5-{[4-(3-methyl-5-{[4-(trifluoromethyl)pyrimidin-2-yl]amino}phenyl)-1H-pyrazol-1-yl]methyl}-1,3-oxazolidin-2-one;
(R)-5-{[4-(3-{[4-(1,1-difluoroethyl)pyrimidin-2-yl]amino}-5-methylphenyl)-1H-pyrazol-1-yl]methyl}-4,4-dimethyl-1,3-oxazolidin-2-one;
(R)-5-{[4-(3-{[4-(difluoromethyl)pyrimidin-2-yl]amino}-5-methylphenyl)-1H-pyrazol-1-yl]methyl}-4,4-dimethyl-1,3-oxazolidin-2-one;
(S)-5-{[4-(3-{[4-(difluoromethyl)pyrimidin-2-yl]amino}-5-methylphenyl)-1H-pyrazol-1-yl]methyl}-4,4-dimethyl-1,3-oxazolidin-2-one;
(S)-5-{[4-(3-{[4-(1,1-difluoroethyl)pyrimidin-2-yl]amino}-5-methylphenyl)-1H-pyrazol-1-yl]methyl}-4,4-dimethyl-1,3-oxazolidin-2-one;
(R)-4,4-dimethyl-5-[(4-{3-methyl-5-[(4-methylpyrimidin-2-yl)amino]phenyl}-1H-pyrazol-1-yl)methyl]-1,3-oxazolidin-2-one;
(S)-4,4-dimethyl-5-[(4-{3-methyl-5-[(4-methylpyrimidin-2-yl)amino]phenyl}-1H-pyrazol-1-yl)methyl]-1,3-oxazolidin-2-one;
5-methyl-4-{[4-(3-methyl-5-{[4-(trifluoromethyl)pyrimidin-2-yl]amino}phenyl)-1H-pyrazol-1-yl]methyl}-1,3-oxazolidin-2-one;
4-(difluoromethyl)-N-(3-methyl-5-{1-[(2-methyl-1H-imidazol-5-yl)methyl]-1H-pyrazol-4-yl}phenyl)pyrimidin-2-amine;
4-(difluoromethyl)-N-(3-methyl-5-{1-[(4-methyl-1H-imidazol-5-yl)methyl]-1H-pyrazol-4-yl}phenyl)pyrimidin-2-amine;
4-(difluoromethyl)-N-{3-[1-(1H-imidazol-4-ylmethyl)-1H-pyrazol-4-yl]-5-methylphenyl}pyrimidin-2-amine;
4-(difluoromethyl)-N-(3-methyl-5-{1-[2-(1H-pyrazol-4-yl)ethyl]-1H-pyrazol-4-yl}phenyl)pyrimidin-2-amine;
3-[4-(3-{[4-(difluoromethyl)pyrimidin-2-yl]amino}-5-methylphenyl)-1H-pyrazol-1-yl]propane-1,2-diol;
(R)-1-[4-(3-{[4-(difluoromethyl)pyrimidin-2-yl]amino}-5-methylphenyl)-1H-pyrazol-1-yl]-2-methylbutan-2-ol;
(S)-1-[4-(3-{[4-(difluoromethyl)pyrimidin-2-yl]amino}-5-methylphenyl)-1H-pyrazol-1-yl]-2-methylbutan-2-ol;
(5R)-5-({4-[3-methyl-5-(pyrimidin-2-ylamino)phenyl]-1H-pyrazol-1-yl}methyl)-1,3-oxazolidin-2-one;
(5S)-5-({4-[3-methyl-5-(pyrimidin-2-ylamino)phenyl]-1H-pyrazol-1-yl}methyl)-1,3-oxazolidin-2-one;
(5R)-5-methyl-5-{[4-(3-methyl-5-{[4-(trifluoromethyl)pyrimidin-2-yl]amino}phenyl)-1H-pyrazol-1-yl]methyl}-1,3-oxazolidin-2-one;
(5S)-5-methyl-5-{[4-(3-methyl-5-{[4-(trifluoromethyl)pyrimidin-2-yl]amino}phenyl)-1H-pyrazol-1-yl]methyl}-1,3-oxazolidin-2-one;
4-methyl-5-{[4-(3-methyl-5-{[4-(trifluoromethyl)pyrimidin-2-yl]amino}phenyl)-1H-pyrazol-1-yl]methyl}-1,3-oxazolidin-2-one;
(5R)-5-methyl-5-[(4-{3-methyl-5-[(4-methylpyrimidin-2-yl)amino]phenyl}-1H-pyrazol-1-yl)methyl]-1,3-oxazolidin-2-one;
(5S)-5-methyl-5-[(4-{3-methyl-5-[(4-methylpyrimidin-2-yl)amino]phenyl}-1H-pyrazol-1-yl)methyl]-1,3-oxazolidin-2-one;
(5R)-5-{[4-(3-{[4-(difluoromethyl)pyrimidin-2-yl]amino}-5-methylphenyl)-1H-pyrazol-1-yl]methyl}-5-methyl-1,3-oxazolidin-2-one;
(5S)-5-{[4-(3-{[4-(difluoromethyl)pyrimidin-2-yl]amino}-5-methylphenyl)-1H-pyrazol-1-yl]methyl}-5-methyl-1,3-oxazolidin-2-one;

(5R)-5-{[4-(3-{[4-(1,1-difluoroethyl)pyrimidin-2-yl] amino}-5-methylphenyl)-1H-pyrazol-1-yl]methyl}-1,3-oxazolidin-2-one;

(5S)-5-{[4-(3-{[4-(1,1-difluoroethyl)pyrimidin-2-yl] amino}-5-methylphenyl)-1H-pyrazol-1-yl]methyl}-1,3-oxazolidin-2-one;

(R)-4-{1-hydroxy-1-[1-(3-methyl-5-{[4-(trifluoromethyl) pyrimidin-2-yl]amino}phenyl)-1H-pyrazol-4-yl] ethyl}benzoic acid;

(S)-4-{1-hydroxy-1-[1-(3-methyl-5-{[4-(trifluoromethyl) pyrimidin-2-yl]amino}phenyl)-1H-pyrazol-4-yl] ethyl}benzoic acid;

N-[3-(3-chloro-1H-pyrazol-1-yl)-5-methylphenyl]-4-(trifluoromethyl)pyrimidin-2-amine;

4-hydroxy-4-[1-(3-methyl-5-{[4-(trifluoromethyl)pyrimidin-2-yl]amino}phenyl)-1H-pyrazol-4-yl]cyclohexanecarboxylic acid;

(1R)-trans-4-{1-hydroxy-1-[1-(3-methyl-5-{[4-(trifluoromethyl)pyrimidin-2-yl]amino}phenyl)-1H-pyrazol-4-yl] ethyl}cyclohexanecarboxylic acid;

(1S)-trans-4-{1-hydroxy-1-[1-(3-methyl-5-{[4-(trifluoromethyl)pyrimidin-2-yl]amino}phenyl)-1H-pyrazol-4-yl] ethyl}cyclohexanecarboxylic acid;

4-hydroxy-2,2-dimethyl-4-[1-(3-methyl-5-{[4-(trifluoromethyl)pyrimidin-2-yl]amino}phenyl)-1H-pyrazol-4-yl]cyclohexanecarboxylic acid;

(R)-3-hydroxy-3-methyl-4-(4-(4-methyl-6-((4-(trifluoromethyl)pyridin-2-yl)amino)pyridin-2-yl)-1H-pyrazol-1-yl) butanenitrile;

(R)-3-hydroxy-3-methyl-4-[4-(3-methyl-5-{[4-(trifluoromethyl)pyrimidin-2-yl]amino}phenyl)-1H-pyrazol-1-yl] butanenitrile;

(S)-3-hydroxy-3-methyl-4-[4-(3-methyl-5-{[4-(trifluoromethyl)pyrimidin-2-yl]amino}phenyl)-1H-pyrazol-1-yl] butanenitrile;

(S)-3-hydroxy-3-methyl-4-[4-(4-methyl-6-{[4-(trifluoromethyl)pyridin-2-yl]amino}pyridin-2-yl)-1H-pyrazol-1-yl] butanenitrile;

(R)-4-[4-(3-{[4-(difluoromethyl)-5-fluoropyrimidin-2-yl] amino}-5-methylphenyl)-1H-pyrazol-1-yl]-3-hydroxy-3-methylbutanenitrile;

(S)-4-[4-(3-{[4-(difluoromethyl)-5-fluoropyrimidin-2-yl] amino}-5-methylphenyl)-1H-pyrazol-1-yl]-3-hydroxy-3-methylbutanenitrile;

(R)-4-[4-(3-{[4-(difluoromethyl)pyrimidin-2-yl]amino}-5-methylphenyl)-1H-pyrazol-1-yl]-3-hydroxy-3-methylbutanenitrile;

(S)-4-[4-(3-{[4-(difluoromethyl)pyrimidin-2-yl]amino}-5-methylphenyl)-1H-pyrazol-1-yl]-3-hydroxy-3-methylbutanenitrile;

(R)-4-[4-(3-{[4-(1,1-difluoroethyl)pyrimidin-2-yl]amino}-5-methylphenyl)-1H-pyrazol-1-yl]-3-hydroxy-3-methylbutanenitrile;

(S)-4-[4-(3-{[4-(1,1-difluoroethyl)pyrimidin-2-yl]amino}-5-methylphenyl)-1H-pyrazol-1-yl]-3-hydroxy-3-methylbutanenitrile;

(R)-2-methyl-3-(4-(3-methyl-5-((4-(trifluoromethyl)pyrimidin-2-yl)amino)phenyl)-1H-pyrazol-1-yl)propane-1,2-diol;

(S)-2-methyl-3-(4-(3-methyl-5-((4-(trifluoromethyl)pyrimidin-2-yl)amino)phenyl)-1H-pyrazol-1-yl)propane-1,2-diol;

3-[4-(3-{[4-(difluoromethyl)pyrimidin-2-yl]amino}-5-methylphenyl)-1H-pyrazol-1-yl]butan-2-one;

(R)-2-methyl-3-[4-(4-methyl-6-{[4-(trifluoromethyl)pyridin-2-yl]amino}pyridin-2-yl)-1H-pyrazol-1-yl]propane-1,2-diol;

(S)-2-methyl-3-[4-(4-methyl-6-{[4-(trifluoromethyl)pyridin-2-yl]amino}pyridin-2-yl)-1H-pyrazol-1-yl]propane-1,2-diol;

(R)-1-[4-(3-{[4-(difluoromethyl)pyrimidin-2-yl]amino}-5-methylphenyl)-1H-pyrazol-1-yl]-2,3-dimethylbutane-2,3-diol;

(S)-1-[4-(3-{[4-(difluoromethyl)pyrimidin-2-yl]amino}-5-methylphenyl)-1H-pyrazol-1-yl]-2,3-dimethylbutane-2,3-diol;

(2R,3S)-2-methyl-3-[4-(3-methyl-5-{[4-(trifluoromethyl)pyrimidin-2-yl]amino}phenyl)-1H-pyrazol-1-yl]butane-1,2-diol;

(2S,3R)-2-methyl-3-[4-(3-methyl-5-{[4-(trifluoromethyl)pyrimidin-2-yl]amino}phenyl)-1H-pyrazol-1-yl]butane-1,2-diol;

(2R,3R)-2-methyl-3-[4-(3-methyl-5-{[4-(trifluoromethyl)pyrimidin-2-yl]amino}phenyl)-1H-pyrazol-1-yl]butane-1,2-diol;

(2S,3S)-2-methyl-3-[4-(3-methyl-5-{[4-(trifluoromethyl)pyrimidin-2-yl]amino}phenyl)-1H-pyrazol-1-yl]butane-1,2-diol;

3-(4-(3-((4-(difluoromethyl)pyrimidin-2-yl)amino)-5-methylphenyl)-1H-pyrazol-1-yl)-2-methylbutane-1,2-diol;

(R)-1-[4-(3-{[4-(1,1-difluoroethyl)pyrimidin-2-yl]amino}-5-methylphenyl)-1H-pyrazol-1-yl]-2,3-dimethylbutane-2,3-diol;

(S)-1-[4-(3-{[4-(1,1-difluoroethyl)pyrimidin-2-yl]amino}-5-methylphenyl)-1H-pyrazol-1-yl]-2,3-dimethylbutane-2,3-diol;

3-[4-(3-{[4-(difluoromethyl)pyrimidin-2-yl]amino}-5-methylphenyl)-1H-pyrazol-1-yl]-1-methylcyclohexane-1,2-diol;

6-[4-(3-{[4-(difluoromethyl)pyrimidin-2-yl]amino}-5-methylphenyl)-1H-pyrazol-1-yl]-3,3-dimethylcyclohexane-1,2-diol;

3-[4-(3-{[4-(difluoromethyl)pyrimidin-2-yl]amino}-5-methylphenyl)-1H-pyrazol-1-yl]-1,5,5-trimethylcyclohexane-1,2-diol;

3-[4-(3-{[4-(difluoromethyl)pyrimidin-2-yl]amino}-5-methylphenyl)-1H-pyrazol-1-yl]-1,2-dimethylcyclohexane-1,2-diol;

5-[4-(3-{[4-(difluoromethyl)pyrimidin-2-yl]amino}-5-methylphenyl)-1H-pyrazol-1-yl]-1-methylcyclopentane-1,2-diol;

3-[4-(3-{[4-(difluoromethyl)pyrimidin-2-yl]amino}-5-methylphenyl)-1H-pyrazol-1-yl]cycloheptane-1,2-diol;

(4S,5S)-4-methyl-5-((4-(3-methyl-5-((4-(trifluoromethyl)pyrimidin-2-yl)amino)phenyl)-1H-pyrazol-1-yl)methyl) oxazolidin-2-one;

4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one;

4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one;

4-methyl-5-[(4-{3-methyl-5-[(4-methylpyrimidin-2-yl) amino]phenyl}-1H-pyrazol-1-yl)methyl]-1,3-oxazolidin-2-one;

5-{[4-(3-{[4-(difluoromethyl)pyrimidin-2-yl]amino}-5-methylphenyl)-1H-pyrazol-1-yl]methyl}-4-methyl-1,3-oxazolidin-2-one;

5-{[4-(3-{[4-(1,1-difluoroethyl)pyrimidin-2-yl]amino}-5-methylphenyl)-1H-pyrazol-1-yl]methyl}-4-methyl-1,3-oxazolidin-2-one;

5-{[4-(3-{[4-(difluoromethyl)pyrimidin-2-yl]amino}-5-methylphenyl)-1H-pyrazol-1-yl]methyl}-4-methyl-1,3-oxazolidin-2-one;

4-(1-methylethyl)-5-[(4-{3-methyl-5-[(4-methylpyrimidin-2-yl)amino]phenyl}-1H-pyrazol-1-yl)methyl]-1,3-oxazolidin-2-one;

4-cyclopropyl-5-{[4-(3-{[4-(difluoromethyl)pyrimidin-2-yl]amino}-5-methylphenyl)-1H-pyrazol-1-yl]methyl}-1,3-oxazolidin-2-one;

5-{[4-(3-{[4-(difluoromethyl)-5-fluoropyrimidin-2-yl]amino}-5-methylphenyl)-1H-pyrazol-1-yl]methyl}-4-methyl-1,3-oxazolidin-2-one;

(R)-3-(4-(3-((4-(difluoromethyl)pyrimidin-2-yl)amino)-5-methylphenyl)-1H-pyrazol-1-yl)-1,1,1-trifluoro-2-methylpropan-2-ol;

(S)-3-(4-(3-((4-(difluoromethyl)pyrimidin-2-yl)amino)-5-methylphenyl)-1H-pyrazol-1-yl)-1,1,1-trifluoro-2-methylpropan-2-ol;

2-((4-(3-((4-(difluoromethyl)pyrimidin-2-yl)amino)-5-methylphenyl)-1H-pyrazol-1-yl)methyl)-3,3,3-trifluoropropane-1,2-diol;

(R)-2-methyl-3-(4-{3-methyl-5-[(4-methylpyrimidin-2-yl)amino]phenyl}-1H-pyrazol-1-yl)propane-1,2-diol;

(R)-3-[4-(3-{[4-(difluoromethyl)pyrimidin-2-yl]amino}-5-methylphenyl)-1H-pyrazol-1-yl]-2-methylpropane-1,2-diol;

(S)-2-methyl-3-(4-{3-methyl-5-[(4-methylpyrimidin-2-yl)amino]phenyl}-1H-pyrazol-1-yl)propane-1,2-diol;

(S)-3-[4-(3-{[4-(difluoromethyl)pyrimidin-2-yl]amino}-5-methylphenyl)-1H-pyrazol-1-yl]-2-methylpropane-1,2-diol;

3-{4-[3-({4-[(1R)-1-fluoroethyl]pyrimidin-2-yl}amino)-5-methylphenyl]-1H-pyrazol-1-yl}-2-methylpropane-1,2-diol;

3-{4-[3-({4-[(1S)-1-fluoroethyl]pyrimidin-2-yl}amino)-5-methylphenyl]-1H-pyrazol-1-yl}-2-methylpropane-1,2-diol;

3-[4-(3-{[4-(difluoromethyl)-5-fluoropyrimidin-2-yl]amino}-5-methylphenyl)-1H-pyrazol-1-yl]-2-methylpropane-1,2-diol;

3-[4-(3-{[4-(difluoromethyl)-5-fluoropyrimidin-2-yl]amino}-5-methylphenyl)-1H-pyrazol-1-yl]-2-methylpropane-1,2-diol;

N-(2-(4-(3-((4-(Difluoromethyl)pyrimidin-2-yl)amino)-5-methylphenyl)-1H-pyrazol-1-yl)ethyl)cyclopropanecarboxamide;

N-{2-[4-(3-{[4-(difluoromethyl)pyrimidin-2-yl]amino}-5-methylphenyl)-1H-pyrazol-1-yl]-1,1-dimethylethyl}cyclopropanecarboxamide;

N-{2-[4-(3-{[4-(difluoromethyl)pyrimidin-2-yl]amino}-5-methylphenyl)-1H-pyrazol-1-yl]-1,1-dimethylethyl}-2-methoxyacetamide;

2-cyano-N-{2-[4-(3-{[4-(difluoromethyl)pyrimidin-2-yl]amino}-5-methylphenyl)-1H-pyrazol-1-yl]ethyl}acetamide;

N-{2-[4-(3-{[4-(difluoromethyl)pyrimidin-2-yl]amino}-5-methylphenyl)-1H-pyrazol-1-yl]ethyl}-2-methoxyacetamide;

N-(2-(4-(3-((4-(difluoromethyl)pyrimidin-2-yl)amino)-5-methylphenyl)-1H-pyrazol-1-yl)ethyl)methanesulfonamide;

methyl {2-[4-(3-{[4-(difluoromethyl)pyrimidin-2-yl]amino}-5-methylphenyl)-1H-pyrazol-1-yl]ethyl}carbamate;

2-methoxyethyl {2-[4-(3-{[4-(difluoromethyl)pyrimidin-2-yl]amino}-5-methylphenyl)-1H-pyrazol-1-yl]ethyl}carbamate;

N-{2-[4-(3-{[4-(difluoromethyl)pyrimidin-2-yl]amino}-5-methylphenyl)-1H-pyrazol-1-yl]-1,1-dimethylethyl}methanesulfonamide;

N-{2-[4-(3-{[4-(difluoromethyl)pyrimidin-2-yl]amino}-5-methylphenyl)-1H-pyrazol-1-yl]-1,1-dimethylethyl}cyclopropanesulfonamide;

N-{2-[4-(3-{[4-(difluoromethyl)pyrimidin-2-yl]amino}-5-methylphenyl)-1H-pyrazol-1-yl]-1,1-dimethylethyl}morpholine-4-sulfonamide;

1-tert-butyl-3-{2-[4-(3-{[4-(difluoromethyl)pyrimidin-2-yl]amino}-5-methylphenyl)-1H-pyrazol-1-yl]-1,1-dimethylethyl}urea;

1-{2-[4-(3-{[4-(difluoromethyl)pyrimidin-2-yl]amino}-5-methylphenyl)-1H-pyrazol-1-yl]-1,1-dimethylethyl}-3-ethylurea;

1-{2-[4-(3-{[4-(difluoromethyl)pyrimidin-2-yl]amino}-5-methylphenyl)-1H-pyrazol-1-yl]-1,1-dimethylethyl}-3-(tetrahydro-2H-pyran-4-ylmethyl)urea;

2-fluoroethyl-{2-[4-(3-{[4-(difluoromethyl)pyrimidin-2-yl]amino}-5-methylphenyl)-1H-pyrazol-1-yl]-1,1-dimethylethyl}carbamate;

methyl {2-[4-(3-{[4-(difluoromethyl)pyrimidin-2-yl]amino}-5-methylphenyl)-1H-pyrazol-1-yl]-1,1-dimethylethyl}carbamate;

2-methoxyethyl {2-[4-(3-{[4-(difluoromethyl)pyrimidin-2-yl]amino}-5-methylphenyl)-1H-pyrazol-1-yl]-1,1-dimethylethyl}carbamate;

N-{2-[4-(3-{[4-(difluoromethyl)pyrimidin-2-yl]amino}-5-methylphenyl)-1H-pyrazol-1-yl]ethyl}cyclopropanesulfonamide;

N-{2-[4-(3-{[4-(difluoromethyl)pyrimidin-2-yl]amino}-5-methylphenyl)-1H-pyrazol-1-yl]ethyl}morpholine-4-sulfonamide;

1-tert-butyl-3-{2-[4-(3-{[4-(difluoromethyl)pyrimidin-2-yl]amino}-5-methylphenyl)-1H-pyrazol-1-yl]ethyl}urea;

1-{2-[4-(3-{[4-(difluoromethyl)pyrimidin-2-yl]amino}-5-methylphenyl)-1H-pyrazol-1-yl]ethyl}-3-ethylurea;

1-{2-[4-(3-{[4-(difluoromethyl)pyrimidin-2-yl]amino}-5-methylphenyl)-1H-pyrazol-1-yl]ethyl}-3-(tetrahydro-2H-pyran-4-ylmethyl)urea;

2-fluoroethyl-{2-[4-(3-{[4-(difluoromethyl)pyrimidin-2-yl]amino}-5-methylphenyl)-1H-pyrazol-1-yl]ethyl}carbamate;

(R)-4-(1-(4-(3-Methyl-5-(pyrimidin-2-ylamino)phenyl)-1H-pyrazol-1-yl)ethyl)benzamide;

(S)-4-(1-(4-(3-Methyl-5-(pyrimidin-2-ylamino)phenyl)-1H-pyrazol-1-yl)ethyl)benzamide;

1-((4-(3-((4-(Difluoromethyl)pyrimidin-2-yl)amino)-5-methylphenyl)-1H-pyrazol-1-yl)methyl)cyclobutanol;

1-{[4-(6-{[4-(difluoromethyl)pyridin-2-yl]amino}-4-methylpyridin-2-yl)-1H-pyrazol-1-yl]methyl}cyclobutanol;

1-[(4-{4-methyl-6-[(4-methylpyrimidin-2-yl)amino]pyridin-2-yl}-1H-pyrazol-1-yl)methyl]cyclobutanol;

1-{[4-(3-{[4-(difluoromethyl)pyrimidin-2-yl]amino}phenyl)-1H-pyrazol-1-yl]methyl}cyclobutanol;

1-[(4-{3-methyl-5-[(4-methylpyrimidin-2-yl)amino]phenyl}-1H-pyrazol-1-yl)methyl]cyclobutanol;

1-{[4-(3-{[4-(difluoromethyl)-5-fluoropyrimidin-2-yl]amino}-5-methylphenyl)-1H-pyrazol-1-yl]methyl}cyclobutanol;

1-[(4-{6-[(4-cyclopropylpyridin-2-yl)amino]-4-methylpyridin-2-yl}-1H-pyrazol-1-yl)methyl]cyclobutanol;

3-(4-(3-methyl-5-(pyrimidin-2-ylamino)phenyl)-1H-pyrazol-1-yl)cyclobutanecarboxamide;

3-(4-(3-Methyl-5-(pyrimidin-2-ylamino)phenyl)-1H-pyrazol-1-yl)cyclobutanecarboxamide;

(R)-2-((4-(3-((4-(difluoromethyl)pyrimidin-2-yl)amino)-5-methylphenyl)-1H-pyrazol-1-yl)methyl)-3,3,3-trifluoropropane-1,2-diol;

(S)-2-((4-(3 ((4-(difluoromethyl)pyrimidin-2-yl)amino)-5-methylphenyl)-1H-pyrazol-1-yl)methyl)-3,3,3-trifluoropropane-1,2-diol;

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one;

(R)-5-[4-(6-{[4-(difluoromethyl)pyridin-2-yl]amino}-4-methylpyridin-2-yl)-1H-pyrazol-1-yl]-5-ethyl-1,3-oxazolidin-2-one; and (S)-5-[4-(6-{[4-(difluoromethyl)pyridin-2-yl]amino}-4-methylpyridin-2-yl)-1H-pyrazol-1-yl]-5-ethyl-1,3-oxazolidin-2-one.

In another embodiment, the compounds (including pharmaceutically acceptable salts thereof) are selected from the following compounds:

3-[4-(3-{[4-(difluoromethyl)pyrimidin-2-yl]amino}-5-methylphenyl)-1H-pyrazol-1-yl]cyclohexane-1,2-diol;

3-(4-{3-methyl-5-[(4-methylpyrimidin-2-yl)amino]phenyl}-1H-pyrazol-1-yl)cyclohexane-1,2-diol;

3-[4-(3-{[4-(difluoromethyl)pyrimidin-2-yl]amino}-5-methylphenyl)-1H-pyrazol-1-yl]-1,5,5-trimethylcyclohexane-1,2-diol;

6-[4-(3-{[4-(difluoromethyl)pyrimidin-2-yl]amino}-5-methylphenyl)-1H-pyrazol-1-yl]-3,3-dimethylcyclohexane-1,2-diol;

3-[4-(3-{[4-(difluoromethyl)pyrimidin-2-yl]amino}-5-methylphenyl)-1H-pyrazol-1-yl]-1,2-dimethylcyclohexane-1,2-diol;

5-{[4-(3-{[4-(difluoromethyl)pyrimidin-2-yl]amino}-5-methylphenyl)-1H-pyrazol-1-yl]methyl}-1,3-oxazolidin-2-one;

5-{[4-(3-{[4-(difluoromethyl)-5-fluoropyrimidin-2-yl]amino}-5-methylphenyl)-1H-pyrazol-1-yl]methyl}-4-methyl-1,3-oxazolidin-2-one;

7-{[4-(3-{[4-(difluoromethyl)pyrimidin-2-yl]amino}-5-methylphenyl)-1H-pyrazol-1-yl]methyl}-6-oxa-4-azaspiro[2.4]heptan-5-one;

4-methyl-5-((4-(3-methyl-5-((4-(trifluoromethyl)pyrimidin-2-yl)amino)phenyl)-1H-pyrazol-1-yl)methyl)oxazolidin-2-one;

5-methyl-5-{[4-(3-methyl-5-{[4-(trifluoromethyl)pyrimidin-2-yl]amino}phenyl)-1H-pyrazol-1-yl]methyl}-1,3-oxazolidin-2-one;

2-methyl-3-(4-(3-methyl-5-((4-(trifluoromethyl)pyrimidin-2-yl)amino)phenyl)-1H-pyrazol-1-yl)propane-1,2-diol;

1-[4-(3-{[4-(difluoromethyl)pyrimidin-2-yl]amino}-5-methylphenyl)-1H-pyrazol-1-yl]-2,3-dimethylbutane-2,3-diol;

1-[4-(3-{[4-(1,1-difluoroethyl)pyrimidin-2-yl]amino}-5-methylphenyl)-1H-pyrazol-1-yl]-2,3-dimethylbutane-2,3-diol;

2-methyl-3-[4-(3-methyl-5-{[4-(trifluoromethyl)pyrimidin-2-yl]amino}phenyl)-1H-pyrazol-1-yl]butane-1,2-diol; and 3-[4-(3-{[4-(1-hydroxyethyl)pyrimidin-2-yl]amino}-5-methylphenyl)-1H-pyrazol-1-yl]-2-methylpropane-1,2-diol.

In the application various terms are as defined below, unless otherwise specified:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

Aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, $(CR^aR^b)_nO_2R^c$; and $(CR^aR^b)_n$-$CONR^dR^e$. Examples or aryl are benzene or naphthalene.

"Carbocyclyl" refers to a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated (non-aromatic) and that ring being isolated or fused (including ortho-fused, spiro-fused and bridged) to one or two such rings or to a benzene ring. In the case of a polycyclic carbocyclyl the attachment point may be on any ring; the carbocyclyl may optionally be substituted with one to four substituents selected from hydroxyl, $C_1$-$C_3$-alkyl, $C_1$-$C_3$-alkoxyl, $(CR^aR^b)_nO_2R^c$; $(CR^aR^b)_nCONR^dR^e$; and a spiro-linked —OCH$_2$CH$_2$O—. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-6}$ cycloalkyl" refers to a saturated ring having from 3 to 6 ring carbon atoms. Exemplary "cycloalkyl" groups useful in the present invention include, but are not limited to, cyclopropyl, cyclobutyl, cyclopentyl and cyclohexyl. The carbocyclyl may be optionally be substituted with one or more substituents selected from oxo, halo, hydroxyl, $C_1$-$C_3$-alkyl, $C_1$-$C_6$-alkenyl, $C_1$-$C_3$-alkoxyl, $(CR^aR^b)_nCO_2R^c$; $(CR^aR^b)_nCONR^dR^e$; $(CHR^a)_nNHCONR^dR^e$.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

"Heterocyclyl" refers to a 4-, 5-, 6-, or 7-membered monocyclic ring or 8-, 9-, 10-membered bicyclic ring, or 13- or 14-membered tricyclic ring, saturated, unsaturated or aromatic, containing 1, 2, 3 or 4 heteroatoms selected from O, N. or S, the heterocyclyl may optionally be substituted with one to four substituents selected from oxo, halo, hydroxyl, $C_1$-$C_3$-alkyl, $C_1$-$C_6$-alkenyl, $C_1$-$C_3$-alkoxyl, $(CR^aR^b)_nO_2R^c$; $(CR^aR^b)_nCONR^dR^e$; $(CHR^a)_nNHCONR^dR^e$; $(CHR^a)_p$—C(O)-heterocyclyl; and heterocycles having a N-atom may by the point of attachment. Representative heterocycles are: azetidinyl, pyrrolidinyl, pyrrolyl, tetrahydrofuran, imidazolyl, imidazolinyl, 1,3-oxazolidinyl, 1,2-oxazolidinyl, isoxazolyl, 1,2,4-oxadiazolyl, 1,3,4-oxadiazolyl, tetrahydropyranyl, piperidinyl, piperazinyl, morpholinyl, pyrimidinyl, pyrrolopyrazine, pyrrolopyridine, and indolyl.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one $R^7$ substituents on the "A" ring, each substituent is independently selected at each occurrence, and each substituent can be the same or different from the other(s).

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psorasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula I or a salt, solvate or physiologically functional derivative thereof.

As used herein, the term "solvate" refers to a complex of variable stoichiometry formed by a solute (in this invention, a compound of formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula I may have the ability to crystallize in more than one form, a characteristic known as polymorphism, and it is understood that such polymorphic forms ("polymorphs") are within the scope of formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of formula I may contain asymmetric or chiral centers, and, therefore, exist in different stereoisomeric forms. It is intended that all stereoisomeric forms of the compounds of formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of formula I may be atropisomers (e.g., substituted biaryls) and are considered as part of this invention.

It is also noted that the compounds of formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallization and filtration. A pharmaceutically acceptable acid addition salt of a compound of formula I can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of formula I.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula I can be prepared without undue experimentation by conventional techniques well known to those skilled in the art or by processes analogous to those described in the Schemes and Examples herein using appropriate isotopically-enriched reagents and/or intermediates The compounds of formula I and salts, solvates and physiologically functional derivatives thereof are believed to be inhibitors of Syk activity, and thus be potentially useful in the treatment of diseases and conditions associated with inappropriate Syk activity.

Compound of formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula I or a pharmaceutically acceptable salt, solvate, or a physiologically functional derivative thereof.

In a further embodiment, the present invention provides for the use of a compound of formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 3 g, preferably 1 mg to 700 mg, more preferably 5 mg to 100 mg of a compound of the formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (WAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler® (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
| --- | --- |
| Compound of formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of formula I | 25 |
| Lactose Powder | 573.5 |

-continued

| Capsule | mg/capsule |
|---|---|
| Magnesium Stearate | 1.5 |
| | 600 |

| Inhalation Aerosol | Per dose |
|---|---|
| Compound of formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
|---|---|
| Compound of formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I for the treatment of diseases or conditions associated with inappropriate Syk activity, will generally be in the range of 5 µg to 100 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula I or a pharmaceutically acceptable salt or solvate thereof, or a physiologically functional derivative thereof, and the use of at least one other pharmaceutically active agent. The compound(s) of formula I and the other pharmaceutically active agent(s) may be administered together or separately and, when administered separately this may occur simultaneously or sequentially in any order. The amounts of the compound(s) of formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate), salmeterol or a pharmaceutically acceptable salt thereof (e.g., salmeterol xinafoate) and fluticasone propionate.

For the treatment of cancer a compound of formula I may be combined with one or more of an anticancer agent. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl) methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxyl)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refers to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; mechlorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:

Biological Assay

Homogeneous Time-Resolved Fluorescence (HTRF) Assay for the Recombinant Human Syk Enzyme:

A recombinant GST-hSyk fusion protein was used to measure potency of compounds to inhibit human Syk activity. The recombinant human GST-Syk (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45 minutes at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on an EnVision (Perkin-Elmer) reader using a time-resolved fluorescence protocol. IC$_{50}$ was determined following 10-dose titration (10 µM to 0.508 nM) and four parameter logistic curve fitting using the Merck Assay Data Analyzer. The rhSyk activity (IC$_{50}$) is expressed as +++(100 nM or less), ++(between 100 and 1000 nM), +(between 1 and 10 µM).

| Example No. | rhSYK Activity |
| --- | --- |
| 1.1 | +++ |
| 1.2 | +++ |
| 1.3 | +++ |
| 1.4 | + |
| 1.5 | +++ |
| 1.6 | +++ |
| 1.7 | +++ |
| 1.8 | ++ |
| 1.9 | ++ |
| 1.10 | + |
| 1.11 | +++ |
| 1.12 | +++ |
| 1.13 | +++ |
| 1.14 | +++ |
| 1.15 | +++ |
| 1.16 | +++ |
| 1.17 | +++ |
| 1.18 | ++ |
| 1.19 | +++ |
| 1.20 | ++ |
| 1.21 | +++ |
| 1.22 | +++ |
| 1.23 | ++ |
| 1.24 | ++ |
| 1.25 | ++ |
| 1.26 | ++ |
| 1.27 | ++ |
| 1.28 | +++ |
| 1.29 | +++ |
| 1.30 | +++ |
| 1.31 | +++ |
| 1.32 | +++ |
| 1.33 | +++ |
| 1.34 | +++ |
| 1.35 | +++ |
| 1.36 | +++ |
| 1.37 | +++ |
| 1.38 | +++ |
| 1.39 | +++ |
| 1.40 | +++ |
| 1.41 | +++ |
| 1.42 | +++ |
| 1.43 | ++ |
| 1.44 | ++ |
| 1.45 | ++ |
| 1.46 | + |
| 1.47 | +++ |
| 1.48 | +++ |
| 1.49 | +++ |
| 1.50 | +++ |
| 1.51 | +++ |
| 1.52 | +++ |
| 1.53 | +++ |
| 1.54 | +++ |
| 1.55 | +++ |
| 1.56 | +++ |
| 1.57 | +++ |
| 1.58 | +++ |
| 1.59 | +++ |
| 1.60 | +++ |
| 1.61 | +++ |
| 1.62 | +++ |
| 1.63 | +++ |
| 1.64 | +++ |
| 1.65 | +++ |
| 1.66 | +++ |
| 2.1 | +++ |
| 2.2 | ++ |
| 2.3 | +++ |
| 2.4 | +++ |
| 2.5 | +++ |
| 2.6 | +++ |
| 2.7 | +++ |
| 2.8 | +++ |
| 2.9 | +++ |
| 2.10 | ++ |
| 2.11 | +++ |
| 2.12 | +++ |
| 2.13 | +++ |
| 2.14 | +++ |
| 2.15 | +++ |
| 2.16 | ++ |
| 2.17 | +++ |
| 2.18 | +++ |
| 2.19 | +++ |
| 2.20 | +++ |
| 2.21 | +++ |
| 2.22 | +++ |
| 2.23 | +++ |
| 2.24 | +++ |
| 2.25 | +++ |
| 2.26 | +++ |
| 2.27 | +++ |
| 2.28 | +++ |
| 2.29 | +++ |
| 2.30 | +++ |
| 2.31 | +++ |
| 2.32 | +++ |
| 2.33 | +++ |
| 2.34 | +++ |
| 2.35 | +++ |
| 2.36 | +++ |
| 2.37 | ++ |

| Example No. | rhSYK Activity |
|---|---|
| 2.38 | ++ |
| 2.39 | ++ |
| 2.40 | +++ |
| 2.41 | +++/++ |
| 2.42 | +++ |
| 2.43 | +++ |
| 2.44 | +++ |
| 2.45 | +++ |
| 2.46 | +++ |
| 2.47 | ++ |
| 2.48 | ++ |
| 2.49 | +++ |
| 2.50 | +++ |
| 2.51 | +++ |
| 2.52 | +++ |
| 2.53 | +++ |
| 2.54 | +++ |
| 2.55 | +++ |
| 2.56 | +++ |
| 2.57 | +++ |
| 2.58 | +++ |
| 2.59 | +++ |
| 2.60 | +++ |
| 2.61 | +++ |
| 2.62 | +++ |
| 2.63 | +++ |
| 2.64 | +++ |
| 2.65 | +++ |
| 2.66 | +++ |
| 2.67 | +++ |
| 2.68 | +++ |
| 2.69 | +++ |
| 2.70 | +++ |
| 2.71 | +++ |
| 2.72 | +++ |
| 2.73 | +++ |
| 2.74 | +++ |
| 2.75 | +++ |
| 2.76 | +++ |
| 2.77 | +++ |
| 2.78 | +++ |
| 2.79 | +++ |
| 2.80 | +++ |
| 2.81 | +++ |
| 2.82 | +++ |
| 2.83 | +++ |
| 2.84 | +++ |
| 2.85 | +++ |
| 2.86 | +++ |
| 2.87 | +++ |
| 2.88 | +++ |
| 2.89 | +++ |
| 2.90 | +++ |
| 2.91 | +++ |
| 2.92 | +++ |
| 2.93 | +++ |
| 2.94 | +++ |
| 2.95 | ++ |
| 2.96 | +++ |
| 2.97 | +++ |
| 2.98 | +++ |
| 3.1 | +++ |
| 3.2 | +++ |
| 3.3 | +++ |
| 3.4 | +++ |
| 3.5 | +++ |
| 3.6 | +++ |
| 3.7 | +++ |
| 3.8 | +++ |
| 3.9 | +++ |
| 3.10 | +++ |
| 3.11 | +++ |
| 3.12 | ++ |
| 3.13 | ++ |
| 3.14 | ++ |
| 3.15 | +++ |
| 3.16 | +++ |
| 3.17 | +++ |
| 3.18 | +++ |
| 3.19 | +++ |
| 3.20 | +++ |
| 3.21 | +++ |
| 3.22 | +++ |
| 3.23 | ++ |
| 3.24 | +++ |
| 3.25 | +++ |
| 3.26 | +++ |
| 3.27 | +++ |
| 3.28 | +++ |
| 3.29 | +++ |
| 3.30 | +++ |
| 3.31 | +++ |
| 3.32 | +++ |
| 3.33 | +++ |
| 3.34 | +++ |
| 3.35 | +++ |
| 3.36 | +++ |
| 3.37 | +++ |
| 3.38 | +++ |
| 3.39 | +++ |
| 3.40 | +++ |
| 3.41 | +++ |
| 3.42 | +++ |
| 3.43 | +++ |
| 3.44 | +++ |
| 3.45 | +++ |
| 3.46 | +++ |
| 3.47 | +++ |
| 3.48 | +++ |
| 3.49 | +++ |
| 3.50 | +++ |
| 3.51 | +++ |
| 3.52 | ++ |
| 3.53 | +++ |
| 3.54 | +++ |
| 3.81 | +++ |
| 3.82 | +++ |
| 3.83 | +++ |
| 3.84 | +++ |
| 3.85 | +++ |
| 3.86 | +++ |
| 3.87 | +++ |
| 3.88 | +++ |
| 3.89 | +++ |
| 3.90 | +++ |
| 3.91 | +++ |
| 3.92 | +++ |
| 3.93 | +++ |
| 3.94 | +++ |
| 3.95 | +++ |
| 3.96 | +++ |
| 3.97 | +++ |
| 3.98 | +++ |
| 3.99 | +++ |
| 3.100 | +++ |
| 3.101 | +++ |
| 3.102 | +++ |
| 3.103 | +++ |
| 3.104 | +++ |
| 3.105 | +++ |
| 3.106 | +++ |
| 3.107 | +++ |
| 3.108 | +++ |
| 3.109 | +++ |
| 3.110 | +++ |
| 3.111 | +++ |
| 3.112 | +++ |
| 3.113 | +++ |
| 3.114 | +++ |
| 3.115 | +++ |
| 3.116 | +++ |
| 3.117 | +++ |
| 3.118 | +++ |
| 3.119 | +++ |

| Example No. | rhSYK Activity |
|---|---|
| 3.120 | +++ |
| 3.121 | +++ |
| 3.122 | +++ |
| 3.123 | +++ |
| 3.124 | +++ |
| 3.125 | +++ |
| 3.126 | +++ |
| 3.127 | +++ |
| 3.128 | +++ |
| 3.129 | +++ |
| 4.1 | +++ |
| 5.1 | +++ |
| 5.2 | +++ |
| 5.3 | +++ |
| 5.4 | +++ |
| 5.5 | +++ |
| 5.6 | +++ |
| 5.7 | +++ |
| 5.8 | ++ |
| 5.9 | +++ |
| 5.10 | +++ |
| 5.11 | ++ |
| 5.12 | +++ |
| 5.13 | ++ |
| 5.14 | +++ |
| 5.15 | +++ |
| 5.16 | +++ |
| 5.17 | +++ |
| 5.18 | +++ |
| 5.19 | +++ |
| 5.20 | +++ |
| 5.21 | +++ |
| 5.22 | +++ |
| 5.23 | +++ |
| 5.24 | +++ |
| 5.25 | +++ |
| 5.26 | +++ |
| 5.27 | +++ |
| 5.28 | +++ |
| 5.29 | +++ |
| 5.30 | +++ |
| 5.31 | +++ |
| 5.32 | +++ |
| 5.33 | +++ |
| 5.34 | +++ |
| 5.35 | +++ |
| 5.36 | +++ |
| 5.37 | +++ |
| 5.38 | +++ |
| 5.39 | +++ |
| 5.40 | +++ |
| 5.41 | +++ |
| 5.42 | +++ |
| 6.1 | +++ |
| 6.2 | +++ |
| 6.3 | +++ |
| 6.4 | +++ |
| 6.5 | +++ |
| 6.6 | +++ |
| 6.7 | +++ |
| 6.8 | +++ |
| 6.9 | +++ |
| 6.10 | ++ |
| 6.11 | +++ |
| 6.12 | +++ |
| 6.13 | +++ |
| 6.14 | +++ |
| 6.15 | +++ |
| 6.16 | +++ |
| 7.1 | +++ |
| 7.2 | +++ |
| 7.3 | +++ |
| 7.4 | +++ |
| 7.5 | +++ |
| 7.6 | +++ |
| 8.1 | +++ |
| 8.2 | +++ |
| 8.3 | +++ |
| 8.4 | +++ |
| 8.5 | +++ |
| 8.6 | +++ |
| 8.7 | +++ |
| 8.8 | +++ |
| 8.9 | +++ |
| 8.10 | ++ |
| 8.11 | +++ |
| 8.12 | +++ |
| 8.13 | +++ |
| 8.14 | +++ |
| 8.15 | +++ |
| 8.16 | +++ |
| 8.17 | +++ |
| 8.18 | +++ |
| 8.19 | +++ |
| 8.20 | +++ |
| 8.21 | +++ |
| 8.22 | ++ |
| 8.23 | +++ |
| 8.24 | +++ |
| 9.1 | +++ |
| 9.2 | +++ |
| 10.1 | +++ |
| 10.2 | +++ |
| 10.3 | +++ |
| 10.4 | +++ |
| 10.5 | +++ |
| 10.6 | +++ |
| 10.7 | +++ |
| 10.8 | +++ |
| 10.9 | +++ |
| 10.10 | +++ |
| 10.11 | +++ |
| 10.12 | +++ |
| 11.1 | +++ |
| 11.2 | +++ |
| 11.3 | +++ |
| 11.4 | +++ |
| 11.5 | +++ |
| 11.6 | +++ |
| 11.7 | +++ |
| 11.8 | +++ |
| 11.9 | +++ |
| 11.10 | +++ |
| 11.11 | +++ |
| 11.12 | +++ |
| 11.13 | +++ |
| 11.14 | +++ |
| 11.15 | +++ |
| 11.16 | +++ |
| 11.17 | +++ |
| 11.18 | +++ |
| 11.19 | ++ |
| 11.20 | +++ |
| 12.1 | ++ |
| 12.2 | +++ |
| 12.3 | +++ |
| 12.4 | ++ |
| 12.5 | +++ |
| 12.6 | +++ |
| 12.7 | +++ |
| 12.8 | +++ |
| 12.9 | +++ |
| 12.10 | +++ |
| 12.11 | +++ |
| 12.12 | +++ |
| 12.13 | ++ |
| 12.14 | +++ |
| 12.15 | +++ |
| 13.1 | +++ |
| 13.2 | +++ |
| 13.3 | +++ |
| 14 (2 isomers) | +++, +++ |
| 15 | +++ |
| 16 | +++ |

| Example No. | rhSYK Activity |
|---|---|
| 17 | +++ |
| 18.1 | +++ |
| 18.2 | ++ |
| 18.3 | +++ |
| 18.4 | ++ |
| 19.1 | +++ |
| 19.2 | ++ |
| 19.3 | +++ |
| 19.4 | ++ |
| 19.5 | ++ |
| 19.6 | ++ |
| 19.7 | +++ |
| 19.8 | +++ |
| 19.9 | ++ |
| 19.10 | ++ |
| 19.11 | +++ |
| 19.12 | +++ |
| 19.13 | +++ |
| 19.14 | ++ |
| 19.15 | ++ |
| 20.1 | +++ |
| 20.2 | +++ |
| 20.3 | +++ |
| 20.4 | +++ |
| 20.5 | +++ |
| 20.6 | +++ |
| 20.7 | +++ |
| 20.8 | +++ |
| 20.9 | +++ |
| 20.10 | +++ |
| 21.1 | +++ |
| 21.2 | +++ |
| 21.3 | +++ |
| 21.4 | +++ |
| 21.5 | +++ |
| 21.6 | +++ |
| 21.7 | +++ |
| 21.8 | +++ |
| 21.9 | +++ |
| 21.10 | +++ |
| 21.11 | +++ |
| 22.1 | +++ |
| 22.2 | +++ |
| 22.3 | +++ |
| 22.4 | +++ |
| 22.5 | +++ |
| 22.6 | +++ |
| 22.7 | +++ |
| 22.8 | +++ |
| 22.9 | +++ |
| 22.10 | +++ |
| 22.11 | +++ |
| 22.12 | +++ |
| 22.13 | +++ |
| 22.14 | +++ |
| 22.15 | +++ |
| 23.1 | +++ |
| 23.2 | +++ |
| 23.3 | +++ |
| 23.4 | +++ |
| 23.5 | +++ |
| 23.6 | +++ |
| 23.7 | +++ |
| 23.8 | +++ |
| 23.9 | +++ |
| 23.10 | +++ |
| 23.11 | +++ |
| 23.12 | +++ |
| 23.13 | +++ |
| 23.14 | +++ |
| 23.15 | +++ |
| 23.16 | +++ |
| 23.17 | +++ |
| 23.18 | +++ |
| 23.19 | +++ |
| 23.20 | +++ |
| 23.21 | +++ |
| 24.1 | +++ |
| 24.2 | +++ |
| 25.1 | +++ |
| 25.2 | +++ |
| 25.3 | +++ |
| 25.4 | +++ |
| 25.5 | +++ |
| 25.6 | +++ |
| 25.7 | +++ |
| 25.8 | +++ |
| 25.9 | +++ |
| 25.10 | +++ |
| 26.1 | +++ |
| 26.2 | +++ |
| 26.3 | +++ |
| 26.4 | +++ |
| 26.5 | +++ |
| 27.1 | +++ |
| 27.2 | +++ |
| 27.3 | +++ |
| 27.4 | +++ |
| 27.5 | +++ |
| 27.6 | +++ |
| 27.7 | +++ |
| 27.8 | +++ |
| 27.9 | +++ |
| 27.10 | +++ |
| 27.11 | +++ |
| 27.12 | +++ |
| 27.13 | +++ |
| 27.14 | +++ |
| 27.15 | +++ |
| 27.16 | +++ |
| 27.17 | +++ |
| 27.18 | +++ |
| 28.1 | +++ |
| 28.2 | +++ |
| 29.1 | +++ |
| 29.2 | +++ |
| 29.3 | +++ |
| 29.4 | +++ |
| 29.5 | +++ |
| 29.6 | +++ |
| 29.7 | +++ |
| 30.1 | +++ |
| 31.1 | +++ |
| 32.1 | +++ |
| 32.2 | +++ |
| 33.1 | +++ |
| 33.2 | +++ |
| 33.3 | +++ |
| 33.4 | +++ |

$IC_{50}$ values are also provided for the following representative compounds:

| Ex. No. | rhSYK $IC_{50}$ |
|---|---|
| 1.1 | 65.8 |
| 2.1 | 22.1 |
| 3.1 | 31.2 |
| 4.1 | 27.4 |
| 5.1 | 58.5 |
| 6.1 | 21.1 |
| 7.1 | 1.1 |
| 8.1 | 1.0 |
| 9.1 | 9.0 |
| 10.1 | 7.4 |
| 10.4 | 3.7 |
| 10.5 | 5.24 |
| 10.6 | 1.3 |
| 10.7 | 0.7 |
| 10.8 | 7.8 |
| 10.9 | 4.8 |
| 10.10 | 29.4 |

-continued

| Ex. No. | rhSYK IC$_{50}$ |
|---|---|
| 10.11 | 3.5 |
| 10.12 | 4.7 |
| 11.1 | 6.2 |
| 12.1 | 110.5 |
| 13.1 | 10.7 |
| 14.1 (enantiomer 1, 2) | 28.0, 10.1 |
| 15 | 5.9 |
| 16 | 2.7 |
| 17 | 13.9 |
| 18 | 56 |
| 19.1 | 61 |
| 20.1 | 1.7 |
| 21.1 | 3.66 |
| 22.1 | 1.3 |
| 22.6 | 1.7 |
| 22.7 | 2.6 |
| 22.8 | 5.9 |
| 22.9 | 1.1 |
| 22.10 | 6.7 |
| 22.11 | 2.5 |
| 22.12 | 7.4 |
| 22.13 | 3.6 |
| 22.14 | 5.8 |
| 22.15 | 2.6 |
| 23.1 | 1.2 |
| 24.1 | 2.6 |
| 24.2 | 6.2 |
| 25.1 | 3.2 |
| 26.1 | 25.2 |
| 27.1 | 8.6 |
| 28.1 | 57.5 |
| 28.2 | 7.2 |
| 29.1 | 2.0 |
| 30.1 | 48.3 |
| 31.1 | 34.9 |
| 32.1 | 1.6 |
| 32.2 | 3.3 |
| 33.1 | 1.6 |

The suitability of the compounds of formula I as prodrugs of Syk inhibitors can be tested as described below.

Analysis of Hydrolysis of Prodrug to Parent Species

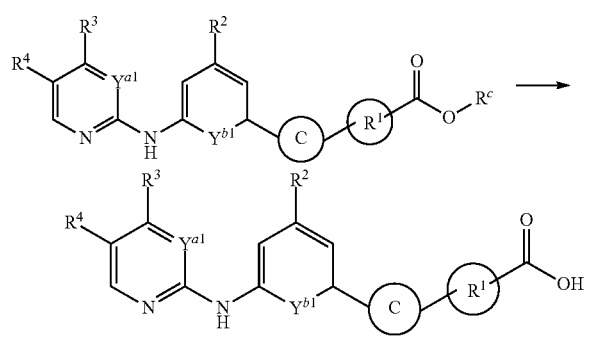

Hydrolysis Assay:

The stability of prodrugs is investigated in human liver S9 microsomes. Incubations of prodrugs (10 µM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treat with 4 volumes of acetonitrile containing 2% formic acid and an internal standard, and centrifuge. The supernatants are analyzed by LC-MS/MS for prodrug disappearance and appearance of active drug. The half-life of the prodrug is calculated from the % prodrug remaining at different time points calculated from on the peak area ratio relative to t=0. The amount of active drug generated at the different time points is determined using a standard curve.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of formula I. Those skilled in the art will recognize if a stereocenter exists in compounds of formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; ACN=Acetontrile; AcOH=Acetic acid; Bn=benzyl; Boc (t-Boc)=t-butyloxycarbonyl; bispin-bis(pinacolato)diborane; BOP=(Benzotriazol-1-yloxy)tris(dimethylamino)phosphonium hexafluorophosphate; DAST=(Diethylamino)sulfur trifluoride; dba=dibenzylideneacetone; DBAD=di-tert-butyl azodicarboxylate; DBU=1,8-Diazabicyclo[5.4.0]undec-7-ene; DCE=1,2-dichloroethane; DCM=Dichloromethane; Dibal/Dibal-H=Diisobutylaluminum hydride; DIPEA/DIEA=Diisopropylethylamine; DMA=N,N-Dimethylaniline; DMAP=N,N-dimethyl-aminopyridine; DME=1,2-dimethoxyethane; DMF=Dimethyl formamide; DMSO=Dimethyl-sulfoxide; Dppf=1,1'-Bis(diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl)uronium hexafluorophosphate; HMDS=Hexamethyldisilazane; HOBT=1-Hydroxybenzo-triazole; HPLC=High Pressure Liquid Chromatography IPA=Isopropyl alcohol; LDA=Lithium diisopropylamide; M=Molar; mCPBA=Meta-chloroperoxybenzoic acid; Ms=Methanesulfonyl (mesyl); MTBE=Methyl t-butyl ether; NBS=N-bromosuccinimide; Ph=phenyl; NMR=Nuclear Magnetic Resonance; SiDMT=Si-Dimercaptotriazole; TBAF=t-butylammonium fluoride; TBDMS/TBS=t-butyl dimethylsilyl; TFA=Trifluoroacetic acid/trifluroacetate; THF=Tetrahydrofuran; TLC=Thin-layer chromatography; TMS=Trimethylsilyl; Ts=Toluenesulfonyl (tosyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

Certain compounds set forth below in the examples below were isolated as isomerically pure or isomerically enriched compounds, but the configuration, or absolute configuration of such compounds was not determined at the time of isolation. Such compounds are identified in the full representative examples or in accompanying tables using such designations as "R or S", "chiral R or S", and "single stereoisomer." Typically, such compounds are further described by referring to the relative elution characteristic of the isomer from a chiral chromatography column using descriptions such as "early eluting", "late eluting", "peak 1 of 4", and the like.

SCHEME 1

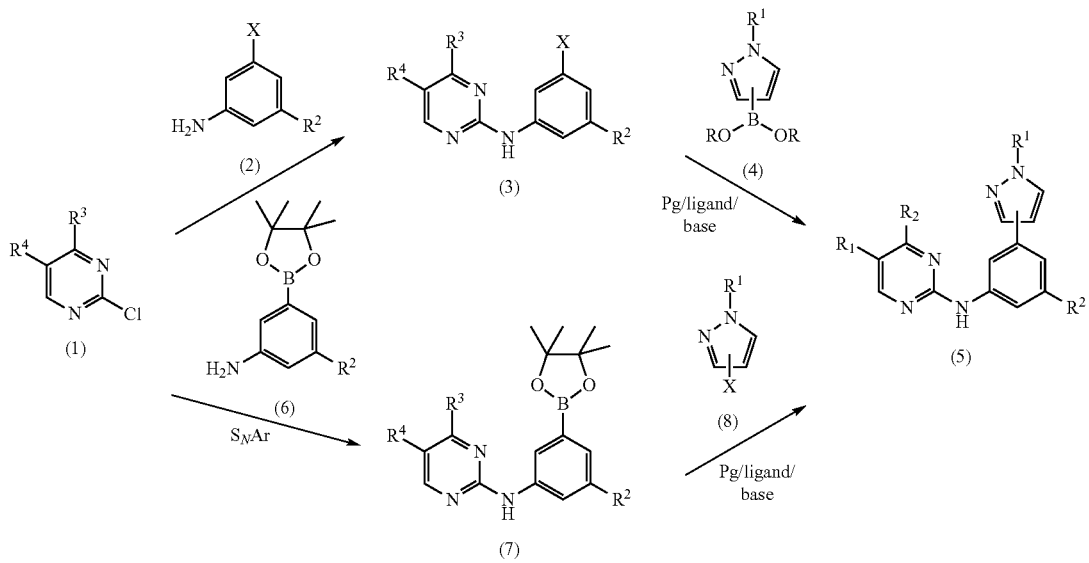

Compounds of formula (5) are prepared by reacting chloropyrimidines (1) with anilines (2), followed by Suzuki coupling with boronic ester-substituted pyrazoles (4). Alternatively, compounds of formula (5) are also prepared by reacting chloropyrimidines (1) with boronic ester-substituted-anilines (6) by $S_NAr$ reaction, followed by Suzuki coupling with halo-pyrazoles (8).

SCHEME 2

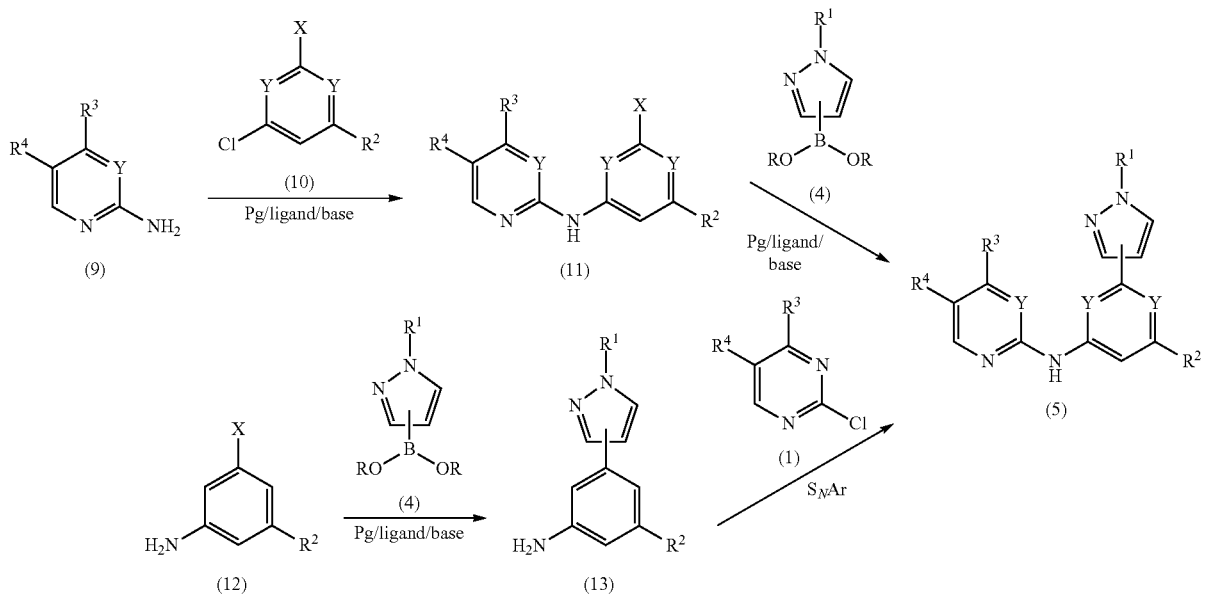

Reaction of substituted-aryl amines (9) with aryl chlorides (10) in the presence of Pd catalyst, followed by Suzuki coupling with boronic ester-substituted-pyrazoles (4) affords compound 5. Anilines (12) reacted with boronic ester-substituted-pyrazoles (6), followed by S_NAr with chloropyrimdines (1) also affords compounds (5).

SCHEME 3

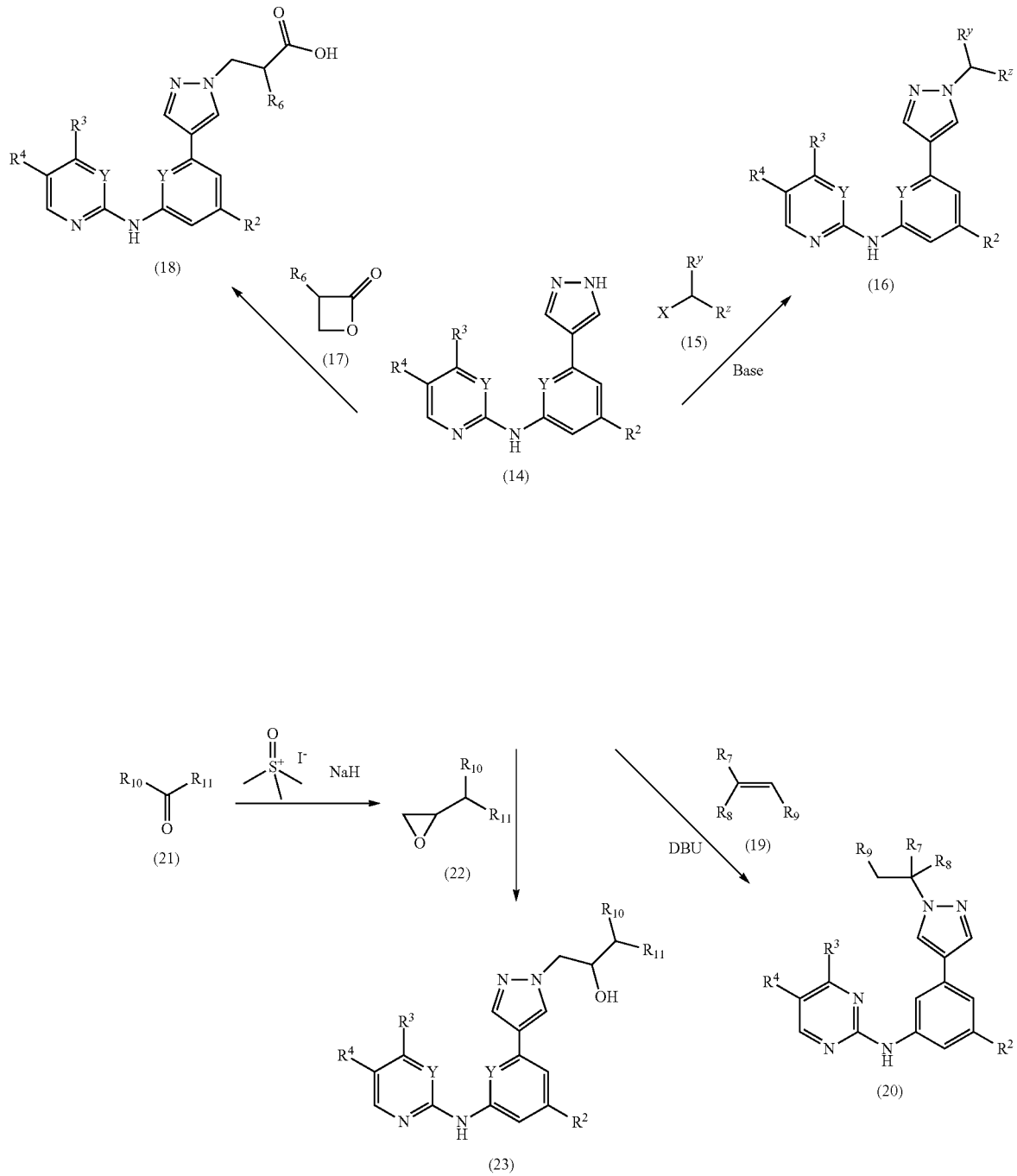

Pyrazoles (14) are reacted in several ways. Compounds of formula (16) are prepared by reaction of pyrazoles (14) with alkyl halides (15) in the presence of base. Reaction of pyrazoles 14 with β-lactones (17) yields compound (18) while reaction of (14) with epoxides (22), commercially available or prepared from the corresponding ketone (21), yields compounds (23). Alternatively, pyrazoles 14 are reacted with alkenes (19) to afford compounds (20).

SCHEME 4

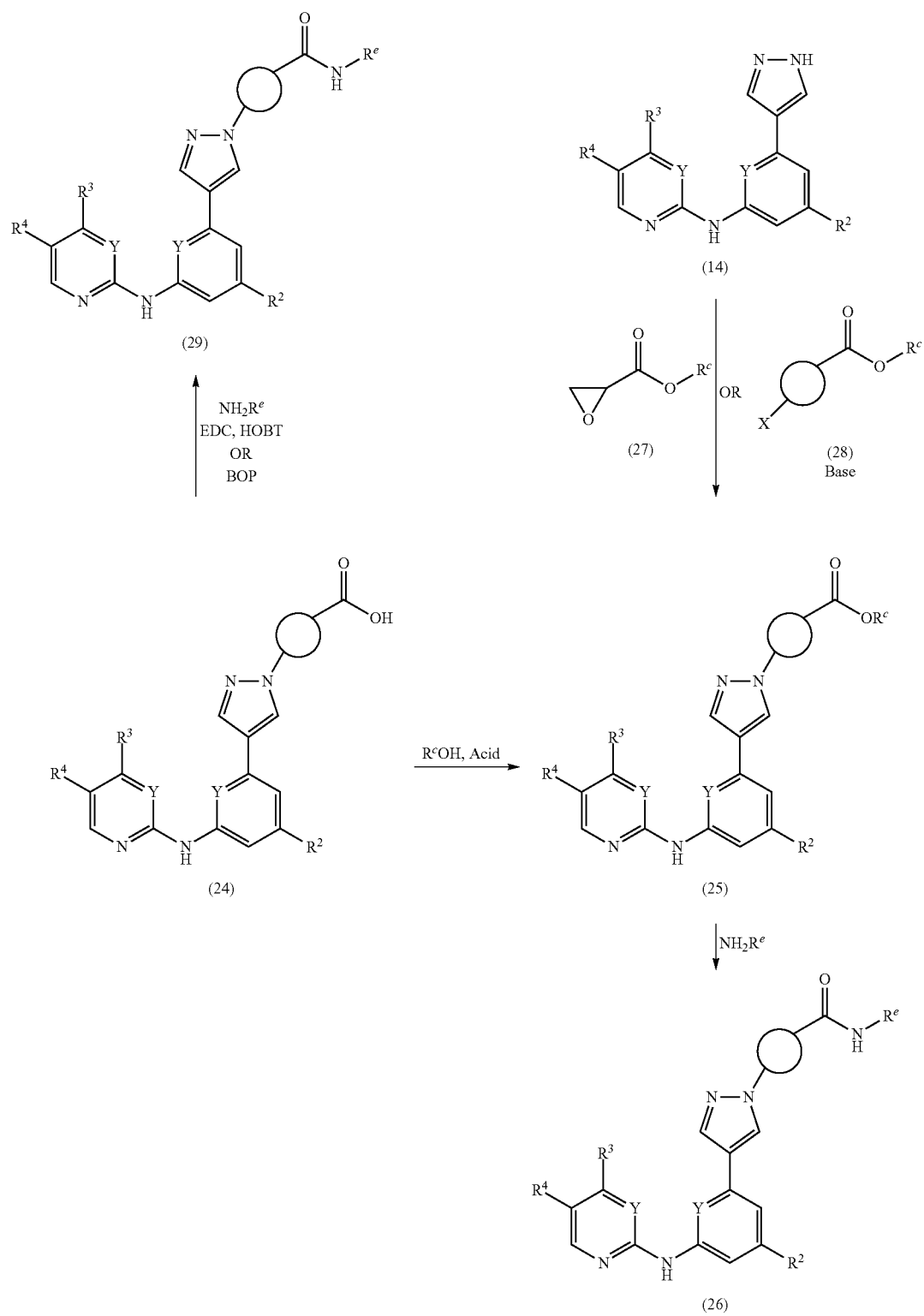

Carboxylic acids (24) are converted to the esters (25) in the presence of an alcohol and acid. Subsequently, esters (25) react with a commercially available amine to afford amide (26). Esters (25) are also prepared by reaction of pyrazole (14) with an ester-substituted-epoxide (27) or ester-substituted-alkyl halide (28). Carboxylic acid (24) can be directly converted to the amide (29) by EDC or BOP coupling with commercially available amines.

SCHEME 5
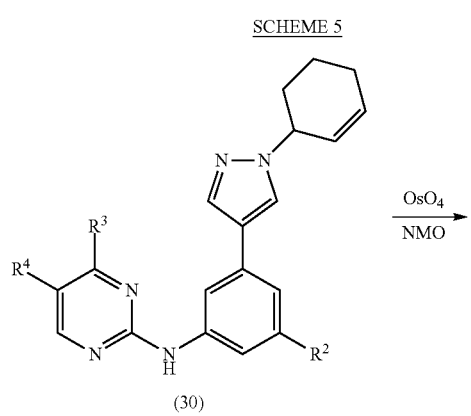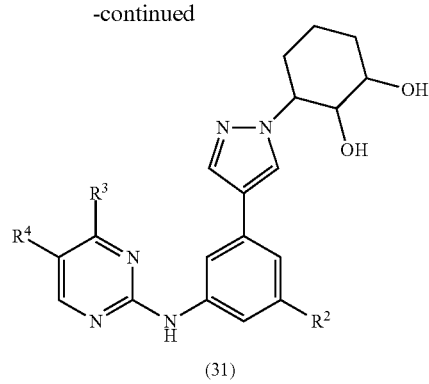
Dihydroxylation of the olefins (30) provides diols 31.
SCHEME 6
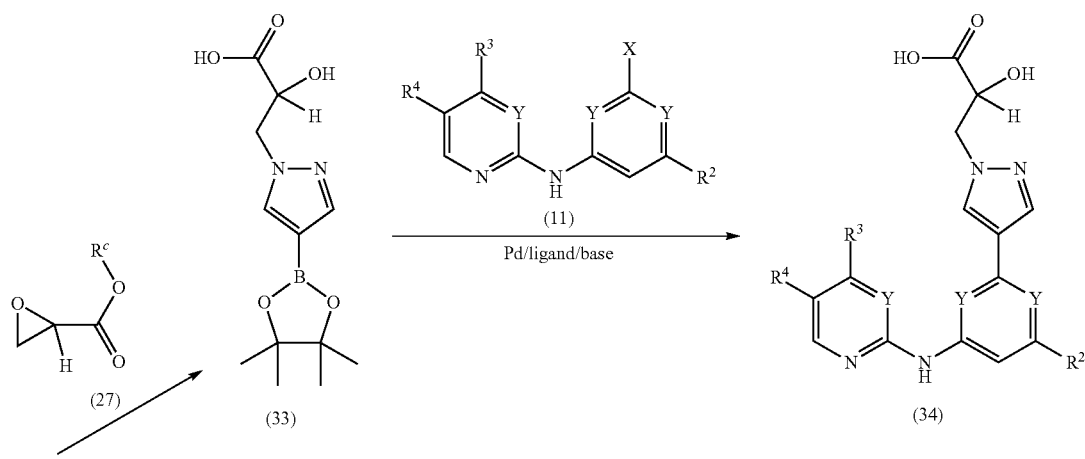
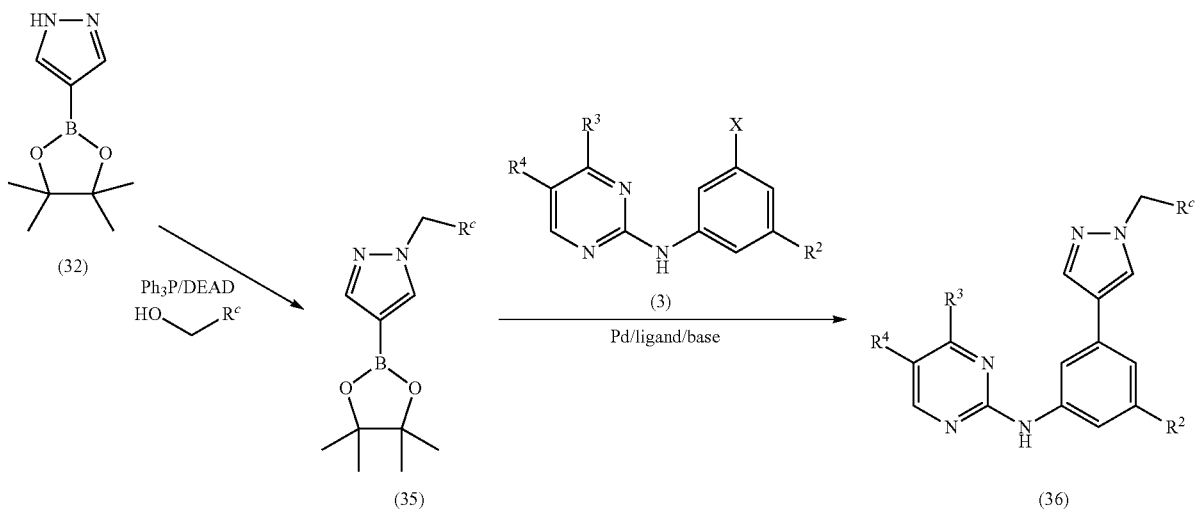

Boronic ester-substituted-pyrazoles (32) are alkylated by reaction with epoxides (27) or by Mitsonobu reaction with commercially available alcohols. Boronic esters (33) and (35) subsequently undergo Suzuki reaction to afford compounds (34) and (36), respectively.

SCHEME 7

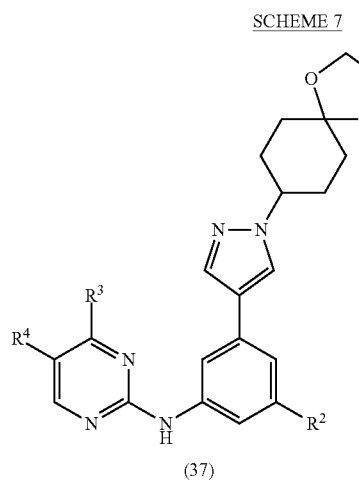

(37)

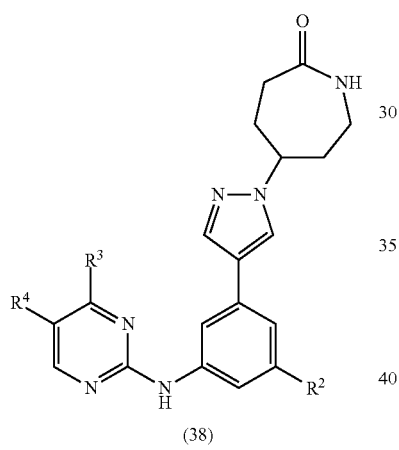

(38)

Compounds (38) are prepared by azido-Schmidt reaction of (37).

SCHEME 8

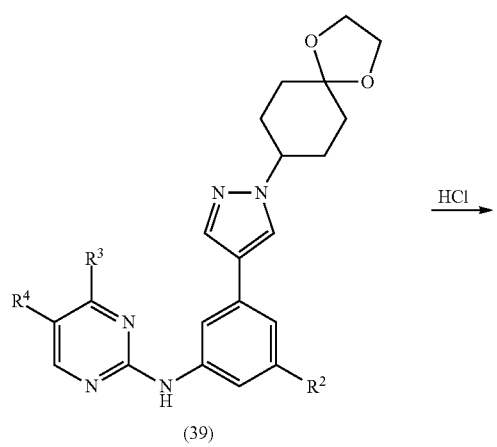

(39)

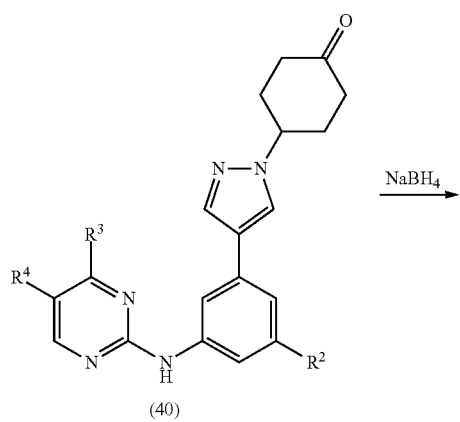

(40)

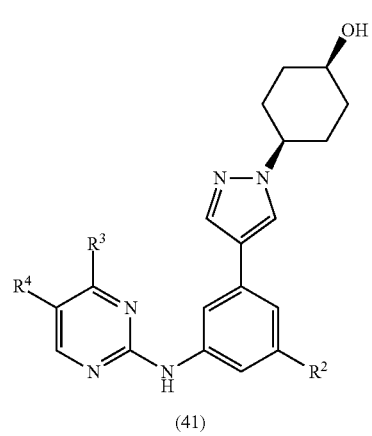

(41)

Acid deprotection of ketals (39), followed by NaBH$_4$ reduction of ketones (40) affords alcohols (41).

SCHEME 9

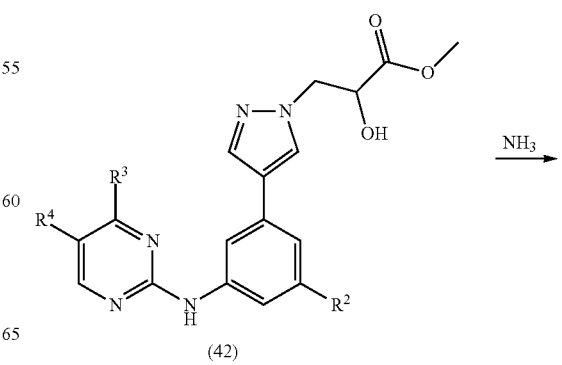

(42)

Compounds (44) are prepared by reaction of (42) with ammonia to afford amide (43) and subsequent S$_N$Ar reaction with chloropyrimidine (1).

Compounds (46) are prepared by treating amines (45) with potassium cyanate.

Compounds of formula (49) are prepared by S$_N$Ar reaction with aryl bromides (47) and substituted pyrazoles (48), followed by base hydrolysis.

71
-continued
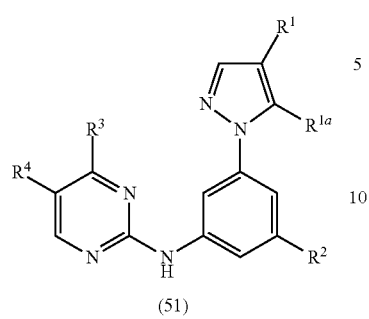
(51)
Compounds of formula (51) are prepared by a Cu promoted coupling with aryl bromides (50) and substituted pyrazoles (48), followed by base hydrolysis.
SCHEME 13
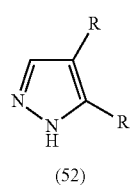
(52)
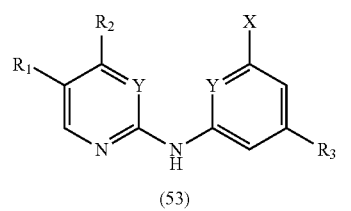
(53)
1. Cu coupling
2. Hydrolysis (optional)
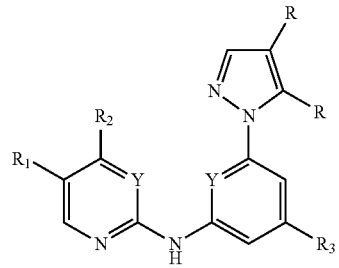
(54)
72
-continued
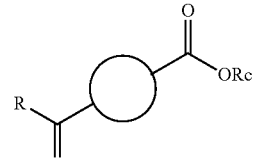
(56)
OR
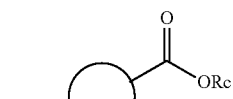
(57)
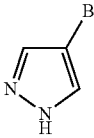
(55)
BuLi, -78 C.
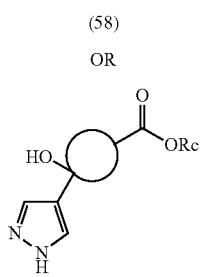
(58)
OR
(59)
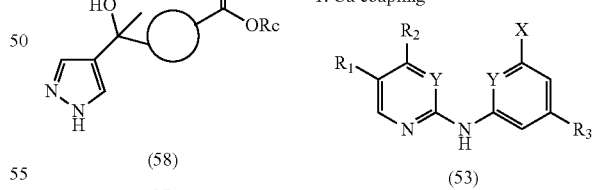
(53)
1. Cu coupling
2. Hydrolysis

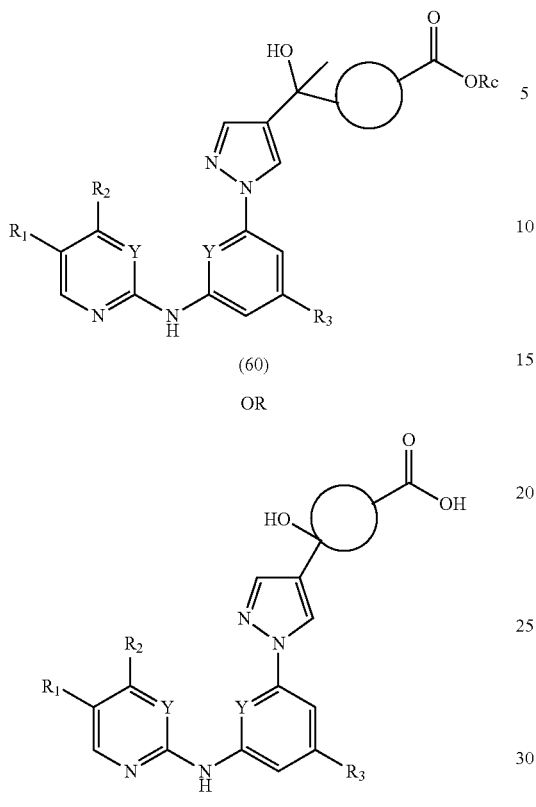
(60)
OR
(61)
Pyrazole (52) can undergo Cu coupling with an aryl halide (53) to afford substituted pyrazole (54). In a more specific fashion, bromopyrazole (55) can react with ketones (56) or (57) to afford a substituted pyrazole (58) or (59) which can undergo Cu coupling with aryl halide (53). Hydrolysis of the ester moiety affords (60) or (61).
SCHEME 14
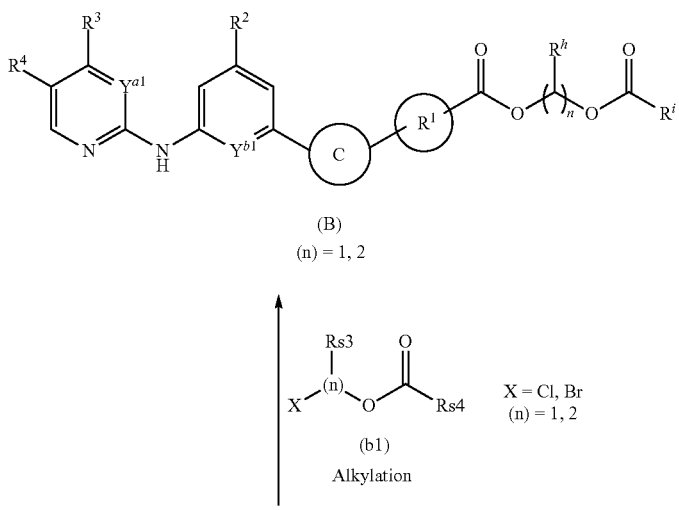

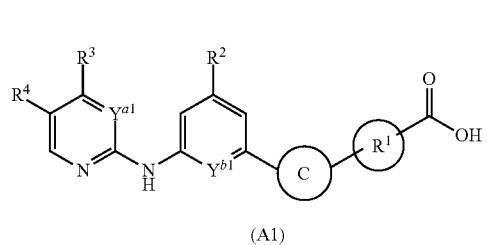

(A1)

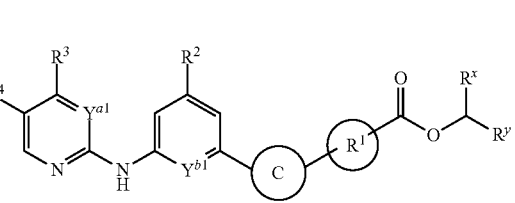

(A)

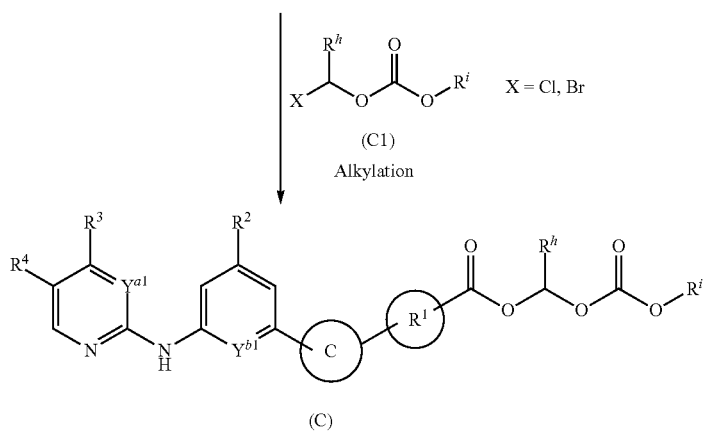

(C)

As shown in Scheme 14, compounds of structural subtype (A) are prepared from compounds of structural type (A1) (where substituent $R^1$ contains a carboxylic acid) by a Mitsonobu reaction with various primary and secondary alcohols, $R^xR^yCHOH$. Compounds of structural subtype (B) are prepared by the alkylation of compounds of structural type (A1) (where $R^1$ contains a carboxylic acid) by alkyl halides of formula (B1). Compounds of structural subtype (C) are prepared by the alkylation of compounds of structural type (A1, where $R^1$ contains a carboxylic acid) by alkyl halides of formula (C1). Note: Ring C as depicted in Schemes 14 and 15 represent the various pyrazolyl isomers and $R^1$ represents those $R^1$ substituents capable of bearing a carboxylic acid group.

SCHEME 15

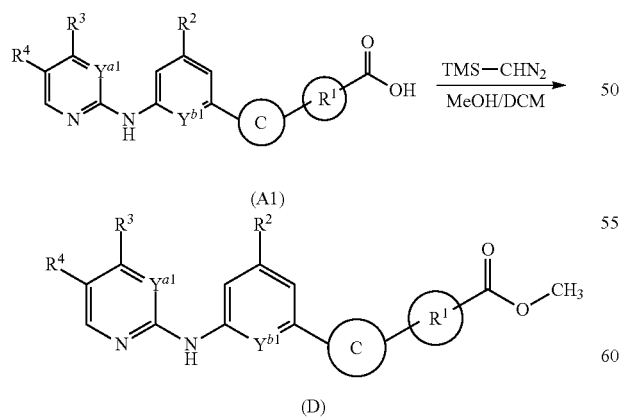

As shown in Scheme 15, compounds of structural subtype (D) are prepared by the reaction of the carboxylic acid (A1) with trimethylsilyldiazomethane and methanol.

SCHEME 16

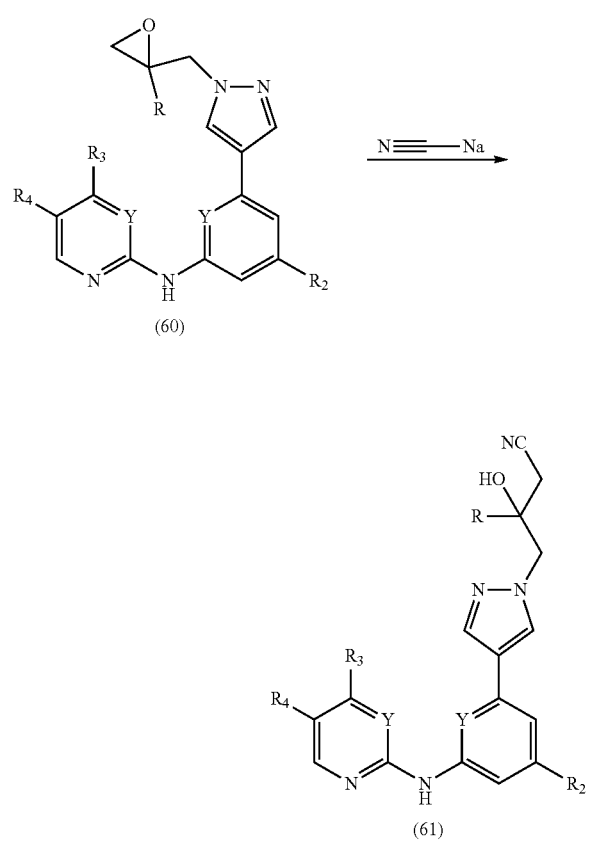

As shown in Scheme 16, epoxide (60) can react with sodium cyanide to afford aryl hydroxy nitrile (61).

SCHEME 17

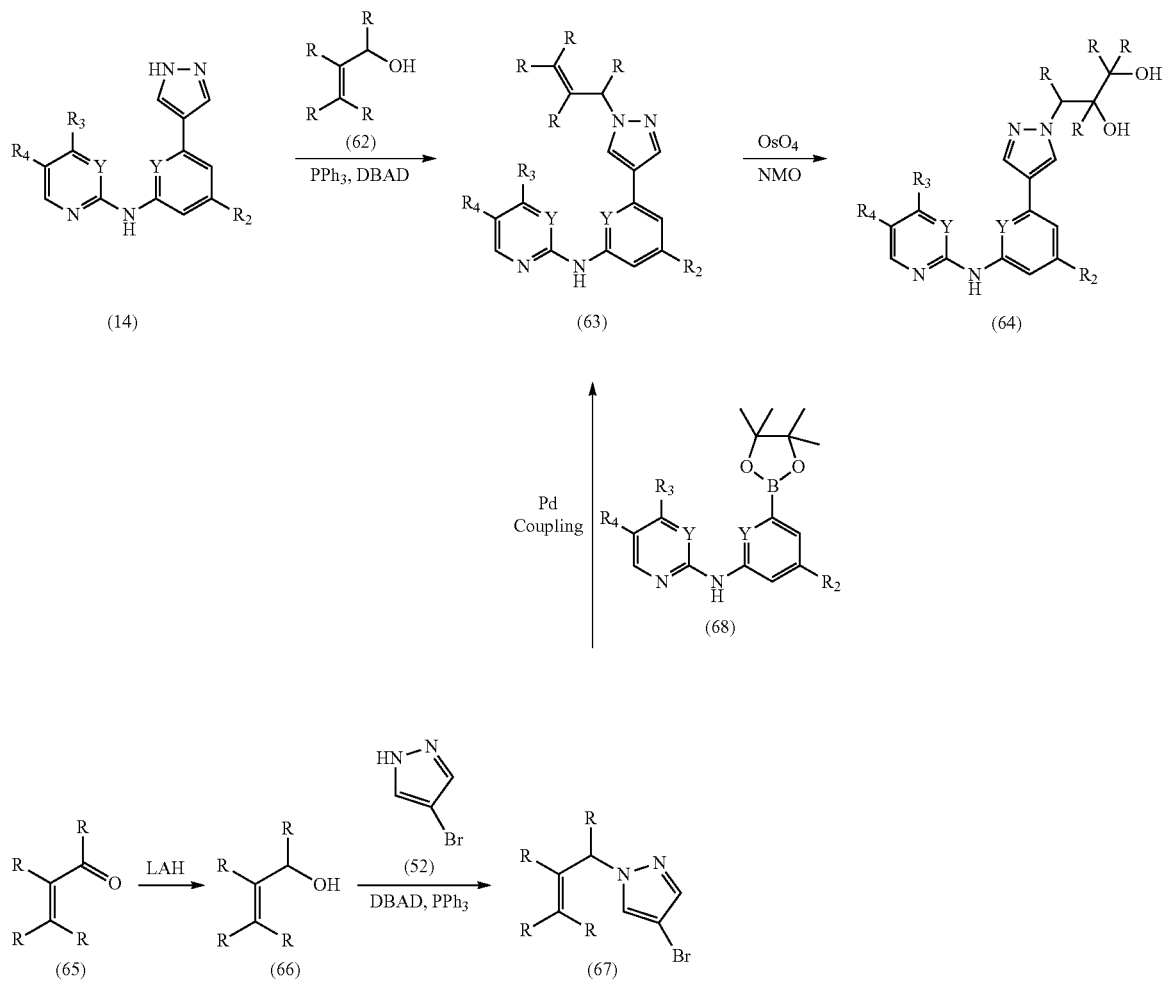

A shown in Scheme 17, Mitsonobu-type reaction of pyrazole (14) with alcohol (62), followed by dihydroxylation affords diol (64). Alternatively, reduction of ketone (65) with LiAlH$_4$ affords alcohol (66) which can undergo a Mitsonobu-type reaction with bromopyrazole (52). A palladium-catalyzed coupling of bromide (67) and boronic ester (68), followed by dihydroxylation also affords (64).

SCHEME 18

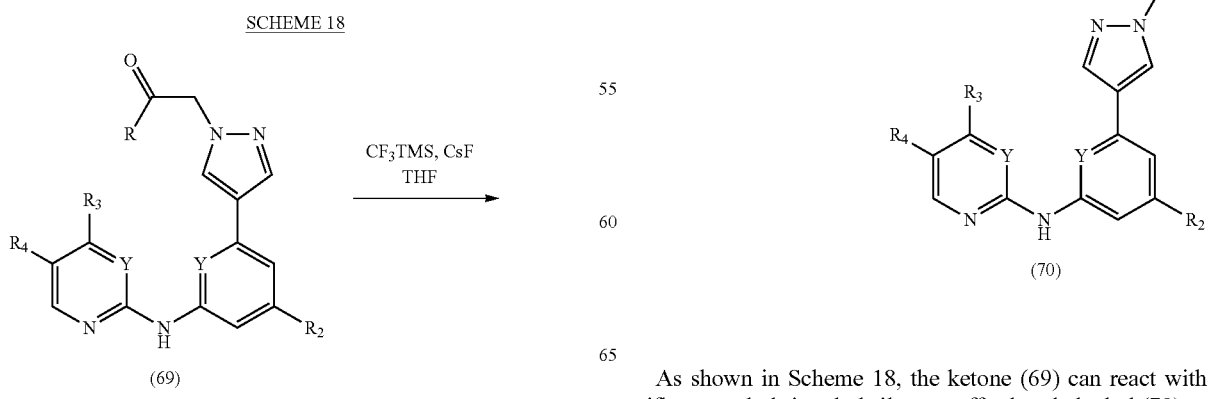

As shown in Scheme 18, the ketone (69) can react with trifluoromethyltrimethyl silane to afford aryl alcohol (70).

SCHEME 19
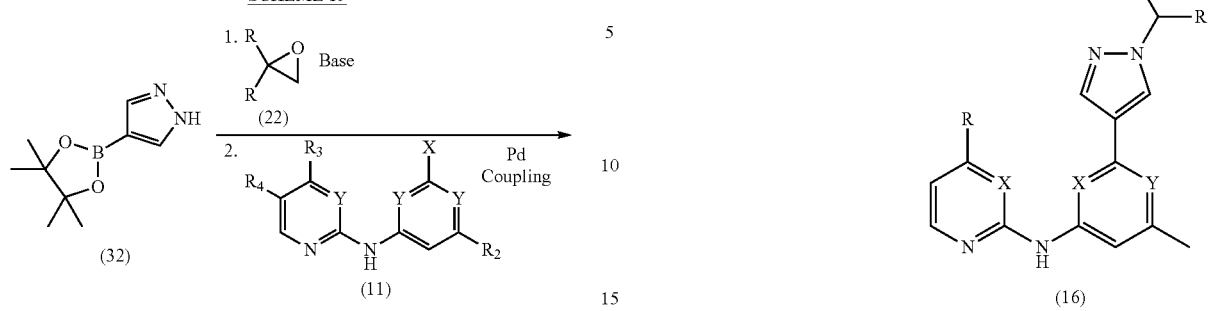
As shown in Scheme 19, reaction of the epoxide (22) with pyrazole (32), directly followed by palladium-catalyzed coupling with aryl halide (11) affords compound (16).
SCHEME 20
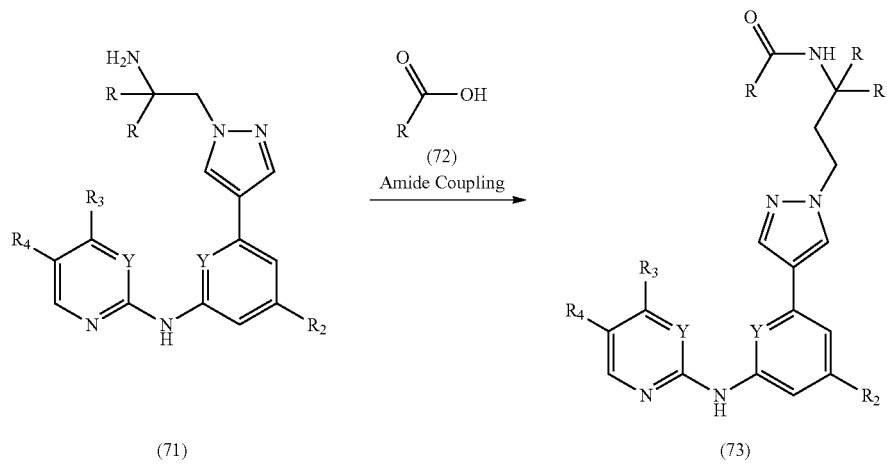
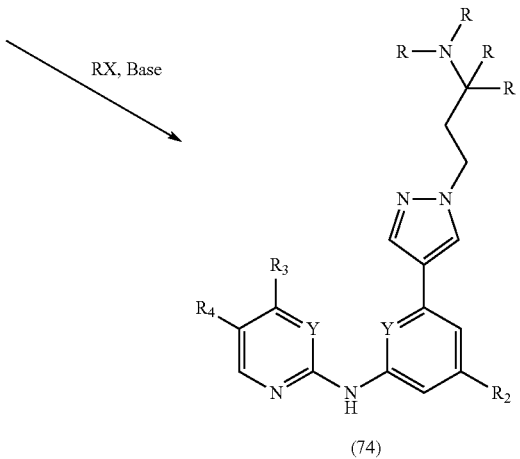
As shown in Scheme 20, amine (71) can undergo an amide coupling to afford compound (73). Amine (71) can also be alkylated to afford compound (74).

SCHEME 21

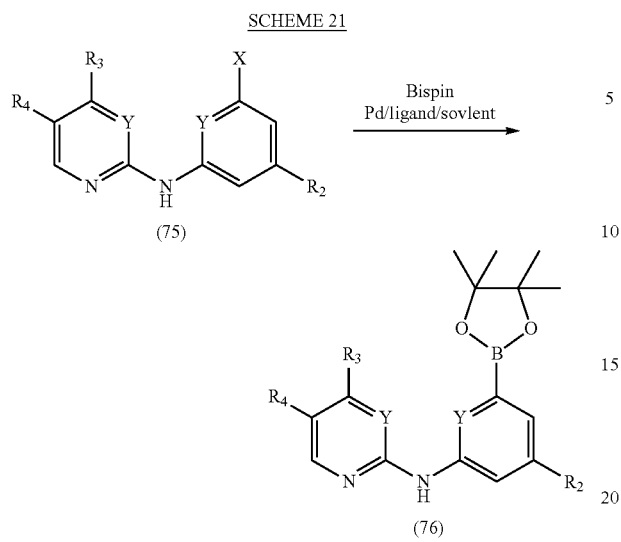

As shown in Scheme 21, reaction of aryl halides (75) with bispin affords boronic esters (76).

Compounds of Formula I can be prepared according to the procedures described in the Schemes (above) and the Examples herein, using appropriate materials and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

EXAMPLES

Preparative Example 1

Preparation of Precursors Useful in Preparing Compounds of Formula (I) Containing Pyrimidinylaminophenyl Substructures The following representative methods in this example were used to prepare synthetic intermediates useful in preparation of final compounds which contain pyrimidinylaminophenyl substructures, and are indicated in the tables as applied.

Preparative Example 1.1

N-(3-bromo-5-methylphenyl)-4-(trifluoromethyl)pyrimidin-2-amine

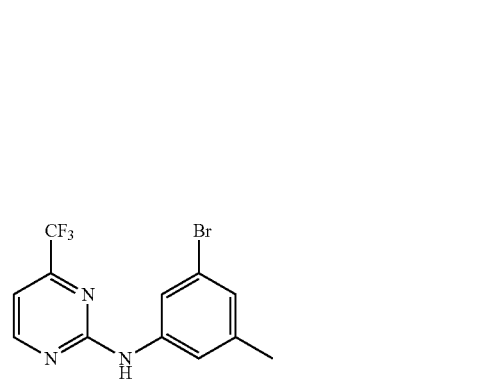 [SMILES: Cc1cc(Br)cc(Nc2nccc(C(F)(F)F)n2)c1]

2-Chloro-4-(trifluoromethyl)pyrimidine (182 g, 995 mmol) and methanesulfonic acid (97.5 g, 1.02 mol) were added sequentially to a solution of 3-bromo-5-methylaniline (162.5 g, 874 mmol) in 1,4-dioxane (2 L). The resulting solution was heated to reflux overnight then cooled and concentrated under reduced pressure. The residue was diluted with water (2 L), adjusted to pH 7-8 with aqueous sodium bicarbonate solution and extracted with EtOAc (2×2 L). The organic layers were combined, washed with water (2×2 L), dried over anhydrous sodium sulfate and concentrated under reduced pressure to afford N-(3-bromo-5-methylphenyl)-4-(trifluoromethyl)pyrimidin-2-amine (200 g, 602 mmol, 69%) as a light yellow solid. MS ESI calcd. For $C_{11}H_8BrF_3N_4$ $[M+H]^+$ 332, 334.0. found 332, 334. $^1$H NMR (400 MHz, $CDCl_3$): δ 8.68 (d, J=4.9 Hz, 1H), 7.79 (s, 1H), 7.30 (s, 2H), 7.10-7.06 (m, 2H), 2.36 (s, 3H). Synthetic Reference: PCT Int. Appl., 2011075517; PCT Int. Appl., 2011075515.

The intermediates in the following table were prepared according to the method described for Preparative Example 1.1 or methods described in PCT publication No. WO2011/075517. $^1$H NMR data is provided when $[M+H]^+$ was not available.

| Prep. Ex. | Structure | Chemical Name | $[M + H]^+$ Calc'd | $[M + H]^+$ Observed |
|---|---|---|---|---|
| 1.2 | 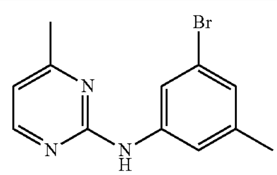 [SMILES: Cc1cc(Br)cc(Nc2nccc(C)n2)c1] | N-(3-bromo-5-methylphenyl)-4-methylpyrimidin-2-amine | 278 | 278 |

| Prep. Ex. | Structure | Chemical Name | [M + H]+ Calc'd | [M + H]+ Observed |
|---|---|---|---|---|
| 1.3 | 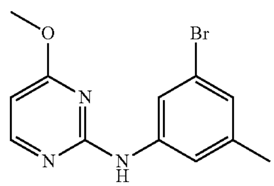 [SMILES: COc1ccnc(Nc2cc(C)cc(Br)c2)n1] | N-(3-bromo-5-methylphenyl)-4-methoxypyrimidin-2-amine | 294 | 294 |
| 1.4 | 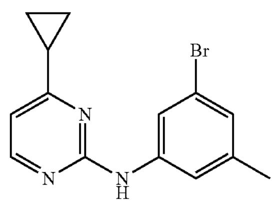 [SMILES: Cc1cc(Br)cc(Nc2nccc(C3CC3)n2)c1] | N-(3-bromo-5-methylphenyl)-4-cyclopropylpyrimidin-2-amine | 304 | 304 |
| 1.5 | 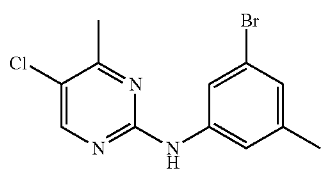 [SMILES: Cc1cc(Br)cc(Nc2ncc(Cl)c(C)n2)c1] | N-(3-bromo-5-methylphenyl)-5-chloro-4-methylpyrimidin-2-amine | 312 | 312, 314 |
| 1.6 | 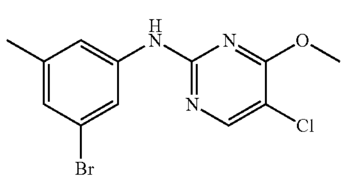 | N-(3-bromo-5-methylphenyl)-5-chloro-4-methoxypyrimidin-2-amine | 328 | $^1$H NMR (600 MHz, DMSO-d$^6$) δ 9.81 (s, 1H), 8.28 (s, 1H), 7.84 (s, 1H), 7.46 (s, 1H), 6.93 (s, 1H), 3.97 (s, 3H), 2.22 (s, 3H). |
| 1.7 | 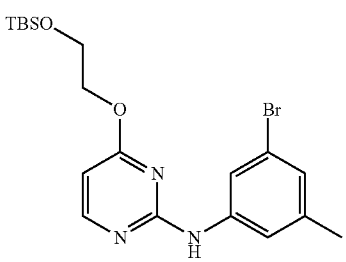 [SMILES: Cc1cc(Br)cc(Nc2nccc(OCCO[Si](C)(C)C(C)(C)C)n2)c1] | N-(3-bromo-5-methylphenyl)-4-(2-{[tert-butyl(dimethyl)silyl]oxy}ethoxy)pyrimidin-2-amine-methane (1:2) | 440 | 440 |
| 1.8 | 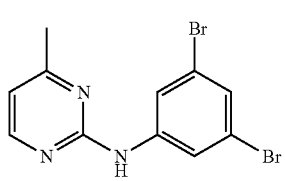 [SMILES: Cc1ccnc(Nc2cc(Br)cc(Br)c2)n1] | N-(3,5-dibromophenyl)-4-methylpyrimidin-2-amine | 343 | |

Preparative Example 1.9

N-(3-bromo-5-cyclopropylphenyl)-4-methylpyrimidin-2-amine

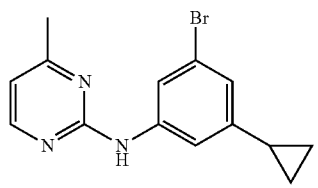 [SMILES: Cc1ccnc(Nc2cc(Br)cc(C3CC3)c2)n1]

N-(3,5-bibromophenyl)-4-methylpyrimidin-2-amine (3.6 g, 10.5 mmol) and PdCl2(dppf)-CH$_2$Cl$_2$ adduct (0.69 g, 0.84 mmol) were added to a solution of dioxane (40 mL) and sodium carbonatel (10.50 mL, 20.99 mmol) followed by cyclopropyl boronic acid (1.04 g, 12.07 mmol). A condenser was placed on top and the flask with evacuated and purged with Argon gas then the reaction mixture was heated to 112° C. overnight. The reaction mixture was cooled, diluted with EtOAc (100 mL), saturated sodium bicarbonate (30 mL) and the layers were separated. The organic layer was washed with brine, dried over anhydrous sodium sulfate and concentrated under reduced pressure. The residue was purified by reverse phase HPLC (ACN/water with 0.1% TFA modifier). The desired fractions were diluted with brine and saturated sodium bicarbonate, extracted with EtOAc. The organic layer was dried over anhydrous sodium sulfate and concentrated to afford N-(3-bromo-5-cyclopropylphenyl)-4-methylpyrimidin-2-amine. MS ESI calc'd for $C_{14}H_{14}BrN_3$ [M+H]$^+$ 304. found 304.

Preparative Example 1.10

N-(3-bromo-5-{[4-(trifluoromethyl)pyrimidin-2-yl]amino}phenyl)acetamide

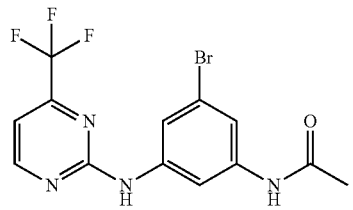 [SMILES: CC(=O)Nc1cc(Br)cc(Nc2nccc(C(F)(F)F)n2)c1]

Step 1:

pTsOH (2.98 g, 15.67 mmol). was added to a solution of 3-bromo-5-nitroaniline (3.4 g, 15.7 mmol) and 2-chloro-4-(trifluoromethyl)pyrimidine) (2.27 mL, 18.80 mmol) in dioxane (78 ml) at room temperature, under nitrogen. The mixture became heterogeneous instantly and upon heating, a solution was obtained. The mixture was stirred at 100° C. for 18 hours then cooled to room temperature and concentrated under reduced pressure. Saturated sodium bicarbonate and dichloromethane were added, the organic phase was recovered using a phase separator and then concentrated under reduced pressure. The residue was washed in hexanes/ether and filtered to afford N-(3-bromo-5-nitrophenyl)-4-(trifluoromethyl)pyrimidin-2-amine.

Step 2:

N-(3-Bromo-5-nitrophenyl)-4-(trifluoromethyl)pyrimidin-2-amine (4.76 g, 13.11 mmol) was dissolved in ethanol (131 ml) and saturated solution of NH$_4$Cl (1 mL) was added followed by Fe (3.66 g, 65.5 mmol). The reaction mixture was stirred at 80° C. for 30 minutes then cooled to room temperature. The solution was filtered through a short pad of silica gel and eluted with EtOAc. The phase were separated, the organics were dried, filtered, concentrated under reduced pressure to afford 5-bromo-N-[4-(trifluoromethyl)pyrimidin-2-yl]benzene-1,3-diamine as a beige powder.

Step 3:

5-Bromo-N-[4-(trifluoromethyl)pyrimidin-2-yl]benzene-1,3-diamine (1.06 g, 3.19 mmol) was dissolved in dichloromethane (15.9 ml) and pyridine (0.28 ml, 3.51 mmol) was added. The solution was cooled to 0° C. and then, acetyl chloride (0.23 ml, 3.19 mmol) was added drop wise. The reaction mixture was stirred at 0° C. for 1 hour. Water and dichloromethane were added and the organic phase was separated, dried and concentrated under reduced pressure to afford N-(3-bromo-5-{[4-(trifluoromethyl)pyrimidin-2-yl]amino}phenyl)acetamide as a beige powder. $^1$H NMR (400 MHz, Acetone-d$_6$) δ 9.37 (s, 1H), 9.32 (s, 1H), 8.83 (d, J=6 Hz, 1H), 7.97 (s, 1H), 7.95 (s, 1H), 7.74 (s, 1H), 7.27 (d, J=6 Hz, 1H), 2.10 (s, 3H).

Preparative Example 1.11

5-Fluoro-4-methoxy-N-[3-methyl-5-(4,4,5,5-tetramethyl-1,3,2-dioxaborolan-2-yl)phenyl]pyrimidin-2-amine

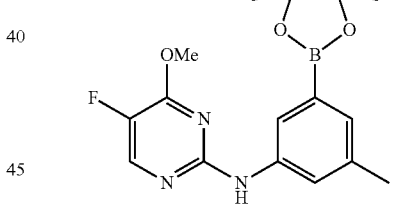

Methanesulfonic acid (0.13 mL, 1.97 mmol) was added to a solution of 2-chloro-5-fluoro-4-methoxypyrimidine (0.32 g, 1.97 mmol) and 3-methyl-5-(4,4,5,5-tetramethyl-1,3,2-dioxaborolan-2-yl)aniline (0.40 g, 1.72 mmol) in dioxane (17 mL). The reaction mixture was heated at 100° C. overnight. The reaction was then cooled to room temperature, diluted with EtOAc, washed with water, dried over magnesium sulfate, filtered and concentrated under reduced pressure. The residue was purified by column chromatography on silica gel to afford 5-fluoro-4-methoxy-N-[3-methyl-5-(4,4,5,5-tetramethyl-1,3,2-dioxaborolan-2-yl)phenyl]-pyrimidin-2-amine MS ESI calc'd for $C_{18}H_{24}BFN_3O_3$ [M+H]$^+$ 360. found 360. $^1$H NMR (500 MHz, DMSO-d$_6$) δ 9.51 (s, 1H), 8.27 (d, J=3.2, 1H), 8.00 (s, 1H), 7.57 (s, 1H), 7.07 (s, 1H), 4.01 (s, 3H), 2.25 (s, 3H), 1.26 (s, 12H).

The intermediates in the following table were prepared according to the method described for Preparative Example 1.11, or according to methods described in U.S. Patent Application Publication No. 2012-0277192 A1.

| Prep. Ex. | Structure | Chemical Name | Exact Mass [M + H]+ | [M + H]+ Found |
|---|---|---|---|---|
| 1.12 | 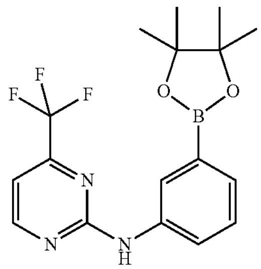 [SMILES: CC1(C)OB(c2cccc(Nc3nccc(C(F)(F)F)n3)c2)OC1(C)C] | N-[3-(4,4,5,5-tetramethyl-1,3,2-dioxaborolan-2-yl)phenyl]-4-(trifluoromethyl)pyrimidin-2-amine | 366 | 366 |
| 1.13 | 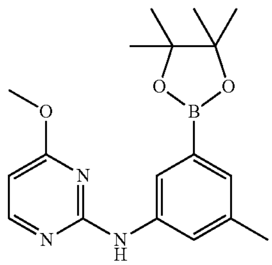 [SMILES: COc1ccnc(Nc2cc(C)cc(B3OC(C)(C)C(C)(C)O3)c2)n1] | 4-methoxy-N-[3-methyl-5-(4,4,5,5-tetramethyl-1,3,2-dioxaborolan-2-yl)phenyl]pyrimidin-2-amine | 342 | 342 |
| 1.14 | 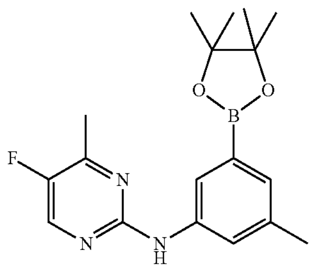 [SMILES: Cc1cc(Nc2ncc(F)c(C)n2)cc(B2OC(C)(C)C(C)(C)O2)c1] | 5-fluoro-4-methyl-N-[3-methyl-5-(4,4,5,5-tetramethyl-1,3,2-dioxaborolan-2-yl)phenyl]pyrimidin-2-amine | 344 | 344 |
| 1.15 | 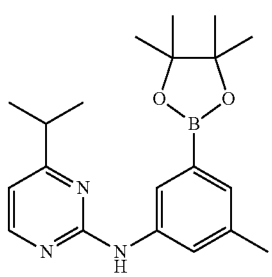 [SMILES: Cc1cc(Nc2nccc(C(C)C)n2)cc(B2OC(C)(C)C(C)(C)O2)c1] | 4-(1-methylethyl)-N-[3-methyl-5-(4,4,5,5-tetramethyl-1,3,2-dioxaborolan-2-yl)phenyl]pyrimidin-2-amine | 354 | 354 |
| 1.16 | 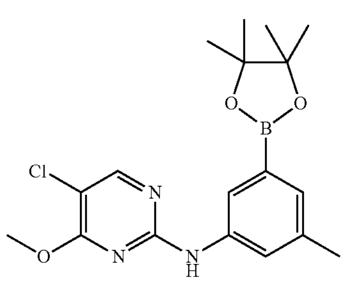 | 5-chloro-4-methoxy-N-[3-methyl-5-(4,4,5,5-tetramethyl-1,3,2-dioxaborolan-2-yl)phenyl]pyrimidin-2-amine | 376 | 376 |

-continued

| Prep. Ex. | Structure | Chemical Name | Exact Mass [M + H]+ | [M + H]+ Found |
|---|---|---|---|---|
| 1.17 | 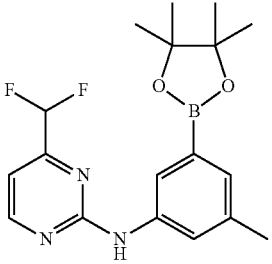 [SMILES: Cc1cc(Nc2nccc(C(F)F)n2)cc(B2OC(C)(C)C(C)(C)O2)c1] | 4-(difluoromethyl)-N-[3-methyl-5-(4,4,5,5-tetramethyl-1,3,2-dioxaborolan-2-yl)phenyl]pyrimidin-2-amine | 362 | 362 |
| 1.18 | 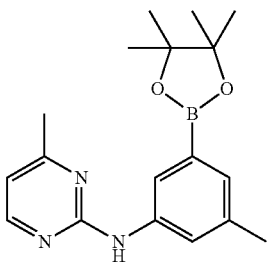 [SMILES: Cc1cc(Nc2nccc(C)n2)cc(B2OC(C)(C)C(C)(C)O2)c1] | 4-methyl-N-[3-methyl-5-(4,4,5,5-tetramethyl-1,3,2-dioxaborolan-2-yl)phenyl]pyrimidin-2-amine | 326 | 326 |
| 1.19 | 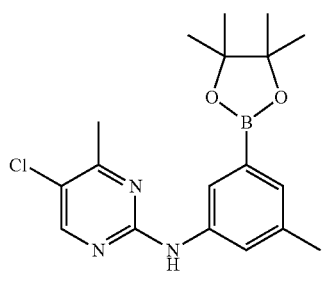 [SMILES: Cc1cc(Nc2ncc(Cl)c(C)n2)cc(B2OC(C)(C)C(C)(C)O2)c1] | 5-chloro-4-methyl-N-[3-methyl-5-(4,4,5,5-tetramethyl-1,3,2-dioxaborolan-2-yl)phenyl]pyrimidin-2-amine | 360 | 360 |
| 1.20 | 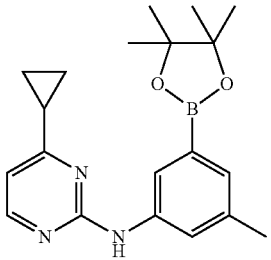 [SMILES: Cc1cc(Nc2nccc(C3CC3)n2)cc(B2OC(C)(C)C(C)(C)O2)c1] | 4-cyclopropyl-N-[3-methyl-5-(4,4,5,5-tetramethyl-1,3,2-dioxaborolan-2-yl)phenyl]pyrimidin-2-amine | 352 | 352 |
| 1.21 | 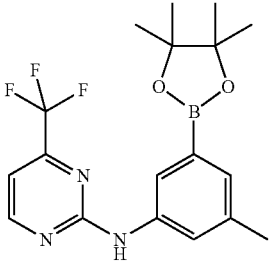 [SMILES: Cc1cc(Nc2nccc(C(F)(F)F)n2)cc(B2OC(C)(C)C(C)(C)O2)c1] | N-[3-methyl-5-(4,4,5,5-tetramethyl-1,3,2-dioxaborolan-2-yl)phenyl]-4-(trifluoromethyl)pyrimidin-2-amine | 380 | 380 |

-continued

| Prep. Ex. | Structure | Chemical Name | Exact Mass [M + H]+ | [M + H]+ Found |
|---|---|---|---|---|
| 1.22 | 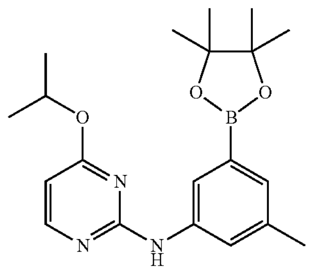 [SMILES: Cc1cc(Nc2nccc(OC(C)C)n2)cc(B2OC(C)(C)C(C)(C)O2)c1] | 4-(1-methylethoxy)-N-[3-methyl-5-(4,4,5,5-tetramethyl-1,3,2-dioxaborolan-2-yl)phenyl]pyrimidin-2-amine | 370 | 370 |
| 1.23 | 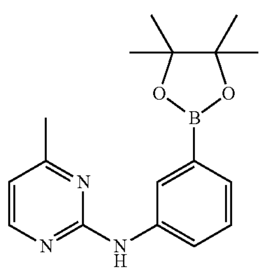 [SMILES: Cc1ccnc(Nc2cccc(B3OC(C)(C)C(C)(C)O3)c2)n1] | 4-methyl-N-[3-(4,4,5,5-tetramethyl-1,3,2-dioxaborolan-2-yl)phenyl]pyrimidin-2-amine | 312 | 312 |

Preparative Example 1.24

Methyl (2S)-3-[4-(3-{[4-(1-fluoroethyl)pyrimidin-2-yl]amino}-5-methylphenyl)-1H-pyrazol-1-yl]-2-hydroxypropanoate

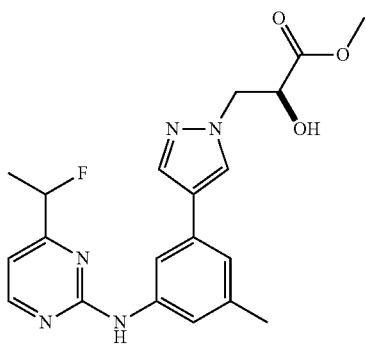 [SMILES: COC(=O)[C@@H](O)Cn1cc(-c2cc(C)cc(Nc3nccc(C(C)F)n3)c2)cn1]

2-Chloro-4-(1-fluoroethyl)pyrimidine (58 mg, 0.36 mmol) and acetic acid (0.022 mL, 0.38 mmol) were added to an oven-dried flask containing methyl (2S)-3-[4-(3-amino-5-methylphenyl)-1H-pyrazol-1-yl]-2-hydroxypropanoate (100 mg, 0.36 mmol) in dioxane (1.2 mL). The mixture was stirred for 3 hours at 120° C. then cooled to room temperature, diluted with water, and extracted with EtOAc (3×). The combined organic layers were dried over sodium sulfate, filtered and concentrated under reduced pressure. The residue was purified by column chromatography on silica gel (2 to 100% EtOAc/hexanes) to afford methyl (2S)-3-[4-(3-{[4-(1-fluoroethyl)pyrimidin-2-yl]amino}-5-methylphenyl)-1H-pyrazol-1-yl]-2-hydroxypropanoate. MS ESI calcd. for $C_{20}H_{23}FN_5O_3$ [M+H]+ 400. found 400.

The intermediates in the following table were prepared according to the method described for Preparative Example 1.24

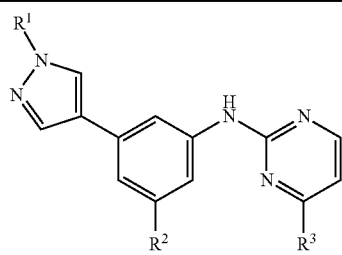

| Prep. Ex. | R¹ | R² | R³ | Chemical Name | Exact Mass [M + H]⁺ | [M + H]⁺ Found |
|---|---|---|---|---|---|---|
| 1.25 | ![structure with HO and methyl ester] | CH₃ | t-butyl | Methyl (2S)-3-(4-{3-[(4-tert-butylpyrimidin-2-yl)amino]-5-methylphenyl}-1H-pyrazol-1-yl)-2-hydroxypropanoate | 410 | 410 |
| 1.26 | ![structure with HO and methyl ester] | CH₃ | i-propyl | Methyl (2S)-2-hydroxy-3-[4-(3-methyl-5-{[4-(propan-2-yl)pyrimidin-2-yl]amino}phenyl)-1H-pyrazol-1-yl]propanoate | 396 | 396 |
| 1.27 | ![structure with HO and methyl ester] | CH₃ | CHF₂ | Methyl (2S)-3-[4-(3-{[4-(difluoromethyl)pyrimidin-2-yl]amino}-5-methylphenyl)-1H-pyrazol-1-yl]-2-hydroxypropanoate | 404 | 404 |

Preparative Example 1.28

4-(2-{[tert-Butyl(dimethyl)silyl]oxy}ethoxy)-2-chloropyrimidine

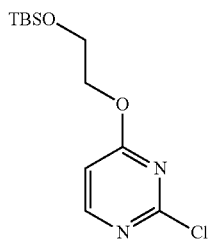 [SMILES: CC(C)(C)[Si](C)(C)OCCOc1ccnc(Cl)n1]

Step 1:

mCPBA (3.92 g, 17.5 mmol) was added to a stirred mixture of 2-chloro-4-(methylsulfanyl)pyrimidine (1.5 g, 7.0 mmol) in dichloromethane (35.0 mL) at 0° C. The reaction mixture was warmed to room temperature, stirred for 1.5 h and then diluted with aqueous sodium thiosulfate. The solution was stirred for 10 min then saturated sodium bicarbonate was added and the mixture was extracted with dichloromethane. The combined organics were washed with brine, dried over sodium sulfate, filtered, and concentrated under reduced pressure. The residue was purified by column chromatography on silica gel (0 to 100% EtOAc/hexanes) to afford 2-chloro-4-(methylsulfonyl)pyrimidine as a white solid. MS ESI calcd. for $C_5H_6ClN_2O_2S$ [M+H]⁺ 193. found 193.

Step 2:

Potassium carbonate (0.89 g, 6.45 mmol) was added at room temperature to an oven-dried, nitrogen cooled flask containing a suspension of ethylene glycol (1.3 mL, 23.4 mmol) in DMF (29 mL) and the mixture was then stirred for 15 minutes. 2-Chloro-4-(methylsulfonyl)pyrimidine (1.13 g, 5.86 mmol) was then added. The solution was stirred for 1.5 h at room temperature, then diluted with EtOAc (30 mL) and washed with 1:1 water:brine (3×50 mL). The organic extracts were dried over sodium sulfate, filtered, concentrated under reduced pressure. The residue was purified by column chromatography on silica gel (0 to 100% EtOAc/hexanes) to afford 2-[(2-chloropyrimidin-4-yl)oxy]ethanol as a pale yellow solid. MS ESI calcd. for $C_6H_8ClN_2O_2$ [M+H]⁺ 175. found 175.

Step 3:

2-[(2-Chloropyrimidin-4-yl)oxy]ethanol (416 mg, 2.38 mmol) in dichloromethane (9.5 mL) at 0° C. was added to an oven-dried, nitrogen cooled vial containing imidazole (389 mg, 5.72 mmol). The solution was stirred for 10 minutes. TBS-Cl (424 mg, 2.81 mmol) was added and the reaction mixture was stirred at room temperature for 2 h then, diluted with water. The organic layer was separated, dried over sodium sulfate, filtered, and concentrated under reduced pressure to afford 4-(2-{[tert-butyl(dimethyl)silyl]oxy}ethoxy)-2-chloropyrimidine as a clear, yellow oil. MS ESI calcd. for $C_{12}H_{22}ClN_2O_2Si$ [M+H]⁺ 289. found 289. ¹H NMR (500

MHz, CDCl₃) δ 8.28 (d, J=5.7, 1H), 6.67 (d, J=5.7, 1H), 4.62-4.30 (m, 2H), 4.02-3.87 (m, 2H), 0.87 (s, 9H), 0.06 (s, 6H).

Preparative Example 1.29

Methyl (2S)-3-[4-(3-amino-5-methylphenyl)-1H-pyrazol-1-yl]-2-hydroxypropanoate

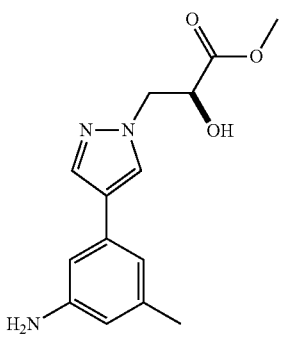 [SMILES: COC(=O)[C@@H](O)Cn1cc(-c2cc(C)cc(N)c2)cn1]

Butyl di-1-adamantylphosphine (1.07 g, 2.98 mmol), Pd(OAc)₂ (0.33 mg, 1.49 mmol), dioxane (12 mL) and water (2.4 mL) were added to an oven-dried flask and stirred for 10 minutes. 3-bromo-5-methylaniline (1.58 g, 8.51 mmol), methyl (2S)-2-hydroxy-3-[4-(4,4,5,5-tetramethyl-1,3,2-dioxaborolan-2-yl)-1H-pyrazol-1-yl]propanoate (3.5 g, 10.64 mmol), and potassium fluoride (1.24 g, 21.3 mmol) were added followed by additional dioxane (12 mL). The mixture was heated to 95° C. overnight then cooled to room temperature, filtered and diluted with water. The mixture was extracted with EtOAc (3×) and the combined organic layers were washed with brine, dried over sodium sulfate, filtered, and concentrated under reduced pressure. The residue was purified by column chromatography on silica gel (0 to 80% EtOAc/hexanes) to afford methyl (2S)-3-[4-(3-amino-5-methylphenyl)-1H-pyrazol-1-yl]-2-hydroxypropanoate. MS ESI calcd. for $C_{14}H_{18}N_3O_3$ [M+H]⁺ 276. found 276. ¹H NMR (500 MHz, DMSO-d₆) δ 7.88 (s, 1H), 7.67 (s, 1H), 6.51 (s, 2H), 6.21 (s, 1H), 5.90 (d, J=6.1 Hz, 1H), 4.93 (s, 2H), 4.43 (tt, J=4.6 Hz, 9.2 Hz, 1H), 4.36 (d, J=4.2 Hz, 1H), 4.27-4.21 (m, 1H), 3.63 (s, 3H), 2.14 (s, 3H).

The intermediates in the following table were prepared according to the method described for Example 1.29.

| Prep. Ex. | R¹ | R² | R³ | Chemical Name | Exact Mass [M + H]+ | [M + H]+ Found |
|---|---|---|---|---|---|---|
| 1.30 | (S)-CH₂-CH(OH)-C(O)OCH₃ | CH₃ | CH₃ | Methyl (2S)-2-hydroxy-3-(4-{3-methyl-5-[(4-methylpyrimidin-2-yl)amino]phenyl}-1H-pyrazol-1-yl)propanoate | 368 | 368 |
| 1.31 | (S)-CH₂-CH(OH)-C(O)OCH₃ | CH₃ | OCH₃ | Methyl (2S)-2-hydroxy-3-(4-{3-methoxypyrimidin-2-yl)amino]-5-methylphenyl}-1H-pyrazol-1-yl)propanoate | 384 | 384 |
| 1.32 | (S)-CH₂-CH(OH)-C(O)OCH₃ | CH₃ | c-propyl | Methyl (2S)-3-(4-{3-[(4-cyclopropyl-pyrimidin-2-yl)amino]-5-methylphenyl}-11H-pyrazol-1-yl)-propanoate | 394 | 394 |
| 1.33 | (S)-CH₂-CH(OH)-C(O)OCH₃ | CH₃ | i-propoxyl | Methyl (2S)-2-hydroxy-3-(4-{3-[(4-isopropoxy-pyrimidin-2-yl)amino]-5-methylphen 1H-pyrazol-1-yl)-propanoate | 412 | 412 |

-continued

| Prep. Ex. | R¹ | R² | R³ | Chemical Name | Exact Mass [M + H]+ | [M + H]+ Found |
|---|---|---|---|---|---|---|
| 1.34 | (cyclohexanecarboxylate tert-butyl ester, Mixt. cis & trans) | CH₃ | OCH₂CH₂OTBS | tert-Butyl 4-[4-(3-{[4-(2-{[tert-butyl-(dimethyl)silyl]oxy}ethoxy)pyrimidin-2-yl]amino}-5-methylphenyl)-1H-pyrazol-1-yl]cyclohexanecarboxylate | 608 | 608 |
| 1.35 | (cyclohexanecarboxylate tert-butyl ester, Mixt. cis & trans) | CH₃ | CF₃ | tert-Butyl 4-[4-(3-methyl-5-{[4-(trifluoromethyl)pyrimidin-2-yl]amino}-phenyl)-1H-pyrazol-1-yl]cyclohexane-carboxylate | 502 | 502 |
| 1.36 | (2,2,4-trimethylcyclohexanecarboxylate tert-butyl ester, Racemic) | CH₃ | CF₃ | Methyl 2,2-dimethyl-4-[4-(3-methyl-5-{[4-(trifluoromethyl)pyrimidin-2-yl]amino}-phenyl)-1H-pyrazol-1-yl] cyclohexane-carboxylate | 488 | 488 |
| 1.37 | H | CH₃ | OCH₃ | 4-methoxy-N-[3-methyl-5-(1H-pyrazol-4-yl)phenyl]pyrimidin-2-amine | 282 | 282 |

Prep. Examples 1.38 and 1.39 were prepared according to the method described in Example 3.1 below. Example 1.40 was prepared according the method described in Example 4. Prep. Examples 1.41, 1.42 and 1.43 were prepared according to the method described in Example 5.1.

| Prep. Ex. | R¹ | R² | R³ | Chemical Name | Exact Mass [M + H]+ | [M + H]+ Found |
|---|---|---|---|---|---|---|
| 1.38 | (methyl butanoate chain) | CH₃ | CF₃ | Methyl 4-[4-(3-methyl-5-{[4-(trifluoromethyl)pyrimidin-2-yl]amino}-phenyl)-1H-pyrazol-1-yl]butanoate | 420 | 420 |
| 1.39 | (methyl 2,2-dimethylpropanoate) | CH₃ | CH₃ | Methyl 2-methyl-2-(4-{3-methyl-5-[(4-methylpyrimidin-2-yl)amino]phenyl}-1H-pyrazol-1-yl)propanoate | 366 | 366 |

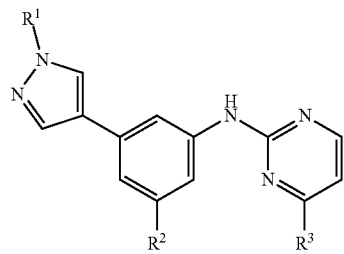

| Prep. Ex. | R¹ | R² | R³ | Chemical Name | Exact Mass [M + H]+ | [M + H]+ Found |
|---|---|---|---|---|---|---|
| 1.40 | (structure with NH2, OH, C=O) | CH₃ | CF₃ | 3-[4-(3-methyl-5-{[4-(trifluoromethyl)pyrimidin-2-yl]amino}-phenyl)-1H-pyrazol-1-yl]-L-alanine | 407 | 407 |
| 1.41 | (structure with OH, OH, C=O) | CH₃ | CF₃ | (2S)-2-hydroxy-3-[4-(3-methyl-5-{[4-(trifluoromethyl)pyrimidin-2-yl]amino}-phenyl)-1H-pyrazol-1-yl]propanoic acid | 408 | 408 |
| 1.42 | (structure, (2S, 3R or 2R, 3R)) | CH₃ | CF₃ | (2R, 3R) or (2S, 3R) 2-hydroxy-3-[4-(3-methyl-5-{[4-(trifluoromethyl)pyrimidin-2-yl]amino}-phenyl)-1H-pyrazol-1-yl]butanoic acid | 422 | 422 |
| 1.43 | (structure, Racemic (TFA salt)) | CH₃ | CF₃ | 4-{1-hydroxy-2-[4-(3-methyl-5-{[4-(trifluoromethyl)-pyrimidin-2-yl]amino}-phenyl)-1H-pyrazol-1-yl]ethyl}benzoic acid | 484 | 484 |

Preparative Example 1.44

N-(3-(1-(Cyclohex-2-en-1-yl)-1H-pyrazol-4-yl)-5-methylphenyl)-4-(difluoromethyl)pyrimidin-2-amine

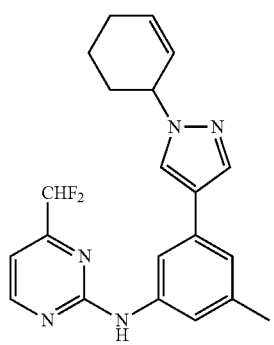 [SMILES: Cc1cc(Nc2nccc(C(F)F)n2)cc(-c2cnn(C3C=CCCC3)c2)c1]

1-(Cyclohex-2-en-1-yl)-4-(4,4,5,5-tetramethyl-1,3,2-dioxaborolan-2-yl)-1H-pyrazole (436 mg, 1.59 mmol), sodium carbonate (337 mg, 3.18 mmol), and 1,1'-Bis(diphenylphosphino)ferrocene-palladium(II)dichloride dichloromethane complex (130 mg, 0.159 mmol) were added to a solution of N-(3-bromo-5-methylphenyl)-4-(difluoromethyl)pyrimidin-2-amine (500 mg, 1.59 mmol) in dioxane (7.5 mL). The mixture was purged with nitrogen for 5 minutes and stirred at 110° C. for 18 h. The mixture was allowed to cool to room temperature, diluted with water (30 mL) and extracted with ethyl acetate (3×50 mL). The organic layer was dried over anhydrous magnesium sulfate and concentrated under reduced pressure. The residue was purified by column chromatography on silica gel (0-50% EtOAc/hexane) to afford N-(3-(1-(cyclohex-2-en-1-yl)-1H-pyrazol-4-yl)-5-methylphenyl)-4-(difluoromethyl)pyrimidin-2-amine ESI calc'd. for $C_{21}H_{22}F_2N_5$ [M+H]⁺ 382. found 382.

The intermediates in the following table were prepared according to the method described for Preparative Example 1.44.

| Prep. Ex. | Structure | Chemical Name | Exact Mass [M + H]+ | [M + H]+ Found |
|---|---|---|---|---|
| 1.45 | 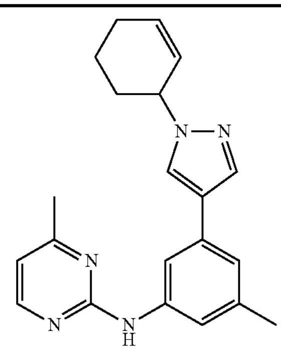 | N-(3-(1-(cyclohex-2-en-1-yl)-1H-pyrazol-4-yl)-5-methylphenyl)-4-methylpyrimidin-2-amine | 346 | 346 |

Preparative Example 1.46

2-Chloro-4-(1-fluoroethyl)pyrimidine

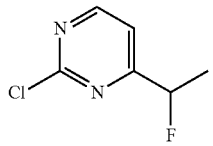

Bis(2-methoxyethyl)aminosulfur trifluoride (7.70 g, 17.4 mmol) was added drop wise to a solution of 1-(2-chloropyrimidin-4-yl)ethanol (2.30 g, 14.5 mmol) in dichloromethane (20 mL) at 0° C. and the mixture was stirred at 0° C. for 15 minutes. The mixture was diluted with dichloromethane and washed with aqueous sodium bicarbonate. The organic layers were separated, dried over anhydrous magnesium sulfate, filtered, and concentrated under reduced pressure. The residue was purified by column chromatography on silica gel (0-50% EtOAc/Hexane) to afford 2-chloro-4-(1-fluoroethyl) pyrimidine. $^1$H NMR (500 MHz, DMSO-$d_6$) δ 8.66 (d, J=5.0 Hz, 1H), 7.45 (d, J=5.0 Hz, 1H), 5.65-5.51 (m, 1H), 1.71-1.65 (m, 3H).

Preparative Example 1.47

3-Methyl-5-(1-(2-methylallyl)-1H-pyrazol-4-yl)aniline

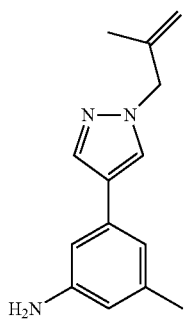 [SMILES: C=C(C)Cn1cc(-c2cc(C)cc(N)c2)cn1]

Step 1:

tert-Butyl 4-(4,4,5,5-tetramethyl-1,3,2-dioxaborolan-2-yl)-1H-pyrazole-1-carboxylate (8.17 g, 27.8 mmol), tetrakis(triphenylphosphine)palladium(0) (2.67 g, 2.31 mmol) and potassium carbonate (12.8 g, 93.0 mmol) were added to a solution of 1-bromo-3-methyl-5-nitrobenzene (5.0 g, 23.1 mmol) in dioxane (7.5 mL). The mixture was degassed with nitrogen for 5 minutes and stirred at 100° C. for 18 h. The mixture was passed through CELITE, washed with methanol and concentrated under reduced pressure. The residue was purified by column chromatography on silica gel (0-50% EtOAc/Hexane) to afford 4-(3-methyl-5-nitrophenyl)-1H-pyrazole. MS ESI calc'd. for $C_{10}H_{10}N_3O_2$ [M+H]$^+$ 204. found 204.

Step 2:

3-Bromo-2-methylprop-1-ene (4.19 g, 31.0 mmol) and cesium carbonate (13.5 g, 41.3 mmol) were added to a solution of 4-(3-methyl-5-nitrophenyl)-1H-pyrazole (4.20 g, 20.7 mmol) in dimethylacetamide (41 mL) and stirred at 70° C. for 18 h. The mixture was allowed to cool to room temperature, passed through CELITE, washed with methanol, and concentrated under reduced pressure. The residue was purified by column chromatography on silica gel (0-50% EtOAc/Hexane) to afford 4-(3-methyl-5-nitrophenyl)-1-(2-methylallyl)-1H-pyrazole. MS ESI calc'd. for $C_{14}H_{16}N_3O_2$ [M+H]$^+$ 258. found 258.

Step 3:

Iron (1.57 g, 28.2 mmol) and saturated aqueous ammonium chloride (11 mL) were added to a solution of 4-(3-methyl-5-nitrophenyl)-1-(2-methylallyl)-1H-pyrazole (2.42 g, 9.41 mmol) in ethanol (7 mL) and water (11 mL). The mixture was heated at 70° C. for 18 h, then allowed to cool to room temperature, passed through CELITE, washed with methanol, and concentrated under reduced pressure. The residue was diluted with EtOAc and washed with water, saturated aqueous sodium bicarbonate and brine. The organic layers were separated, dried over anhydrous magnesium sulfate, filtered, and concentrated under reduced pressure to give 3-methyl-5-(1-(2-methylallyl)-1H-pyrazol-4-yl)aniline. MS ESI calc'd. for $C_{14}H_{18}N_3$ [M+H]$^+$ 228. found 228. $^1$H NMR (500 MHz, DMSO-$d_6$) δ 7.92 (s, 1H), 7.68 (s, 1H), 6.52 (s, 2H), 6.21 (s, 1H), 4.92 (s, 2H), 4.87 (s, 1H), 4.70 (s, 1H), 4.66 (s, 2H), 2.14 (s, 3H). 1.60 (s, 3H).

Preparative Example 1.48

2-Chloro-4-(difluoromethyl)pyrimidine

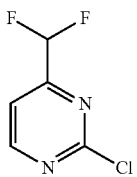

Step 1:

2,2-difluoroacetic anhydride and DMAP in DCM were cooled to −20° C. and ethyl vinyl ether was added drop wise at such a rate that the internal temperature did not exceed −10° C. When complete the reaction mixture was stirred over night while slowly warming to room temperature. Water and DCM were added and the layers were cut. The organic layer was washed sequentially with aqueous saturated sodium bicarbonate then brine. The aqueous layers were sequentially back extracted with a second portion of DCM and the combined organics were dried with anhydrous magnesium sulfate, filtered and concentrated under reduced pressure. The residue was then taken up in EtOH, urea was added followed by concentrated hydrochloric acid. The resulting mixture stirred for 18 h then concentrated under reduced pressure. Ethanol was added and again concentrated under reduced pressure. This was repeated then repeated with EtOAc (2×). The resulting residue was diluted with EtOAc stirred for 1 h then filtered and washed with EtOAc/Hexanes (1:1) to afford 4-(difluoromethyl)pyrimidin-2-ol as a brown solid.

Step 2:

4-(difluoromethyl)pyrimidin-2-ol was diluted with phosphorus oxychloride (80 mL) then heated at 85° C. for 3 hours with periodic venting of the reaction mixture. The mixture was cooled to rt, diluted with DCM (500 mL) and poured into water (~1 L) cooled in an ice bath at such a rate the exotherm was maintained at ~30° C. The mixture was transferred to a separatory funnel and the layers were separated. The aqueous layer was extracted with DCM (2×500 mL) and the organics were combined and dried with anhydrous magnesium sulfate, filtered and concentrated under reduced pressure to afford 2-chloro-4-(difluoromethyl) as a light yellow oil. MS ESI calcd. for $C_5H_4ClF_2N_2$ [M+H]$^+$ 165. found 165. $^1$H NMR δ ppm DMSO-d$_6$): 8.18 (1H, d, J=6.25 Hz), 6.63 (1H, t, J=54.22 Hz). 6.57 (2H, d, J=6.26 Hz).

Preparative Example 1.49

2-Chloro-4-(difluoromethyl)-5-fluoropyrimidine

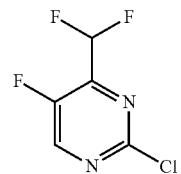

Step 1:

2,4-Dichloro-5-fluoropyrimidine (111 g, 661.47 mmol, 1.00 equiv., 99.5%), potassium trifluoro(vinyl)borate (98 g, 716.72 mmol, 1.08 equiv., 98%), TEA (67 g, 98%), 1-propanol (1100 mL), PdCl$_2$(dppf).CH$_2$Cl$_2$ (27 g, 33.06 mmol, 0.05 equiv) were added into five 2000-mL pressure tank reactors which purged and maintained with an inert atmosphere of nitrogen. The resulting solution was stirred overnight at 105° C. The reaction mixture of five batches was combined and then cooled to room temperature with a water bath. The solid was filtered out. The filtrate was concentrated under reduced vacuum. The residue was applied onto a silica gel column and eluted with ethyl acetate/petroleum ether (1:20) to afford 2-chloro-4-ethenyl-5-fluoropyrimidin as a highly volatile yellow oil.

Step 2:

A solution of OsO$_4$ in water (0.015 g/ml, 265 mL) was added into a 10-L 4-necked round-bottom flask with 2-chloro-4-ethenyl-5-fluoropyrimidine (303 g, 1.24 mol, 1.00 equiv, 65%), tetrahydrofuran (2400 mL) and water (1600 mL). This was followed by the addition of NaIO$_4$(424 g, 1.94 mol, 1.56 equiv, 98%), in portions at 0-10° C. The resulting solution was stirred for 60 min at 0-10° C. in a water/ice bath. The resulting solution was diluted with water (4 L), then extracted with ethyl acetate (5×1000 mL). The organic layers were combined, dried over anhydrous sodium sulfate and concentrated under reduced pressure. The residue was applied onto a silica gel column and eluted with ethyl acetate/petroleum ether (1:5) to afford (2-chloro-5-fluoropyrimidin-4-yl)methanediol as a white solid and (2-chloro-5-fluoropyrimidin-4-yl)methanediol as a yellow oil.

Step 3:

(2-Chloro-5-fluoropyrimidin-4-yl)methanediol (80 g, 426 mmol, 1.00 equiv, 95%), dichloromethane (1300 mL), ethyl acetate (7.3 mL) were added to a 3-L 4-necked round-bottom flask purged and maintained with an inert atmosphere of nitrogen. This was followed by the addition of DAST (86.7 g, 537.87 mmol, 1.26 equiv) drop wise with stirring at 15-25° C. The resulting solution was stirred overnight at 25° C. The reaction was then quenched by the addition of saturated aqueous ammonium chloride (1500 mL). The resulting solution was extracted with dichloromethane (2×1000 mL). The organic layers were combined, dried over anhydrous magnesium sulfate and concentrated under reduced pressure. The crude product was purified by distillation under reduced pressure (20 mmHg) and the fraction was collected at 80-85° C. to afford 2-chloro-4-(difluoromethyl)-5-fluoropyrimidine as brown oil. MS ESI calcd. for $C_5HClF_3N_2$ [M+H]$^+$ 182. found 182. $^1$H NMR (300 MHz, CDCl$_3$) δ 8.68 (1H, m), 6.99-6.49 (1H, m).

Preparative Example 1.50

N-(3-Bromo-5-methylphenyl)-4-(1,1-difluoroethyl)pyrimidin-2-amine

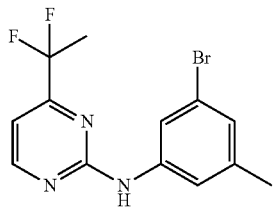 [SMILES: Cc1cc(Br)cc(Nc2nccc(C(C)(F)F)n2)c1]

Step 1:

1-(2-Chloropyrimidin-4-yl)ethanol (5.25 g, 33.1 mmol) and 3-bromo-5-methylaniline (9.24 g, 49.7 mmol) were suspended in 1,4-dioxane (30 mL). Acetic acid (1.90 ml, 33.1 mmol) was added, and the resultant mixture was heated to 100° C. for 14 h. The reaction mixture was allowed to cool to room temperature and then was diluted with dichloromethane. The resultant solution was adsorbed on silica gel and purified by column chromatography on silica (10-100% ethyl acetate/hexanes) to afford 1-(2-((3-bromo-5-methylphenyl)amino)pyrimidin-4-yl)ethanol as a black semi-solid. MS ESI calc'd. for $C_{13}H_{15}BrN_3O$ [M+H]$^+$ 308, 310. found 308, 310.

Step 2:

1-(2-((3-Bromo-5-methylphenyl)amino)pyrimidin-4-yl)ethanol (3.27 g, 10.59 mmol) was dissolved in dichloromethane (14 mL). Dess-Martin Periodinane (9.0 g, 21.2 mmol) was added, and the resultant suspension was stirred vigorously for 14 h at room temperature. The mixture was diluted with saturated aqueous sodium bicarbonate and sodium thiosulfate. The heterogeneous mixture was extracted with dichloromethane (2×). The combined organic extracts were dried over anhydrous sodium sulfate, filtered, and concentrated under reduced pressure. The residue was purified by column chromatography on silica (10-40% ethyl acetate/hexanes) to afford 1-(2-((3-bromo-5-methylphenyl)amino)pyrimidin-4-yl)ethanone as a yellow solid. MS ESI calc'd. for $C_{13}H_{13}BrN_3O$ [M+H]$^+$ 306, 308. found 306, 308. $^1$H NMR (500 MHz, CDCl$_3$) δ 8.64 (d, J=4.9 Hz, 1H), 7.93 (s, 1H), 7.35-7.30 (m, 2H), 7.05 (s, 1H), 2.71 (s, 3H), 2.35 (s, 3H).

Step 3:

1-(2-((3-Bromo-5-methylphenyl)amino)pyrimidin-4-yl)ethanone (30 mg, 0.10 mmol) was dissolved in dichloromethane (2 mL). Diethylaminosulfur trifluoride (0.04 mL, 0.29 mmol) was added, and the mixture was stirred vigorously for 14 h. The mixture was diluted via the slow addition of saturated aqueous sodium bicarbonate. The layers were separated, and the aqueous portion was extracted with dichloromethane (2×). The combined organic extracts were dried over anhydrous sodium sulfate, filtered, and concentrated under reduced pressure. The residue was purified by column chromatography n silica (10-100% ethyl acetate/hexanes) to afford N-(3-bromo-5-methylphenyl)-4-(1,1-difluoroethyl)pyrimidin-2-amine as a white solid. MS ESI calc'd. for $C_{13}H_{13}BrF_2N_3$ [M+H]+328, 330. found 328, 330. $^1$H NMR (500 MHz, CDCl$_3$) δ 8.59 (d, J=4.7 Hz, 1H), 7.84 (s, 1H), 7.32-7.18 (m, 2H), 7.11-6.99 (m, 2H), 2.36 (s, 3H), 2.00 (t, J=18.7 Hz, 3H).

Preparative Example 1.51

N-(3-(1-(2-Aminoethyl)-1H-pyrazol-4-yl)-5-methylphenyl)-4-(difluoromethyl)pyrimidin-2-amine hydrochloride

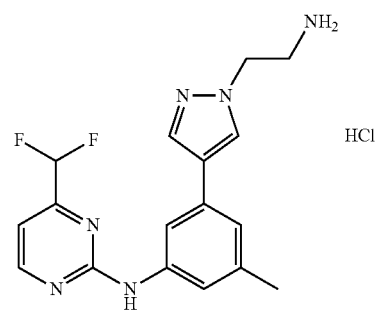 [SMILES: Cc1cc(Nc2nccc(C(F)F)n2)cc(-c2cnn(CCN)c2)c1 ; Cl]

Step 1:

Di-tert-butyl dicarbonate (9.97 ml, 42.9 mmol) was added to a flask containing 2-(4-chloro-1H-pyrazol-1-yl)ethanamine (2.50 g, 17.2 mmol) and tetrahydrofuran (60 ml). The reaction was stirred for 2 hours and concentrated under reduced pressure. The residue was purified by column chromatography on silica gel (0-80% ethyl acetate/hexanes) to afford tert-butyl (2-(4-chloro-1H-pyrazol-1-yl)ethyl)carbamate. MS ESI calc'd. for $C_{10}H_{17}ClN_3O_2$ [M+H]$^+$246. found 246.

Step 2:

1,4-Dioxane (40 mL) and water (9 mL) were added to a flask containing 4-(difluoromethyl)-N-(3-methyl-5-(4,4,5,5-tetramethyl-1,3,2-dioxaborolan-2-yl)phenyl)pyrimidin-2-amine (3.00 g, 8.31 mmol), tert-butyl (2-(4-chloro-1H-pyrazol-1-yl)ethyl)carbamate (3.06 g, 12.5 mmol), SiliaCat Si-DPP-Pd (9.58 g, 2.49 mmol, 0.26 mmol/g), and sodium carbonate (4.40 g, 41.5 mmol). The reaction was heated at 110° C. overnight. The reaction mixture was filtered, washed with 1,4-dioxane, and then concentrated under reduced pressure. The residue was purified by column chromatography on silica gel (0-100% ethyl acetate/hexanes) and dissolved in a small amount of 1,4-dioxane. Hydrochloric acid (4N in 1,4-dioxane, 10 mL) in was added and the mixture was allowed to stir for 3 hours. The mixture was diluted with diethyl ether, filtered, washed with diethyl ether, and dried over anhydrous sodium sulfate to afford N-(3-(1-(2-aminoethyl)-1H-pyrazol-4-yl)-5-methylphenyl)-4-(difluoromethyl)pyrimidin-2-amine hydrochloride. MS ESI calc'd. for $C_{17}H_{19}F_2N_6$ [M+H]$^+$ 345. found 345. $^1$H NMR (500 MHz, DMSO-d$_6$): δ 9.92 (s, 1H), 8.68 (d, J=4.9 Hz, 1H), 8.29 (s, 3H), 8.15 (s, 1H), 7.87 (s, 1H), 7.85 (s, 1H), 7.34 (s, 1H), 7.04 (t, J=5.3 Hz, 2H), 6.89 (t, J=54.5 Hz, 1H), 4.42 (t, J=6.3 Hz, 2H), 3.27-3.25 (m, 2H), 2.28 (s, 3H).

Preparative Example 1.52

N-(3-(1-(2-Amino-2-methylpropyl)-1H-pyrazol-4-yl)-5-methylphenyl)-4-(difluoromethyl)pyrimidin-2-amine hydrochloride

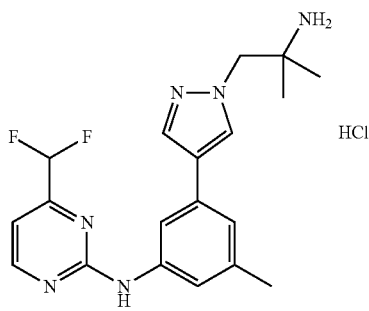 [SMILES: Cc1cc(Nc2nccc(C(F)F)n2)cc(-c2cnn(CC(C)(C)N)c2)c1 ; Cl]

Step 1:

Dichloromethane (50 mL) and triethylamine (9.72 ml, 69.7 mmol) were added to a flask containing tert-butyl (1-hydroxy-2-methylpropan-2-yl)carbamate (3.30 g, 17.4 mmol). The reaction mixture was stirred and then chilled to 0° C. for 10 minutes. Methanesulfonyl chloride (2.72 ml, 34.9 mmol) was dissolved in dichloromethane (15 mL) and slowly added to the reaction mixture, which was then allowed to stir at 0° C. for 2 hours. The reaction was quenched with saturated aqueous sodium bicarbonate solution and the organic layer was separated. The organic layer was dried over anhydrous sodium sulfate, filtered, and concentrated under reduced pressure to afford 2-((tert-butoxycarbonyl)amino)-2-methylpropyl methanesulfonate. $^1$H NMR (500 MHz, DMSO-$d_6$): δ 6.73 (s, 1H), 4.20 (s, 2H), 3.12 (s, 3H), 1.36 (s, 9H), 1.17 (s, 6H).

Step 2:

A flask containing 4-(difluoromethyl)-N-(3-methyl-5-(1H-pyrazol-4-yl)phenyl)pyrimidin-2-amine (1.00 g, 3.32 mmol), 2-((tert-butoxycarbonyl)amino)-2-methylpropyl methanesulfonate (2.66 g, 9.96 mmol), cesium carbonate (5.41 g, 16.6 mmol) and DMSO (15 mL) was heated at 110° C. overnight. The reaction mixture was quenched with hydrochloric acid (2 N) and the aqueous layer was extracted with dichloromethane followed by ethyl acetate. The aqueous layer was then filtered and the collected solids were washed with hydrochloric acid (2 N). The aqueous layer placed in a flask and, while stirring, sodium hydroxide (10 N) was added to the aqueous layer until the mixture was slightly basic (pH 8). The aqueous layer was then extracted with isopropyl alcohol/chloroform (20%) and the resulting organic layer was concentrated under reduced pressure. The residue was taken up in 1,4-dioxane, then hydrochloric acid (4 N in 1,4-dioxane, 5 mL) was then added and the resulting solids were collected by filtration to afford N-(3-(1-(2-amino-2-methylpropyl)-1H-pyrazol-4-yl)-5-methylphenyl)-4-(difluoromethyl)pyrimidin-2-amine hydrochloride. MS ESI calc'd. for $C_{19}H_{23}F_2N_6$ [M+H]$^+$ 373. found 373. $^1$H NMR (600 MHz, DMSO): δ 9.82 (s, 1H), 8.66 (d, J=4.9 Hz, 1H), 8.08 (s, 1H), 7.87 (s, 1H), 7.75 (s, 1H), 7.28 (s, 1H), 7.06 (s, 1H), 7.02 (d, J=4.9 Hz, 1H), 6.85 (t, J=54.5 Hz, 1H), 2.84 (s, 2H), 2.26 (s, 3H), 1.46 (s, 6H).

Preparative Example 1.53

N-(3-Bromophenyl)-4-(difluoromethyl)pyrimidin-2-amine

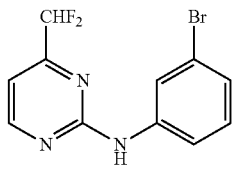 [SMILES: FC(F)c1ccnc(Nc2cccc(Br)c2)n1]

2-Chloro-4-(difluoromethyl)pyrimidine (69 wt % in DCM, 24.2 g, 101 mmol) was diluted with 1,4-dioxane (200 mL) to which was added 3-bromoaniline (14.9 mL, 137 mmol) followed by methanesulfonic acid (8.89 mL, 137 mmol). The resulting mixture was heated to an internal temperature of 95° C. where it was stirred for 10 h at which point the reaction mixture was cooled to room temperature and diluted with dichloromethane and water. NaOH (1N) was added until the pH of the aq layer was ~7, the layers were separated and the aqueous layer was extracted a second time with additional of dichloromethane. The combined organics were dried with anhydrous magnesium sulfate, filtered, and concentrated under reduced pressure. To facilitate purification, the crude residue was diluted with dichloromethane (200 mL) and DMAP (0.84 g, 6.84 mmol) followed by acetic anhydride (3.87 mL, 41.1 mmol) were added. After stirring for 30 min all excess 3-bromoaniline had been acetylated, silica gel was added and the mixture concentrated under reduced pressure and the desired product isolated by purification by column chromatography on silida (0 to 100% EtOAc/Hex) to afford N-(3-bromophenyl)-4-(difluoromethyl)pyrimidin-2-amine as a white solid, MS ESI calcd. for $C_{11}H_9BrF_2N_3$ [M+H]$^+$ 300. found 300. $^1$H NMR (600 MHz, DMSO-d$^6$) δ 10.15 (s, 1H), 8.71 (d, J=4.9 Hz, 1H), 8.06 (s, 1H), 7.70 (dd, J=8.2, 1.3 Hz, 1H), 7.22 (t, J=8.1 Hz, 1H), 7.12 (d, J=7.9 Hz, 1H), 7.09 (d, J=4.9 Hz, 1H), 6.85 (t, J=54.4 Hz, 1H).

Preparative Example 1.54

N-(3-Bromo-5-methylphenyl)-4-(difluoromethyl)-5-fluoropyrimidin-2-amine

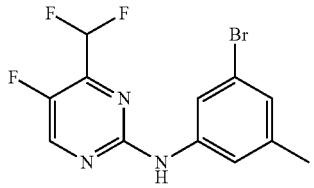

2-Chloro-4-(difluoromethyl)-5-fluoropyrimidine (30 g, 162 mmol, 1.00 equiv) p-TsOH (37 g, 215 mmol, 1.33 equiv), 1,4-dioxane (600 mL), 3-bromo-5-methylaniline (46 g, 247 mmol, 1.53 equiv) were added into a 1000-mL pressure tank reactor purged and maintained with an inert atmosphere of nitrogen. The resulting solution was stirred for 72 h at 105° C.

The reaction mixture was cooled to room temperature. The solid was filtered out and the filtrate was concentrated under reduced pressure. The residue was applied onto a silica gel and purified column chromatography on silica (1:20 ethyl acetate/petroleum ether) to afford N-(3-bromo-5-methylphenyl)-4-(difluoromethyl)-5-fluoropyrimidin-2-amine as a yellow solid. MS ESI calc'd. for $C_{12}H_{10}BrF_3N_3$ $[M+H]^+$ 332/334. found 332/334. $^1$H NMR (400 MHz, CDCl$_3$): δ 8.45 (1H, s), 7.73 (1H, s), 7.21 (1H, s), 7.18 (1H, s), 7.05 (1H, s), 6.63 (1H, t, J=53.37 Hz), 2.34 (3H, s).

The intermediates in the following table were prepared according to the method described for Preparative Example 1.54.

4-yl)phenyl)-4-(trifluoromethyl)pyrimidin-2-amine (371 mg, 1.16 mmol) in THF (3.5 mL). The reaction was stirred for 10 min and allowed to warm to RT for 18 hours. The reaction was quenched into aqueous potassium hydrogen sulfate (5%, 20 mL) and product extracted with ethyl acetate (2×20 mL). The organic extracts were combined dried over anhydrous magnesium sulfate, filtered and concentrated under reduced pressure. The residue was purified by column chromatography on silica (10-50% ethyl acetate/hexanes) to afford N-(3-methyl-5-(1-(3-methylbut-3-en-2-yl)-1H-pyrazol-4-yl)phenyl)-4-(trifluoromethyl)pyrimidin-2-amine MS ESI calcd. for $C_{20}H_{21}F_3N_5$ $[M+H]^+$ 388. found 388.

| Prep. Ex. | Structure | Chemical Name | Exact Mass [M + H]+ | [M + H]+ Found |
|---|---|---|---|---|
| 1.55 | 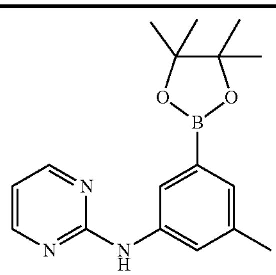 | N-(3-methyl-5-(4,4,5,5-tetramethyl-1,3,2-dioxaborolan-2-yl)phenyl)pyrimidin-2-amine | 312 | 312 |
| 1.56 | 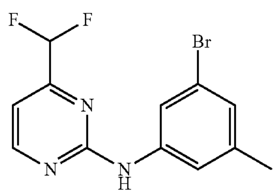 [SMILES: Cc1cc(Br)cc(Nc2nccc(C(F)F)n2)c1] | N-(3-bromo-5-methylphenyl)-4-(difluoromethyl)pyrimidin-2-amine | 314/316 | 314/316 |

Preparative Example 1.57

N-(3-methyl-5-(1-(3-methylbut-3-en-2-yl)-1H-pyrazol-4-yl)phenyl)-4-(trifluoromethyl)pyrimidin-2-amine

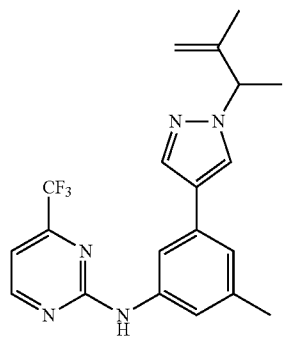 [SMILES: C=C(C)C(C)n1cc(-c2cc(C)cc(Nc3nccc(C(F)(F)F)n3)c2)cn1]

(E)-di-tert-butyl diazene-1,2-dicarboxylate (321 mg, 1.39 mmol) was added slowly to a 0° C. well stirred solution of 3-methylbut-3-en-2-ol (100 mg, 1.16 mmol), triphenylphosphine (365 mg, 1.39 mmol) and N-(3-methyl-5-(1H-pyrazol- Preparative Example 1.58

N-(3-bromo-5-chlorophenyl)-4-(trifluoromethyl)pyrimidin-2-amine

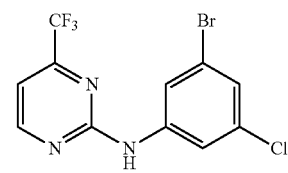 [SMILES: FC(F)(F)c1ccnc(Nc2cc(Cl)cc(Br)c2)n1]

Potassium tert-butoxide (750 mg, 6.69 mmol) was added to a solution of 2-chloro-4-(trifluoromethyl)pyrimidine (406 mg, 2.23 mmol) and 3-bromo-5-chloroaniline (460 mg 2.23 mmol) in THF (20 mL) at 0° C. under a nitrogen atmosphere. The mixture was stirred at 70° C. for 12 hours. The mixture was then diluted with saturated aqueous ammonium chloride solution and extracted with ethyl acetate. The organic layer was dried over sodium sulfate, filtered, and concentrated under reduced pressure. The product was purified by chromatography on silica gel to give N-(3-bromo-5-chlorophenyl)-4-(trifluoromethyl)pyrimidin-2-amine MS ESI calc'd. for $C_{11}H_7BrClF_3N_3$ $[M+H]^+$ 352 and 354. found 352 and 354.

The intermediates in the following table were prepared according to the method described for Preparative Example 1.58.

| Prep. Ex. | Structure | Chemical Name | Exact Mass [M + H]+ | [M + H]+ Found |
|---|---|---|---|---|
| 1.59 | ![structure] | N-bromo-N-(4-(difluoromethyl) pyridin-2-yl) pyridin-2-amine | 300, 302 | 300, 302 |

Preparative Example 2

Preparation of Precursors Useful in Preparing Compounds of Formula (I) Containing Aminobispyridine Substructures The following representative methods in this example were used to prepare synthetic intermediates useful in preparation of final compounds which contain aminobispyridine substructures, and are indicated in the tables as applied.

Preparative Example 2.1

6-Bromo-4-methyl-N-[4-(trifluoromethyl)pyridine-2-yl]pyridine-2-amine

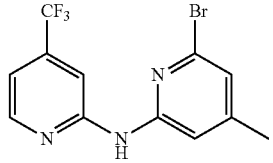 [SMILES: Cc1cc(Br)nc(Nc2cc(C(F)(F)F)ccn2)c1]

Sodium tert-butoxide (5.87 g, 61.1 mmol) and 1,1'-bis(di-tert-butylphsophino)ferrocene palladium dichloride (0.91 g, 1.4 mmol) were added to a solution of 2,6-dibromo-4-methyl pyridine (13.9 g, 55.5 mmol) and 2-amino-4-trifluoromethyl pyridine (9.0 g, 55.5 mmol) in nitrogen sparged dioxane (180 mL). The slurry was evacuated and refilled with nitrogen. The mixture was stirred at 25° C. for 15 minutes and then heated to 75° C. for 12 hours. The reaction mixture was cooled to 25° C., water (20 mL) was added, and the mixture was extracted with EtOAc (2×200 mL). The combined extracts were dried over sodium sulfate, filtered, concentrated under reduced pressure. The residue was purified by column chromatography on silica gel to afford 6-bromo-4-methyl-N-[4-(trifluoromethyl)pyridine-2-yl]pyridine-2-amine as a white solid. MS ESI calc'd. for $C_{12}H_{10}BrF_3N_3$ [M+H]+ 332 and 334. found 332 and 334. $^1$H NMR (600 MHz, DMSO-$d_6$) δ 10.40 (s, 1H), 8.46 (d, J=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following table were prepared according to the method described for Preparative Example 2.1. $^1$H NMR data is provided when [M+H]+ was not available. Preparative Example 2.5 was prepared following the procedures described in PCT Publication Nos. WO2006/093247 and WO2011/086085.

| Prep. Ex. | Structure | Chemical Name | Exact Mass [M + H]+ | [M + H]+ Found |
|---|---|---|---|---|
| 2.2 | | 6-bromo-4-methyl-N-4-methylpyridin-2-yl)pyridin-2-amine | 278 | 278, 280 |
| 2.2 | | 6-bromo-N-(4-cyclopropylpyridin-2-yl)-4-methylpyridin-2-amine | 304 | 304, 306 |
| 2.3 | 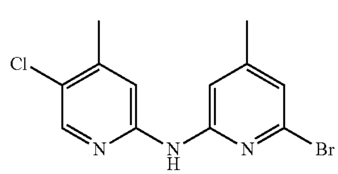 [SMILES: Cc1cc(Br)nc(Nc2cc(C)c(Cl)cn2)c1] | N-(6-bromo-4-methyl-pyridin-2-yl)-5-chloro-4-methylpyridin-2-amine | 312 | $^1$H NMR (600 MHz, DMSO-$d^6$) δ 10.01 (s, 1H), 8.18 (s, 1H), 7.63 (s, 1H), 7.40 (s, 1H), 6.94 (s, 1H), 2.26 (s, 3H), 2.23 (s, 3H). |

-continued

| Prep. Ex. | Structure | Chemical Name | Exact Mass [M + H]+ | [M + H]+ Found |
|---|---|---|---|---|
| 2.4 | 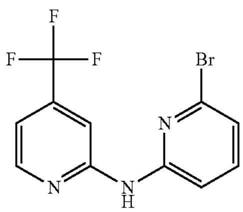 [SMILES: FC(F)(F)c1ccnc(Nc2cccc(Br)n2)c1] | N-(6-bromopyridin-2-yl)-4-(trifluoromethyl)-pyridin-2-amine | 318 | 318 |
| 2.5 | 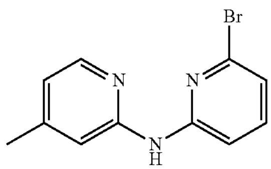 | N-(6-bromopyridin-2-yl)-4-methylpyridin-2-amine | 264 | 264 |
| 2.6 | 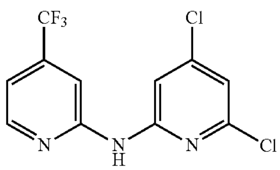 [SMILES: FC(F)(F)c1ccnc(Nc2cc(Cl)cc(Cl)n2)c1] | 4,6-dichloro-N-[4-(trifluoromethyl)pyridin-2-yl]pyridin-2-amine | 308 | 308 |
| 2.7 | 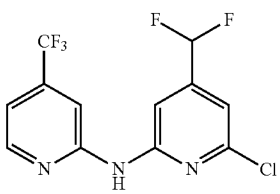 [SMILES: FC(F)c1cc(Cl)nc(Nc2cc(C(F)(F)F)ccn2)c1] | 6-chloro-4-(difluoromethyl)-N-[4-(trifluoromethyl)-pyridin-2-yl]pyridin-2-amine | 324 | 324 |
| 2.8 | 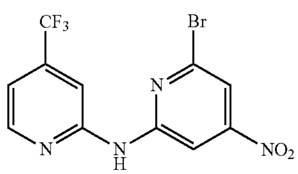 [SMILES: O=[N+]([O-])c1cc(Br)nc(Nc2cc(C(F)(F)F)ccn2)c1] | 6-bromo-4-nitro-N-[4-(trifluoromethyl)-pyridin-2-yl]pyridin-2-amine | 363 | 363, 365 |
| 2.9 | 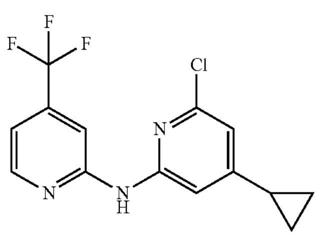 [SMILES: FC(F)(F)c1ccnc(Nc2cc(C3CC3)cc(Cl)n2)c1] | 6-chloro-4-cyclopropyl-N-[4-(trifluoromethyl)pyridin-2-yl]pyridin-2-amine | 314 | 314 |
| 2.10 | 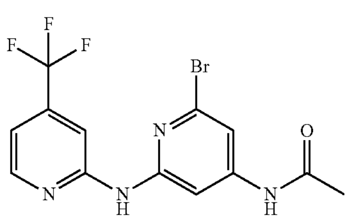 [SMILES: CC(=O)Nc1cc(Br)nc(Nc2cc(C(F)(F)F)ccn2)c1] | N-(2-bromo-6-{[4-(trifluoromethyl)pyridin-2-yl]amino}-pyridin-4-yl)-acetamide | 375 | 375 |

| Prep. Ex. | Structure | Chemical Name | Exact Mass [M + H]+ | [M + H]+ Found |
|---|---|---|---|---|
| 2.11 | ![structure] | 6-bromo-N-(4-(difluoromethyl)pyridin-2-yl)-4-methylpyridin-2-amine | 314, 316 | 314, 316 |
| 2.12 | ![structure] | 6-bromo-N-(4-(1,1-difluoroethyl)pyridin-2-yl)-4-methylpyridin-2-amine | 328, 330 | 328, 330 |

Preparative Example 2.13

6-Bromo-$N^2$-[4-(trifluoromethyl)pyridin-2-yl]pyridine-2,4-diamine

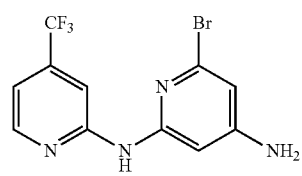

A suspension of 6-bromo-4-nitro-N-[4-(trifluoromethyl)pyridin-2-yl]pyridin-2-amine (586 mg, 1.614 mmol) and iron (361 mg, 6.46 mmol) in acetic acid (7 mL) was heated to 50° C. for 1 hour. The reaction mixture was partitioned between ethyl acetate (70 mL) and water (70 mL). The aqueous layer was further extracted with ethyl acetate (70 mL), and the combined organic layers were washed with water (70 mL), saturated aqueous sodium bicarbonate solution (2×70 mL), brine (50 mL), dried over sodium sulfate, filtered, and concentrated under reduced pressure. The residue was purified by chromatography on silica gel (10-60% ethyl acetate/hexanes) to afford 6-bromo-$N^2$-[4-(trifluoromethyl)pyridin-2-yl]pyridine-2,4-diamine MS ESI calc'd. for $C_{11}H_9BrF_3N_4$ [M+H]+ 333 and 335. found 333 and 335. $^1$H NMR (500 MHz, DMSO-$d_6$) δ 11.08 (s, 1H), 8.63 (s, 1H), 8.59 (d, J=5.4 Hz, 1H), 7.85 (s, 1H), 7.83-7.76 (m, 2H), 7.48-7.42 (m, 1H), 7.37-7.32 (m, 1H).

Preparative Example 2.14

2,6-Dichloro-4-cyclopropylpyridine

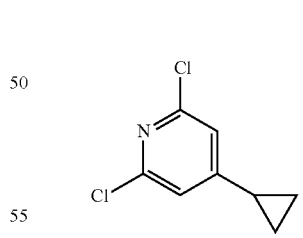

Cyclopropylzinc bromide (0.5 M in tetrahydrofuran, 15 mL, 7.3 mmol) was added to a mixture of 2,6-dichloro-4-iodopyridine (1.0 g, 3.65 mmol) and tetrakis(triphenylphosphine)palladium(0) (211 mg, 0.182 mmol) in anhydrous tetrahydrofuran (10 mL) at 0° C. After being stirred at room temperature for 4 hours, the reaction mixture was filtered, and the filtrate was concentrated under reduced pressure. The residue was purified by column chromatography on silica gel (petroleum ether: ethyl acetate=100:1) to provide 2,6-dichloro-4-cyclopropylpyridine. MS ESI calc'd. for $C_8H_8Cl_2N$ [M+H]$^+$ 188. found 188. $^1$H NMR: (400 MHz, CDCl$_3$) δ 6.89 (s, 2H), 1.87-1.80 (m, 1H), 1.18-1.13 (m, 2H), 0.84-0.80 (m, 2H).

Preparative Example 2.15

N-(2,6-dibromopyridin-4-yl)acetamide

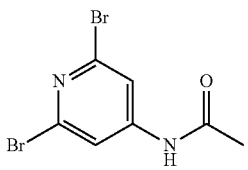

2,6-Dibromopyridin-4-amine, DMAP (0.048 g, 0.397 mmol) and pyridine (0.48 ml, 5.95 mmol) were taken-up in THF (7.9 ml) under argon. Acetic anhydride (0.41 ml, 4.37 mmol) was slowly added and the mixture was stirred overnight at room temperature. The reaction was then heated to 65° C. for 5 days and cooled to room temperature, diluted with methanol, and concentrated under reduced pressure. The residue was purified by chromatography on silica gel (0-100% EtOAc/hexanes) to afford N-(2,6-dibromopyridin-4-yl)acetamide as a light yellow solid. MS ESI calc'd. for $C_7H_6Br_2N_2O$ [M+H]$^+$ 294. found 294.

Preparative Example 2.16

4,6-Dichloro-N-[4-(trifluoromethyl)pyridin-2-yl]pyridin-2-amine

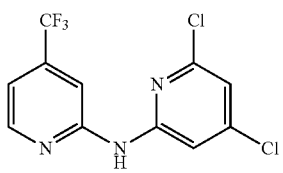 [SMILES: FC(F)(F)c1ccnc(Nc2cc(Cl)cc(Cl)n2)c1]

A mixture of 4-(trifluoromethyl)pyridin-2-amine (3.24 g, 20.0 mmol) and sodium hydride (1.2 g, 30 mmol) in THF (60 mL) was stirred at 0° C. under nitrogen for 1 hour, and then 2,4,6-trichloropyridine (3.62 g, 20.0 mmol) was added. The reaction was stirred at 25° C. for 3 hours. The mixture was diluted with water and extracted with ethyl acetate. The organic layer was dried over sodium sulfate, filtered, and concentrated under reduced pressure. The residue was purified by chromatography on silica gel (ethyl acetate/petroleum ether) to give 4,6-dichloro-N-[4-(trifluoromethyl)pyridin-2-yl]pyridin-2-amine. MS ESI calc'd. for $C_{11}H_7Cl_2F_3N_3$ [M+H]$^+$ 308. found 308. $^1$H NMR (400 MHz, CD$_3$OD): δ 8.49 (d, J=5.6 Hz, 1H), 7.99 (s, 1H), 7.87 (s, 1H), 7.19 (d, J=1.2 Hz, 1H), 7.05 (d, J=1.2 Hz, 1H).

Preparative Example 2.17

4-(1,1-Difluoroethyl)pyridin-2-amine

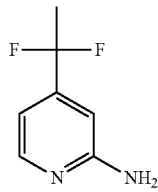

Lithium bis(trimethylsilyl)amide (1.0 M in THF, 11.87 mL, 11.87 mmol) was added to a solution of 2-chloro-4-(1,1-diflurorethyl)pyridine (1.916 g, 10.79 mmol) and chloro(2-dicyclohexylphosphino-2',4',6'-triisopropyl-1,1'-biphenyl)[2-(2-aminoethyl)phenyl)]palladium(II) under nitrogen. The resulting solution was heated to 50° C. for two hours and then cooled to 0° C. Hydrochloric acid (1 M in water, 20 mL) was added and the THF was removed under reduced pressure. MTBE was added, the mixture was filtered, and the layers were separated. The aqueous layer pH was adjusted to 10 with 45% KOH in water and then extracted with ethyl acetate. The organic layer was dried over sodium sulfate, filtered, and concentrated under reduced pressure to afford 4-(1,1-difluoroethyl)pyridin-2-amine $^1$H NMR (400 MHz, CDCl$_3$): δ 8.13 (d, J=5.5 Hz, 1H), 7.22 (dd, J=5.4, 1.3 Hz, 1H), 6.64 (s, 1H), 4.71 (br s, 2H), 1.88 (t, J=18.3 Hz, 3H).

Preparative Example 2.18

2-(Benzyloxy)-5-(bromomethyl)pyridine

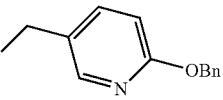

Step 1:
Sulfurous dichloride (6.8 g, 57 mmol) was added to a solution of 6-chloronicotinic acid (4.5 g, 28.5 mmol) in toluene (40 mL) at 0° C. The mixture was stirred at 110° C. for 2 hours. After cooling to room temperature, the mixture was concentrated under reduced pressure. Benzyl alcohol (4.65 g, 43.1 mmol), pyridine (6.9 mL) and toluene (50 mL) were added to the residue. The mixture was stirred at 25° C. for 3 hours. HCl (20 mL, 4 N) was added and the mixture was extracted with toluene. The toluene layer was dried over anhydrous sodium sulfate, filtered, and concentrated under reduced pressure to afford benzyl 6-chloronicotinate. MS ESI calc'd. for $C_{13}H_{11}ClNO_2$ [M+H]$^+$ 248. found 248. $^1$HNMR (400 MHz, DMSO-d$_6$) δ 8.94 (d, J=2.0 Hz, 1H), 8.34-8.31 (m, 1H), 7.67 (d, J=8.4 Hz, 1H), 7.50-7.17 (m, 5H), 5.38 (s, 2H).
Step 2:
Sodium hydride (1.2 g, 30.3 mmol, 60 wt %) was added to a solution of benzyl alcohol (3.28 g, 30.3 mmol) in THF (40 mL). The mixture was stirred at 0° C. under N$_2$ for 1 hour. A solution of benzyl 6-chloronicotinate (5 g, 20.2 mmol) in THF (2 mL) was added to the mixture. The mixture was stirred at 20° C. for 12 hours. The mixture was diluted with saturated ammonium chloride solution and extracted with EtOAc. The organic layer was dried over anhydrous sodium sulfate, filtered, and concentrated under reduced pressure. The residue was purified by column chromatography on silica gel (petroleum ether/EtOAc) to afford benzyl 6-(benzyloxy) nicotinate. MS ESI calc'd. for $C_{20}H_{18}NO_3$ [M+H]$^+$ 320. found 320. $^1$H NMR (400 MHz, DMSO-d$_6$) δ 8.80 (d, J=2.4 Hz, 1H), 8.22-8.19 (m, 1H), 7.48-7.34 (m, 10H), 6.98 (d, J=8.4 Hz, 1H), 5.43 (s, 2H), 5.35 (s, 2H).

Step 3:

Lithium borohydride (517 mg, 23.5 mmol) and MeOH (752 mg, 23.5 mmol) were added to a solution of benzyl 6-(benzyloxy)nicotinate (5 g, 15.7 mmol) in THF (50 mL) under N$_2$ at 0° C. The mixture was stirred at 70° C. for 2 hours. The mixture was diluted with saturated aqueous ammonium chloride solution and extracted with EtOAc. The organic layer was dried over anhydrous sodium sulfate, filtered, and concentrated under reduced pressure. The residue was purified by column chromatography on silica gel (petroleum ether/EtOAc) to afford (6-(benzyloxy)pyridin-3-yl)methanol. MS ESI calc'd. for $C_{13}H_{14}NO_2$ [M+H]$^+$ 216. found 216. $^1$H NMR (400 MHz, DMSO-d$_6$) δ 8.11 (d, J=2.0 Hz, 1H), 7.69-7.67 (m, 1H), 7.45-7.33 (m, 5H), 6.86 (d, J=8.4 Hz, 1H), 5.35 (s, 2H), 5.23-5.20 (m, 1H), 4.52-4.44 (m, 2H).

Step 4:

(6-(Benzyloxy)pyridin-3-yl)methanol (3 g, 14 mmol) was added to a solution of phosphorus oxybromide (4.8 g, 16.8 mmol) in DCM (40 mL) under N$_2$ at 0° C. The mixture was stirred at 20° C. for 1 hour. The mixture was diluted with saturated aqueous sodium bicarbonate solution and extracted with EtOAc. The organic layer was dried over anhydrous sodium sulfate, filtered, and concentrated under reduced pressure. The residue was purified by column chromatography on silica gel (petroleum ether/EtOAc) to afford 2-(benzyloxy)-5-(bromomethyl)pyridine. MS ESI calc'd. for $C_{13}H_{13}BrNO$ [M+H]$^+$ 278 and 280. found 278 and 280. $^1$H NMR (400 MHz, DMSO-d$_6$) δ 8.27 (d, J=2.4 Hz, 1H), 7.81-7.79 (m, 1H), 7.45-7.31 (m, 5H), 6.90 (d, J=8.4 Hz, 1H), 5.35 (s, 2H), 4.72 (s, 2H).

Preparative Example 3

Preparation of Precursors Useful in Preparing Compounds of Formula (I) Containing Pyrimidinylaminopyridyl and Pyridylaminopyrmidine Substructures The following representative methods in this example were used to prepare synthetic intermediates useful in preparation of final compounds which contain a pyrimidinylaminopyridine or pyridylaminopyrimidine substructures.

Preparative Example 3.1

2-Chloro-6-methyl-N-[4-(trifluoromethyl)pyridin-2-yl]pyrimidin-4-amine

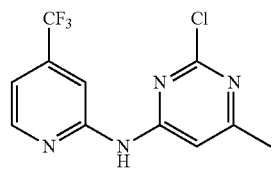 [SMILES: Cc1cc(Nc2cc(C(F)(F)F)ccn2)nc(Cl)n1]

Nitrogen was bubbled through a solution of 4-(trifluoromethyl)pyridin-2-amine (10.96 g, 67.6 mmol), 2,4-dichloro-6-methylpyrimidine (11.02 g, 67.6 mmol) in dioxane (198 mL) for 10 minutes. Sodium tert-butoxide (6.50 g, 67.6 mmol) and 1,1' bis(di-t-butylphosphino ferrocene) (3.21 g, 6.76 mmol) were added, followed by Pd$_2$(dba)$_3$ (3.10 g, 3.38 mmol) and the solution was evacuated and then purged with nitrogen. After heating to reflux for 3 h, the reaction mixture was cooled to room temperature and EtOAc (1 L) was added. The organic layer was washed with saturated sodium bicarbonate, water and brine, then dried over anhydrous sodium sulfate, filtered and concentrated under reduced pressure. The residue was purified by column chromatography on silica gel (EtOAc/hexanes; to afford 2-chloro-6-methyl-N-[4-(trifluoromethyl) pyridin-2-yl]pyrimidin-4-amine as a yellow solid. MS ESI calcd. for $C_{11}H_{18}ClF_3N_4$[M+H]$^+$ 289. found 289.

The intermediates in the following Table were prepared according to the method described for Preparative Example 3.1.

| Prep. Ex. | Structure | Chemical Name | Exact Mass [M + H]+ | [M + H]+ Found |
|---|---|---|---|---|
| 3.2 | 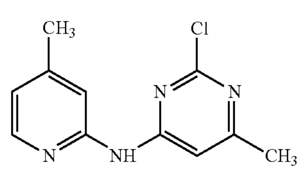 [SMILES: Cc1ccnc(Nc2cc(C)nc(Cl)n2)c1] | 2-chloro-6-methyl-N-(4-methylpyridin-2-yl)pyrimidin-4-amine | 235 | NA |
| 3.3 | 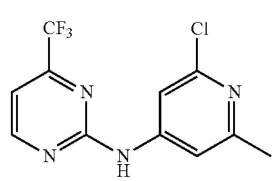 [SMILES: Cc1cc(Nc2nccc(C(F)(F)F)n2)cc(Cl)n1] | N-(2-chloro-6-methyl-pyridin-4-yl)-4-(trifluoromethyl)-pyrimidin-2-amine | 289 | 289 |

Preparative Example 4

Preparation of Substituted C-Ring Precursors Useful in Preparing Compounds of Formula (I)

The following representative methods in this example were used to prepare synthetic intermediates containing substituted C-rings which useful in preparation of final compounds.

Preparative Example 4.1

(R or S) 5-((4-iodo-1H-pyrazol-1-yl)methyl)oxazolidin-2-one (early and late eluting enantiomers)

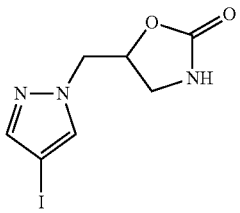 [SMILES: O=C1NCC(Cn2cc(I)cn2)O1]

Potassium phosphate tribasic (6.6 g, 31 mmol), 4-iodo-1H-pyrazole (2.0 g, 10 mmol), and 5-(chloromethyl)oxazolidin-2-one (2.8 g, 21 mmol) were suspended in dioxane (0.10 L, 0.10 M). The reaction vessel was heated to 110° C. for 48 hours, then cooled to room temperature and diluted with dichloromethane (0.25 L). The organics were washed with H$_2$O (2×0.20 L) and were concentrated under reduced pressure. The residue was suspended in methanol:hexanes for 3 hours at ambient temperature with stirring. The precipitate was filtered to afford 5-((4-iodo-1H-pyrazol-1-yl)methyl)oxazolidin-2-one. MS ESI calcd. for C$_7$H$_9$IN$_3$O$_2$ [M+H]$^+$ 294. found 294. $^1$H NMR (500 MHz, DMSO-d$_6$) δ 7.90 (s, 1H), 7.56 (s, 1H), 7.54 (s, 1H), 4.94-4.77 (m, 1H), 4.42-4.32 (m, 2H), 3.54 (t, J=9.0, 1H), 3.24 (dd, J=6.4, 8.8, 1H). The racemic compound, thus obtained, was resolved by chiral super critical fluid chromatography (IC column, 1:4 Isopropanol/CO$_2$) to afford (R or S) 5-((4-iodo-1H-pyrazol-1-yl)methyl)oxazolidin-2-one (early eluting enantiomer): MS ESI calcd. for C$_7$H$_9$IN$_3$O$_2$ [M+H]$^+$ 294. found 294. $^1$H NMR (500 MHz, DMSO-d$_6$) δ 7.90 (s, 1H), 7.56 (s, 1H), 7.54 (s, 1H), 4.94-4.77 (m, 1H), 4.42-4.32 (m, 2H), 3.54 (t, J=9.0, 1H), 3.24 (dd, J=6.4, 8.8, 1H); and (R or S) 5-((4-iodo-1H-pyrazol-1-yl)methyl)oxazolidin-2-one (late eluting enantiomer), MS ESI calcd. for C$_7$H$_9$IN$_3$O$_2$ [M+H]$^+$ 294. found 294. $^1$H NMR (500 MHz, DMSO-d$_6$) δ 7.90 (s, 1H), 7.56 (s, 1H), 7.54 (s, 1H), 4.94-4.77 (m, 1H), 4.42-4.32 (m, 2H), 3.54 (t, J=9.0, 1H), 3.24 (dd, J=6.4, 8.8, 1H).

Preparative Example 4.2 tert-butyl 4-[4-(4,4,5,5-tetramethyl-1,3,2-dioxaborolan-2-yl)-1H-pyrazol-1-yl]cyclohexanecarboxylate (mixture of cis and trans)

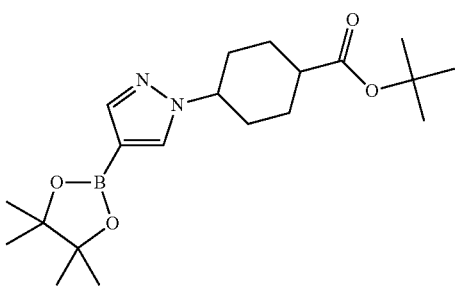 [SMILES: CC(C)(C)OC(=O)C1CCC(n2cc(B3OC(C)(C)C(C)(C)O3)cn2)CC1]

Step 1:

Methanesulfonyl chloride (0.53 mL, 6.80 mmol) was added to a −20° C. solution of tert-butyl 4-hydroxycyclohexanecarboxylate (1.05 g, 5.25 mmol) and triethylamine (1.46 mL, 10.5 mmol) in dichloromethane (21 mL). The reaction was stirred for 2 hours, then saturated aqueous sodium bicarbonate was added and the mixture was extracted with EtOAc (3×). The combined organic layers were dried over sodium sulfate, filtered and concentrated under reduced pressure to afford tert-butyl 4-[(methylsulfonyl)oxy]cyclohexanecarboxylate. $^1$H NMR (500 MHz, CDCl$_3$) δ 4.96-4.55 (m, 1H), 3.00 (s, 3H), 2.23-2.12 (m, 2H), 2.03-1.98 (m, 2H), 1.93-1.81 (m, 1H), 1.79-1.66 (m, 1H), 1.66-1.48 (m, 3H), 1.42 (s, 9H).

Step 2:

4-(4,4,5,5-Tetramethyl-1,3,2-dioxaborolan-2-yl)-1H-pyrazole (325 mg, 1.67 mmol), cesium carbonate (600 mg, 1.84 mmol), and tert-butyl 4-[(methylsulfonyl)oxy]cyclohexanecarboxylate (513 mg, 1.84 mmol) followed by DMF (5.6 mL) were added to an oven-dried flask. The reaction mixture was stirred at 90° C. for 22 hours then cooled to room temperature, diluted with diethyl ether, washed with water (3×50 mL), and then brine. The organic layer was dried over sodium sulfate, filtered, and concentrated under reduced pressure to afford tert-butyl 4-[4-(4,4,5,5-tetramethyl-1,3,2-dioxaborolan-2-yl)-1H-pyrazol-1-yl]cyclohexanecarboxylate (mixture of cis and trans). $^1$H NMR (500 MHz, CDCl$_3$) δ 7.99

(s, 1H), 7.86 (s, 1H), 2.98 (s, 1H), 2.24-1.85 (m, 5H), 1.75-1.43 (m, 4H), 1.41 (s, 9H), 1.29 (s, 12H).

Preparative Example 4.3

Racemic 1-(cyclohex-2-en-1-yl)-4-(4,4,5,5-tetramethyl-1,3,2-dioxaborolan-2-yl)-1H-pyrazole

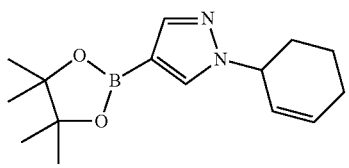 [SMILES: CC1(C)OB(c2cnn(C3C=CCCC3)c2)OC1(C)C]

4-(4,4,5,5-Tetramethyl-1,3,2-dioxaborolan-2-yl)-1H-pyrazole (250 mg, 1.29 mmol), 3-bromocyclohexene (0.17 mL, 1.42 mmol), and cesium carbonate (462 mg, 1.42 mmol) were added to an oven-dried flask, followed by DMF (4.3 mL). The reaction mixture was stirred at 90° C. overnight then cooled to room temperature, diluted with diethyl ether, washed with water (3×50 mL) and brine. The organic layer was dried over sodium sulfate, filtered, and concentrated under reduced pressure to afford 1-(cyclohex-2-en-1-yl)-4-(4,4,5,5-tetramethyl-1,3,2-dioxaborolan-2-yl)-1H-pyrazole. $^1$H NMR (500 MHz, CD$_3$OD) δ 7.82 (s, 1H), 7.69 (s, 1H), 5.81-5.62 (m, 2H), 4.15-4.09 (m, 1H), 2.24-1.41 (m, 6H), 1.31 (s, 12H).

Preparative Example 4.4

Racemic methyl 2,2-dimethyl-4-[4-(4,4,5,5-tetramethyl-1,3,2-dioxaborolan-2-yl)-1H-pyrazol-1-yl]cyclohexanecarboxylate

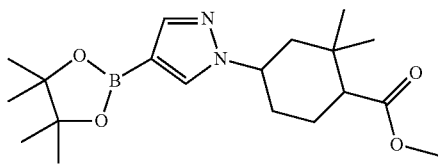

Step 1:
Sodium borohydride (1.85 g, 48.9 mmol) was added to a solution of methyl 2,2-dimethyl-4-oxocyclohexanecarboxylate (3.0 g, 16.3 mmol) in ethanol (65 mL) at −20° C. The solution was stirred at −20° C. for 2 hours. Aqueous hydrochloric acid (1M) was added drop wise and the mixture was extracted with dichloromethane (3×). The combined organic layers were dried over sodium sulfate, filtered, and concentrated under reduced pressure to afford methyl 4-hydroxy-2,2-dimethylcyclohexanecarboxylate. $^1$H NMR (500 MHz, DMSO-d$_6$) δ 3.70-3.58 (m, 1H), 3.54 (s, 3H), 2.16-2.11 (m, 1H), 1.73-1.68 (m, 1H), 1.65-1.48 (m, 4H), 1.07-0.99 (m, 1H), 0.91 (s, 6H).
Step 2:
Methanesulfonyl chloride (1.69 mL, 21.7 mmol) was added at −20° C. to a solution of racemic methyl 4-hydroxy-2,2-dimethylcyclohexanecarboxylate (3.11 g, 16.7 mmol) and triethylamine (4.65 mL, 33.4 mmol) in dichloromethane (67 mL). The reaction was stirred for 3 hours. Saturated aqueous sodium bicarbonate was added to the mixture and extracted with dichloromethane (3×). The combined organic layers were washed with brine, dried over sodium sulfate, filtered and concentrated under reduced pressure to afford methyl 2,2-dimethyl-4-[(methylsulfonyl)oxy]cyclohexanecarboxylate. $^1$H NMR (500 MHz, CDCl$_3$) δ 4.92-4.72 (m, 1H), 3.64 (s, 3H), 2.99 (s, 3H), 2.29-2.15 (m, 1H), 2.15-2.00 (m, 1H), 1.99-1.87 (m, 1H), 1.83-1.71 (m, 2H), 1.63-1.59 (m, 1H), 1.49-1.32 (m, 1H), 1.01 (s, 6H).
Step 3:
4-(4,4,5,5-Tetramethyl-1,3,2-dioxaborolan-2-yl)-1H-pyrazole (700 mg, 3.61 mmol), 2,2-dimethyl-4-[(methylsulfonyl)oxy]cyclohexanecarboxylate (1.50 g, 3.97 mmol), and cesium carbonate (1.29 g, 3.97 mmol) were added to an oven-dried flask. DMF (12 mL) was added and the mixture was stirred at 90° C. for 22 hours. The mixture was cooled to room temperature, diluted with diethyl ether, washed with water (3×50 mL), and then brine. The organic layer was dried over sodium sulfate, filtered, and concentrated under reduced pressure. The residue was purified by column chromatography on silica gel (10 to 80% EtOAc/hexanes) to afford racemic methyl 2,2-dimethyl-4-[4-(4,4,5,5-tetramethyl-1,3,2-dioxaborolan-2-yl)-1H-pyrazol-1-yl]cyclohexanecarboxylate. $^1$H NMR (500 MHz, DMSO-d$_6$) δ 7.91 (s, 1H), 7.54 (s, 1H), 4.10 (q, J=7.3 Hz, 1H), 3.54 (s, 3H), 2.20-1.98 (m, 1H), 1.83-1.65 (m, 2H), 1.64-1.49 (m, 2H), 1.43-1.38 (m, 1H), 1.34-1.31 (m, 1H), 1.22 (s, 12H), 0.90 (s, 6H).

Preparative Example 4.5

Ethyl 3-(4-iodo-1H-pyrazol-1-yl) propanoate

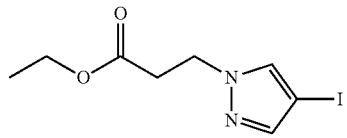

DBU (38.5 mL, 0.26 mol) was added to a stirred solution of 4-iodo-1H-pyrazole (100 g, 0.52 mol) in acetonitrile (1.5 L) at 0° C., followed by drop wise addition of ethyl acrylate (112 mL, 1.03 mol). The reaction mixture was allowed to warm to room temperature and stirred for 2 h. The reaction progress was monitored by TLC. After completion of reaction (TLC), the reaction mixture was concentrated under reduced pressure. The residue was purified by column chromatography on silica gel (0 to 8% EtOAc/petroleum ether) to afford ethyl 3-(4-iodo-1H-pyrazol-1-yl) propanoate. MS ESI calc. for $C_8H_{13}IN_2O_2$ [M+H]$^+$ 250. found 250.

Preparative Example 4.6

Ethyl 3-[4-(4,4,5,5-tetramethyl-1.3.2-dioxaborolan-2-yl)-1H-pyrazol-1-yl]propanoate

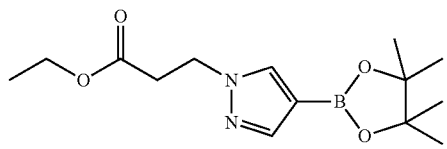 [SMILES: CCOC(=O)CCn1cc(B2OC(C)(C)C(C)(C)O2)cn1]

Potassium acetate (33.3 g, 340 mmol), bis(pinacolato)diboron (30.2 g, 119 mmol) followed by Pd(PPh$_3$)$_4$ (4.91 g, 4.25 mmol) were added to a degassed solution of ethyl 3-(4-iodo-1H-pyrazol-1-yl) propanoate (25.0 g, 85.0 mmol) in anhydrous dimethylsulfoxide (250 mL) under argon atmosphere and stirred for 30 min. The reaction mixture was slowly heated to 80° C. and stirred for 2 h then cooled to room temperature. The mixture was filtered through CELITE and the filtrate was diluted with water (500 mL) and extracted into tertiary butyl methyl ether (2×250 mL). The combined organic layer was washed with brine (200 mL), dried over anhydrous sodium sulfate and concentrated under reduced pressure. The residue was purified by (0 to 15% ethyl acetate/petroleum ether) afford ethyl 3-[4-(4,4,5,5-tetramethyl-1,3,2-dioxaborolan-2-yl)-1H-pyrazol-1-yl]propanoate as a colorless liquid. MS ESI calc. for $C_{14}H_{24}BN_2O_4[M+H]^+$ 295. found 295. $^1$H NMR (300 MHz, DMSO-$d_6$) δ: 7.90 (s, 1H), 7.56 (s, 1H), 4.35 (t, J=6.6 Hz, 2H), 4.04 (q, J=6.9 Hz, 2H), 2.84 (t, J=6.6 Hz, 2H), 1.24 (s, 12H), 1.15 (m, 3H). $^{13}$C NMR (75 MHz, CD$_3$OD) δ: 172.8, 147.0, 139.0, 85.1, 84.5, 76.2, 62.3, 36.1, 25.6, 25.5, 25.4, 14.9.

Preparative Example 4.7

Racemic 1-(2,4-dimethoxybenzyl)-4-{1-[4-(4,4,5,5-tetramethyl-1,3,2-dioxaborolan-2-yl)-1H-pyrazol-1-yl]ethyl}pyrrolidin-2-one

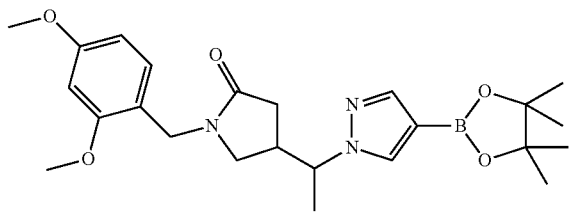

Step 1:

The mixture of 1-(2,4-dimethoxyphenyl)methanamine (5.2 g, 32 mmol) and 2-methylene-succinic acid dimethyl ester (5.0 g, 32 mmol) in MeOH (200 mL) was stirred at 30° C. for 10 hours. The solvent was removed under reduced pressure. The residue was recrystallized by petroleum ether to afford compound methyl 1-(2,4-dimethoxybenzyl)-5-oxopyrrolidine-3-carboxylate. $^1$H NMR (400 MHz, CDCl$_3$) δ 7.13~7.14 (m, 1H), 6.43-6.45 (m, 2H), 4.41-4.42 (m, 2H), 3.79-3.82 (m, 6H), 3.69 (s, 3H), 3.46-3.49 (m, 2H), 3.19-3.23 (m, 2H), 2.70-2.77 (m, 1H). MS ESI calc'd. for $C_{15}H_{20}NO_5$ [M+H]$^+$ 294. found 294.

Step 2:

Isopropylmagnesium chloride (15.3 mL, 30.6 mmol) was added to a solution of 1-(2,4-dimethoxybenzyl)-5-oxopyrrolidine-3-carboxylate (3.0 g, 10 mmol) and O,N-dimethylhydroxylamine (1.5 g, 15 mmol) in THF (100 mL) at −10° C. The mixture was stirred at 0° C. for 1 hour then the mixture was added to water and concentrated under reduced pressure to afford 1-(2,4-dimethoxybenzyl)-N-methoxy-N-methyl-5-oxopyrrolidine-3-carboxamide. $^1$H NMR (400 MHz, CDCl$_3$) δ 7.13-7.15 (m, 1H), 6.43-6.45 (m, 2H), 4.41-4.42 (m, 2H), 3.79-3.82 (m, 6H), 3.67 (s, 3H), 3.46-3.49 (m, 3H), 3.18 (s, 3H), 2.70-2.77 (m, 1H), 2.57-2.63 (m, 1H). MS ESI calc'd. for $C_{16}H_{23}N_2O_5$ [M+H]$^+$ 323. found 323.

Step 3:

MeMgBr (2.3 mL, 6.8 mmol) was added to a mixture of 1-(2,4-dimethoxybenzyl)-N-methoxy-N-methyl-5-oxopyrrolidine-3-carboxamide (2.0 g, 6.2 mmol) in THF (40 mL) at −10° C. The mixture was stirred at 0° C. for 1 hour then diluted with water and the mixture was extracted with EtOAc. The EtOAc layer was dried over sodium sulfate and concentrated under reduced pressure to afford 4-acetyl-1-(2,4-dimethoxybenzyl)pyrrolidin-2-one. $^1$H NMR (400 MHz, CDCl$_3$) δ 7.10-7.13 (m, 1H), 6.43-6.45 (m, 2H), 4.41-4.42 (m, 2H), 3.79-3.82 (m, 6H), 3.46-3.20 (m, 3H), 2.61-2.64 (m, 2H), 2.04-2.15 (d, J=7.2 Hz, 3H). MS ESI calc'd. for $C_{15}H_{20}NO_4$ [M+H]$^+$ 278. found 278.

Step 4:

To a stirred solution of 4-acetyl-1-(2,4-dimethoxybenzyl)pyrrolidin-2-one (1.5 g, 7.2 mmol) in MeOH (15 mL), NaBH$_4$ (400 mg, 10.8 mmol) was added at 0° C. The reaction mixture was stirred at 0° C. for 1 hour then diluted with water and extracted with EtOAc. The organic layers were dried over sodium sulfate and concentrated under reduced pressure to afford 1-(2,4-dimethoxybenzyl)-4-(1-hydroxyethyl)pyrrolidin-2-one. $^1$H NMR (400 MHz, CDCl$_3$) δ 7.10-7.13 (m, 1H), 6.43-6.45 (m, 2H), 4.41-4.42 (m, 2H), 3.79-3.82 (m, 6H), 3.67-3.70 (m, 1H), 3.06-3.46 (m, 2H), 2.03-2.50 (m, 3H), 1.26-1.42 (d, J=7.2 Hz, 3H). MS ESI calc'd. for $C_{15}H_{22}NO_4$ [M+H]$^+$ 280. found 280.

Step 5:

MsCl (3.3 g, 28 mmol) and Et$_3$N (3.8 g, 38 mmol) were added to a mixture of 1-(2,4-dimethoxybenzyl)-4-(1-hydroxyethyl)pyrrolidin-2-one (5.0 g, 19 mmol) in dichloromethane (50 mL) at 0° C. The mixture was stirred at room temperature for 10 hours then diluted with water and extracted with EtOAc. The EtOAc layer was dried over sodium sulfate and concentrated under reduced pressure to afford 1-[1-(2,4-dimethoxybenzyl)-5-oxopyrrolidin-3-yl]ethyl methanesulfonate. $^1$H NMR (400 MHz, CDCl$_3$) δ 7.10~7.13 (m, 1H), 6.43-6.45 (m, 2H), 4.76-4.78 (m, 1H), 4.41-4.42 (m, 2H), 3.79-3.82 (m, 6H), 3.36-3.42 (m, 1H), 3.12-3.19 (m, 1H), 2.98 (s, 3H), 2.23-2.59 (m, 3H), 1.26-1.42 (d, J=7.2 Hz, 3H). MS ESI calc'd. for $C_{16}H_{24}NO_6S$ [M+H]$^+$ 358. found 358.

Step 6:

The mixture of 4-(4,4,5,5-tetramethyl-[1,3,2]dioxaborolan-2-yl)-1H-pyrazole (1.0 g, 5.0 mmol), 1-[1-(2,4-dimethoxybenzyl)-5-oxopyrrolidin-3-yl]ethyl methanesulfonate (1.5 g, 4.2 mmol), NaI (64.0 mg, 0.04 mmol) and K$_2$CO$_3$ (1.2 g, 8.4 mmol) in DMF (15 mL) was stirred at 80° C. for 8 hours. The mixture was then diluted with water and extracted with EtOAc. The EtOAc layer was dried over sodium sulfate and concentrated under reduced pressure to afford racemic 1-(2,4-dimethoxybenzyl)-4-{1-[4-(4,4,5,5-tetramethyl-1,3,2-dioxaborolan-2-yl)-1H-pyrazol-1-yl]

ethyl}pyrrolidin-2-one which was used in next step without purification. MS ESI calc'd. for $C_{24}H_{35}BN_3O_5$ [M+H]$^+$ 456. found 456.

Preparative Example 4.8

Racemic 1-(2,4-dimethoxybenzyl)-4-{[4-(4,4,5,5-tetramethyl-1,3,2-dioxaborolan-2-yl)-1H-pyrazol-1-yl]methyl}pyrrolidin-2-one

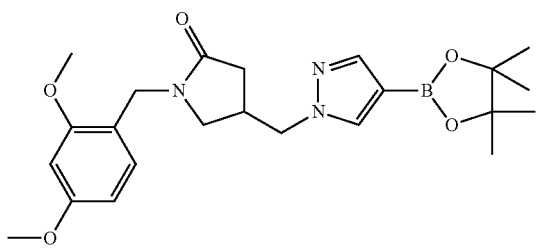

Step 1:

MsCl (3.3 g, 28 mmol) and Et$_3$N (3.8 g, 38 mmol) were added to a mixture of 1-(2,4-dimethoxybenzyl)-4-(hydroxymethyl)pyrrolidin-2-one (5.0 g, 19 mmol) in dichloromethane (50 mL) at 0° C. The mixture was stirred at room temperature for 10 hours then diluted with water and extracted with EtOAc. The EtOAc layer was dried over sodium sulfate and concentrated under reduced pressure to afford [1-(2,4-dimethoxybenzyl)-5-oxopyrrolidin-3-yl]methyl methanesulfonate. $^1$H NMR (400 MHz, CDCl$_3$) δ 7.13-7.15 (m, 1H), 6.43-6.45 (m, 2H), 4.41-4.42 (m, 2H), 4.09-4.14 (m, 2H), 3.79-3.82 (m, 6H), 3.36-3.42 (m, 1H), 3.12-3.19 (m, 1H), 2.98 (s, 3H), 2.62-2.75 (m, 2H), 2.21-2.25 (m, 1H). MS ESI calc'd. for $C_{15}H_{22}NO_6S$ [M+H]$^+$ 344. found 344.

Step 2:

A mixture of [1-(2,4-dimethoxybenzyl)-5-oxopyrrolidin-3-yl]methyl methanesulfonate (1.5 g, 4.2 mmol), 4-(4,4,5,5-Tetramethyl-[1,3,2]dioxaborolan-2-yl)-1H-pyrazole (1.0 g, 5.0 mmol), NaI (64.0 mg, 0.04 mmol) and K$_2$CO$_3$ (1.2 g, 8.4 mmol) in DMF (15 mL) was stirred at 80° C. for 8 hours. The mixture was diluted with water and extracted with EtOAc. The EtOAc layer was dried over sodium sulfate and concentrated under reduced pressure to afford racemic 1-(2,4-dimethoxybenzyl)-4-{[4-(4,4,5,5-tetramethyl-1,3,2-dioxaborolan-2-yl)-1H-pyrazol-1-yl]methyl}pyrrolidin-2-one which was used in next step without purification. MS ESI calc'd. for $C_{23}H_{33}BN_3O_5$ [M+H]$^+$ 442. found 442.

Preparative Example 4.9

4-Bromo-1-(3-methylbut-3-en-2-yl)-1H-pyrazole

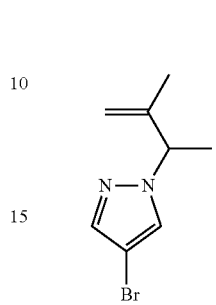

(E)-Di-tert-butyl diazene-1,2-dicarboxylate (940 mg, 4.08 mmol) was added slowly to a stirred solution of 3-methylbut-3-en-2-ol (293 mg, 3.40 mmol), triphenylphosphine (1.07 g, 4.08 mmol), and 4-bromo-1H-pyrazole (500 mg, 3.40 mmol) in THF (10 mL) at 0° C. The reaction was stirred for 10 min at 0° C. and then allowed to warm to RT for 1 hour. The reaction was quenched into water and the product was extracted with ethyl acetate (2×20 mL), dried over anhydrous magnesium sulfate, filtered, and concentrated under reduced pressure to afford an oil. The oil was dissolved in 20% trifluoroacetic acid in dichloromethane (5 mL) and stirred for 20 minutes. The reaction mixture was concentrated under reduced pressure and the residue was dissolved in ethyl acetate, washed with 10% aqueous sodium bicarbonate, dried over anhydrous sodium sulfate, filtered, and concentrated under reduced pressure to afford the crude residue. The crude residue was purified by column chromatography on silica (20-100% ethyl acetate/hexanes) to afford 4-bromo-1-(3-methylbut-3-en-2-yl)-1H-pyrazole. MS ESI calcd. for $C_8H_{12}BrN_2$ [M+H]$^+$ 215 and 217. found 215 and 217.

Preparative Example 4.10

3-(4-Bromo-1H-pyrazol-1-yl)hexane-2,5-diol

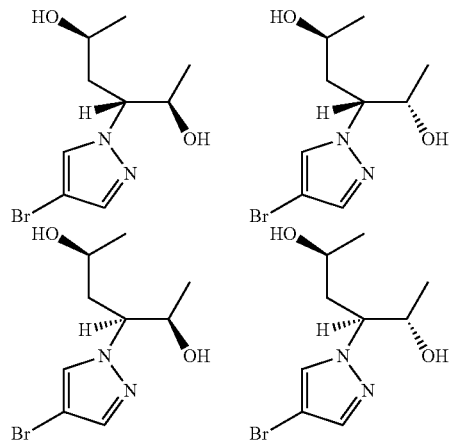

NaBH$_4$ (657 mg, 17.4 mmol) was added to a solution of 3-(4-bromo-1H-pyrazol-1-yl)hexane-2,5-dione (4.5 g, 17.4 mmol) in MeOH (30 mL) and the resulting mixture stirred at room temperature for 2 hours. The mixture was concentrate under reduced pressure, the residue diluted with $CH_2Cl_2$ and washed with hydrochloric acid (aq. 1N). The organic layer was dried with anhydrous magnesium sulfate, filtered, concentrated under reduced pressure. The crude residue was absorbed on silica and purified by column chromatography on silica (0 to 100% EtOAc/Hex) to afford a mixture of diols. The mixture was purified by achiral SFC (ES Basic, 21×250 in series w/ES Pyridyl Amide, 21×250 mm, 10% MeOH w/0.25% DMEA in 90% $CO_2$) to provide 4 raceimc diol products as single diastereomers.

(Isomer 1, first eluting) MS ESI calcd. for $C_9H_{16}BrN_2O_2$ $[M+H]^+$ 263. found 263.

(Isomer 2, second eluting) MS ESI calcd. for $C_9H_{16}BrN_2O_2$ $[M+H]^+$ 263. found 263.

(Isomer 3, third eluting) MS ESI calcd. for $C_9H_{16}BrN_2O_2$ $[M+H]^+$ 263. found 263.

(Isomer 4, fourth eluting) MS ESI calcd. for $C_9H_{16}BrN_2O_2$ $[M+H]^+$ 263. found 263.

Preparative Example 4.11

1-(4-Bromo-1H-pyrazol-1-yl)-2-methylbut-3-en-2-ol

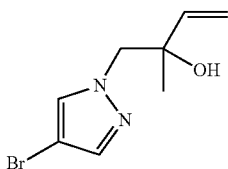

To a cooled (0° C.) solution of 1-(4-bromo-1H-pyrazol-1-yl)propan-2-one (660 mg, 3.25 mmol) in THF (1 mL) was added vinyl magnesium bromide (1M in THF, 3.9 mL, 3.9 mmol) dropwise over 5 min. The resulting mixture was stirred for 1 h, diluted with 0.5 M $HCl_{aq}$ and EtOAc and the layers separated. The organic phase was dried with $MgSO_4$, filtered and concentrated in vacuo, then the crude residue was absorbed on silica gel and purified by column chromatography (0 to 100% EtOAc/Hex) to afford 1-(4-bromo-1H-pyrazol-1-yl)-2-methylbut-3-en-2-ol, MS ESI calcd. for $C_8H_{12}BrN_2O$ $[M+H]^+$ 231. found 231.

Preparative Example 4.12

4-Bromo-1-((2,2-dimethyl-1,3-dioxolan-4-yl)methyl)-1H-pyrazole

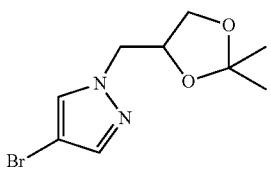

$Cs_2CO_3$ (5.3 g, 16.3 mmol) was added to a solution of 4-bromo-1H-pyrazole (2 g, 13.6 mmol) in DMF (10 mL), followed by 4-(chloromethyl)-2,2-dimethyl-1,3-dioxolane (2.46 g, 16.3 mmol) and the resulting mixture heated to an internal temperature of 65° C. After stirring for 14 h, water and EtOAc was added and the layers separated. The organic layer was washed a second time with water, dried with over anhydorus magnesium sulfate, filtered and concentrated under reduced pressure. The resulting crude residue was absorbed on silica gel and purified by column chromatography on silica (0 to 100% EtOAc/Hex) to afford 4-bromo-1-((2,2-dimethyl-1,3-dioxolan-4-yl)methyl)-1H-pyrazole as a light yellow oil, MS ESI calcd. for $C_9H_{14}BrN_2O_2$ $[M+H]^+$ 261. found 261.

Preparative Example 4.13

1-(4-Bromo-1H-pyrazol-1-yl)propan-2-one and 3-(4-bromo-1H-pyrazol-1-yl)hexane-2,5-dione

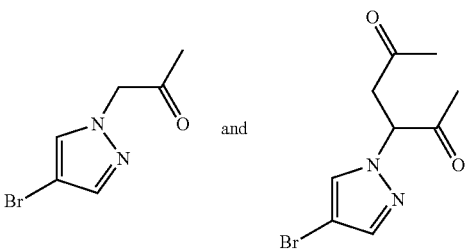

$Cs_2CO_3$ (21.6 g, 66.4 mmol) was added to a cooled (4° C.) solution of 4-bromo-1H-pyrazole (9.76 g, 66.4 mmol) in DMF (30 mL), followed by the slow addition 1-chloropropan-2-one (6.1 g, 66.4 mmol) at such a rate that the internal temperature did not exceed 15° C. The cooling bath was then removed and the yellow mixture stirred at room temperature for 90 min, water and EtOAc were added, the layers separated and the organic washed a second time with water, then dried with anhydorus magnesium sulfate, filtered and concentrated under reduced pressure. The crude residue was absorbed on silica gel and purified by column chromatography on silica (0 to 100% EtOAc/Hex) to afford separately 3-(4-bromo-1H-pyrazol-1-yl)hexane-2,5-dione, MS ESI calcd. for $C_9H_{12}BrN_2O_2$ $[M+H]^+$ 259. found 259, and 1-(4-bromo-1H-pyrazol-1-yl)propan-2-one, MS EIS cald. for $C_6H_8BrN_2O$ $[M+H]^+$ 203. found 203.

Preparative Example 4.14

(S)-3-(4-Iodo-1H-pyrazol-1-yl)-2-methylpropane-1,2-diol

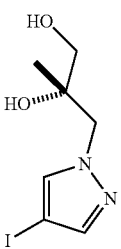

Step 1:

(S)-(2-Methyloxiran-2-yl)methyl 4-nitrobenzoate (2.0 g, 8.4 mmol) and cesium carbonate (4.12 g, 12.7 mmol) were added to a solution of 4-iodo-1H-pyrazole (1.64 g, 8.43 mmol) in DMF (30 mL). The mixture was stirred at room temperature for 14 h, then diluted with EtOAc, and washed with hydrochloric acid (1N). The organic layers were separated, dried over anhydrous magnesium sulfate, filtered, and concentrated under reduced pressure. The residue was purified by column chromatography on silica gel (0-60% EtOAc/Hexane) to afford (S)-2-hydroxy-3-(4-iodo-1H-pyrazol-1-yl)-2-methylpropyl 4-nitrobenzoate. MS ESI calc'd. for $C_{14}H_{15}IN_2O_5$ [M+H]$^+$ 432. found 432.

Step 2:

Sodium hydroxide (3 M in water, 3.25 mL, 9.74 mmol) was added to a solution of (S)-2-hydroxy-3-(4-iodo-1H-pyrazol-1-yl)-2-methylpropyl 4-nitrobenzoate (2.80 g, 6.49 mmol) in acetonitrile (40 mL). The mixture was stirred at room temperature for 1 h, then concentrated under reduced pressure, diluted with EtOAc, and washed with hydrochloric acid (1N), water and brine. The organic layers were separated, dried over anhydrous magnesium sulfate and concentrated under reduced pressure. The residue was purified by column chromatography on silica gel (0-10% MeOH/DCM) to afford (S)-3-(4-iodo-1H-pyrazol-1-yl)-2-methylpropane-1,2-diol. MS ESI calc'd. for $C_7H_{12}N_2O_2$ [M+H]$^+$ 283. found 283. $^1$H NMR (500 MHz, DMSO-d$_6$) δ 7.76 (s, 1H), 7.48 (s, 1H), 4.79 (t, J=5.5 Hz, 1H), 4.53 (s, 1H), 4.09-4.00 (m, 2H), 3.17-3.11 (m, 2H), 0.89 (s, 3H).

Preparative Example 4.15

4-((4-Bromo-1H-pyrazol-1-yl)methyl)benzamide

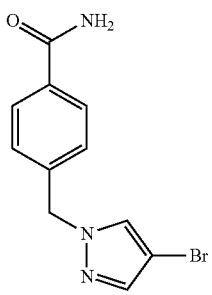 [SMILES: NC(=O)c1ccc(Cn2cc(Br)cn2)cc1]

A mixture of 4-bromo-1H-pyrazole (400 mg, 2.72 mmol), 4-(chloromethyl)benzamide (462 mg, 2.72 mmol), and potassium carbonate (940 mg, 6.80 mmol) in DMF (5 mL) was stirred for 2 hours at 80° C. The reaction mixture was then cooled to ambient temperature and diluted with diethyl ether (400 mL). The mixture was washed with water (2×100 mL) and brine (25 mL). The organic layer was dried over magnesium sulfate, filtered, and concentrated under reduced pressure to afford the crude product residue. The crude product residue was suspended in ethyl acetate (10 mL) and then diluted by the drop wise addition of n-heptane (40 mL). After stirring for 18 hours, the mixture was filtered and the collected solids were washed with n-heptane (3×10 mL). The collected solids were dried under reduced pressure to afford 4-((4-bromo-1H-pyrazol-1-yl)methyl)benzamide. MS ESI calcd. for $C_{11}H_{11}BrN_3O$ [M+H]$^+$ 280 and 282. found 280 and 282. $^1$H NMR (500 MHz, DMSO-d$_6$) δ 8.10 (s, 1H), 7.93 (s, 1H), 7.81 (d, J=8.5 Hz, 2H), 7.57 (s, 1H), 7.35 (s, 1H), 7.26 (d, J=8.0 Hz, 2H), 5.35 (s, 2H).

Preparative Example 4.16

4-((4-Bromo-1H-pyrazol-1-yl)methyl)phenol

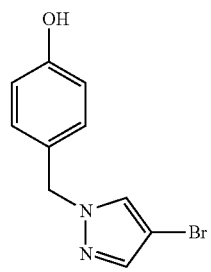 [SMILES: Oc1ccc(Cn2cc(Br)cn2)cc1]

A mixture of 4-bromo-1H-pyrazole (500 mg, 3.40 mmol), 4-(chloromethyl)phenyl acetate (659 mg, 3.57 mmol), and potassium carbonate (1.18 g, 8.50 mmol) was diluted with DMF (5 mL) at ambient temperature. The reaction mixture was heated to 40° C. for 4 hours. The reaction mixture was then diluted with sodium hydroxide (2.0 M in water, 3.40 mL, 6.80 mmol) and stirred for an additional 30 minutes at 40° C. The reaction mixture was then cooled to ambient temperature and diluted with ethyl acetate (200 mL) and saturated aqueous ammonium chloride solution (50 mL). The organic layer was separated and washed with water (50 mL) and then brine (25 mL). The organic layer was separated, dried over anhydrous magnesium sulfate, filtered, and concentrated under reduced pressure to afford the crude product residue. The crude product residue was purified by column chromatography on silica (0-100% ethyl acetate/hexanes) to afford 4-((4-bromo-1H-pyrazol-1-yl)methyl)phenol. MS ESI calc'd. for $C_{10}H_{10}BrN_2O$ [M+H]$^+$ 253 and 255. found 253 and 255. $^1$H NMR (500 MHz, DMSO-d$_6$) δ 9.45 (s, 1H), 7.98 (s, 1H), 7.51 (s, 1H), 7.08 (d, J=8.5 Hz, 2H), 6.69 (dd, J=7.0 Hz, 2.0 Hz, 2H), 5.14 (s, 2H).

Preparative Example 4.17

1-(2,3-Dimethylbut-2-en-1-yl)-4-(4,4,5,5-tetramethyl-1,3,2-dioxaborolan-2-yl)-1H-pyrazole

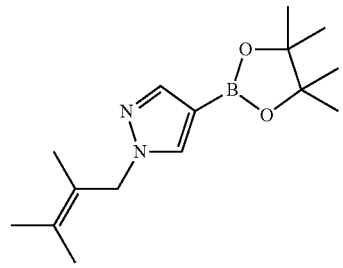 [SMILES: CC(C)=C(C)Cn1cc(B2OC(C)(C)C(C)(C)O2)cn1]

1-Bromo-2,3-dimethylbut-2-ene (3.78 g, 23.19 mmol), and cesium carbonate (15.11 g, 46.4 mmol) were added to a solution of 4-(4,4,5,5-tetramethyl-1,3,2-dioxaborolan-2-yl)-1H-pyrazole (3.0 g, 15.46 mmol) in DMF (52 mL), and the mixture was stirred at 90° C. for 18 h. The mixture was allowed to cool to room temperature, diluted with diethyl ether, washed with water (3×50 mL) and brine. The organic layers were separated, dried over anhydrous magnesium sulfate and concentrated under reduced pressure. The residue was purified by column chromatography on silica gel (0-40% EtOAc/hexane) to afford 1-(2,3-dimethylbut-2-en-1-yl)-4-(4,4,5,5-tetramethyl-1,3,2-dioxaborolan-2-yl)-1H-pyrazole. $^1$H NMR (500 MHz, CDCl$_3$) δ 7.79 (s, 1H), 7.62 (s, 1H), 4.74 (s, 2H), 1.83 (s, 3H), 1.74 (s, 3H), 1.59 (s, 3H), 1.31 (s, 12H).

Preparative Example 4.18 tert-Butyl (2S)-2-[(4-bromo-1H-pyrazol-1-yl)methyl]morpholine-4-carboxylate

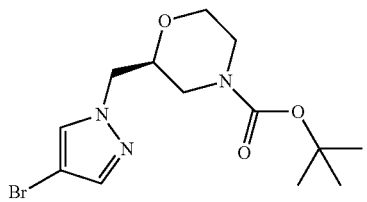 [SMILES: CC(C)(C)OC(=O)N1CCO[C@H](Cn2cc(Br)cn2)C1]

Tetrahydrofuran was added to a mixture of (S)-tert-butyl 2-(hydroxymethyl)morpholine-4-carboxylate (250 mg, 1.15 mmol), 4-bromo-1H-pyrazole (186 mg, 1.27 mmol), di-tert-butyl azodicarboxylate (530 mg, 2.30 mmol), and triphenylphosphine resin (3 mmol/g loading, 601 mg, 2.30 mmol) under argon. The resulting suspension was stirred for 8 days and then filtered through CELITE. The supernatant was concentrated under reduced pressure, and the residue was purified by chromatography on silica gel (5-100% ethyl acetate/hexanes) to afford tert-butyl (2S)-2-[(4-bromo-1H-pyrazol-1-yl)methyl]morpholine-4-carboxylate. ESI calc'd. for C$_9$H$_{13}$BrN$_3$O$_3$ [M+H t-Bu]$^+$ 289 and 291. found 289 and 291. $^1$H NMR (500 MHz, CDCl$_3$) δ 7.49 (s, 1H), 7.46 (s, 1H), 4.22-4.08 (m, 2H), 4.04-3.78 (m, 3H), 3.76-3.69 (br s, 1H), 3.52-3.46 (m, 1H), 2.99-2.82 (br s, 1H), 2.63-2.51 (br s, 1H), 1.45 (s, 9H).

The intermediates in the following table were prepared according to the method described for Preparative Example 4.18.

Preparative Example 4.20

Methyl 4-{1-[4-(4,4,5,5-tetramethyl-1,3,2-dioxaborolan-2-yl)-1H-pyrazol-1-yl]ethyl}benzoate

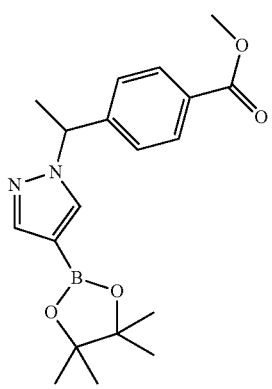 [SMILES: COC(=O)c1ccc(C(C)n2cc(B3OC(C)(C)C(C)(C)O3)cn2)cc1]

The mixture of 4-(4,4,5,5-tetramethyl-[1,3,2]dioxaborolan-2-yl)-1H-pyrazole (0.20 g, 1.0 mmol), methyl 4-(1-chloroethyl)benzoate (0.2 g, 1.0 mmol), potassium carbonate (0.28 g, 2.0 mmol), and 18-crown-6 (3 mg) in DMF (5 mL) was stirred at 80° C. for 8 hours. After cooling to room temperature, the mixture was diluted with water and extracted with ethyl acetate. The organic layer was dried over sodium sulfate, filtered, and concentrated to afford methyl 4-{1-[4-(4,4,5,5-tetramethyl-1,3,2-dioxaborolan-2-yl)-1H-pyrazol-

| Prep. Ex. | Structure | Chemical Name | Exact Mass [M + H]+ | [M + H]+ Found |
|---|---|---|---|---|
| 4.19 | 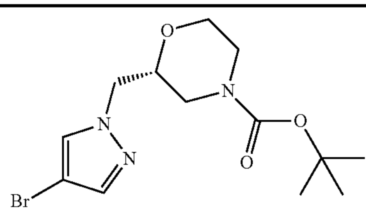 | (R)-tert-butyl 2-((4-bromo-1H-pyrazol-1-yl)methyl)morpholine-4-carboxylate | 289/291 | 289/291 |

1-yl]ethyl}benzoate, which was used in next step without purification. MS ESI calc'd. for $C_{19}H_{26}BN_2O_4$ [M+H]$^+$ 357. found 357.

Preparative Example 4.21

Ethyl 4-[4-(4,4,5,5-tetramethyl-1,3,2-dioxaborolan-2-yl)-1H-pyrazol-1-yl]cyclohexanecarboxylate

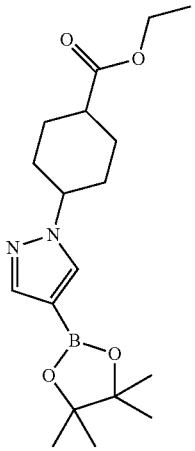 [SMILES: CCOC(=O)C1CCC(n2cc(B3OC(C)(C)C(C)(C)O3)cn2)CC1]

Step 1:

Cesium carbonate (1.96 g, 6 mmol) and 4-bromopyrazole (321 mg, 2.2 mmol) were added to a solution of ethyl 4-[(methylsulfonyl)oxy]cyclohexanecarboxylate (0.50 g, 2 mmol) in DMF (10 mL). The mixture was stirred at 80° C. for 16 hours. Upon cooling to room temperature, the mixture was diluted with water and extracted with ethyl acetate. The organic layer was dried over sodium sulfate, filtered, and concentrated under reduced pressure. The residue was purified by chromatography on silica gel (ethyl acetate/petroleum ether) to give ethyl 4-(4-bromo-1H-pyrazol-1-yl)cyclohexanecarboxylate. MS ESI calc'd. for $C_{12}H_{18}BrN_2O_2$ [M+H]$^+$ 301 and 303. found 301 and 303. $^1$H NMR (400 MHz, CDCl$_3$): δ 7.45 (s, 1H), 7.44 (s, 1H), 4.23 (q, J=7.2 Hz, 2H), 2.46-2.38 (m, 1H), 2.26-2.18 (m, 4H), 2.06-1.98 (m, 2H), 1.86-1.78 (m, 3H), 1.36 (t, J=7.2 Hz, 3H).

Step 2:

Bis(pinacolato)diboron (213 mg, 0.84 mmol), potassium acetate (137 mg, 1.4 mmol), and [1,1'-bis(diphenylphosphino)ferrocene]dichloropalladium(II), complex with dichloromethane (51 mg, 0.07 mmol) were added to a solution of ethyl 4-(4-bromo-1H-pyrazol-1-yl)cyclohexanecarboxylate (210 mg, 0.7 mmol) in dioxane (5 mL). The mixture was stirred under nitrogen at 110° C. for 12 hours. After cooling to room temperature, the mixture was diluted with water and extracted with ethyl acetate. The organic layer was dried over sodium sulfate, filtered, and concentrated under reduced pressure. The residue was purified by chromatography on silica gel (ethyl acetate/petroleum ether) to give ethyl 4-[4-(4,4,5,5-tetramethyl-1,3,2-dioxaborolan-2-yl)-1H-pyrazol-1-yl]cyclohexanecarboxylate (132 mg, yield: 54%). MS ESI calc'd. for $C_{18}H_{30}BN_2O_4$ [M+H]$^+$ 349. found 349. $^1$H NMR (400 MHz, DMSO-d$_6$): δ 7.90 (s, 1H), 7.62 (s, 1H), 4.26-4.18 (m, 1H), 4.13 (q, J=7.2 Hz, 2H) 2.36-2.34 (m, 1H), 2.26-1.98 (m, 4H), 1.66-1.58 (m, 4H), 1.26 (s, 12H), 1.21 (t, J=7.2 Hz, 3H).

Preparative Example 4.22

Methyl 4-(4-bromo-1H-pyrazol-1-yl)-2,2-dimethyl-cyclohexanecarboxylate

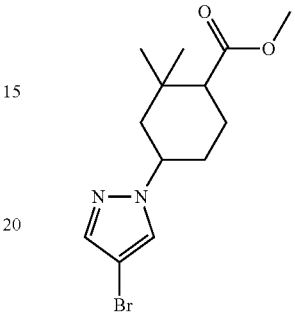

Step 1:

Sodium borohydride (6.19 g, 163 mmol) was added in portions at 0° C. to a solution of methyl 2,2-dimethyl-4-oxocyclohexanecarboxylate (10.0 g, 54.3 mmol) in methanol (200 mL). The mixture was stirred at room temperature for 30 minutes. Then the mixture was diluted with water and extracted with ethyl acetate. The organic layer was dried over sodium sulfate, filtered, and concentrated under reduced pressure to give methyl 4-hydroxy-2,2-dimethylcyclohexanecarboxylate. $^1$H NMR (400 MHz, CDCl$_3$): δ 3.89-3.84 (m, 1H), 3.65 (s, 3H), 2.21 (s, 1H), 1.79-1.73 (m, 1H), 1.70-1.68 (m, 3H), 1.49-1.35 (m, 2H), 1.06 (s, 6H).

Step 2:

Methanesulfonyl chloride (2.6 g, 22 mmol) and triethylamine (2.4 g, 22 mmol) were added to a solution of methyl 4-hydroxy-2,2-dimethylcyclohexanecarboxylate (1.38 g, 7.4 mmol) in dichloromethane (30 mL) at 0° C. The mixture was stirred at room temperature for 16 hours. Then the mixture was diluted with water and extracted with ethyl acetate. The ethyl acetate layer was dried over sodium sulfate, filtered, and concentrated under reduced pressure. The residue was purified by chromatography on silica gel (ethyl acetate/petroleum ether) to give methyl 2,2-dimethyl-4-[(methylsulfonyl)oxy] cyclohexanecarboxylate. $^1$H NMR (400 MHz, CDCl$_3$): δ 5.30-4.78 (m, 1H), 3.65 (s, 3H), 3.05 (s, 3H), 2.25-2.21 (m, 1H), 2.19-2.13 (m, 2H), 1.90-1.88 (m, 1H), 1.79-1.75 (m, 2H), 1.63 (s, 1H), 1.06 (s, 6H).

Step 3:

Cesium carbonate (2.93 g, 9 mmol) and 4-bromopyrazole (482 mg, 3.3 mmol) were added to a solution of methyl 2,2-dimethyl-4-[(methylsulfonyl)oxy]cyclohexanecarboxylate (0.79 g, 3 mmol) in DMF (10 mL). The mixture was stirred at 80° C. for 16 hours. Then the mixture was diluted with water and extracted with ethyl acetate. The organic layer was dried over sodium sulfate, filtered, and concentrated under reduced pressure. The residue was purified by chromatography on silica gel (ethyl acetate/petroleum ether) to give methyl 4-(4-bromo-1H-pyrazol-1-yl)-2,2-dimethylcyclohexanecarboxylate. MS ESI calc'd. for $C_{13}H_{20}BrN_2O_2$ [M+H]$^+$ 315 and 317. found 315 and 317. $^1$H NMR (400 MHz, CDCl$_3$): δ 7.35 (s, 1H), 7.22 (s, 1H), 4.53-4.50 (m, 1H), 3.69 (s, 3H), 2.26-2.18 (m, 1H), 2.06-1.78 (m, 4H), 1.36-1.28 (m, 2H), 1.06 (s, 3H), 0.97 (s, 3H).

Preparative Example 4.23

5-[(4-Iodo-1H-pyrazol-1-yl)methyl]-1,3-oxazolidin-2-one, isomer 1 and isomer 2

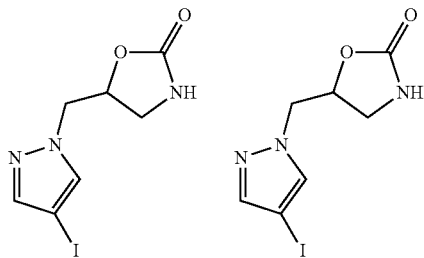 [SMILES: O=C1NCC(Cn2cc(I)cn2)O1 ; O=C1NCC(Cn2cc(I)cn2)O1]

A mixture of potassium phosphate tribasic (6.57 g, 30.9 mmol), 4-iodo pyrazole (2.00 g, 10.3 mmol), and 5-(chloromethyl)-1,3-oxazolidin-2-one (2.80 g, 20.6 mmol) in 1,4-dioxane (103 mL) was sealed in a pressure vessel and heated for 72 hours at 110° C. Upon cooling to room temperature, the mixture was diluted with water and dichloromethane. The organic layer was separated, washed with water, and concentrated under reduced pressure. The residue was triturated with a mixture of methanol and hexanes for several hours at room temperature, and then the precipitate was collected by filtration to afford 5-[(4-iodo-1H-pyrazol-1-yl)methyl]-1,3-oxazolidin-2-one. MS ESI calc'd. for $C_7H_8IN_3O_2$ [M+H]$^+$ 294. found 294. The enantiomers were separated by chiral SFC (supercritical fluid chromatography), IC column with 20% isopropyl alcohol in $CO_2$ to give isomer 1 (faster eluting) and isomer 2 (slower eluting).

Preparative Example 4.24

1-(2,4-Dimethoxybenzyl)-4-[(4-iodo-1H-pyrazol-1-yl)methyl]-4-methylpyrrolidin-2-one

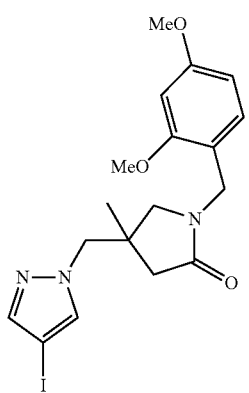 [SMILES: COc1ccc(CN2CC(C)(Cn3cc(I)cn3)CC2=O)c(OC)c1]

Step 1:

Sodium hydride (327 mg, 13.6 mmol) ws added to a solution of methyl 1-(2,4-dimethoxybenzyl)-5-oxopyrrolidine-3-carboxylate (2.0 g, 6.8 mmol) in THF (50 mL) at 0° C. The mixture was stirred at room temperature for 2 hours. Then the mixture was added methyl iodide (4.8 g, 34 mmol) dropwise at 0° C. The mixture was stirred at room temperature for 16 hours and then was diluted with water and extracted with ethyl acetate. The organic layer was dried over sodium sulfate, filtered, and concentrated under reduced pressure. The residue purified by chromatography on silica gel (ethyl acetate/petroleum ether) to give methyl 1-(2,4-dimethoxybenzyl)-3-methyl-5-oxopyrrolidine-3-carboxylate. MS ESI calc'd. for $C_{16}H_{22}NO_5$ [M+H]$^+$ 308. found 308. $^1$H NMR (400 MHz, CD$_3$OD): δ 7.11 (d, J=8.8 Hz, 1H), 6.56 (s, 1H), 6.50 (d, J=8.8 Hz, 1H), 4.39 (s, 2H), 3.82 (s, 3H), 3.80 (s, 3H), 3.68 (s, 3H), 3.64 (d, J=16.8 Hz, 1H), 3.10 (d, J=16.8 Hz, 1H), 2.93 (d, J=16.8 Hz, 1H), 2.32 (d, J=16.8 Hz, 1H), 1.33 (s, 3H).

Step 2:

Lithium borohydride (28 mg, 1.3 mmol) was added to a solution of methyl 1-(2,4-dimethoxybenzyl)-3-methyl-5-oxopyrrolidine-3-carboxylate (200 mg, 0.65 mmol) in THF (2 mL) at 0° C. The mixture was stirred at room temperature for 16 hours and then diluted with water and extracted with ethyl acetate. The organic layer was dried over sodium sulfate, filtered, and concentrated under reduced pressure. The residue was purified by chromatography on silica gel (ethyl acetate/petroleum ether) to give 1-(2,4-dimethoxybenzyl)-4-(hydroxymethyl)-4-methylpyrrolidin-2-one. MS ESI calc'd. for $C_{15}H_{22}NO_4$ [M+H]$^+$ 280. found 280. $^1$H NMR (400 MHz, CD$_3$OD): δ 7.08 (d, J=8.4 Hz, 1H), 6.52 (s, 1H), 6.46 (d, J=8.4 Hz, 1H), 4.40-4.31 (m, 2H), 3.79 (s, 3H), 3.77 (s, 3H), 3.30-3.20 (m, 3H), 2.88-2.86 (m, 1H), 2.43 (d, J=16.8 Hz, 1H), 2.08 (d, J=16.8 Hz, 1H), 1.04 (s, 3H).

Step 3:

Methanesulfonyl chloride (305 mg, 2.65 mmol) and triethylamine (540 mg, 5.35 mmol) were added to a solution of 1-(2,4-dimethoxybenzyl)-4-(hydroxymethyl)-4-methylpyrrolidin-2-one (500 mg, 1.75 mmol) in DCM (5 mL) at 0° C. The mixture was stirred at room temperature for 16 hours and then diluted with water and extracted with ethyl acetate. The organic layer was dried over sodium sulfate, filtered, and concentrated under reduced pressure. The residue was purified by chromatography on silica gel (ethyl acetate/petroleum ether) to give [1-(2,4-dimethoxybenzyl)-3-methyl-5-oxopyrrolidin-3-yl]methyl methanesulfonate. MS ESI calc'd. for $C_{16}H_{24}NO_6S$ [M+H]$^+$ 358. found 358. $^1$H NMR (400 MHz, CDCl$_3$): δ 7.15 (d, J=8.4 Hz, 1H), 6.46-6.44 (m, 2H), 4.41 (s, 2H), 4.02-3.96 (m, 2H), 3.81 (s, 3H), 3.80 (s, 3H), 3.22 (d, J=6.4 Hz, 1H), 2.99-2.95 (m, 4H), 2.41 (d, J=16.8 Hz, 1H), 2.24 (d, J=16.8 Hz, 1H), 1.19 (s, 3H).

Step 4:

A mixture of 4-iodo-1H-pyrazole (270 mg, 1.4 mmol), [1-(2,4-dimethoxybenzyl)-3-methyl-5-oxopyrrolidin-3-yl] methyl methanesulfonate (500 mg, 1.4 mmol), cesium carbonate (910 mg, 2.8 mmol), and potassium iodide (10 mg, 0.05 mmol) in DMF (80 mL) was stirred at 80° C. for 12 hours. The mixture was diluted with water and extracted with ethyl acetate. The organic layer was dried over sodium sulfate, filtered, and concentrated under reduced pressure. The residue was purified by chromatography on silica gel (ethyl acetate/petroleum ether) to give 1-(2,4-Dimethoxybenzyl)-4-[(4-iodo-1H-pyrazol-1-yl)methyl]-4-methylpyrrolidin-2-one. MS ESI calc'd. for $C_{18}H_{23}IN_3O_3$ [M+H]$^+$ 456. found 456. $^1$H NMR (400 MHz, MeOD): δ 7.49 (s, 1H), 7.44 (s, 1H), 7.05 (d, J=8 Hz, 1H), 6.54 (d, J=2.4 Hz, 1H), 6.49-6.47 (m, 1H), 4.30 (d, J=4 Hz, 2H), 4.06 (d, J=2 Hz, 2H), 3.78 (s, 6H), 3.33-3.29 (m, 1H), 2.91 (d, J=6.4 Hz, 1H), 2.54 (d, J=16.8 Hz, 1H), 2.17 (d, J=16.8 Hz, 1H), 1.01 (s, 3H).

Preparative Example 4.25 rac-(4R,5R)-4-[(4-iodo-1H-pyrazol-1-yl)methyl]-1-(4-methoxybenzyl)-5-methylpyrrolidin-2-one

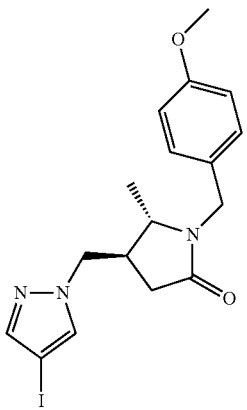 [SMILES: COc1ccc(CN2C(=O)C[C@@H](Cn3cc(I)cn3)[C@@H]2C)cc1]

Step 1:

Ethyl rac-(2R,3S)-2-methyl-5-oxopyrrolidine-3-carboxylate (30 g, 0.18 mol) in DMF (100 mL) was carefully added to a suspension of sodium hydride (7.6 g, 0.19 mol, 60% in mineral oil) in DMF (400 mL) at 0° C. The resulting mixture was stirred for 1 hour before 4-methoxybenzyl chloride (32.8 g, 28.5 mL, 0.21 mol) was added dropwise, followed by tert-butylammonium iodide (13 g, 35 mmol). The reaction mixture was stirred at room temperature for 10 hours and then quenched by adding saturated aqueous ammonium chloride solution (30 mL). The reaction mixture was diluted with water (100 mL) and extracted with ethyl acetate (500 mL×3). The combined organic layers were washed with brine (100 mL), dried over sodium sulfate, filtered, and concentrated under reduced pressure to afford the crude product, which was purified by chromatography on silica gel (ethyl acetate/petroleum ether) to afford ethyl rac-(2R,3S)-1-(4-methoxybenzyl)-2-methyl-5-oxopyrrolidine-3-carboxylate. MS ESI calc'd. for $C_{16}H_{22}NO_4$ [M+H]$^+$ 292. found 292. $^1$H NMR (CDCl$_3$, 400 MHz) δ: 7.13 (d, J=8.4 Hz, 2H), 6.82 (d, J=8.4 Hz, 2H), 4.91 (d, J=14.4 Hz, 1H), 4.08-4.15 (m, 2H), 3.89 (d, J=14.4 Hz, 1H), 3.76 (s, 3H), 3.62-3.63 (m, 1H), 2.71 (s, 3H), 1.18-1.26 (m, 6H).

Step 2:

Lithium borohydride (3.5 g, 0.16 mol) in THF (50 mL) was slowly added dropwise to a solution of ethyl rac-(2R,3S)-1-(4-methoxybenzyl)-2-methyl-5-oxopyrrolidine-3-carboxylate (18.5 g, 0.064 mol) in THF (350 mL) at 0° C. The reaction mixture was allowed to stir at room temperature for 16 hours and then quenched by the slow addition of saturated aqueous ammonium chloride solution (30 mL). After removal of THF under reduced pressure, the mixture was diluted with water (100 mL) and extracted with ethyl acetate (300 mL×3). The combined organic layers were dried over sodium sulfate, filtered, and concentrated under reduced pressure. The residue was purified by chromatography on silica gel (ethyl acetate/petroleum ether) to give rac-(4R,5S)-4-(hydroxymethyl)-1-(4-methoxybenzyl)-5-methylpyrrolidin-2-one. MS ESI calc'd. for $C_{14}H_{20}NO_3$ [M+H]$^+$ 250. found 250. $^1$H NMR (CDCl$_3$, 400 MHz): δ 7.10 (d, J=8.4 Hz, 2H), 6.79 (d, J=8.4 Hz, 2H), 4.83 (d, J=14.8 Hz, 1H), 3.85 (d, J=14.8 Hz, 1H), 3.74 (s, 3H), 3.47 (d, J=6.4 Hz, 2H), 3.30-3.27 (m, 1H), 2.76 (s, br, 1H), 2.58-2.52 (m, 1H), 2.24-2.18 (m, 1H), 2.06-2.02 (m, 1H), 1.15 (d, J=6.4 Hz, 3H).

Step 3:

Triethylamine (1.47 g, 14.57 mmol) and methanesulfonyl chloride (1.25 g, 10.93 mmol) were added to a solution of rac-(4R,5S)-4-(hydroxymethyl)-1-(4-methoxybenzyl)-5-methylpyrrolidin-2-one (1.8 g, 7.29 mmol) in DCM (36 mL) at 0° C. The mixture was stirred at 0° C. for 1 hour, and then water (70 mL) was added and the mixture was extracted with ethyl acetate (100 mL×3). The combined organic layers were dried over sodium sulfate, filtered, and concentrated under reduced pressure. The residue was purified by chromatography on silica gel (ethyl acetate/petroleum ether) to afford [(2R,3S)-1-(4-methoxybenzyl)-2-methyl-5-oxopyrrolidin-3-yl]methyl rac-methanesulfonate. MS ESI calc'd. for $C_{15}H_{22}NO_5S$ [M+H]$^+$ 328. found 328. $^1$H NMR (400 MHz, CDCl$_3$): δ 7.17 (d, J=8.4 Hz, 2H), 6.86 (d, J=8.4 Hz, 2H), 4.96-4.91 (m, 1H), 4.10-4.05 (m, 2H), 3.91-3.86 (m, 1H), 3.81 (s, 3H), 3.36-3.30 (m, 1H), 2.92 (s, 3H), 2.76-2.68 (m, 1H), 2.39-2.29 (m, 1H), 2.27-2.20 (m, 1H), 1.24 (d, J=6.4 Hz, 3H).

Step 4:

4-Iodo-1H-pyrazole (0.93 g, 4.77 mmol) and cesium carbonate (2.59 g, 7.95 mmol) were added to a solution of [(2R,3S)-1-(4-methoxybenzyl)-2-methyl-5-oxopyrrolidin-3-yl]methyl rac-methanesulfonate (1.3 g, 3.98 mmol) in DMF (26 mL). The mixture was stirred at 90° C. under a nitrogen atmosphere for 3 hours. After cooling to room temperature, the mixture was diluted with water (50 mL) and extracted with ethyl acetate (100 mL×3). The combined organic layers were dried over sodium sulfate, filtered, and concentrated under reduced pressure. The residue was purified by chromatography on silica gel (ethyl acetate/petroleum ether) to afford rac-(4R,5R)-4-[(4-iodo-1H-pyrazol-1-yl)methyl]-1-(4-methoxybenzyl)-5-methylpyrrolidin-2-one. MS ESI calc'd. for $C_{17}H_{21}IN_3O_2$ [M+H]$^+$ 426. found 426. $^1$H NMR (400 MHz, CDCl$_3$): δ 7.47 (s, 1H), 7.17 (d, J=8.5 Hz, 2H), 6.95 (s, 1H), 6.90 (d, J=8.5 Hz, 2H), 4.99-4.94 (m, 1H), 4.02-3.99 (m, 1H), 3.90-3.85 (m, 1H), 3.85 (s, 3H), 3.82-3.79 (m, 1H), 3.15-3.06 (m, 1H), 2.69-2.63 (m, 1H), 2.58-2.48 (m, 1H), 2.18-2.09 (m, 1H), 1.06 (d, J=6.5 Hz, 3H).

Preparative Example 4.26

3-((4-Iodo-1H-pyrazol-1-yl)methyl)pyrrolidine-2,5-dione, Isomer 1 and Isomer 2

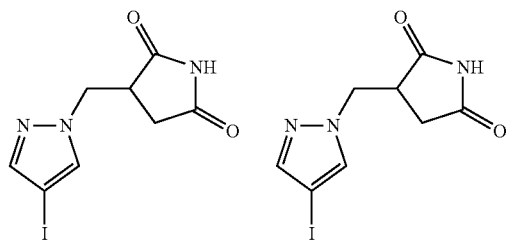

Step 1:

1,8-Diazabicyclo[5.4.0]undec-7-ene (753 mg, 3 mmol) was added to a stirred mixture of dimethyl 2-methylenesuccinate (158 mg, 1.00 mmol) and 4-iodo-1H-pyrazole (194 mg, 1.00 mmol) in acetonitrile (2 mL) and the mixture was stirred at room temperature under $N_2$ for 12 hours. The mixture was diluted with water and extracted with EtOAc. The EtOAc layer was dried over anhydrous sodium sulfate, filtered, and concentrated under reduced pressure. The residue was purified by prep-TLC on silica gel (petroleum ether/EtOAc) to afford dimethyl 2-((4-iodo-1H-pyrazol-1-yl)methyl)succinate. MS ESI calcd. for $C_{10}H_{14}IN_2O_4$ [M+H]$^+$ 353, found 353. $^1$H NMR (400 MHz, CDCl$_3$) δ 7.52 (s, 1H), 7.39 (s, 1H), 4.55-4.36 (m, 2H), 3.72 (s, 3H), 3.68 (s, 3H), 3.42-3.33 (m, 1H), 2.70-2.47 (m, 2H).

Step 2:

A solution of dimethyl 2-((4-iodo-1H-pyrazol-1-yl)methyl)succinate (200 mg, 0.61 mmol) and lithium hydroxide (40 mg, 1.80 mmol) in THF/water (4 mL/1 mL) was stirred at 60° C. for 12 hours. After cooling to room temperature, the mixture was diluted with water and extracted with EtOAc. The organic layer was dried over anhydrous sodium sulfate, filtered, and concentrated under reduced pressure to afford 2-((4-iodo-1H-pyrazol-1-yl)methyl)succinic acid. MS ESI calc'd. for $C_8H_{10}IN_2O_4$ [M+H]$^+$ 325. found 325. $^1$H NMR (400 MHz, CD$_3$OD) δ 7.76 (s, 1H), 7.50 (s, 1H), 4.60-4.48 (m, 2H), 3.46-3.38 (m, 1H), 2.83-2.73 (m, 1H), 2.60-2.51 (m, 1H).

Step 3:

The solution of 2-((4-iodo-1H-pyrazol-1-yl)methyl)succinic acid (170 mg, 0.52 mmol) and urea (72 mg, 1.50 mmol) was stirred neat at 130° C. for 12 hours. After cooling to room temperature, the mixture was diluted with water and extracted with EtOAc. The organic layer was dried over anhydrous sodium sulfate, filtered, and concentrated under reduced pressure to afford 3-((4-iodo-1H-pyrazol-1-yl)methyl)pyrrolidine-2,5-dione. MS ESI calc'd. for $C_8H_9IN_3O_2$ [M+H]$^+$ 306. found 306. $^1$H NMR (400 MHz, CD$_3$OD) δ 7.70 (s, 1H), 7.50 (s, 1H), 4.62-4.43 (m, 2H), 3.48-3.37 (m, 1H), 2.85-2.68 (m, 1H), 2.61-2.49 (m, 1H).

The racemic mixture was purified by chiral SFC (ethanol/CO$_2$) to afford (R or S)-3-((4-iodo-1H-pyrazol-1-yl)methyl)pyrrolidine-2,5-dione (Isomer 1, first eluting) and (R or S)-3-((4-iodo-1H-pyrazol-1-yl)methyl)pyrrolidine-2,5-dione (Isomer 2, second eluting).

Preparative Example 4.27

4-Hydroxy-4-((4-iodo-1H-pyrazol-1-yl)methyl)pyrrolidin-2-one

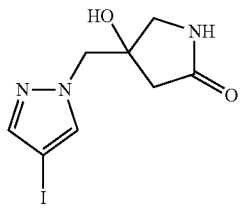 [SMILES: O=C1CC(O)(Cn2cc(I)cn2)CN1]

Step 1:

Sodium hydride (6 g, 250 mmol, 60 wt % in mineral oil) was added to mixture of 4-iodo-1H-pyrazole (10 g, 50 mmol) in THF (200 mL) at room temperature under $N_2$. The mixture was stirred at room temperature for 1 hour. Ethyl 4-chloro-3-oxobutanoate (11.6 g, 75 mmol) was added and the mixture was stirred at room temperature for 12 hours. The mixture was diluted with water and extracted with EtOAc. The organic layer was dried over anhydrous sodium sulfate, filtered, and concentrated under reduced pressure. The residue was purified by column chromatography on silica gel (petroleum ether: EtOAc) to afford ethyl 4-(4-iodo-1H-pyrazol-1-yl)-3-oxobutanoate. MS ESI calc'd. for $C_9H_{12}IN_2O_3$ [M+H]$^+$ 323. found 323. $^1$H NMR (400 MHz, CDCl$_3$) δ 7.57 (s, 1H), 7.48 (s, 1H), 5.05 (s, 2H), 4.19-4.15 (m, 2H), 3.40 (s, 2H), 1.28-1.24 (m, 3H).

Step 2:

Trimethylsilyl cyanide (3.0 g, 30 mmol) was added to a mixture of ethyl 4-(4-iodo-1H-pyrazol-1-yl)-3-oxobutanoate (8 g, 25 mmol), triphenylphosphine (195 mg, 0.75 mmol) and methyl acrylate (64 mg, 0.75 mmol) in chloroform (100 mL) at 0° C. under $N_2$. The mixture was allowed to warm to room temperature and was stirred at room temperature for 12 hours. The mixture was diluted with water and extracted with EtOAc. The organic layer was dried over anhydrous sodium sulfate, filtered, and concentrated under reduced pressure. The residue was purified by column chromatography on silica gel (petroleum ether: EtOAc) to afford ethyl 3-cyano-4-(4-iodo-1H-pyrazol-1-yl)-3-((trimethylsilyl)oxy)butanoate. MS ESI calc'd. for $C_{13}H_{21}IN_3O_3Si$ [M+H]$^+$ 422. found 422. $^1$H NMR (400 MHz, CDCl$_3$) δ 7.57 (d, J=4.4 Hz, 2H), 4.65-4.56 (m, 2H), 4.26-4.19 (m, 2H), 2.78-2.69 (m, 2H), 1.32-1.28 (m, 3H), 0.24-0.20 (m, 9H).

Step 3:

Sodium borohydride (2 g, 52 mmol) was slowly added at −20° C. over 15 minutes to a solution of ethyl 3-cyano-4-(4-iodo-1H-pyrazol-1-yl)-3-((trimethylsilyl)oxy)butanoate (4 g, 9 mmol) and cobalt(II) chloride (9 g, 36 mmol) in methanol (40 mL). After allowing to warm to room temperature, the mixture was diluted with aqueous ammonium chloride solution and extracted with DCM. The organic layer was dried over anhydrous sodium sulfate, filtered, and concentrated under reduced pressure to afford ethyl 4-amino-3-(4-iodo-1H-pyrazol-1-yl)methyl)-3-((trimethylsilyl)oxy)butanoate. MS ESI calc'd. for $C_{13}H_{25}IN_3O_3Si$ [M+H]$^+$ 426. found 426. $^1$H NMR (400 MHz, CD$_3$OD) δ 7.57 (s, 1H), 7.52 (s, 1H), 4.60-4.49 (m, 2H), 4.20-4.07 (m, 2H), 2.81-2.62 (m, 4H), 1.32-1.28 (m, 3H), 0.24-0.20 (m, 9H).

Step 4:

Sodium hydroxide (113 mg, 2.8 mmol) was added to a mixture of ethyl 4-amino-3-((4-iodo-1H-pyrazol-1-yl)methyl)-3-((trimethylsilyl)oxy)butanoate (1.2 g, 2.8 mmol) in methanol (10 mL) and the mixture was stirred at room temperature for 2 hours. The mixture was diluted with water and extracted with DCM. The organic layer was dried over anhydrous sodium sulfate, filtered, and concentrated under reduced pressure. The residue was purified by prep-TLC (petroleum ether/EtOAc) to afford 4-hydroxy-4-((4-iodo-1H-pyrazol-1-yl)methyl)pyrrolidin-2-one. MS ESI calc'd. for $C_8H_{11}IN_3O_2$ [M+H]⁺ 308. found 308. ¹H NMR (400 MHz, CDCl₃) δ 7.58 (s, 1H), 7.51 (s, 1H), 4.28 (s, 2H), 3.34 (s, 2H), 2.29-2.05 (m, 2H).

Preparative Example 4.28

5-((4-Iodo-1H-pyrazol-1-yl)methyl)oxazolidine-2,4-dione

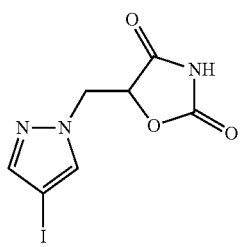 [SMILES: O=C1NC(=O)C(Cn2cc(I)cn2)O1]

Step 1:

A mixture of 4-iodo-1H-pyrazole (10 g, 51 mmol), methyl oxirane-2-carboxylate (6.8 g, 67 mmol) and tripotassium phosphate (12 g, 57 mmol) in dioxane (80 mL) was stirred at 90° C. for 4 hours. After cooling to room temperature, the mixture was diluted with water and extracted with DCM. The organic layer was dried over anhydrous sodium sulfate, filtered, and concentrated under reduced pressure. The residue was purified by silica gel column chromatography (petroleum ether/EtOAc) to afford methyl 2-hydroxy-3-(4-iodo-1H-pyrazol-1-yl)propanoate. MS ESI calc'd. for $C_7H_{10}IN_2O_3$ [M+H]⁺ 297. found 297. ¹H NMR (400 MHz, CDCl₃) δ 7.50 (d, J=3.2 Hz, 2H), 4.51-4.46 (m, 3H), 4.27-4.25 (m, 1H), 1.31-1.28 (m, 3H).

Step 2:

A mixture of methyl 2-hydroxy-3-(4-iodo-1H-pyrazol-1-yl)propanoate (4 g, 13 mmol) and ammonia (saturated in methanol, 100 mL) in a sealed tube was stirred at 60° C. for 12 hours. After cooling to room temperature, the mixture was concentrated under reduced pressure to afford 2-hydroxy-3-(4-iodo-1H-pyrazol-1-yl)propanamide. MS ESI calc'd. for $C_6H_9IN_3O_2$ [M+H]⁺ 282. found 282. ¹H NMR (400 MHz, CDCl₃) δ 7.72 (s, 1H), 7.50 (s, 1H), 4.53-4.49 (m, 1H), 4.36-4.29 (m, 2H).

Step 3:

1,1'-Carbonyldiimidazole (3.5 g, 21 mmol) and sodium hydride (0.85 g, 21 mmol, 60 wt %) were added to a mixture of 2-hydroxy-3-(4-iodo-1H-pyrazol-1-yl)propanamide (2 g, 7 mmol) in diethyl carbonate (50 mL). The mixture was stirred at 50° C. for 5 hours. After cooling to room temperature, the mixture was diluted with aqueous ammonium chloride solution and extracted with DCM. The organic layer was dried over anhydrous sodium sulfate, filtered, and concentrated under reduced pressure. The residue was purified by silica gel column chromatography (petroleum ether/EtOAc) to afford 5-((4-iodo-1H-pyrazol-1-yl)methyl)oxazolidine-2,4-dione. MS ESI calc'd. for $C_7H_7IN_3O_3$ [M+H]⁺ 308. found 308. ¹H NMR (400 MHz, CDCl₃) δ 7.55 (s, 1H), 7.50 (s, 1H), 5.16 (s, 1H), 4.68 (d, J=4 Hz, 2H).

Preparative Example 4.29

6-((4-Iodo-1H-pyrazol-1-yl)methyl)-1,3-oxazinan-2-one

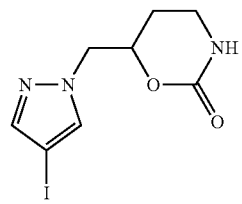 [SMILES: O=C1NCCC(Cn2cc(I)cn2)O1]

Step 1:

Benzyl chloroformate (38 g, 0.22 mol) was added at 0° C. over 15 minutes to a mixture of but-3-en-1-amine (10 g, 0.14 mol) and sodium bicarbonate (35 g, 0.52 mol) in DCM (500 mL) and water (40 mL). The mixture was diluted with water and extracted with DCM. The organic layer was dried over anhydrous sodium sulfate, filtered, and concentrated under reduced pressure. The residue was purified by silica gel column chromatography (petroleum ether/EtOAc) to afford benzyl but-3-en-1-ylcarbamate. MS ESI calc'd. for $C_{12}H_{16}NO_2$ [M+H]⁺ 206. found 206. ¹H NMR (400 MHz, CDCl₃) δ 7.36-7.30 (m, 5H), 5.80-5.70 (m, 1H), 5.11-5.01 (m, 4H), 3.79-3.25 (m, 2H), 2.29-2.24 (m, 2H).

Step 2:

Bromine (11 g, 68 mmol) was added to a mixture of benzyl but-3-en-1-ylcarbamate (7 g, 34 mmol) in DCM at room temperature under N₂. The mixture was stirred at room temperature for 4 hours. The mixture was diluted with water and extracted with DCM. The organic layer was dried over anhydrous sodium sulfate, filtered, and concentrated under reduced pressure. The residue was purified by silica gel column chromatography (petroleum ether/EtOAc) to afford 6-(bromomethyl)-1,3-oxazinan-2-one. ¹H NMR (400 MHz, CDCl₃) δ 6.14 (s, 1H), 4.49-4.45 (m, 1H), 3.59-3.56 (m, 1H), 3.46-3.39 (m, 3H), 2.24-2.20 (m, 1H), 1.95-1.89 (m, 1H).

Step 3:

A mixture of 4-iodo-1H-pyrazole (1 g, 5 mmol), 6-(bromomethyl)-1,3-oxazinan-2-one (1 g, 5 mmol), cesium carbonate (3.2 g, 10 mmol) and potassium iodide (20 mg, 0.1 mmol) in DMF (80 mL) was stirred at 80° C. for 12 hours. After cooling to room temperature, the mixture was diluted with water and extracted with DCM. The organic layer was concentrated under reduced pressure to afford 6-((4-iodo-1H- pyrazol-1-yl)methyl)-1,3-oxazinan-2-one. MS ESI calc'd. for $C_8H_{11}IN_3O_2$ [M+H]$^+$ 308. found 308.

Preparative Example 4.30

4-[(4-iodo-1H-pyrazol-1-yl)methyl]pyridin-2(1H)-one

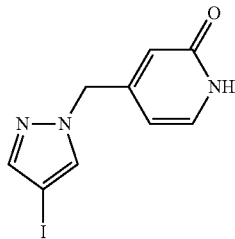 [SMILES: O=c1cc(Cn2cc(I)cn2)cc[nH]1]

Step 1:

Borane-THF (29 mL, 1.0 M) was added to a solution of 2-oxo-1,2-dihydropyridine-4-carboxylic acid (1 g, 7.19 mmol) in THF (15 mL) at 0° C. The mixture was stirred at 25° C. for 2 hours. Methanol was added and the mixture was concentrated under reduced pressure to afford 4-(hydroxymethyl)pyridin-2(1H)-one. MS ESI calc'd. for $C_6H_8NO_2$ [M+H]$^+$ 126. found 126. $^1$H NMR (400 MHz, CD$_3$OD) δ 7.40 (d, J=6.8 Hz, 1H), 6.58 (s, 1H), 6.38 (d, J=6.4 Hz, 1H), 4.52 (s, 2H).

Step 2:

Hydrobromic acid (2 mL) was added to a solution of 4-(hydroxymethyl)pyridin-2(1H)-one (200 mg, 1.6 mmol) was at 0° C. The mixture was stirred at 110° C. for 3 hours. After cooling to room temperature, the mixture was concentrated under reduced pressure. The residue was purified by column chromatography on silica gel (EtOAc/MeOH) to afford the 4-(bromomethyl)pyridin-2(1H)-one. MS ESI calc'd. for $C_6H_7BrNO$ [M+H]$^+$ 188 and 190. found 188 and 190. $^1$H NMR (400 MHz, DMSO-d$_6$) δ 11.55 (s, 1H), 7.36 (d, J=6.8 Hz, 1H), 6.39 (s, 1H), 6.17 (d, J=6.8 Hz, 1H), 4.45 (s, 2H).

Step 3:

Sodium hydride (19 mg, 0.48 mmol, 60 wt %) was added to a solution of 4-iodo-1H-pyrazole (47 mg, 0.24 mmol) in THF (2 mL) at 0° C. After 30 minutes, 4-(bromomethyl)pyridin-2(1H)-one (30 mg, 0.16 mmol) was added. The mixture was stirred at 25° C. for 12 hours. The organic layer was dried over anhydrous sodium sulfate, filtered, and concentrated under reduced pressure. The residue was purified by silica gel column chromatography (EtOAc/MeOH) to afford 4-((4-iodo-1H-pyrazol-1-yl)methyl)pyridin-2(1H)-one. MS ESI calc'd. for $C_9H_9IN_3O$ [M+H]$^+$ 302. found 302. $^1$H NMR (400 MHz, DMSO-d$_6$) δ 11.54 (s, 1H), 8.05 (s, 1H), 7.61 (s, 1H), 7.32 (d, J=6.8 Hz, 1H), 5.93-5.90 (m, 2H), 5.19 (s, 2H).

Preparative Example 5

Preparation of Precursors of R$^1$ Moieties Useful in Preparing Compounds of Formula (I)

The following representative methods in this example were used to prepare synthetic precursors of R$^1$ moieties useful in the preparation of final compounds.

Preparative Example 5.1

1,4-dioxaspiro[4.5]dec-8-yl methanesulfonate

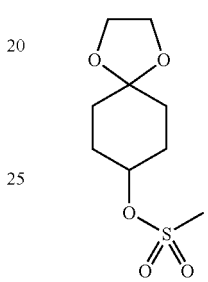

Triethylamine (2.4 mL, 17 mmol) was added to a solution of 1,4-dioxaspiro[4,5]decan-9-ol (884 mg, 5.59 mmol) in dichloromethane (22 mL) under a nitrogen atmosphere. The solution was cooled to 0° C. in an ice bath. Methanesulfonyl chloride (0.87 mL, 11.2 mmol) was added and the reaction stirred for 4 h while warming up to room temperature. Water was added and the mixture was extracted with dichloromethane (2×). The combined organic layers were washed with brine (1×), dried with magnesium sulfate, and concentrated under reduced pressure. The residue was purified by column chromatography on silica gel (0 to 100% EtOAc/hexane) to afford 1,4-dioxaspiro[4.5]dec-8-yl methanesulfonate as a light yellow oil. $^1$H NMR (500 MHz, DMSO-d$_6$) δ 4.81-4.68 (m, 1H), 3.91-3.78 (m, 4H), 3.16 (s, 3H), 1.87 (ddd, J=4.2, 8.1, 16.6, 2H), 1.82-1.71 (m, 2H), 1.67 (ddd, J=4.3, 7.9, 12.3, 2H), 1.58 (ddd, J=4.8, 8.7, 13.3, 2H).

Preparative Example 5.2

Racemic 5-(chloromethyl)-3-methyl-1,3-oxazolidin-2-one

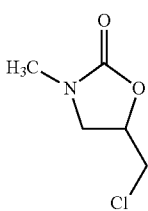

5-(Chloromethyl)-1,3-oxazolidin-2-one (500 mg, 3.69 mmol) and iodomethane (0.27 mL, 4.43 mmol) were dissolved in DMF (5 mL) and the resulting solution was cooled to 0° C. Sodium hydride (60%, 177 mg, 4.43 mmol) was added followed by additional DMF (2 mL). The reaction was warmed to room temperature and stirred for 4 hours. Additional iodomethane (0.14 mL, 2.22 mmol) and sodium hydride (60%, 88 mg, 2.2 mmol) were then added and the reaction mixture stirred at room temperature for two hours. The reaction was diluted with EtOAc, washed with brine, dried over sodium sulfate, filtered and concentrated under reduced pressure. The residue was purified by column chromatography on silica gel (12 to 100% EtOAc/hexanes) to afford racemic 5-(chloromethyl)-3-methyl-1,3-oxazolidin-2-one as a yellow liquid. $^1$H NMR (500 MHz, CDCl$_3$) δ 4.82-4.60 (m, 1H), 3.81-3.55 (m, 3H), 3.48-3.44 (m, 1H), 2.90 (s, 3H).

Preparative Example 5.3

2-Methyl-1,6-dioxaspiro[2.5]octane

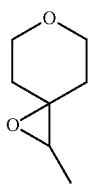

Step 1:
n-Butyllithium (2.5 M in hexanes, 4.40 mL, 11.0 mmol) was added drop wise at 0° C. to a solution of ethyltriphenylphosphonium bromide (4.08 g, 11.0 mmol) in diethyl ether (80 mL). The reaction mixture was stirred for 20 minutes then tetrahydro-4H-pyran-4-one (1.0 g, 10.0 mmol) in diethyl ether (15 mL) was added. The mixture was warmed to room temperature and stirred for 4.5 hours. The crude reaction mixture was diluted with diethyl ether and washed with water. The layers were separated and the aqueous layer was re-extracted with diethyl ether (2×). The combined organic layers were dried over sodium sulfate, filtered, and concentrated under reduced pressure. The white solid was diluted with hexanes and filtered. The filtrate was concentrated under reduced pressure to afford 4-ethylidenetetrahydro-2H-pyran. $^1$H NMR (500 MHz, CDCl$_3$) δ 5.30-5.20 (m, 1H), 3.65 (dd, J=4.7, 9.8 Hz, 4H), 2.27 (t, J=5.3 Hz, 2H), 2.19 (t, J=5.0 Hz, 2H), 1.59 (d, J=6.7 Hz, 3H).
Step 2:
3-Chloroperoxybenzoic acid (1.23 g, 7.13 mmol) was added to a solution of 4-ethylidenetetrahydro-2H-pyran (800 mg, 7.13 mmol) in dichloromethane (80 mL) at 0° C. The reaction mixture was warmed to room temperature and stirred for two hours. The mixture was diluted with dichloromethane and washed with saturated sodium bicarbonate then saturated sodium thiosulfate. The layers were separated and the aqueous layer was re-extracted with dichloromethane (2×). The combined organic layers were dried over magnesium sulfate, filtered, and concentrated under reduced pressure to afford 2-methyl-1,6-dioxaspiro[2.5]octane as a yellow oil. $^1$H NMR (500 MHz, CDCl$_3$) δ 3.88-3.76 (m, 4H), 2.92 (q, J=5.5 Hz, 1H), 1.91-1.81 (m, 2H), 1.58-145 (m, 2H), 1.30 (d, J=5.5 Hz, 3H).

Preparative Example 5.4 cis-2,6-Dimethyltetrahydro-4H-pyran-4-one

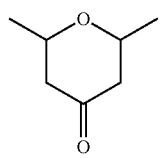

2,6-Dimethyl-4H-pyran-4-one (2.0 g, 16 mmol) was dissolved in ethanol (10 mL) and purged under nitrogen. Palladium on carbon (5%, 200 mg) was then added and the reaction mixture stirred under hydrogen gas (40 psi) for 24 hours. The reaction mixture was filtered over CELITE, rinsed with ethanol, and concentrated under reduced pressure. The residue was purified by column chromatography on silica gel (5 to 30% EtOAc/hexanes) to afford cis-2,6-dimethyltetrahydro-4H-pyran-4-one as a colorless liquid. $^1$H NMR (500 MHz, CDCl$_3$) δ 3.77-3.70 (m, 2H), 2.38-2.32 (m, 2H), 2.25-2.20 (m, 2H), 1.32 (d, J=6.1 Hz, 6H).

Preparative Example 5.5

1-Oxaspiro[2.3]hexane

Sodium hydride (188 mg, 7.85 mmol) was added to a slurry of trimethylsulfoxonium iodide (1.74 g, 7.91 mmol) and DMSO (5 mL). Vigorous gas evolution resulted. After stirring at room temperature for 45 minutes, gas evolution ceased and a clear solution resulted. Cyclobutanone (500 mg, 7.13 mmol) in DMSO (2 mL) was added drop wise. The resulting mixture was stirred at 55° C. for 5 hours. The cooled reaction mixture was poured into ice-water and extracted with EtOAc. The combined organic phase was washed with water, brine, dried over sodium sulfate, filtered and concentrated under reduced pressure to afford crude product, which was used in the next step directly.

Preparative Example 5.6

Racemic methyl 4-bromo-1,2,3,4-tetrahydronaphthalene-1-carboxylate

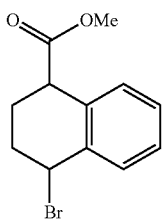 [SMILES: COC(=O)C1CCC(Br)c2ccccc21]

Step 1:
4-Oxo-1,2,3,4-tetrahydronaphthalene-1-carboxylic acid (3.50 g, 18.4 mmol) in THF (18.4 ml) was added to a dry flask and the solution was purged and then evacuated with argon. Sodium borohydride (1.74 g, 46.0 mmol) was added in one portion and the mixture was stirred at room temperature overnight. The reaction was diluted with aqueous HCl and the mixture was extracted with EtOAc (3×). The organic layer was dried over anhydrous magnesium sulfate and concentrated under reduced pressure. The resulting oily solid was taken-up in methanol/dichloromethane (1:1, 20 ml). Trimethylsilyldiazomethane (18.4 ml, 36.8 mmol) was added drop wise until the solution turned bright yellow and then the mixture was concentrated under reduced pressure. The residue was purified by column chromatography on silica gel (0 to 100% EtOAc/hexanes) to afford methyl 4-hydroxy-1,2,3,4-tetrahydronaphthalene-1-carboxylate as a yellow oil.

Step 2:
Methyl 4-hydroxy-1,2,3,4-tetrahydronaphthalene-1-carboxylate (3.68 g, 17.84 mmol) was taken-up in dichloromethane (17.8 ml) and the solution was purged and then evacuated with argon. Phosphorus tribromide (3.4 ml, 36 mmol) was added, and the resulting mixture was allowed to stir at room temperature over the weekend. The reaction was diluted with aqueous sodium bicarbonate and product was extracted with dichloromethane (3×). The organic layer was dried over anhydrous sodium sulfate and concentrated under reduced pressure. The residue was purified by column chromatography on silica gel (0 to 100% EtOAc/hexanes) to afford racemic methyl 4-bromo-1,2,3,4-tetrahydronaphthalene-1-carboxylate as a light yellow oil.

Preparative Example 5.7

3-(4,4,5,5-Tetramethyl-1,3,2-dioxaborolan-2-yl)-5,6-dihydro-4H-pyrrolo[1,2-]pyrazole

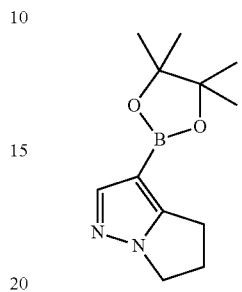

Step 1:
SOCl$_2$ (60.0 mL, 820 mmol) was added to a solution of 4-chloro-butyric acid (50.0 g, 410 mmol) in EtOH (1.2 L) at 0° C. The mixture was heated to reflux for 2 hr then cooled to room temperature and concentrated under reduced pressure to afford the crude 4-chloro-butyric acid ethyl ester.

Step 2:
EtMgBr (3.0 M, 288 mL) was added drop wise at 18-20° C. to a solution of crude 4-chloro-butyric acid ethyl ester and Ti(Oi-Pr)$_4$ (11.0 mL, 36.8 mmol) in Et$_2$O (1000 mL). The mixture was stirred at the same temperature for 1.5 hr then diluted by addition of HCl (10% in water) at 0° C. The aqueous layer was extracted by EtOAc (250×3 mL) and the organic extracts were washed with sodium bicarbonate, brine, dried over magnesium sulfate and concentrated under reduced pressure. The residue was purified by column chromatography on silica gel to afford 1-(3-chloro-propyl)-cyclopropanol.

Step 3:
Bromine (2.0 mL, 39 mmol) was added slowly to a solution of 1-(3-chloro-propyl)-cyclopropanol (5.0 g, 34 mmol) in i-PrOH (80% in water, 30 mL) at 0° C. The reaction mixture was stirred at room temperature for 1 hr then diluted with water (15 mL). The aqueous layer was extracted with EtOAc (3×30 mL) and the organic extracts were dried over magnesium sulfate, filtered and concentrated under reduced pressure to afford crude 1-bromo-6-chloro-hexan-3-one.

Step 4:
Triethylamine (7.1 mL, 50 mmol) was added to the solution of crude 1-bromo-7-chloro-hexan-3-one in diethyl ether (30 mL) slowly at room temperature. The mixture was stirred at the same temperature overnight then concentrated under reduced pressure to afford crude 6-chloro-hexa-1-en-3-one.

Step 5:
Potassium bromide (4.8 g, 40 mmol) and bromine (2.0 mL, 39 mmol) were added to the solution of crude 7-chloro-hexa-1-en-3-one in i-PrOH (80% in water, 30 mL) at 0° C. The reaction mixture was stirred at the same temperature for 1 hr then diluted with water (15 mL). The aqueous layer was extracted by EtOAc (3×30 mL) and the organic extracts were dried over magnesium sulfate, filtered and concentrated under reduced pressure to afford crude 1,2-dibromo-6-chloro-hexa-3-one.

Step 6:
Hydrazine hydrate (8.40 g, 170 mmol) was added to the solution of the crude 1,2-dibromo-6-chloro-hexa-3-one in i-PrOH (80% in water, 30 mL) at the room temperature. The reaction mixture was stirred at the same temperature overnight then diluted with water (15 mL). The aqueous layer was extracted by EtOAc (3×30 mL) and the organic extracts were dried over magnesium sulfate, filtered and concentrated under reduced pressure to afford the crude 3-(3-chloro-propyl)-1H-pyrazole.

Step 7:

Potassium hydroxide (2.0 g, 36 mmol) was added to the solution of the crude 3-(3-chloro-propyl)-1H-pyrazole in i-PrOH (80% in water, 30 mL). The mixture was heated to reflux for 4 hr then cooled to room temperature and diluted with water (15 mL). The aqueous layer was extracted with dichloromethane (3×30 mL) and the organic extracts were dried over magnesium sulfate, filtered and concentrated under reduced pressure. The residue was purified by column chromatography on silica gel to give 5,6-dihydro-4H-pyrrolo[1,2-b]pyrazole.

Step 8:

Bromine (22.4 mL, 435 mmol) was added to a solution of 5,6-dihydro-4H-pyrrolo[1,2-b]pyrazole 8 (47.2 g, 437 mmol) and NaOAc (36.2 g, 440 mmol) in AcOH (750 mL) drop wise at 0° C. The mixture was stirred at the same temperature for 10 minutes then neutralized by the addition of aqueous sodium bicarbonate. The aqueous layer was extracted with EtOAc (5×200 mL) and the organic extracts were dried over magnesium sulfate and concentrated under reduced pressure to afford 3-bromo-5,6-dihydro-4H-pyrrolo[1,2-b]pyrazole (73.5 g).

Step 9:

n-BuLi (1.6 M in THF, 300 mL) was slowly added to a solution of 3-bromo-5,6-dihydro-4H-pyrrolo[1,2-b]pyrazole (73.5 g, 390 mmol) in THF (600 mL) at −78° C. The resulting mixture was allowed to stir at the same temperature for 45 min. A solution of triisopropylborate (111 mL, 480 mmol) was then added and the mixture was allowed to warm up to room temperature and stir for additional 1 hr. A solution of pinacol (63.8 g, 540 mmol) in THF (300 mL) was then added. Five minutes later, a solution of AcOH (24 mL, 420 mmol) was added and the reaction mixture was stirred for 30 minutes then, filtered through CELITE and washed with aqueous saturated sodium bicarbonate. The aqueous layer was extracted with EtOAc (2×500 mL) and the organic extracts were dried over magnesium sulfate and concentrated under reduced pressure. The residue was purified by column chromatography on silica gel to afford 3-(4,4,5,5-tetramethyl-1,3,2-dioxaborolan-2-yl)-5,6-dihydro-4H-pyrrolo[1,2-]pyrazole.

Preparative Example 5.8

2-chloro-1-(4,4-dimethyloxazolidin-3-yl)ethanone

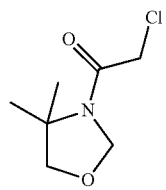

Formaldehyde (37% in water, 300 mL) was added to a solution of 2-amino-2-methylpropan-1-ol (100 g) in toluene (500 mL). The mixture was heated to 70-75° C. for 3 hr, then water was removed by toluene, cooled and concentrated under reduced pressure. The residue was dissolved in dichloromethane (800 mL), saturated sodium bicarbonate (600 mL). Chloroacetyl chloride (95 g) was added drop wise at room temperature and the mixture was reacted for 1.5 hr, and then extracted by dichloromethane. The organic extracts were dried over anhydrous sodium sulfate and concentrated under reduced pressure. The residue was purified by column chromatography on silica gel to afford 2-chloro-1-(4,4-dimethyloxazolidin-3-yl)ethanone as a white solid. MS ESI calcd. $C_7H_{13}ClNO_2[M+H]^+$ 178. found for 178. $^1H$ NMR (300 MHz, CDCl$_3$) 5.04 (s, 2H), 3.85 (s, 2H), 3.76 (s, 2H), 1.49 (s, 6H).

Preparative Example 5.9

2-Chloro-(1-methoxy-2-methylpropan-2-yl)acetamide

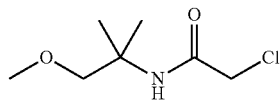

Step 1:

Et$_3$N (140 mL) and 2-methyl-2-aminopropan-1-ol (100 mL) were dissolved in dry THF (1.5 L) and the mixture was cooled to 0° C. (Boc)$_2$O (230 g) was added and the cooling bath was removed. After stirring for 90 min at room temperature, the solvent was removed by vacuum distillation. Water was added to the residue, and the mixture was extracted with EtOAc. The organic layer was recrystallized from EtOAc/petroleum ether to afford a white solid. To a 0° C. solution of the recrystallized solid (200 g) in THF (1000 mL) and water (500 mL), KOH (250 g) was added in a single portion and the cold bath was removed. The mixture was stirred for 15 min at room temperature, and Me$_2$SO$_4$ (133.5 g) was added drop wise via additional funnel by over a period of 45 min then stirred for 4 h at room temperature. The reaction mixture was filtered to remove excess KOH, poured into a mixture of EtOAc and saturated aqueous ammonium chloride and the layers were separated. The combined organic layers were dried over sodium sulfate, filtered, concentrated under reduced pressure and directly used in the next step.

Step 2:

KOH (250 g) was added in a single portion to a 0° C. cooled solution of the recrystallized solid from step 1 (200 g) in THF (1000 mL) and 500 mL of water. The cold bath was removed and the mixture was stirred for 15 min at room temperature. Me$_2$SO$_4$ (133.5 g) was added drop wise via additional funnel by over a period of 45 min and then stirred for 4 h at room temperature. The reaction mixture was filtered to remove excess KOH, poured into a mixture of EtOAc and saturated aqueous ammonium chloride and the layers were separated. The combined organic layers were dried over sodium sulfate, filtered, concentrated under reduced pressure and directly used in the next step.

Step 3:

tert-Butyl (1-methoxy-2-methylpropan-2-yl)methylcarbamate (170 g) was added to a saturated solution of MeOH/HCl at 5° C. and the mixture was stirred for 16 h at room temperature. Upon consumption of the starting materials, the solvent was distilled off. The crude product was purified by reduced pressure distillation and directly used in the next step.

Step 4:

1-Methoxy-2-dimethylpropan-2-amine was dissolved in the mixture of THF and water (1000 mL:500 mL) and cooled to room temperature. NaOH (160 g) was added and the mixture was stirred for 15 min at 0° C. ClCH$_2$COCl (65 mL) was added drop wise to the reaction mixture (keeping below 20° C.). The reaction mixture was stirred at room temperature for 30 min and saturated ammonium chloride solution was added. The organic layer was separated and concentrated under reduced pressure. The residue was washed with hexane (3×) to afford 2-chloro-(1-methoxy-2-methylpropan-2-yl)acetamide as a white crystalline solid. $^1$H NMR (300 MHz, CDCl$_3$) 61.37 (s, 6H), 3.36 (s, 2H), 3.38 (s, 3H), 3.39 (s, 2H), 6.6 (bs, 1H).

Preparative Example 5.10

(3R,5S)-tert-butyl-3,5-dimethylmorpholin-4-carboxylate

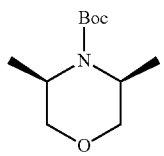

Step 1:

Platinum dioxide (800 mg) was added to a solution of dl-2-amino-1-propanol (100 g) and hydroxyacetone (115 g) in methanol (1100 mL). The reaction mixture was hydrogenated at 60 psi for 20 hours, after which time, the catalyst was filtered off and the solvent was removed under reduced pressure to afford crude 2,2'-iminodipropan-1-ol.

Step 2:

With vigorous stirring, 2,2'-iminodipropan-1-ol was added in one portion to concentrated sulfuric acid (800 mL) and cooled to 0° C. The reaction mixture was heated to 160° C. for 8 hours with stirring. Aqueous potassium hydroxide solution was added to the cooled mixture and the pH was adjusted to 7-8. The mixture was then filtered. NaOH (310 g) and the filtrate were added to di-tert-butyl-dicarbonate (355 g) in one portion at room temperature. The mixture was stirred overnight and then poured into water and extracted with ether. The combined organic layers were dried and concentrated under reduced pressure. The residue was purified by column chromatography on silica gel (EtOAc/petroleum ether, 1:30) to give tert-butyl (3S,5S)-3,5-dimethylmorpholine-4-carboxylate and tert-butyl (3R,5S)-3,5-dimethylmorpholine-4-carboxylate.

Step 3:

tert-Butyl (3R,5S)-3,5-dimethylmorpholine-4-carboxylate (80 g) was dissolved in methanol (500 mL) and HCl (8N in methanol, 500 mL) and stirred at 0° C. for 10 min. The mixture was allowed to warm to room temperature, stirred for 6 hours and then concentrated under reduced pressure to give the hydrochloric salt which was dissolved in dichloromethane (200 mL) and cooled to 0° C. Sodium carbonate (32 g in 70 mL of water) was added and stirred. Subsequently 2-chloroacetyl chloride (25 g) in dichloromethane was added drop wise at 0° C. The mixture was stirred for 30 min at 0° C., warmed to room temperature and continuously stirred for 5 hr. After this time, the reaction was diluted with water and extracted with dichloromethane. The organic layer was separated and washed with water (2×), dried over sodium sulfate, concentrated under reduced pressure and crystallized in ether to afford (3R,5S)-tert-butyl-3,5-dimethylmorpholin-4-carboxylate.

Preparative Example 5.11

(3S,5S)-tert-butyl-3,5-dimethylmorpholine-4-carboxylate

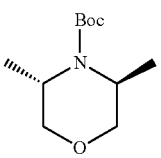

tert-Butyl (3S,5S)-3,5-dimethylmorpholine-4-carboxylate (80 g) was dissolved in methanol (500 mL) and HCl (8N in methanol, 500 mL) and stirred at 0° C. for 10 min. The mixture was allowed to warm to room temperature for 6 hours. The mixture was concentrated to give the hydrochloric salt product which was dissolved in dichloromethane (200 mL) and cooled to 0° C. Sodium carbonate (32 g in 70 mL of water) was added and stirred. Subsequently 2-chloroacetyl chloride (25 g) in dichloromethane was added drop wise at 0° C. The mixture was stirred for 30 min at 0° C., warmed to room temperature and continuously stirred for 5 hr. After this time, the reaction was diluted with water and extracted with dichloromethane. The organic layer was separated and washed with water (2×), dried over sodium sulfate, concentrated under reduced pressure and crystallized in ether to afford (3S,5S)-tert-butyl-3,5-dimethylmorpholine-4-carboxylate.

Preparative Example 5.12

3-methoxycyclobutanone

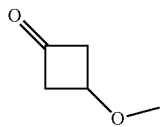

Step 1:

Concentrated sulfuric acid (3 drops) was added to a mixture of glycerol (55.1 g, 0.60 mmol) and benzaldehyde (50.0 g, 0.47 mmol) in toluene (69 mL) and the resulting mixture was heated to reflux in a Dean-Stark water separator under nitrogen. When the separation of water was complete, the solvent was concentrated under reduced pressure to give a white solid which was recrystallized from ether/petroleum ether. Repeated recrystallization from the same solvent gave pure 2-phenyl-1,3-dioxan-5-ol. $^1$H NMR (300 MHz, CDCl$_3$)

δ 7.51-7.48 (m, 2H), 7.41-7.37 (m, 3H), 5.55 (s, 1H), 4.21-4.17 (m, 2H), 4.14-4.10 (m, 2H), 3.63 (s, 1H), 2.78 (bs, 1H).
Step 2:

Sodium hydride (0.7 g, 18 mmol) was added in three portions to a solution of 2-phenyl-1,3-dioxan-5-ol. (3.0 g, 17 mmol) in THF (50 mL) at −10° C. The reaction mixture was stirred at 0° C. until no gas was generated. MeI (3.5 g, 25 mmol) was then added at room temperature, and reaction mixture was stirred at room temperature for 2 h. The reaction was diluted with water (50 mL). The solvent was removed; the residue was extracted with ethyl acetate (3×50 mL). The combined organic layer was dried over sodium sulfate, filtered and concentrated under reduced pressure to give a brown crude oil which was recrystallized from THF/hexane to afford 5-methoxy-2-phenyl-1,3-dioxane as a white solid. $^1$H NMR (300 MHz, CDCl$_3$) δ 7.51-7.48 (m, 2H), 7.41-7.37 (m, 3H), 5.56 (s, 1H), 4.25-4.19 (m, 2H), 4.07-4.03 (m, 2H), 3.48 (s, 3H).
Step 3:

TsOH (8.8 g, 0.1 mol) was added to a solution of 5-methoxy-2-phenyl-1,3-dioxane (100 g, 0.50 mol) in MeOH (1 L) and stirred was at 50° C. for 18 h. The mixture was cooled to room temperature and then Et$_3$N (10.1 g, 0.10 mol) was added in one portion. The solvent was removed under reduced pressure. The residue was purified by column chromatography on silica gel to afford 2-methoxypropane-1,3-diol as a yellow oil. $^1$H NMR (300 MHz, CDCl$_3$) δ 3.82-3.67 (m, 4H), 3.47 (s, 3H), 3.37-3.34 (m, 1H) 2.58 (bs, 2H).
Step 4:

Carbon tetrabromide (3.38 g, 10.2 mmol) and triphenylphosphine (2.67 g, 10.2 mmol) were added at 0° C., respectively, to a solution of 2-methoxypropane-1,3-diol (0.36 g, 3.40 mmol) in dichloromethane (20 mL). The reaction mixture was stirred at room temperature overnight then concentrated under reduced pressure. The residue was purified by column chromatography on silica gel (petroleum ether) to afford 1,3-dibromo-2-methoxypropane as light yellow oil. $^1$H NMR (300 MHz, CDCl$_3$) δ 3.63-3.60 (m, 5H), 3.51 (s, 3H).
Step 5:

n-Butyl lithium (1.6 M in hexane, 243 mL, 0.39 mol) was added drop wise to a solution of methyl methyl sulfide (41.0 mL, 0.39 mol) in THF (400 mL) at −10° C. The reaction mixture was stirred at −10° C. for 2 h and then cooled to −70° C. A solution of 1,3-dibromo-2-methoxypropane (37.3 g, 0.16 mol) in THF (100 mL) was added drop wise. The reaction mixture was allowed to warm to room temperature overnight and then diluted with brine and extracted with EtOAc (3×500 mL). The combined organic extracts were concentrated under reduced pressure and the residue was purified by column chromatography on silica gel (petroleum ether:EtOAc, 3:1) to afford (3-methoxy-1-(methylsulfinyl)cyclobutyl)(methyl)-sulfane as dark oil.
Step 6:

A solution of (3-methoxy-1-(methylsulfinyl)cyclobutyl)(methyl)sulfane (3.2 g, 12 mmol) in Et$_2$O (109 mL) was treated with perchloric acid (30%, 6.2 mL) and stirred at room temperature overnight. The reaction mixture was neutralized with saturated sodium bicarbonate. The mixture was extracted with EtOAc (100 mL×3). The combined organic extracts were washed with brine, dried over sodium sulfate, filtered and concentrated under reduced pressure. The residue was distilled to afford 3-methoxycyclobutanone as a yellow oil. $^1$H NMR (300 MHz, CDCl$_3$) δ 4.20-4.17 (1H, m) 3.34 (3H, s) 3.20-3.17 (2H, m) 3.09-3.03 (2H, m).

Preparative Example 5.13

(4R)-5-(Chloromethyl)-4-methyloxazolidin-2-one

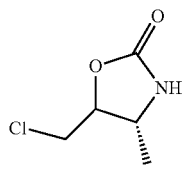

Step 1:

N,N-Diisopropylethylamine (4.7 mL, 27 mmol) and isobutyl carbonochloridate (3.11 ml, 23.78 mmol) were added to a solution of (R)-2-((tert-butoxycarbonyl)amino)propanoic acid (3.0 g, 15.9 mmol) in tetrahydrofuran (34.5 ml) at 0° C. and the mixture was stirred at 0° C. for four hours. The mixture was then diluted with acetonitrile (22 mL). TMS-diazomethane (2.0 M in diethyl ether, 15.9 ml, 31.7 mmol) was then added slowly to the mixture at 0° C. The mixture was allowed to stir at 0° C. for 3 hours and was then allowed to warm to room temperature for 14 hours. The mixture was concentrated under reduced pressure and then purified by column chromatography on silica to afford (R)-tert-butyl (4-diazo-3-oxobutan-2-yl)carbamate. $^1$H NMR (500 MHz, DMSO-d$_6$) δ 7.27 (d, J=7.4 Hz, 1H), 6.01 (s, 1H), 3.97-3.87 (m, 1H), 1.37 (s, 9H), 1.13 (d, J=7.3 Hz, 3H).
Step 2:

Hydrochloric acid (2.0 M in water, 21.4 mL, 42.8 mmol) was added to a mixture of (R)-tert-butyl (4-diazo-3-oxobutan-2-yl)carbamate (1.89 g, 8.86 mmol) in diethyl ether (19.27 mL) at 0° C.0. The mixture was stirred vigorously for 20 minutes and then allowed to warm to room temperature and stirred vigorously until the mixture went from yellow to colorless. The mixture was washed with saturated aqueous sodium bicarbonate, dried over anhydrous magnesium sulfate, filtered and concentrated under reduced pressure to afford (R)-tert-butyl (4-chloro-3-oxobutan-2-yl)carbamate. $^1$H NMR (500 MHz, DMSO-d$_6$) δ 7.34 (d, J=7.0 Hz, 1H), 4.64-4.51 (m, 2H), 4.23-4.02 (m, 1H), 1.36 (s, 9H), 1.16 (d, J=7.2 Hz, 3H).
Step 3:

Sodium borohydride (621 mg, 16.42 mmol) was added to a mixture of (R)-tert-butyl (4-chloro-3-oxobutan-2-yl)carbamate (910 mg, 4.10 mmol) in methanol (9 mL) at 0° C., and the mixture was stirred for one hour at 0° C. A few drops of acetic acid were added then the mixture was concentrated under reduced pressure. The residue was diluted with ethyl acetate, washed with water, dried over anhydrous magnesium sulfate, filtered and concentrated under reduced pressure to afford tert-butyl ((2R)-4-chloro-3-hydroxybutan-2-yl)carbamate. $^1$H NMR (500 MHz, DMSO-d$_6$) δ 6.65 (d, J=8.1 Hz, 1H), 5.24 (d, J=5.6 Hz, 1H), 3.58-3.53 (m, 1H), 3.50-3.44 (m, 2H), 3.44-3.34 (m, 1H), 1.36 (s, 9H), 0.99 (d, J=6.3 Hz, 3H).
Step 4:

Trifluoroacetic acid (0.70 mL, 9.0 mmol) was added to a mixture of tert-butyl ((2R)-4-chloro-3-hydroxybutan-2-yl)carbamate (200 mg, 0.89 mmol) in dichloromethane (1.4 mL) and the mixture was stirred for one hour. The mixture was concentrated to afford (R)-3-chloro-2-hydroxypropan-1-aminium 2,2,2-trifluoroacetate. $^1$H NMR (500 MHz, DMSO-$d_6$) δ 7.80 (s, 3H), 3.84 (td, J=6.8, 3.2 Hz, 1H), 3.76-3.63 (m, 1H), 3.61 (dd, J=11.3, 6.0 Hz, 1H), 3.51 (dd, J=11.2, 7.1 Hz, 1H), 3.39-3.30 (m, 1H), 1.08 (d, J=6.8 Hz, 3H).

Step 5:

Triethylamine (370 μl, 2.65 mmol) was added slowly to a mixture of (R)-3-chloro-2-hydroxypropan-1-aminium 2,2,2-trifluoroacetate (210 mg, 0.88 mmol) in dichloromethane (2.0 mL) at 0° C. The mixture was stirred for 15 minutes. A mixture of triphosgene (89 mg, 0.30 mmol) in dichloromethane (15 mL) was added drop wise via addition funnel. The mixture was allowed to warm to room temperature for 14 h, and then diethyl ether (2.0 mL) was added and the mixture was cooled to −78° C. The solids were filtered and the filtrate was concentrated under reduced pressure to about 1 mL. The mixture was then added to a plug of silica gel and washed slowly with ethyl acetate (50 mL). The filtrate was concentrated under reduced pressure and dried under vacuum to afford crude (4R)-5-(chloromethyl)-4-methyloxazolidin-2-one that was used without further purification or characterization.

The intermediates in the following table were prepared according to the method described above for Preparative Example 5.13

Preparative Example 5.18

5-(Chloromethyl)-4,4-dimethyloxazolidin-2-one

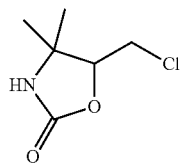

Thionyl chloride (0.13 ml, 1.72 mmol) was added to a mixture of 5-(hydroxymethyl)-4,4-dimethyloxazolidin-2-one (50 mg, 0.34 mmol) in pyridine (1 mL) at −20° C. The mixture was allowed to stir for 15 minutes and then warmed to 60° C. for 1 hour. The mixture was concentrated under reduced pressure and the residue was purified by column chromatography on silica (20-100% ethyl acetate/hexanes) to afford 5-(chloromethyl)-4,4-dimethyloxazolidin-2-one. $^1$H

| Prep Ex. | Structure | Name | NMR Data |
|---|---|---|---|
| 5.14 | (structure: OH, Cl, NHBoc) | tert-butyl ((2S)-4-chloro-3-hydroxybutan-2-yl)carbamate | $^1$H NMR (500 MHz, DMSO-$d_6$) δ 6.66 (d, J = 8.1 Hz, 1H), 5.24 (d, J = 5.6 Hz, 1H), 3.64-3.57 (m, 1H), 3.55 (dd, J = 10.8, 3.0 Hz, 1H), 3.50-3.35 (m, 2H), 1.36 (s, 9H), 0.99 (d, J = 6.2 Hz, 3H). |
| 5.15 | (structure: OH, Cl, NHBoc) | tert-butyl ((3S)-1-chloro-2-hydroxy-4-methylpentan-3-yl)carbamate | $^1$H NMR (500 MHz, DMSO-$d_6$) δ 6.55 (d, J = 10.0 Hz, 1H), 5.17 (d, J = 6.7 Hz, 1H), 3.59 (dd, J = 11.0, 2.2 Hz, 1H), 3.56-3.49 (m, 1H), 3.41 (dd, J = 11.1, 6.8 Hz, 1H), 3.37-3.32 (m, 1H), 2.15- 1.99 (m, 1H), 1.36 (s, 9H), 0.77 (d, J = 6.9 Hz, 3H), 0.72 (d, J = 6.8 Hz, 3H). |
| 5.16 | (structure: OH, Cl, NHBoc) | tert-butyl ((3S)-1-chloro-2-hydroxy-4-methylpentan-3-yl)carbamate | $^1$H NMR (500 MHz, DMSO-$d_6$) δ 6.55 (d, J = 10.0 Hz, 1H), 5.16 (d, J = 6.7 Hz, 1H), 3.59 (dd, J = 11.0, 2.2 Hz, 1H), 3.56-3.49 (m, 1H), 3.41 (dd, J = 11.0, 6.8 Hz, 1H), 3.38-3.31 (m, 1H), 2.12- 2.00 (m, 1H), 1.36 (d, J = 2.9 Hz, 9H), 0.76 (t, J = 9.0 Hz, 3H), 0.74 (s, 3H). |
| 5.17 | (structure: OH, Cl, NHBoc, cyclopropyl) | tert-butyl ((1R)-3-chloro-1-cyclopropyl-2-hydroxypropyl)carbamate | $^1$H NMR (500 MHz, DMSO-$d_6$) δ 6.60 (d, J = 8.7 Hz, 1H), 5.28 (d, J = 5.5 Hz, 1H), 3.68-3.59 (m, 2H), 3.52-3.43 (m, 1H), 3.10-3.03 (m, 1H), 1.35 (s, 9H), 1.03-0.90 (m, 1H), 0.48-0.35 (m, 2H), 0.28-0.21 (m, 2H). |

NMR (500 MHz, CDCl$_3$) δ 6.20 (br s, 1H), 4.38-4.35 (m, 1H), 3.75-3.70 (m, 1H), 3.62-3.57 (m, 1H), 1.42 (s, 3H), 1.31 (s, 3H).

Preparative Example 5.19

(4S,5R)-4-(Chloromethyl)-5-methyloxazolidin-2-one

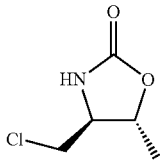

Step 1:

Triethylamine (7.40 mL, 53.1 mmol) was added slowly to a mixture of (2S,3R)-methyl 2-amino-3-hydroxybutanoate hydrochloride (3.0 g, 17.7 mmol) in dichloromethane (41 mL) at 0° C. The mixture was stirred for 15 minutes. A mixture of triphosgene (1.79 g, 6.01 mmol) in dichloromethane (15 mL) was added drop wise via addition funnel. The mixture was allowed to warm to room temperature for 14 hours. Diethyl ether (20 mL) was added, and the mixture was cooled to −78° C. for 15 minutes. The solids were filtered and the filtrate was concentrated under reduced pressure to about 10 mL. The mixture was then added to a plug of silica gel and washed slowly with ethyl acetate (~75 mL). The filtrate was then concentrated under reduced pressure and dried under vacuum to afford (4S,5R)-methyl 5-methyl-2-oxooxazolidine-4-carboxylate. $^1$H NMR (500 MHz, CDCl$_3$) δ 5.96 (s, 1H), 4.77-4.71 (m, 1H), 3.99 (d, J=5.4 Hz, 1H), 3.81 (s, 3H), 1.56 (d, J=6.3 Hz, 3H).

Step 2:

Sodium borohydride (0.55 g, 14.65 mmol) was added to a mixture of (4S,5R)-methyl 5-methyl-2-oxooxazolidine-4-carboxylate (2.12 g, 13.32 mmol) in ethanol (29 mL) at 0° C. The mixture was stirred for 3 hours and then 2 mL of saturated aqueous ammonium chloride was added. The mixture was stirred for 30 minutes and the white solids were filtered through CELITE and the filter cake was washed with ethanol. The filtrate was concentrated under reduced pressure and dried under vacuum to afford (4R,5R)-4-(hydroxymethyl)-5-methyloxazolidin-2-one. $^1$H NMR (500 MHz, D$_2$O) δ 4.56-4.37 (m, 1H), 3.60-3.38 (m, 3H), 1.27 (d, J=6.4 Hz, 3H).

Step 3:

Thionyl chloride (5.07 ml, 69.4 mmol) was added to a mixture of (4R,5R)-4-(hydroxymethyl)-5-methyloxazolidin-2-one (1.82 g, 13.88 mmol) in pyridine (35 mL) at 0° C. and the mixture was allowed to warm to room temperature for one hour. The mixture was then heated to 60° C. for one hour, allowed to cool to room temperature and then concentrated under reduced pressure. The crude oil was purified by column chromatography on silica to afford (4S,5R)-4-(chloromethyl)-5-methyloxazolidin-2-one. $^1$H NMR (500 MHz, CDCl$_3$) δ 6.23 (s, 1H), 4.50 (qd, J=6.3, 4.6 Hz, 1H), 3.74-3.63 (m, 1H), 3.59-3.48 (m, 2H), 1.48 (d, J=6.4 Hz, 3H).

The intermediates in the following table were prepared according to the method described for Preparative Example 5.19.

| Prep. Ex. | Structure | Name | NMR Data |
| --- | --- | --- | --- |
| 5.20 | 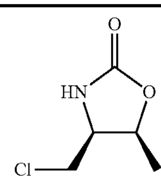 | (4S,5S)-4-(chloromethyl)-5-methyloxazolidin-2-one | $^1$H NMR (500 MHz, CDCl$_3$) δ 5.97 (s, 1H), 4.85 (dq, J = 13.5, 6.7 Hz, 1H), 4.02 (td, J = 7.8 5.1 Hz, 1H), 3.61 (dd, J = 11.3, 5.0 Hz, 1H), 3.53 (dd, J = 11.3, 8.1 Hz, 1H), 1.44 (d, J = 6.1 Hz, 3H). |
| 5.21 | 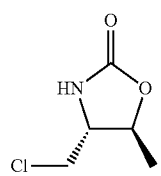 | (4R,5S)-4-(chloromethyl)-5-methyloxazolidin-2-one | $^1$H NMR (500 MHz, CDCl$_3$) δ 6.06 (s, 1H), 4.50 (qd, J = 6.4, 4.7 Hz, 1H), 3.74-3.63 (m, 1H), 3.59-3.47 (m, 2H), 1.49 (d, J = 6.4 Hz, 3H). |
| 5.22 | 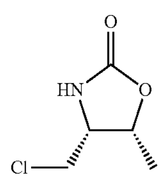 | (4R,5R)-4-(chloromethyl)-5-methyloxazolidin-2-one | $^1$H NMR (500 MHz, CDCl$_3$) δ 5.79 (s, 1H), 4.85 (dq, J = 13.5, 6.7 Hz, 1H), 4.02 (td, J = 7.9, 4.9 Hz, 1H), 3.61 (dd, J = 11.3, 4.8 Hz, 1H), 3.53 (dd, J = 11.3, 8.3 Hz, 1H), 1.44 (d, J = 6.7 Hz, 3H). |

Preparative Example 5.23

(5-oxo-6-oxa-4-azaspiro[2.4]hept-7-yl)methyl methanesulfonate

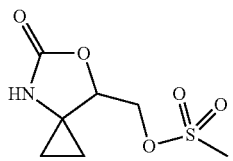

Step 1:

A catalytic amount of osmium tetroxide (<1 mg) and 4-methylmorpholine N-oxide (70 mg, 0.6 mmol) were added to a solution of tert-butyl(1-ethenylcyclopropyl)carbamate (0.10 g, 0.55 mmol) in THF/water (5 mL/5 mL). The mixture was stirred at room temperature overnight and then concentrated under reduced pressure. The residue was purified by chromatography on silica gel (methanol/dichloromethane) to give tert-butyl [1-(1,2-dihydroxyethyl)cyclopropyl]carbamate. $^1$H NMR (400 MHz, CD$_3$OD): δ 3.63-3.60 (m, 1H), 3.52-3.48 (m, 1H), 3.21-3.18 (m, 1H), 1.43 (s, 9H), 0.91-0.89 (m, 1H), 0.80-0.75 (m, 2H), 0.68-0.67 (m, 1H).

Step 2:

Sodium hydride (197 mg, 4.92 mmol) was added to a solution of tert-butyl [1-(1,2-dihydroxyethyl)cyclopropyl]carbamate (100 mg, 0.46 mmol) in THF (1 mL) at room temperature. The mixture was stirred at 30° C. under a nitrogen atmosphere for 16 hours. After being cooled to 20° C., the mixture was diluted with ice water (1 mL) and then extracted with ethyl acetate. The organic layer was dried over sodium sulfate, filtered, and concentrated under reduced pressure. The residue was purified by chromatography on silica gel (methanol/dichloromethane) to give 7-(hydroxymethyl)-6-oxa-4-azaspiro[2.4]heptan-5-one. $^1$H NMR (300 MHz, DMSO-d$_6$): δ 7.62 (br s, 1H), 5.00-4.96 (m, 1H), 4.40-4.35 (m, 1H), 3.51-3.40 (m, 2H), 1.01-0.88 (m, 1H), 0.80-0.55 (m, 3H).

Step 3:

Methanesulfonyl chloride (1.36 g, 11.1 mmol) and triethylamine (2.51 mL, 18.4 mmol) were added to a solution of 7-(hydroxymethyl)-6-oxa-4-azaspiro[2.4]heptan-5-one (1.32 g, 9.2 mmol) in DCM (47 mL) at 0° C. and this mixture was stirred at room temperature for 3 hours. The reaction mixture was then poured into water and extracted with ethyl acetate (10 mL×3). The combined organic layer was dried over sodium sulfate, filtered, and concentrated under reduced pressure. The residue was purified by chromatography on silica gel (ethyl acetate) to afford (5-oxo-6-oxa-4-azaspiro[2.4]hept-7-yl)methyl methanesulfonate. MS ESI calc'd. for C$_7$H$_{12}$NO$_5$S [M+H]$^+$ 222. found 222.

Preparative Example 5.24

5-(1-bromoethyl)-1,3-oxazolidin-2-one

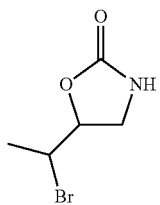

Bromine (0.049 mL, 0.96 mmol) in dichloromethane (0.27 mL) was added to a solution of ethyl (2E)-but-2-en-1-ylcarbamate (138 mg, 0.96 mmol) in dichloromethane (1.6 mL) under a nitrogen atmosphere at 20° C. The mixture was stirred for 3 hours at 20° C. under a nitrogen atmosphere. TLC showed that the ethyl (2E)-but-2-en-1-ylcarbamate was not consumed completely and additional bromine (0.049 mL, 0.96 mmol) in dichloromethane (0.27 mL) was added. After 3 hours, the reaction mixture was concentrated under reduced pressure. The residue was purified by prep-TLC (ethyl acetate/petroleum ether) to give a mixture of 5-(1-bromoethyl)-1,3-oxazolidin-2-one and 5-bromo-6-methyl-1,3-oxazinan-2-one. MS ESI calc'd. for C$_5$H$_9$BrNO$_2$ [M+H]$^+$ 194 and 196. found 194 and 196. $^1$H NMR (400 MHz, CDCl$_3$) δ 5.24 (s, 1H), 4.62-4.58 (m, 1H), 4.12-4.08 (s, 1H), 3.79-3.75 (m, 1H), 3.55-3.51 (m, 1H), 1.79 (d, J=6.8 Hz, 3H).

Preparative Example 5.25

(5-oxo-4-azaspiro[2.4]hept-7-yl)methyl methanesulfonate

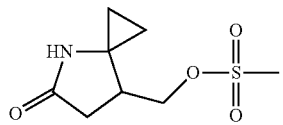

Step 1:

n-Butyllithium (2.5 M in THF, 33 mL, 82 mmol) was added dropwise to a solution of diisopropylamine (9.0 g, 90 mmol) in THF at −78° C. The reaction mixture was stirred at −78° C. for 1 hour. To the mixture was added a solution of 3-butenenitrile (5.0 g, 74.6 mmol) in THF (30 mL) dropwise at −78° C. The resultant mixture was stirred at the temperature for 1 hour, then a solution of ethyl bromoacetate (13.7 g, 82.06 mmol) in THF (30 mL) was added dropwise at −78° C. to the reaction mixture. The reaction mixture was stirred at −78° C. for an additional 1 hour. The reaction mixture was poured into a solution of saturated aqueous ammonium chloride and extracted with tert-butyl methyl ether (3×300 mL). The organic layers were combined, dried over sodium sulfate, filtered, and concentrated under reduced pressure to afford the crude product residue. The crude product residue was purified by silica gel chromatography (ethyl acetate/petroleum ether) to afford ethyl 3-cyanopent-4-enoate as a colorless oil. $^1$H NMR (400 MHz, CDCl$_3$) δ 5.83-5.71 (m, 1H), 5.53-5.49 (m, 1H), 5.36-5.33 (m, 1H), 4.20 (q, J=7.2 Hz, 2H), 3.79-3.71 (m, 1H), 2.81-2.73 (m, 1H), 2.69-2.61 (m, 1H), 1.28 (t, J=7.2 Hz, 3H).

Step 2:

Ethyl magnesium bromide (3.0 M in ether, 2.2 mL, 6.6 mmol) was added dropwise over a period of 1 hour to a solution of ethyl 3-cyanopent-4-enoate (500 mg, 3.27 mmol) and Ti(Oi-Pr)$_4$ (1.1 mL, 3.6 mmol) in diethylether (16.4 mL) at room temperature. The reaction mixture was diluted by the dropwise addition of water (3.27 mL) and stirred at room temperature for an additional 30 minutes. The reaction mixture was filtered and the filtrate was concentrated under reduced pressure to afford the crude product residue. The crude product residue was purified by silica gel chromatography (1:1 ethyl acetate/petroleum ether, R$_f$=0.3) to afford 7-ethenyl-4-azaspiro[2.4]heptan-5-one as a white solid. MS ESI calc'd. for C$_8$H$_{12}$NO [M+H]$^+$ 138. found 138. $^1$H NMR (400 MHz, CDCl$_3$) δ 6.09 (br s, 1H), 5.68-5.60 (m, 1H), 5.08-5.00 (m, 2H), 3.01-2.96 (m, 1H), 2.70-2.64 (m, 1H), 2.40-2.36 (m, 1H), 0.83-0.75 (m, 2H), 0.65-0.58 (m, 2H).

Step 3:

Osmium tetroxide (55 mg, 0.22 mmol) and sodium periodate (1.4 g, 6.6 mmol) were added in portions to a solution of 7-ethenyl-4-azaspiro[2.4]heptan-5-one (0.50 g, 3.3 mmol) in methanol (8 mL) and water (12 mL) at room temperature. The reaction mixture was stirred at room temperature for 4 hours. The reaction mixture was filtered and the filtrate was dried under reduced pressure to afford 5-oxo-4-azaspiro[2.4]heptane-7-carbaldehyde. The material was used in the next step without purification. MS ESI calc'd. for C$_7$H$_{10}$NO$_2$ [M+H]$^+$ 140. found 140.

Step 4:

Sodium borohydride (1.4 g, 6.6 mmol) was added to a stirred solution of 5-oxo-4-azaspiro[2.4]heptane-7-carbaldehyde (0.51 g, 3.3 mmol) in methanol (8 mL) and water (12 mL) at 0° C. The reaction mixture was allowed to warm to room temperature and stirred for 1 hour. The reaction mixture was dried over sodium sulfate and concentrated under reduced pressure to afford the crude product residue. The crude product residue was purified by silica gel chromatography (1:10 methanol in dichloromethane, $R_f$=0.4) to give 7-(hydroxymethyl)-4-azaspiro[2.4]heptan-5-one. $^1$H NMR (400 MHz, CD$_3$OD) δ 3.65-3.42 (m, 2H), 2.73-2.55 (m, 1H), 2.46-2.22 (m, 2H), 1.11-0.92 (m, 1H), 0.83-0.59 (m, 3H).

Step 5:

Methanesulfonyl chloride (0.40 g, 1.0 mmol) and triethylamine (0.22 mL, 1.6 mmol) were added to a solution of 7-(hydroxymethyl)-4-azaspiro[2.4]heptan-5-one (0.11 g, 0.78 mmol) in DCM (4 mL) at 0° C. The reaction mixture was stirred at room temperature for 3 hours. The reaction mixture was diluted with water and extracted with ethyl acetate (10 mL×3). The organic layers were combined and concentrated under reduced pressure to afford the crude product residue. The crude product residue was purified by silica gel chromatography (neat ethyl acetate, $R_f$=0.6) to afford (5-oxo-4-azaspiro[2.4]hept-7-yl)methyl methanesulfonate. $^1$H NMR (400 MHz, CDCl$_3$) δ 5.87 (br s, 1H), 4.35-4.01 (m, 2H), 2.95 (s, 3H), 2.87-2.54 (m, 2H), 2.41-2.35 (m, 1H), 1.05-0.72 (m, 4H).

Preparative Example 6

Ultimate Synthetic Step Methods of Precursors

The following representative methods were used as the ultimate synthetic step in preparation of final compounds and are indicated in the tables as applied.

Preparative Example 6.1

Ester Hydrolysis

LiOH (10.6 mg, 0.44 mmol) was added to a solution of methyl 2-[4-(3-methyl-5-{[4-(trifluoromethyl)pyrimidin-2-yl]amino}phenyl)-1H-pyrazol-1-yl]propanoate (18 mg, 0.04 mmol) in methanol (870 μL) and water (87 μL). The reaction mixture was allowed to stir at room temperature for 3 hours then concentrated using under reduced pressure. The residue was purified by reverse phase HPLC (ACN/water with 0.1% TFA modifier) to afford 2-[4-(3-methyl-5-{[4-(trifluoromethyl)pyrimidin-2-yl]amino}phenyl)-1H-pyrazol-1-yl]propanoic acid. MS ESI calcd. for C$_{18}$H$_{17}$F$_3$N$_5$O$_2$[M+H]$^+$ 392. found, 392. $^1$H NMR (500 MHz, DMOS-d$^6$) δ 13.04 (s, 1H), 10.11 (s, 1H), 8.80 (d, J=4.9, 1H), 8.12 (s, 1H), 7.84 (s, 1H), 7.75 (s, 1H), 7.32 (s, 1H), 7.24 (d, J=4.9, 1H), 7.09 (s, 1H), 5.11 (q, J=7.3, 1H), 2.29 (s, 3H), 1.67 (d, J=7.3, 3H).

Preparative Example 6.2

TBS Deprotection

HCl (550 μL, 0.55 mmol) was added to a solution of 3-[4-(3-{[4-(2-{[tert-butyl(dimethyl)silyl]oxy}ethoxy)pyrimidin-2-yl]amino}-5-methylphenyl)-1H-pyrazol-1-yl]propanamide (91 mg, 0.18 mmol) in THF (1000 μL). The reaction mixture was stirred for 18 h at room temperature then diluted with water and extracted with EtOAc (2×) and chloroform:IPA (3:1). The organic layer was dried over sodium sulfate, filtered, concentrated under reduced pressure, triturated with dichloromethane:hexanes (1:1) and then purified by reverse phase HPLC (ACN/water with 0.1% formic acid modifier) to afford 3-[4-(3-{[4-(2-hydroxyethoxy)pyrimidin-2-yl]amino}-5-methylphenyl)-1H-pyrazol-1-yl]propanamide as a white solid. MS ESI calcd. for C$_{19}$H$_{23}$N$_6$O$_3$ [M+H]$^+$ 382. found 382.

Preparative Example 6.3

TBDMS Deprotection

TFA (24 μL, 0.31 mmol) was added to a solution of N-{3-[1-(2-{[tert-butyl(dimethyl)silyl]-oxy}ethyl)-1H-pyrazol-4-yl]-5-methylphenyl}-4-(trifluoromethyl)pyrimidin-2-amine in dichloromethane (2 mL), and the reaction was allowed to stir for 30 minutes. The competed reaction was concentrated under reduced pressure. The residue was purified by reverse phase HPLC (ACN/water with 0.1% formic acid modifier to afford 2-[4-(3-methyl-5-{[4-(trifluoromethyl)pyrimidin-2-yl]amino}phenyl)-1H-pyrazol-1-yl]ethanol. MS ESI calcd. for C$_{17}$H$_{17}$F$_3$N$_5$O [M+H]$^+$ 364. found 364. $^1$H NMR (500 MHz, DMSO-d$^6$) δ 10.10 (s, 1H), 8.79 (d, J=4.9, 1H), 8.00 (s, 1H), 7.81 (s, 1H), 7.73 (s, 1H), 7.31 (s, 1H), 7.23 (d, J=4.9, 1H), 7.05 (s, 1H), 4.92 (t, J=5.2, 1H), 4.14 (t, J=5.6, 2H), 3.73 (q, J=5.6, 2H), 2.27 (s, 3H).

Preparative Example 6.4

Esterification of Carboxylic Acid

Example 4, Step 2 exemplifies an esterification of a carboxylic acid.

Preparative Example 6.5

TMS Deprotection

TBAF (1.0 M, 0.11 mL, 0.11 mmol) was added to a solution of 6-[1-(2-{[tert-butyl(dimethyl)silyl]oxy}ethyl)-1H-pyrazol-4-yl]-4-methyl-N-[4-(trifluoromethyl)pyridin-2-yl]pyridin-2-amine in dichloromethane (2 mL). The reaction mixture was stirred overnight and then concentrated under reduced pressure. The residue was purified by column chromatography on silica gel (0 to 10% MeOH/dichloromethane) to afford 2-[4-(4-methyl-6-{[4-(trifluoromethyl)pyridin-2-yl]amino}pyridin-2-yl)-1H-pyrazol-1-yl]ethanol. MS ESI C$_{17}$H$_{16}$F$_3$N$_5$O [M+H]$^+$ 364. found 364.

Preparative Example 6.6

Methoxybenzyl or Dimethoxybenzyl Deprotection

A mixture of 1-(2,4-dimethoxybenzyl)-4-{1-[4-(4-methyl-6-{[4-(trifluoromethyl)-pyridin-2-yl]amino}pyridin-2-yl)-1H-pyrazol-1-yl]ethyl}pyrrolidin-2-one (100 mg, 0.17 mmol) in TFA (5 mL) was stirred at 60° C. for 3 hours. The solvent was removed under reduced pressure and the crude product was purified by reverse phase HPLC (ACN/water with 0.1% formic acid modifier) to afford 4-{1-[4-(4-methyl-6-{[4-(trifluoromethyl)pyridin-2-yl]amino}pyridin-2-yl)-1H-pyrazol-1-yl]ethyl}pyrrolidin-2one.

Preparative Example 6.7 tert-Butyl Ester Hydrolysis

TFA (1.17 ml, 15.2 mmol) was added to a stirred solution of tert-butyl [4-(4-methyl-6-{[4-(trifluoromethyl)pyridin-2- yl]amino}pyridin-2-yl)-1H-pyrazol-1-yl]acetate (330 mg, 0.76 mmol) in DCM (3.8 ml) at room temperature. The reaction mixture was stirred at 40° C. overnight. Upon cooling, the reaction mixture was poured into phosphate buffer pH 4 and extracted with EtOAc (2×30 mL). The combined organic layers were washed with brine, dried with magnesium sulfate and concentrated under reduced pressure. The residue was triturated in Et₂O to afford [4-(4-methyl-6-{[4-(trifluoromethyl)pyridin-2-yl]amino}pyridin-2-yl)-1H-pyrazol-1-yl]acetic acid as a pale yellow solid. [M+H]⁺ 378. found, 378

Preparative Example 6.8

Acetal Hydrolysis

Hydrochloric acid (6N, 6.6 mL, 39.7 mmol) was added to 4-(difluoromethyl)-N-(3-(1-((2,2-dimethyl-1,3-dioxolan-4-yl)methyl)-1H-pyrazol-4-yl)-5-methylphenyl)pyrimidin-2-amine (16.5 g, 39.7 mmol) in MeOH (150 mL). The mixture heated at reflux for 2 h then cooled to RT. Water (200 mL) was added and then the pH was adjusted to 7 with NaOH (6N). The solution was seeded with crystalline product (prepared via an earlier small scale) and crystallization occurred. Additional water (150 ml) was added and the mixture was stirred for 30 min, then filtered, washed with water (2×50 mL) and dried for 14 h under a nitrogen bag to afford 3-(4-(3-((4-(difluoromethyl)pyrimidin-2-yl)amino)-5-methylphenyl)-1H-pyrazol-1-yl)propane-1,2-diol an off white solid.

Preparative Example 6.9

Benzyl Dehydrogenation

To a solution of N-[3-(1-{[6-(benzyloxy)pyridin-3-yl]methyl}-1H-pyrazol-4-yl)-5-methylphenyl]-4-(difluoromethyl)pyrimidin-2-amine (80 mg, 0.16 mmol) in methanol (20 mL) was added palladium hydroxide on carbon (20 wt %, 8 mg). The reaction mixture was stirred at 25° C. under a hydrogen atmosphere (1 atm) for 12 hours. The mixture was then filtered and concentrated under reduced pressure. The residue was purified by reverse phase HPLC to give the 5-{[4-(3-{[4-(difluoromethyl)pyrimidin-2-yl]amino}-5-methylphenyl)-1H-pyrazol-1-yl]methyl}pyridin-2(1H)-one. MS ESI calc'd. for $C_{21}H_{19}F_2N_6O$ [M+H]⁺ 409. found 409.

Preparative Example 7

Coupline of C-Ring Pyrazole to Pyrimidinylaminophenyl or Bisaminopyridyl Moeities The following representative methods were used as the ultimate synthetic step in preparation of final compounds and are indicated in the tables as applied.

Preparative Example 7.1

4-(1,1-Difluoroethyl)-N-(3-methyl-5-(1H-pyrazol-4-phenyl)pyrimidin-2-amine

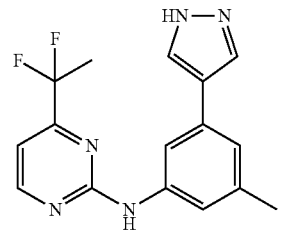 [SMILES: Cc1cc(Nc2nccc(C(C)(F)F)n2)cc(-c2cn[nH]c2)c1]

N-(3-Bromo-5-methylphenyl)-4-(1,1-difluoroethyl)pyrimidin-2-amine (2.0 g, 6.1 mmol), tert-butyl 4-(4,4,5,5-tetramethyl-1,3,2-dioxaborolan-2-yl)-1H-pyrazole-1-carboxylate (1.79 g, 6.09 mmol), and [1,1'-bis(diphenylphosphino)ferrocene]dichloropalladium(II), complex with dichloromethane (0.249 g, 0.305 mmol) were combined in a flask. 1,4-Dioxane (30 mL) and aqueous sodium carbonate (9.1 mL, 18.3 mmol, 2.0 M in water) were added, and the resultant suspension was heated to 100° C. for 4 h. The mixture was allowed to cool to room temperature and then filtered, and concentrated under reduced pressure. Purification by gel column chromatography on silica (10-100% ethyl acetate/hexanes) afforded 4-(1,1-difluoroethyl)-N-(3-methyl-5-(1H-pyrazol-4-yl)phenyl)pyrimidin-2-amine as a brown solid. MS ESI calc'd. for $C_{16}H_{16}F_2N_5$ [M+H]⁺ 316. found 316. ¹H NMR (500 MHz, DMSO-d₆) δ 12.91 (s, 1H), 9.83 (s, 1H), 8.67 (d, J=4.9 Hz, 1H), 8.04 (s, 1H), 7.84 (d, J=18.9 Hz, 1H), 7.78 (s, 1H), 7.32 (s, 1H), 7.08-7.02 (m, 2H), 2.28 (s, 3H), 1.98 (t, J=18.7 Hz, 3H).

The intermediates in the following table were prepared according to the method described for Preparative Example 5.6

| Prep. Ex. | Structure | Chemical Name | Exact Mass [M + H]⁺ | [M + H]⁺ Found |
|---|---|---|---|---|
| 7.2 | 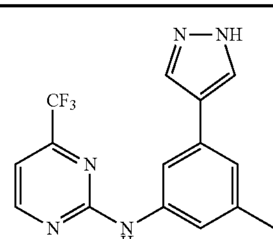 | N-(3-methyl-5-(1H-pyrazol-4-yl)phenyl)-4-(trifluoromethyl)pyrimidin-2-amine | 320 | 320 |

-continued

| Prep. Ex. | Structure | Chemical Name | Exact Mass [M + H]+ | [M + H]+ Found |
|---|---|---|---|---|
| 7.3 | 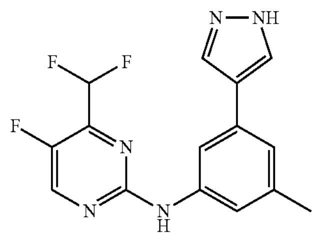 [SMILES: Cc1cc(Nc2ncc(F)c(C(F)F)n2)cc(-c2cn[nH]c2)c1] | 4-(difluoromethyl)-5-fluoro-N-(3-methyl-5-(1H-pyrazol-4-yl)phenyl)pyrimidin-2-amine | 320 | 320 |
| 7.4 | 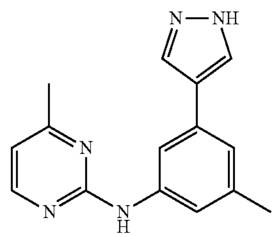 [SMILES: Cc1cc(Nc2nccc(C)n2)cc(-c2cn[nH]c2)c1] | 4-methyl-N-(3-methyl-5-(1H-pyrazol-4-yl)phenyl)pyrimidin-2-amine | 266 | 266 |
| 7.5 | 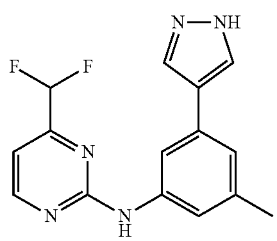 [SMILES: Cc1cc(Nc2nccc(C(F)F)n2)cc(-c2cn[nH]c2)c1] | 4-(difluoromethyl)-N-(3-methyl-5-(1H-pyrazol-4-yl)phenyl)pyrimidin-2-amine | 302 | 302 |
| 7.6 | 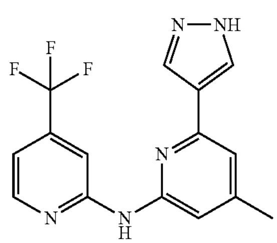 [SMILES: Cc1cc(Nc2cc(C(F)(F)F)ccn2)nc(-c2cn[nH]c2)c1] | 4-methyl-6-(1H-pyrazol-4-yl)-N-(4-(trifluoromethyl)pyridin-2-yl)pyridin-2-amine | 320 | 320 |
| 7.7 | 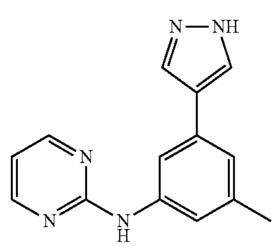 [SMILES: Cc1cc(Nc2ncccn2)cc(-c2cn[nH]c2)c1] | N-(3-methyl-5-(1H-pyrazol-4-yl)phenyl)pyrimidin-2-amine | 252 | 252 |
| 7.8 | 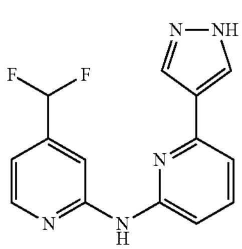 [SMILES: FC(F)c1ccnc(Nc2cccc(-c3cn[nH]c3)n2)c1] | N-(6-(1H-pyrazol-4-yl)pyridin-2-yl)-4-(difluoromethyl)pyridin-2-amine | 288 | 288 |

-continued

| Prep. Ex. | Structure | Chemical Name | Exact Mass [M + H]+ | [M + H]+ Found |
|---|---|---|---|---|
| 7.9 | 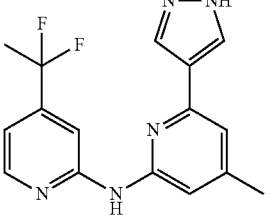 | N-(4-(1,1-difluoroethyl)pyridin-2-yl)-4-methyl-6-(1H-pyrazol-4-yl)pyridin-2-amine | 316 | 316 |
| 7.10 | 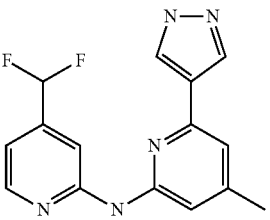 [SMILES: Cc1cc(Nc2cc(C(F)F)ccn2)nc(-c2cn[nH]c2)c1] | N-(4-(difluoromethyl)pyridin-2-yl)-4-methyl-6-(1H-pyrazol-4-yl)pyridin-2-amine | 302 | 302 |
| 7.11 | 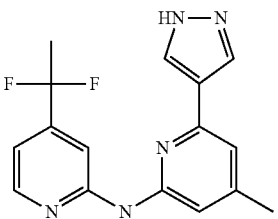 | N-(4-(1,1-difluoroethyl)pyridin-2-yl)-4-methyl-6-(1H-pyrazol-4-yl)pyridin-2-amine | 316 | 316 |
| 7.12 | 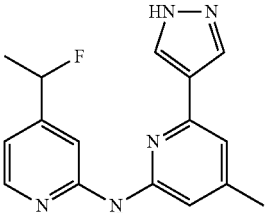 | N-(4-(1-fluoroethyl)pyridin-2-yl)-4-methyl-6-(1H-pyrazol-4-yl)pyridin-2-amine | 298 | 298 |

Preparative Example 7.13

4-(Difluoromethyl)-5-fluoro-N-(3-methyl-5-(4,4,5,5-tetramethyl-1,3,2-dioxaborolan-2-yl)phenyl)pyrimidin-2-amine

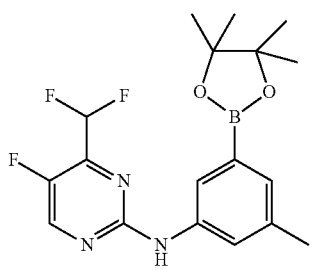 [SMILES: Cc1cc(Nc2ncc(F)c(C(F)F)n2)cc(B2OC(C)(C)C(C)(C)O2)c1]

N-(3-Bromo-5-methylphenyl)-4-(difluoromethyl)-5-fluoropyrimidin-2-amine (30 mg, 0.09 mmol), bis(pinacolato) diboron (28 mg, 0.11 mmol), PdCl$_2$(dppf)-CH$_2$Cl$_2$ adduct (4.0 mg, 4.5 μmol), potassium acetate (27 mg, 0.27 mmol) and dioxane (500 μL) were combined. The vial was sealed and placed under argon through 3 cycles of evacuation and argon flushing. The reaction mixture was stirred at 100° C. overnight then filtered through a CELITE plug, washing with EtOAc and concentrated under reduced pressure to afford crude 4-(difluoromethyl)-5-fluoro-N-(3-methyl-5-(4,4,5,5-tetramethyl-1,3,2-dioxaborolan-2-yl)phenyl)pyrimidin-2-amine as brown oil. MS ESI calcd. for C$_{18}$H$_{22}$BF$_3$N$_3$O$_2$ [M+H]+ 380. found 380.

The intermediates in the following table were prepared according to the method described for Preparative Example 7.11.

| Prep. Ex. | Structure | Chemical Name | Exact Mass [M + H]+ | [M + H]+ Found |
|---|---|---|---|---|
| 7.14 | 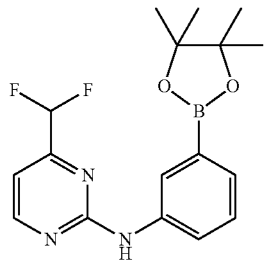 [SMILES: CC1(C)OB(c2cccc(Nc3nccc(C(F)F)n3)c2)OC1(C)C] | 4-(difluoromethyl)-N-(3-(4,4,5,5-tetramethyl-1,3,2-dioxaborolan-2-yl)phenyl)pyrimidin-2-amine | 348 | 348 |
| 7.15 | 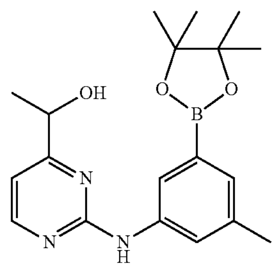 [SMILES: Cc1cc(Nc2nccc(C(C)O)n2)cc(B2OC(C)(C)C(C)(C)O2)c1] | 1-(2-((3-methyl-5-(4,4,5,5-tetramethyl-1,3,2-dioxaborolan-2-yl)phenyl)amino)pyrimidin-4-yl)ethanol | 356 | 356 |
| 7.16 | 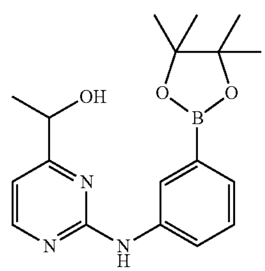 [SMILES: CC(O)c1ccnc(Nc2cccc(B3OC(C)(C)C(C)(C)O3)c2)n1] | 1-(2-((3-(4,4,5,5-tetramethyl-1,3,2-dioxaborolan-2-yl)phenyl)amino)pyrimidin-4-yl)ethanol | 342 | 342 |
| 7.17 | 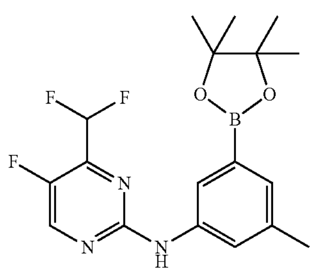 [SMILES: Cc1cc(Nc2ncc(F)c(C(F)F)n2)cc(B2OC(C)(C)C(C)(C)O2)c1] | 4-(difluoromethyl)-5-fluoro-N-(3-methyl-5-(4,4,5,5-tetramethyl-1,3,2-dioxaborolan-2-yl)phenyl)pyrimidin-2-amine | 380 | 380 |

Preparative Example 7.18

6-Bromo-N-[4-(1-fluoroethyl)pyridin-2-yl]-4-methylpyridin-2-amine

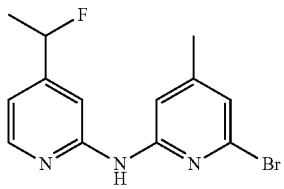 [SMILES: Cc1cc(Br)nc(Nc2cc(C(C)F)ccn2)c1]

Step 1:

2-Chloropyridine-4-carbonitrile (250 g, 1.80 mol, 1.00 equiv) and ether (3750 mL) were combined in a 10000-mL 4-necked round-bottom flask purged and maintained with an inert atmosphere of nitrogen. A solution of MeMgI in ether (1200 mL) was added dropwise with stirring at 0° C. in 30 min. The resulting solution was stirred for 6 h at room temperature and then poured into water/ice/6N hydrogen chloride (3000 mL) and stirred for 10 min. The organic phase was separated and the aqueous phase was extracted with ether (3×2000 mL). The combined organic layer was washed with brine (2×2000 mL), dried over anhydrous sodium sulfate and concentrated under vacuum. The residue was purified by column chromatography on silica gel (1:20 ethyl acetate/petroleum ether) to afford 1-(2-chloropyridin-4-yl)ethan-1-one as a light yellow solid.

Step 2:

1-(2-Chloropyridin-4-yl)ethan-1-one (110 g, 707 mmol, 1.00 equiv) and methanol (1500 mL) were added to a 3000-mL 4-necked round-bottom flask purged and maintained with an inert atmosphere of nitrogen. NaBH$_4$ (26.4 g, 698 mmol, 1.00 equiv) was added in portions at 0° C. The reaction mixture was stirred overnight at room temperature. The reaction was then quenched by the addition of water (1000 mL). The resulting mixture was concentrated under vacuum and extracted with dichloromethane (3×2000 mL). The combined organic layer was washed with brine (2×2000 mL), dried over anhydrous sodium sulfate and concentrated under vacuum. The residue was purified by column chromatography on silica gel (1:5 ethyl acetate/petroleum ether) to afford 1-(2-chloropyridin-4-yl)ethan-1-ol as colorless oil.

Step 3:

1-(2-Chloropyridin-4-yl)ethan-1-ol (115 g, 729 mmol, 1.00 equiv) and dichloromethane (3300 mL) were added to a 5000-mL 4-necked round-bottom flask purged and maintained with an inert atmosphere of nitrogen. DAST (144 g, 893 mmol, 1.25 equiv) was added dropwise with stirring at −78° C. in 30 min. The resulting solution was stirred overnight at room temperature. The reaction was then slowly quenched by the addition of water (1000 mL). The resulting solution was extracted with dichloromethane (3×1000 mL). The combined organic layer was washed with brine (3×1000 mL), dried over anhydrous sodium sulfate and concentrated under vacuum. The residue was purified by column chromatography on silica gel column (1:10 ethyl acetate/petroleum ether) to afford 2-chloro-4-(1-fluoroethyl)pyridine as light yellow oil.

Step 4:

2-Chloro-4-(1-fluoroethyl)pyridine (70 g, 439 mmol, 1.00 equiv), NaI (661 g, 4.41 mol, 10.00 equiv), ACN (700 mL) and acetyl chloride (56 g, 713 mmol, 1.60 equiv) were combined in a 2000-mL 4-necked round-bottom flask. The resulting solution was stirred overnight at 80° C. in an oil bath and then cooled to r.t, diluted with ice aqueous saturated sodium carbonate (500 mL) and extracted with dichloromethane (3×500 mL). The combined organic layer was washed with $NaS_2O_3$ (10%, 3×300 mL) and the aqueous phase was extracted with dichloromethane (2×200 mL). The combined organic layer was washed with brine (2×500 mL), dried over anhydrous sodium sulfate and concentrated under vacuum. The residue was purified by column chromatography on silica gel column (1:10 ethyl acetate/petroleum ether) to afford 4-(1-fluoroethyl)-2-iodopyridine as yellow oil.

Step 5:

4-(1-Fluoroethyl)-2-iodopyridine (90 g, 359 mmol, 1.05 equiv), 6-bromo-4-methylpyridin-2-amine (63.7 g, 341 mmol, 1.00 equiv), toluene (900 mL), t-BuOK (57.6 g, 1.50 equiv), BINAP (10.8 g, 17.3 mmol, 0.05 equiv) and $Pd_2(dba)_3$ (15.7 g, 17.1 mmol, 0.05 equiv) were combined into a 2000-mL 4-necked round-bottom flask purged and maintained with an inert atmosphere of nitrogen. The reaction mixture was stirred overnight at 90° C. in an oil bath and then cooled to r.t, diluted with DCM (500 mL). The solid was filtered out, washed with DCM and the filtrate was concentrated under vacuum. The residue was purified by column chromatography on silica gel column (1:15 ethyl acetate/petroleum ether) to afford 6-bromo-N-[4-(1-fluoroethyl)pyridin-2-yl]-4-methylpyridin-2-amine as a light yellow solid. ESI calc'd for $C_{13}H_{14}BrFN_3$ $[M+H]^+$ 309. found 309. $^1$H NMR ($CD_3OD$, 400 MHz, ppm): δ 8.23-8.22 (m, 1H), 7.66 (s, 1H), 7.45 (s, 1H), 6.93-6.91 (m, 2H), 5.72-5.51 (m, 1H), 2.32 (s, 3H), 1.68-1.61 (m, 3H).

Example 1.1

Preparation of N-(3-methyl-5-(pyrazolo[1,5-a]pyridin-3-yl)phenyl)-4-(trifluoromethyl)pyrimidin-2-amine

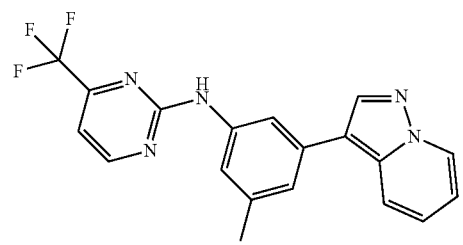 [SMILES: Cc1cc(Nc2nccc(C(F)(F)F)n2)cc(-c2cnn3ccccc23)c1]

N-(3-Bromo-5-methylphenyl)-4-(trifluoromethyl)pyrimidin-2-amine (70 mg, 0.21 mmol), pyrazolo[1,5-a]pyridin-3-ylboronic acid (68 mg, 0.42 mmol), $PdCl_2(dppf)$-$CH_2Cl_2$ adduct (34 mg, 0.04 mmol), sodium carbonate (2M in water, 211 μL, 0.42 mmol), and 2-methyl-tetrahydrofuran (1055 mL) were added to a microwave vial. The vial was sealed and allowed to react overnight at 60° C. Si-Dimercaptotriazole (Si-DMT) (222 mg, 0.13 mmol) and acetonitrile (3 mL) were added as a means of scavenging the palladium and the vial was resealed and allowed to stir for 4 hours at room temperature. The reaction mixture was filtered, washing with 1.5 mL DMSO, and the acetonitrile was removed under reduced pressure at 40° C. via Genevac. The sample, still in 1.5 mL DMSO, was filtered and purified by mass triggered reverse phase HPLC (ACN/water with 0.1% formic acid modifier) to afford N-(3-methyl-5-(pyrazolo[1,5-a]pyridin-3-yl)phenyl)-4-(trifluoromethyl)pyrimidin-2-amine as the formate salt. MS ESI calcd. for $C_{15}H_{15}F_3N_5$ $[M+H]^+$ 370. found 370. $^1$H NMR (600 MHz, DMSO-$d_6$) δ 10.19 (s, 1H), 8.81 (d, J=4.9, 1H), 8.70 (d, J=7.0, 1H), 8.29 (s, 1H), 8.01 (d, J=8.9, 2H), 7.38 (s, 1H), 7.33-7.27 (m, 1H), 7.24 (d, J=4.8, 1H), 7.16 (s, 1H), 6.93 (td, J=1.1, 6.9, 1H), 2.32 (s, 3H).

The following compounds in Tables 1A-1E were prepared according to the method described for Example 1.1.

TABLE 1A

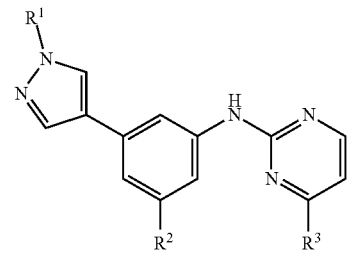

| Ex. No. | $R^1$ | $R^2$ | $R^3$ | Chemical Name | $[M + H]^+$ Calc'd | $[M + H]^+$ Found |
|---|---|---|---|---|---|---|
| 1.2 | —$(CH_2)_2CO_2H$ ammonium salt | $CH_3$ | $CF_3$ | 3-[4-(3-methyl-5-{[4-(trifluoromethyl)-pyrimidin-2-yl]amino}- | 392 | 392 |

TABLE 1A-continued

[structure shown: pyrazole-phenyl-pyrimidine scaffold with R¹ on pyrazole N, R² on phenyl, R³ on pyrimidine]

| Ex. No. | R¹ | R² | R³ | Chemical Name | [M + H]⁺ Calc'd | [M + H]⁺ Found |
|---|---|---|---|---|---|---|
| | | | | phenyl)-1H-pyrazol-1-yl]-propanoic acid | | |
| 1.3 | CH₃ free base | CH₃ | CF₃ | N-[3-methyl-5-(1-methyl-1H-pyrazol-4-yl)phenyl]-4-(trifluoromethyl)-pyrimidin-2-amine | 334 | 334 |
| 1.4 | 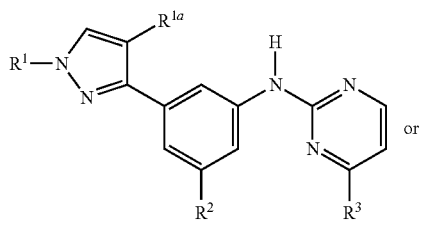 free base | CH₃ | CF₃ | tert-butyl 4-[4-(3-methyl-5-{[4-(trifluoromethyl)-pyrimidin-2-yl]amino}-phenyl)-1H-pyrazol-1-yl]-cyclohexanecarboxylate | 502 | 502 |
| 1.5 | 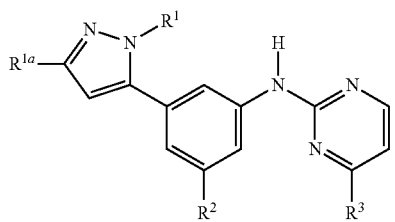 free base | CH₃ | CF₃ | N-[3-(1-cyclohex-2-en-1-yl-1H-pyrazol-4-yl)-5-methylphenyl]-4-(trifluoromethyl)-pyrimidin-2-amine | 400 | 400 |
| 1.6 | H free base | CH₃ | CF₃ | N-[3-methyl-5-(1H-pyrazol-4-yl)phenyl]-4-(trifluoromethyl)-pyrimidin-2-amine | 320 | 320 |

TABLE 1B

[structures Ic and Id shown: pyrazole regioisomers with R¹, R¹ᵃ, R², R³ substituents]

| Ex. No. | R¹ | R² | R³ | Chemical Name | [M + H]⁺ Calc'd | [M + H]⁺ Found |
|---|---|---|---|---|---|---|
| 1.7 | H (IC, R¹ᴬ = H) free base | CH₃ | CF₃ | N-[3-methyl-5-(1H-pyrazol-3-yl)phenyl]-4-(trifluoromethyl)pyrimidin-2-amine | 320 | 320 |

TABLE 1B-continued

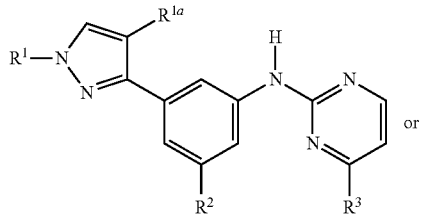
Ic or

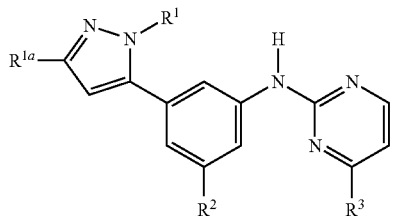
Id

| Ex. No. | R¹ | R² | R³ | Chemical Name | [M + H]⁺ Calc'd | [M + H]⁺ Found |
|---|---|---|---|---|---|---|
| 1.8 | i-propyl (ID, R¹ᴬ = H) free base | CH₃ | CF₃ | N-{3-methyl-5-[1-(1-methylethyl)-1H-pyrazol-5-yl]phenyl}-4-(trifluoromethyl)pyrimidin-2-amine | 362 | 362 |
| 1.9 | CH₃ (ID, R¹ᴬ = H) free base, formate salt | CH₃ | CF₃ | N-[3-methyl-5-(1-methyl-1H-pyrazol-5-yl)phenyl]-4-(trifluoromethyl)pyrimidin-2-amine | 334 | 334 |
| 1.10 | CH₃ (ID, R¹ᴬ = CF₃) formate salt | CH₃ | CF₃ | N-{3-methyl-5-[1-methyl-3-(trifluoromethyl)-1H-pyrazol-5-yl]phenyl}-4-(trifluoromethyl)pyrimidin-2-amine | 402 | 402 |

TABLE 1C

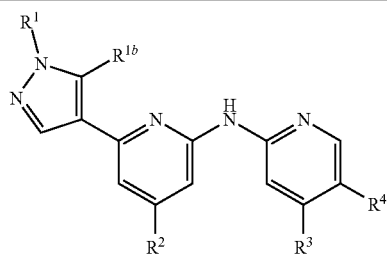

| Ex. No. | R¹ (R¹ᴮ is H unless specified) | R² | R³ (R⁴ is H unless specified) | Chemical Name | [M + H]⁺ Calc'd | [M + H]⁺ Found |
|---|---|---|---|---|---|---|
| 1.11 | —CO₂t-butyl free base | CH₃ | CF₃ | tert-butyl 4-(4-methyl-6-{[4-(trifluoromethyl)pyridin-2-yl]amino}-pyridin-2-yl)-1H-pyrazole-1-carboxylate | 420 | 420 |
| 1.12 | H free base | CH₃ | CF₃ | 4-methyl-6-(1H-pyrazol-4-yl)-N-[4-(trifluoromethyl)pyridin-2-yl]pyridin-2-amine | 320 | 320 |
| 1.13 | CH₃ free base | CH₃ | CF₃ | 4-methyl-6-(1-methyl-1H-pyrazol-4-yl)-N-[4-(trifluoromethyl)pyridin-2-yl]pyridin-2-amine | 334 | 334 |

TABLE 1C-continued

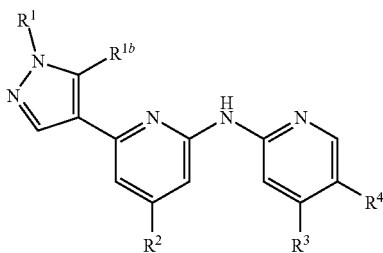

| Ex. No. | $R^1$ ($R^{1B}$ is H unless specified) | $R^2$ | $R^3$ ($R^4$ is H unless specified) | Chemical Name | $[M+H]^+$ Calc'd | $[M+H]^+$ Found |
|---|---|---|---|---|---|---|
| 1.14 | —(CH$_2$)$_2$CH(CH$_3$)$_2$ free base | CH$_3$ | CF$_3$ | 4-methyl-6-[1-(3-methylbutyl)-1H-pyrazol-4-yl]-N-[4-(trifluoromethyl)pyridin-2-yl]pyridin-2-amine | 390 | — |
| 1.15 | $R^1$ + $R^{1B}$ = —CH$_2$CH$_2$CH$_2$— free base | CH$_3$ | CF$_3$ | 6-(5,6-dihydro-4H-pyrrolo[1,2-b]pyrazol-3-yl)-4-methyl-N-[4-(trifluoromethyl)pyridin-2-yl]pyridin-2-amine | 360 | 360 |
| 1.16 | —(CH$_2$)$_2$CO$_2$ethyl free base | CH$_3$ | CF$_3$ | ethyl 3-[4-(4-methyl-6-{[4-(trifluoromethyl)pyridin-2-yl]amino}pyridin-2-yl)-1H-pyrazol-1-yl]propanoate | 420 | 420 |
| 1.17 | —(CH$_2$)$_2$CO$_2$ethyl free base | CH$_3$ | c-propyl | ethyl 3-(4-{6-[(4-cyclopropylpyridin-2-yl)amino]-4-methylpyridin-2-yl}-1H-pyrazol-1-yl)propanoate | 392 | 392 |
| 1.18 | —(CH$_2$)$_2$CO$_2$H ammonium salt | H | CH$_3$ | 3-(4-{6-[(4-methylpyridin-2-yl)amino]pyridin-2-yl}-1H-pyrazol-1-yl)propanoic acid | 324 | 324 |
| 1.19 | —(CH$_2$)$_2$CO$_2$H ammonium salt | H | CF$_3$ | 3-[4-(6-{[4-(trifluoromethyl)pyridin-2-yl]amino}pyridin-2-yl)-1H-pyrazol-1-yl]propanoic acid | 378 | 378 |
| 1.20 | —(CH$_2$)$_2$CO$_2$H ammonium salt | CH$_3$ | CH$_3$ | 3-(4-{4-methyl-6-[(4-methylpyridin-2-yl)amino]pyridin-2-yl}-1H-pyrazol-1-yl)propanoic acid | 338 | 338 |
| 1.21 | —(CH$_2$)$_2$CO$_2$H ammonium salt | CH$_3$ | CF$_3$ | 3-[4-(4-methyl-6-{[4-(trifluoromethyl)pyridin-2-yl]amino}pyridin-2-yl)-1H-pyrazol-1-yl]propanoic acid | 392 | 392 |
| 1.22 | —(CH$_2$)$_2$CO$_2$H ammonium salt | CH$_3$ | c-propyl | 3-(4-{6-[(4-cyclopropylpyridin-2-yl)amino]-4-methylpyridin-2-yl}-1H-pyrazol-1-yl)propanoic acid | 364 | 364 |
| 1.23 | —(CH$_2$)$_2$CO$_2$ethyl formate salt | H | CH$_3$ | ethyl 3-(4-{6-[(4-methylpyridin-2-yl)amino]pyridin-2-yl}-1H-pyrazol-1- | 352 | 352 |
| 1.24 | —(CH$_2$)$_2$CO$_2$ethyl formate salt | H | CF$_3$ | ethyl 3-[4-(6-{[4-(trifluoromethyl)pyridin-2-yl]amino}pyridin-2-yl)-1H-pyrazol-1-yl]propanoate | 406 | 406 |
| 1.25 | —(CH$_2$)$_2$CO$_2$ethyl formate salt | CH$_3$ | CH$_3$ ($R^4$ = Cl) | ethyl 3-(4-{6-[(5-chloro-4-methylpyridin-2-yl)amino]-4-methylpyridin-2-yl}- | 400 | 400 |

TABLE 1C-continued

*[Structure: pyrazole-pyridine-NH-pyridine scaffold with R¹, R¹ᵇ, R², R³, R⁴ substituents]*

| Ex. No. | R¹ (R¹ᴮ is H unless specified) | R² | R³ (R⁴ is H unless specified) | Chemical Name | [M + H]⁺ Calc'd | [M + H]⁺ Found |
|---|---|---|---|---|---|---|
| 1.26 | —(CH₂)₂CO₂ethyl formate salt | CH₃ | CH₃ | ethyl 3-(4-{4-methyl-6-[(4-methylpyridin-2-yl)amino]pyridin-2-yl}-1H-pyrazol-1-yl)propanoate | 366 | 366 |
| 1.27 | —(CH₂)₂CO₂H formate salt | CH₃ | CH₃ (R⁴ = Cl) | 3-(4-{6-[(5-chloro-4-methylpyridin-2-yl)amino]-4-methylpyridin-2-yl}-1H-pyrazol-1-yl)propanoic acid | 372 | 372 |
| 1.28 | *[oxazolidin-2-one-CH₂- group]* TFA salt | CH₃ | CF₃ | 5-{[4-(4-methyl-6-{[4-(trifluoromethyl)pyridin-2-yl]amino}pyridin-2-yl)-1H-pyrazol-1-yl]methyl}-1,3-oxazolidin-2-one | 419 | 419 |
| 1.29 | *[oxazolidin-2-one-CH₂- group, alternate stereochem]* TFA salt | CH₃ | CF₃ | 5-{[4-(4-methyl-6-{[4-(trifluoromethyl)pyridin-2-yl]amino}pyridin-2-yl)-1H-pyrazol-1-yl]methyl}-1,3-oxazolidin-2-one | 419 | 419 |
| 1.30 | —(CH₂)₂CO₂t-butyl free base | CH₃ | CF₃ | tert-butyl [4-(4-methyl-6-{[4-(trifluoromethyl)pyridin-2-yl]amino}pyridin-2-yl)-1H-pyrazol-1-yl]acetate | 434 | 434 |
| 1.31[1] | —CH₂CO₂H free base | CH₃ | CF₃ | [4-(4-methyl-6-{[4-(trifluoromethyl)pyridin-2-yl]amino}pyridin-2-yl)-1H-pyrazol-1-yl]acetic acid | 378 | 378 |
| 1.32[2] | *[pyrrolidin-2-one-CH(CH₃)- group]* R or S, S or R TFA salt | CH₃ | CF₃ | 4-{1-[4-(4-methyl-6-{[4-(trifluoromethyl)pyridin-2-yl]amino}pyridin-2-yl)-1H-pyrazol-1-yl]ethyl}pyrrolidin-2-one | 431 | 431 |

TABLE 1C-continued

| Ex. No. | R¹ (R¹ᴮ is H unless specified) | R² | R³ (R⁴ is H unless specified) | Chemical Name | [M + H]⁺ Calc'd | [M + H]⁺ Found |
|---|---|---|---|---|---|---|
| 1.33² | R or S, S or R TFA salt | CH₃ | CF₃ | 4-{1-[4-(4-methyl-6-{[4-(trifluoromethyl)pyridin-2-yl]amino}pyridin-2-yl)-1H-pyrazol-1-yl]ethyl}pyrrolidin-2-one | 431 | 431 |
| 1.34² | S or R, S or R TFA salt | CH₃ | CF₃ | 4-{1-[4-(4-methyl-6-{[4-(trifluoromethyl)pyridin-2-yl]amino}pyridin-2-yl)-1H-pyrazol-1-yl]ethyl}pyrrolidin-2-one | 431 | 431 |
| 1.35² | chiral-R or S TFA salt | CH₃ | CHF₂ | 4-{[4-(6-{[4-(difluoromethyl)pyridin-2-yl]amino}-4-methylpyridin-2-yl)-1H-pyrazol-1-yl]methyl}pyrrolidin-2-one | 431 | 431 |
| 1.36² | S or R, S or R TFA salt | CH₃ | CF₃ | 4-{1-[4-(4-methyl-6-{[4-(trifluoromethyl)pyridin-2-yl]amino}pyridin-2-yl)-1H-pyrazol-1-yl]ethyl}pyrrolidin-2-one | 431 | 431 |
| 1.37² | chiral-S or R TFA salt | CH₃ | CHF₂ | 4-{[4-(6-{[4-(difluoromethyl)pyridin-2-yl]amino}-4-methylpyridin-2-yl)-1H-pyrazol-1-yl)methyl}pyrrolidin-2-one | 399 | 399 |
| 1.38² | racemic TFA salt | CH₃ | CF₃ | 4-{[4-(4-methyl-6-{[4-(trifluoromethyl)pyridin-2-yl]amino}pyridin-2-yl)-1H-pyrazol-1-yl]-methyl}pyrrolidin-2-one | 417 | 417 |
| 1.39² | | CH₃ | CF₃ | 4-{[4-(4-methyl-6-{[4-(trifluoromethyl)-pyridin-2-yl]amino}-pyridin-2-yl)-1H-pyrazol-1-yl]methyl}- | 417 | 417 |

TABLE 1C-continued

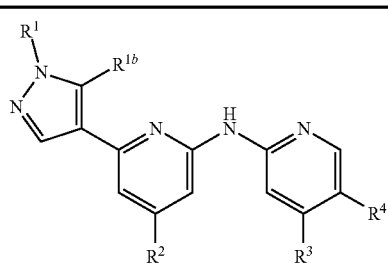

| Ex. No. | $R^1$ ($R^{1B}$ is H unless specified) | $R^2$ | $R^3$ ($R^4$ is H unless specified) | Chemical Name | $[M+H]^+$ Calc'd | $[M+H]^+$ Found |
|---|---|---|---|---|---|---|
| | racemic TFA salt | | | pyrrolidin-2-one | | |

TABLE 1D

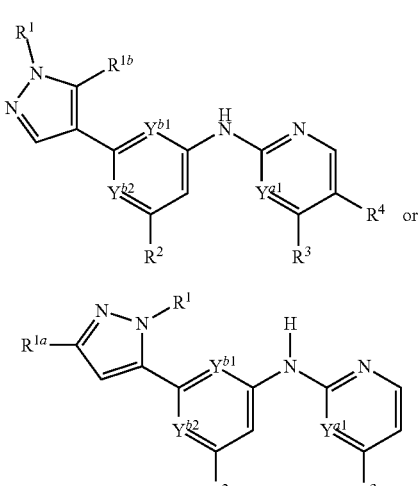

Ie (1) [$Y^{b1} = Y^{b2} = N$; $Y^{a1} = CH$ and $R^4 = H$]
Ie (2) [$Y^{b1} = CH$; $Y^{a1} = Y^{b2} = N$ and $R^4 = H$]
If [$Y^{b1} = Y^{b2} = N$; $Y^{a1} = CH$ and $R^4 = H$]

| Ex. No. | $R^1$ ($R^{1A}$ and $R^{1B}$ is H unless specified) | $R^2$ | $R^3$ | Chemical Name | $[M+H]^+$ Found | $[M+H]^+$ Calc'd |
|---|---|---|---|---|---|---|
| 1.40 | —(CH$_2$)$_2$CO$_2$H (IE (1)) ammonium salt | CH$_3$ | CF$_3$ | 3-[4-(4-methyl-6-{[4-(trifluoromethyl)pyridin-2-yl]amino}pyrimidin-2-yl)-1H-pyrazol-1-yl]propanoic acid | 393 | 393 |
| 1.41 | H (IE (1)) formate salt | CH$_3$ | CF$_3$ | 6-methyl-2-(1H-pyrazol-4-yl)-N-[4-(trifluoromethyl)pyridin-2-yl]pyrimidin-4-amine | 321 | 321 |
| 1.42 | $R^1 + R^{1B}$ = —CH=CH—CH=CH— (IE (1)) formate salt | CH$_3$ | CF$_3$ | 6-methyl-2-pyrazolo-[1,5-a]pyridin-3-yl-N-[4-(trifluoromethyl)-pyridin-2-yl]pyrimidin-4-amine | 371 | 371 |
| 1.43 | CH$_3$ (IE (2)) free base | CH$_3$ | CF$_3$ | N-[2-methyl-6-(1-methyl-1H-pyrazol-4-yl)pyridin-4-yl]-4- | 335 | 335 |

TABLE 1D-continued

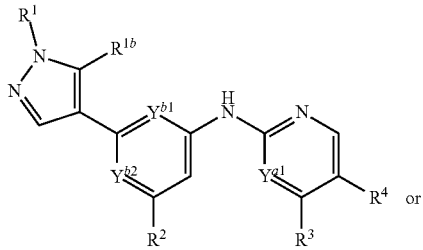

Ie

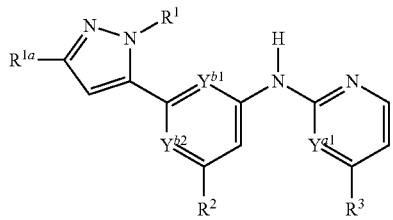

If

Ie (1) [$Y^{b1} = Y^{b2} = N; Y^{a1} = CH$ and $R^4 = H$]
Ie (2) [$Y^{b1} = CH; Y^{a1} = Y^{b2} = N$ and $R^4 = H$]
If [$Y^{b1} = Y^{b2} = N; Y^{a1} = CH$ and $R^4 = H$]

| Ex. No. | $R^1$ ($R^{1A}$ and $R^{1B}$ is H unless specified) | $R^2$ | $R^3$ | Chemical Name | $[M+H]^+$ Found | $[M+H]^+$ Calc'd |
|---|---|---|---|---|---|---|
| 1.44 | $CH_3$ (IE (2)) free base | $CH_3$ | $CF_3$ | (trifluoromethyl)-pyrimidin-2-amine N-[2-methyl-6-(1H-pyrazol-4-yl)pyridin-4-yl]-4-(trifluoromethyl)pyrimidin-2-amine | 321 | 321 |
| 1.45 | $CH_3$ (IF, $R^{1A}$ = H) formate salt | $CH_3$ | $CF_3$ | 6-methyl-2-(1-methyl-1H-pyrazol-5-yl)-N-[4-(trifluoromethyl)pyridin-2-yl]pyrimidin-4-amine | 335 | 335 |
| 1.46 | $CH_3$ (IF, $R^{1A}$ = $CF_3$) formate salt | $CH_3$ | $CF_3$ | 6-methyl-2-[1-methyl-3-(trifluoromethyl)-1H-pyrazol-5-yl]-N-[4-(trifluoromethyl)pyridin-2-yl]pyrimidin-4-amine | 403 | 403 |

TABLE 1E

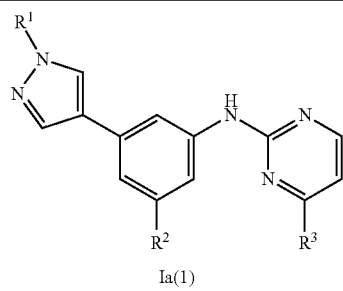 or 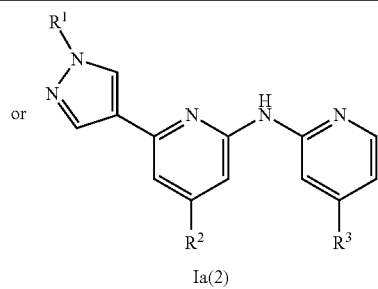

Ia(1)                                Ia(2)

| Ex. No. | $R^1$ (Structural Template) | $R^2$ | $R^3$ | Chemical Name | $[M+H]^+$ Calc'd | $[M+H]^+$ Found | Form |
|---|---|---|---|---|---|---|---|
| 1.47 | H (Ia(1)) | $CH_3$ | $C(F_2)CH_3$ | 4-(1,1-difluoroethyl)-N-[3-methyl-5-(1H-pyrazol-4-yl)phenyl]pyrimidin-2-amine | 316.1 | 316 | Free Base |

TABLE 1E-continued

| Ex. No. | R¹ (Structural Template) | R² | R³ | Chemical Name | [M + H]⁺ Calc'd | [M + H]⁺ Found | Form |
|---|---|---|---|---|---|---|---|
| 1.48 | 4-(1-carboxyphenyl)ethyl, R or S (Ia(1)) | CH₃ | CF₃ | 4-{1-[4-(3-methyl-5-{[4-(trifluoromethyl)pyrimidin-2-yl]amino}phenyl)-1H-pyrazol-1-yl]ethyl}benzoic acid | 468.2 | 468 | TFA Salt |
| 1.49 | 4-(1-carboxyphenyl)ethyl, S or R (Ia(1)) | CH₃ | CF₃ | 4-{1-[4-(3-methyl-5-{[4-(trifluoromethyl)pyrimidin-2-yl]amino}phenyl)-1H-pyrazol-1-yl]ethyl}benzoic acid | 468.2 | 468 | TFA Salt |
| 1.50 | 4-carboxycyclohexyl (Ia(1)) | NH₂ | CF₃ | 4-[4-(3-amino-5-{[4-(trifluoromethyl)pyrimidin-2-yl]amino}phenyl)-1H-pyrazol-1-yl]cyclohexanecarboxylic acid | 447.2 | 447 | TFA Salt |
| 1.51 | 4-carboxycyclohexyl (Ia(1)) | NH₂ | CF₃ | 4-[4-(3-amino-5-{[4-(trifluoromethyl)pyrimidin-2-yl]amino}phenyl)-1H-pyrazol-1-yl]cyclohexanecarboxylic acid | 447.2 | 447 | TFA Salt |
| 1.52 | 4-carboxycyclohexyl (Ia(1)) | NHC(O)CH₃ | CF₃ | 4-{4-[3-(acetylamino)-5-{[4-(trifluoromethyl)pyrimidin-2-yl]amino}phenyl]-1H-pyrazol-1-yl}cyclohexanecarboxylic acid | 489.2 | 489 | TFA Salt |

TABLE 1E-continued

Structural templates Ia(1) and Ia(2): pyrazole-substituted arylamine pyrimidine/pyridine scaffolds with R¹, R², R³ substituents.

| Ex. No. | R¹ (Structural Template) | R² | R³ | Chemical Name | [M + H]⁺ Calc'd | [M + H]⁺ Found | Form |
|---|---|---|---|---|---|---|---|
| 1.53 | 4-carboxycyclohexyl (Ia(1)) | NHC(O)CH₃ | CF₃ | 4-{4-[3-(acetylamino)-5-{[4-(trifluoromethyl)pyrimidin-2-yl]amino}phenyl]-1H-pyrazol-1-yl}cyclohexanecarboxylic acid | 489.2 | 489 | TFA Salt |
| 1.54 | 4-carboxycyclohexyl (Ia(2)) | Cl | CF₃ | 4-[4-(4-chloro-6-{[4-(trifluoromethyl)pyridin-2-yl]amino}pyridin-2-yl)-1H-pyrazol-1-yl]cyclohexanecarboxylic acid | 466.1 | 466 | TFA Salt |
| 1.55 | 4-carboxycyclohexyl (Ia(2)) | Cl | CF₃ | 4-[4-(4-chloro-6-{[4-(trifluoromethyl)pyridin-2-yl]amino}pyridin-2-yl)-1H-pyrazol-1-yl]cyclohexanecarboxylic acid | 466.1 | 466 | TFA Salt |
| 1.56 | 4-carboxycyclohexyl (Ia(1)) | CH₃ | CF₃ | 4-[4-(3-methyl-5-{[4-(trifluoromethyl)pyrimidin-2-yl]amino}phenyl)-1H-pyrazol-1-yl]cyclohexanecarboxylic acid | 446.2 | 446 | Free Base |
| 1.57 | 4-carboxycyclohexyl (Ia(1)) | CH₃ | CF₃ | 4-[4-(3-methyl-5-{[4-(trifluoromethyl)pyrimidin-2-yl]amino}phenyl)-1H-pyrazol-1-yl]cyclohexanecarboxylic acid | 446.2 | 446 | Free Base |

TABLE 1E-continued

| Ex. No. | R¹ (Structural Template) | R² | R³ | Chemical Name | [M + H]⁺ Calc'd | [M + H]⁺ Found | Form |
|---|---|---|---|---|---|---|---|
| 1.58 | (cyclohexanecarboxylic acid) (Ia(1)) | $CH_3$ | $CH_3$ | 4-(4-{3-methyl-5-[(4-methylpyrimidin-2-yl)amino]phenyl}-1H-pyrazol-1-yl)cyclohexanecarboxylic acid | 392.2 | 392 | Free Base |
| 1.59 | (cyclohexanecarboxylic acid) (Ia(1)) | $CH_3$ | $CH_3$ | 4-(4-{3-methyl-5-[(4-methylpyrimidin-2-yl)amino]phenyl}-1H-pyrazol-1-yl)cyclohexanecarboxylic acid | 392.2 | 392 | Free Base |
| 1.60 | (cyclohexanecarboxylic acid) (Ia(1)) | Cl | $CF_3$ | 4-[4-(3-chloro-5-{[4-(trifluoromethyl)pyrimidin-2-yl]amino}phenyl)-1H-pyrazol-1-yl]cyclohexanecarboxylic acid | 466.1 | 466 | Free Base |
| 1.61 | (cyclohexanecarboxylic acid) (Ia(1)) | Cl | $CF_3$ | 4-[4-(3-chloro-5-{[4-(trifluoromethyl)pyrimidin-2-yl]amino}phenyl)-1H-pyrazol-1-yl]cyclohexanecarboxylic acid | 466.1 | 466 | Free Base |
| 1.62[2] | (pyrrolidin-2-one) "R or S, S or R" (Ia(2)) | $CH_3$ | $C(H)F_2$ | 4-{1-[4-(6-{[4-(difluoromethyl)pyridin-2-yl]amino}-4-methylpyridin-2-yl)-1H-pyrazol-1-yl]ethyl}pyrrolidin-2-one | 413.2 | 413 | Free Base |

TABLE 1E-continued

| Ex. No. | R¹ (Structural Template) | R² | R³ | Chemical Name | [M + H]⁺ Calc'd | [M + H]⁺ Found | Form |
|---|---|---|---|---|---|---|---|
| 1.63[2] | "S or R, R or S" (Ia(2)) | CH₃ | C(H)F₂ | 4-{1-[4-(6-{[4-(difluoromethyl)pyridin-2-yl]amino}-4-methylpyridin-2-yl)-1H-pyrazol-1-yl]ethyl}pyrrolidin-2-one | 413.2 | 413 | Free Base |
| 1.64[2] | "S or R, S or R" (Ia(2)) | CH₃ | C(H)F₂ | 4-{1-[4-(6-{[4-(difluoromethyl)pyridin-2-yl]amino}-4-methylpyridin-2-yl)-1H-pyrazol-1-yl]ethyl}pyrrolidin-2-one | 413.2 | 413 | Free Base |
| 1.65 | H (Ia(1)) | CH₃ | C(H)F₂ | 4-(difluoromethyl)-N-[3-methyl-5-(1H-pyrazol-4-yl)phenyl]pyrimidin-2-amine | 302.1 | 302 | Free Base |
| 1.66[2] | "R or S, R or S" (Ia(2)) | CH₃ | C(H)F₂ | 4-{1-[4-(6-{[4-(difluoromethyl)pyridin-2-yl]amino}-4-methylpyridin-2-yl)-1H-pyrazol-1-yl]ethyl}pyrrolidin-2-one | 413.2 | 413 | Free Base |

Footnotes:

[1] In Example 1.31, the corresponding tert-butyl ester, used the method described in Preparative Example 6.7, tert-Butyl Ester Hydrolysis, as the ultimate synthetic step.

[2] Examples 1.32-1.39, 1.62-1.64, and 1.66 used the method described in Preparative Example 6.6, dimethoxybenzyl deprotection, as the ultimate synthetic step

Example 2.1

Preparation of 3-(4-(3-((4-methoxypyrimidin-2-yl)amino)-5-methylphenyl)-1H-pyrazol-1-yl)propanoic acid

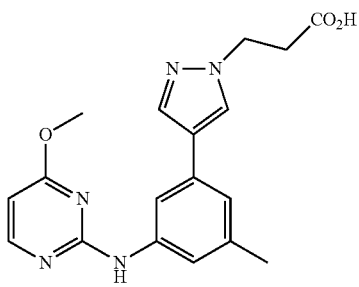 [SMILES: COc1ccnc(Nc2cc(C)cc(-c3cnn(CCC(=O)O)c3)c2)n1]

Step 1:

4-Methoxy-N-(3-methyl-5-(4,4,5,5-tetramethyl-1,3,2-dioxaborolan-2-yl)phenyl)pyrimidin-2-amine (0.05 g, 0.13 mmol), ethyl 3-(4-iodo-1H-pyrazol-1-yl)propanoate (0.04 g, 0.15 mmol), PdCl$_2$(dppf)-CH$_2$Cl$_2$ (0.02 g, 0.02 mmol), and Na$_2$CO$_3$ (2.0 M in water, 0.13 mL, 0.26 mmol) suspended in dioxane (0.75 mL) were added to vial. The vial was evacuated and then purged with argon, sealed and heated to 110° C. for 12 hours. The resulting mixture was used directly in the next step.

Step 2:

NaOH (1.0 M in water, 0.50 mL) and MeOH (0.50 mL) were added. The vial was sealed and irradiated in the microwave at 110° C. for 10 minutes. Silica supported-DMT (0.09 g, 0.13 mmol, 0.57 mmol/g) was added and the mixture was allowed to shake for 5 hrs at ambient temperature. The reaction was passed through a syringe filter, the eluent was collected and evaporated to dryness in vacuo. The crude residue was suspended in DMSO (1.5 mL) and was purified by reverse phase preparative HPLC (0 to 95% ACN/water with 0.1% formic acid modifier) to 3-(4-(3-((4-methoxypyrimidin-2-yl)amino)-5-methylphenyl)-1H-pyrazol-1-yl)propanoic acid. MS ESI calcd. for $C_{18}H_{20}N_5O_3$ [M+H]$^+$ 354. found 354. $^1$H NMR (600 MHz, DMSO-$d_6$) δ 9.41 (s, 1H), 8.17 (d, J=5.6, 1H), 7.99 (s, 1H), 7.78 (s, 1H), 7.72 (s, 1H), 7.35 (s, 1H), 6.94 (s, 1H), 6.24 (d, J=5.6, 1H), 4.29 (t, J=6.7, 2H), 3.90 (s, 3H), 2.79 (t, J=6.7, 2H), 2.26 (s, 3H).

The following compounds in Tables 2A-2C were prepared according to the method described for Example 2.1. Step 2 may not apply to all compounds exemplified in Table 2. Chiral separation was performed as necessary.

TABLE 2A

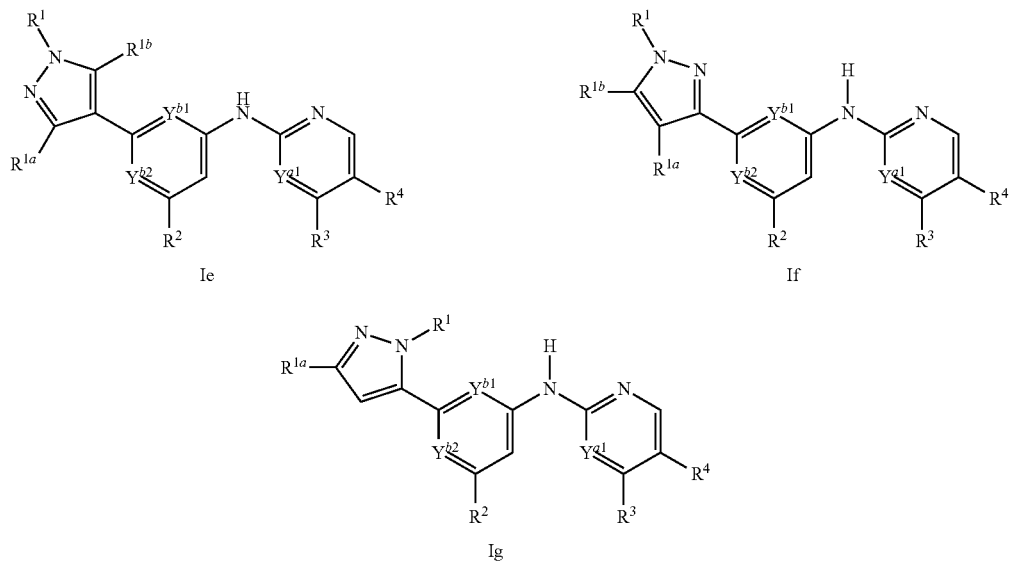

The below Examples are the formula IE [$Y^{b1} = Y^{b2}$ = CH, $Y^{a1}$ = N, and $R^{1a} = R^{1b} = R^4$ = H] unless specified to be of formulae If [$Y^{b1} = Y^{b2}$ = CH, $Y^{a1}$ = N, and $R^{1b} = R^4$ = H] or Ig [$Y^{b1} = Y^{b2}$ = CH, $Y^{a1}$ = N, and $R^{1a} = R^4$ = H].

| Ex. No. | $R^1$ | $R^2$ | $R^3$ | Chemical Name | [M + H]$^+$ Calc'd | [M + H]$^+$ Found |
|---|---|---|---|---|---|---|
| 2.2 | —(CH$_2$)$_2$CO$_2$ethyl formate salt | H | CF$_3$ | ethyl 3-[4-(3-{[4-(trifluoromethyl)-pyrimidin-2-yl]-amino}phenyl)-1H-pyrazol-1-yl]-propanoate | 406 | 406 |
| 2.3 | —(CH$_2$)$_2$CO$_2$ethyl formate salt | CH$_3$ | OCH$_3$ | ethyl 3-(4-{3-[(4-methoxypyrimidin-2-yl)amino]-5-methylphenyl}-1H-pyrazol-1-yl)-propanoate | 382 | 382 |

TABLE 2A-continued

| | | | | | | |
|---|---|---|---|---|---|---|
| 2.4 | (oxazolidin-2-one structure shown) chiral-R or S (late eluting enantiomer free base | $CH_3$ | $CF_3$ | 5-{[4-(3-methyl-5-{[4-(trifluoromethyl)-pyrimidin-2-yl]-amino}phenyl)-1H-pyrazol-1-yl]methyl}-1,3-oxazolidin-2-one | 419 | 419 |
| 2.5 | —$(CH_2)_2CO_2H$ ammonium salt | H | $CF_3$ | 3-[4-(3-{[4-(trifluoromethyl)pyrimidin-2-yl]amino}phenyl)-1H-pyrazol-1-yl]-propanoic acid | 378 | 378 |
| 2.6 | —$(CH_2)_2CONH_2$ formate salt | $CH_3$ | $CH_3$, $R^4 = F$ | 3-(4-{3-[(5-fluoro-4-methylpyrimidin-2-yl)amino]-5-methylphenyl}-1H-pyrazol-1-yl)propanamide | 355 | 355 |
| 2.7 | —$(CH_2)_2CONH_2$ formate salt | $CH_3$ | $OCH_3$, $R^4 = Cl$ | 3-(4-{3-[(5-chloro-4-methoxypyrimidin-2-yl)amino]-5-methylphenyl}-1H-pyrazol-1-yl)propanamide | 387 | 387 |
| 2.8 | —$(CH_2)_2CONH_2$ formate salt | $CH_3$ | —$CH(CH_3)_2$ | 3-[4-(3-methyl-5-{[4-(1-methylethyl)-pyrimidin-2-yl]-amino}phenyl)-1H-pyrazol-1-yl]propanamide | 365 | 365 |
| 2.9 | —$(CH_2)_2CONH_2$ formate salt | $CH_3$ | —$CHF_2$ | 3-[4-(3-{[4-(difluoromethyl)pyrimidin-2-yl]amino}-5-methylphenyl)-1H-pyrazol-1-yl]propanamide | 373 | 373 |
| 2.10 | —$(CH_2)_2CONH_2$ formate salt | H | $CH_3$ | 3-(4-{3-[(4-methylpyrimidin-2-yl)amino]phenyl}-1H-pyrazol-1-yl)propanamide | 323 | 323 |
| 2.11 | —$(CH_2)_2CONH_2$ formate salt | $CH_3$ | $OCH_3$, $R^4 = F$ | 3-(4-{3-[(5-fluoro-4-methoxypyrimidin-2-yl)amino]-5-methylphenyl}-1H-pyrazol-1-yl)propanamide | 371 | 371 |
| 2.12 | —$(CH_2)_2CONH_2$ formate salt | $CH_3$ | $CH_3$ | 3-(4-{3-methyl-5-[(4-methylpyrimidin-2-yl)amino]phenyl}-1H-pyrazol-1-yl)propanamide | 337 | 337 |
| 2.13 | —$(CH_2)_2CONH_2$ formate salt | $CH_3$ | $CH_3$, $R^4 = Cl$ | 3-(4-{3-[(5-chloro-4-methylpyrimidin-2-yl)amino]-5-methylphenyl}-1H-pyrazol-1-yl)propanamide | 371 | 371 |
| 2.14 | —$(CH_2)_2CONH_2$ formate salt | $CH_3$ | c-propyl | 3-(4-{3-[(4-cyclopropylpyrimidin-2-yl)amino]-5-methylphenyl}-1H-pyrazol-1-yl)propanamide | 363 | 363 |
| 2.15 | —$(CH_2)_2CONH_2$ formate salt | H | $CF_3$ | 3-[4-(3-{[4-(trifluoromethyl)pyrimidin-2-yl]amino}phenyl)-1H-pyrazol-1-yl]propanamide | 377 | 377 |

TABLE 2A-continued

| # | Structure | R | R' | Name | MS1 | MS2 |
|---|---|---|---|---|---|---|
| 2.16 | oxazolidinone-CH2- (chiral-R or S, free base) | H | CH₃ | 5-[(4-{3-[(4-methylpyrimidin-2-yl)amino]phenyl}-1H-pyrazol-1-yl)methyl]-1,3-oxazolidin-2-one | 351 | 351 |
| 2.17 | oxazolidinone-CH2- (racemic, free base) | CH₃ | OCH₃ | 5-[(4-{3-[(4-methoxypyrimidin-2-yl)amino]-5-methylphenyl}-1H-pyrazol-1-yl)methyl]-1,3-oxazolidin-2-one | 381 | 381 |
| 2.18 | oxazolidinone-CH2- (racemic, free base) | CH₃ | CH₃ | 5-[(4-{3-methyl-5-[(4-methylpyrimidin-2-yl)amino]phenyl}-1H-pyrazol-1-yl)methyl]-1,3-oxazolidin-2-one | 365 | 365 |
| 2.19 | oxazolidinone-CH2- (racemic, free base) | CH₃ | c-propyl | 5-[(4-{3-[(4-cyclopropylpyrimidin-2-yl)amino]-5-methylphenyl}-1H-pyrazol-1-yl)methyl]-1,3-oxazolidin-2-one | 391 | 391 |
| 2.20 | oxazolidinone-CH2- (racemic, free base) | H | CH₃ | 5-[(4-{3-[(4-methylpyrimidin-2-yl)amino]phenyl}-1H-pyrazol-1-yl)methyl]-1,3-oxazolidin-2-one | 351 | 351 |
| 2.21 | oxazolidinone-CH2- (racemic, free base) | CH₃ | OCH₃ | 5-[(4-{3-[(4-methoxypyrimidin-2-yl)amino]-5-methylphenyl}-1H-pyrazol-1-yl)methyl]-1,3-oxazolidin-2-one | 381 | 381 |
| 2.22 | oxazolidinone-CH2- (racemic, free base) | CH₃ | CH₃, R⁴ = F | 5-[(4-{3-[(5-fluoro-4-methylpyrimidin-2-yl)amino]-5-methylphenyl}-1H-pyrazol-1-yl)methyl]-1,3-oxazolidin-2-one | 383 | 383 |
| 2.23 | oxazolidinone-CH2- (chiral-R or S, free base) | CH₃ | OCH₃, R⁴ = Cl | 5-[(4-{3-[(5-chloro-4-methoxypyrimidin-2-yl)amino]-5-methylphenyl}-1H-pyrazol-1-yl)methyl]-1,3-oxazolidin-2-one | 415 | 415 |
| 2.24 | oxazolidinone-CH2- (chiral-R or S, free base) | CH₃ | i-propyl | 5-{[4-(3-methyl-5-{[4-(1-methylethyl)pyrimidin-2-yl]amino}phenyl)-1H-pyrazol-1-yl]methyl}-1,3-oxazolidin-2-one | 393 | 393 |
| 2.25 | oxazolidinone-CH2- (chiral-R or S, free base) | CH₃ | OCH₃, R⁴ = F | 5-[(4-{3-[(5-fluoro-4-methoxypyrimidin-2-yl)amino]-5-methylphenyl}-1H-pyrazol-1-yl)methyl]-1,3-oxazolidin-2-one | 399 | 399 |

TABLE 2A-continued

| | | | | | | |
|---|---|---|---|---|---|---|
| 2.26 | 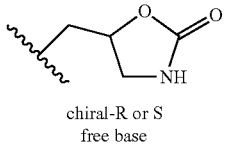 [SMILES: *CC1CNC(=O)O1] chiral-R or S free base | CH₃ | CH₃, R⁴ = Cl | 5-[(4-{3-[(5-chloro-4-methylpyrimidin-2-yl)amino]-5-methylphenyl}-1H-pyrazol-1-yl)methyl]-1,3-oxazolidin-2-one | 399 | 399 |
| 2.27 | 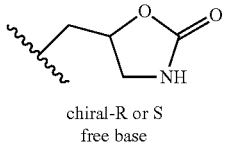 chiral-R or S free base | H | CF₃ | 5-{4-[3-{[4-(trifluoromethyl)pyrimidin-2-yl]amino}phenyl)-1H-pyrazol-1-yl]methyl}-1,3-oxazolidin-2-one | 405 | 405 |
| 2.28 | 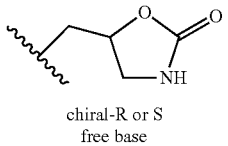 [SMILES: *CC1CNC(=O)O1] chiral-R or S free base | CH₃ | OCH₃, R⁴ = Cl | 5-[(4-{3-[(5-chloro-4-methoxypyrimidin-2-yl)amino]-5-methylphenyl}-1H-pyrazol-1-yl)methyl]-1,3-oxazolidin-2-one | 415 | 415 |
| 2.29 | 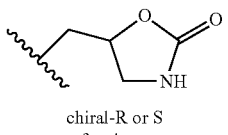 chiral-R or S free base | CH₃ | i-propyl | 5-{[4-(3-methyl-5-{[4-(1-methylethyl)pyrimidin-2-yl]amino}phenyl)-1H-pyrazol-1-yl]methyl}-1,3-oxazolidin-2-one | 393 | 393– |
| 2.30 | 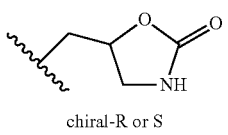 chiral-R or S free base | CH₃ | OCH₃, R⁴ = F | 5-[(4-{3-[(5-fluoro-4-methoxypyrimidin-2-yl)amino]-5-methylphenyl}-1H-pyrazol-1-yl)methyl]-1,3-oxazolidin-2-one | 399 | 399 |
| 2.31 | 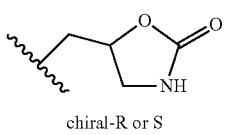 [SMILES: *CC1CNC(=O)O1] chiral-R or S | CH₃ | CH₃ | 5-[(4-{3-methyl-5-[(4-methylpyrimidin-2-yl)amino]phenyl}-1H-pyrazol-1-yl)methyl]-1,3-oxazolidin-2-one | 365 | 365 |
| 2.32 | 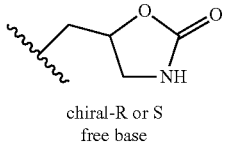 [SMILES: *CC1CNC(=O)O1] chiral-R or S free base | CH₃ | CH₃, R⁴ = Cl | 5-[(4-{3-[(5-chloro-4-methylpyrimidin-2-yl)amino]-5-methylphenyl}-1H-pyrazol-1-yl)methyl]-1,3-oxazolidin-2-one | 399 | 399 |
| 2.33 | 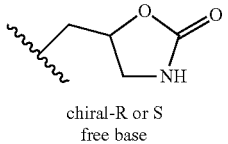 [SMILES: *CC1CNC(=O)O1] chiral-R or S free base | CH₃ | c-propyl | 5-[(4-{3-[(4-cyclopropylpyrimidin-2-yl)amino]-5-methylphenyl}-1H-pyrazol-1-yl)methyl]-1,3-oxazolidin-2-one | 391 | 391 |
| 2.34 | 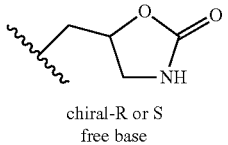 [SMILES: *CC1CNC(=O)O1] chiral-R or S free base | H | CF₃ | 5-{4-(3-{[4-(trifluoromethyl)pyrimidin-2-yl]amino}phenyl)-1H-pyrazol-1-yl]methyl}-1,3-oxazolidin-2-one | 405 | 405 |
| 2.35 | R¹ + R¹ᴮ = —N=CH—CH=CH— (IE(1)) free base | CH₃ | CF₃ | N-(3-methyl-5-pyrazolo[1,5-b]pyridazin-3-ylphenyl)-4-(trifluoromethyl)pyrimidin-2-amine | 371 | 371 |
| 2.36 | —N=C(OCH₃)—CH=CH— (IE(1)) free base | CH₃ | CF₃ | N-[3-(6-methoxypyrazolo[1,5-b]pyridazin-3-yl)-5- | 401 | 401 |

TABLE 2A-continued

| | | | | | | |
|---|---|---|---|---|---|---|
| 2.37 | —CH=CH—CH=N— (IE(1)) free base | CH$_3$ | CF$_3$ | methylphenyl]-4-(trifluoromethyl)pyrimidin-2-amine N-(3-methyl-5-pyrazolo[1,5-a]pyrimidin-3-ylphenyl)-4-(trifluoromethyl)pyrimidin-2-amine | 371 | 371 |
| 2.38 | H, R$^{1A}$ = R$^{1B}$ = CH$_3$ free base | CH$_3$ | CF$_3$ | N-[3-(3,5-dimethyl-1H-pyrazol-4-yl)-5-methylphenyl]-4-(trifluoromethyl)pyrimidin-2-amine | 348 | 348 |
| 2.39 | H, R$^{1A}$ = CH$_3$ free base | CH$_3$ | CF$_3$ | N-[3-methyl-5-(3-methyl-1H-pyrazol-4-yl)phenyl]-4-(trifluoromethyl)pyrimidin-2-amine | 334 | 334 |
| 2.40 | (CH$_2$)$_2$CO$_2$H formate salt | CH$_3$ | c-propyl | 3-(4-{3-[(4-cyclopropylpyrimidin-2-yl)amino]-5-methylphenyl}-1H-pyrazol-1-yl)propanoic acid | 364 | 364, 364 |
| 2.41 | (CH$_2$)$_2$CO$_2$ethyl free base, formate salt | CH$_3$ | c-propyl | ethyl 3-(4-{3-[(4-cyclopropylpyrimidin-2-yl)amino]-5-methylphenyl}-1H-pyrazol-1-yl)propanoate | 392 | 392 |
| 2.42 | (CH$_2$)$_2$CO$_2$ethyl formate salt | CH$_3$ | CH$_3$ | ethyl 3-(4-{3-methyl-5-[(4-methylpyrimidin-2-yl)amino]phenyl}-1H-pyrazol-1-yl)propanoate | 366 | 366 |
| 2.43 | (CH$_2$)$_2$CO$_2$ethyl free base, formate salt | CH$_3$ | CF$_3$ | ethyl 3-[4-(3-methyl-5-{[4-(trifluoromethyl)pyrimidin-2-yl]amino}phenyl)-1H-pyrazol-1-yl]propanoate | 420 | 420 |
| 2.44 | (CH$_2$)$_2$CO$_2$H formate salt | CH$_3$ | CH$_3$ | 3-(4-{3-methyl-5-[(4-methylpyrimidin-2-yl)amino]phenyl}-1H-pyrazol-1-yl)propanoic acid | 338 | 338 |
| 2.45 | 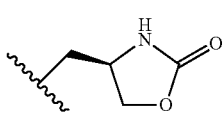 chiral-R or S (early eluting enantiomer) free base | CH$_3$ | CF$_3$ | 5-{[4-(3-methyl-5-{[4-(trifluoromethyl)pyrimidin-2-yl]amino}phenyl)-1H-pyrazol-1-yl]methyl}-1,3-oxazolidin-2-one | 419 | 419 |
| 2.46 | CH$_3$, IG free base | CH$_3$ | CF$_3$ | N-[3-methyl-5-(1-methyl-1H-pyrazol-3-yl)phenyl]-4-(trifluoromethyl)-pyrimidin-2-amine | 334 | 334 |
| 2.47 | R$^{1A}$ + R$^{1B}$ = —CH=CH—CH=CH— (IF) free base | CH$_3$ | CF$_3$ | N-[3-(1H-indazol-3-yl)-5-methylphenyl]-4-(trifluoromethyl)-pyrimidin-2-amine | 370 | 370 |
| 2.48 | CH$_3$, IF free base, formate salt | CH$_3$ | CF$_3$ | N-[3-methyl-5-(1-methyl-1H-pyrazol-5-yl)phenyl]-4-(trifluoromethyl)-pyrimidin-2-amine | 334 | 334 |

TABLE 2B

| Ex No. | R¹ | R² | R³ | Chemical Name | [M + H]⁺ Calc'd | [M + H]⁺ Found | Form |
|---|---|---|---|---|---|---|---|
| 2.49 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.50 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.51 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.52 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.53 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.54 | (structure with OH groups) single isomer, early eluting | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |

TABLE 2B-continued

| Ex No. | R¹ | R² | R³ | Chemical Name | [M + H]⁺ Calc'd | [M + H]⁺ Found | Form |
|---|---|---|---|---|---|---|---|
| 2.55 | (single isomer, early eluting) | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.56 | (single isomer, early eluting) | CH₃ | CHF₂ | 3-[4-(3-{[4-(difluoromethyl)pyrimidin-2-yl]amino}-5-methylphenyl)-1H-pyrazol-1-yl]hexane-2,5-diol | 418.2 | 418 | Free Base |
| 2.57 | benzamide-CH₂ | CH₃ | H | 4-({4-[3-methyl-5-(pyrimidin-2-ylamino)phenyl]-1H-pyrazol-1-yl}methyl)benzamide | 385.2 | 385 | Free Base |
| 2.58 | phenol-CH₂ | CH₃ | H | 4-({4-[3-methyl-5-(pyrimidin-2-ylamino)phenyl]-1H-pyrazol-1-yl}methyl)phenol | 358.2 | 358 | Free Base |
| 2.59 | 2,2-dimethyl-cyclohexanecarboxamide ("R or S, R or S") | CH₃ | CF₃ | 2,2-dimethyl-4-[4-(3-methyl-5-{[4-(trifluoromethyl)pyrimidin-2-yl]amino}phenyl)-1H-pyrazol-1-yl]cyclohexanecarboxylic acid | 474.2 | 474 | TFA Salt |
| 2.60 | cyclohexanecarboxylic acid | CH₃ | CHF₂ | 4-[4-(3-{[4-(difluoromethyl)pyrimidin-2-yl]amino}-5-methylphenyl)-1H-pyrazol-1-yl]cyclohexanecarboxylic acid | 428.2 | 428 | TFA Salt |

TABLE 2B-continued

| Ex No. | R¹ | R² | R³ | Chemical Name | [M + H]⁺ Calc'd | [M + H]⁺ Found | Form |
|---|---|---|---|---|---|---|---|
| 2.61 | (trans-cyclohexane-carboxylic acid), trans | CH₃ | CHF₂ | trans-4-[4-(3-{[4-(difluoromethyl)pyrimidin-2-yl]amino}-5-methylphenyl)-1H-pyrazol-1-yl]cyclohexanecarboxylic acid | 428.2 | 428 | Free Base |
| 2.63 | (oxazolidin-2-one-methyl), R or S | CH₃ | CHF₂ | 5-{[4-(3-{[4-(difluoromethyl)pyrimidin-2-yl]amino}-5-methylphenyl)-1H-pyrazol-1-yl]methyl}-1,3-oxazolidin-2-one | 401.2 | 401 | Free Base |
| 2.64 | (oxazolidin-2-one-methyl), S or R | CH₃ | CHF₂ | 5-{[4-(3-{[4-(difluoromethyl)pyrimidin-2-yl]amino}-5-methylphenyl)-1H-pyrazol-1-yl]methyl}-1,3-oxazolidin-2-one | 401.2 | 401 | Free Base |
| 2.65 | (oxazolidin-2-one-methyl), R or S | H | CHF₂ | 5-{[4-(3-{[4-(difluoromethyl)pyrimidin-2-yl]amino}phenyl)-1H-pyrazol-1-yl]methyl}-1,3-oxazolidin-2-one | 387.1 | 387 | Free Base |
| 2.66 | (oxazolidin-2-one-methyl), S or R | H | CHF₂ | 5-{[4-(3-{[4-(difluoromethyl)pyrimidin-2-yl]amino}phenyl)-1H-pyrazol-1-yl]methyl}-1,3-oxazolidin-2-one | 387.1 | 387 | Free Base |
| 2.67[3] | (pyrrolidin-2-one ethyl), "R or S, R or S" | CH₃ | CHF₂ | 4-{1-[4-(3-{[4-(difluoromethyl)pyrimidin-2-yl]amino}-5-methylphenyl)-1H-pyrazol-1-yl]ethyl}pyrrolidin-2-one | 413.2 | 413 | Free Base |

TABLE 2B-continued

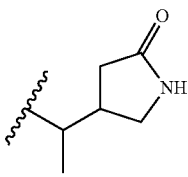

| Ex No. | R¹ | R² | R³ | Chemical Name | [M + H]⁺ Calc'd | [M + H]⁺ Found | Form |
|---|---|---|---|---|---|---|---|
| 2.68[3] | 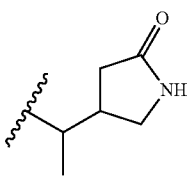<br>"R or S, S or R" | $CH_3$ | $CHF_2$ | 4-{1-[4-(3-{[4-(difluoromethyl)pyrimidin-2-yl]amino}-5-methylphenyl)-1H-pyrazol-1-yl]ethyl}pyrrolidin-2-one | 413.2 | 413 | Free Base |
| 2.69[3] | 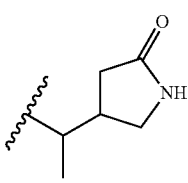<br>"S or R, R or S" | $CH_3$ | $CHF_2$ | 4-{1-[4-(3-{[4-(difluoromethyl)pyrimidin-2-yl]amino}-5-methylphenyl)-1H-pyrazol-1-yl]ethyl}pyrrolidin-2-one | 413.2 | 413 | Free Base |
| 2.70[3] | 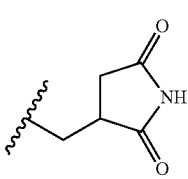<br>"S or R, S or R" | $CH_3$ | $CHF_2$ | 4-{1-[4-(3-{[4-(difluoromethyl)pyrimidin-2-yl]amino}-5-methylphenyl)-1H-pyrazol-1-yl]ethyl}pyrrolidin-2-one | 413.2 | 413 | Free Base |
| 2.71 | 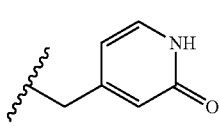 [SMILES: *Cc1cc[nH]c(=O)c1]<br>R or S | $CH_3$ | $CHF_2$ | 3-{[4-(3-{[4-(difluoromethyl)pyrimidin-2-yl]amino}-5-methylphenyl)-1H-pyrazol-1-yl]methyl}pyrrolidine-2,5-dione | 413.2 | 413 | TFA Salt |
| 2.72 | 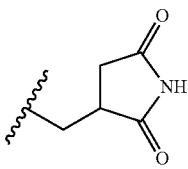 | $CH_3$ | $CHF_2$ | 4-{[4-(3-{[4-(difluoromethyl)pyrimidin-2-yl]amino}-5-methylphenyl)-1H-pyrazol-1-yl]methyl}pyridin-2(1H)-one | 409.2 | 409 | Free Base |
| 2.73 | <br>S or R | $CH_3$ | $CHF_2$ | 3-{[4-(3-{[4-(difluoromethyl)pyrimidin-2-yl]amino}-5-methylphenyl)-1H-pyrazol-1-yl]methyl}pyrrolidine-2,5-dione | 413.2 | 413 | TFA Salt |

TABLE 2B-continued

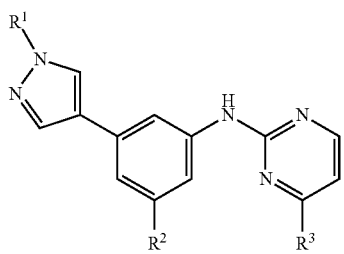

| Ex No. | R¹ | R² | R³ | Chemical Name | [M + H]⁺ Calc'd | [M + H]⁺ Found | Form |
|---|---|---|---|---|---|---|---|
| 2.74 | (oxazolidine-2,4-dione, R or S) | CH₃ | CHF₂ | 5-{[4-(3-{[4-(difluoromethyl)pyrimidin-2-yl]amino}-5-methylphenyl)-1H-pyrazol-1-yl]methyl}-1,3-oxazolidine-2,4-dione | 415.1 | 415 | Free Base |
| 2.75 | (oxazolidine-2,4-dione, S or R) | CH₃ | CHF₂ | 5-{[4-(3-{[4-(difluoromethyl)pyrimidin-2-yl]amino}-5-methylphenyl)-1H-pyrazol-1-yl]methyl}-1,3-oxazolidine-2,4-dione | 415.1 | 415 | Free Base |
| 2.76[4] | (5-methylpyrrolidin-2-one, "R or S, R or S") | CH₃ | CHF₂ | 4-{[4-(3-{[4-(difluoromethyl)pyrimidin-2-yl]amino}-5-methylphenyl)-1H-pyrazol-1-yl]methyl}-5-methylpyrrolidin-2-one | 413.2 | 413 | TFA Salt |
| 2.77[4] | (4-methylpyrrolidin-2-one, R or S) | CH₃ | CHF₂ | 4-{[4-(3-{[4-(difluoromethyl)pyrimidin-2-yl]amino}-5-methylphenyl)-1H-pyrazol-1-yl]methyl}-4-methylpyrrolidin-2-one | 413.2 | 413 | Free Base |
| 2.78 | (1,3-oxazinan-2-one, R or S) | CH₃ | CHF₂ | 6-{[4-(3-{[4-(difluoromethyl)pyrimidin-2-yl]amino}-5-methylphenyl)-1H-pyrazol-1-yl]methyl}-1,3-oxazinan-2-one | 415.2 | 415 | Free Base |
| 2.79[4] | (5-methylpyrrolidin-2-one, "R or S, S or R") | CH₃ | CHF₂ | 4-{[4-(3-{[4-(difluoromethyl)pyrimidin-2-yl]amino}-5-methylphenyl)-1H-pyrazol-1-yl]methyl}-5-methylpyrrolidin-2-one | 413.2 | 413 | TFA Salt |

TABLE 2B-continued

| Ex No. | R¹ | R² | R³ | Chemical Name | [M + H]⁺ Calc'd | [M + H]⁺ Found | Form |
|---|---|---|---|---|---|---|---|
| 2.80[4] | (4-methyl-2-oxopyrrolidin-4-yl)methyl, S or R | $CH_3$ | $CHF_2$ | 4-{[4-(3-{[4-(difluoromethyl)pyrimidin-2-yl]amino}-5-methylphenyl)-1H-pyrazol-1-yl]methyl}-4-methylpyrrolidin-2-one | 413.2 | 413 | TFA Salt |
| 2.81 | (2-oxo-1,3-oxazinan-6-yl)methyl, S or R | $CH_3$ | $CHF_2$ | 6-{[4-(3-{[4-(difluoromethyl)pyrimidin-2-yl]amino}-5-methylphenyl)-1H-pyrazol-1-yl]methyl}-1,3-oxazinan-2-one | 415.2 | 415 | Free Base |
| 2.82 | 2-aminoethyl | $CH_3$ | $CHF_2$ | N-{3-[1-(2-aminoethyl)-1H-pyrazol-4-yl]-5-methylphenyl}-4-(difluoromethyl)pyrimidin-2-amine | 345.2 | 345 | Free Base |
| 2.83 | (morpholin-2-yl)methyl, S | $CH_3$ | $CHF_2$ | 4-(difluoromethyl)-N-(3-methyl-5-{1-[(2S)-morpholin-2-ylmethyl]-1H-pyrazol-4-yl}phenyl)pyrimidin-2-amine | 401.2 | 401 | Free Base |
| 2.84 | (morpholin-2-yl)methyl, R | $CH_3$ | $CHF_2$ | 4-(difluoromethyl)-N-(3-methyl-5-{1-[(2R)-morpholin-2-ylmethyl]-1H-pyrazol-4-yl}phenyl)pyrimidin-2-amine | 401.2 | 401 | Free Base |
| 2.85[5] | 2-amino-2-methylpropyl | $CH_3$ | $CHF_2$ | N-{3-[1-(2-amino-2-methylpropyl)-1H-pyrazol-4-yl]-5-methylphenyl}-4-(difluoromethyl)pyrimidin-2-amine | 373.2 | 373 | Free Base |

Footnotes:

[3]Example Nos. 2.67-2.70 used the method described in Preparative Example 6.6 - Methoxybenzyl or Dimethoxybenzyl Deprotection as the ultimate synthetic step

[4]Example Nos. 2.76, 2.77, 2.79, and 2.80, aand 2.85 used the method described in Preparative Example 6.9 - Benzyl deprotection as the ultimate synthetic step

[5]Example No. 2.85 - OMs used as starting material

TABLE 2C

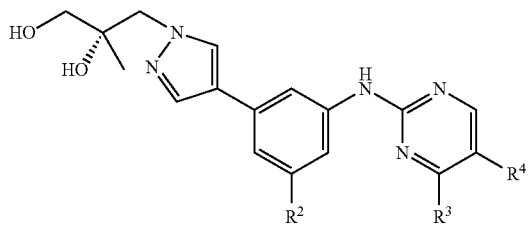

| Ex No. | R² | R³ | R⁴ | Chemical Name | [M + H]⁺ Calc'd | [M + H]⁺ Found | Form |
|---|---|---|---|---|---|---|---|
| 2.86 | H | H | CF₃ | (2S)-2-methyl-3-[4-(3-{[4-(trifluoromethyl)pyrimidin-2-yl]amino}phenyl)-1H-pyrazol-1-yl]propane-1,2-diol | 394.1 | 394 | TFA Salt |
| 2.87 | CH₃ | H | C(H)(OH)CH₃ R or S | (2S)-3-[4-(3-{[4-(1-hydroxyethyl)pyrimidin-2-yl]amino}-5-methylphenyl)-1H-pyrazol-1-yl]-2-methylpropane-1,2-diol | 384.2 | 384 | TFA Salt |
| 2.88 | CH₃ | H | OCH₃ | (2S)-3-(4-{3-[(4-methoxypyrimidin-2-yl)amino]-5-methylphenyl}-1H-pyrazol-1-yl)-2-methylpropane-1,2-diol | 370.2 | 370 | TFA Salt |
| 2.89 | CH₃ | OCH₃ | F | (2S)-3-(4-{3-[(5-fluoro-4-methoxypyrimidin-2-yl)amino]-5-methylphenyl}-1H-pyrazol-1-yl)-2-methylpropane-1,2-diol | 388.2 | 388 | TFA Salt |
| 2.90 | CH₃ | H | c-propyl | (2S)-3-(4-{3-[(4-cyclopropylpyrimidin-2-yl)amino]-5-methylphenyl}-1H-pyrazol-1-yl)-2-methylpropane-1,2-diol | 380.2 | 380 | TFA Salt |
| 2.91 | F | H | CF₃ | (2S)-3-[4-(3-fluoro-5-{[4-(trifluoromethyl)pyrimidin-2-yl]amino}phenyl)-1H-pyrazol-1-yl]-2-methylpropane-1,2-diol | 412.1 | 412 | TFA Salt |
| 2.92 | H | H | CHF₂ | (2S)-3-[4-(3-{[4-(difluoromethyl)pyrimidin-2-yl]amino}phenyl)-1H-pyrazol-1-yl]-2-methylpropane-1,2-diol | 376.2 | 376 | Free Base |
| 2.93 | H | H | C(H)(OH)CH₃ R or S | (2S)-3-[4-(3-{[4-(1-hydroxyethyl)pyrimidin-2-yl]amino}phenyl)-1H-pyrazol-1-yl]-2-methylpropane-1,2-diol | 370.2 | 370 | Free Base |
| 2.94 | CH₃ | CH₃ | F | (2S)-3-(4-{3-[(5-fluoro-4-methylpyrimidin-2-yl)amino]-5-methylphenyl}-1H-pyrazol-1-yl)-2-methylpropane-1,2-diol | 372.2 | 372 | Free Base |
| 2.95 | H | H | CH₃ | (2S)-2-methyl-3-(4-{3-[(4-methylpyrimidin-2-yl)amino]phenyl}-1H-pyrazol-1-yl)propane-1,2-diol | 340.2 | 340 | Free Base |
| 2.96 | CH₃ | H | OC(H)(CH₃)₂ | (2S)-2-methyl-3-[4-(3-methyl-5-{[4-(1-methylethoxy)pyrimidin-2-yl]amino}phenyl)-1H-pyrazol-1-yl]propane-1,2-diol | 398.2 | 398 | Free Base |
| 2.97 | CH₃ | CH₃ | Cl | (2S)-3-(4-{3-[(5-chloro-4-methylpyrimidin-2-yl)amino]-5-methylphenyl}-1H-pyrazol-1-yl)-2-methylpropane-1,2-diol | 388.2 | 388 | Free Base |
| 2.98 | CH₃ | OCH₃ | Cl | (2S)-3-(4-{3-[(5-chloro-4-methoxypyrimidin-2-yl)amino]-5-methylphenyl}-1H-pyrazol-1-yl)-2-methylpropane-1,2-diol | 404.1 | 404 | Free Base |

Example 3.1

Preparation of 3-methyl-5-{[4-(3-methyl-5-{[4-(trifluoromethyl)pyrimidin-2-yl]amino}phenyl)-1H-pyrazol-1-yl]methyl}-1,3-oxazolidin-2-one (early eluting enantiomer)

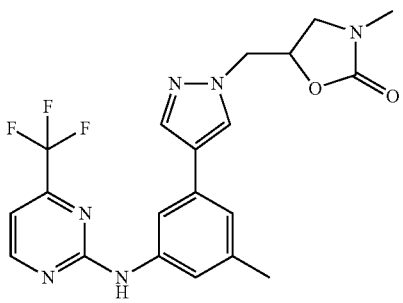 [SMILES: Cc1cc(Nc2nccc(C(F)(F)F)n2)cc(-c2cnn(CC3CN(C)C(=O)O3)c2)c1]

Step 1:

N-[3-Methyl-5-(1H-pyrazol-4-yl)phenyl]-4-(trifluoromethyl)pyrimidin-2-amine (100 mg, 0.31 mmol), 5-(chloromethyl)-3-methyl-1,3-oxazolidin-2-one (56.2 mg, 0.38 mmol), and cesium carbonate (122 mg, 0.38 mmol) were dissolved in DMA (1 mL). The mixture was then heated by microwave irradiation to 140° C. for 1.5 hours. Additional 5-(chloromethyl)-3-methyl-1,3-oxazolidin-2-one (30 mg, 0.19 mmol) was added and the mixture heated by microwave irradiation to 140° C. for 30 minutes. The reaction was cooled to room temperature, diluted with water (3 mL) and ACN (3 mL) then filtered through a syringe filter and concentrated under reduced pressure. The residue was purified by reverse phase preparative HPLC (45 to 80% ACN/water with 0.1% TFA modifier). The free base was liberated using PL-HCO$_3$ cartridges (Stratospheres™, 0.9 mmol) and lyophilized to afford racemic 3-methyl-5-{[4-(3-methyl-5-{[4-(trifluoromethyl)pyrimidin-2-yl]amino}phenyl)-1H-pyrazol-1-yl]methyl}-1,3-oxazolidin-2-one. MS ESI calcd. for $C_{20}H_{20}F_3N_6O_2$ [M+H]$^+$ 433. found 433. $^1$H NMR (500 MHz, DMSO-d$_6$) δ 10.12 (s, 1H), 8.80 (d, J=3.9 Hz, 1H), 8.04 (s, 1H), 7.82 (s, 1H), 7.80 (s, 1H), 7.35 (s, 1H), 7.24 (d, J=3.4 Hz, 1H), 7.06 (s, 1H), 4.90-4.79 (m, 1H), 4.45-4.32 (m, 2H), 3.65 (t, J=8.9 Hz, 1H), 3.40 (dd, J=6.2, 9.0, 1H), 2.68 (s, 3H), 2.29 (s, 3H).

Step 2:

3-Methyl-5-{[4-(3-methyl-5-{[4-(trifluoromethyl)pyrimidin-2-yl]amino}phenyl)-1H-pyrazol-1-yl]methyl}-1,3-oxazolidin-2-one (29.3 mg, 0.07 mmol) enantiomers were separated by chiral super critical fluid chromatography (IC-H 2.1×25 cm, 5 uM, mobile phase: 35% to 65% 2-propanol in CO$_2$, flow rate: 70 mL/min, 7 min run time) to afford –3-methyl-5-{[4-(3-methyl-5-{[4-(trifluoromethyl)pyrimidin-2-yl]amino}phenyl)-1H-pyrazol-1-yl]methyl}-1,3-oxazolidin-2-one (early eluting enantiomer) as a white solid. MS ESI calcd. for $C_{20}H_{20}F_3N_6O_2$ [M+H]$^+$ 433. found 433. $^1$H NMR (500 MHz, DMSO-d$_6$) δ 10.13 (s, 1H), 8.80 (d, J=4.9, 1H), 8.04 (s, 1H), 7.82 (s, 1H), 7.80 (s, 1H), 7.35 (s, 1H), 7.24 (d, J=4.9 Hz, 1H), 7.06 (s, 1H), 4.95-4.76 (m, 1H), 4.46-4.33 (m, 2H), 3.65 (t, J=8.9, 1H), 3.37 (dd, J=6.2, 9.0 Hz, 1H), 2.68 (s, 3H), 2.32 (s, 3H).

The following compounds in Tables 3A-3C were prepared according to the method described for Example 3.

TABLE 3A

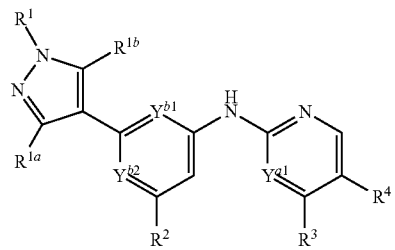

Ie

Ie [$R^{1a} = R^{1b} = R^4 = H$; $Y^{b1} = Y^{b2} = CH$; $Y^{a1} = N$]

| Ex. | R$^1$ | R$^2$ | R$^3$ | Chemical Name | [M + H]$^+$ Calc'd | [M + H]$^+$ Found |
|---|---|---|---|---|---|---|
| 3.2 | CH$_2$CH(OH)CH$_2$CN<br>R<br>formate salt, TFA salt | CH$_3$ | CF$_3$ | (3R)-3-hydroxy-4-[4-(3-methyl-5-{[4-(trifluoromethyl)-pyrimidin-2-yl]amino}phenyl)-1H-pyrazol-1-yl]-butanenitrile | 403 | 403 |
| 3.3 | (CH$_2$)$_2$CONH$_2$<br>free base, formate salt | CH$_3$ | CF$_3$ | 3-[4-(3-methyl-5-{[4-(trifluoromethyl)-pyrimidin-2-yl]aminol-phenyl)-1H-pyrazol-1-yl]-propanamide | 391 | 391 |
| 3.4 | CH$_2$CH(OH)CH$_2$CN<br>R<br>formate salt | CH$_3$ | CF$_3$ | (2r)-2-methyl-3-[4-(3-methyl-5-{[4-(trifluoromethyl)-pyrimidin-2-yl]-amino}phenyl)-1H-pyrazol-1-yl]-propan-1-ol | 392 | 392 |
| 3.5 | CH$_2$CH(OH)CH$_2$CN<br>S<br>formate salt | CH$_3$ | CF$_3$ | (2s)-2-methyl-3-[4-(3-methyl-5-{[4-(trifluoromethyl)- | 392 | 392 |

TABLE 3A-continued

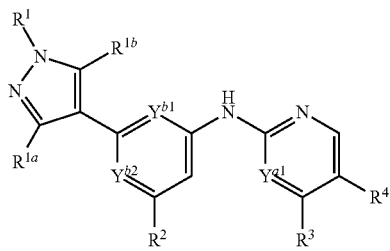

Ie [$R^{1a} = R^{1b} = R^4 = H$; $Y^{b1} = Y^{b2} = CH$; $Y^{a1} = N$]

| Ex. | $R^1$ | $R^2$ | $R^3$ | Chemical Name | [M + H]+ Calc'd | [M + H]+ Found |
|---|---|---|---|---|---|---|
| | | | | pyrimidin-2-yl]amino}-phenyl)-1H-pyrazol-1-yl]-propan-1-ol | | |
| 3.6 | 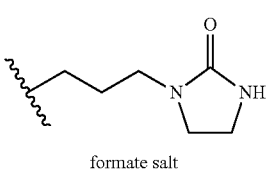 [SMILES: *CCCN1CCNC1=O]<br>formate salt | CH₃ | CF₃ | 1-{3-[4-(3-methyl-5-{[4-(trifluoro-methyl)pyrimidin-2-yl]amino}-phenyl)-1H-pyrazol-1-yl]-propyl}imidazolidin-2-one | 446 | 446 |
| 3.7 | 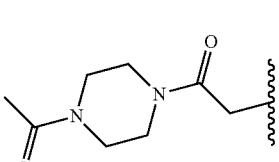<br>formate salt | CH₃ | CF₃ | N-(3-{1-[2-(4-acetylpiperazin-1-yl)-2-oxoethyl]-1H-pyrazol-4-yl}-5-methylphenyl)-4-(trifluoromethyl)-pyrimidin-2-amine | 488 | 488 |
| 3.8 | CH₂CONHt-butyl<br>formate salt | CH₃ | CF₃ | N-tert-butyl-2-[4-(3-methyl-5-{[4-(trifluoromethyl)pyrimidin-2-yl]amino}-phenyl)-1H-pyrazol-1-yl]acetamide | 433 | 433 |
| 3.9 | 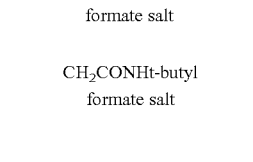<br>racemic<br>formate salt | CH₃ | CF₃ | N-{3-[1-(1,4-dioxan-2-ylmethyl)-1H-pyrazol-4-yl]-5-methyl-phenyl}-4-(trifluoro-methyl)pyrimidin-2-amine | 420 | 420 |
| 3.10 | 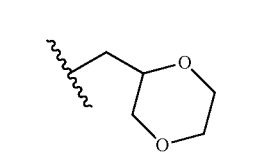<br>formate salt | CH₃ | CF₃ | N-(3-methyl-5-{1-[(5-methyl-1,2,4-oxadiazol-3-yl)methyl]-1H-pyrazol-4-yl}phenyl)-4-(trifluoromethyl)-pyrimidin-2-amine | 416 | 416 |
| 3.11 | 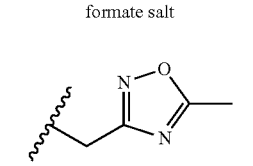<br>formate salt | CH₃ | CF₃ | N-(3-{1-[2-(4,4-dimethyl-1,3-oxazolidin-3-yl)-2-oxoethyl]-1H-pyrazol-4-yl}-5-methylphenyl)-4-(trifluoromethyl)pyrimidin-2-amine | 461 | 461 |

TABLE 3A-continued

Ie [$R^{1a} = R^{1b} = R^4 = H; Y^{b1} = Y^{b2} = CH; Y^{a1} = N$]

| Ex. | $R^1$ | $R^2$ | $R^3$ | Chemical Name | [M + H]$^+$ Calc'd | [M + H]$^+$ Found |
|---|---|---|---|---|---|---|
| 3.12 | (acetamide group with N-methoxy-1,1-dimethylethyl) formate salt | CH$_3$ | CF$_3$ | N-(2-methoxy-1,1-dimethylethyl)-2-[4-(3-methyl-5-{[4-(trifluoromethyl)pyrimidin-2-yl]amino}phenyl)-1H-pyrazol-1-yl]acetamide | 463 | 463 |
| 3.13 | (3,3-dimethylmorpholine acyl) formate salt | CH$_3$ | CF$_3$ | N-(3-{1-[2-(3,3-dimethylmorpholin-4-yl)-2-oxoethyl]-1H-pyrazol-4-yl}-5-methylphenyl)-4-(trifluoromethyl)pyrimidin-2-amine | 475 | 475 |
| 3.14 | (3,5-dimethylmorpholine acyl, R,S) formate salt | CH$_3$ | CF$_3$ | N-[3-(1-{2-[(3r,5s)-3,5-dimethyl-morpholin-4-yl]-2-oxoethyl}-1H-pyrazol-4-yl)-5-methylphenyl]-4-(trifluoromethyl)-pyrimidin-2-amine | 475 | 475 |
| 3.15 | (3,5-dimethylmorpholine acyl, R,R) formate salt | CH$_3$ | CF$_3$ | N-[3-(1-{2-[(3r,5r)-3,5-dimethylmorpholin-4-yl]-2-oxoethyl}-1H-pyrazol-4-yl)-5-methylphenyl]-4-(trifluoromethyl)-pyrimidin-2-amine | 475 | 475 |
| 3.16 | —(CH$_2$)$_2$NHCONH$_2$ formate salt | CH$_3$ | CF$_3$ | 1-{2-[4-(3-methyl-5-{[4-(trifluoromethyl)-pyrimidin-2-yl]-amino}phenyl)-1H-pyrazol-1-yl]ethyl}urea | 406 | 406 |
| 3.17 | (dihydrofuran-2(3H)-one) racemic formate salt | CH$_3$ | CF$_3$ | 3-[4-(3-methyl-5-{[4-(trifluoromethyl)pyrimidin-2-yl]amino}-phenyl)-1H-pyrazol-1-yl]dihydrofuran-2(3h)-one | 404 | 404 |

TABLE 3A-continued

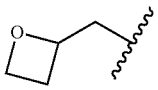

Ie [$R^{1a} = R^{1b} = R^4 = H; Y^{b1} = Y^{b2} = CH; Y^{a1} = N$]

| Ex. | $R^1$ | $R^2$ | $R^3$ | Chemical Name | [M + H]⁺ Calc'd | [M + H]⁺ Found |
|---|---|---|---|---|---|---|
| 3.18 | 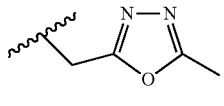<br>racemic<br>formate salt | CH₃ | CF₃ | N-{3-methyl-5-[1-(oxetan-2-ylmethyl)-1H-pyrazol-4-yl]-phenyl}-4-(trifluoro-methyl)-pyrimidin-2-amine | 390 | 390 |
| 3.19 | —(CH₂)₂O(CH₂)₂OH<br>formate salt | CH₃ | CF₃ | 2-{2-[4-(3-methyl-5-{[4-(trifluoromethyl)-pyrimidin-2-yl]-amino}phenyl)-1H-pyrazol-1-yl]ethoxy} ethanol | 408 | 408 |
| 3.20 | —(CH₂)₃NH₂<br>formate salt | CH₃ | CF₃ | N-{3-[1-(3-aminopropyl)-1H-pyrazol-4-yl]-5-methylphenyl}-4-(trifluoromethyl)pyrimidin-2-amine | 377 | 377 |
| 3.21 | —CH₂c-propyl<br>formate salt | CH₃ | CF₃ | N-{3-[1-(cyclopropylmethyl)-1H-pyrazol-4-yl]-5-methylphenyl}-4-(trifluoromethyl)pyrimidin-2-amine | 374 | 374 |
| 3.22 | —CH₂C(O)CH₃<br>formate salt | CH₃ | CF₃ | 1-[4-(3-methyl-5-{[4-(trifluoromethyl)pyrimidin-2-yl]amino}phenyl)-1H-pyrazol-1-yl]propan-2-one | 376 | 376 |
| 3.23 | —CH₂CH(OCH₂CH₃)₂<br>formate salt | CH₃ | CF₃ | N-{3-[1-(2,2-diethoxyethyl)-1H-pyrazol-4-yl]-5-methylphenyl}-4-(trifluoromethyl)pyrimidin-2-amine | 436 | 436 |
| 3.24 | 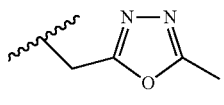<br>formate salt | CH₃ | CF₃ | N-(3-methyl-5-{1-[(5-methyl-1,3,4-oxadiazol-2-yl)methyl]-1H-pyrazol-4-yl}phenyl)-4-(trifluoromethyl)pyrimidin-2-amine | 416 | 416 |
| 3.25 | 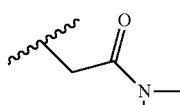<br>formate salt | CH₃ | CF₃ | N-(3-methyl-5-{1-[(3-methylisoxazol-5-yl)methyl]-1H-pyrazol-4-yl}phenyl)-4-(trifluoromethyl)-pyrimidin-2-amine | 415 | 415 |
| 3.26 | <br>formate salt | CH₃ | CF₃ | N-{3-[1-(2-azetidin-1-yl-2-oxoethyl)-1H-pyrazol-4-yl]-5-methylphenyl}-4-(trifluoromethyl)pyrimidin-2-amine | 417 | 417 |

TABLE 3A-continued

Ie [$R^{1a} = R^{1b} = R^4 = H$; $Y^{b1} = Y^{b2} = CH$; $Y^{a1} = N$]

| Ex. | $R^1$ | $R^2$ | $R^3$ | Chemical Name | $[M + H]^+$ Calc'd | $[M + H]^+$ Found |
|---|---|---|---|---|---|---|
| 3.27 | (acetyl-pyrrolidine group) formate salt | $CH_3$ | $CF_3$ | N-{3-methyl-5-[1-(2-oxo-2-pyrrolidin-1-ylethyl)-1H-pyrazol-4-yl]phenyl}-4-(trifluoromethyl)pyrimidin-2-amine | 431 | 431 |
| 3.28 | methyl 2-ethylpropanoate group, racemic formate salt | $CH_3$ | $CF_3$ | methyl 2-[4-(3-methyl-5-{[4-(trifluoromethyl)pyrimidin-2-yl]amino}-phenyl)-1H-pyrazol-1-yl]butanoate | 420 | 420 |
| 3.29 | methyl 2-methylpropanoate group, racemic formate salt | $CH_3$ | $CF_3$ | methyl 2-[4-[3-methyl-5-{[4-(trifluoromethyl)-pyrimidin-2-yl]amino}-phenyl)-1H-pyrazol-1-yl]propanoate | 406 | 406 |
| 3.30 | ethyl 2-methylpropanoate group, racemic formate salt | $CH_3$ | $CF_3$ | ethyl 2-[4-(3-methyl-5-{[4-(trifluoromethyl)-pyrimidin-2-yl]amino}phenyl)-1H-pyrazol-1-yl]propanoate | 420 | 420 |
| 3.31 | —$(CH_2)_3OH$ formate salt | $CH_3$ | $CF_3$ | 3-[4-(3-methyl-5-{[4-(trifluoromethyl)pyrimidin-2-yl]amino}-phenyl)-1H-pyrazol-1-yl]propan-1-ol | 378 | 378 |
| 3.32 | (pyridazin-4-ylmethyl group) formate salt | $CH_3$ | $CF_3$ | N-{3-methyl-5-[1-(pyridazin-4-ylmethyl)-1H-pyrazol-4-yl]phenyl}-4-(trifluoromethyl)pyrimidin-2-amine | 412 | 412 |

TABLE 3A-continued

Ie

Ie [R$^{1a}$ = R$^{1b}$ = R$^4$ = H; Y$^{b1}$ = Y$^{b2}$ = CH; Y$^{a1}$ = N]

| Ex. | R$^1$ | R$^2$ | R$^3$ | Chemical Name | [M + H]$^+$ Calc'd | [M + H]$^+$ Found |
|---|---|---|---|---|---|---|
| 3.33 | (oxazolidin-2-one-CH$_2$-) formate salt | CH$_3$ | CF$_3$ | 5-{[4-(3-methyl-5-{[4-(trifluoromethyl)pyrimidin-2-yl]amino}-phenyl)-1H-pyrazol-1-yl]methyl}-1,3-oxazolidin-2-one | 419 | 419 |
| 3.34[6] | (CH(Et)COOH-) racemic formate salt | CH$_3$ | CF$_3$ | 2-[4-(3-methyl-5-{[4-(trifluoromethyl)pyrimidin-2-yl]amino}-phenyl)-1H-pyrazol-1-yl]butanoic acid | 406 | 406 |
| 3.35[6] | (CH(Me)COOH-) racemic free base | CH$_3$ | CF$_3$ | 2-[4-(3-methyl-5-{[4-(trifluoromethyl)pyrimidin-2-yl]amino}-phenyl)-1H-pyrazol-1-yl]propanoic acid | 392 | 392 |
| 3.36[7] | —(CH$_2$)$_2$OH formate salt | CH$_3$ | CF$_3$ | 2-[4-(3-methyl-5-{[4-(trifluoromethyl)-pyrimidin-2-yl]amino}-phenyl)-1H-pyrazol-1-yl]ethanol | 364 | 364 |
| 3.37 | —CH$_2$CONH$_2$ free base formate salt | CH$_3$ | CF$_3$ | 2-[4-(3-methyl-5-{[4-(trifluoromethyl)pyrimidin-2-yl]amino}-phenyl)-1H-pyrazol-1-yl]acetamide | 377 | 377 |
| 3.38[8] | —(CH$_2$)$_2$CONH$_2$ formate salt | CH$_3$ | —O(CH$_2$)$_2$OH | 3-[4-(3-{[4-(2-hydroxyethoxy)pyrimidin-2-yl]amino}-5-methylphenyl)-1H-pyrazol-1-yl]propanamide | 383 | 383 |
| 3.39 | —CH$_2$SO$_2$NH$_2$ free base | CH$_3$ | CF$_3$ | 1-[4-(3-methyl-5-{[4-(trifluoromethyl)pyrimidin-2-yl]amino}-phenyl)-1H-pyrazol-1-yl]methane-sulfonamide | 413 | 413 |
| 3.40 | —(CH$_2$)$_2$CONH$_2$ free base | CH$_3$ | OCH$_3$ | 3-(4-{3-[(4-methoxypyrimidin-2-yl)amino]-5-methylphenyl}-1H-pyrazol-1-yl)propanamide | 353 | 353 |
| 3.41 | —CH$_2$CH(OH)CH$_2$OH R free base | CH$_3$ | CF$_3$ | (2R)-3-[4-(3-methyl-5-{[4-(trifluoromethyl)pyrimidin-2-yl]amino}-phenyl)-1H-pyrazol-1-yl]propane-1,2-diol | 394 | 394 |

TABLE 3A-continued

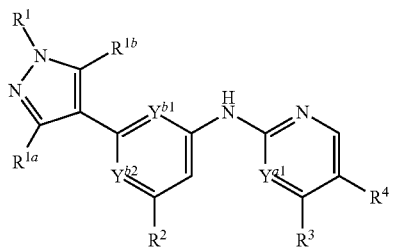

Ie [R$^{1a}$ = R$^{1b}$ = R$^4$ = H; Y$^{b1}$ = Y$^{b2}$ = CH; Y$^{a1}$ = N]

| Ex. | R$^1$ | R$^2$ | R$^3$ | Chemical Name | [M + H]$^+$ Calc'd | [M + H]$^+$ Found |
|---|---|---|---|---|---|---|
| 3.42 | —CH$_2$CH(OH)CH$_2$OH<br>S<br>free base | CH$_3$ | CF$_3$ | (2S)-3-[4-(3-methyl-5-{[4-(trifluoromethyl)pyrimidin-2-yl]amino}phenyl)-1H-pyrazol-1-yl]propane-1,2-diol | 394 | 394 |
| 3.43 | —CH$_2$CH(OH)CF$_3$<br>racemic<br>free base | CH$_3$ | CF$_3$ | 1,1,1-trifluoro-3-[4-(3-methyl-5-{[4-(trifluoromethyl)pyrimidin-2-yl]amino}phenyl)-1H-pyrazol-1-yl]propan-2-ol | 432 | 432 |
| 3.44 | —CH$_2$CH(OH)CF$_3$<br>chiral-R or S<br>free base | CH$_3$ | CF$_3$ | 1,1,1-trifluoro-3-[4-(3-methyl-5-{[4-(trifluoromethyl)pyrimidin-2-yl]amino}phenyl)-1H-pyrazol-1-yl]propan-2-ol | 432 | 432 |
| 3.45 | —CH$_2$CH(OH)CF$_3$<br>chiral-S or R<br>free base | CH$_3$ | CF$_3$ | 1,1,1-trifluoro-3-[4-(3-methyl-5-{[4-(trifluoromethyl)pyrimidin-2-yl]amino}phenyl)-1H-pyrazol-1-yl]propan-2-ol | 432 | 432 |
| 3.46 | (oxazolidinone structure)<br>chiral-R OR S<br>(late eluting peak)<br>free base | CH$_3$ | CF$_3$ | (3-methyl-5-{[4-(3-methyl-5-{[4-(trifluoromethyl)pyrimidin-2-yl]amino}-phenyl)-1H-pyrazol-1-yl]methyl}-1,3-oxazolidin-2-one | 433 | 433 |
| 3.47 | —CH$_2$CH(OH)CH$_2$CN<br>S<br>TFA salt | CH$_3$ | CF$_3$ | (3S)-3-hydroxy-4-[4-(3-methyl-5-{[4-(trifluoromethyl)pyrimidin-2-yl]amino}-phenyl)-1H-pyrazol-1-yl]butanenitrile | 403 | 403 |
| 3.48 | —CH$_2$CH$_2$SO$_2$CH$_3$<br>TFA salt | CH$_3$ | CF$_3$ | N-(3-methyl-5-{1-[2-(methylsulfonyl)ethyl]-1H-pyrazol-4-yl}phenyl)-4-(trifluoromethyl)pyrimidin-2-amine | 426 | 426 |
| 3.49 | —(CH$_2$)$_3$CO$_2$CH$_3$<br>free base | CH$_3$ | CF$_3$ | methyl 4-[4-(3-methyl-5-{[4-(trifluoromethyl)-pyrimidin-2-yl]amino}-phenyl)-1H-pyrazol-1-yl]butanoate | 420 | 420 |
| 3.50[6] | —(CH$_2$)$_3$CO$_2$H<br>free base | CH$_3$ | CF$_3$ | 4-[4-(3-methyl-5-{[4-(trifluoromethyl)-pyrimidin-2-yl]amino}-phenyl)-1H-pyrazol-1-yl]butanoic acid | 406 | 406 |

TABLE 3A-continued

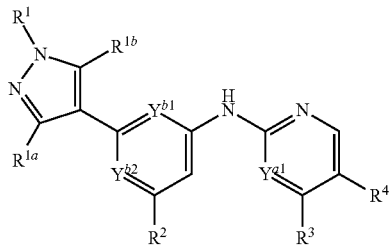

Ie [$R^{1a} = R^{1b} = R^4 = H$; $Y^{b1} = Y^{b2} = CH$; $Y^{a1} = N$]

| Ex. | $R^1$ | $R^2$ | $R^3$ | Chemical Name | [M + H]$^+$ Calc'd | [M + H]$^+$ Found |
|---|---|---|---|---|---|---|
| 3.51 | (4-carboxy-1,2,3,4-tetrahydronaphthalen-1-yl) racemic TFA salt | CH$_3$ | CF$_3$ | 4-[4-(3-methyl-5-{[4-(trifluoromethyl)pyrimidin-2-yl]amino}phenyl)-1H-pyrazol-1-yl]-1,2,3,4-tetrahydronaphthalene-1-carboxylic acid | 494 | 494 |
| 3.52 | (4-methoxycarbonyl-1,2,3,4-tetrahydronaphthalen-1-yl) racemic TFA salt | CH$_3$ | CF$_3$ | methyl 4-[4-(3-methyl-5-{[4-(trifluoromethyl)pyrimidin-2-yl]amino}-phenyl)-1H-pyrazol-1-yl]-1,2,3,4-tetrahydronaphthalene-1-carboxylate | 508 | 508 |
| 3.53 | 1-hydroxy-2-(4-carboxyphenyl)ethyl racemic TFA salt | CH$_3$ | CF$_3$ | 4-{1-hydroxy-2-[4-(3-methyl-5-{[4-(trifluoromethyl)pyrimidin-2-yl]amino}-phenyl)-1H-pyrazol-1-yl]ethyl}benzoic acid | 484 | 484 |
| 3.54 | 1-hydroxy-2-(4-methoxycarbonylphenyl)ethyl racemic TFA salt | CH$_3$ | CF$_3$ | methyl 4-{1-hydroxy-2-[4-(3-methyl-5-{[4-(trifluoromethyl)pyrimidin-2-yl]amino}phenyl)-1H-pyrazol-1-yl]ethyl}benzoate | 498 | 498 |
| 3.55 | 1,4-dioxaspiro[4.5]dec-8-yl free base | CH$_3$ | CF$_3$ | N-{3-[1-(1,4-dioxaspiro[4.5]dec-8-yl)-1H-pyrazol-4-yl]-5-methylphenyl}-4-(trifluoromethyl)pyrimidin-2-amine | 460 | 460 |
| 3.56 | —CH(CH$_3$)CH$_2$CONH$_2$ TFA salt | CH$_3$ | CF$_3$ | 3-[4-(3-methyl-5-{[4-(trifluoromethyl)pyrimidin-2-yl]amino}phenyl)-1H-pyrazol-1-yl]butanamide | 405 | 405 |

TABLE 3A-continued

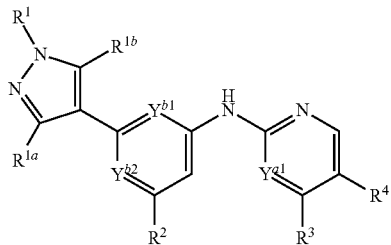

Ie [R$^{1a}$ = R$^{1b}$ = R$^4$ = H; Y$^{b1}$ = Y$^{b2}$ = CH; Y$^{a1}$ = N]

| Ex. | R$^1$ | R$^2$ | R$^3$ | Chemical Name | [M + H]$^+$ Calc'd | [M + H]$^+$ Found |
|---|---|---|---|---|---|---|
| 3.57 | ![piperidine-Boc structure]<br>free base | CH$_3$ | CF$_3$ | tert-butyl 4-[4-(3-methyl-5-{[4-(trifluoromethyl)pyrimidin-2-yl]amino}-phenyl)-1H-pyrazol-1-yl]piperidine-1-carboxylate | 503 | 503 |
| 3.58[9] | —CH(CH$_2$CH$_2$OH)CO$_2$H<br>racemic<br>formate salt | CH$_3$ | CF$_3$ | 4-hydroxy-2-[4-(3-methyl-5-{[4-(trifluoromethyl)-pyrimidin-2-yl]amino}phenyl)-1H-pyrazol-1-yl]butanoic acid | 422 | 422 |

TABLE 3B

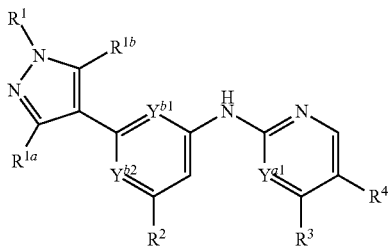

Ie [R$^{1a}$ = R$^{1b}$ = R$^4$ = H; Y$^{b1}$ = N; Y$^{b2}$ = Y$^{a1}$ = CH]

| Ex. No. | R$^1$ | R$^2$ | R$^3$ | Chemical Name | [M + H]$^+$ Calc'd | [M + H]$^+$ Found |
|---|---|---|---|---|---|---|
| 3.59 | —C(O)CH$_2$OCH$_3$<br>free base | CH$_3$ | CF$_3$ | 6-[1-(methoxyacetyl)-1H-pyrazol-4-yl]-4-methyl-N-[4-(trifluoromethyl)-pyridin-2-yl]pyridin-2-amine | 392 | 392 |
| 3.60 | —(CH$_2$)$_3$OH<br>formate salt | CH$_3$ | CF$_3$ | 3-[4-(4-methyl-6-{[4-(trifluoromethyl)pyridin-2-yl]amino}pyridin-2-yl)-1H-pyrazol-1-yl]propan-1-ol | 378 | 378 |
| 3.61 | —CH$_2$CH$_2$CONH$_2$<br>free base,<br>formate salt | CH$_3$ | CF$_3$ | 3-[4-(4-methyl-6-{[4-(trifluoromethyl)pyridin-2-yl]amino}pyridin-2-yl)-1H-pyrazol-1-yl]propanamide | 391 | 391 |
| 3.62 | —CH$_2$CONH$_2$<br>formate salt | CH$_3$ | CF$_3$ | 2-[4-(4-methyl-6-{[4-(trifluoromethyl)pyridin-2-yl]amino}pyridin-2-yl)-1H-pyrazol-1-yl]acetamide | 377 | 377 |

TABLE 3B-continued

Ie [R$^{1a}$ = R$^{1b}$ = R$^4$ = H; Y$^{b1}$ = N; Y$^{b2}$ = Y$^{a1}$ = CH]

| Ex. No. | R$^1$ | R$^2$ | R$^3$ | Chemical Name | [M + H]$^+$ Calc'd | [M + H]$^+$ Found |
|---|---|---|---|---|---|---|
| 3.63 | (imidazolidin-2-one-propyl) formate salt | CH$_3$ | CF$_3$ | 1-{3-[4-(4-methyl-6-{[4-(trifluoromethyl)pyridin-2-yl]amino}pyridin-2-yl)-1H-pyrazol-1-yl]propyl}imidazolidin-2-one | 446 | 446 |
| 3.64 | (1,4-dioxan-2-ylmethyl) racemic formate salt | CH$_3$ | CF$_3$ | 6-[1-(1,4-dioxan-2-ylmethyl)-1H-pyrazol-4-yl]-4-methyl-N-[4-(trifluoromethyl)pyridin-2-yl]pyridin-2-amine | 420 | 420 |
| 3.65 | (N-(2-methoxy-1,1-dimethylethyl)acetamide) formate salt | CH$_3$ | CF$_3$ | N-(2-methoxy-1,1-dimethylethyl)-2-[4-(4-methyl-6-{[4-(trifluoromethyl)pyridin-2-yl]amino}-pyridin-2-yl)-1H-pyrazol-1-yl]-acetamide | 463 | 463 |
| 3.66 | ((3R,5S)-3,5-dimethylmorpholin-4-yl oxoethyl) R,S formate salt | CH$_3$ | CF$_3$ | 6-(1-{2-[(3R,5S)-3,5-dimethylmorpholin-4-yl]-2-oxoethyl}-1H-pyrazol-4-yl)-4-methyl-N-[4-(trifluoromethyl)pyridin-2-yl]pyridin-2-amine | 475 | 475 |
| 3.67 | (3-morpholin-4-ylpropyl) formate salt | CH$_3$ | CF$_3$ | 4-methyl-6-[1-(3-morpholin-4-ylpropyl)-1H-pyrazol-4-yl]-N-[4-(trifluoromethyl)-pyridin-2-yl]pyridin-2-amine | 447 | 447 |
| 3.68 | (oxetan-2-ylmethyl) racemic formate salt | CH$_3$ | CF$_3$ | 4-methyl-6-[1-(oxetan-2-ylmethyl)-1H-pyrazol-4-yl]-N-[4-(trifluoromethyl)-pyridin-2-yl]pyridin-2-amine | 390 | 390 |
| 3.69 | —(CH$_2$)$_2$O(CH$_2$)$_2$OH formate salt | CH$_3$ | CF$_3$ | 2-{2-[4-(4-methyl-6-{[4-(trifluoromethyl)-pyridin-2-yl]amino}-pyridin-2-yl)-1H-pyrazol-1-yl]-ethoxy}ethanol | 408 | 408 |

TABLE 3B-continued

Ie [$R^{1a} = R^{1b} = R^4 = H$; $Y^{b1} = N$; $Y^{b2} = Y^{a1} = CH$]

| Ex. No. | R¹ | R² | R³ | Chemical Name | [M + H]⁺ Calc'd | [M + H]⁺ Found |
|---|---|---|---|---|---|---|
| 3.70 | —(CH₂)₃NH₂ formate salt | CH₃ | CF₃ | 6-[1-(3-aminopropyl)-1H-pyrazol-4-yl]-4-methyl-N-[4-(trifluoromethyl)-pyridin-2-yl]pyridin-2-amine | 377 | 377 |
| 3.71 | —CH₂c-propyl | CH₃ | CF₃ | 6-[1-(cyclopropyl-methyl)-1H-pyrazol-4-yl]-4-methyl-N-[4-(trifluoromethyl)pyridin-2-yl]pyridin-2-amine | 374 | 374 |
| 3.72 | —CH₂CH(OCH₂CH₃)₂ formate salt | CH₃ | CF₃ | 6-[1-(2,2-diethoxyethyl)-1H-pyrazol-4-yl]-4-methyl-N-[4-(trifluoromethyl)pyridin-2-yl]pyridin-2-amine | 436 | 436 |
| 3.73 | i-propyl formate salt | CH₃ | CF₃ | 4-methyl-6-[1-(1-methylethyl)-1H-pyrazol-4-yl]-N-[4-(trifluoromethyl)pyridin-2-yl]pyridin-2-amine | 362 | 362 |
| 3.74[10] | —CH₂CH₂OH free base | CH₃ | CF₃ | 2-[4-(4-methyl-6-{[4-(trifluoro-methyl)pyridin-2-yl]amino}pyridin-2-yl)-1H-pyrazol-1-yl]ethanol | 364 | 364 |
| 3.75 | (1,2,3,4-tetrahydronaphthalene-1-carboxylic acid substituent) racemic TFA salt | CH₃ | CF₃ | 4-[4-(4-methyl-6-{[4-(trifluoro-methyl)pyridin-2-yl]amino}pyridin-2-yl)-1H-pyrazol-1-yl]-1,2,3,4-tetrahydro-naphthalene-1-carboxylic acid | 494 | 494 |
| 3.76 | (methyl 1,2,3,4-tetrahydronaphthalene-1-carboxylate substituent) racemic TFA salt | CH₃ | CF₃ | methyl 4-[4-(4-methyl-6-{[4-(trifluoromethyl)pyridin-2-yl]amino}-pyridin-2-yl)-1H-pyrazol-1-yl]-1,2,3,4-tetrahydro-naphthalene-1-carboxylate | 508 | 508 |

TABLE 3B-continued

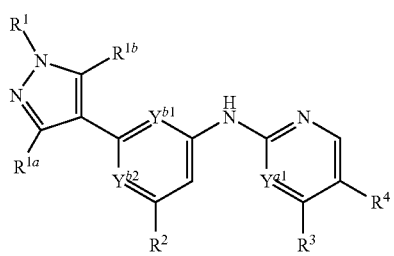

Ie [$R^{1a} = R^{1b} = R^4 = H$; $Y^{b1} = N$; $Y^{b2} = Y^{a1} = CH$]

| Ex. No. | $R^1$ | $R^2$ | $R^3$ | Chemical Name | $[M+H]^+$ Calc'd | $[M+H]^+$ Found |
|---|---|---|---|---|---|---|
| 3.77 | HO—(CH)—C6H4—COOH  racemic TFA salt | CH₃ | CF₃ | 4-{1-hydroxy-2-[4-(4-methyl-6-{[4-(trifluoromethyl)pyridin-2-yl]amino}-pyridin-2-yl)-1H-pyrazol-1-yl]ethyl}-benzoic acid | 484 | 484 |
| 3.78 | HO—(CH)—C6H4—COOCH3  racemic TFA salt | CH₃ | CF₃ | methyl 4-{1-hydroxy-2-[4-(4-methyl-6-{[4-(trifluoromethyl)pyridin-2-yl]amino}-pyridin-2-yl)-1H-pyrazol-1-yl]ethyl}-benzoate | 498 | 498 |
| 3.79 | Boc-piperidin-4-yl  free base | CH₃ | CF₃ | tert-butyl 4-[4-(4-methyl-6-{[4-(trifluoromethyl)pyridin-2-yl]amino}-pyridin-2-yl)-1H-pyrazol-1-yl]piperidine-1-carboxylate | 503 | 503 |
| 3.80 | CH₂CN  free base | CH₃ | CF₃ | [4-(4-methyl-6-{[4-(trifluoromethyl)pyridin-2-yl]amino}-pyridin-2-yl)-1H-pyrazol-1-yl]-acetonitrile | 359 | 359 |

Footnotes:

[6] Example 3.34, 3.35 and 3.50, from the corresponding methyl esters, used the method described in Preparative Example 6.1 - ester hydrolysis as the ultimate synthetic step.

[7] Example 3.36 used the method described in Preparative Example 6.3 - TBDMS deprotection as the ultimate synthetic step.

[8] Example 3.38 used the method described in Preparative Example 6.3 - TBS deprotection as the ultimate synthetic step.

[9] Example 3.58 used 5-bromodihydrofuran-2(3H)-one as a starting material.

[10] Example 3.74 used the method described in Preparative Example 6.5 - TMS deprotection as the ultimate synthetic step.

TABLE 3C

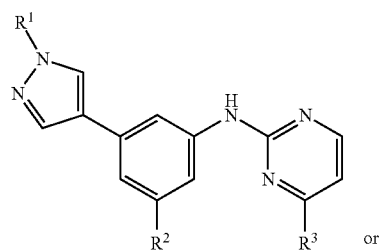

Ia(1)

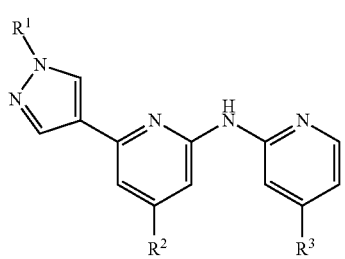

Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.81 | R or S (Ia(2)) | CH₃ | C(H)F₂ | 5-{[4-(6-{[4-(difluoromethyl)pyridin-2-yl]amino}-4-methylpyridin-2-yl)-1H-pyrazol-1-yl]methyl}-1,3-oxazolidin-2-one | 401.2 | 401 | Free Base |
| 3.82 | R or S (Ia(2)) | H | C(H)F₂ | 5-{[4-(6-{[4-(difluoromethyl)pyridin-2-yl]amino}pyridin-2-yl)-1H-pyrazol-1-yl]methyl}-1,3-oxazolidin-2-one | 387.1 | 387 | Free Base |
| 3.83 | S or R (Ia(2)) | CH₃ | C(H)F₂ | 5-{[4-(6-{[4-(difluoromethyl)pyridin-2-yl]amino}-4-methylpyridin-2-yl)-1H-pyrazol-1-yl]methyl}-1,3-oxazolidin-2-one | 401.2 | 401 | Free Base |
| 3.84 | S or R (Ia(2)) | H | C(H)F₂ | 5-{[4-(6-{[4-(difluoromethyl)pyridin-2-yl]amino}pyridin-2-yl)-1H-pyrazol-1-yl]methyl}-1,3-oxazolidin-2-one | 387.1 | 387 | Free Base |

TABLE 3C-continued

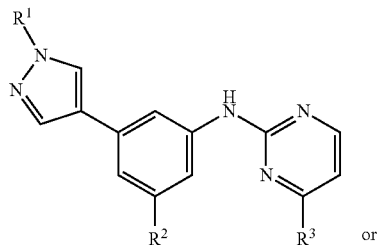
Ia(1)

or

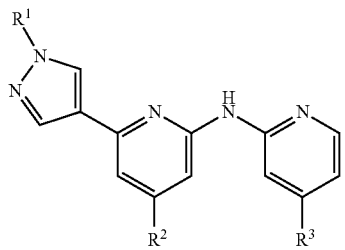
Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.85 | ![oxazolidinone] R or S (Ia(2)) | CH₃ | C(H)(F₂)CH₃ | 5-{[4-(6-{[4-(1,1-difluoroethyl)pyridin-2-yl]amino}-4-methylpyridin-2-yl)-1H-pyrazol-1-yl]methyl}-1,3-oxazolidin-2-one | 415.2 | 415 | Free Base |
| 3.86 | ![oxazolidinone] S or R (Ia(2)) | CH₃ | C(H)(F₂)CH₃ | 5-{[4-(6-{[4-(1,1-difluoroethyl)pyridin-2-yl]amino}-4-methylpyridin-2-yl)-1H-pyrazol-1-yl]methyl}-1,3-oxazolidin-2-one | 415.2 | 415 | Free Base |
| 3.87 | ![oxazolidinone] "R or S, R or S" (Ia(2)) | CH₃ | C(H)F₂ | 5-{1-[4-(6-{[4-(difluoromethyl)pyridin-2-yl]amino}-4-methylpyridin-2-yl)-1H-pyrazol-1-yl]ethyl}-1,3-oxazolidin-2-one | 415.2 | 415 | Free Base |
| 3.88 | ![oxazolidinone] "R or S, R or S" (Ia(2)) | CH₃ | C(H)F₂ | 5-{1-[4-(6-{[4-(difluoromethyl)pyridin-2-yl]amino}-4-methylpyridin-2-yl)-1H-pyrazol-1-yl]ethyl}-1,3-oxazolidin-2-one | 415.2 | 415 | Free Base |

TABLE 3C-continued

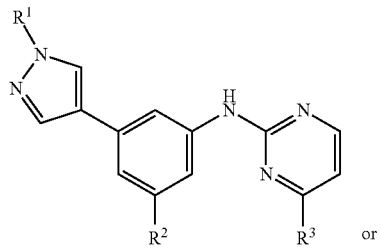

Ia(1)

or

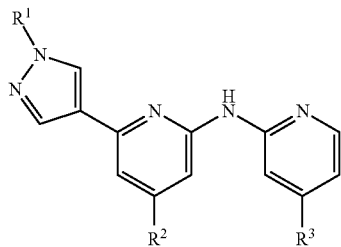

Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.89 | ![structure] R or S (Ia(1)) | CH₃ | C(H)F₂ | 7-{[4-(3-{[4-(difluoromethyl)pyrimidin-2-yl]amino}-5-methylphenyl)-1H-pyrazol-1-yl]methyl}-4-azaspiro[2.4]heptan-5-one | 425.2 | 425 | Free Base |
| 3.90 | ![structure] S or R (Ia(1)) | CH₃ | C(H)F₂ | 7-{[4-(3-{[4-(difluoromethyl)pyrimidin-2-yl]amino}-5-methylphenyl)-1H-pyrazol-1-yl]methyl}-4-azaspiro[2.4]heptan-5-one | 425.2 | 425 | Free Base |
| 3.91 | ![structure] "R or S, R or S" (Ia(1)) | CH₃ | C(H)F₂ | 5-{1-[4-(3-{[4-(difluoromethyl)pyrimidin-2-yl]amino}-5-methylphenyl)-1H-pyrazol-1-yl]ethyl}-1,3-oxazolidin-2-one | 415.2 | 415 | TFA Salt |
| 3.92 | ![structure] R or S (Ia(1)) | CH₃ | C(H)F₂ | 7-{[4-(3-{[4-(difluoromethyl)pyrimidin-2-yl]amino}-5-methylphenyl)-1H-pyrazol-1-yl]methyl}-6-oxa-4-azaspiro[2.4]heptan-5-one | 427.2 | 427 | Free Base |

TABLE 3C-continued

| Ex. No. | R¹ (Substructure) | R² | R³ | Chemical Name | [M + H]⁺ Calc'd | [M + H]⁺ Found | Form |
|---|---|---|---|---|---|---|---|
| 3.93 | "R or S, S or R" (Ia(1)) | $CH_3$ | $C(H)F_2$ | 5-{1-[4-(3-{[4-(difluoromethyl)pyrimidin-2-yl]amino}-5-methylphenyl)-1H-pyrazol-1-yl]ethyl}-1,3-oxazolidin-2-one | 415.2 | 415 | TFA Salt |
| 3.94 | S or R (Ia(1)) | $CH_3$ | $C(H)F_2$ | 7-{[4-(3-{[4-(difluoromethyl)pyrimidin-2-yl]amino}-5-methylphenyl)-1H-pyrazol-1-yl]methyl}-6-oxa-4-azaspiro[2.4]heptan-5-one | 427.2 | 427 | Free Base |
| 3.95[11] | (Ia(1)) | $CH_3$ | $C(H)F_2$ | 5-{[4-(3-{[4-(difluoromethyl)pyrimidin-2-yl]amino}-5-methylphenyl)-1H-pyrazol-1-yl]methyl}pyridin-2(1H)-one | 409.2 | 409 | TFA Salt |
| 3.96 | 4S (Ia(1)) | $CH_3$ | $CF_3$ | (4S)-4-{[4-(3-methyl-5-{[4-(trifluoromethyl)pyrimidin-2-yl]amino}phenyl)-1H-pyrazol-1-yl]methyl}-1,3-oxazolidin-2-one | 419.1 | 419 | Free Base |

TABLE 3C-continued

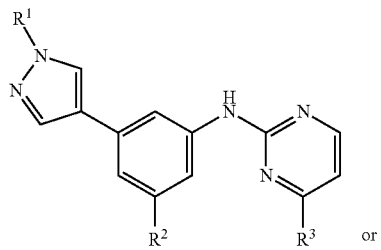
Ia(1)

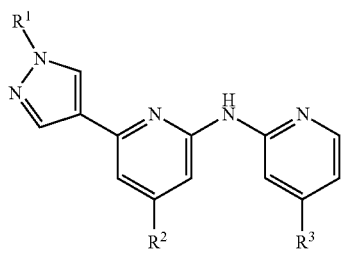
Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.97 | ![structure] 4R (Ia(1)) | $CH_3$ | $CF_3$ | (4R)-4-{[4-(3-methyl-5-{[4-(trifluoromethyl)pyrimidin-2-yl]amino}phenyl)-1H-pyrazol-1-yl]methyl}-1,3-oxazolidin-2-one | 419.1 | 419 | Free Base |
| 3.98 | ![structure] single isomer, early eluting (Ia(1)) | $CH_3$ | $C(H)F_2$ | 3-[4-(3-{[4-(difluoromethyl)pyrimidin-2-yl]amino}-5-methylphenyl)-1H-pyrazol-1-yl]butan-2-one | 372.2 | 372 | Free Base |
| 3.99 | ![structure] single isomer, early eluting (Ia(1)) | $CH_3$ | $CF_3$ | 4,4-dimethyl-5-{[4-(3-methyl-5-{[4-(trifluoromethyl)pyrimidin-2-yl]amino}phenyl)-1H-pyrazol-1-yl]methyl}-1,3-oxazolidin-2-one | 447.2 | 447 | Free Base |
| 3.100 | ![structure] single isomer, late eluting (Ia(1)) | $CH_3$ | $CF_3$ | 4,4-dimethyl-5-{[4-(3-methyl-5-{[4-(trifluoromethyl)pyrimidin-2-yl]amino}phenyl)-1H-pyrazol-1-yl]methyl}-1,3-oxazolidin-2-one | 447.2 | 447 | Free Base |

TABLE 3C-continued

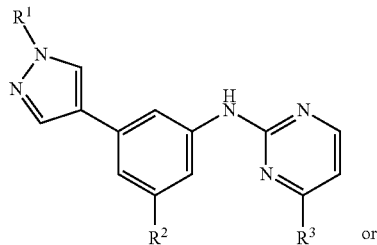

Ia(1)

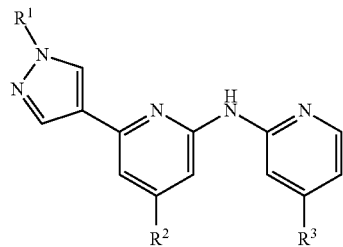

Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.101 | single isomer, early eluting (Ia(1)) | CH₃ | C(H)(F₂)CH₃ | 5-{[4-(3-{[4-(1,1-difluoroethyl)pyrimidin-2-yl]amino}-5-methylphenyl)-1H-pyrazol-1-yl]methyl}-4,4-dimethyl-1,3-oxazolidin-2-one | 443.2 | 443 | Free Base |
| 3.102 | single isomer, early eluting (Ia(1)) | CH₃ | C(H)F₂ | 5-{[4-(3-{[4-(difluoromethyl)pyrimidin-2-yl]amino}-5-methylphenyl)-1H-pyrazol-1-yl]methyl}-4,4-dimethyl-1,3-oxazolidin-2-one | 429.2 | 429 | Free Base |
| 3.103 | single isomer, late eluting (Ia(1)) | CH₃ | C(H)F₂ | 5-{[4-(3-{[4-(difluoromethyl)pyrimidin-2-yl]amino}-5-methylphenyl)-1H-pyrazol-1-yl]methyl}-4,4-dimethyl-1,3-oxazolidin-2-one | 429.2 | 429 | Free Base |
| 3.104 | single isomer, late eluting (Ia(1)) | CH₃ | C(H)(F₂)CH₃ | 5-{[4-(3-{[4-(1,1-difluoroethyl)pyrimidin-2-yl]amino}-5-methylphenyl)-1H-pyrazol-1-yl]methyl}-4,4-dimethyl-1,3-oxazolidin-2-one | 443.2 | 443 | Free Base |

TABLE 3C-continued

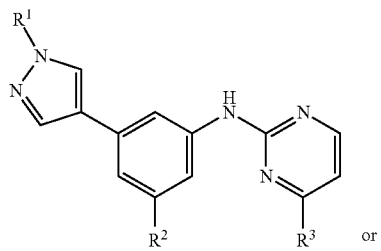
Ia(1)

or

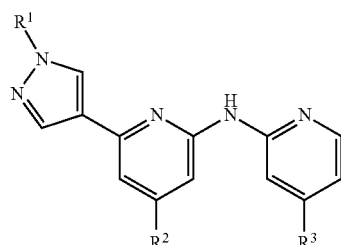
Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.105 | single isomer, early eluting (Ia(1)) | CH₃ | CH₃ | 4,4-dimethyl-5-[(4-{3-methyl-5-[(4-methylpyrimidin-2-yl)amino]phenyl}-1H-pyrazol-1-yl)methyl]-1,3-oxazolidin-2-one | 393.2 | 393 | Free Base |
| 3.106 | single isomer, late eluting (Ia(1)) | CH₃ | CH₃ | 4,4-dimethyl-5-[(4-{3-methyl-5-[(4-methylpyrimidin-2-yl)amino]phenyl}-1H-pyrazol-1-yl)methyl]-1,3-oxazolidin-2-one | 393.2 | 393 | Free Base |
| 3.107 | single enantiomer, derived from chiral starting material (Ia(1)) | CH₃ | CF₃ | 5-methyl-4-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 3.108 | (Ia(1)) | CH₃ | C(H)F₂ | 4-(difluoromethyl)-N-(3-methyl-5-{1-[(2-methyl-1H-imidazol-5-yl)methyl]-1H-pyrazol-4-yl}phenyl)pyrimidin-2-amine | 396.2 | 396 | TFA Salt |

TABLE 3C-continued

| Ex. No. | R¹ (Substructure) | R² | R³ | Chemical Name | [M + H]⁺ Calc'd | [M + H]⁺ Found | Form |
|---|---|---|---|---|---|---|---|
| 3.109 | (imidazole with two methyls) (Ia(1)) | CH₃ | C(H)F₂ | 4-(difluoromethyl)-N-(3-methyl-5-{1-[(4-methyl-1H-imidazol-5-yl)methyl]-1H-pyrazol-4-yl}phenyl)pyrimidin-2-amine | 396.2 | 396 | TFA Salt |
| 3.110 | (imidazole) (Ia(1)) | CH₃ | C(H)F₂ | 4-(difluoromethyl)-N-{3-[1-(1H-imidazol-4-ylmethyl)-1H-pyrazol-4-yl]-5-methylphenyl}pyrimidin-2-amine | 382.2 | 382 | TFA Salt |
| 3.111 | (pyrazolylethyl) (Ia(1)) | CH₃ | C(H)F₂ | 4-(difluoromethyl)-N-(3-methyl-5-{1-[2-(1H-pyrazol-4-yl)ethyl]-1H-pyrazol-4-yl}phenyl)pyrimidin-2-amine | 396.2 | 396 | Free Base |
| 3.112[12] | (diol) racemic (Ia(1)) | CH₃ | C(H)F₂ | 3-[4-(3-{[4-(difluoromethyl)pyrimidin-2-yl]amino}-5-methylphenyl)-1H-pyrazol-1-yl]propane-1,2-diol | 376.2 | 376 | Free Base |
| 3.113 | (tertiary alcohol) single isomer, late eluting (Ia(1)) | CH₃ | C(H)F₂ | 1-[4-(3-{[4-(difluoromethyl)pyrimidin-2-yl]amino}-5-methylphenyl)-1H-pyrazol-1-yl]-2-methylbutan-2-ol | 388.2 | 388 | Free Base |

TABLE 3C-continued

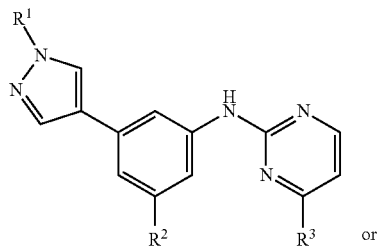

Ia(1)

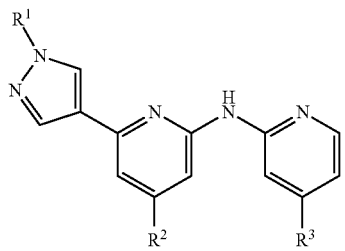

Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.114 | HO, ethyl group; single isomer, early eluting (Ia(1)) | CH₃ | C(H)F₂ | 1-[4-(3-{[4-(difluoromethyl)pyrimidin-2-yl]amino}-5-methylphenyl)-1H-pyrazol-1-yl]-2-methylbutan-2-ol | 388.2 | 388 | Free Base |
| 3.115 | oxazolidinone; single isomer, early eluting (Ia(1)) | CH₃ | H | 5-({4-[3-methyl-5-(pyrimidin-2-ylamino)phenyl]-1H-pyrazol-1-yl}methyl)-1,3-oxazolidin-2-one | 351.2 | 351 | Free Base |
| 3.116 | oxazolidinone; single isomer, late eluting (Ia(1)) | CH₃ | H | 5-({4-[3-methyl-5-(pyrimidin-2-ylamino)phenyl]-1H-pyrazol-1-yl}methyl)-1,3-oxazolidin-2-one | 351.2 | 351 | Free Base |
| 3.117 | oxazolidinone; single enantiomer, early eluting (Ia(1)) | CH₃ | CF₃ | 5-methyl-5-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |

TABLE 3C-continued

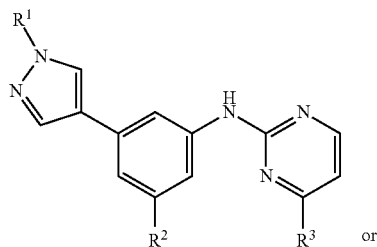
Ia(1)

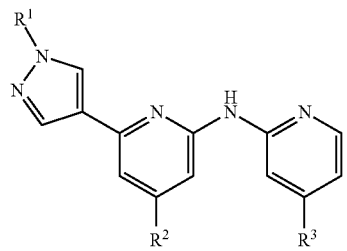
Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.118 | single enantiomer, late eluting (Ia(1)) | CH₃ | CF₃ | 5-methyl-5-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 3.119 | single isomer, early eluting (Ia(1)) | CH₃ | CF₃ | 4-methyl-5-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 3.120 | single isomer, late eluting (Ia(1)) | CH₃ | CF₃ | 4-methyl-5-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 3.121 | single enantiomer, early eluting (Ia(1)) | CH₃ | CH₃ | 5-methyl-5-[(4-{3-methyl-5-[(4-methylpyrimidin-2-yl)amino]phenyl}-1H-pyrazol-1-yl)methyl]-1,3-oxazolidin-2-one | 379.2 | 379 | Free Base |

TABLE 3C-continued

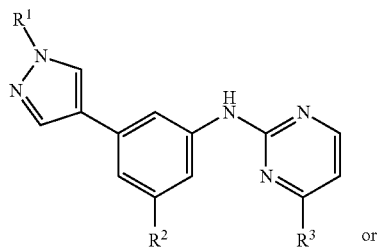
Ia(1)

or

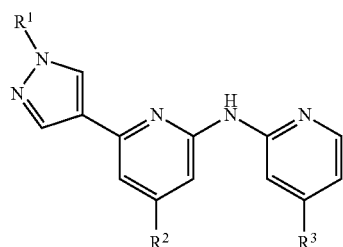
Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.122 | oxazolidinone substituent, single enantiomer, late eluting (Ia(1)) | $CH_3$ | $CH_3$ | 5-methyl-5-[(4-{3-methyl-5-[(4-methylpyrimidin-2-yl)amino]phenyl}-1H-pyrazol-1-yl)methyl]-1,3-oxazolidin-2-one | 379.2 | 379 | Free Base |
| 3.123 | oxazolidinone substituent, single enantiomer, early eluting (Ia(1)) | $CH_3$ | $C(H)F_2$ | 5-{[4-(3-{[4-(difluoromethyl)pyrimidin-2-yl]amino}-5-methylphenyl)-1H-pyrazol-1-yl]methyl}-5-methyl-1,3-oxazolidin-2-one | 415.2 | 415 | Free Base |
| 3.124 | oxazolidinone substituent, single enantiomer, late eluting (Ia(1)) | $CH_3$ | $C(H)F_2$ | 5-{[4-(3-{[4-(difluoromethyl)pyrimidin-2-yl]amino}-5-methylphenyl)-1H-pyrazol-1-yl]methyl}-5-methyl-1,3-oxazolidin-2-one | 415.2 | 415 | Free Base |
| 3.125 | oxazolidinone substituent, single enantiomer, early eluting (Ia(1)) | $CH_3$ | $C(H)(F_2)CH_3$ | 5-{[4-(3-{[4-(1,1-difluoroethyl)pyrimidin-2-yl]amino}-5-methylphenyl)-1H-pyrazol-1-yl]methyl}-1,3-oxazolidin-2-one | 415.2 | 415 | Free Base |

TABLE 3C-continued

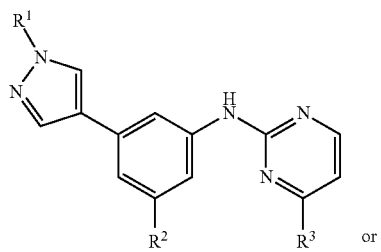

Ia(1)

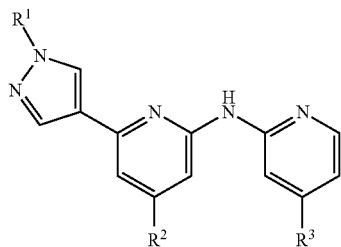

Ia(2)

| Ex. No. | R¹ (Substructure) | R² | R³ | Chemical Name | [M + H]⁺ Calc'd | [M + H]⁺ Found | Form |
|---|---|---|---|---|---|---|---|
| 3.126 | ![structure] single enantiomer, late eluting (Ia(1)) | CH₃ | C(H)(F₂)CH₃ | 5-{[4-(3-{[4-(1,1-difluoroethyl)pyrimidin-2-yl]amino}-5-methylphenyl)-1H-pyrazol-1-yl]methyl}-1,3-oxazolidin-2-one | 415.2 | 415 | Free Base |
| 3.127 | ![structure] single enantiomer, derived from chiral starting material (Ia(1)) | CH₃ | CF₃ | 5-methyl-4-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 3.128 | ![structure] single enantiomer, derived from chiral starting material (Ia(1)) | CH₃ | CF₃ | 5-methyl-4-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |

TABLE 3C-continued

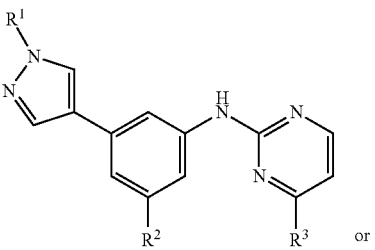

| Ex. No. | R¹ (Substructure) | R² | R³ | Chemical Name | [M + H]⁺ Calc'd | [M + H]⁺ Found | Form |
|---|---|---|---|---|---|---|---|
| 3.129 | 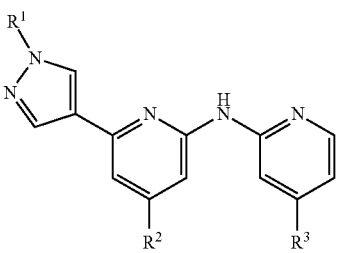<br>single enantiomer, derived from chiral starting material (Ia(1)) | $CH_3$ | $CF_3$ | 5-methyl-4-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |

Footnotes:
[11] Example No. 3.95 used the method described in Preparative Example 6.9-Benzyl Deprotection as the ultimate synthetic step.
[12] Example No. 3.112 used the method described in Preparative Example 6.8-Acetal Deprotection as the ultimate synthetic step.

Example 4

Preparation of (S) methyl 3-[4-(3-methyl-5-{[4-(trifluoromethyl)pyrimidin-2-yl]amino}phenyl)-1H-pyrazo(-1-yl]-L-alaninate

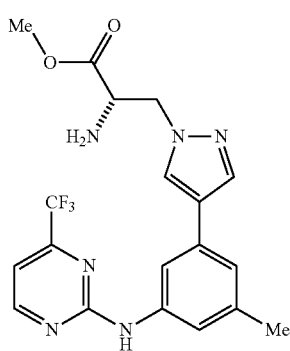 [SMILES: COC(=O)[C@@H](N)Cn1cc(-c2cc(C)cc(Nc3nccc(C(F)(F)F)n3)c2)cn1]

Step 1:

(3S)-2-Oxooxetan-3-aminium tetrafluoroborate (870 mg, 5.0 mmol) was added to a stirred solution of N-[3-methyl-5-(1H-pyrazol-4-yl)phenyl]-4-(trifluoromethyl)pyrimidin-2-amine (400 mg, 1.3 mmol) in DMF (6.3 mL). The reaction mixture was left to stir for 2 days and then directly purified by reverse phase HPLC (ACN/water with 0.1% TFA modifier) to afford s-3-[4-(3-methyl-5-{[4-(trifluoromethyl)pyrimidin-2-yl]amino}phenyl)-1H-pyrazol-1-yl]-L-alanine. MS ESI calcd. for $C_{18}H_{15}F_3N_6O_2$ [M+H]⁺ 407. found 407. ¹H NMR (500 MHz, DMSO-d₆) δ 10.15 (s, 1H), 8.82 (d, J=4.9 Hz, 1H), 8.03 (s, 1H), 7.82 (s, 1H), 7.80 (s, 1H), 7.36 (s, 1H), 7.26 (d, J=4.6 Hz, 1H), 7.07 (s, 1H), 4.57-4.60 (m, 1H), 4.33-4.38 (m, 1H), 3.63-3.64 (m, 1H), 2.30 (s, 3H).

Step 2:

Concentrated sulfuric acid (16 uL, 0.3 mmol) was added to a stirred solution of 3-[4-(3-methyl-5-{[4-(trifluoromethyl)pyrimidin-2-yl]amino}phenyl)-1H-pyrazol-1-yl]-L-alanine (100 mg, 0.3 mmol) in MeOH (1 mL). The reaction mixture was heated to 70° C. overnight, cooled to room temperature, and treated with aqueous sodium bicarbonate solution. The mixture was extracted with EtOAc, washed with sodium hydroxide solution (1N, 2×) and brine, dried over sodium sulfate, concentrated under reduced pressure to afford methyl 3-[4-(3-methyl-5-{[4-(trifluoromethyl)pyrimidin-2-yl]amino}phenyl)-1H-pyrazol-1-yl]-L-alaninate. MS ESI calcd. for $C_{19}H_{26}F_3N_6O_2$ [M+H]⁺ 421. found 421. ¹H NMR (500 MHz, DMSO-d₆) δ 10.13 (s, 1H), 8.82 (d, J=4.9 Hz, 1H), 8.00 (s, 1H), 7.81 (s, 1H), 7.76 (s, 1H), 7.34 (s, 1H), 7.26

(d, J=4.6 Hz, 1H), 7.06 (s, 1H), 4.25-4.34 (m, 2H), 3.78-3.80 (m, 1H), 3.62 (s, 3H), 2.30 (s, 3H).

Example 5.1

Preparation of racemic 2-(4-(3-methyl-5-((4-(trifluoromethyl)pyrimidin-2-yl)amino)phenyl)-1H-pyrazol-1-yl)-1-phenylethanol

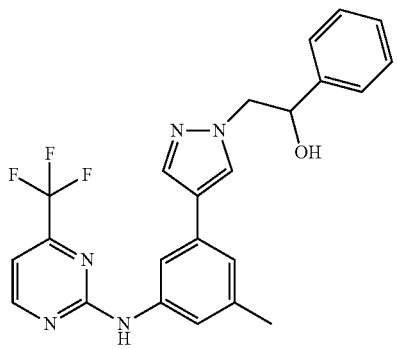 [SMILES: Cc1cc(Nc2nccc(C(F)(F)F)n2)cc(-c2cnn(CC(O)c3ccccc3)c2)c1]

NaH (0.0075 g, 0.19 mmol, 60% dispersion) was added to N-(3-methyl-5-(1H-pyrazol-4-yl)phenyl)-4-(trifluoromethyl)pyrimidin-2-amine (0.02 g, 0.06 mmol) suspended in DMF (1 mL, 0.06 mmol). The reaction mixture was allowed to stir at ambient temperature for 15 minutes. Styrene oxide (0.01 g, 0.08 mmol) was then added. The vial was capped and allowed to stir at 45° C. for 12 hours. H$_2$O (0.2 mL) was added and the reaction was concentrated under reduced pressure. The residue was taken up in DMSO (1.0 mL) and was passed through a syringe filter. The eluent was purified by reverse phase HPLC (0 to 95% ACN/water with 0.1% formic acid modifier) to afford racemic 2-(4-(3-methyl-5-((4-(trifluoromethyl)pyrimidin-2-yl)amino)phenyl)-1H-pyrazol-1-yl)-1-phenylethanol. MS ESI calcd. for $C_{23}H_{21}F_3N_5O$ [M+H]$^+$ 440. found 440. $^1$H NMR (600 MHz, DMSO-d$_6$) δ 10.05 (s, 1H), 8.77 (d, J=4.8, 1H), 7.91 (s, 1H), 7.75 (s, 1H), 7.72 (s, 1H), 7.34-7.27 (m, 5H), 7.25-7.19 (m, 2H), 7.01 (s, 1H), 5.69 (d, J=4.6, 1H), 4.94 (d, J=5.2, 1H), 4.20 (d, J=6.4, 2H), 2.26 (s, 3H).

The following compounds in Tables 5A and 5B were prepared according to the method described for Example 5.1.

TABLE 5A

Ie

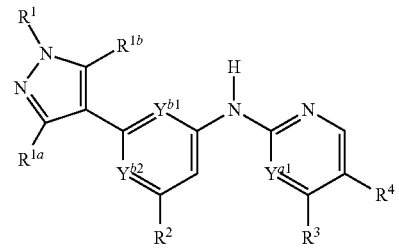

[$R^{1a} = R^{1b} = R^4 = H; Y^{b1} = Y^{b2} = CH; Y^{a1} = N$]

| Ex. No. | R$^1$ | R$^2$ | R$^3$ | Chemical Name | [M + H]$^+$ Calc'd | [M + H]$^+$ Found |
|---|---|---|---|---|---|---|
| 5.2[13] | —CH$_2$CHOHCO$_2$CH$_3$<br>S<br>free base | CH$_3$ | CF$_3$ | methyl (2S)-2-hydroxy-3-[4-(3-methyl-5-{[4-(trifluoromethyl)-pyrimidin-2-yl]amino}phenyl)-1H-pyrazol-1-yl]propanoate | 422 | 422 |
| 5.3[13] | —CH$_2$CHOHCO$_2$CH$_3$<br>R<br>free base | CH$_3$ | CF$_3$ | methyl (2R)-2-hydroxy-3-[4-(3-methyl-5-{[4-(trifluoromethyl)pyrimidin-2-yl]amino}phenyl)-1H-pyrazol-1-yl]propanoate | 422 | 422 |
| 5.4 | —CH$_2$CCH$_3$OHCO$_2$CH$_3$<br>racemic<br>TFA salt | CH$_3$ | CF$_3$ | methyl 2-hydroxy-2-methyl-3-[4-(3-methyl-5-{[4-(trifluoromethyl)pyrimidin-2-yl]amino}phenyl)-1H-pyrazol-1-yl]propanoate | 436 | 436 |

TABLE 5A-continued

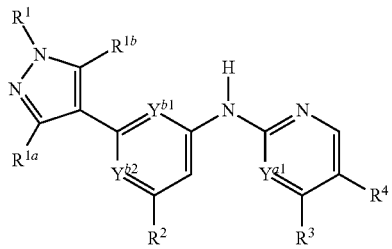

[$R^{1a} = R^{1b} = R^4 = H$; $Y^{b1} = Y^{b2} = CH$; $Y^{a1} = N$]

Ie

| Ex. No. | $R^1$ | $R^2$ | $R^3$ | Chemical Name | [M + H]$^+$ Calc'd | [M + H]$^+$ Found |
|---|---|---|---|---|---|---|
| 5.5 | (cyclohexane structure with OH and CO₂H) formate salt | CH₃ | CF₃ | cis-4-hydroxy-4-{[4-(3-methyl-5-{[4-(trifluoro-methyl)pyrimidin-2-yl]amino}-phenyl)-1H-pyrazol-1-yl]methyl}-cyclohexanecarboxylic acid | 476 | 476 |
| 5.6 | —CH₂CCH₃OHCO₂H racemic formate salt | CH₃ | CF₃ | 2-hydroxy-2-methyl-3-[4-(3-methyl-5-{[4-(trifluoro-methyl)pyrimidin-2-yl]amino}-phenyl)-1H-pyrazol-1-yl]propanoic acid | 422 | 422 |
| 5.7 | (isopropoxy-hydroxypropyl structure) racemic formate salt | CH₃ | CF₃ | 1-(1-methylethoxy)-3-[4-(3-methyl-5-{[4-(trifluoro-methyl)pyrimidin-2-yl]amino}-phenyl)-1H-pyrazol-1-yl]propan-2-ol | 436 | 436 |
| 5.8 | (phenoxy-hydroxypropyl structure) racemic formate salt | CH₃ | CF₃ | 1-[4-(3-methyl-5-{[4-(trifluoro-methyl)pyrimidin-2-yl]amino}-phenyl)-1H-pyrazol-1-yl]-3-phenoxypropan-2-ol | 470 | 470 |
| 5.9 | —CH₂CHOHC₂H₅ racemic formate salt | CH₃ | CF₃ | 1-[4-(3-methyl-5-{[4-(trifluoro-methyl)pyrimidin-2-yl]amino}-phenyl)-1H-pyrazol-1-yl]butan-2-ol | 392 | 392 |

TABLE 5A-continued

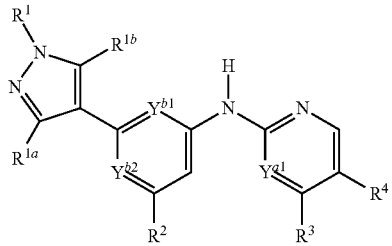

[$R^{1a} = R^{1b} = R^4 = H$; $Y^{b1} = Y^{b2} = CH$; $Y^{a1} = N$]

Ie

| Ex. No. | $R^1$ | $R^2$ | $R^3$ | Chemical Name | [M + H]$^+$ Calc'd | [M + H]$^+$ Found |
|---|---|---|---|---|---|---|
| 5.10 | morpholine-CH2-CH(OH)-CH2- racemic formate salt | CH$_3$ | CF$_3$ | 1-[4-(3-methyl-5-{[4-(trifluoroethyl)pyrimidin-2-yl]amino}-phenyl)-1H-pyrazol-1-yl]-3-morpholin-4-ylpropan-2-ol | 463 | 463 |
| 5.11 | (4-methoxyphenoxy)-CH2-CH(OH)-CH2- racemic formate salt | CH$_3$ | CF$_3$ | 1-(4-methoxyphenoxy)-3-[4-(3-methyl-5-{[4-(trifluoromethyl)-pyrimidin-2-yl]amino}phenyl)-1H-pyrazol-1-yl]propan-2-ol | 500 | 500 |
| 5.12 | —CH$_2$CH(CH$_3$)$_2$OH formate salt | CH$_3$ | CF$_3$ | 2-methyl-1-[4-(3-methyl-5-{[4-(trifluoromethyl)pyrimidin-2-yl]amino}-phenyl)-1H-pyrazol-1-yl]propan-2-ol | 392 | 392 |
| 5.13 | —CH$_2$CH(OH)CH$_2$F $R^5$ = —CH$_2$CH(OH)CH$_2$F racemic formate salt | CH$_3$ | CF$_3$ | 1-fluoro-3-({3-[1-(3-fluoro-2-hydroxy-propyl)-1H-pyrazol-4-yl]-5-methyl-phenyl}-[4-(trifluoromethyl)-pyrimidin-2-yl]-amino)propan-2-ol | 472 | 472 |
| 5.14 | —CH$_2$CH(OH)CO$_2$H racemic formate salt | CH$_3$ | CF$_3$ | 2-hydroxy-3-[4-(3-methyl-5-{[4-(trifluoro-methyl)pyrimidin-2-yl]amino}-phenyl)-1H-pyrazol-1-yl]propanoic acid | 408 | 408 |
| 5.15 | —CH$_2$CH(OH)CO$_2$OH racemic formate salt | CH$_3$ | CF$_3$ | 3-[4-(3-methyl-5-{[4-(trifluoromethyl)-pyrimidin-2-yl]amino}-phenyl)-1H-pyrazol-1-yl]propane-1,2-diol | 394 | 394 |
| 5.16 | —CH$_2$CH(OH)CO$_2$H R TFA salt | CH$_3$ | CF$_3$ | (2R)-2-hydroxy-3-[4-(3-methyl-5-{[4-(trifluoromethyl)-pyrimidin-2-yl]amino}phenyl)-1H-pyrazol-1-yl]propanoic acid | 408 | 408 |

TABLE 5A-continued

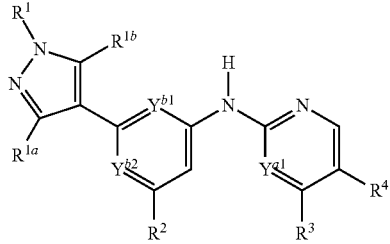

Ie

[R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| 5.17 | —CH$_2$CH(OH)CO$_2$H<br>S<br>TFA salt | CH$_3$ | CF$_3$ | (2S)-2-hydroxy-3-[4-(3-methyl-5-{[4-(trifluoromethyl)pyrimidin-2-yl]amino}-phenyl)-1H-pyrazol-1-yl]propanoic acid | 408 | 408 |

Footnote:

[13]Examples 5.2 and 5.3 used the method described in Preparative Example 6.4-esterification of a carboxylic acid as the ultimate synthetic step.

TABLE 5B

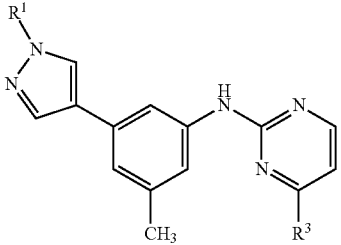

| Ex. No. | R$^1$ | R$^3$ | Chemical Name | [M + H]$^+$ Calc'd | [M + H]$^+$ Found | Form |
|---|---|---|---|---|---|---|
| 5.18 | 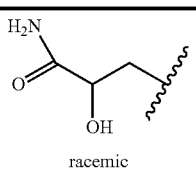<br>racemic | C(H)F$_2$ | 3-[4-(3-{[4-(difluoromethyl)pyrimidin-2-yl]amino}-5-methylphenyl)-1H-pyrazol-1-yl]-2-hydroxypropanamide | 389.2 | 389 | TFA Salt |
| 5.19 | 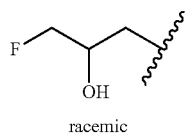<br>racemic | C(H)F$_2$ | 1-[4-(3-{[4-(difluoromethyl)pyrimidin-2-yl]amino}-5-methylphenyl)-1H-pyrazol-1-yl]-3-fluoropropan-2-ol | 378.2 | 378 | TFA Salt |
| 5.20 | 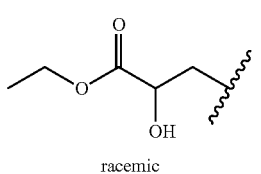 [SMILES: *CC(O)C(=O)OCC]<br>racemic | C(H)F$_2$ | ethyl 3-[4-(3-{[4-(difluoromethyl)pyrimidin-2-yl]amino}-5-methylphenyl)-1H-pyrazol-1-yl]-2-hydroxypropanoate | 418.2 | 418 | TFA Salt |

TABLE 5B-continued

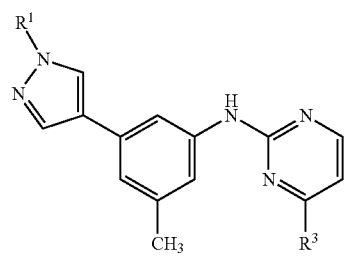

| Ex. No. | R¹ | R³ | Chemical Name | [M + H]⁺ Calc'd | [M + H]⁺ Found | Form |
|---|---|---|---|---|---|---|
| 5.21 | *tert*-butyl ester with OH, racemic | C(H)F₂ | tert-butyl {3-[4-(3-{[4-(difluoromethyl)pyrimidin-2-yl]amino}-5-methylphenyl)-1H-pyrazol-1-yl]-2-hydroxypropyl}carbamate | 475.2 | 475 | TFA Salt |
| 5.22 | methoxy, OH, racemic | C(H)F₂ | 1-[4-(3-{[4-(difluoromethyl)pyrimidin-2-yl]amino}-5-methylphenyl)-1H-pyrazol-1-yl]-3-methoxypropan-2-ol | 390.2 | 390 | TFA Salt |
| 5.23 | isopropyl, OH, racemic | C(H)F₂ | 1-[4-(3-{[4-(difluoromethyl)pyrimidin-2-yl]amino}-5-methylphenyl)-1H-pyrazol-1-yl]-3-methylbutan-2-ol | 388.2 | 388 | TFA Salt |
| 5.24 | CF₃, OH, racemic | C(H)F₂ | 3-[4-(3-{[4-(difluoromethyl)pyrimidin-2-yl]amino}-5-methylphenyl)-1H-pyrazol-1-yl]-1,1,1-trifluoropropan-2-ol | 414.1 | 414 | TFA Salt |
| 5.25 | pyrazolyl, OH, racemic | C(H)F₂ | 1-[4-(3-{[4-(difluoromethyl)pyrimidin-2-yl]amino}-5-methylphenyl)-1H-pyrazol-1-yl]-3-(1H-pyrazol-1-yl)propan-2-ol | 426.2 | 426 | TFA Salt |
| 5.26 | pyridin-2-yl, OH, racemic | C(H)F₂ | 2-[4-(3-{[4-(difluoromethyl)pyrimidin-2-yl]amino}-5-methylphenyl)-1H-pyrazol-1-yl]-1-pyridin-2-ylethanol | 423.2 | 423 | TFA Salt |
| 5.27 | 1-hydroxycyclohexyl, OH, racemic | C(H)F₂ | 1-{3-[4-(3-{[4-(difluoromethyl)pyrimidin-2-yl]amino}-5-methylphenyl)-1H-pyrazol-1-yl]-2-hydroxypropyl}cyclohexanol | 458.2 | 458 | TFA Salt |

TABLE 5B-continued

| Ex. No. | R¹ | R³ | Chemical Name | [M + H]⁺ Calc'd | [M + H]⁺ Found | Form |
|---|---|---|---|---|---|---|
| 5.28 | (dihydrofuran-2(3H)-one-yl-methyl with OH); mixture of diastereomers | C(H)F₂ | 4-{3-[4-(3-{[4-(difluoromethyl)pyrimidin-2-yl]amino}-5-methylphenyl)-1H-pyrazol-1-yl]-2-hydroxypropyl}dihydrofuran-2(3H)-one | 444.2 | 444 | TFA Salt |
| 5.29 | HO, OH (pentyl diol); mixture of diastereomers | C(H)F₂ | 1,3,5-trideoxy-1-[4-(3-{[4-(difluoromethyl)pyrimidin-2-yl]amino}-5-methylphenyl)-1H-pyrazol-1-yl]pentitol | 404.2 | 404 | TFA Salt |
| 5.30 | tert-butyl CH(OH)CH₂–; racemic | C(H)F₂ | 1-[4-(3-{[4-(difluoromethyl)pyrimidin-2-yl]amino}-5-methylphenyl)-1H-pyrazol-1-yl]-3,3-dimethylbutan-2-ol | 402.2 | 402 | TFA Salt |
| 5.31 | CF₃CH₂OCH₂CH(OH)CH₂–; racemic | C(H)F₂ | 1-[4-(3-{[4-(difluoromethyl)pyrimidin-2-yl]amino}-5-methylphenyl)-1H-pyrazol-1-yl]-3-(2,2,2-trifluoroethoxy)propan-2-ol | 458.2 | 458 | TFA Salt |
| 5.32 | (Et)₂C(OH)CH₂– | C(H)F₂ | 3-{[4-(3-{[4-(difluoromethyl)pyrimidin-2-yl]amino}-5-methylphenyl)-1H-pyrazol-1-yl]methyl}pentan-3-ol | 402.2 | 402 | TFA Salt |
| 5.33 | pyrrolidin-2-one-N-CH₂CH(OH)CH₂– | C(H)F₂ | 1-{3-[4-(3-{[4-(difluoromethyl)pyrimidin-2-yl]amino}-5-methylphenyl)-1H-pyrazol-1-yl]-2-hydroxypropyl}pyrrolidin-2-one | 443.2 | 443 | TFA Salt |
| 5.34 | piperidin-3-yl-CH(OH)CH₂– | C(H)F₂ | 2-[4-(3-{[4-(difluoromethyl)pyrimidin-2-yl]amino}-5-methylphenyl)-1H-pyrazol-1-yl]-1-piperidin-3-ylethanol | 429.2 | 429 | TFA Salt |
| 5.35 | (CH₃)₂C(OH)CH₂– | C(H)F₂ | 1-[4-(3-{[4-(difluoromethyl)pyrimidin-2-yl]amino}-5-methylphenyl)-1H-pyrazol-1-yl]-2-methylpropan-2-ol | 374.2 | 374 | TFA Salt |

TABLE 5B-continued

| Ex. No. | R¹ | R³ | Chemical Name | [M + H]⁺ Calc'd | [M + H]⁺ Found | Form |
|---|---|---|---|---|---|---|
| 5.36 | (HO-C(=O)-CH(OH)-CH₂-) racemic | C(H)F₂ | 3-[4-(3-{[4-(difluoromethyl)pyrimidin-2-yl]amino}-5-methylphenyl)-1H-pyrazol-1-yl]-2-hydroxypropanoic acid | 390.1 | 390 | TFA Salt |
| 5.37 | (H₂N-CH₂-CH(OH)-CH₂-) racemic | C(H)F₂ | 1-amino-3-[4-(3-{[4-(difluoromethyl)pyrimidin-2-yl]amino}-5-methylphenyl)-1H-pyrazol-1-yl]propan-2-ol | 375.2 | 375 | TFA Salt |
| 5.38 | (3-hydroxy-4-carboxycyclohexyl) "trans, 3S or 3R, 4S or 4R" | CF₃ | 3-hydroxy-4-[3-(3-methyl-5-{[4-(trifluoromethyl)pyrimidin-2-yl]amino}phenyl)-1H-pyrazol-1-yl]cyclohexanecarboxylic acid | 462.2 | 462 | Free Base |
| 5.39 | (3-hydroxy-4-carboxycyclohexyl) "trans, 3R or 3S, 4S or 4R" | CF₃ | 3-hydroxy-4-[3-(3-methyl-5-{[4-(trifluoromethyl)pyrimidin-2-yl]amino}phenyl)-1H-pyrazol-1-yl]cyclohexane-carboxylic acid | 462.2 | 462 | Free Base |
| 5.40 | (3-cyano-1-hydroxycyclobutyl-methyl) | C(H)F₂ | trans-3-{[4-(3-{[4-(difluoromethyl)pyrimidin-2-yl]amino}-5-methylphenyl)-1H-pyrazol-1-yl]methyl}-3-hydroxycyclobutane-carbonitrile | 411.2 | 411 | TFA Salt |
| 5.41 | (1-hydroxycyclobutyl-methyl) | C(H)F₂ | 1-{[4-(3-{[4-(difluoromethyl)pyrimidin-2-yl]amino}-5-methylphenyl)-1H-pyrazol-1-yl]methyl}cyclobutanol | 386.2 | 386 | TFA Salt |
| 5.42 | (4-hydroxy-1,1-dioxotetrahydrothiopyran-4-ylmethyl) | C(H)F₂ | 4-{[4-(3-{[4-(difluoromethyl)pyrimidin-2-yl]amino}-5-methylphenyl)-1H-pyrazol-1-yl]methyl}tetrahydro-2H-thiopyran-4-ol 1,1-dioxide | 464.2 | 464 | TFA Salt |

Example 6.1

Preparation of (2S)-2-hydroxy-N-(2-hydroxyethyl)-3-[4-(3-methyl-5-{[4-(trifluoromethyl)pyrimidin-2-yl]amino}phenyl)-1H-pyrazol-1-yl]propanamide

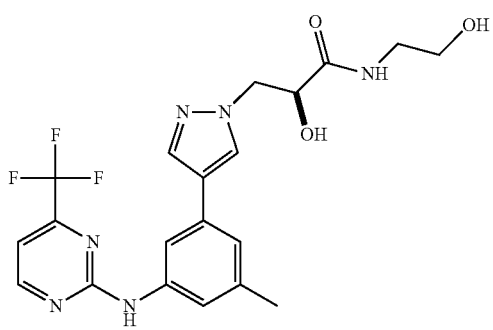 [SMILES: Cc1cc(Nc2nccc(C(F)(F)F)n2)cc(-c2cnn(C[C@H](O)C(=O)NCCO)c2)c1]

Methyl (2S)-2-hydroxy-3-[4-(3-methyl-5-{[4-(trifluoromethyl)pyrimidin-2-yl]amino}phenyl)-1H-pyrazol-1-yl]propanoate (40 mg, 0.10 mmol) in methanol (1 mL) was treated with ethanolamine (0.03 mL, 0.48 mmol). The mixture was stirred overnight at 70° C. Upon cooling to room temperature, the mixture was filtered and purified by reverse phase HPLC (0 to 95% ACN/water with 0.1% TFA modifier) to afford (2S)-2-hydroxy-N-(2-hydroxyethyl)-3-[4-(3-methyl-5-{[4-(trifluoromethyl)pyrimidin-2-yl]amino}phenyl)-1H-pyrazol-1-yl]propanamide. MS ESI calcd. for $C_{20}H_{21}F_3N_6O_3$ $[M+H]^+$ 451. found 451. $^1$H NMR (500 MHz, DMSO-$d_6$) δ 10.11 (s, 1H), 8.80 (d, J=4.9 Hz, 1H), 7.94 (s, 1H), 7.84 (t, J=5.6 Hz, 1H), 7.80 (s, 1H), 7.75 (s, 1H), 7.33 (s, 1H), 7.23 (d, J=6.3 Hz, 1H), 7.05 (s, 1H), 4.39 (dd, J=2.9 Hz, 13.7 Hz, 1H), 4.26 (d, J=7.7 Hz, 1H), 4.17-4.12 (m, 1H), 3.38 (t, J=5.9 Hz, 2H), 3.16 (q, J=6.1 Hz, 2H), 2.28 (s, 3H).

The following compounds in Tables 6A and 6B were prepared according to the method described for Example 6.1.

TABLE 6A

Ie

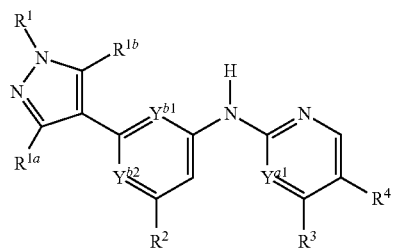

[$R^{1a} = R^{1b} = R^4 = H; Y^{b1} = Y^{b2} = CH; Y^{a1} = N$]

| Ex. No. | $R^1$ | $R^2$ | $R^3$ | Chemical Name | $[M+H]^+$ Calc'd | $[M+H]^+$ Found |
|---|---|---|---|---|---|---|
| 6.2[14] | —CH$_2$CHOHCONH$_2$ S free base | CH$_3$ | —OCH$_2$CH$_2$OH | (2S)-2-hydroxy-3-[4-(3-{[4-(2-hydroxyethoxy)pyrimidin-2-yl]amino}-5-methylphenyl)-1H-pyrazol-1-yl]propanamide | 399 | 399 |
| 6.3 | —CH$_2$CHOHCONH$_2$ S free base | CH$_3$ | CH$_3$ | (2S)-2-hydroxy-3-(4-{3-methyl-5-[(4-methylpyrimidin-2-yl)amino]phenyl}-1H-pyrazol-1-yl)propanamide | 353 | 353 |
| 6.4 | —CH$_2$CHOHCONH$_2$ S free base | CH$_3$ | OCH$_3$ | (2S)-2-hydroxy-3-(4-{3-[(4-methoxypyrimidin-2-yl)amino]-5-methylphenyl}-1H-pyrazol-1-yl)propanamide | 369 | 369 |
| 6.5 | —CH$_2$CHOHCONH$_2$ S TFA salt | CH$_3$ | c-propyl | (2S)-3-(4-{3-[(4-cyclopropyl-pyrimidin-2-yl)amino]-5-methylphenyl}-1H-pyrazol-1-yl)-2-hydroxypropanamide | 379 | 379 |
| 6.6 | —CH$_2$CHOHCONH$_2$ S free base | CH$_3$ | —OCH(CH$_3$)$_2$ | (2S)-2-hydroxy-3-[4-(3-methyl-5-{[4-(1-methylethoxy)pyrimidin-2- | 397 | 397 |

TABLE 6A-continued

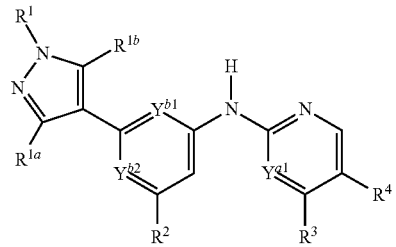

[$R^{1a} = R^{1b} = R^4 = H$; $Y^{b1} = Y^{b2} = CH$; $Y^{a1} = N$]

Ie

| Ex. No. | $R^1$ | $R^2$ | $R^3$ | Chemical Name | $[M + H]^+$ Calc'd | $[M + H]^+$ Found |
|---|---|---|---|---|---|---|
| 6.7 | —CH$_2$CHOHCONH$_2$ S free base | CH$_3$ | t-butyl | (2S)-3-(4-{3-[(4-tert-butyl-pyrimidin-2-yl)amino]-5-methylphenyl}-1H-pyrazol-1-yl)-2-hydroxy-propanamide | 395 | 395 |
| 6.8 | —CH$_2$CHOHCONH$_2$ S free base | CH$_3$ | —OCHFCH$_3$ | (2S)-3-[4-(3-{[4-(1-fluoroethyl)-pyrimidin-2-yl]amino}-5-methylphenyl)-1H-pyrazol-1-yl]-2-hydroxy-propanamide | 385 | 385 |
| 6.9 | —CH$_2$CHOHCONH$_2$ S free base | CH$_3$ | i-propyl | (2S)-2-hydroxy-3-[4-(3-methyl-5-{[4-(1-methyl-ethyl)pyrimidin-2-yl]-amino}phenyl)-1H-pyrazol-1-yl]propanamide | 381 | 381 |
| 6.10 | ![structure] S free base | CH$_3$ | CF$_3$ | (2S)-2-hydroxy-3-[4-(3-methyl-5-{[4-(trifluoromethyl)pyrimidin-2-yl]amino}phenyl)-1H-pyrazol-1-yl]-N-[3-(2-oxopyrrolidin-1-yl)propyl]propan-amide | 532 | 532 |
| 6.11 | —CH$_2$CHOHCONHCH$_3$ S free base | CH$_3$ | CF$_3$ | (2S)-2-hydroxy-N-methyl-3-[4-(3-methyl-5-{[4-(trifluoromethyl)pyrimidin-2-yl]amino}phenyl)-1H-pyrazol-1-yl]propanamide | 421 | 421 |
| 6.12 | ![structure] S free base | CH$_3$ | CF$_3$ | (2S)-2-hydroxy-N-(3-methoxypropyl)-3-[4-(3-methyl-5-{[4-(trifluoromethyl)pyrimidin-2-yl]amino}phenyl)-1H-pyrazol-1-yl]propanamide | 479 | 479 |

TABLE 6A-continued

Ie

[R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| 6.13 | (structure with methoxyethylamide, OH, S configuration) free base | CH$_3$ | CF$_3$ | (2S)-2-hydroxy-N-(2-methoxyethyl)-3-[4-(3-methyl-5-{[4-(trifluoromethyl)pyrimidin-2-yl]amino}phenyl)-1H-pyrazol-1-yl]propanamide | 465 | 465 |

Footnote:
[14]Example 6.2 used the method described in Preparative Example 6.2-TBS deprotection as the ultimate synthetic step.

TABLE 6B

Ie

[R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| 6.14 | (tetrahydronaphthalene-carboxamide structure) racemic TFA salt | CH$_3$ | CF$_3$ | 4-[4-(4-methyl-6-{[4-(trifluoromethyl)-pyridin-2-yl]amino}-pyridin-2-yl)-1H-pyrazol-1-yl]-1,2,3,4-tetrahydronaphthalene-1-carboxamide | 493 | 493 |
| 6.15 | —CH$_2$CHOHCONH$_2$ S TFA salt | CH$_3$ | CF$_3$ | (2S)-2-hydroxy-3-[4-(4-methyl-6-{[4-(trifluoromethyl)-pyridin-2-yl]amino}-pyridin-2-yl)-1H-pyrazol-1-yl]-propanamide | 407 | 407 |

TABLE 6B-continued

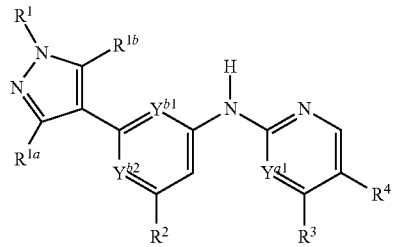

[$R^{1a} = R^{1b} = R^4 = H; Y^{b1} = Y^{b2} = CH; Y^{a1} = N$]

| Ex. No. | $R^1$ | $R^2$ | $R^3$ | Chemical Name | $[M+H]^+$ Calc'd | $[M+H]^+$ Found |
|---|---|---|---|---|---|---|
| 6.16 | 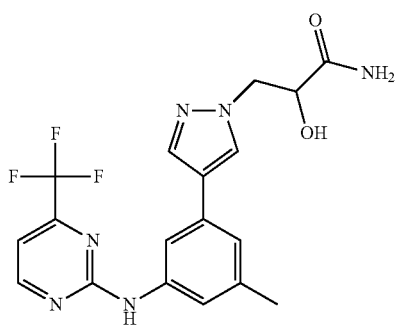 racemic TFA salt | $CH_3$ | $CF_3$ | 4-{1-hydroxy-2-[4-(4-methyl-6-{[4-(trifluoromethyl)-pyridin-2-yl]amino}-pyridin-2-yl)-1H-pyrazol-1-yl]ethyl}-benzamide | 483 | 483 |

Example 7.1

Preparation of (R or S)-2-hydroxy-3-[4-(3-methyl-5-{[4-(trifluoromethyl)pyrimidin-2-yl]amino}phenyl)-1H-pyrazol-1-yl]propanamide

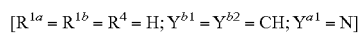

Step 1:

Sulfuric acid (0.10 ml, 1.83 mmol) was added to an oven-dried vial containing 2-hydroxy-3-[4-(3-methyl-5-{[4-(trifluoromethyl)pyrimidin-2-yl]amino}phenyl)-1H-pyrazol-1-yl]propanoic acid (1.78 g, 1.83 mmol) in MeOH (12.2 ml) and the solution was warmed to 70° C. and stirred for 1 h. The reaction mixture was cooled to room temperature, diluted with water, and extracted with EtOAc (3×). The combined organic layers were washed with brine, dried over sodium sulfate, filtered, concentrated under reduced pressure. The residue was purified by column chromatography on silica gel (0 to 80% EtOAc/hexanes) to afford racemic methyl (2R)-2-hydroxy-3-[4-(3-methyl-5-{[4-(trifluoromethyl)pyrimidin-2-yl]amino}phenyl)-1H-pyrazol-1-yl]propanoate. The racemic sample was purified by super critical fluid chiral chromatography (AD-H 2.1×25 cm, 5 μm, 45%/55% 2-propanol/$CO_2$, 70 mL/min, 12 min. run time, 220 nM) to afford (R or S) 2-methyl-2-hydroxy-3-[4-(3-methyl-5-{[4-(trifluoromethyl)pyrimidin-2-yl]amino}phenyl)-1H-pyrazol-1-yl]propanoate (early eluting enantiomer). MS ESI calcd. for $C_{19}H_{19}F_3N_5O_3$ $[M+H]^+$ 422. found 422.

Step 2:

2-Methyl-2-hydroxy-3-[4-(3-methyl-5-{[4-(trifluoromethyl)pyrimidin-2-yl]amino}phenyl)-1H-pyrazol-1-yl]propanoate (early eluting enantiomer) (50 mg, 0.12 mmol) was treated with ammonia (7.0 M in MeOH, 750 μL, 5.25 mmol) and stirred at 70° C. for 2 h. The reaction mixture was then concentrated under reduced pressure to afford (R or S) 2-hydroxy-3-[4-(3-methyl-5-{[4-(trifluoromethyl)pyrimidin-2-yl]amino}phenyl)-1H-pyrazol-1-yl]propanamide as a yellow solid. MS ESI calcd. for $C_{18}H_{18}F_3N_6O_2$ $[M+H]^+$ 407. found 407. $^1$H NMR (500 MHz, DMSO-$d_6$) δ 10.11 (s, 1H), 8.80 (d, J=4.9, 1H), 7.96 (s, 1H), 7.81 (s, 1H), 7.75 (s, 1H), 7.37 (s, 1H), 7.33 (s, 2H), 7.24 (d, J=4.9, 1H), 7.05 (s, 1H), 5.87 (d, J=6.0, 1H), 4.38 (dd, J=2.7, 13.4, 1H), 4.25-4.11 (m, 2H), 2.28 (s, 3H).

The following compounds in Table 7 were prepared according to the method described for Example 7.1.

TABLE 7

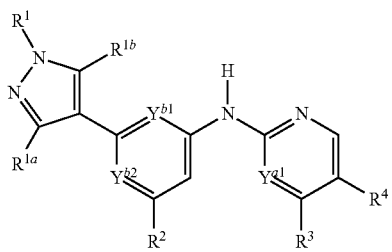

Ie

[$R^{1a}$ = $R^{1b}$ = $R^4$ = H; $Y^{b1}$ = $Y^{b2}$ = CH; $Y^{a1}$ = N]

| Ex. No. | $R^1$ | $R^2$ | $R^3$ | Chemical Name | $[M + H]^+$ Calc'd | $[M + H]^+$ Found |
|---|---|---|---|---|---|---|
| 7.2 | —CH₂CHNH₂CONH₂<br>S<br>free base | CH₃ | CF₃ | 3-[4-(3-methyl-5-{[4-(trifluoromethyl)pyrimidin-2-yl]amino}phenyl)-1H-pyrazol-1-yl]-1-alaninamide | 406 | 406 |
| 7.3 | —CH₂CHOHCONH₂<br>R<br>free base | CH₃ | CF₃ | (2R)-2-hydroxy-3-[4-(3-methyl-5-{[4-(trifluoromethyl)pyrimidin-2-yl]amino}-phenyl)-1H-pyrazol-1-yl]propanamide | 407 | 407 |
| 7.4 | —CH₂CHOHCONH₂<br>S<br>free base | CH₃ | CF₃ | (2S)-2-hydroxy-3-[4-(3-methyl-5-{[4-(trifluoromethyl)pyrimidin-2-yl]amino}-phenyl)-1H-pyrazol-1-yl]propanamide | 407 | 407 |
| 7.5 | —CHCH₃CHOHCONH₂<br>free base | CH₃ | CF₃ | 2-hydroxy-3-[4-(3-methyl-5-{[4-(trifluoromethyl)pyrimidin-2-yl]amino}-phenyl)-1H-pyrazol-1-yl]butanamide | 421 | 421 |
| 7.6 | —CHCH₃CHOHCONH₂<br>free base | CH₃ | CF₃ | 2-hydroxy-3-[4-(3-methyl-5-{[4-(trifluoromethyl)pyrimidin-2-yl]amino}-phenyl)-1H-pyrazol-1-yl]butanamide | 421 | 421 |

Example 8.1

Preparation of (R or S) 2-hydroxy-2-methyl-3-[4-(3-methyl-5-{[4-(trifluoromethyl)pyrimidin-2-yl]amino}phenyl)-1H-pyrazol-1-yl]propanamide (early eluting enantiomer)

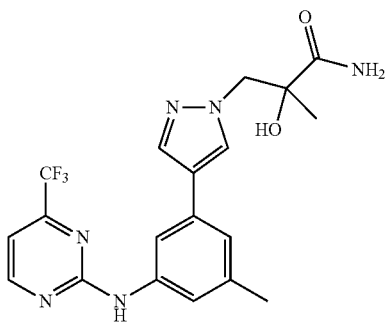

Step 1:

Sodium hydride (23.5 mg, 0.59 mmol) at 0° C. was added to an oven-dried vial containing N-[3-methyl-5-(1H-pyrazol-4-yl)phenyl]-4-(trifluoromethyl)pyrimidin-2-amine (75 mg, 0.24 mmol) in DMF (0.8 mL). The mixture was stirred for 10 minutes, and then methyl 2-methylglycidate (0.03 mL, 0.24 mmol) was added. The reaction was warmed to room temperature and stirred overnight, followed by subsequent heating to 70° C. overnight. The mixture was cooled to room temperature, diluted with EtOAc, washed with water (3×), then brine, dried over sodium sulfate, filtered, and concentrated under reduced pressure. The residue was purified by reverse phase HPLC (45 to 85% ACN/water with 0.1% TFA modifier) to afford racemic 2-hydroxy-2-methyl-3-[4-(3-methyl-5-{[4-(trifluoromethyl)pyrimidin-2-yl]amino}phenyl)-1H-pyrazol-1-yl]propanoic acid. MS ESI calcd. for $C_{19}H_{18}F_3N_5O_3$ $[M+H]^+$ 422. found 422.

Step 2:

Racemic 2-hydroxy-2-methyl-3-[4-(3-methyl-5-{[4-(trifluoromethyl)pyrimidin-2-yl]amino}phenyl)-1H-pyrazol-1-yl]propanoic acid (142 mg, 0.26 mmol), HOBT (61 mg, 0.4 mmol), EDC (76 mg, 0.4 mmol), and ammonium chloride (42.5 mg, 0.8 mmol) were combined with DMF (2.5 mL) in a flask. Triethylamine (0.35 mL, 2.51 mmol) was added and the mixture was stirred for 3 days at room temperature. The mixture was diluted with EtOAc and diluted with 1:1 water:brine (3×). The organic layer was dried over sodium sulfate, filtered and concentrated under reduced pressure to afford racemic 2-hydroxy-2-methyl-3-[4-(3-methyl-5-{[4-(trifluoromethyl)pyrimidin-2-yl]amino}phenyl)-1H-pyrazol-1-yl]propanamide. MS ESI calcd. for $C_{19}H_{19}F_3N_6O_2$ $[M+H]^+$ 421. found 421.

Step 3:

Racemic 2-hydroxy-2-methyl-3-[4-(3-methyl-5-{[4-(trifluoromethyl)pyrimidin-2-yl]amino}phenyl)-1H-pyrazol-1-yl]propanamide (23 mg, 0.05 mmol) enantiomers were separated by chiral supercritical fluid chromatography (OJ 21×250 mm, 10 μM column, 30%/70% methanol/$CO_2$ with a flow rate of 70 mL/min with a 5.75 minute run time) to afford (R or S) 2-hydroxy-2-methyl-3-[4-(3-methyl-5-{[4-(trifluoromethyl)pyrimidin-2-yl]amino}phenyl)-1H-pyrazol-1-yl]propanamide (early eluting enantiomer). MS ESI calcd. for $C_{19}H_{20}F_3N_6O_2$ $[M+H]^+$ 421. found 421. $^1$H NMR (500 MHz, DMSO-$d_6$) δ 10.09 (s, 1H), 8.80 (d, J=4.8 Hz, 1H), 7.91 (s, 1H), 7.80 (s, 1H), 7.73 (s, 1H), 7.34 (s, 1H), 7.24 (s, 1H), 7.23 (s, 1H) 7.21 (s, 1H), 7.04 (s, 1H), 4.32 (d, J=13.9 Hz, 1H), 4.20 (d, J=13.9 Hz, 1H), 2.28 (s, 3H), 1.19 (s, 3H).

The following compounds in Table 8 were prepared according to the method described for Example 8.1.

TABLE 8

Ie

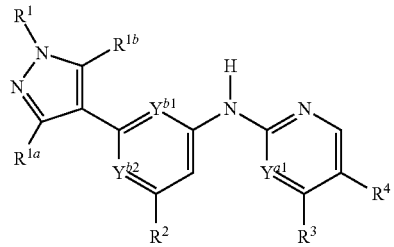

$[R^{1a} = R^{1b} = R^4 = H; Y^{b1} = Y^{b2} = CH; Y^{a1} = N]$

| Ex. No. | $R^1$ | $R^2$ | $R^3$ | Chemical Name | $[M + H]^+$ Calc'd | $[M + H]^+$ Found |
|---|---|---|---|---|---|---|
| 8.2 | —CH$_2$CHOHCONH$_2$ R<br>TFA salt, formate salt | CH$_3$ | CF$_3$ | (2R)-2-hydroxy-3-[4-(3-methyl-5-{[4-(trifluoromethyl)pyrimidin-2-yl]amino}phenyl)-1H-pyrazol-1-yl]propanamide | 407 | 407 |
| 8.3 | —CH$_2$CCH$_3$OHCONH$_2$ chiral-R OR S<br>free base | CH$_3$ | CF$_3$ | 2-hydroxy-2-methyl-3-[4-(3-methyl-5-{[4-(trifluoromethyl)pyrimidin-2-yl]amino}phenyl)-1H-pyrazol-1-yl]propanamide | 421 | 421 |

TABLE 8-continued

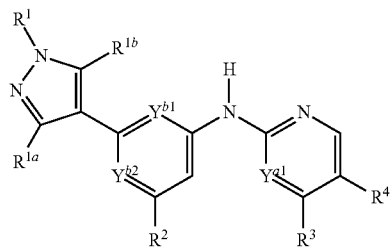

[$R^{1a}$ = $R^{1b}$ = $R^4$ = H; $Y^{b1}$ = $Y^{b2}$ = CH; $Y^{a1}$ = N]

| Ex. No. | $R^1$ | $R^2$ | $R^3$ | Chemical Name | [M + H]$^+$ Calc'd | [M + H]$^+$ Found |
|---|---|---|---|---|---|---|
| 8.4 | —CH$_2$CHOHCONH$_2$ S free base, formate salt | CH$_3$ | CF$_3$ | (2S)-2-hydroxy-3-[4-(3-methyl-5-{[4-(trifluoromethyl)-pyrimidin-2-yl]amino}-phenyl)-1H-pyrazol-1-yl]propanamide | 407 | 407 |
| 8.5 | (cyclohexane-CONH$_2$) free base | CH$_3$ | —OCH$_2$CH$_2$OH | 4-[4-(3-{[4-(2-hydroxy-ethoxy)pyrimidin-2-yl]amino}-5-methylphenyl)-1H-pyrazol-1-yl]-cyclo-hexanecarboxamide | 437 | 437 |
| 8.6 | (cyclohexane-CONH$_2$) free base | CH$_3$ | CF$_3$ | 4-[4-(3-methyl-5-{[4-(trifluorometh-yl)pyrimidin-2-yl]amino}-phenyl)-1H-pyrazol-1-yl]cyclohexane-carboxamide | 445 | 445 |
| 8.7 | (dimethyl-cyclohexane-CONH$_2$) free base | CH$_3$ | CF$_3$ | 2,2-dimethyl-4-[4-(3-methyl-5-{[4-(trifluoromethyl)-pyrimidin-2-yl]amino}-phenyl)-1H-pyrazol-1-yl]cyclohexane-carboxamide | 473 | 473 |
| 8.8 | —CHCH$_3$CONH$_2$ racemic tfa salt | CH$_3$ | CF$_3$ | 2-[4-(3-methyl-5-{[4-(trifluoromethyl)-pyrimidin-2-yl]amino}phenyl)-1H-pyrazol-1-yl]propanamide | 391 | 391 |
| 8.9 | —(CH$_2$)$_3$CONH$_2$ free base | CH$_3$ | CF$_3$ | 4-[4-(3-methyl-5-{[4-(trifluoromethyl)-pyrimidin-2-yl]amino}phenyl)-1H-pyrazol-1-yl]butanamide | 405 | 405 |
| 8.10 | —C(CH$_3$)$_2$CONH$_2$ free base | CH$_3$ | CH$_3$ | 2-methyl-2-(4-{3-methyl-5-[(4-methyl-pyrimidin-2-yl)amino]-phenyl}-1H-pyrazol-1-yl)propanamide | 351 | 351 |
| 8.11 | —CH$_2$COHCH$_3$CONH$_2$ racemic free base | CH$_3$ | CF$_3$ | 2-hydroxy-2-methyl-3-[4-(3-methyl-5-{[4-(trifluorometh-yl)pyrimidin-2- | 421 | 421 |

TABLE 8-continued

Ie

[R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| | | | | yl]amino}-phenyl)-1H-pyrazol-1-yl]propanamide | | |
| 8.12 | (structure: CH$_2$CH(OH)-C$_6$H$_4$-C(O)NH$_2$) racemic TFA salt | CH$_3$ | CF$_3$ | 4-{1-hydroxy-2-[4-(3-methyl-5-{[4-(trifluoromethyl)-pyrimidin-2-yl]amino}-phenyl)-1H-pyrazol-1-yl]ethyl}benzamide | 483 | 483 |
| 8.13 | —CH$_2$CHOHCONH$_2$ R TFA salt, formate salt | CH$_3$ | CF$_3$ | (2r)-2-hydroxy-3-[4-(3-methyl-5-{[4-(trifluoromethyl)pyrimidin-2-yl]amino}phenyl)-1H-pyrazol-1-yl]propanamide | 407 | 407 |
| 8.14 | —CH$_2$CCH$_3$OHCONH$_2$ chiral-R or S free base | CH$_3$ | CF$_3$ | 2-hydroxy-2-methyl-3-[4-(3-methyl-5-{[4-(trifluoromethyl)pyrimidin-2-yl]amino}phenyl)-1H-pyrazol-1-yl]propanamide | 421 | 421 |
| 8.15 | —CH$_2$CCH$_3$OHCONH$_2$ chiral-R OR S free base | CH$_3$ | CF$_3$ | 2-hydroxy-2-methyl-3-[4-(3-methyl-5-{[4-(trifluoromethyl)pyrimidin-2-yl]amino}phenyl)-1H-pyrazol-1-yl]propanamide | 421 | 421 |
| 8.16 | —CH$_2$CHOHCONH$_2$ S free base, formate salt | CH$_3$ | CF$_3$ | (2s)-2-hydroxy-3-[4-(3-methyl-5-{[4-(trifluoromethyl)pyrimidin-2-yl]amino}phenyl)-1H-pyrazol-1-yl]propanamide | 407 | 407 |
| 8.17 | (cyclohexyl-C(O)NH$_2$) free base | CH$_3$ | —OCH$_2$CH$_2$OH | 4-[4-(3-{[4-(2-hydroxy-ethoxy)pyrimidin-2-yl]amino}-5-methylphenyl)-1H-pyrazol-1-yl]-cyclohexanecarboxamide | 437 | 437 |

TABLE 8-continued

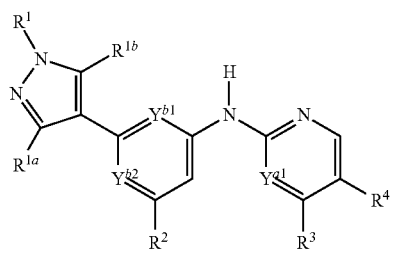

[$R^{1a}$ = $R^{1b}$ = $R^4$ = H; $Y^{b1}$ = $Y^{b2}$ = CH; $Y^{a1}$ = N]

| Ex. No. | $R^1$ | $R^2$ | $R^3$ | Chemical Name | [M + H]$^+$ Calc'd | [M + H]$^+$ Found |
|---|---|---|---|---|---|---|
| 8.18 | cyclohexyl-C(=O)NH$_2$ free base | CH$_3$ | CF$_3$ | 4-[4-(3-methyl-5-{[4-(trifluoromethyl)pyrimidin-2-yl]amino}phenyl)-1H-pyrazol-1-yl]-cyclohexane-carboxamide | 445 | 445 |
| 8.19 | 3,3-dimethylcyclohexyl-C(=O)NH$_2$ racemic free base | CH$_3$ | CF$_3$ | 2,2-dimethyl-4-[4-(3-methyl-5-{[4-(trifluoromethyl)pyrimidin-2-yl]amino}phenyl)-1H-pyrazol-1-yl]-cyclohexanecarboxamide | 473 | 473 |
| 8.20 | —CHCH$_3$CONH$_2$ TFA Salt | CH$_3$ | CF$_3$ | 2-[4-(3-methyl-5-{[4-(trifluoromethyl)pyrimidin-2-yl]amino}phenyl)-1H-pyrazol-1-yl]propanamide | 391 | 391 |
| 8.21 | —(CH$_2$)$_3$CONH$_2$ free base | CH$_3$ | CF$_3$ | 4-[4-(3-methyl-5-{[4-(trifluoromethyl)pyrimidin-2-yl]amino}phenyl)-1H-pyrazol-1-yl]butanamide | 405 | 405 |
| 8.22 | —C(CH$_3$)$_2$CONH$_2$ free base | CH$_3$ | CH$_3$ | 2-methyl-2-(4-{3-methyl-5-[(4-methylpyrimidin-2-yl)amino]phenyl}-1H-pyrazol-1-yl)propanamide | 351 | 351 |
| 8.23 | —CH$_2$COHCH$_3$CONH$_2$ free base | CH$_3$ | CF$_3$ | 2-hydroxy-2-methyl-3-[4-(3-methyl-5-{[4-(trifluoromethyl)-pyrimidin-2-yl]amino}-phenyl)-1H-pyrazol-1-yl]propanamide | 421 | 421 |

TABLE 8-continued

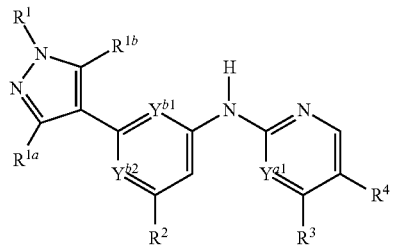

[$R^{1a} = R^{1b} = R^4 = H; Y^{b1} = Y^{b2} = CH; Y^{a1} = N$]

| Ex. No. | $R^1$ | $R^2$ | $R^3$ | Chemical Name | [M + H]$^+$ Calc'd | [M + H]$^+$ Found |
|---|---|---|---|---|---|---|
| 8.24 | 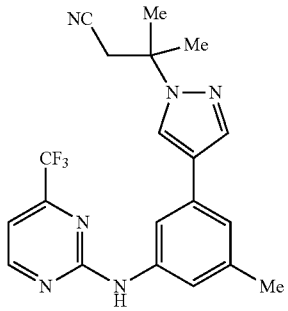<br>racemic<br>TFA salt | CH$_3$ | CF$_3$ | 4-{1-hydroxy-2-[4-(3-methyl-5-{[4-(trifluoromethyl)pyrimidin-2-yl]amino}-phenyl)-1H-pyrazol-1-yl]ethyl}-benzamide | 483 | 483 |

Example 9.1

Preparation of 3-methyl-3-[4-(3-methyl-5-{[4-(trifluoromethyl)pyrimidin-2-yl]amino}phenyl)-1H-pyrazol-1-yl]butanenitrile 3-Methylbut-2-enenitrile (179 mg, 1.57 mmol) and DBU (143 mg, 0.94 mmol) were added to a stirred solution of N-[3-methyl-5-(1H-pyrazol-4-yl)phenyl]-4-(trifluoromethyl)pyrimidin-2-amine (250 mg, 0.73 mmol) in acetonitrile (3.9 mL). The mixture was heated to 75° C. overnight and concentrated under reduced pressure The residue was purified by column chromatography on silica gel to afford 3-methyl-3-[4-(3-methyl-5-{[4-(trifluoromethyl)pyrimidin-2-yl]amino}phenyl)-1H-pyrazol-1-yl]butanenitrile. MS ESI calcd. for C$_{20}$H$_{20}$F$_3$N$_6$ [M+H]$^+$ 401. found 401. $^1$H NMR (500 MHz, DMSO-d$_6$) δ 10.13 (s, 1H), 8.82 (d, J=4.9 Hz, 1H), 8.27 (s, 1H), 7.91 (s, 1H), 7.84 (s, 1H), 7.32 (s, 1H), 7.26 (d, J=4.9 Hz, 1H), 7.15 (s, 1H), 3.24 (s, 2H), 2.31 (s, 3H), 1.67 (s, 6H).

The following compounds in Table 9 were prepared according to the method described for Example 9.1.

TABLE 9

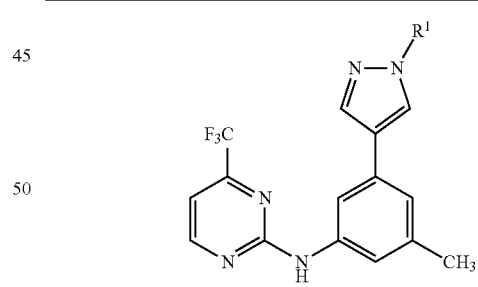

| Ex. No. | $R^1$ | Chemical Name | [M + H]$^+$ Calc'd | [M + H]$^+$ Found |
|---|---|---|---|---|
| 9.2 | —CH$_2$CH$_2$SO$_2$NH$_2$<br>TFA salt | 2-[4-(3-methyl-5-{[4-(trifluoromethyl)pyrimidin-2-yl]amino}-phenyl)-1H-pyrazol-1-yl]-ethanesulfonamide | 427 | 427 |

Example 10.1

Preparation of (R or S) 3-[4-(3-methyl-5-{[4-(trifluoromethyl)pyrimidin-2-yl]amino}phenyl)-1H-pyrazol-1-yl]cyclohexane-1,2-diol

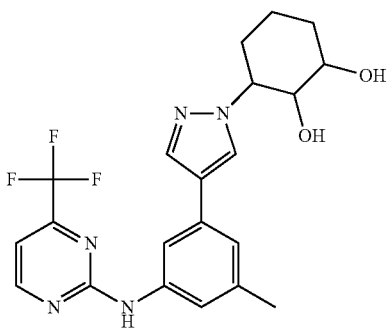 [SMILES: Cc1cc(Nc2nccc(C(F)(F)F)n2)cc(-c2cnn(C3CCCC(O)C3O)c2)c1]

Step 1:

3-Bromocyclohexene (0.18 mL, 1.57 mmol) and cesium carbonate (1.02 g, 3.13 mmol) were added to an oven-dried flask containing N-[3-methyl-5-(1H-pyrazol-4-yl)phenyl]-4-(trifluoromethyl)pyrimidin-2-amine (500 mg, 1.57 mmol) dissolved in DMF (5 mL). The mixture was warmed to 80° C. and stirred overnight. The mixture was cooled to room temperature, diluted with EtOAc, and washed with 1:1 water:brine (3×). The organic layer was dried over sodium sulfate, filtered, and concentrated under reduced pressure. The residue was purified by column chromatography on silica gel (0 to 80% EtOAc/hexanes) to afford racemic N-{3-[1-(cyclohex-2-en-1-yl)-1H-pyrazol-4-yl]-5-methylphenyl}-4-(trifluoromethyl)pyrimidin-2-amine. MS ESI calcd. for $C_{21}H_{21}F_3N_5$ [M+H]$^+$ 400. found 400.

Step 2:

Osmium tetroxide (2.08 mL, 0.34 mmol) and 4-methylmorpholine N-oxide (398 mg, 3.4 mmol) were added to a flask containing racemic N-{3-[1-(cyclohex-2-en-1-yl)-1H-pyrazol-4-yl]-5-methylphenyl}-4-(trifluoromethyl)pyrimidin-2-amine (339 mg, 0.85 mmol) dissolved in acetone (7.5 mL) and water (0.94 mL). The suspension was stirred for 2.5 hours at room temperature. The mixture was diluted with saturated aqueous sodium thiosulfate and stirred for 15 minutes at room temperature. The mixture was extracted with EtOAc (3×). The combined organic layers were dried over sodium sulfate, filtered, and concentrated under reduced pressure to afford racemic 3-[4-(3-methyl-5-{[4-(trifluoromethyl)pyrimidin-2-yl]amino}phenyl)-1H-pyrazol-1-yl]cyclohexane-1,2-diol. MS ESI calcd. for $C_{21}H_{23}F_3N_5O_2$ [M+H]$^+$ 434. found 434.

Step 3:

Racemic 3-[4-(3-methyl-5-{[4-(trifluoromethyl)pyrimidin-2-yl]amino}phenyl)-1H-pyrazol-1-yl]cyclohexane-1,2-diol enantiomers were separated by chiral super critical fluid chromatography (AS-H 21×250 mm, 5 μM column, 30%/70% methanol/CO$_2$ with a flow rate of 70 mL/min at 35° C. with a 6 minute run time) to afford (R or S) 3-[4-(3-methyl-5-{[4-(trifluoromethyl)pyrimidin-2-yl]amino}phenyl)-1H-pyrazol-1-yl]cyclohexane-1,2-diol (early eluting enantiomer). MS ESI calcd. for $C_{21}H_{23}F_3N_5O_2$ [M+H]$^+$ 434. found 434. $^1$H NMR (500 MHz, DMSO-d$_6$) δ 10.10 (s, 1H), 8.80 (d, J=4.8 Hz, 1H), 8.00 (s, 1H), 7.81 (s, 1H), 7.71 (s, 1H), 7.30 (s, 1H), 7.23 (d, J=4.9 Hz, 1H), 7.04 (s, 1H), 4.63-4.55 (m, 2H), 4.23 (td, J=4.3 Hz, 11.0 Hz, 1H), 3.91 (s, 1H), 3.73-3.65 (m, 1H), 2.28 (s, 3H), 1.92-1.63 (m, 4H), 1.48-1.44 (m, 2H).

The following compounds in Tables 10A-10C were prepared according to the method described for Example 10.1 and may include step 1.

TABLE 10A

| Ex. No. | Structure | Chemical Name | [M + H]$^+$ Calc'd | [M + H]$^+$ Found |
|---|---|---|---|---|
| 10.2 | chiral, mix enantiomers 2 & 3 free base | 3-[4-(3-methyl-5-{[4-(trifluoromethyl)pyrimidin-2-yl]amino}phenyl)-1H-pyrazol-1-yl]cyclohexane-1,2-diol | 434 | 434 |
| 10.3 | chiral, enantiomer 4 free base | 3-[4-(3-methyl-5-[4-(trifluoromethyl)pyrimidin-2-yl]amino}phenyl)-1H-pyrazol-1-yl]cyclohexane-1,2-diol | 434 | 434 |

TABLE 10B

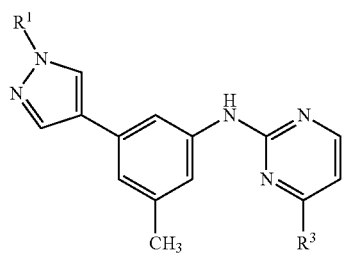

| Ex. No. | R¹ | R³ | Chemical Name | [M + H]⁺ Calc'd | [M + H]⁺ Found | Form |
|---|---|---|---|---|---|---|
| 10.4 | cyclohexane-1,2-diol (OH, OH) single stereoisomer, peak 2 of 4 | C(H)F$_2$ | 3-[4-(3-{[4-(difluoromethyl)pyrimidin-2-yl]amino}-5-methylphenyl)-1H-pyrazol-1-yl]cyclohexane-1,2-diol | 416.2 | 416 | Free Base |
| 10.5 | cyclohexane-1,2-diol (OH, OH) single stereoisomer, peak 3 of 4 | C(H)F$_2$ | 3-[4-(3-{[4-(difluoromethyl)pyrimidin-2-yl]amino}-5-methylphenyl)-1H-pyrazol-1-yl]cyclohexane-1,2-diol | 416.2 | 416 | Free Base |
| 10.6 | cyclohexane-1,2-diol (OH, OH) single stereoisomer, peak 1 of 4 | C(H)F$_2$ | 3-[4-(3-{[4-(difluoromethyl)pyrimidin-2-yl]amino}-5-methylphenyl)-1H-pyrazol-1-yl]cyclohexane-1,2-diol | 416.2 | 416 | Free Base |
| 10.7 | cyclohexane-1,2-diol (OH, OH) single stereoisomer, peak 4 of 4 | C(H)F$_2$ | 3-[4-(3-{[4-(difluoromethyl)pyrimidin-2-yl]amino}-5-methylphenyl)-1H-pyrazol-1-yl]cyclohexane-1,2-diol | 416.2 | 416 | Free Base |
| 10.8 | cyclohexane-1,2-diol (OH, OH) single stereoisomer, peak 1 of 3 | CH$_3$ | 3-(4-{3-methyl-5-[(4-methylpyrimidin-2-yl)amino]phenyl}-1H-pyrazol-1-yl)cyclohexane-1,2-diol | 380.2 | 380 | TFA Salt |

TABLE 10B-continued

[Structure: R¹-pyrazole connected to phenyl (with CH₃) connected to NH-pyrimidine with R³]

| Ex. No. | R¹ | R³ | Chemical Name | [M + H]⁺ Calc'd | [M + H]⁺ Found | Form |
|---|---|---|---|---|---|---|
| 10.9 | cyclohexane-1,2-diol (racemic) | CH₃ | 3-(4-{3-methyl-5-[(4-methylpyrimidin-2-yl)amino]phenyl}-1H-pyrazol-1-yl)cyclohexane-1,2-diol | 380.2 | 380 | TFA Salt |
| 10.10 | cyclohexane-1,2-diol (single stereoisomer, peak 3 of 3) | CH₃ | 3-(4-{3-methyl-5-[(4-methylpyrimidin-2-yl)amino]phenyl}-1H-pyrazol-1-yl)cyclohexane-1,2-diol | 380.2 | 380 | TFA Salt |

TABLE 10C

[Structure: R¹-pyrazole connected to phenyl (with CH₃) connected to NH-pyrimidine with F and CHF₂ substituents]

| Ex. No. | R¹ | Chemical Name | [M + H]⁺ Calc'd | [M + H]⁺ Found | Form |
|---|---|---|---|---|---|
| 10.11 | cyclohexane-1,2-diol (single stereoisomer, late eluting) | 3-[4-(3-{[4-(difluoromethyl)-5-fluoro-pyrimidin-2-yl]amino}-5-methylphenyl)-1H-pyrazol-1-yl]cyclohexane-1,2-diol | 434.2 | 434 | Free Base |
| 10.12 | cyclohexane-1,2-diol (single stereoisomer, early eluting) | 3-[4-(3-{[4-(difluoromethyl)-5-fluoro-pyrimidin-2-yl]amino}-5-methylphenyl)-1H-pyrazol-1-yl]cyclohexane-1,2-diol | 434.2 | 434 | Free Base |

Example 11.1

Preparation of (R)-3-(4-(3-(4-cyclopropylpyrimidin-2-ylamino)-5-methylphenyl)-1H-pyrazol-1-yl)-2-hydroxypropanoic acid

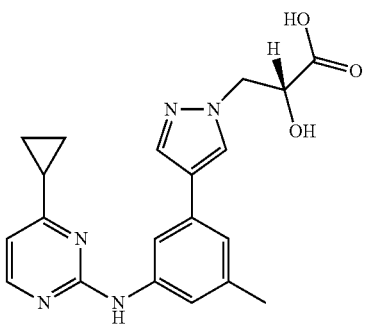 [SMILES: Cc1cc(Nc2nccc(C3CC3)n2)cc(-c2cnn(C[C@@H](O)C(=O)O)c2)c1]

Cesium carbonate (65.2 mg, 0.20 mmol) was added along with 4-(4,4,5,5-tetramethyl-1,3,2-dioxaborolan-2-yl)-1H-pyrazole (19.40 mg, 0.100 mmol) dissolved in DMF (1000 μL) and (R)-methylglycidate (10 μL, 0.11 mmol) was added to vial. The reaction was warmed to 80° C. and stirred overnight. PdCl₂(dppf)-CH₂Cl₂ (8.17 mg, 10.00 μmol) was added directly to the reaction mixture along with N-(3-bromo-5-methylphenyl)-4-cyclopropyl-pyrimidin-2-amine (30 mg, 0.1 mmol) and sodium carbonate (2M in water, 100 μL, 0.200 mmol). The mixture was stirred at 90° C. overnight and then stirred at 100° C. for 72 hours. Si-Dimercaptotriazole (Si-DMT) (222 mg, 0.126 mmol) was added as a means of scavenging the palladium and the vial was resealed and allowed to stir for 6 hours at room temperature. The reaction mixture was filtered through an activated CELITE cartridge (HM-N) and washed with DMSO (2×1 mL). The solution was purified by reverse phase HPLC (ACN/water with ammonium hydroxide buffer) to afford (R)-3-(4-(3-(4-cyclopropylpyrimidin-2-ylamino)-5-methylphenyl)-1H-pyrazol-1-yl)-2-hydroxypropanoic acid as the ammonium salt. MS ESI calcd. for $C_{20}H_{22}N_5O_3$ [M+H]$^+$ 380. found 380. $^1$H NMR (600 MHz, DMSO-d$_6$) δ 9.26 (s, 1H), 8.22 (d, J=5.0, 1H), 7.92 (s, 1H), 7.79 (s, 1H), 7.68 (s, 1H), 7.30 (s, 1H), 6.91 (s, 1H), 6.75 (d, J=5.0, 1H), 4.37 (dd, J=2.7, 13.6, 1H), 3.95 (dd, J=8.7, 13.6, 1H), 3.89 (d, J=7.4, 1H), 2.24 (s, 3H), 2.03-1.94 (m, 1H), 1.09-0.98 (m, 5H).

The following compounds in Tables 11A and 11B were prepared according to the method described for Example 11.1.

TABLE 11A

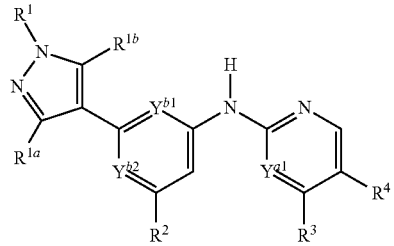

Ie [R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| 11.2 | —CH$_2$CHOHCO$_2$H S ammonium salt | CH$_3$ | OCH$_3$ | (2S)-2-hydroxy-3-(4-{3-[(4-methoxy-pyrimidin-2-yl)amino]-5-methylphenyl}-1H-pyrazol-1-yl)-propanoic acid | 370 | 370 |
| 11.3 | —CH$_2$CHOHCO$_2$H S ammonium salt | CH$_3$ | CH$_3$ | (2S)-2-hydroxy-3-(4-{3-methyl-5-[(4-methylpyrimidin-2-yl)amino]phenyl}-1H-pyrazol-1-yl)-propanoic acid | 354 | 354 |
| 11.4 | —CH$_2$CHOHCO$_2$H S ammonium salt | H | OCH$_3$ | (2S)-2-hydroxy-3-(4-{3-[(4-methoxy-pyrimidin-2-yl)-amino]phenyl}-1H-pyrazol-1-yl)-propanoic acid | 356 | 356 |
| 11.5 | —CH$_2$CHOHCO$_2$H S ammonium salt | CH$_3$ | c-propyl | (2S)-3-(4-{3-[(4-cyclopropylpyrimidin-2-yl)amino]-5-methyl-phenyl}-1H-pyrazol-1-yl)-2-hydroxy-propanoic acid | 380 | 380, 380 |
| 11.6 | —CH$_2$CHOHCO$_2$H S ammonium salt | CH$_3$ | OCH$_3$, R$^4$ = Cl | (2S)-3-(4-{3-[(5-chloro-4-methoxy-pyrimidin-2-yl)-amino]-5-methyl-phenyl}-1H-pyrazol-1-yl)-2-hydroxy-propanoic acid | 404 | 404 |
| 11.7 | —CH$_2$CHOHCO$_2$H R ammonium salt | CH$_3$ | CH$_3$, R$^4$ = Cl | (2R)-3-(4-{3-[(5-chloro-4-methyl-pyrimidin-2-yl)-amino]-5-methyl-phenyl}-1H-pyrazol-1-yl)-2-hydroxy-propanoic acid | 388 | 388 |
| 11.8 | —CH$_2$CHOHCO$_2$H R ammonium salt | CH$_3$ | OCH$_3$, | (2R)-2-hydroxy-3-(4-{3-[(4-methoxy-pyrimidin-2-yl)-amino]-5-methyl-phenyl}-1H-pyrazol-1-yl)propanoic acid | 370 | 370 |
| 11.9 | —CH$_2$CHOHCO$_2$H R ammonium salt | CH$_3$ | OCH$_3$, R$^4$ = Cl | (2R)-3-(4-{3-[(5-chloro-4-methoxy-pyrimidin-2-yl)-amino]-5-methyl-phenyl}-1H-pyrazol-1-yl)-2-hydroxy-propanoic acid | 404 | 404 |
| 11.10 | —CH$_2$CHOHCO$_2$H R ammonium salt | CH$_3$ | CH$_3$ | (2R)-2-hydroxy-3-(4-{3-methyl-5-[(4-methylpyrimidin-2-yl)amino]phenyl}-1H- | 354 | 354 |

TABLE 11A-continued

Ie [$R^{1a}$ = $R^{1b}$ = $R^4$ = H; $Y^{b1}$ = $Y^{b2}$ = CH; $Y^{a1}$ = N]

| Ex. No. | $R^1$ | $R^2$ | $R^3$ | Chemical Name | $[M+H]^+$ Calc'd | $[M+H]^+$ Found |
|---|---|---|---|---|---|---|
| | | | | pyrazol-1-yl)propanoic acid | | |
| 11.11 | —CH$_2$CHOHCO$_2$H R ammonium salt | H | OCH$_3$ | (2R)-2-hydroxy-3-(4-{3-[(4-methoxy-pyrimidin-2-yl)amino]phenyl}-1H-pyrazol-1-yl)propanoic acid | 356 | 356 |
| 11.12 | —CH$_2$CHOHCO$_2$H R ammonium salt | CH$_3$ | c-propyl | (2R)-3-(4-{3-[(4-cyclopropylpyrimidin-2-yl)amino]-5-methylphenyl}-1H-pyrazol-1-yl)-2-hydroxypropanoic acid | 380 | 380 |
| 11.13 | —CH$_2$CHOHCO$_2$H R ammonium salt | CH$_3$ | CH$_3$, $R^4$ = F | (2R)-3-(4-{3-[(5-fluoro-4-methylpyrimidin-2-yl)amino]-5-methylphenyl}-1H-pyrazol-1-yl)-2-hydroxypropanoic acid | 372 | 372 |
| 11.14 | —CH$_2$CHOHCO$_2$H R ammonium salt | CH$_3$ | OCH(CH$_3$)$_2$ | (2R)-2-hydroxy-3-[4-(3-methyl-5-{[4-(1-methylethoxy)-pyrimidin-2-yl]amino}-phenyl)-1H-pyrazol-1-yl]propanoic acid | 398 | 398 |
| 11.15 | —CH$_2$CHOHCO$_2$H R ammonium salt | CH$_3$ | OCH$_3$, $R^4$ = Cl | (2R)-3-(4-{3-[(5-chloro-4-methoxy-pyrimidin-2-yl)amino]-5-methyl-phenyl}-1H-pyrazol-1-yl)-2-hydroxy-propanoic acid | 404 | 404 |
| 11.16 | —CH$_2$CHOHCO$_2$H R ammonium salt | CH$_3$ | CH(CH$_3$)$_2$ | (2R)-2-hydroxy-3-[4-(3-methyl-5-{[4-(1-methylethyl)-pyrimidin-2-yl]amino}phenyl)-1H-pyrazol-1-yl]propanoic acid | 382 | 382 |

TABLE 11B

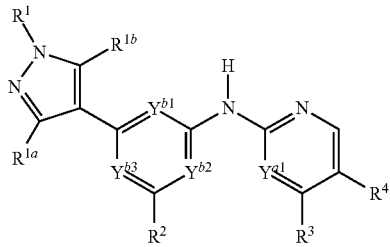

Ie [$R^{1a} = R^{1b} = R^4 = H$; $Y^{b1} = Y^{b2} = N$; $Y^{b3} = Y^{a1} = CH$]

| Ex. No. | $R^1$ | $R^2$ | $R^3$ | Chemical Name | $[M+H]^+$ Calc'd | $[M+H]^+$ Found |
|---|---|---|---|---|---|---|
| 11.17 | —CH₂CHOHCO₂H S ammonium salt | CH₃ | CH₃ | (2S)-2-hydroxy-3-(4-{4-methyl-6-[(4-methyl-pyridin-2-yl)amino]-pyrimidin-2-yl}-1H-pyrazol-1-yl)propanoic acid | 355 | 355 |
| 11.18 | —CH₂CHOHCO₂H S ammonium salt | CH₃ | CF₃ | (2S)-2-hydroxy-3-[4-(6-methyl-4-{[4-(trifluoromethyl)pyrimidin-2-yl]amino}pyridin-2-yl)-1H-pyrazol-1-yl]propanoic acid | 409 | 409 |
| 11.19 | —CH₂CHOHCO₂H R ammonium salt | CH₃ | CH₃ | (2R)-2-hydroxy-3-(4-{4-methyl-6-[(4-methyl-pyridin-2-yl)amino]-pyrimidin-2-yl}-1H-pyrazol-1-yl)propanoic acid | 355 | 355 |
| 11.20 | —CH₂CHOHCO₂H R ammonium salt | CH₃ | CF₃ | (2R)-2-hydroxy-3-[4-(6-methyl-4-{[4-(trifluoromethyl)pyrimidin-2-yl]amino}pyridin-2-yl)-1H-pyrazol-1-yl]propanoic acid | 409 | 409 |

Example 12.1

Preparation of 4-((4-(3-methyl-5-((4-(trifluoromethyl)pyrimidin-2-yl)amino)phenyl)-1H-pyrazol-1-yl)methyl)piperidin-4-ol

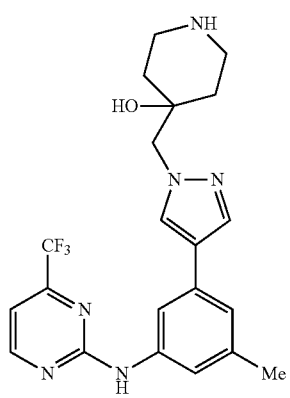 [SMILES: Cc1cc(Nc2nccc(C(F)(F)F)n2)cc(-c2cnn(CC3(O)CCNCC3)c2)c1]

Step 1:
Sodium hydride (27 mg, 0.68 mmol) was added to a mixture of N-(3-methyl-5-(1H-pyrazol-4-yl)phenyl)-4-(trifluoromethyl)pyrimidin-2-amine (145 mg, 0.46 mmol), ten-butyl 1-oxa-6-azaspiro[2.5]octane-6-carboxylate (112 mg, 0.525 mmol) in DMF (2 mL). The resulting brown solution was stirred at 90° C. for 5 hours. The mixture was partitioned between EtOAc and saturated ammonium chloride. The organic layer was washed with water, brine, dried over sodium sulfate, filtered and concentrated under reduced pressure. The residue was purified by column chromatography on silica gel (50% EtOAc/hexanes) to afford racemic tert-butyl 4-hydroxy-4-((4-(3-methyl-5-((4-(trifluoromethyl)pyrimidin-2-yl)amino)phenyl)-1H-pyrazol-1-yl)methyl)piperidine-1-carboxylate MS ESI calc'd for $C_{26}H_{32}F_3N_6O_3$ $[M+H]^+$ 533. found 533.

Step 2:
TFA (0.1 mL 1.298 mmol) was added to the solution of racemic tert-butyl 4-hydroxy-4-((4-(3-methyl-5-((4-(trifluoromethyl) pyrimidin-2-yl)amino)phenyl)-1H-pyrazol-1-yl)methyl)piperidine-1-carboxylate (120 mg, 0.23 mmol) in dichloromethane (1 mL). The mixture was stirred at room temperature for 2 days. Additional TFA (0.2 mL) was added and the mixture was stirred for 16 hours. The mixture was purified on reverse phase HPLC (ACN/water with 0.1% TFA modifier) to afford 4-((4-(3-methyl-5-((4-(trifluoromethyl) pyrimidin-2-yl)amino)phenyl)-1H-pyrazol-1-yl)methyl)piperidin-4-ol. MS ESI calc'd for $C_{21}H_{24}F_3N_6O$ $[M+H]^+$ 433. found 433. ¹H NMR (500 MHz, CD₃OD) δ 8.65 (d, J=4.8, 1H), 7.96 (s, 1H), 7.86 (s, 1H), 7.83 (s, 1H), 7.31 (s, 1H), 7.06 (s, 1H), 7.05 (d, J=4.2, 1H), 4.20 (s, 2H), 3.31-3.17 (m, 4H), 2.33 (s, 3H), 1.94-1.78 (m, 2H), 1.73-1.65 (m, 2H).

The following compounds in Table 12 were prepared according to the method described for Example 12.1 and may not include Step 2.

TABLE 12

Ie [R$^{1a}$ = R$^{1b}$ = R$^4$ = H; Y$^{b1}$ = Y$^{b2}$ = CH; Y$^{a1}$ = N;]

| Ex. No. | R$^1$ | R$^2$ | R$^3$ | Chemical Name | [M + H]$^+$ Calc'd | [M + H]$^+$ Found |
|---|---|---|---|---|---|---|
| 12.2 | (1-hydroxycyclobutyl)methyl, TFA salt | CH$_3$ | CF$_3$ | 1-{[4-(3-methyl-5-{[4-(trifluoromethyl)pyrimidin-2-yl]amino}-phenyl)-1H-pyrazol-1-yl]-methyl}-cyclobutanol | 404 | 404 |
| 12.3 | (3-methoxy-1-hydroxycyclobutyl)methyl, TFA salt | CH$_3$ | CH$_3$ | 3-methoxy-1-[(4-{3-methyl-5-[(4-methylpyrimidin-2-yl)amino]phenyl}-1H-pyrazol-1-yl)methyl]-cyclobutanol | 380 | 380 |
| 12.4 | tert-butyl (4-hydroxypiperidin-1-yl)acetate, TFA salt | CH$_3$ | CF$_3$ | tert-butyl (4-hydroxy-4-{[4-(3-methyl-5-{[4-(trifluoromethyl)pyrimidin-2-yl]amino}phenyl)-1H-pyrazol-1-yl]methyl}-piperidin-1-yl)acetate | 547 | 547 |
| 12.5 | (4-hydroxytetrahydro-2H-pyran-4-yl)methyl, free base | CH$_3$ | CF$_3$ | 4-{[4-(3-methyl-5-{[4-(trifluoromethyl)pyrimidin-2-yl]amino}phenyl)-1H-pyrazol-1-yl]methyl}-tetrahydro-2H-pyran-4-ol | 434 | 434 |
| 12.6[15] | 4-hydroxy-2,2-dimethylcyclohexanecarboxylic acid, syn racemic free base | CH$_3$ | CF$_3$ | 4-hydroxy-2,2-dimethyl-4-{[4-(3-methyl-5-{[4-(trifluoromethyl)pyrimidin-2-yl]amino}phenyl)-1H-pyrazol-1-yl]methyl}-cyclohexanecarboxylic acid | 504 | 504 |

TABLE 12-continued

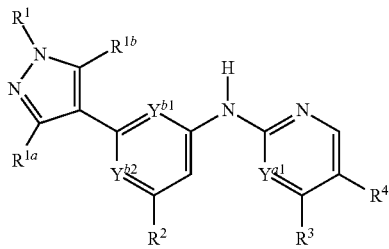

Ie [$R^{1a}$ = $R^{1b}$ = $R^4$ = H; $Y^{b1}$ = $Y^{b2}$ = CH; $Y^{a1}$ = N;]

| Ex. No. | $R^1$ | $R^2$ | $R^3$ | Chemical Name | $[M + H]^+$ Calc'd | $[M + H]^+$ Found |
|---|---|---|---|---|---|---|
| 12.7 | (HO-tetrahydropyran-3-yl methyl) free base | CH₃ | CF₃ | 3-{[4-(3-methyl-5-{[4-(trifluoromethyl)pyrimidin-2-yl]amino}phenyl)-1H-pyrazol-1-yl]methyl}-tetrahydro-2H-pyran-3-ol | 434 | 434 |
| 12.8 | (2,6-dimethyl-4-hydroxy-tetrahydropyran-4-yl methyl) chiral-alcohol trans to the cis methyl groups free base | CH₃ | CF₃ | meso (2R,4S,6S)-2,6-dimethyl-4-{[4-(3-methyl-5-{[4-(trifluoromethyl)pyrimidin-2-yl]amino}phenyl)-1H-pyrazol-1-yl]methyl}-tetrahydro-2H-pyran-4-ol; | 462 | 462 |
| 12.9 | (2,2-dimethyl-4-hydroxy-tetrahydropyran-4-yl methyl) chiral-R or S (early eluting peak) free base | CH₃ | CF₃ | 2,2-dimethyl-4-{[4-(3-methyl-5-{[4-(trifluoromethyl)pyrimidin-2-yl]amino}phenyl)-1H-pyrazol-1-yl]methyl}-tetrahydro-2H-pyran-4-ol | 462 | 462 |
| 12.10 | (2,2-dimethyl-4-hydroxy-tetrahydropyran-4-yl methyl) chiral-R or S (late eluting peak) free base | CH₃ | CF₃ | 2,2-dimethyl-4-{[4-(3-methyl-5-{[4-(trifluoromethyl)pyrimidin-2-yl]amino}phenyl)-1H-pyrazol-1-yl]methyl}-tetrahydro-2H-pyran-4-ol | 462 | 462 |
| 12.11 | (3-hydroxy-tetrahydropyran-3-yl methyl) free base | CH₃ | CF₃ | 3-{[4-(3-methyl-5-{[4-(trifluoromethyl)pyrimidin-2-yl]amino}phenyl)-1H-pyrazol-1-yl]methyl}-tetrahydro-2H-pyran-3-ol | 434 | 434 |

TABLE 12-continued

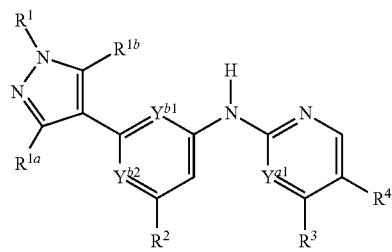

Ie [$R^{1a} = R^{1b} = R^4 = H$; $Y^{b1} = Y^{b2} = CH$; $Y^{a1} = N$;]

| Ex. No. | $R^1$ | $R^2$ | $R^3$ | Chemical Name | [M + H]$^+$ Calc'd | [M + H]$^+$ Found |
|---|---|---|---|---|---|---|
| 12.12 | HO (tetrahydropyran), chiral-R or S (late eluting peak) free base | CH$_3$ | CF$_3$ | 3-{[4-(3-methyl-5-{[4-(trifluoromethyl)pyrimidin-2-yl]amino}phenyl)-1H-pyrazol-1-yl]methyl}-tetrahydro-2H-pyran-4-ol | 434 | 434 |
| 12.13 | HO (tetrahydropyran), free base | CH$_3$ | CH$_3$ | 4-[(4-{3-methyl-5-[(4-methylpyrimidin-2-yl)amino]phenyl}-1H-pyrazol-1-yl)methyl]-tetrahydro-2H-pyran-4-ol | 380 | 380 |
| 12.14 | HO (tetrahydropyran with methyl), racemic (methyl and alcohol are cis) free base | CH$_3$ | CF$_3$ | 4-{1-[4-(3-methyl-5-{[4-(trifluoromethyl)pyrimidin-2-yl]amino}phenyl)-1H-pyrazol-1-yl]ethyl}-tetrahydro-2H-pyran-4-ol | 448 | 448 |
| 12.15[16] | HO-piperidine-CH$_2$-COOH, TFA salt | CH$_3$ | CF$_3$ | (4-hydroxy-4-{[4-(3-methyl-5-{[4-(trifluoromethyl)-pyrimidin-2-yl]amino}-phenyl)-1H-pyrazol-1-yl]methyl}piperidin-1-yl)acetic acid | 491 | 491 |

Footnotes: [15]Example 12.6 used methyl syn-5,5-dimethyl-1-oxaspiro[2.5]octane-6-carboxylate as the starting material which afforded 5,5-dimethyl-1-{[4-(3-methyl-5-{[4-(trifluoromethyl)pyrimidin-2-yl]amino}phenyl)-1H-pyrazol-1-yl]methyl}-2-oxabicyclo[2.2.2]octan-3-one followed by method described in Preparative Example 6.1—ester hydrolysis as the ultimate synthetic step.

[16]Example 12.15, from the corresponding tert-butyl ester, used by the method described in Preparative Example 6.—tert-Butyl ester hydrolysis as the ultimate synthetic step.

Example 13.1

Preparation of N-(3-(1-isopropyl-1H-pyrazol-4-yl)-5-methylphenyl)-4-(trifluoromethyl)-pyrimidin-2-amine

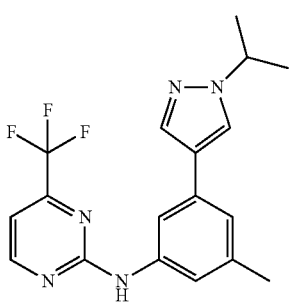 [SMILES: Cc1cc(Nc2nccc(C(F)(F)F)n2)cc(-c2cnn(C(C)C)c2)c1]

4-(4,4,5,5-Tetramethyl-1,3,2-dioxaborolan-2-yl)-1H-pyrazole (0.02 g, 0.10 mmol), polystyrene supported-triphenylphosphine (0.12 g, 0.24 mmol, 1.92 mmol/g), diisopropyl hydrazine-1,2-dicarboxylate (0.04 g, 0.19 mmol), and isopropanol (0.01 g, 0.21 mmol) were suspended in THF (1.0 mL). The reaction was allowed to shake at ambient temperature for 48 hours. The reaction mixture was filtered, the eluent was collected and concentrated under reduced pressure. Pd(dppf)Cl$_2$ (0.011 g, 0.015 mmol), N-(3-bromo-5-methylphenyl)-4-(trifluoromethyl)pyrimidin-2-amine (0.03 g, 0.08 mmol), sodium carbonate (0.10 mL, 0.20 mmol, 2 M) suspended in THF (1.0 mL) were added. The vial was capped and irradiated in a microwave for 15 minutes at 110° C. Silica supported-DMT (0.055 g, 0.05 mmol, 0.94 mmol/g) was added, the vial was sealed and allowed to stir for 4 hours. The reaction mixture was passed through a syringe filter, the eluent was collected and concentrated under reduced pressure. The residue was purified by reverse phase HPLC (0 to 95% ACN/water with 0.1% TFA modifier) to afford N-(3-(1-isopropyl-1H-pyrazol-4-yl)-5-methylphenyl)-4-(trifluoromethyl)pyrimidin-2-amine. MS ESI calc'd for C$_{18}$H$_{19}$F$_3$N$_5$ [M+H]$^+$ 362. found 362. $^1$H NMR (500 MHz, DMSO-d$_6$) δ 10.10 (s, 1H), 8.80 (d, J=4.8, 1H), 8.08 (s, 1H), 7.84 (s, 1H), 7.71 (s, 1H), 7.29 (s, 1H), 7.23 (d, J=4.9, 1H), 7.07 (s, 1H), 4.49 (dt, J=6.6, 13.3, 1H), 2.28 (s, 3H), 1.43 (d, J=6.7, 6H).

The following compounds in Table 13 were prepared according to the method described for Example 13.1.

TABLE 13

Ie [R$^{1a}$ = R$^{1b}$ = R$^4$ = H; Y$^{b1}$ = Y$^{b2}$ = CH; Y$^{a1}$ = N]

| Ex. No. | R$^1$ | R$^2$ | R$^3$ | Chemical Name | [M + H]$^+$ Calc'd | [M + H]$^+$ Found |
|---|---|---|---|---|---|---|
| 13.2 | (2-pyrrolidinyl)ethyl, racemic formate salt | CH$_3$ | CF$_3$ | N-{3-methyl-5-[1-(2-pyrrolidin-2-ylethyl)-1H-pyrazol-4-yl]phenyl}-4-(trifluoromethyl)-pyrimidin-2-amine | 417 | 417 |
| 13.3 | (tetrahydrofuran-2-yl)methyl, formate salt | CH$_3$ | CF$_3$ | N-{3-methyl-5-[1-(tetrahydrofuran-2-ylmethyl)-1H-pyrazol-4-yl]phenyl}-4-(trifluoromethyl)-pyrimidin-2-amine | 404 | 404 |

Example 14

Preparation of (R or S) 5-[4-(3-methyl-5-{[4-(trifluoromethyl)pyrimidin-2-yl]amino}phenyl)-1H-pyrazol-1-yl]azepan-2-one (early eluting enantiomer and late eluting enantiomer)

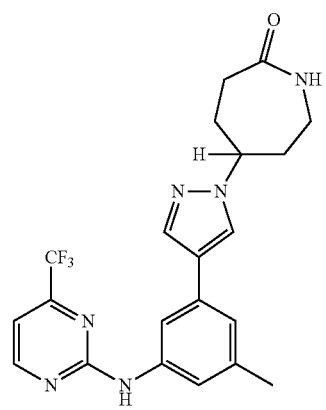

-continued

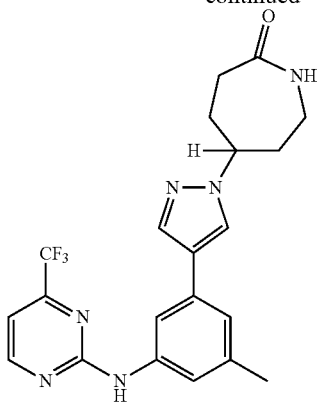

Step 1:

Sodium azide (155 mg, 2.39 mL) was added to a solution of N-{3-[1-(1,4-dioxaspiro[4.5]dec-8-yl)-1H-pyrazol-4-yl]-5-methylphenyl}-4-(trifluoromethyl)pyrimidin-2-amine (732 mg, 1.59 mmol) in chloroform (8.0 mL) followed by methanesulfonic acid (1.24 mL, 19.1 mmol). The reaction was heated to 65° C. for 2 h. The reaction was cooled to room temperature and water was added, followed by NaOH (1N). The organic layer was extracted with EtOAc (3×). The combined layers were dried over magnesium sulfate and concentrated under reduced pressure. The residue was purified by column chromatography on silica gel (10% methanol/dichloromethane) to afford racemic 5-[4-(3-methyl-5-{[4-(trifluoromethyl)pyrimidin-2-yl]amino}phenyl)-1H-pyrazol-1-yl]azepan-2-one as a white solid. MS ESI calcd. for $C_{21}H_{21}F_3N_6O$ [M+H]$^+$ 431. found 431.

Step 2:

Racemic 5-[4-(3-methyl-5-{[4-(trifluoromethyl)pyrimidin-2-yl]amino}phenyl)-1H-pyrazol-1-yl]azepan-2-one (549 mg, 1.28 mmol) enantiomers were separated by chiral super critical fluid chromatography (OJ 2.1×25 cm, 5 µM at a wavelength of 275 nm, 35/65 methanol/$CO_2$ and a flow rate of 70 mL/min) to afford (5R or S)-5-[4-(3-methyl-5-{[4-(trifluoromethyl)pyrimidin-2-yl]amino}phenyl)-1H-pyrazol-1-yl]azepan-2-one (early eluting enantiomer), MS ESI calcd. for $C_{21}H_{21}F_3N_6O$ [M+H]$^+$ 431. found 431. $^1$H NMR (500 MHz, DMSO-$d_6$) δ 10.10 (s, 1H), 8.80 (d, J=4.8, 1H), 8.12 (s, 1H), 7.82 (s, 1H), 7.72 (s, 1H), 7.58 (t, J=15.4, 1H), 7.29 (s, 1H), 7.24 (d, J=4.9, 1H), 7.06 (s, 1H), 4.47-4.36 (m, 1H), 3.27 (ddd, J=4.4, 11.1, 15.3, 1H), 3.19-3.05 (m, 1H), 2.31-2.19 (m, 5H), 2.11 (t, J=13.2, 2H), 1.97-1.79 (m, 2H); and (5R or S)-5-[4-(3-methyl-5-{[4-(trifluoromethyl)pyrimidin-2-yl]amino}phenyl)-1H-pyrazol-1-yl]azepan-2-one (late eluting enantiomer), MS ESI calcd. for $C_{21}H_{21}F_3N_6O$ [M+H]$^+$ 431. found 431. $^1$H NMR (500 MHz, DMSO-$d_6$) δ 10.10 (s, 1H), 8.80 (d, J=4.8, 1H), 8.12 (s, 1H), 7.82 (s, 1H), 7.72 (s, 1H), 7.58 (t, J=15.4, 1H), 7.29 (s, 1H), 7.24 (d, J=4.9, 1H), 7.06 (s, 1H), 4.47-4.36 (m, 1H), 3.27 (ddd, J=4.4, 11.1, 15.3, 1H), 3.19-3.05 (m, 1H), 2.31-2.19 (m, 5H), 2.11 (t, J=13.2, 2H), 1.97-1.79 (m, 2H).

Example 15

Preparation of cis-4-[4-(3-methyl-5-{[4-(trifluoromethyl)pyrimidin-2-yl]amino}phenyl)-1H-pyrazol-1-yl]cyclohexanol

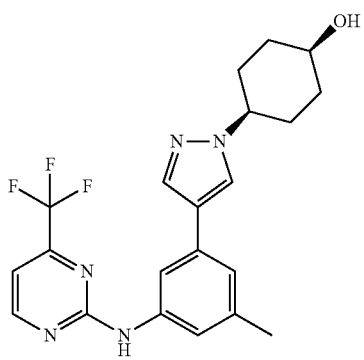 [SMILES: Cc1cc(Nc2nccc(C(F)(F)F)n2)cc(-c2cnn([C@H]3CC[C@@H](O)CC3)c2)c1]

Step 1:

N-{3-[1-(1,4-dioxaspiro[4.5]dec-8-yl)-1H-pyrazol-4-yl]-5-methylphenyl}-4-(trifluoromethyl)pyrimidin-2-amine (62.4 mg, 0.14 mmol) was dissolved in THF (1 mL) and hydrochloric acid (0.45 mL, 2.72 mmol) was added. The reaction mixture was stirred at room temperature for two hours. The mixture was diluted with EtOAc, washed with saturated sodium bicarbonate, dried over sodium sulfate, filtered and concentrated under reduced pressure. The residue was purified by column chromatography on silica gel (10-80% EtOAc/hexanes) to afford 4-[4-(3-methyl-5-{[4-(trifluoromethyl)pyrimidin-2-yl]amino}phenyl)-1H-pyrazol-1-yl]cyclohexanone as a colorless foam. MS ESI calcd. for $C_{21}H_{21}F_3N_5O$ [M+H]$^+$ 416. found 416. $^1$H NMR (500 MHz, DMSO-$d_6$) δ 10.11 (s, 1H), 8.80 (d, J=4.7 Hz, 1H), 8.17 (s, 1H), 7.82 (s, 1H), 7.80 (s, 1H), 7.35 (s, 1H), 7.27 (d, J=4.7 Hz, 1H), 7.08 (s, 1H), 4.77-4.68 (m, 1H), 2.61-2.48 (m, 4H), 2.35-2.17 (m, 4H), 2.22 (s, 3H).

Step 2:

Sodium borohydride (3.39 mg, 0.09 mmol) was added to 4-[4-(3-methyl-5-{[4-(trifluoromethyl)pyrimidin-2-yl]amino}phenyl)-1H-pyrazol-1-yl]cyclohexanone (24.8 mg, 0.06 mmol) dissolved in methanol (0.5 mL). The reaction mixture was stirred at room temperature for one hour. The mixture was diluted with EtOAc, washed with water, dried over sodium sulfate, filtered, and concentrated under reduced pressure. The residue was purified by reverse phase HPLC (45 to 80% ACN/Water with 0.1% TFA modifier). The free base was liberated using PL-HCO$_3$ cartridges (Stratospheres™, 0.9 mmol) and lyophilized to afford cis-4-[4-(3-methyl-5-{[4-(trifluoromethyl)pyrimidin-2-yl]amino}phenyl)-1H-pyrazol-1-yl]cyclohexanol. MS ESI calcd. for $C_{21}H_{23}F_3N_5O$ [M+F]$^+$ 418. found 418. $^1$H NMR (500 MHz, DMSO-$d_6$) δ 10.10 (s, 1H), 8.80 (d, J=4.7 Hz, 1H), 8.06 (s, 1H), 7.82 (s, 1H), 7.70 (s, 1H), 7.38 (s, 1H), 7.25 (d, J=4.7 Hz, 1H), 7.05 (s, 1H), 4.67 (s, 1H), 4.19-4.07 (m, 1H), 3.50-3.41 (m, 1H), 2.27 (s, 3H), 2.02-1.99 (m, 2H), 1.94-1.85 (m, 2H), 1.78 (q, J=11.7 Hz, 2H), 1.35 (q, J=11.7 Hz, 2H).

Example 16

Preparation of (2S)-3-[4-(3-{[4-(difluoromethyl) pyrimidin-2-yl]amino}-5-methylphenyl)-1H-pyrazol-1-yl]-2-hydroxypropanamide

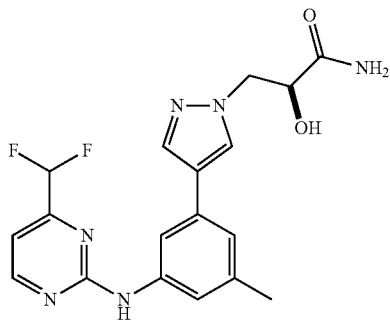 [SMILES: Cc1cc(Nc2nccc(C(F)F)n2)cc(-c2cnn(C[C@H](O)C(N)=O)c2)c1]

Step 1:

Ammonia (7.0 M in methanol, 1.5 mL, 10.5 mmol) was added to a flask containing methyl (2S)-3-[4-(3-{[4-(difluoromethyl)pyrimidin-2-yl]amino}-5-methylphenyl)-1H-pyrazol-1-yl]-2-hydroxypropanoate (57.2 mg, 0.14 mmol) and the mixture was stirred overnight at 60° C. The mixture was cooled to room temperature and concentrated under reduced pressure. The residue was purified by reverse phase HPLC (0 to 95% ACN/water with 0.1% TFA modifier) to afford (2S)-3-[4-(3-amino-5-methylphenyl)-1H-pyrazol-1-yl]-2-hydroxypropanamide. MS ESI calcd. for $C_{13}H_{17}N_4O_2$ [M+H]$^+$ 261. found 261.

Step 2:

2-Chloro-4-(difluoromethyl)pyrimidine (24.8 mg, 0.12 mmol) and acetic acid (0.0074 mL, 0.130 mmol) were added to an oven-dried flask containing (2S)-3-[4-(3-amino-5-methylphenyl)-1H-pyrazol-1-yl]-2-hydroxypropanamide (46.2 mg, 0.12 mmol) dissolved in dioxane (0.41 mL). The mixture was stirred for 3 hours at 120° C. The mixture was then cooled to room temperature, diluted with water, and extracted with EtOAc (3×). The combined organic layers were dried over sodium sulfate, filtered, and concentrated under reduced pressure. The residue was purified by column chromatography on silica gel (2 to 100% EtOAc/hexanes) to afford (2S)-3-[4-(3-{[4-(difluoromethyl)pyrimidin-2-yl]amino}-5-methylphenyl)-1H-pyrazol-1-yl]-2-hydroxypropanamide. MS ESI calcd. for $C_{18}H_{19}F_2N_6O_2$ [M+H]$^+$ 389. found 389. $^1$H NMR (500 MHz, DMSO-d$_6$) δ 9.88 (s, 1H), 8.68 (d, J=4.9 Hz, 1H), 7.96 (s, 1H), 7.82 (s, 1H), 7.76 (s, 1H), 7.37 (s, 1H), 7.34 (s, 1H), 7.32 (s, 1H), 7.04 (d, J=4.9 Hz, 1H), 7.01 (s, 1H), 6.87 (t, J=54.4 Hz, 1H), 5.86 (d, J=5.9 Hz, 1H), 4.41-4.33 (m, 1H), 4.24-4.18 (m, 1H), 4.17-4.13 (m, 1H), 2.28 (s, 3H).

Example 17

Preparation of 4-hydroxy-4-((4-(3-methyl-5-((4-(trifluoromethyl)pyrimidin-2-yl)amino)phenyl)-1H-pyrazol-1-yl)methyl)piperidine-1-carboxamide

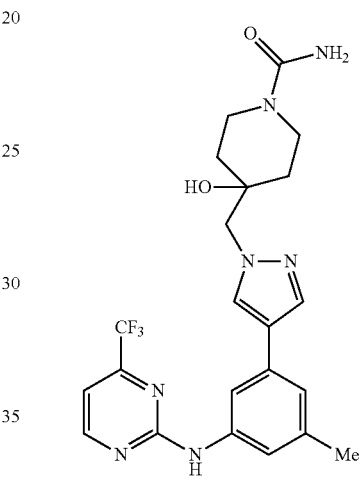

Potassium cyanate (55.6 mg, 0.69 mmol), water (2.4 mL) and hydrochloric acid (2.0 M in water, 0.3 mL, 0.60 mmol) were added to a solution of racemic 4-((4-(3-methyl-5-((4-(trifluoromethyl)pyrimidin-2-yl)amino)phenyl)-1H-pyrazol-1-yl)methyl)piperidin-4-ol (49 mg, 0.11 mmol) in THF (0.8 mL). The mixture was stirred at 55° C. for 3.5 hours. Additional hydrochloric acid standard solution (2.0 M in water, 0.15 mL, 0.30 mmol) and potassium cyanate (20.0 mg, 0.25 mmol) were added. The mixture was heated for another 2 hours then saturated sodium bicarbonate and EtOAc were added. The organic phase was washed with water, brine, dried over sodium sulfate, filtered and concentrated under reduced pressure. The residue was purified on reverse phase HPLC (ACN/water with 0.1% TFA modifier) to afford 4-hydroxy-4-((4-(3-methyl-5((4-(trifluoromethyl) pyrimidin-2-yl) amino)phenyl)-1H-pyrazol-1-yl)methyl) piperidine-1-carboxamide. MS ESI calc'd for $C_{22}H_{25}F_3N_7O_2$ [M+H]$^+$476. found 476. $^1$H NMR (500 MHz, CD$_3$OD) δ 8.68 (d, J=4.9, 1H), 7.96 (s, 1H), 7.84 (s, 1H), 7.82 (s, 1H), 7.37 (s, 1H), 7.10

(s, 1H), 7.09 (d, J=4.9, 1H), 4.16 (s, 2H), 3.78 (d, J=13.2, 2H), 3.20 (t, J=11.3, 2H), 2.35 (s, 3H), 1.71-1.56 (m, 2H), 1.48 (d, J=13.1, 2H).

Example 18.1

Preparation of 3-(1-(6-((4-(trifluoromethyl)pyridin-2-yl)amino)pyridin-2-yl)-1H-pyrazol-4-yl)propanoic acid

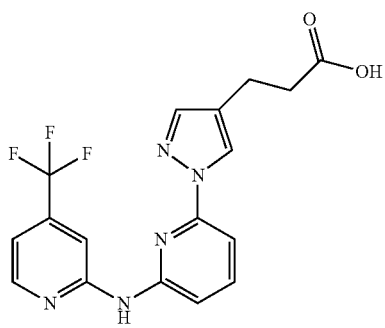 [SMILES: O=C(O)CCc1cnn(-c2cccc(Nc3cc(C(F)(F)F)ccn3)n2)c1]

N-(6-Bromopyridin-2-yl)-4-(trifluoromethyl)pyrimidin-2-amine (0.015 g, 0.047 mmol), ethyl 3-(1H-pyrazol-4-yl)propanoate (0.008 g, 0.047 mmol), potassium phosphate tribasic (0.030 g, 0.14 mmol), and DMSO (0.48 mL) were added to a microwave vial. The reaction tube was sealed and heated to 130° C. for 12 hours. The completed reaction was diluted DMSO (0.5 mL) and passed through a syringe filtered where the eluent was collected and concentrated under reduced pressure. The residue was taken up in dichloromethane (1.0 mL), MeOH (0.5 mL), and NaOH (0.5 mL, 1.0 M) and was allowed to stir at ambient temperature for 4 hours. The reaction was concentrated under reduced pressure. The residue was taken up in DMSO (1.0 mL), passed through a syringe filter and purified by reverse phase preparative HPLC (0 to 95% ACN/$H_2O$ with 0.1% ammonium hydroxide modifier) to afford 3-(1-(6-((4-(trifluoromethyl)pyridin-2-yl)amino)pyridin-2-yl)-1H-pyrazol-4-yl)propanoic acid. MS ESI calc. for $C_{12}H_{15}F_3N_5O_2$ [M+H]$^+$ 378. found 378. $^1$H NMR (600 MHz, DMSO-$d_6$) δ 10.35 (s, 1H), 8.48 (d, J=5.2, 1H), 8.19 (s, 1H), 8.18 (s, 1H), 7.80 (t, J=8.0, 1H), 7.60 (s, 1H), 7.49 (d, J=8.2, 1H), 7.34 (d, J=7.8, 1H), 7.20 (d, J=5.3, 1H), 2.62 (t, J=7.6, 2H), 2.23 (t, 2H).

The following compounds in Table 18 were prepared according to the methods described in Example 18.1

TABLE 18

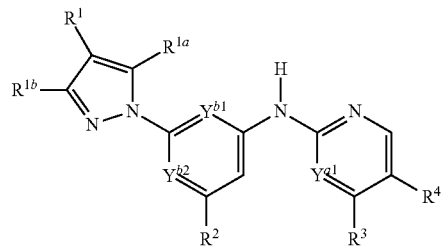

Ib [$R^{1a} = R^{1b} = R^4 = H$; $Y^{a1} = Y^{b2} = CH$; $Y^{b1} = N$;]

| Ex. No. | $R^1$ | $R^2$ | $R^3$ | Chemical Name | [M + H]$^+$ Calc'd | [M + H]$^+$ Found |
|---|---|---|---|---|---|---|
| 18.2 | $CH_2CH_2CO_2H$ Ammonium Salt | H | $CH_3$ | 3-(1-{6-[(4-methylpyridin-2-yl)amino]pyridin-2-yl}-1H-pyrazol-4-yl)propanoic acid | 324 | 324 |
| 18.3 | $CH_2CH_2CO_2H$ Ammonium Salt | $CH_3$ | c-propyl | 3-(1-{6-[(4-cyclopropylpyridin-2-yl)amino]-4-methylpyridin-2-yl}-1H-pyrazol-4-yl)propanoic acid | 364 | 364 |
| 18.4 | $CH_2CH_2CO_2H$ Ammonium Salt | $CH_3$ | $CH_3$ $R^4$ = Cl | 3-(1-{6-[(5-chloro-4-methylpyridin-2-yl)amino]-4-methylpyridin-2-yl}-1H-pyrazol-4-yl)propanoic acid | 372 | 372 |

Example 19.1

Preparation of 3-(1-(3-methyl-5-((4-(trifluoromethyl)pyrimidin-2-yl)amino)phenyl)-1H-pyrazol-4-yl)propanoic acid

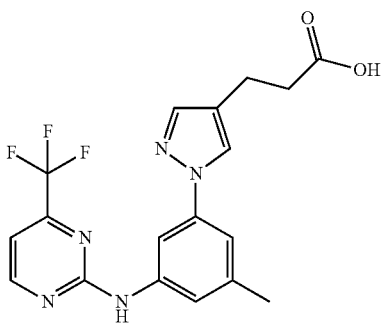 [SMILES: Cc1cc(Nc2nccc(C(F)(F)F)n2)cc(-n2cc(CCC(=O)O)cn2)c1]

Step 1:

N-(3-Bromo-5-methylphenyl)-4-(trifluoromethyl)pyrimidin-2-amine (0.036 g, 0.11 mmol), ethyl 3-(1H-pyrazol-4-yl)propanoate (0.020 g, 0.12 mmol), copper iodide (0.0050 g, 0.026 mmol), potassium carbonate (0.029 g, 0.21 mmol) and L-proline (0.0060 g, 0.053 mmol) were suspended in DMSO (0.70 mL, 0.15 M). The reaction vessel was sealed and heated to 120° C. for 12 hours. The completed reaction was diluted with DMSO (0.5 mL) was passed through a syringe filter where the eluent was collected and concentrated reduced pressure.

Step 2:

The residue was taken up in dichloromethane (1.0 mL), MeOH (0.5 mL), and NaOH (0.5 mL, 1.0 M) and was allowed to stir at ambient temperature for 4 hours. The reaction was concentrated under reduced pressure. The residue was taken up in DMSO (1.0 mL), passed through a syringe filter and purified by reverse phase preparative HPLC (0 to 95% ACN/$H_2O$ with 0.1% ammonium hydroxide modifier) to afford 3-(1-(3-methyl-5-((4-(trifluoromethyl)-pyrimidin-2-yl)amino)phenyl)-1H-pyrazol-4-yl)propanoic acid. MS ESI calc. for $C_{18}H_{12}F_3N_5O_2$ $[M+H]^+$ 392. found 392. $^1H$ NMR (600 MHz, DMSO-$d_6$) δ 10.27 (s, 1H), 8.81 (d, J=4.8, 1H), 8.11 (s, 1H), 8.06 (s, 1H), 7.55 (s, 1H), 7.40 (s, 1H), 7.26 (d, J=4.9, 1H), 7.21 (s, 1H), 2.68 (t, J=7.5, 2H), 2.55-2.49 (m, 2H), 2.31 (s, 3H).

The following compounds in Table 19A were prepared according to the method described in Example 19.1. Esters were optionally hydrolyzed according to the procedure in Example 19.1, Step 2.

TABLE 19A

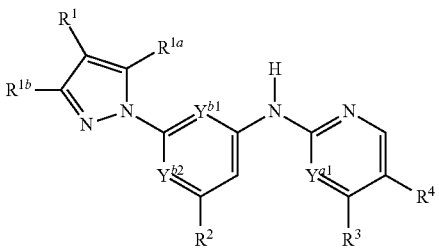

Ib [$R^{1a} = R^{1b} = R^4 = H$; $Y^{b1} = Y^{b2} = CH$; $Y^{a1} = N$;]

| Ex. No. | $R^1$ | $R^2$ | $R^3$ | Chemical Name | $[M+H]^+$ Calc'd | $[M+H]^+$ Found |
|---|---|---|---|---|---|---|
| 19.2 | $CH_2CH_2CO_2Et$ Formate Salt | $CH_3$ | $CF_3$ | Ethyl 3-[1-(3-methyl-5-{[4-(trifluoromethyl)-pyrimidin-2-yl]amino}phenyl)-1H-pyrazol-4-yl]propanoate | 420 | 420 |
| 19.3 | $CH_2CH_2CO_2H$ Formate Salt | $CH_3$ | c-propyl | 3-(1-{3-[(4-cyclopropylpyrimidin-2-yl)amino]-5-methylphenyl}-1H-pyrazol-4-yl)propanoic acid | 364 | 364 |
| 19.4 | $CH_2CH_2CO_2Et$ Formate Salt | $CH_3$ | c-propyl | Ethyl 3-(1-{3-[(4-cyclopropylpyrimidin-2-yl)amino]-5-methylphenyl}-1H-pyrazol-4-yl)propanoate | 392 | 392 |
| 19.5 | $CH_2CH_2CO_2Et$ Formate Salt | $CH_3$ | $OCH_3$ | Ethyl 3-(1-{3-[(4-methoxypyrimidin-2-yl)amino]-5-methylphenyl}-1H-pyrazol-4-yl)propanoate | 382 | 382 |
| 19.6 | $CH_2CH_2CO_2Et$ Formate Salt | $CH_3$ | $CH_3$ | Ethyl 3-(1-{3-methyl-5-[(4-methyl-pyrimidin- | 366 | 366 |

TABLE 19A-continued

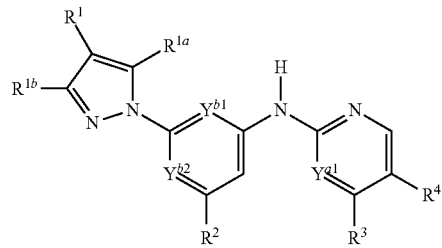

Ib [$R^{1a} = R^{1b} = R^4 = H$; $Y^{b1} = Y^{b2} = CH$; $Y^{a1} = N$;]

| Ex. No. | $R^1$ | $R^2$ | $R^3$ | Chemical Name | [M + H]$^+$ Calc'd | [M + H]$^+$ Found |
|---|---|---|---|---|---|---|
| | | | | 2-yl)amino]-phenyl}-1H-pyrazol-4-yl)propanoate | | |

Example 19.7 and 19.8

4-{1-Hydroxy-1-[1-(3-methyl-5-{[4-(trifluoromethyl)pyrimidin-2-yl]amino}phenyl)-1H-pyrazol-4-yl]ethyl}benzoic acid, R and S

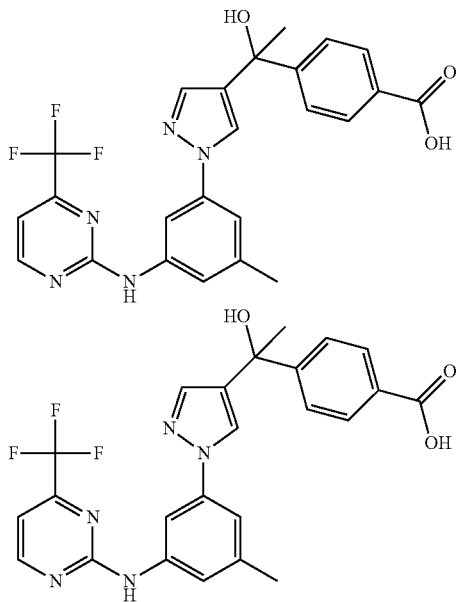

Step 1:

Ph₃CCl (10.4 g, 37 mmol) was added to a mixture of 4-bromopyrazole (5.0 g, 34 mmol) and potassium tert-butoxide (4.58 g, 41 mmol) in DMF (15 mL) at 0° C. then the mixture was stirred at 28° C. for 12 hours. The mixture was diluted with water and extracted with ethyl acetate, filtrated and recrystallized. The solid was dried under reduced pressure to afford 4-bromo-1-trityl-1H-pyrazole. MS ESI calc'd. for $C_{22}H_{18}BrN_2$ [M+H]+389 and 391. found 389 and 391. $^1$H NMR (400 MHz, DMSO-d₆): δ 7.74 (s, 1H), 7.50 (s, 1H), 7.38-7.34 (m, 10H), 7.04-7.01 (m, 5H).

Step 2:

n-BuLi (1.65 mL, 4 mmol) was added dropwise to a mixture of 4-bromo-1-trityl-1H-pyrazole (1.5 g, 3.8 mmol) in THF (15 mL) cooled to −78° C. Then the mixture was stirred at −78° C. for 1 hour. After methyl 4-acetylbenzoate (0.71 g, 3.8 mmol) in THF (1 mL) was added, the mixture was stirred at −78° C. for 2 hours, and then quenched with saturated aqueous ammonium chloride solution. The mixture was extracted with ethyl acetate. The organic layer was concentrated and the residue was purified by chromatography on silica gel to afford methyl 4-[1-hydroxy-1-(1-trityl-1H-pyrazol-4-yl)ethyl]benzoate. MS ESI calc'd. for $C_{32}H_{29}N_2O_3$ [M+H]$^+$ 489. found 489.

Step 3:

TFA (0.1 mL) in DCM (2 mL) were added dropwise to a mixture of methyl 4-[1-hydroxy-1-(1-trityl-1H-pyrazol-4-yl)ethyl]benzoate (0.2 g, 0.8 mmol), triethylsilane (0.2 mL) in DCM (5 mL) cooled to −40° C. Then the mixture was stirred at −40° C. for 2 hours. The mixture was adjusted to pH 7 by adding aqueous sodium bicarbonate solution at −40° C. After the reaction warmed to room temperature, the mixture was extracted with ethyl acetate. The organic layer was concentrated and the residue was purified by preparative thin layer chromatography to afford methyl 4-[1-hydroxy-1-(1H-pyrazol-4-yl)ethyl]benzoate. MS ESI calc'd. for $C_{13}H_{15}N_2O_3$ [M+H]$^+$ 247. found 247. $^1$H NMR (400 MHz, CD₃OD): δ 7.98 (d, J=8.4 Hz, 2H), 7.59 (d, J=8.4 Hz, 2H), 7.50 (s, 2H), 3.90 (s, 3H), 1.89 (s, 3H).

Step 4:

A mixture of methyl 4-[1-hydroxy-1-(1H-pyrazol-4-yl)ethyl]benzoate (17 mg, 0.053 mmol), N-(3-bromo-5-methylphenyl)-4-(trifluoromethyl)pyrimidin-2-amine (13 mg, 0.053 mmol), copper(I) iodide (1 mg, 0.005 mmol), $N^1,N^2$-dimethylethane-1,2-diamine (0.47 mg, 0.005 mmol), and cesium carbonate (52 mg, 0.16 mmol) in 1,4-dioxane (2 mL) was stirred at 130° C. for 50 minutes. After being cooled to room temperature, the mixture was diluted with ethyl acetate and washed with brine. The organic layer was concentrated and the residue was purified by preparative thin layer chromatography to afford methyl 4-{1-hydroxy-1-[1-(3-methyl-5-{[4-(trifluoromethyl)pyrimidin-2-yl]amino}phenyl)-1H-pyrazol-4-yl]ethyl}benzoate. MS ESI calc'd. for $C_{25}H_{23}F_3N_5O_3$ [M+H]$^+$ 498. found 498. $^1$H NMR (400 MHz, CDCl₃): δ 8.66 (s, 1H), 8.02-8.06 (m, 3H), 7.78 (s, 1H), 7.59-7.63 (m, 3H), 7.51 (s, 1H), 7.18 (s, 1H), 7.06 (s, 1H), 3.92 (s, 3H), 3.79 (s, 1H), 3.49 (s, 1H), 2.41 (s, 3H), 1.97 (s, 3H).

Step 5:

Methyl 4-{1-hydroxy-1-[1-(3-methyl-5-{[4-(trifluoromethyl)pyrimidin-2-yl]amino}phenyl)-1H-pyrazol-4-yl]ethyl}benzoate was separated by SFC (Column, Chiralpak AS-H 150*4.6 mm; I.D., 5-40% methanol (0.05% diethylamine) in $CO_2$). to afford methyl 4-{1-hydroxy-1-[1-(3-methyl-5-{[4-(trifluoromethyl)pyrimidin-2-yl]amino}phenyl)-1H-pyrazol-4-yl]ethyl}benzoate (isomer 1, early eluting) and methyl 4-{1-hydroxy-1-[1-(3-methyl-5-{[4-(trifluoromethyl)pyrimidin-2-yl]amino}phenyl)-1H-pyrazol-4-yl]ethyl}benzoate (isomer 2, late eluting):

Step 6:

A mixture of methyl 4-{1-hydroxy-1-[1-(3-methyl-5-{[4-(trifluoromethyl)pyrimidin-2-yl]amino}phenyl)-1H-pyrazol-4-yl]ethyl}benzoate (isomer 1, early eluting) (100 mg, 0.2 mmol) and lithium hydroxide monohydrate (26 mg, 0.6 mmol) in 1,4-dioxane (2 mL) and water (0.5 mL) was stirred at 60° C. for 3 hours. After being cooled to 0° C., the mixture was adjusted to pH 7 with aqueous sodium bicarbonate solution. Then the mixture was extracted with ethyl acetate and washed by brine. The organic layer was concentrated and the residue was purified by reverse phase chromatography to afford 4-{1-hydroxy-1-[1-(3-methyl-5-{[4-(trifluoromethyl)pyrimidin-2-yl]amino}phenyl)-1H-pyrazol-4-yl]ethyl}benzoic acid (Example 19.7). MS ESI calc'd. for $C_{24}H_{21}F_3N_5O_3$ [M+H]$^+$ 484. found 484. $^1$H NMR (400 MHz, DMSO-$d_6$): δ 11.11 (s, 1H), 9.66 (s, 1H), 8.99 (s, 1H), 8.93 (s, 1H), 8.69-8.71 (m, 2H), 8.42-8.44 (m, 2H), 8.24 (s, 1H), 8.10-8.11 (m, 2H), 6.67 (s, 1H), 3.16 (s, 3H), 2.64 (s, 3H).

The procedure for 4-{1-hydroxy-1-[1-(3-methyl-5-{[4-(trifluoromethyl)pyrimidin-2-yl]amino}phenyl)-1H-pyrazol-4-yl]ethyl}benzoic acid (from step 5 as isomer 2, late eluting) was similar to that of 4-{1-hydroxy-1-[1-(3-methyl-5-{[4-(trifluoromethyl)pyrimidin-2-yl]amino}phenyl)-1H-pyrazol-4-yl]ethyl}benzoic acid (Example 19.8, derived from step 5 as isomer 1, late eluting). MS ESI calc'd. for $C_{24}H_{21}F_3N_5O_3$ [M+H]$^+$ 484. found 484. $^1$H NMR (400 MHz, DMSO-$d_6$): δ 10.30 (s, 1H), 8.84 (s, 1H), 8.19 (s, 1H), 8.12 (s, 1H), 7.88-7.90 (m, 2H), 7.61-7.63 (m, 3H), 7.43 (s, 1H), 7.29-7.30 (m, 2H), 5.86 (s, 1H), 2.35 (s, 3H), 1.83 (s, 3H).

The following compounds in Tables 19B and 19C were prepared according to the method described in Example 19.1 or 19.7. Esters were optionally hydrolyzed according to the procedure in Example 19.1, Step 2.

TABLE 19B

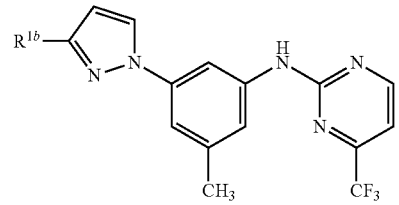

| Ex. No. | R$^{1b}$ | Chemical Name | [M + H]$^+$ Calc'd | [M + H]$^+$ Found | Form |
|---|---|---|---|---|---|
| 19.9 | Cl | N-[3-(3-chloro-1H-pyrazol-1-yl)-5-methylphenyl]-4-(trifluoromethyl)pyrimidin-2-amine | 354.1 | 354 | TFA Salt |

TABLE 19C

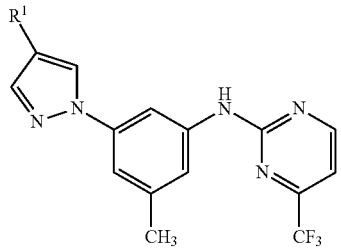

| Ex. No. | R$^1$ | Chemical Name | [M + H]$^+$ Calc'd | [M + H]$^+$ Found | Form |
|---|---|---|---|---|---|
| 19.10 | ![structure] | 4-hydroxy-4-[1-(3-methyl-5-{[4-(trifluoromethyl)pyrimidin-2-yl]amino}phenyl)-1H-pyrazol-4-yl]cyclohexanecarboxylic acid | 462.2 | 462 | Free Base |
| 19.11 | ![structure] | 4-hydroxy-4-[1-(3-methyl-5-{[4-(trifluoromethyl)pyrimidin-2-yl]amino}phenyl)-1H-pyrazol-4-yl]cyclohexanecarboxylic acid | 462.2 | 462 | Free Base |

TABLE 19C-continued

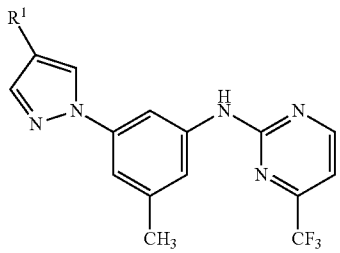

| Ex. No. | R¹ | Chemical Name | [M + H]⁺ Calc'd | [M + H]⁺ Found | Form |
|---|---|---|---|---|---|
| 19.12 | (R or S) cyclohexane with HO, C(CH₃), COOH | trans-4-{1-hydroxy-1-[1-(3 methyl-5-{[4-(trifluoromethyl)pyrimidin-2-yl]amino}phenyl)-1H-pyrazol-4-yl]ethyl}cyclohexanecarboxylic acid | 490.2 | 490 | Free Base |
| 19.13 | (S or R) cyclohexane with HO, C(CH₃), COOH | trans-4-{1-hydroxy-1-[1-(3-methyl-5-{[4-(trifluoromethyl)pyrimidin-2-yl]amino}phenyl)-1H-pyrazol-4-yl]ethyl}cyclohexanecarboxylic acid | 490.2 | 490 | Free Base |
| 19.14 | "R or S, R or S" | 4-hydroxy-2,2-dimethyl-4-[1-(3-methyl-5-{[4-(trifluoromethyl)pyrimidin-2-yl]amino}phenyl)-1H-pyrazol-4-yl]cyclohexanecarboxylic acid | 490.2 | 472 (observed as —H₂O) | Free Base |
| 19.15 | "R or S, S or R" | 4-hydroxy-2,2-dimethyl-4-[1-(3-methyl-5-{[4-(trifluoromethyl)pyrimidin-2-yl]amino}phenyl)-1H-pyrazol-4-yl]cyclohexanecarboxylic acid | 490.2 | 472 (observed as —H₂O) | Free Base |

Example 20.1

(R or S)-3-Hydroxy-3-methyl-4-(4-(4-methyl-6-((4-(trifluoromethyl)pyridin-2-yl)amino)pyridin-2-yl)-1H-pyrazol-1-yl)butanenitrile

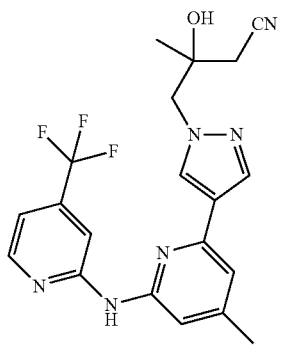 [SMILES: Cc1cc(Nc2cc(C(F)(F)F)ccn2)nc(-c2cnn(CC(C)(O)CC#N)c2)c1]

Step 1:

Sodium hydride (20.7 mg, 0.52 mmol) was added to a solution of 4-methyl-6-(1H-pyrazol-4-yl)-N-(4-(trifluoromethyl)pyridin-2-yl)pyridin-2-amine (150 mg, 0.47 mmol) in DMF (2 mL). The mixture was stirred for ten minutes after which time 2-(chloromethyl)-2-ethyloxirane (150 mg, 1.41 mmol) was added. The mixture was stirred at room temperature for 2 h, water was added, and the mixture was extracted with EtOAc. The organic layer was dried over anhydrous magnesium sulfate, filtered, and concentrated under reduced pressure to afford 4-methyl-6-(1-((2-methyloxiran-2-yl)methyl)-1H-pyrazol-4-yl)-N-(4-(trifluoromethyl)pyridin-2-yl)pyridin-2-amine. MS ESI calc'd. for $C_{19}H_{19}F_3N_5O$ [M+H]$^+$ 390. found 390.

Step 2:

Sodium cyanide (113 mg, 2.3 mmol) was added to 4-methyl-6-(1-((2-methyloxiran-2-yl)methyl)-1H-pyrazol-4-yl)-N-(4-(trifluoromethyl)pyridin-2-yl)pyridin-2-amine (180 mg, 0.46 mmol) in ethanol (5 mL) and water (3 mL), and the mixture was stirred at room temperature for 18 h. The mixture was passed through CELITE, washed with methanol, and concentrated under reduced pressure. The resultant residue was purified by column chromatography on silica gel (0-20% EtOAc/Hexane) to afford 3-hydroxy-3-methyl-4-(4-(4-methyl-6-((4-(trifluoromethyl)pyridin-2-yl)amino)pyridin-2-yl)-1H-pyrazol-1-yl)butanenitrile. The racemic mixture was purified by chiral SFC (Chiralpak column, MeOH+0.25% DMEA) to afford (S or R)-3-hydroxy-3-methyl-4-(4-(4-methyl-6-((4-(trifluoromethyl)pyridin-2-yl)amino)pyridin-2-yl)-1H-pyrazol-1-yl)butanenitrile (Isomer 1, first eluting): MS ESI calc'd. for $C_{20}H_{20}F_3N_6O$ [M+H]$^+$ 417. found 417. $^1$H NMR (500 MHz, DMSO-d$_6$) δ 10.07 (s, 1H), 8.61 (s, 1H), 8.46 (d, J=5 Hz, 1H), 8.15 (s, 1H), 7.96 (s, 1H), 7.17 (d, J=5 Hz, 1H), 7.11 (s, 1H), 7.02 (s, 1H), 5.55 (s, 1H), 4.15 (s, 2H), 2.71-2.64 (m, 2H), 2.28 (s, 3H), 1.18 (s, 3H).

The following compounds in Table 20 were prepared according to the method described for Example 20.1.

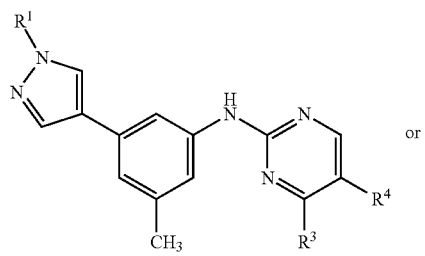

Ie(1)

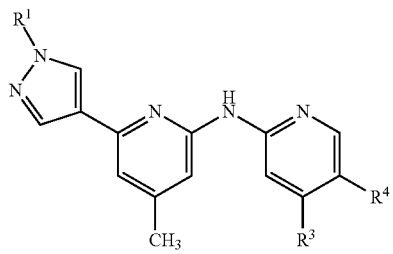

Ie(2)

| Ex. No. | R$^1$ Substructure | R$^3$ | R$^4$ | Chemical Name | [M + H]$^+$ Calc'd | [M + H]$^+$ Found | Form(s) |
|---|---|---|---|---|---|---|---|
| 20.2 | ![structure] single stereoisomer, early eluting Ie(1) | CF$_3$ | H | 3-hydroxy-3-methyl-4-[4-(3-methyl-5-{[4-(trifluoromethyl)pyrimidin-2-yl]amino}phenyl)-1H-pyrazol-1-yl]butanenitrile | 417.2 | 417 | Free Base |

-continued

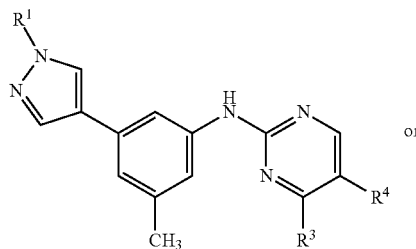

Ie(1)

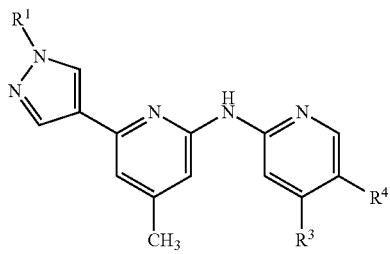

Ie(2)

| Ex. No. | R¹ Substructure | R³ | R⁴ | Chemical Name | [M + H]⁺ Calc'd | [M + H]⁺ Found | Form(s) |
|---|---|---|---|---|---|---|---|
| 20.3 | (CH3)-CH2-) single stereoisomer, late eluting Ie(1) | $CF_3$ | H | 3-hydroxy-3-methyl-4-[4-(3-methyl-5-{[4-(trifluoromethyl)pyrimidin-2-yl]amino}phenyl)-1H-pyrazol-1-yl]butanenitrile | 417.2 | 417 | Free Base |
| 20.4 | (CH3)-CH2-) single stereoisomer, early eluting Ie(2) | $CF_3$ | H | 3-hydroxy-3-methyl-4-[4-(4-methyl-6-{[4-(trifluoromethyl)pyridin-2-yl]amino}pyridin-2-yl)-1H-pyrazol-1-yl]butanenitrile | 417.2 | 417 | Free Base |
| 20.5 | (CH3)-CH2-) single siomer, early eluting Ie(1) | $C(H)F_2$ | F | 4-[4-(3-{[4-(difluoromethyl)-5-fluoropyrimidin-2-yl]amino}-5-methylphenyl)-1H-pyrazol-1-yl]-3-hydroxy-3-methylbutanenitrile | 417.2 | 417 | Free Base |
| 20.6 | (CH3)-CH2-) single isomer, late eluting Ie(1) | $C(H)F_2$ | F | 4-[4-(3-{[4-(difluoromethyl)-5-fluoropyrimidin-2-yl]amino}-5-methylphenyl)-1H-pyrazol-1-yl]-3-hydroxy-3-methylbutanenitrile | 417.2 | 417 | Free Base |
| 20.7 | (CH3)-CH2-) single isomer, early eluting Ie(1) | $C(H)F_2$ | H | 4-[4-(3-{[4-(difluoromethyl)pyrimidin-2-yl]amino}-5-methylphenyl)-1H-pyrazol-1-yl]-3-hydroxy-3-methylbutanenitrile | 399.2 | 399 | Free Base |

-continued

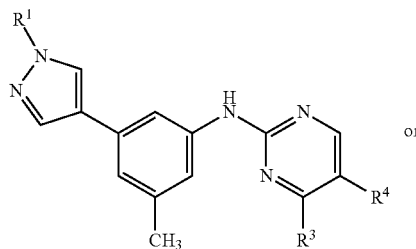

Ie(1)

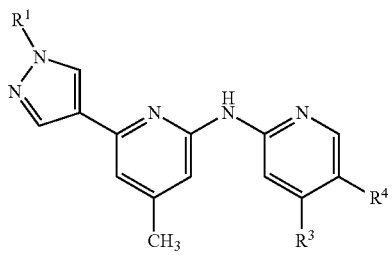

Ie(2)

| Ex. No. | R¹ Substructure | R³ | R⁴ | Chemical Name | [M + H]⁺ Calc'd | [M + H]⁺ Found | Form(s) |
|---|---|---|---|---|---|---|---|
| 20.8 | (N≡C-CH₂-C(OH)(CH₃)-CH₂-) single isomer, late eluting Ie(1) | C(H)F₂ | H | 4-[4-(3-{[4-(difluoromethyl)pyrimidin-2-yl]amino}-5-methylphenyl)-1H-pyrazol-1-yl]-3-hydroxy-3-methylbutanenitrile | 399.2 | 399 | Free Base |
| 20.9 | (N≡C-CH₂-C(OH)(CH₃)-CH₂-) single isomer, early eluting Ie(1) | C(H)(F₂)CH₃ | H | 4-[4-(3-{[4-(1,1-difluoroethyl)pyrimidin-2-yl]amino}-5-methylphenyl)-1H-pyrazol-1-yl]-3-hydroxy-3-methylbutanenitrile | 413.2 | 413 | Free Base |
| 20.10 | (N≡C-CH₂-C(OH)(CH₃)-CH₂-) single isomer, late eluting Ie(1) | C(H)(F₂)CH₃ | H | 4-[4-(3-{[4-(1,1-difluoroethyl)pyrimidin-2-yl]amino}-5-methylphenyl)-1H-pyrazol-1-yl]-3-hydroxy-3-methylbutanenitrile | 413.2 | 413 | Free Base |

Example 21.1 and 21.2

2-Methyl-3-(4-(3-methyl-5-((4-(trifluoromethyl)pyrimidin-2-yl)amino)phenyl)-1H-pyrazol-1-yl)propane-1,2-diol

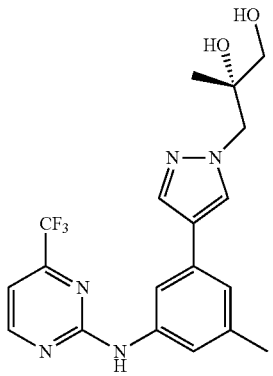 [SMILES: Cc1cc(Nc2nccc(C(F)(F)F)n2)cc(-c2cnn(C[C@](C)(O)CO)c2)c1]

Step 1:

N-(3-Methyl-5-(1H-pyrazol-4-yl)phenyl)-4-(trifluoromethyl)pyrimidin-2-amine (34 mg, 0.11 mmol), 3-bromo-2-methylprop-1-ene (11 µl, 0.11 mmol), cesium carbonate (69 mg, 0.21 mmol) and DMA (210 µL) were combined in a vial and stirred at 100° C. for 1.25 hours. The reaction mixture was diluted with EtOAc, washed with aqueous sodium bicarbonate, then brine, dried over anhydrous sodium sulfate, filtered and concentrated under reduced pressure to afford crude N-(3-methyl-5-(1-(2-methylallyl)-1H-pyrazol-4-yl)phenyl)-4-(trifluoromethyl)pyrimidin-2-amine as a yellow oil. MS ESI calcd. for $C_{19}H_{19}F_3N_5$ $[M+H]^+$ 374. found 374.

Step 2:

Osmium tetroxide (290 µl, 0.04 mmol) was added to a flask containing N-(3-methyl-5-(1-(2-methylallyl)-1H-pyrazol-4-yl)phenyl)-4-(trifluoromethyl)pyrimidin-2-amine (56 mg, 0.15 mmol), N-methylmorpholine N-oxide (26.4 mg, 0.225 mmol), THF (1000 µL) and water (500 µL). The reaction mixture was stirred at room temperature for 3.5 hours. Silica was added and the mixture concentrated under reduced pressure. The residue was purified by column chromatography on silica (0-10% MeOH/DCM) and concentrated under reduced pressure. The racemic mixture was purified by chiral SFC (IA column, 40% MeOH with 0.25% DMEA/$CO_2$) to afford 2-methyl-3-(4-(3-methyl-5-((4-(trifluoromethyl)pyrimidin-2-yl)amino)phenyl)-1H-pyrazol-1-yl)propane-1,2-diol (Example 21.1, Isomer 1, early eluting): MS ESI calcd. for $C_{19}H_{21}F_3N_5O_2$ $[M+H]^+$ 408. found 408, $^1$H NMR δ ppm (DMSO-$d_6$): 10.11 (1H, s), 8.80 (1H, d, J=4.88 Hz), 7.95 (1H, s), 7.81 (1H, s), 7.73 (1H, s), 7.33 (1H, s), 7.24 (1H, d, J=4.88 Hz), 7.05 (1H, s), 4.80 (1H, t, J=5.61 Hz), 4.67 (1H, s), 4.11 (1H, d, J=13.94 Hz), 4.05 (1H, d, J=13.90 Hz), 3.18-3.20 (2H, m), 2.29 (3H, s), 0.95 (3H, s), and 2-methyl-3-(4-(3-methyl-5-((4-(trifluoromethyl)pyrimidin-2-yl)amino)phenyl)-1H-pyrazol-1-yl)propane-1,2-diol (Example 21.2, Isomer 2, late eluting): MS ESI calcd. for $C_{19}H_{21}F_3N_5O_2$ $[M+H]^+$ 408. found 408, $^1$H NMR δ ppm (DMSO-$d_6$): 10.11 (1H, s), 8.80 (1H, d, J=4.88 Hz), 7.95 (1H, s), 7.81 (1H, s), 7.73 (1H, s), 7.33 (1H, s), 7.24 (1H, d, J=4.88 Hz), 7.05 (1H, s), 4.80 (1H, t, J=5.61 Hz), 4.67 (1H, s), 4.11 (1H, d, J=13.94 Hz), 4.05 (1H, d, J=13.90 Hz), 3.18-3.20 (2H, m), 2.29 (3H, s), 0.95 (3H, s).

The following compounds in Table 21A were prepared according to the method described for Examples 21.1 and 21.2.

TABLE 21A

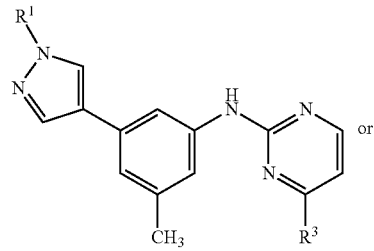

Ie(1)

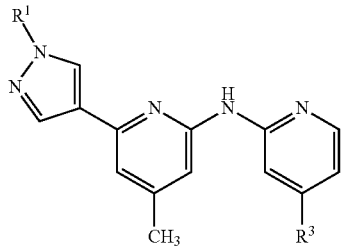

Ie(2)

| Ex. No. | R$^1$ Substructure | R$^3$ | Chemical Name | [M + H]$^+$ Calc'd | [M + H]$^+$ Found | Form |
|---|---|---|---|---|---|---|
| 21.3 | ![structure] single isomer, late eluting Ie(1) | C(H)F$_2$ | 3-[4-(3-{[4-(difluoromethyl)pyrimidin-2-yl]amino}-5-methylphenyl)-1H-pyrazol-1-yl]butan-2-one | 372.2 | 372 | Free Base |

TABLE 21A-continued

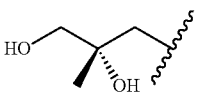

Ie(1)

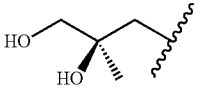

Ie(2)

| Ex. No. | R¹ Substructure | R³ | Chemical Name | [M + H]⁺ Calc'd | [M + H]⁺ Found | Form |
|---|---|---|---|---|---|---|
| 21.4 | <br>single stereoisomer,<br>early eluting<br>Ie(2) | CF₃ | 2-methyl-3-[4-(4-methyl-6-{[4-(trifluoromethyl)pyridin-2-yl]amino}pyridin-2-yl)-1H-pyrazol-1-yl]propane-1,2-diol | 408.2 | 408 | Free Base |
| 21.5 | <br>single stereoisomer,<br>late eluting<br>Ie(2) | CF₃ | 2-methyl-3-[4-(4-methyl-6-{[4-(trifluoromethyl)pyridin-2-yl]amino}pyridin-2-yl)-1H-pyrazol-1-yl]propane-1,2-diol | 408.2 | 408 | Free Base |
| 21.6 | <br>single stereoisomer,<br>early eluting<br>Ie(1) | C(H)F₂ | 1-[4-(3-{[4-(difluoromethyl)pyrimidin-2-yl]amino}-5-methylphenyl)-1H-pyrazol-1-yl]-2,3-dimethylbutane-2,3-diol | 418.2 | 418 | TFA Salt |
| 21.7 | <br>single stereoisomer,<br>late eluting<br>Ie(1) | C(H)F₂ | 1-[4-(3-{[4-(difluoromethyl)pyrimidin-2-yl]amino}-5-methylphenyl)-1H-pyrazol-1-yl]-2,3-dimethylbutane-2,3-diol | 418.2 | 418 | TFA Salt |

The following compounds in Table 21B were prepared according to the method described for Examples 21.1 and 21.2, Step 2.

TABLE 21B

[Structure: R1-N-pyrazole connected to phenyl (with CH3) - NH - pyrimidine-CF3]

| Ex. No. | R¹ | Chemical Name | [M + H]⁺ Calc'd | [M + H]⁺ Found | Form |
|---|---|---|---|---|---|
| 21.8 | HO-CH2-C(CH3)(OH)-CH(CH3)-~ (single isomer, peak 1 of 4) | 2-methyl-3-[4-(3-methyl-5-{[4-(trifluoromethyl)pyrimidin-2-yl]amino}phenyl)-1H-pyrazol-1-yl]butane-1,2-diol | 422.2 | 422 | Free Base |
| 21.9 | HO-CH2-C(CH3)(OH)-CH(CH3)-~ (single isomer, peak 3 of 4) | 2-methyl-3-[4-(3-methyl-5-{[4-(trifluoromethyl)pyrimidin-2-yl]amino}phenyl)-1H-pyrazol-1-yl]butane-1,2-diol | 422.2 | 422 | Free Base |
| 21.10 | HO-CH2-C(CH3)(OH)-CH(CH3)-~ (single isomer, peak 2 of 4) | 2-methyl-3-[4-(3-methyl-5-{[4-(trifluoromethyl)pyrimidin-2-yl]amino}phenyl)-1H-pyrazol-1-yl]butane-1,2-diol | 422.2 | 422 | Free Base |
| 21.11 | HO-CH2-C(CH3)(OH)-CH(CH3)-~ (single isomer, peak 4 of 4) | 2-methyl-3-[4-(3-methyl-5-{[4-(trifluoromethyl)pyrimidin-2-yl]amino}phenyl)-1H-pyrazol-1-yl]butane-1,2-diol | 422.2 | 422 | Free Base |

Example 22.1 and 22.2

3-(4-(3-((4-(Difluoromethyl)pyrimidin-2-yl)amino)-5-methylphenyl)-1H-pyrazol-1-yl)-2-methylbutane-1,2-diol

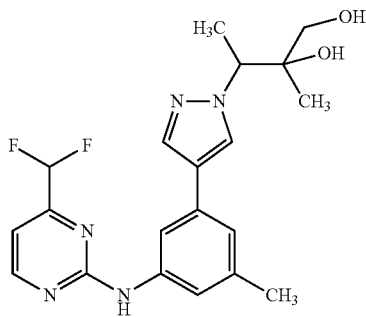 [SMILES: Cc1cc(Nc2nccc(C(F)F)n2)cc(-c2cnn(C(C)C(C)(O)CO)c2)c1]

Step 1:

4-(Difluoromethyl)-N-(3-methyl-5-(4,4,5,5-tetramethyl-1,3,2-dioxaborolan-2-yl)phenyl)pyrimidin-2-amine (400 mg, 1.11 mmol) and 4-bromo-1-(3-methylbut-3-en-2-yl)-1H-pyrazole (238 mg, 1.11 mmol) were dissolved in dioxane (4 ml) and degassed with nitrogen for 5 minutes. PdCl$_2$(dppf)-CH$_2$Cl$_2$ (90 mg, 0.11 mmol) and sodium carbonate (2.0 M in water, 1.1 ml, 2.2 mmol) were added and the reaction was sealed and heated to 90° C. for 12 hours. The reaction was cooled, diluted with water (10 mL), and the product was extracted with ethyl acetate (2×20 mL). The extracts were dried over anhydrous magnesium sulfate, filtered, and concentrated under reduced pressure to afford the crude product residue. The crude product residue was purified by column chromatography on silica two times utilizing (10-50% ethyl acetate/hexanes) and (0-5% acetone/dichloromethane) to afford 4-(difluoromethyl)-N-(3-methyl-5-(1-(3-methylbut-3-en-2-yl)-1H-pyrazol-4-yl)phenyl)pyrimidin-2-amine. MS ESI calcd. for C$_{20}$H$_{22}$F$_2$N$_5$ [M+H]⁺ 370. found 370.

Step 2:

Osmium tetroxide (4% solution in water, 1.06 ml, 0.14 mmol) was added to a flask containing 4-(difluoromethyl)-N-(3-methyl-5-(1-(3-methylbut-3-en-2-yl)-1H-pyrazol-4-yl)phenyl)pyrimidin-2-amine (200 mg, 0.54 mmol), N-methylmorpholine N-oxide (127 mg, 1.08 mmol), THF (2.5 ml) and water (1.25 ml) was. The reaction mixture was allowed to stir at room temperature for 3 hrs. The reaction was diluted with brine and reaction product extracted with ethyl acetate (2×20 mL), dried over anhydrous sodium sulfate, filtered and concentrated under reduced pressure. The residue was purified by column chromatography on silica (20-100% ethyl acetate/hexanes) to afford racemic 3-(4-(3-((4-(difluoromethyl)pyrimidin-2-yl)amino)-5-methylphenyl)-1H-pyrazol-1-yl)-2-methylbutane-1,2-diol. The racemic mixture was purified by chiral SFC (Phenomenex Lux-4, 21×250 mm, 70 mL/min, 20% Methanol/$CO_2$) to afford 3-(4-(3-((4-(difluoromethyl)pyrimidin-2-yl)amino)-5-methylphenyl)-1H-pyrazol-1-yl)-2-methylbutane-1,2-diol. (Example 22.1, Isomer 1, first eluting): MS ESI calcd. for $C_{20}H_{24}F_2N_5O_2$ [M+H]+ 404. found 404. $^1$H NMR (500 MHz, $DMSO_{d-6}$) δ 9.87 (s, 1H), 8.68 (d, J=5.0 Hz, 1H), 7.99 (s, 1H), 7.85 (s, 1H), 7.75 (s, 1H), 7.35 (s, 1H), 7.04 (m, 2H), 6.86 (t, J=54.5 Hz, 1H), 4.65 (t, J=4.5 Hz, 1H), 4.62 (s, 1H), 4.43 (q, J=6.5 Hz, 1H), 3.08 (m, 2H), 2.28 (s, 3H), 1.43 (d, J=6.5 Hz, 3H), 1.03 (s, 3H); and 3-(4-(3-((4-(difluoromethyl)pyrimidin-2-yl)amino)-5-methylphenyl)-1H-pyrazol-1-yl)-2-methylbutane-1,2-diol. (Example 22.2, Isomer 2, second eluting): MS ESI calcd. for $C_{20}H_{24}F_2N_5O_2$ [M+H]+ 404. found 404. $^1$H NMR (500 MHz, $DMSO_{d-6}$) δ 9.85 (s, 1H), 8.66 (d, J=4.0 Hz, 1H), 7.97 (s, 1H), 7.82 (s, 1H), 7.72 (s, 1H), 7.32 (s, 1H), 7.06-7.02 (m, 2H), 6.84 (t, J=45.5 Hz, 1H), 4.62 (t, J=4.5 Hz, 1H), 4.53 (s, 1H), 4.39 (q, J=6.5 Hz, 1H), 3.10-3.06 (m, 2H), 2.26 (s, 3H), 1.41 (d, J=6.5 Hz, 3H), 1.00 (s, 3H).

The following compounds in Table 22 were prepared according to the method described for Example 22.1

TABLE 22

| Ex. No. | R$^1$ | R$^3$ | Chemical Name | [M + H]+ Calc'd | [M + H]+ Found | Form |
|---|---|---|---|---|---|---|
| 22.3 | (single stereoisomer, peak 4) | C(H)F$_2$ | 3-[4-(3-{[4-(difluoromethyl)pyrimidin-2-yl]amino}-5-methylphenyl)-1H-pyrazol-1-yl]-2-methylbutane-1,2-diol | 404.2 | 404 | Free Base |
| 22.4 | (single stereoisomer, early eluting) | C(H)(F$_2$)CH$_3$ | 1-[4-(3-{[4-(1,1-difluoroethyl)pyrimidin-2-yl]amino}-5-methylphenyl)-1H-pyrazol-1-yl]-2,3-dimethylbutane-2,3-diol | 432.2 | 432 | Free Base |
| 22.5 | (single stereoisomer, late eluting) | C(H)(F$_2$)CH$_3$ | 1-[4-(3-{[4-(1,1-difluoroethyl)pyrimidin-2-yl]amino}-5-methylphenyl)-1H-pyrazol-1-yl]-2,3-dimethylbutane-2,3-diol | 432.2 | 432 | Free Base |
| 22.6 | ("racemic, mixture of 4 isomers") | C(H)F$_2$ | 3-[4-(3-{[4-(difluoromethyl)pyrimidin-2-yl]amino}-5-methylphenyl)-1H-pyrazol-1-yl]-1-methylcyclohexane-1,2-diol | 430.2 | 430 | TFA Salt |

TABLE 22-continued

| Ex. No. | R¹ | R³ | Chemical Name | [M + H]⁺ Calc'd | [M + H]⁺ Found | Form |
|---|---|---|---|---|---|---|
| 22.7 | (dimethyl cyclohexane diol group) "racemic, mixture of 4 isomers" | C(H)F₂ | 6-[4-(3-{[4-(difluoromethyl)pyrimidin-2-yl]amino}-5-methylphenyl)-1H-pyrazol-1-yl]-3,3-dimethylcyclohexane-1,2-diol | 444.2 | 444 | TFA Salt |
| 22.8 | (trimethyl cyclohexane diol group) "racemic, mixture of 4 isomers" | C(H)F₂ | 6-[4-(3-{[4-(difluoromethyl)pyrimidin-2-yl]amino}-5-methylphenyl)-1H-pyrazol-1-yl]-1,3,3-trimethylcyclohexane-1,2-diol | 458.2 | 458 | TFA Salt |
| 22.9 | (trimethyl cyclohexane diol group) mixture of 2 enantiomers | C(H)F₂ | 3-[4-(3-{[4-(difluoromethyl)pyrimidin-2-yl]amino}-5-methylphenyl)-1H-pyrazol-1-yl]-1,5,5-trimethylcyclohexane-1,2-diol | 458.2 | 458 | TFA Salt |
| 22.10 | (trimethyl cyclohexane diol group) mixture of 2 enantiomers | C(H)F₂ | 3-[3-{[4-(difluoromethyl)pyrimidin-2-yl]amino}-5-methylphenyl)-1H-pyrazol-1-yl]-1,5,5-trimethylcyclohexane-1,2-diol | 458.2 | 458 | TFA Salt |
| 22.11 | (dimethyl cyclohexane diol group) single enantiomer, peak 3 of 4 | C(H)F₂ | 3-[4-(3-{[4-(difluoromethyl)pyrimidin-2-yl]amino}-5-methylphenyl)-1H-pyrazol-1-yl]-1,2-dimethylcyclohexane-1,2-diol | 444.2 | 444 | Free Base |

TABLE 22-continued

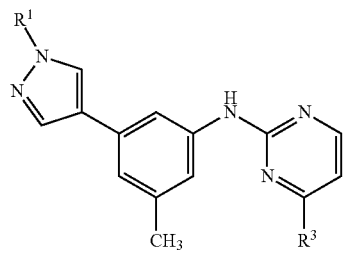

| Ex. No. | R¹ | R³ | Chemical Name | [M + H]⁺ Calc'd | [M + H]⁺ Found | Form |
|---|---|---|---|---|---|---|
| 22.12 | (structure: 1,2-dimethyl-1,2-dihydroxycyclohexane) single enantiomer, peak 4 of 4 | C(H)F₂ | 3-[4-(3-{[4-(difluoromethyl)pyrimidin-2-yl]amino}-5-methylphenyl)-1H-pyrazol-1-yl]-1,2-dimethylcyclohexane-1,2-diol | 444.2 | 444 | Free Base |
| 22.13 | (structure: 1-methyl-1,2-dihydroxycyclopentane) single stereoisomer, early eluting | C(H)F₂ | 5-[4-(3-{[4-(difluoromethyl)pyrimidin-2-yl]amino}-5-methylphenyl)-1H-pyrazol-1-yl]-1-methylcyclopentane-1,2-diol | 416.2 | 416 | Free Base |
| 22.14 | (structure: 1-methyl-1,2-dihydroxycyclopentane) single stereoisomer, late eluting | C(H)F₂ | 5-[4-(3-{[4-(difluoromethyl)pyrimidin-2-yl]amino}-5-methylphenyl)-1H-pyrazol-1-yl]-1-methylcyclopentane-1,2-diol | 416.2 | 416 | Free Base |
| 22.15 | (structure: 1,2-dihydroxycycloheptane) racemic | C(H)F₂ | 3-[4-(3-{[4-(difluoromethyl)pyrimidin-2-yl]amino}-5-methylphenyl)-1H-pyrazol-1-yl]cycloheptane-1,2-diol | 430.2 | 430 | Free Base |

Example 23.1

(4S,5S)-4-Methyl-5-((4-(3-methyl-5-((4-(trifluoromethyl)pyrimidin-2-yl)amino)phenyl)-1H-pyrazol-1-yl)methyl)oxazolidin-2-one

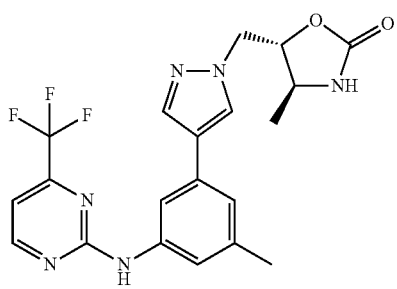 [SMILES: Cc1cc(Nc2nccc(C(F)(F)F)n2)cc(-c2cnn(C[C@@H]3OC(=O)N[C@H]3C)c2)c1]

Sodium hydride (60% dispersion in mineral oil, 28 mg, 0.71 mmol) was added to a mixture of N-(3-methyl-5-(1H-pyrazol-4-yl)phenyl)-4-(trifluoromethyl)pyrimidin-2-amine (150 mg, 0.47 mmol) in DMF (3 mL), and the mixture was stirred for 5 minutes. A mixture of tert-butyl ((2S)-4-chloro-3-hydroxybutan-2-yl)carbamate (110 mg, 0.49 mmol) in DMF (2 mL) was added and the mixture was heated to 40° C. for 4 hours. The mixture was then allowed to cool to room temperature and diluted with ethyl acetate and water. The organic layer was separated, dried over anhydrous magnesium sulfate, filtered and concentrated under reduced pressure. The crude residue was then purified by column chromatography on silica gel. The purified diastereomeric mixture was separated by chiral SFC (Chiralpak ID, 21×250 (mm), 25% $CO_2$ with methanol as the diluent) to afford (4S,5S)-4-methyl-5-((4-(3-methyl-5-((4-(trifluoromethyl)pyrimidin-2-yl)amino)phenyl)-1H-pyrazol-1-yl)methyl)oxazolidin-2-one (Isomer 1, early eluting): MS ESI calc'd. for $C_{20}H_{20}F_3N_6O_2$ $[M+H]^+$ 433. found 433. $^1$H NMR (500 MHz, DMSO-$d_6$) δ 10.12 (s, 1H), 8.80 (d, J=4.3 Hz, 1H), 8.06 (s, 1H), 7.85-7.76 (m, 2H), 7.73 (s, 1H), 7.35 (s, 1H), 7.24 (d, J=4.6 Hz, 1H), 7.06 (s, 1H), 4.47-4.35 (m, 3H), 3.75-3.59 (m, 1H), 2.29 (s, 3H), 1.10 (d, J=5.8 Hz, 3H).

The following compounds in Tables 23A and 23B were prepared according to the method described for Example 23.1.

TABLE 23A

| Ex. No. | $R^1$ | $R^3$ | Chemical Name | $[M+H]^+$ Calc'd | $[M+H]^+$ Found | Form |
|---|---|---|---|---|---|---|
| 23.2 | (single isomer, late eluting) | $CF_3$ | 4-methyl-5-{[4-(3-methyl-5-{[4-(trifluoromethyl)pyrimidin-2-yl]amino}phenyl)-1H-pyrazol-1-yl]methyl}-1,3-oxazolidin-2-one | 433.2 | 433 | Free Base |
| 23.3 | (single isomer, early eluting) | $CF_3$ | 4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one | 461.2 | 461 | Free Base |
| 23.4 | (single isomer, late eluting) | $CF_3$ | 4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one | 461.2 | 461 | Free Base |

TABLE 23A-continued

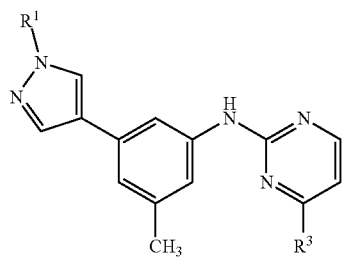

| Ex. No. | R¹ | R³ | Chemical Name | [M + H]⁺ Calc'd | [M + H]⁺ Found | Form |
|---|---|---|---|---|---|---|
| 23.5 | (oxazolidinone with isopropyl) single isomer, late eluting | CF₃ | 4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one | 461.2 | 461 | Free Base |
| 23.6 | (oxazolidinone with isopropyl) single isomer, early eluting | CF₃ | 4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one | 461.2 | 461 | Free Base |
| 23.7 | (oxazolidinone with methyl) single isomer, early eluting | CH₃ | 4-methyl-5-[(4-{3-methyl-5-[(4-methylpyrimidin-2-yl)amino]phenyl}-1H-pyrazol-1-yl)methyl]-1,3-oxazolidin-2-one | 379.2 | 379 | Free Base |
| 23.8 | (oxazolidinone with methyl) single isomer, late eluting | CH₃ | 4-methyl-5-[(4-{3-methyl-5-[(4-methylpyrimidin-2-yl)amino]phenyl}-1H-pyrazol-1-yl)methyl]-1,3-oxazolidin-2-one | 379.2 | 379 | Free Base |
| 23.9 | (oxazolidinone with methyl) single isomer, ealy eluting | C(H)F₂ | 5-{[4-(3-{[4-(difluoromethyl)pyrimidin-2-yl]amino}-5-methylphenyl)-1H-pyrazol-1-yl]methyl}-4-methyl-1,3-oxazolidin-2-one | 415.2 | 415 | Free Base |
| 23.10 | (oxazolidinone with methyl) single isomer, late eluting | C(H)F₂ | 5-{[4-(3-{[4-(difluoromethyl)pyrimidin-2-yl]amino}-5-methylphenyl)-1H-pyrazol-1-yl]methyl}-4-methyl-1,3-oxazolidin-2-one | 415.2 | 415 | Free Base |

TABLE 23A-continued

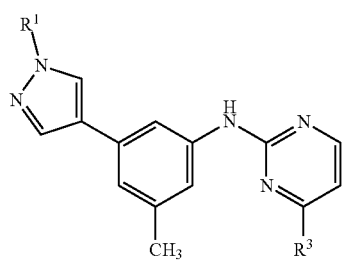

| Ex. No. | R[1] | R[3] | Chemical Name | $[M+H]^+$ Calc'd | $[M+H]^+$ Found | Form |
|---|---|---|---|---|---|---|
| 23.11 | (oxazolidinone with methyl, single isomer, early eluting) | C(H)(F$_2$)CH$_3$ | 5-{[4-(3-{[4-(1,1-difluoromethyl)pyrimidin-2-yl]amino}-5-methylphenyl)-1H-pyrazol-1-yl]methyl}-4-methyl-1,3-oxazolidin-2-one | 429.2 | 429 | Free Base |
| 23.12 | (oxazolidinone with methyl, single isomer, late eluting) | C(H)(F$_2$)CH$_3$ | 5-{[4-(3-{[4-(1,1-difluoroethyl)pyrimidin-2-yl]amino}-5-methylphenyl)-1H-pyrazol-1-yl]methyl}-4-methyl-1,3-oxazolidin-2-one | 429.2 | 429 | Free Base |
| 23.13 | (oxazolidinone with methyl, single isomer, early eluting) | C(H)F$_2$ | 5-{[4-(3-{[4-(difluoromethyl)pyrimidin-2-yl]amino}-5-methylphenyl)-1H-pyrazol-1-yl]methyl}-4-methyl-1,3-oxazolidin-2-one | 415.2 | 415 | Free Base |
| 23.14 | (oxazolidinone with methyl, single isomer, late eluting) | C(H)F$_2$ | 5-{[4-(3-{[4-(difluoromethyl)pyrimidin-2-yl]amino}-5-methylphenyl)-1H-pyrazol-1-yl]methyl}-4-methyl-1,3-oxazolidin-2-one | 415.2 | 415 | Free Base |
| 23.15 | (oxazolidinone with isopropyl, single isomer, early eluting) | CH$_3$ | 4-(1-methylethyl)-5-[(4-{3-methyl-5-[(4-methylpyrimidin-2-yl)amino]phenyl}-1H-pyrazol-1-yl)methyl]-1,3-oxazolidin-2-one | 407.2 | 407 | Free Base |

TABLE 23A-continued

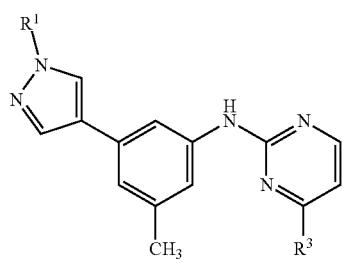

| Ex. No. | R¹ | R³ | Chemical Name | [M + H]⁺ Calc'd | [M + H]⁺ Found | Form |
|---|---|---|---|---|---|---|
| 23.16 single isomer, late eluting | (4-isopropyl oxazolidinone) | CH₃ | 4-(1-methylethyl)-5-[(4-{3-methyl-5-[(4-methylpyrimidin-2-yl)amino]phenyl}-1H-pyrazol-1-yl)methyl]-1,3-oxazolidin-2-one | 407.2 | 407 | Free Base |
| 23.17 mixture of isomers | (4-cyclopropyl oxazolidinone) | C(H)F₂ | 4-cyclopropyl-5-{[4-(3-{[4-(difluoromethyl)pyrimidin-2-yl]amino}-5-methylphenyl)-1H-pyrazol-1-yl]methyl}-1,3-oxazolidin-2-one | 441.2 | 441 | Free Base |
| 23.18 single isomer, early eluting | (4-cyclopropyl oxazolidinone) | C(H)F₂ | 4-cyclopropyl-5-{[4-(3-{[4-(difluoromethyl)pyrimidin-2-yl]amino}-5-methylphenyl)-1H-pyrazol-1-yl]methyl}-1,3-oxazolidin-2-one | 441.2 | 441 | Free Base |
| 23.19 single isomer, late eluting | (4-cyclopropyl oxazolidinone) | C(H)F₂ | 4-cyclopropyl-5-{[4-(3-{[4-(difluoromethyl)pyrimidin-2-yl]amino}-5-methylphenyl)-1H-pyrazol-1-yl]methyl}-1,3-oxazolidin-2-one | 441.2 | 441 | Free Base |

TABLE 23B

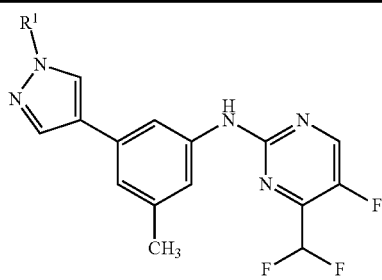

| Ex. No. | R¹ | Chemical Name | [M + H]⁺ Calc'd | [M + H]⁺ Found | Form |
|---|---|---|---|---|---|
| 23.20 | ![HN-oxazolidinone, single isomer, early eluting] | 5-{[4-(3-{[4-(difluoromethyl)-5-fluoropyrimidin-2-yl]amino}-5-methylphenyl)-1H-pyrazol-1-yl]methyl}-4-methyl-1,3-oxazolidin-2-one | 433.2 | 433 | Free Base |
| 23.21 | ![HN-oxazolidinone, single isomer, late eluting] | 5-{[4-(3-{[4-(difluoromethyl)-5-fluoropyrimidin-2-yl]amino}-5-methylphenyl)-1H-pyrazol-1-yl]methyl}-4-methyl-1,3-oxazolidin-2-one | 433.2 | 433 | Free Base |

Examples 24.1 and 24.2

(R and S) 3-(4-(3-((4-(Difluoromethyl)pyrimidin-2-yl)amino)-5-methylphenyl)-1H-pyrazol-1-yl)-1,1,1-trifluoro-2-methylpropan-2-ol

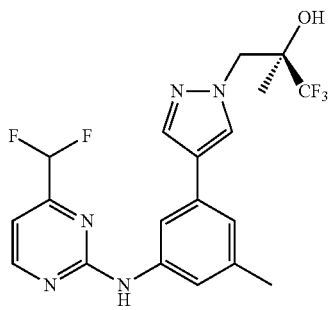

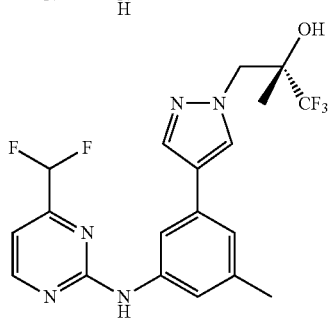

Step 1:

4-(Difluoromethyl)-N-(3-methyl-5-(4,4,5,5-tetramethyl-1,3,2-dioxaborolan-2-yl)phenyl)pyrimidin-2-amine (400 mg, 1.11 mmol) and 1-(4-bromo-1H-pyrazol-1-yl)propan-2-one (225 mg, 1.11 mmol) were dissolved in dioxane (4 mL) and degassed with nitrogen for 5 minutes. $PdCl_2(dppf)\cdot CH_2Cl_2$ (90 mg, 0.11 mmol) and sodium carbonate (2.0 M in water, 1.107 ml, 2.215 mmol) were added, the reaction was sealed and heated to 90° C. for 12 hours. The reaction was cooled to ambient temperature, diluted with water (10 mL) and product extracted with ethyl acetate (2×20 mL). The extracts were dried over anhydrous magnesium sulfate, filtered, and concentrated under reduced pressure to afford the crude product residue. The crude product residue was purified by column chromatography on silica (5-50% ethyl acetate/hexanes) to afford 1-(4-(3-((4-(difluoromethyl)pyrimidin-2-yl)amino)-5-methylphenyl)-1H-pyrazol-1-yl)propan-2-one. MS ESI calcd. for $C_{18}H_{18}F_2N_5O$ [M+H]⁺ 358. found 358.

Step 2:

(Trifluoromethyl)trimethylsilane (0.103 ml, 0.70 mmol) was added to a 20° C. solution of 1-(4-(3-((4-(difluoromethyl)pyrimidin-2-yl)amino)-5-methylphenyl)-1H-pyrazol-1-yl)propan-2-one (100 mg, 0.28 mmol) and cesium fluoride (4.3 mg, 0.028 mmol) in THF (1 mL). The reaction was allowed to stir for 60 minutes at room temperature and additional cesium fluoride (4.25 mg, 0.03 mmol) and (trifluoromethyl)trimethylsilane (0.103 ml, 0.70 mmol) were then added. The reaction was stirred for 18 hours and filtered through a plug of glass wool. The filtrate was treated with hydrochloric acid (6N, 1 mL, 6 mmol) and stirred for 30 minutes. The reaction was concentrated under reduced pressure to afford the crude product residue. The crude product residue was dissolved in DMSO/water and purified by mass triggered reverse phase HPLC (ACN/water+0.1% TFA) to afford racemic 3-(4-(3-((4-(difluoromethyl)pyrimidin-2-yl)amino)-5-methylphenyl)-1H-pyrazol-1-yl)-1,1,1-trifluoro-2-methylpropan-2-ol. MS ESI calcd. for $C_{19}H_{19}F_5N_5O$ [M+H]$^+$ 428. found 428. The racemic mixture was purified by chiral SFC (Chiralpak, IA, 21×250 (mm), 70 mL/min, 25% Methanol/CO$_2$) to afford (S or R)-3-(4-(3-((4-(difluoromethyl)pyrimidin-2-yl)amino)-5-methylphenyl)-1H-pyrazol-1-yl)-1,1,1-trifluoro-2-methylpropan-2-ol Example 24.1

(Isomer 1, first eluting): MS ESI calcd. for $C_{19}H_{19}F_5N_5O$ [M+H]$^+$ 428. found 428. $^1$H NMR (500 MHz, DMSO$_{d-6}$) δ 9.90 (s, 1H), 8.68 (d, J=4.9 Hz, 1H), 8.02 (s, 1H), 7.85 (s, 1H), 7.81 (s, 1H), 7.36 (s, 1H), 7.04-7.00 (m, 2H), 6.87 (t, J=54.5 Hz, 1H), 6.40 (s, 1H), 4.31 (m, 2H), 2.28 (s, 3H), 1.18 (s, 3H).

Example 24.2

(S or R)-3-(4-(3-((4-(difluoromethyl)pyrimidin-2-yl)amino)-5-methylphenyl)-1H-pyrazol-1-yl)-1,1,1-trifluoro-2-methylpropan-2-ol (Isomer 2, second eluting): MS ESI calcd. for $C_{19}H_{19}F_5N_5O$ [M+H]$^+$ 428. found 428. $^1$H NMR (500 MHz, DMSO$_{d-6}$) δ 9.90 (s, 1H), 8.68 (d, J=4.9 Hz, 1H), 8.02 (s, 1H), 7.85 (s, 1H), 7.81 (s, 1H), 7.36 (s, 1H), 7.04-7.00 (m, 2H), 6.87 (t, J=54.5 Hz, 1H), 6.40 (s, 1H), 4.31 (m, 2H), 2.28 (s, 3H), 1.18 (s, 3H).

Examples 25.1

2-((4-(3-((4-(Difluoromethyl)pyrimidin-2-yl)amino)-5-methylphenyl)-1H-pyrazol-1-yl)methyl)-3,3,3-trifluoropropane-1,2-diol

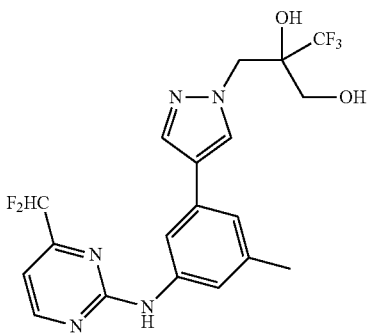 [SMILES: Cc1cc(Nc2nccc(C(F)F)n2)cc(-c2cnn(CC(O)(CO)C(F)(F)F)c2)c1]

Step 1:
2-Chloro-4-(1-fluoroethyl)pyrimidine (170 mg, 1.06 mmol), Palladium(II) acetate (59.3 mg, 0.26 mmol), 4,5-bis(diphenylphosphino)-9,9-dimethylxanthene (229 mg, 0.40 mmol), and cesium carbonate (860 mg, 2.64 mmol) were added to a solution of 3-methyl-5-(1-(2-methylallyl)-1H-pyrazol-4-yl)aniline (300 mg, 1.32 mmol) in dioxane (2.5 mL). The solution was degassed by sparging with Ar for 5 minutes and stirred at 110° C. for 18 h. The mixture was allowed to cool to room temperature, diluted with EtOAc, and washed with brine. The organic layer was dried over anhydrous magnesium sulfate, filtered and concentrated under reduced pressure. The residue was purified by column chromatography on silica gel (10-30% EtOAc/Hexane), then further purified by reverse phase HPLC (ACN/water with 0.1% TFA modifier) to afford 4-(1-fluoroethyl)-N-(3-methyl-5-(1-(2-methylallyl)-1H-pyrazol-4-yl)phenyl)pyrimidin-2-amine MS ESI calc'd. for $C_{20}H_{23}FN_5$ [M+H]$^+$ 352. found 352.

Step 2:
Imidazole (0.28 g, 4.16 mmol) and tert-butylchlorodimethylsilane (0.574 g, 3.81 mmol) were added to a solution of 3-(4-(3-((4-(difluoromethyl)pyrimidin-2-yl)amino)-5-methylphenyl)-1H-pyrazol-1-yl)propane-1,2-diol (1.3 g, 3.46 mmol) in DMF (12 mL) at 0° C. The mixture was stirred at 0° C. for 90 minutes. The mixture was allowed to warm to room temperature, diluted with EtOAc, and washed with water. The organic layer was dried over anhydrous magnesium sulfate, filtered, and concentrated under reduced pressure. The residue was purified by column chromatography on silica gel (0-100% EtOAc/Hexane) to afford 1-((tert-butyldimethylsilyl)oxy)-3-(4-(3-((4-(difluoromethyl)pyrimidin-2-yl)amino)-5-methylphenyl)-1H-pyrazol-1-yl)propan-2-ol. MS ESI calc'd. for $C_{24}H_{34}F_2N_5O_2Si$ [M+H]$^+$ 490. found 490.

Step 3:
Oxalyl chloride (0.21 mL, 2.39 mmol) was added to a solution of dimethyl sulfoxide (0.34 mL, 4.78 mmol) in methylene chloride (20 mL) at −78° C. The mixture was stirred for 10 minutes and 1-((tert-butyldimethylsilyl)oxy)-3-(4-(3-((4-(difluoromethyl)pyrimidin-2-yl)amino)-5-methylphenyl)-1H-pyrazol-1-yl)propan-2-ol (780 mg, 1.59 mmol) was added. After stirring for additional 15 minutes, triethylamine (1.11 mL, 7.97 mmol) was added. The mixture was allowed to warm to room temperature for 2 h. Water was added to the mixture, which was then extracted with methylene chloride. The organic layer was dried over anhydrous magnesium sulfate, filtered, and concentrated under reduced pressure. The residue was purified by column chromatography on silica gel (0-40% EtOAc/Hexane) to afford 1-((tert-butyldimethylsilyl)oxy)-3-(4-(3-((4-(difluoromethyl)pyrimidin-2-yl)amino)-5-methylphenyl)-1H-pyrazol-1-yl)propan-2-one. MS ESI calc'd. for $C_{24}H_{32}F_2N_5O_2Si$ [M+H]$^+$ 488. found 488.

Step 4:
Trifluoromethyl)trimethylsilane (0.197 mL, 1.33 mmol) was added to a solution of 1-((tert-butyldimethylsilyl)oxy)-3-(4-(3-((4-(difluoromethyl)pyrimidin-2-yl)amino)-5-methylphenyl)-1H-pyrazol-1-yl)propan-2-one (260 mg, 0.53 mmol) and cesium fluoride (8.10 mg, 0.05 mmol) in THF (3 mL). The mixture was stirred at room temperature for 2 h. The mixture was passed through CELITE, washed with methanol and concentrated under reduced pressure and used without further purification in the subsequent transformation.

Step 5:
Tetra-n-butyl ammonium fluoride (0.64 mL, 0.64 mmol) was added to the residue from Step 4 in THF (2 mL). The mixture was stirred at room temperature for 20 minutes. The mixture was concentrated under reduced pressure and purified by reverse phase HPLC (ACN/water with 0.1% TFA modifier) to afford 2-((4-(3-((4-(difluoromethyl)pyrimidin-2-yl)amino)-5-methylphenyl)-1H-pyrazol-1-yl)methyl)-3,3,3-trifluoropropane-1,2-diol. The racemic mixture was purified by chiral SFC (Chiralpak column, MeOH+0.25% DMEA) to afford (S or R)-2-((4-(3-((4-(difluoromethyl)pyrimidin-2-yl)amino)-5-methylphenyl)-1H-pyrazol-1-yl)methyl)-3,3,3-trifluoropropane-1,2-diol (Isomer 2, second eluting): MS ESI calc'd. for $C_{19}H_{19}F_5N_5O_2$ [M+H]$^+$ 444. found 444. $^1$H NMR (500 MHz, DMSO-d$_6$) δ 9.89 (s, 1H), 8.68 (d, J=4.5 Hz, 1H), 8.02 (s, 1H), 7.83 (s, 1H), 7.80 (s, 1H), 7.36 (s, 1H), 7.05-7.03 (m, 2H), 6.86 (t, J=54.5 Hz, 1H), 6.30 (s, 1H), 5.26 (t, J=6 Hz, 1H), 4.42 (q, J=14.5 Hz, J=15 Hz, 2H), 3.56-3.52 (m, 1H), 3.43-3.39 (m, 1H), 2.28 (s, 3H).

The following compounds in Table 25 were prepared according to the method described for Examples 25.1.

TABLE 25A

| Ex. No. | R¹ | R³ | Chemical Name | [M + H]⁺ Calc'd | [M + H]⁺ Found | Form |
|---|---|---|---|---|---|---|
| 25.2 | HO, HO (single stereoisomer, late eluting) | CH₃ | 2-methyl-3-(4-{3-methyl-5-[(4-methylpyrimidin-2-yl)amino]phenyl}-1H-pyrazol-1-yl)propane-1,2-diol | 354.2 | 354 | Free Base |
| 25.3 | HO, OH (single stereoisomer, early eluting) | C(H)F₂ | 3-[4-(3-{[4-(difluoromethyl)pyrimidin-2-yl]amino}-5-methylphenyl)-1H-pyrazol-1-yl]-2-methylpropane-1,2-diol | 390.2 | 390 | Free Base |
| 25.4 | HO, OH (single stereoisomer, early eluting) | CH₃ | 2-methyl-3-(4-{3-methyl-5-[(4-methylpyrimidin-2-yl)amino]phenyl}-1H-pyrazol-1-yl)propane-1,2-diol | 354.2 | 354 | Free Base |
| 25.5 | HO, HO (single stereoisomer, late eluting) | C(H)F₂ | 3-[4-(3-{[4-(difluoromethyl)pyrimidin-2-yl]amino}-5-methylphenyl)-1H-pyrazol-1-yl]-2-methylpropane-1,2-diol | 390.2 | 390 | Free Base |
| 25.6 | HO, HO (single stereoisomer, peak 3 of 4) | F, R | 3-{4-[3-({4-[(1R)-1-fluoroethyl]pyrimidin-2-yl}amino)-5-methylphenyl]-1H-pyrazol-1-yl}-2-methylpropane-1,2-diol | 386.2 | 386 | Free Base |
| 25.7 | HO, OH (single stereoisomer, peak 1 of 4) | F, S | 3-{4-[3-({4-[(1S)-1-fluoroethyl]pyrimidin-2-yl}amino)-5-methylphenyl]-1H-pyrazol-1-yl}-2-methylpropane-1,2-diol | 386.2 | 386 | Free Base |
| 25.8 | HO, OH (single stereoisomer, peak 2 of 4) | F, R | 3-{4-[3-({4-[(1R)-1-fluoroethyl]pyrimidin-2-yl}amino)-5-methylphenyl]-1H-pyrazol-1-yl}-2-methylpropane-1,2-diol | 386.2 | 386 | Free Base |

TABLE 25B

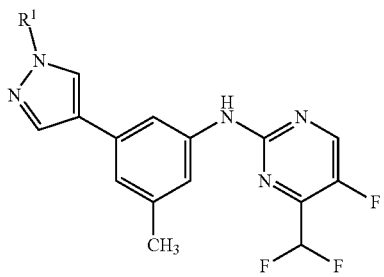

| Ex. No. | R¹ | Chemical Name | [M + H]⁺ Calc'd | [M + H]⁺ Found | Form |
|---|---|---|---|---|---|
| 25.9 | HO—⧸⧹—OH (single stereoisomer, late eluting) | 3-[4-(3-{[4-(difluoromethyl)-5-fluoropyrimidin-2-yl]amino}-5-methylphenyl)-1H-pyrazol-1-yl]-2-methylpropane-1,2-diol | 408.2 | 408 | Free Base |
| 25.10 | HO—⧸⧹—OH (single stereoisomer, early eluting) | 3-[4-(3-{[4-(difluoromethyl)-5-fluoropyrimidin-2-yl]amino}-5-methylphenyl)-1H-pyrazol-1-yl]-2-methylpropane-1,2-diol | 408.2 | 408 | Free Base |

Example 26.1

N-(2-(4-(3-((4-(Difluoromethyl)pyrimidin-2-yl)amino)-5-methylphenyl)-1H-pyrazol-1-yl)ethyl)cyclopropanecarboxamide

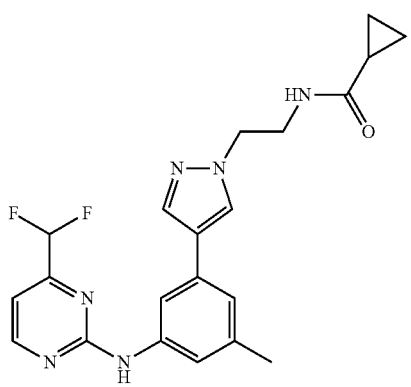 [SMILES: Cc1cc(Nc2nccc(C(F)F)n2)cc(-c2cnn(CCNC(=O)C3CC3)c2)c1]

Dichloromethane (1 mL) and N,N-diisopropylethylamine (0.087 mL, 0.50 mmol) were added to a vial containing cyclopropanecarboxylic acid (17.2 mg, 0.2 mmol) and 2-chloro-1,3-dimethylimidazolinium chloride (0.025 g, 0.15 mmol). The reaction mixture was stirred for 10 minutes and N-(3-(1-(2-amino ethyl)-1H-pyrazol-4-yl)-5-methylphenyl)-4-(difluoromethyl)pyrimidin-2-amine hydrochloride (38 mg, 0.10 mmol) was added. The reaction mixture was stirred for two hours and then concentrated under reduced pressure. The residue was purified by reverse phase chromatography (acetonitrile/water with 0.1% TFA modifier) to afford N-(2-(4-(3-((4-(difluoromethyl)pyrimidin-2-yl)amino)-5-methylphenyl)-1H-pyrazol-1-yl)ethyl)cyclopropanecarboxamide. MS ESI calc'd. for $C_{21}H_{23}F_2N_6O$ [M+H]⁺ 413. found 413. ¹H NMR (600 MHz, DMSO): δ 9.78 (s, 1H), 8.64 (d, J=4.9 Hz, 1H), 8.19 (s, 1H), 7.96 (s, 1H), 7.77 (s, 1H), 7.76 (s, 1H), 7.29 (s, 1H), 7.01 (d, J=4.9 Hz, 1H), 7.00 (s, 1H), 6.80 (t, J=54.5 Hz, 1H), 4.13 (t, J=6.2 Hz, 2H), 3.44 (q, J=6.0 Hz, 2H), 2.25 (s, 3H), 1.47-1.45 (m, 1H), 0.61-0.59 (m, 4H).

The following compounds in Table 26 were prepared according to the method described for Example 26.1.

TABLE 26

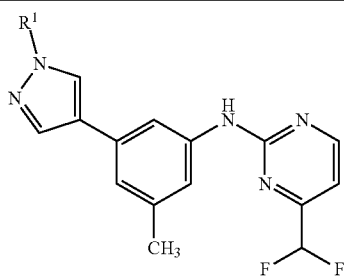

| Ex. No. | R¹ | Chemical Name | [M + H]⁺ Calc'd | [M + H]⁺ Found | Form |
|---|---|---|---|---|---|
| 26.2 | ![] | N-{2-[4-(3-{[4-(difluoromethyl)pyrimidin-2-yl]amino}-5-methylphenyl)-1H-pyrazol-1-yl]-1,1-dimethylethyl}cyclopropanecarboxamide | 441.2 | 441 | TFA Salt |
| 26.3 | ![] | N-{2-[4-(3-{[4-(difluoromethyl)pyrimidin-2-yl]amino}-5-methylphenyl)-1H-pyrazol-1-yl]-1,1-dimethylethyl}-2-methoxyacetamide | 445.2 | 445 | TFA Salt |
| 26.4 | ![] | 2-cyano-N-{2-[4-(3-{[4-(difluoromethyl)pyrimidin-2-yl]amino}-5-methylphenyl)-1H-pyrazol-1-yl]ethyl}acetamide | 412.2 | 412 | TFA Salt |
| 26.5 | ![] | N-{2-[4-(3-{[4-(difluoromethyl)pyrimidin-2-yl]amino}-5-methylphenyl)-1H-pyrazol-1-yl]ethyl}-2-methoxyacetamide | 417.2 | 417 | TFA Salt |

Example 27.1

N-(2-(4-(3-((4-(Difluoromethyl)pyrimidin-2-yl)amino)-5-methylphenyl)-1H-pyrazol-1-yl)ethyl)methanesulfonamide

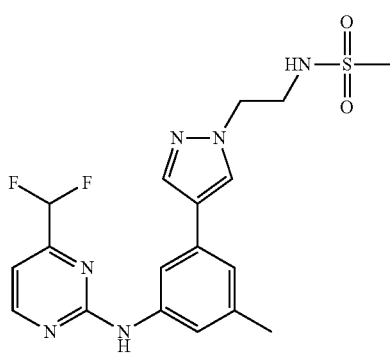 [SMILES: Cc1cc(Nc2nccc(C(F)F)n2)cc(-c2cnn(CCNS(C)(=O)=O)c2)c1]

Dichloromethane (1 mL), N,N-diisopropylethylamine (0.087 mL, 0.50 mmol) and methanesulfonyl chloride (0.023 g, 0.20 mmol) were added to a vial containing N-(3-(1-(2-aminoethyl)-1H-pyrazol-4-yl)-5-methylphenyl)-4-(difluoromethyl)pyrimidin-2-amine hydrochloride (0.038 g, 0.10 mmol). The reaction mixture was stirred for two hours and then concentrated under reduced pressure. The residue was purified by reverse phase chromatography (acetonitrile/water with 0.1% TFA modifier) to afford N-(2-(4-(3-((4-(difluoromethyl)pyrimidin-2-yl)amino)-5-methylphenyl)-1H-pyrazol-1-yl)ethyl)methanesulfonamide. MS ESI calc'd. for $C_{15}H_{21}F_2N_6O_2S$ [M+H]⁺ 423. found 423. ¹H NMR (600 MHz, DMSO-d₆): δ 9.80 (s, 1H), 8.64 (d, J=4.9 Hz, 1H), 8.02 (s, 1H), 7.78 (d, J=5.5 Hz, 2H), 7.31 (s, 1H), 7.19 (t, J=5.9 Hz, 1H), 7.01 (d, J=6.7 Hz, 2H), 6.81 (t, J=54.5 Hz, 1H), 4.18 (t, J=6.2 Hz, 2H), 3.36-3.35 (m, 2H), 2.77 (s, 3H), 2.25 (s, 3H).

The following compounds in Table 27 were prepared according to the method described for Example 27.1.

TABLE 27

| Ex. No. | R¹ | Chemical Name | [M + H]⁺ Calc'd | [M + H]⁺ Found | Form |
|---|---|---|---|---|---|
| 27.2 | (methyl carbamate-ethyl) | methyl {2-[4-(3-{[4-(difluoromethyl)pyrimidin-2-yl]amino}-5-methylphenyl)-1H-pyrazol-1-yl]ethyl}carbamate | 403.2 | 403 | TFA Salt |
| 27.3 | (2-methoxyethyl carbamate-ethyl) | 2-methoxyethyl {2-[4-(3-{[4-(difluoromethyl)pyrimidin-2-yl]amino}-5-methylphenyl)-1H-pyrazol-1-yl]ethyl}carbamate | 447.2 | 447 | TFA Salt |
| 27.4 | (methanesulfonamido-dimethylethyl) | N-{2-[4-(3-{[4-(difluoromethyl)pyrimidin-2-yl]amino}-5-methylphenyl)-1H-pyrazol-1-yl]-1,1-dimethylethyl}methanesulfonamide | 451.2 | 451 | TFA Salt |
| 27.5 | (cyclopropanesulfonamido-dimethylethyl) | N-{2-[4-(3-{[4-(difluoromethyl)pyrimidin-2-yl]amino}-5-methylphenyl)-1H-pyrazol-1-yl]-1,1-dimethylethyl}cyclopropanesulfonamide | 477.2 | 477 | TFA Salt |
| 27.6 | (morpholinosulfonamido-dimethylethyl) | N-{2-[4-(3-{[4-(difluoromethyl)pyrimidin-2-yl]amino}-5-methylphenyl)-1H-pyrazol-1-yl]-1,1-dimethylethyl}morpholine-4-sulfonamide | 522.2 | 522 | TFA Salt |
| 27.7 | (tert-butylurea-dimethylethyl) | 1-tert-butyl-3-{2-[4-(3-{[4-(difluoromethyl)pyrimidin-2-yl]amino}-5-methylphenyl)-1H-pyrazol-1-yl]-1,1-dimethylethyl}urea | 472.3 | 472 | TFA Salt |
| 27.8 | (ethylurea-dimethylethyl) | 1-{2-[4-(3-{[4-(difluoromethyl)pyrimidin-2-yl]amino}-5-methylphenyl)-1H-pyrazol-1-yl]-1,1-dimethylethyl}-3-ethylurea | 444.2 | 444 | TFA Salt |
| 27.9 | (tetrahydropyranylmethylurea-dimethylethyl) | 1-{2-[4-(3-{[4-(difluoromethyl)pyrimidin-2-yl]amino}-5-methylphenyl)-1H-pyrazol-1-yl]-1,1-dimethylethyl}-3-(tetrahydro-2H-pyran-4-ylmethyl)urea | 514.3 | 514 | TFA Salt |

TABLE 27-continued

| Ex. No. | R¹ | Chemical Name | [M + H]⁺ Calc'd | [M + H]⁺ Found | Form |
|---|---|---|---|---|---|
| 27.10 | (2-fluoroethyl carbamate on dimethylethyl) | 2-fluoroethyl {2-[4-(3-{[4-(difluoromethyl)pyrimidin-2-yl]amino}-5-methylphenyl)-1H-pyrazol-1-yl]-1,1-dimethylethyl}carbamate | 463.2 | 463 | TFA Salt |
| 27.11 | (methyl carbamate on dimethylethyl) | methyl {2-[4-(3-{[4-(difluoromethyl)pyrimidin-2-yl]amino}-5-methylphenyl)-1H-pyrazol-1-yl]-1,1-dimethylethyl}carbamate | 431.2 | 431 | TFA Salt |
| 27.12 | (2-methoxyethyl carbamate on dimethylethyl) | 2-methoxyethyl {2-[4-(3-{[4-(difluoromethyl)pyrimidin-2-yl]amino}-5-methylphenyl)-1H-pyrazol-1-yl]-1,1-dimethylethyl}carbamate | 475.2 | 475 | TFA Salt |
| 27.13 | (cyclopropanesulfonamide-ethyl) | N-{2-[4-(3-{[4-(difluoromethyl)pyrimidin-2-yl]amino}-5-methylphenyl)-1H-pyrazol-1-yl]ethyl}cyclopropanesulfonamide | 449.2 | 449 | TFA Salt |
| 27.14 | (morpholine-4-sulfonamide-ethyl) | N-{2-[4-(3-{[4-(difluoromethyl)pyrimidin-2-yl]amino}-5-methylphenyl)-1H-pyrazol-1-yl]ethyl}morpholine-4-sulfonamide | 494.2 | 494 | TFA Salt |
| 27.15 | (1-tert-butyl urea-ethyl) | 1-tert-butyl-3-{2-[4-(3-{[4-(difluoromethyl)pyrimidin-2-yl]amino}-5-methylphenyl)-1H-pyrazol-1-yl]ethyl}urea | 444.2 | 444 | TFA Salt |
| 27.16 | (ethylurea-ethyl) | 1-{2-[4-(3-{[4-(difluoromethyl)pyrimidin-2-yl]amino}-5-methylphenyl)-1H-pyrazol-1-yl]ethyl}-3-ethylurea | 416.2 | 416 | TFA Salt |
| 27.17 | (tetrahydropyran-4-ylmethylurea-ethyl) | 1-{2-[4-(3-{[4-(difluoromethyl)pyrimidin-2-yl]amino}-5-methylphenyl)-1H-pyrazol-1-yl]ethyl}-3-(tetrahydro-2H-pyran-4-ylmethyl)urea | 486.2 | 486 | TFA Salt |
| 27.18 | (2-fluoroethyl carbamate-ethyl) | 2-fluoroethyl {2-[4-(3-{[4-(difluoromethyl)pyrimidin-2-yl]amino}-5-methylphenyl)-1H-pyrazol-1-yl]ethyl}carbamate | 435.2 | 435 | TFA Salt |

Examples 28.1 and 28.2

4-(1-(4-(3-Methyl-5-(pyrimidin-2-ylamino)phenyl)-1H-pyrazol-1-yl)ethyl)benzamide (Isomer 1) and 4-(1-(4-(3-methyl-5-(pyrimidin-2-ylamino)phenyl)-1H-pyrazol-1-yl)ethyl)benzamide (Isomer 2)

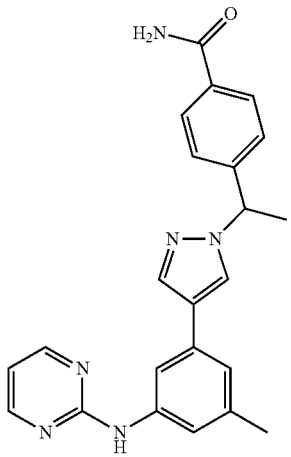

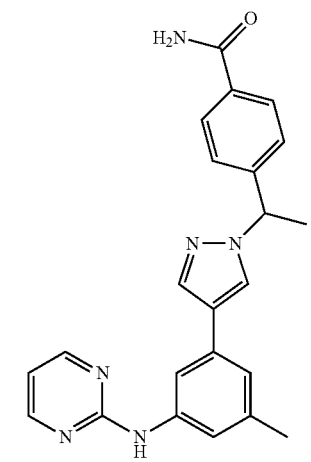

Step 1:

A mixture of 4-bromo-1H-pyrazole (200 mg, 1.36 mmol), methyl 4-(1-hydroxyethyl)benzoate (490 mg, 2.72 mmol), and triphenylphosphine (resin bound: 3 mmol/g loading, 907 mg, 2.72 mmol) in THF (5 mL) was stirred for 5 minutes at ambient temperature. Di-tert-butyl azodicarboxylate (627 mg, 2.72 mmol) was added and the reaction mixture was stirred for 24 hours at ambient temperature. The reaction mixture was filtered, and the filtrate was diluted with dichloromethane (25 mL) and TFA (6 mL) and stirred for 30 minutes. The mixture was concentrated under reduced pressure and then diluted with ethyl acetate (100 mL) and saturated aqueous sodium bicarbonate solution (100 mL). The organic layer was separated, washed with brine (25 mL), dried over magnesium sulfate, filtered, and concentrated under reduced pressure to afford the crude product residue. The crude product residue was purified by column chromatography on silica (0-100% diethyl ether/hexanes) to afford methyl 4-(1-(4-bromo-1H-pyrazol-1-yl)ethyl)benzoate. MS ESI calc'd. for $C_{13}H_{14}BrN_2O_2$ $[M+H]^+$ 309 and 311. found 309 and 311. $^1H$ NMR (500 MHz, DMSO-$d_6$) δ 8.17 (s, 1H), 7.90 (dd, J=6.5 Hz, 1.5 Hz, 2H), 7.58 (s, 1H), 7.33 (d, J=8.5 Hz, 2H), 5.72-5.65 (m, 1H), 3.82 (s, 3H), 1.78 (d, J=7.5 Hz, 3H).

Step 2:

A mixture of N-(3-methyl-5-(4,4,5,5-tetramethyl-1,3,2-dioxaborolan-2-yl)phenyl)pyrimidin-2-amine (100 mg, 0.321 mmol), methyl 4-(1-(4-bromo-1H-pyrazol-1-yl)ethyl)benzoate (139 mg, 0.450 mmol), $Pd_2(dba)_3$ (15 mg, 0.016 mmol), X-phos (15 mg, 0.032 mmol), and cesium carbonate (314 mg, 0.964 mmol) was diluted with 1,4-dioxane (3 mL) and water (0.3 mL) at ambient temperature. The mixture was stirred for 5 minutes under a subsurface argon sparge, after which time the mixture was heated to 90° C. and stirred under an argon atmosphere for 2 hours. The reaction mixture was cooled to ambient temperature and diluted with ethyl acetate (100 mL) and water (25 mL). The organic layer was separated and washed with water (25 mL) and then brine (25 mL). The organic layer was dried over anhydrous magnesium sulfate, filtered, and concentrated under reduced pressure to afford the crude product residue. The crude product residue was purified by column chromatography on silica (0-100% [5% methanol in ethyl acetate]/hexanes) to afford methyl 4-(1-(4-(3-methyl-5-(pyrimidin-2-ylamino)phenyl)-1H-pyrazol-1-yl)ethyl)benzoate. MS ESI calcd. for $C_{24}H_{24}N_5O_2$ $[M+H]^+$ 414. found 414. $^1H$ NMR (500 MHz, DMSO-$d_6$) δ 9.46 (s, 1H), 8.46 (d, J=4.5 Hz, 2H), 8.24 (s, 1H), 7.91 (d, J=8.0 Hz, 2H), 7.80 (s, 1H), 7.72 (s, 1H), 7.41 (s, 1H), 7.37 (d, J=8.0 Hz, 2H), 7.01 (s, 1H), 6.80 (t, J=5.0 Hz, 1H), 5.76-5.70 (m, 1H), 3.82 (s, 3H), 3.27 (s, 3H), 1.83 (d, J=7.0 Hz, 3H).

Step 3:

A solution of methyl 4-(1-(4-(3-methyl-5-(pyrimidin-2-ylamino)phenyl)-1H-pyrazol-1-yl)ethyl)benzoate (125 mg, 0.302 mmol) in THF (5.0 mL), methanol (1.0 mL), and water (1.0 mL) was diluted with sodium hydroxide (1.0 M in water, 1.0 mL, 1.0 mmol). The reaction mixture was stirred and heated to 50° C. for 1 hour. The reaction mixture was cooled to ambient temperature and diluted with hydrochloric acid (1.0 M in water, 1.0 mL, 1.0 mmol) while stirring. The resulting suspension was diluted with ethyl acetate (100 mL) and brine (10 mL). The organic layer was separated, dried over anhydrous magnesium sulfate, filtered, and concentrated under reduced pressure to afford 4-(1-(4-(3-methyl-5-(pyrimidin-2-ylamino)phenyl)-1H-pyrazol-1-yl)ethyl)benzoic acid. The material was used without purification in the subsequent step. MS ESI calcd. for $C_{23}H_{22}N_5O_2$ [M+H]$^+$ 400. found 400.

Step 4:

2-(1H-Benzo[d][1,2,3]triazol-1-yl)-1,1,3,3-tetramethylisouronium tetrafluoroborate (101 mg, 0.315 mmol) was added to a solution of 4-(1-(4-(3-methyl-5-(pyrimidin-2-ylamino)phenyl)-1H-pyrazol-1-yl)ethyl)benzoic acid (105 mg, 0.263 mmol) in THF (5.0 mL) and DMF (1.0 mL). Ammonium hydroxide (0.15 mL, 1.05 mmol) was then added and the reaction mixture was stirred at ambient temperature for 1 hour. The reaction mixture was diluted with ethyl acetate (100 mL) and water (10 mL). The organic layer was separated and washed with water (2×10 mL) followed by brine (10 mL). The organic layer was dried over anhydrous magnesium sulfate, filtered, and concentrated under reduced pressure to afford the crude product residue. The crude product residue was purified by column chromatography on silica (0-100% [5% methanol in ethyl acetate]/hexanes) to afford racemic 4-(1-(4-(3-methyl-5-(pyrimidin-2-ylamino)phenyl)-1H-pyrazol-1-yl)ethyl)benzamide. MS ESI calcd. for $C_{23}H_{23}N_6O$ [M+H]$^+$ 399. found 399. $^1$H NMR (500 MHz, DMSO-$d_6$) δ 9.46 (s, 1H), 8.46 (d, J=5.0 Hz, 2H), 8.22 (s, 1H), 7.92 (s, 1H), 7.82 (s, 1H), 7.79 (d, J=6.5 Hz, 2H), 7.71 (s, 1H), 7.41 (s, 1H), 7.36-7.26 (m, 3H), 7.00 (s, 1H), 6.80 (t, J=5.0 Hz, 1H), 5.70-5.64 (m, 1H), 2.27 (s, 3H), 1.83 (d, J=7.0 Hz, 3H).

Example 28.1

4-(1-(4-(3-methyl-5-(pyrimidin-2-ylamino)phenyl)-1H-pyrazol-1-yl)ethyl)benzamide (racemic mixture of enantiomers) was purified by chiral SFC (ID column, 45% [0.25% w/w dimethylethylamine in methanol]/CO$_2$) to afford 4-(1-(4-(3-methyl-5-(pyrimidin-2-ylamino)phenyl)-1H-pyrazol-1-yl)ethyl)benzamide (Isomer 1, first eluting): MS ESI calcd. for $C_{23}H_{23}N_6O$ [M+H]$^+$ 399. found 399. $^1$H NMR (500 MHz, DMSO$_{d-6}$) δ 9.46 (s, 1H), 8.46 (d, J=5.0 Hz, 2H), 8.22 (s, 1H), 7.92 (s, 1H), 7.82 (s, 1H), 7.79 (d, J=7.0 Hz, 2H), 7.71 (s, 1H), 7.41 (s, 1H), 7.35-7.27 (m, 3H), 7.00 (s, 1H), 6.80 (t, J=5.0 Hz, 1H), 5.71-5.64 (m, 1H), 2.27 (s, 3H), 1.83 (d, J=7.5 Hz, 3H).

Example 28.2

4-(1-(4-(3-methyl-5-(pyrimidin-2-ylamino)phenyl)-1H-pyrazol-1-yl)ethyl)benzamide (Isomer 2, second eluting): MS ESI calcd. for $C_{23}H_{23}N_6O$ [M+H]$^+$ 399. found 399. $^1$H NMR (500 MHz, DMSO$_{d-6}$) δ 9.46 (s, 1H), 8.46 (d, J=5.0 Hz, 2H), 8.22 (s, 1H), 7.92 (s, 1H), 7.81 (s, 1H), 7.79 (d, J=7.0 Hz, 2H), 7.71 (s, 1H), 7.41 (s, 1H), 7.36-7.27 (m, 3H), 7.00 (s, 1H), 6.80 (t, J=5.0 Hz, 1H), 5.70-5.64 (m, 1H), 2.27 (s, 3H), 1.83 (d, J=7.5 Hz, 3H).

Example 29.1

1-((4-(3-((4-(Difluoromethyl)pyrimidin-2-yl)amino)-5-methylphenyl)-1H-pyrazol-1-yl)methyl)cyclobutanol

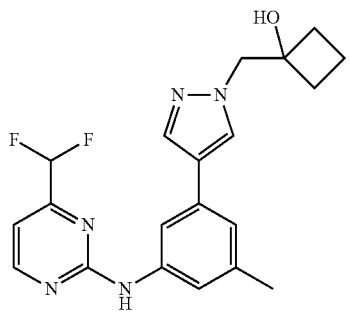 [SMILES: Cc1cc(Nc2nccc(C(F)F)n2)cc(-c2cnn(CC3(O)CCC3)c2)c1]

Acetonitrile (1 mL) was added to a vial containing 1-oxaspiro[2.3]hexane (0.050 g, 0.60 mmol), 4-(4,4,5,5-tetramethyl-1,3,2-dioxaborolan-2-yl)-1H-pyrazole (0.058 g, 0.30 mmol), and potassium carbonate (0.083 g, 0.60 mmol). The reaction mixture was heated at 90° C. overnight. N-(3-bromo-5-methylphenyl)-4-(difluoromethyl)pyrimidin-2-amine (0.063 g, 0.2 mmol), SiliaCat Si-DPP-Pd (0.154 g, 0.040 mmol, 0.26 mmol/g), sodium carbonate (0.064 g, 0.60 mmol), 1,4-dioxane (1.75 mL), and water (0.4 mL) were added and the reaction was heated at 110° C. for four hours. The reaction mixture was filtered, washed with 1,4-dioxane, and concentrated under reduced pressure. The residue was purified by reverse phase chromatography (acetonitrile/water, both with 0.1% TFA) to yield 1-((4-(3-((4-(difluoromethyl)pyrimidin-2-yl)amino)-5-methylphenyl)-1H-pyrazol-1-yl)methyl)cyclobutanol. MS ESI calc'd. for $C_{20}H_{22}F_2N_5O$ [M+H]$^+$ 386. found 386. $^1$H NMR (600 MHz, DMSO-d$_6$): δ 9.84 (s, 1H), 8.66 (d, J=4.9 Hz, 1H), 7.95 (s, 1H), 7.80 (s, 1H), 7.72 (s, 1H), 7.33 (s, 1H), 7.02 (d, J=4.9 Hz, 1H), 7.00 (s, 1H), 6.84 (t, J=54.5 Hz, 1H), 4.15 (s, 2H), 2.26 (s, 3H), 2.07 (t, J=9.6 Hz, 2H), 1.91-1.90 (m, 2H), 1.60 (d, J=10.5 Hz, 1H), 1.43-1.41 (m, 1H).

The following compounds in Table 29 were prepared according to the method described for Example 29.1.

TABLE 29

Ie(3): 1-(hydroxycyclobutyl)methyl-pyrazole linked to phenyl(R²)(R³)-NH-pyrimidine(R⁴)

Ie(4): 1-(hydroxycyclobutyl)methyl-pyrazole linked to pyridine(R²)(R³)-NH-pyridine(R⁴)

| Ex. No. | Substructure | R² | R³ | R⁴ | Chemical Name | [M + H]⁺ Calc'd | [M + H]⁺ Found | Form |
|---|---|---|---|---|---|---|---|---|
| 29.2 | Ie(4) | CH₃ | C(H)F₂ | H | 1-{[4-(6-{[4-(difluoromethyl)pyridin-2-yl]amino}-4-methylpyridin-2-yl)-1H-pyrazol-1-yl]methyl}cyclobutanol | 386.2 | 386 | TFA Salt |
| 29.3 | Ie(4) | CH₃ | CH₃ | H | 1-[(4-{4-methyl-6-[(4-methylpyridin-2-yl)amino]pyridin-2-yl}-1H-pyrazol-1-yl)methyl}cyclobutanol | 350.2 | 350 | TFA Salt |
| 29.4 | Ie(3) | H | C(H)F₂ | H | 1-{[4-(3-{[4-(difluoromethyl)pyrimidin-2-yl]amino}phenyl)-1H-pyrazol-1-yl]methyl}cyclobutanol | 372.2 | 372 | TFA Salt |
| 29.5 | Ie(3) | CH₃ | CH₃ | H | 1-[(4-{3-methyl-5-[(4-methylpyrimidin-2-yl)amino]phenyl}-1H-pyrazol-1-yl)methyl}cyclobutanol | 350.2 | 350 | TFA Salt |
| 29.6 | Ie(3) | CH₃ | C(H)F₂ | F | 1-{[4-(3-{[4-(difluoromethyl)-5-fluoropyrimidin-2-yl]amino}-5-methylphenyl)-1H-pyrazol-1-yl]methyl}cyclobutanol | 404.2 | 404 | TFA Salt |
| 29.7 | Ie(4) | CH₃ | c-propyl | H | 1-[(4-{6-[(4-cyclopropylpyridin-2-yl)amino]-4-methylpyridin-2-yl}-1H-pyrazol-1-yl)methyl]cyclobutanol | 376.2 | 376 | Free Base |

Example 30.1

3-(4-(3-Methyl-5-(pyrimidin-2-ylamino)phenyl)-1H-pyrazol-1-yl)cyclobutanecarboxamide (Isomer 1)

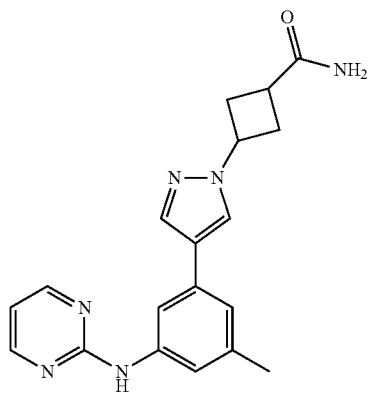 [SMILES: Cc1cc(Nc2ncccn2)cc(-c2cnn(C3CC(C(N)=O)C3)c2)c1]

Step 1:

TMS-diazomethane (2.0 M in diethyl ether, 2.2 ml, 4.4 mmol) was added dropwise to a solution of 3-chlorocyclobutanecarboxylic acid (540 mg, 4.0 mmol) in methanol (5.0 mL) and dichloromethane (5.0 mL) at 0° C. The reaction mixture was concentrated under reduced pressure to afford methyl 3-chlorocyclobutanecarboxylate. The material was used in the subsequent reaction without purification.

Step 2:

A mixture of 4-bromo-1H-pyrazole (500 mg, 3.40 mmol), methyl 3-chlorocyclobutanecarboxylate (607 mg, 4.08 mmol), and potassium carbonate (1.18 g, 8.50 mmol) in DMF (5 mL) was heated to 70° C. for 24 hours. The reaction mixture was cooled to ambient temperature and diluted with diethyl ether (200 mL). The mixture was washed with water (2×50 mL) and then brine (25 mL). The organic layer was dried over magnesium sulfate, filtered, and concentrated under reduced pressure to afford the crude product residue. The crude product residue was purified by column chromatography on silica (0-100% diethyl ether/hexanes) to afford methyl 3-(4-bromo-1H-pyrazol-1-yl)cyclobutanecarboxylate (Isomer 1) and methyl 3-(4-bromo-1H-pyrazol-1-yl)cyclobutanecarboxylate (Isomer 2). Methyl 3-(4-bromo-1H-pyrazol-1-yl)cyclobutanecarboxylate (Isomer 1): MS ESI calc'd. for $C_9H_{12}BrN_2O_2$ $[M+H]^+$ 259 and 261. found 259 and 261. $^1$H NMR (500 MHz, DMSO-$d_6$) δ 8.09 (s, 1H), 7.59 (s, 1H), 5.02-4.95 (m, 1H), 3.65 (s, 3H), 3.20-3.14 (m, 1H), 2.75-2.66 (m, 2H), 2.64-2.56 (m, 2H).

Methyl 3-(4-bromo-1H-pyrazol-1-yl)cyclobutanecarboxylate (Isomer 2): MS ESI calcd. for $C_9H_{12}BrN_2O_2$ $[M+H]^+$ 259 and 261. found 259 and 261. $^1$H NMR (500 MHz, DMSO-$d_6$) δ 8.05 (s, 1H), 7.57 (s, 1H), 4.80-4.72 (m, 1H), 3.61 (s, 3H), 3.02-2.94 (m, 1H), 2.63-2.56 (m, 4H).

Step 3:

A mixture of N-(3-methyl-5-(4,4,5,5-tetramethyl-1,3,2-dioxaborolan-2-yl)phenyl)pyrimidin-2-amine (220 mg, 0.707 mmol), methyl 3-(4-bromo-1H-pyrazol-1-yl)cyclobutanecarboxylate (Isomer 1) (183 mg, 0.707 mmol), $Pd_2(dba)_3$ (32 mg, 0.035 mmol), X-phos (34 mg, 0.071 mmol), and cesium carbonate (691 mg, 2.12 mmol) in 1,4-dioxane (3 mL) and water (0.3 mL) was degassed via a subsurface argon sparge for 5 minutes. The mixture was then heated to 90° C. under an argon atmosphere for 2 hours. The reaction mixture was cooled to ambient temperature and diluted with ethyl acetate (100 mL) and water (25 mL). The organic layer was separated and washed with water (25 mL) and then brine (25 mL). The organic layer was dried over anhydrous magnesium sulfate, filtered, and concentrated under reduced pressure to afford the crude product residue. The crude product residue was purified by column chromatography on silica (0-100% ethyl acetate/hexanes) to afford methyl 3-(4-(3-methyl-5-(pyrimidin-2-ylamino)phenyl)-1H-pyrazol-1-yl)cyclobutanecarboxylate (Isomer 1) MS ESI calc'd. for $C_{20}H_{22}N_5O_2$ $[M+H]^+$ 364. found 364. $^1$H NMR (500 MHz, DMSO-$d_6$) δ 9.48 (s, 1H), 8.46 (d, J=4.5 Hz, 2H), 8.16 (s, 1H), 7.80 (s, 1H), 7.72 (s, 1H), 7.40 (s, 1H), 6.98 (s, 1H), 6.81 (t, J=5.0 Hz, 1H), 5.05-5.00 (m, 1H), 3.67 (s, 3H), 3.24-3.17 (m, 1H), 2.81-2.74 (m, 2H), 2.67-2.60 (m, 2H), 2.27 (s, 3H).

Step 4:

Sodium hydroxide (1.0 M in water, 1.68 mL, 1.68 mmol) was added to a solution of methyl 3-(4-(3-methyl-5-(pyrimidin-2-ylamino)phenyl)-1H-pyrazol-1-yl)cyclobutanecarboxylate (Isomer 1) (203 mg, 0.559 mmol) in methanol (4.0 mL) and water (1.0 mL). The reaction mixture was heated to 50° C. and stirred for 1 hour. The reaction mixture was cooled to ambient temperature and diluted with hydrochloric acid (1.0 M in water, 1.68 mL, 1.68 mmol) while stirring. The resulting suspension was diluted with ethyl acetate (100 mL) and brine (10 mL). The organic layer was separated, washed with brine (10 mL), dried over anhydrous magnesium sulfate, filtered, and concentrated under reduced pressure to afford 3-(4-(3-methyl-5-(pyrimidin-2-ylamino)phenyl)-1H-pyrazol-1-yl)cyclobutanecarboxylic acid (Isomer 1). The material was used without purification in the subsequent step. MS ESI calc'd. for $C_{19}H_{20}N_5O_2$ $[M+H]^+$ 350. found 350.

Step 5:

A solution of 3-(4-(3-methyl-5-(pyrimidin-2-ylamino)phenyl)-1H-pyrazol-1-yl)cyclobutanecarboxylic acid (Isomer 1) (170 mg, 0.49 mmol), 2-(1H-benzo[d][1,2,3]triazol-1-yl)-1,1,3,3-tetramethylisouronium tetrafluoroborate (187 mg, 0.584 mmol), and triethylamine (0.136 mL, 0.973 mmol) in DMF (5.0 mL) was stirred for 10 minutes, after which time ammonium hydroxide (0.20 mL, 1.46 mmol) was added. The reaction mixture was stirred at ambient temperature for 1 hour. The reaction mixture was diluted with ethyl acetate (100 mL) and water (10 mL). The organic layer was separated and washed with water (2×10 mL) followed by brine (10 mL). The organic layer was dried over anhydrous magnesium sulfate, filtered, and concentrated under reduced pressure to afford the crude product residue. The crude product residue was dissolved in a mixture of methanol (6 mL) and dichloromethane (20 mL). The mixture was diluted by the dropwise addition of hexanes (50 mL). The resulting suspension was stirred for 4 hours. The suspension was filtered and the collected solids were washed with hexanes/dichloromethane (1:1, 3×10 mL) followed by neat hexanes (2×10 mL). The collected solids were dried under reduced pressure to afford 3-(4-(3-methyl-5-(pyrimidin-2-ylamino)phenyl)-1H-pyrazol-1-yl)cyclobutanecarboxamide (Isomer 1) MS ESI calcd. for $C_{19}H_{21}N_6O$ $[M+H]^+$ 349. found 349. $^1$H NMR (500 MHz, DMSO-$d_6$) δ 9.47 (s, 1H), 8.46 (d, J=4.5 Hz, 2H), 8.15 (s, 1H), 7.78 (s, 1H), 7.72 (s, 1H), 7.40 (s, 1H), 7.37 (s, 1H), 6.98

(s, 1H), 6.88 (s, 1H), 6.81 (t, J=5.0 Hz, 1H), 5.03-4.96 (m, 1H), 3.05-2.98 (m, 1H), 2.69-2.61 (m, 2H), 2.57-2.51 (m, 2H), 2.27 (s, 3H).

Example 31.1

3-(4-(3-Methyl-5-(pyrimidin-2-ylamino)phenyl)-1H-pyrazol-1-yl)cyclobutanecarboxamide (Isomer 2)

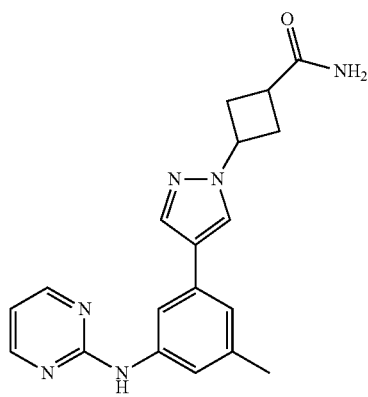 [SMILES: Cc1cc(Nc2ncccn2)cc(-c2cnn(C3CC(C(N)=O)C3)c2)c1]

3-(4-(3-methyl-5-(pyrimidin-2-ylamino)phenyl)-1H-pyrazol-1-yl)cyclobutanecarboxamide (Isomer 2) was prepared from N-(3-methyl-5-(4,4,5,5-tetramethyl-1,3,2-dioxaborolan-2-yl)phenyl)pyrimidin-2-amine and methyl 3-(4-bromo-1H-pyrazol-1-yl)cyclobutanecarboxylate (Isomer 2) using chemistry described for 3-(4-(3-methyl-5-(pyrimidin-2-ylamino)phenyl)-1H-pyrazol-1-yl)cyclobutanecarboxamide (Isomer 1). MS ESI calcd. for $C_{19}H_{21}N_6O$ [M+H]+ 349. found 349. $^1$H NMR (500 MHz, DMSO-d$_6$) δ 9.46 (s, 1H), 8.46 (d, J=4.5 Hz, 2H), 8.10 (s, 1H), 7.77 (s, 1H), 7.71 (s, 1H), 7.42 (s, 1H), 7.33 (s, 1H), 7.00 (s, 1H), 6.86 (s, 1H), 6.81 (t, J=5.0 Hz, 1H), 4.78-4.71 (m, 1H), 2.80-2.72 (m, 1H), 2.61-2.49 (m, 4H), 2.27 (s, 3H).

Examples 32.1 and 32.2

2-((4-(3-((4-(Difluoromethyl)pyrimidin-2-yl)amino)-5-methylphenyl)-1H-pyrazol-1-yl)methyl)-3,3,3-trifluoropropane-1,2-diol

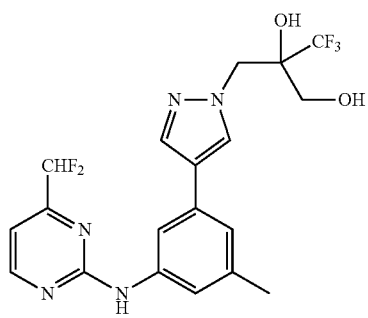 [SMILES: Cc1cc(Nc2nccc(C(F)F)n2)cc(-c2cnn(CC(O)(CO)C(F)(F)F)c2)c1]

Step 1:
Trifluoromethyl)trimethylsilane (0.20 mL, 1.33 mmol) was added to a solution of 1-((tert-butyldimethylsilyl)oxy)-3-(4-(3-((4-(difluoromethyl)pyrimidin-2-yl)amino)-5-methylphenyl)-1H-pyrazol-1-yl)propan-2-one (260 mg, 0.53 mmol) and cesium fluoride (8.10 mg, 0.05 mmol) in THF (3 mL). The mixture was stirred at room temperature for 2 h. The mixture was passed through CELITE, washed with methanol and concentrated under reduced pressure and used without further purification in the subsequent transformation.
Step 2:
Tetra-n-butyl ammonium fluoride (0.64 mL, 0.64 mmol) was added to the residue from step 1 in THF (2 mL). The mixture was stirred at room temperature for 20 minutes. The mixture was concentrated under reduced pressure and purified by reverse phase HPLC (ACN/water with 0.1% TFA modifier) to afford 2-((4-(3-((4-(difluoromethyl)pyrimidin-2-yl)amino)-5-methylphenyl)-1H-pyrazol-1-yl)methyl)-3,3,3-trifluoropropane-1,2-diol. The racemic mixture was purified by chiral SFC (Chiralpak column, MeOH+0.25% DMEA) to afford (S or R)-2-((4-(3-((4-(difluoromethyl)pyrimidin-2-yl)amino)-5-methylphenyl)-1H-pyrazol-1-yl)methyl)-3,3,3-trifluoropropane-1,2-diol Example 32.1

(Isomer 1, first eluting): MS ESI calc'd. for $C_{19}H_{19}F_5N_5O_2$ [M+H]+ 444. found 444. $^1$H NMR (500 MHz, DMSO-d$_6$) δ 9.89 (s, 1H), 8.68 (d, J=4.5 Hz, 1H), 8.02 (s, 1H), 7.83 (s, 1H), 7.80 (s, 1H), 7.36 (s, 1H), 7.05-7.04 (m, 2H), 6.82 (t, J=54.5 Hz, 1H), 6.30 (s, 1H), 5.26 (t, J=6 Hz, 1H), 4.43 (q, J=14.5 Hz, J=15 Hz, 2H), 3.56-3.52 (m, 1H), 3.43-3.39 (m, 1H), 2.28 (s, 3H).

Example 32.2

(S or R)-2-((4-(3-((4-(difluoromethyl)pyrimidin-2-yl)amino)-5-methylphenyl)-1H-pyrazol-1-yl)methyl)-3,3,3-trifluoropropane-1,2-diol (Isomer 2, second eluting): MS ESI calc'd. for $C_{19}H_{19}F_5N_5O_2$ [M+H]+ 444. found 444. $^1$H NMR (500 MHz, DMSO-d$_6$) δ 9.89 (s, 1H), 8.68 (d, J=4.5 Hz, 1H), 8.02 (s, 1H), 7.83 (s, 1H), 7.80 (s, 1H), 7.36 (s, 1H), 7.05-7.03 (m, 2H), 6.86 (t, J=54.5 Hz, 1H), 6.30 (s, 1H), 5.26 (t, J=6 Hz, 1H), 4.42 (q, J=14.5 Hz, J=15 Hz, 2H), 3.56-3.52 (m, 1H), 3.43-3.39 (m, 1H), 2.28 (s, 3H).

Examples 33.1-33.4

5-{[4-(3-{[4-(Difluoromethyl)pyrimidin-2-yl]amino}-5-methylphenyl)-1H-pyrazol-1-yl]methyl}-4-(hydroxymethyl)-1,3-oxazolidin-2-one (Stereoisomers 1, 2, 3, and 4)

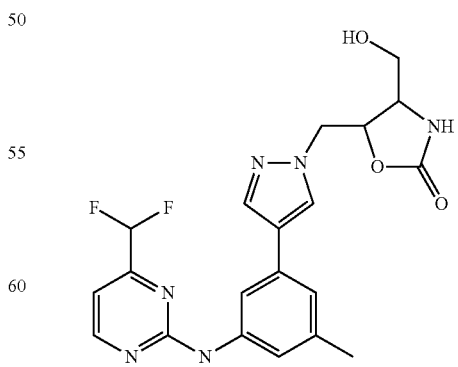

Step 1:
Benzyl bromide (8.0 g, 47 mmol) was added over a period of 30 minutes to a mixture of but-2-ene-1,4-diol (25.0 g, 281 mmol) and sodium hydride (2.2 g, 94 mmol) in DMF (100 mL) at 0° C. The mixture was stirred for 16 hours at room temperature. The mixture was then diluted with saturated aqueous ammonium chloride and extracted with ethyl acetate. The organic layer was dried over sodium sulfate, filtered, and concentrated under reduced pressure to afford the crude product residue. The crude product residue was purified by silica gel chromatography (methanol/ethyl acetate) to afford (2Z)-4-(benzyloxy)but-2-en-1-ol. $^1$H NMR (400 MHz, CD$_3$OD) δ 7.34-7.27 (m, 5H), 5.75-5.64 (m, 2H), 4.50 (s, 2H), 4.12-4.09 (m, 4H).

Step 2:

Sodium hydride (53 mg, 2.4 mmol) was added to a solution of (2Z)-4-(benzyloxy)but-2-en-1-ol (2.0 g, 11 mmol) in THF (50 mL) at 0° C. 2,2,2-trichloroacetonitrile (1.63 g, 12 mmol) was added dropwise to the reaction mixture at 0° C. over a period of 30 minutes. The reaction mixture was stirred at room temperature for an additional 2 hours. The reaction mixture was concentrated under reduced pressure and then diluted with decahydronaphthalene (35.8 g, 259 mmol). The mixture was stirred and heated to 200° C. for 5 hours. The reaction mixture was cooled to ambient temperature, diluted with water, and extracted with ethyl acetate. The organic layer was dried over sodium sulfate, filtered, and concentrated under reduced pressure to afford the crude product residue. The crude product residue was purified by silica gel chromatography (ethyl acetate/petroleum ether) to give N-[1-(benzyloxy)but-3-en-2-yl]-2,2,2-trichloroacetamide. $^1$H NMR (400 MHz, CDCl$_3$) δ 7.38-7.11 (m, 6H), 5.93-5.86 (m, 1H), 5.34-5.27 (m, 2H), 4.60-4.58 (m, 3H), 3.66-3.61 (m, 2H).

Step 3:

A mixture of N-[1-(benzyloxy)but-3-en-2-yl]-2,2,2-trichloroacetamide (7.5 g, 23 mmol) and sodium hydroxide (4.0 M in H$_2$O, 40 mL, 160 mmol) was stirred and heated to 80° C. for 5 hours. The reaction mixture was cooled to ambient temperature, diluted with water, and extracted with ethyl acetate. The organic layer was separated and extracted with hydrochloric acid (2N). The aqueous layer was concentrated under reduced pressure to afford 1-(benzyloxy)but-3-en-2-amine hydrochloride. MS ESI calc'd. for C$_{11}$H$_{16}$NO [M+H]$^+$ 178. found 178. $^1$H NMR (400 MHz, DMSO-d$_6$) δ 8.38 (s, 2H), 7.37-7.28 (m, 5H), 5.89-5.80 (m, 1H), 5.44-5.32 (m, 2H), 4.57-4.50 (m, 2H), 3.99 (s, 1H), 3.62-3.55 (m, 2H).

Step 4:

Benzyl carbonochloridate (4.7 g, 27.4 mmol) was added dropwise over a period of 30 minutes to a mixture of 1-(benzyloxy)but-3-en-2-amine hydrochloride (3.9 g, 18 mmol) and Hunig's base (10.0 mL, 54.8 mmol) in acetonitrile (100 mL) at 0° C. The reaction mixture was stirred at room temperature for 16 hours. The reaction mixture was diluted with water and extracted with ethyl acetate. The organic layer was dried over sodium sulfate, filtered, and concentrated under reduced pressure to afford the crude product residue. The crude product residue was purified by silica gel chromatography (ethyl acetate/petroleum ether) to afford benzyl [1-(benzyloxy)but-3-en-2-yl]carbamate. MS ESI calc'd. for C$_{19}$H$_{22}$NO$_3$ [M+H]$^+$ 312. found 312. $^1$H NMR (300 MHz, CD$_3$OD) δ 7.34-7.25 (m, 10H), 5.87-5.79 (m, 1H), 5.25-5.08 (m, 4H), 4.51 (s, 2H), 4.38-4.36 (m, 1H), 3.54-3.44 (m, 2H).

Step 5:

A mixture of benzyl [1-(benzyloxy)but-3-en-2-yl]carbamate (3.0 g, 9.6 mmol) and iodine (4.9 g, 19 mmol) in dichloromethane (200 mL) was stirred at 20° C. for 16 hours. The reaction mixture was diluted with aqueous sodium thiosulfate and extracted with ethyl acetate. The organic layer was dried over sodium sulfate, filtered, and concentrated under reduced pressure to give the crude product residue. The crude product residue was purified by silica gel chromatography (ethyl acetate/petroleum ether) to give 4-[(benzyloxy)methyl]-5-(iodomethyl)-1,3-oxazolidin-2-one. MS ESI calc'd. for C$_{12}$H$_{15}$INO$_3$ [M+H]$^+$ 348. found 348. $^1$H NMR (300 MHz, CDCl$_3$) δ 7.40-7.27 (m, 5H), 5.53 (s, 1H), 4.57 (s, 2H), 4.37-4.34 (m, 1H), 3.82-3.80 (m, 1H), 3.67-3.51 (m, 2H), 3.38-3.32 (m, 2H).

Step 6:

A mixture of 4-bromo-1H-pyrazole (2.33 g, 15.9 mmol), 4-[(benzyloxy)methyl]-5-(iodomethyl)-1,3-oxazolidin-2-one (5.00 g, 14.4 mmol), and potassium phosphate tribasic (9.17 g, 43.3 mmol) in DMF (50 mL) was stirred and heated to 90° C. for 16 hours. The reaction mixture was cooled to ambient temperature, diluted with water, and extracted with ethyl acetate. The organic layer was dried over sodium sulfate, filtered, and concentrated under reduced pressure to afford the crude product residue. The crude product residue was purified by reverse phase HPLC to afford 4-[(benzyloxy)methyl]-5-[(4-bromo-1H-pyrazol-1-yl)methyl]-1,3-oxazolidin-2-one. MS ESI calc'd. for C$_{15}$H$_{12}$BrN$_3$O$_3$ [M+H]$^+$ 366 and 368. found 366 and 368. $^1$H NMR (400 MHz, DMSO-d$_6$) δ 7.99 (s, 1H), 7.88 (s, 1H), 7.60 (s, 1H), 7.38-7.29 (m, 5H), 4.63-4.60 (m, 1H), 4.54 (s, 2H), 4.39 (d, J=5.6 Hz, 2H), 3.80-3.76 (m, 1H), 3.41 (d, J=4.8 Hz, 2H).

Step 7:

A mixture of 4-(difluoromethyl)-N-[3-methyl-5-(4,4,5,5-tetramethyl-1,3,2-dioxaborolan-2-yl)phenyl]pyrimidin-2-amine (111 mg, 0.307 mmol), 4-[(benzyloxy)methyl]-5-[(4-bromo-1H-pyrazol-1-yl)methyl]-1,3-oxazolidin-2-one (109 mg, 0.298 mmol), potassium phosphate tribasic (239 mg, 1.13 mmol), and Pd(dbpf)Cl$_2$ (4 mg, 0.006 mmol) in dioxane (2 mL) was stirred and heated to 110° C. in a microwave reactor for 30 minutes. The reaction mixture was diluted with water and extracted with ethyl acetate. The organic layer was dried over sodium sulfate, filtered, and concentrated under reduced pressure to afford the crude product residue. The crude product residue was purified by prep-TLC (ethyl acetate/petroleum ether) to give 4-[(benzyloxy)methyl]-5-{[4-(3-{[4-(difluoromethyl)pyrimidin-2-yl]amino}-5-methylphenyl)-1H-pyrazol-1-yl]methyl}-1,3-oxazolidin-2-one. MS ESI calc'd. for C$_{27}$H$_{27}$F$_2$N$_6$O$_3$ [M+H]$^+$ 521. found 521. $^1$H NMR (400 MHz, CD$_3$OD) δ 8.60 (d, J=4.8 Hz, 1H), 7.99 (s, 1H), 7.84 (s, 1H), 7.77 (s, 1H), 7.40 (s, 1H), 7.38-7.26 (m, 5H), 7.15 (s, 1H), 7.05 (d, J=4.8 Hz, 1H), 6.56 (t, J=54.4 Hz, 1H), 4.88-4.76 (m, 1H), 4.54 (s, 2H), 4.48-4.46 (m, 2H), 3.94-3.92 (m, 1H), 3.48-3.46 (m, 2H), 2.35 (s, 3H).

Step 8:

A solution of 4-[(benzyloxy)methyl]-5-{[4-(3-{[4-(difluoromethyl)pyrimidin-2-yl]amino}-5-methylphenyl)-1H-pyrazol-1-yl]methyl}-1,3-oxazolidin-2-one (100 mg, 0.199 mmol) in TFA (1.0 mL) was stirred and heated at 120° C. in a microwave reactor for 40 minutes. The reaction mixture was concentrated under reduced pressure to afford (5-{[4-(3-{[4-(difluoromethyl)pyrimidin-2-yl]amino}-5-methylphenyl)-1H-pyrazol-1-yl]methyl}-2-oxo-1,3-oxazolidin-4-yl)methyl trifluoroacetate, which was used in the next step without further purification. MS ESI calc'd. for C$_{22}$H$_{20}$F$_5$N$_6$O$_4$ [M+H]$^+$ 527. found 527.

Step 9:

A solution of (5-{[4-(3-{[4-(difluoromethyl)pyrimidin-2-yl]amino}-5-methylphenyl)-1H-pyrazol-1-yl]methyl}-2-oxo-1,3-oxazolidin-4-yl)methyl trifluoroacetate (80 mg, 0.15 mmol) and potassium carbonate (80 mg, 0.58 mmol) in methanol (3 mL) was stirred at 25° C. for 30 minutes. The reaction mixture was diluted with water and extracted with ethyl acetate. The organic layer was dried over sodium sulfate, filtered, and concentrated under reduced pressure to afford the crude product residue. The crude product residue was purified by prep-TLC (ethyl acetate) to give racemic 5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one. MS ESI calc'd. for $C_{20}H_{21}F_2N_6O_3$ [M+H]$^+$ 431. found 431.

Racemic 5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one was separated by SFC (Chiralcel OJ-H, 5um; 5-40% [methanol with 0.05% diethylamine] in $CO_2$) to afford 5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one (peaks 1, 2, 3, and 4).

Example 33.1

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one (Peak 1, first eluting). MS ESI calc'd. for $C_{20}H_{21}F_2N_6O_3$ [M+H]$^+$ 431. found 431. $^1$H NMR (300 MHz, CD$_3$OD) δ 8.59 (d, J=5.1 Hz, 1H), 7.97 (s, 1H), 7.85 (s, 1H), 7.77 (s, 1H), 7.34 (s, 1H), 7.06 (s, 1H), 7.00 (d, J=5.1 Hz, 1H), 6.56 (t, J=54.4 Hz, 1H), 4.51-4.47 (m, 1H), 4.44-4.30 (m, 1H), 4.28-4.20 (m, 2H), 3.92-3.86 (m, 2H), 2.34 (s, 3H).

Example 33.2

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one (Peak 2, second eluting). MS ESI calc'd. for $C_{20}H_{21}F_2N_6O_3$ [M+H]$^+$ 431. found 431. $^1$H NMR (300 MHz, CD$_3$OD) δ 8.56 (d, J=5.1 Hz, 1H), 7.96 (s, 1H), 7.83 (s, 1H), 7.72 (s, 1H), 7.32 (s, 1H), 7.03 (s, 1H), 6.97 (d, J=5.1 Hz, 1H), 6.54 (t, J=54.4 Hz, 1H), 4.79-4.78 (m, 1H), 4.45-4.44 (m, 2H), 3.79-3.77 (m, 1H), 3.56-3.54 (m, 2H), 2.31 (s, 3H).

Example 33.3

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one (Peak 3, third eluting). MS ESI calc'd. for $C_{20}H_{21}F_2N_6O_3$ [M+H]$^+$ 431. found 431. $^1$H NMR (300 MHz, CD$_3$OD) δ 8.60 (d, J=4.8 Hz, 1H), 7.98 (s, 1H), 7.85 (s, 1H), 7.79 (s, 1H), 7.36 (s, 1H), 7.06 (s, 1H), 7.00 (d, J=4.8 Hz, 1H), 6.56 (t, J=54.4 Hz, 1H), 4.51-4.47 (m, 1H), 4.44-4.20 (m, 3H), 3.92-3.86 (m, 2H), 2.35 (s, 3H).

Example 33.4

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one (Peak 4, fourth eluting). MS ESI calc'd. for $C_{20}H_{21}F_2N_6O_3$ [M+H]$^+$ 431. found 431. $^1$H NMR (300 MHz, CD$_3$OD) δ 8.60 (d, J=5.1 Hz, 1H), 8.00 (s, 1H), 7.85 (s, 1H), 7.76 (s, 1H), 7.37 (s, 1H), 7.06 (s, 1H), 7.00 (d, J=5.1 Hz, 1H), 6.57 (t, J=54.4 Hz, 1H), 4.79-4.70 (m, 1H), 4.49-4.44 (m, 2H), 3.81-3.71 (m, 1H), 3.55-3.44 (m, 2H), 2.34 (s, 3H).

Example 34.1 and 34.2

5-[4-(6-{[4-(Difluoromethyl)pyridin-2-yl]amino}-4-methylpyridin-2-yl)-1H-pyrazol-1-yl]-5-ethyl-1,3-oxazolidin-2-one (Peak 1, first eluting) and 5-[4-(6-{[4-(difluoromethyl)pyridin-2-yl]amino}-4-methylpyridin-2-yl)-1H-pyrazol-1-yl]-5-ethyl-1,3-oxazolidin-2-one (Peak 2, second eluting)

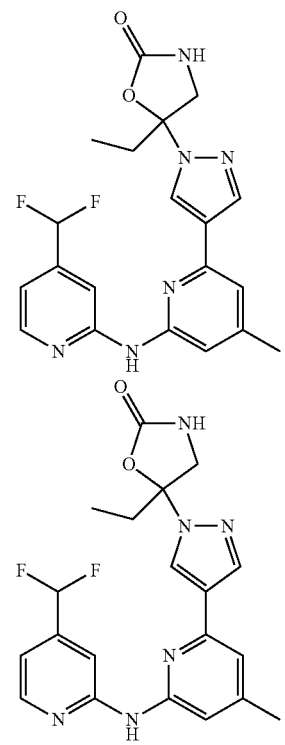

Step 1:
Benzyl carbonochloridate (22.8 mL, 167 mmol) was added to a solution of (2E)-but-2-en-1-amine hydrochloride (12.0 g, 112 mmol) and Hunig's base (43.2 g, 330 mmol) in acetonitrile (120 mL) under a nitrogen atmosphere at 0° C. The reaction mixture was stirred under nitrogen at 0° C. for 1 hour and then allowed to warm to ambient temperature. After 3 hours, the reaction mixture was diluted with brine (50 mL) and was extracted with ethyl acetate (3×50 mL). The organic layers were combined, dried over sodium sulfate, filtered, and concentrated under reduced pressure to afford the crude product residue. The crude product residue was purified by silica gel chromatography (ethyl acetate/petroleum ether) to give benzyl (2E)-but-2-en-1-ylcarbamate. MS ESI calc'd. for $C_{12}H_{16}NO_2$ [M+H]$^+$ 206. found 206.

Step 2:
Iodine (56.4 g, 200 mmol) was added to a solution of benzyl (2E)-but-2-en-1-ylcarbamate (20.4 g, 100 mmol) in DCM (700 mL) under a nitrogen atmosphere at 20° C. The reaction mixture was stirred under nitrogen at 20° C. for 12 hours. The reaction mixture was quenched with saturated aqueous ammonium chloride (100 mL) and was extracted with dichloromethane (3×100 mL). The organic layers were combined, dried over sodium sulfate, filtered, and concentrated under reduced pressure to afford the crude product residue. The crude product residue was purified by silica gel chromatography (ethyl acetate/petroleum ether) to give a mixture of 5-(1-iodoethyl)-1,3-oxazolidin-2-one and 5-iodo-6-methyl-1,3-oxazinan-2-one. MS ESI calc'd. for $C_5H_9INO_2$ [M+H]$^+$ 242. found 242. $^1$H NMR (400 MHz, CDCl$_3$) δ 5.18 (br s, 1H), 4.58-4.52 (m, 1H), 4.16-4.12 (m, 1H), 3.80-3.76 (m, 1H), 3.43-3.39 (m, 1H), 2.00 (d, J=4.0 Hz, 3H).

Step 3:

Cesium carbonate (320 mg, 0.99 mmol) and 5-(1-iodoethyl)-1,3-oxazolidin-2-one (160 mg, 0.66 mmol) were added to a solution of N-[4-(difluoromethyl)pyridin-2-yl]-4-methyl-6-(1H-pyrazol-4-yl)pyridin-2-amine (100 mg, 0.33 mmol) in DMF (1 mL) under a nitrogen atmosphere at 20° C. The mixture was stirred under nitrogen and heated to 80° C. for 12 hours. The reaction mixture was cooled to 20° C. and then diluted with brine (50 mL) and extracted with ethyl acetate (3×50 mL). The organic layers were combined, dried over sodium sulfate, filtered, and concentrated under reduced pressure to afford the crude product residue. The crude product residue was purified by prep-TLC (ethyl acetate) to afford racemic 5-[4-(6-{[4-(difluoromethyl)pyridin-2-yl]amino}-4-methylpyridin-2-yl)-1H-pyrazol-1-yl]-5-ethyl-1,3-oxazolidin-2-one. MS ESI calc'd. for $C_{20}H_{21}F_2N_6O_2$ [M+H]$^+$ 415. found 415. Racemic 5-[4-(6-{[4-(difluoromethyl)pyridin-2-yl]amino}-4-methylpyridin-2-yl)-1H-pyrazol-1-yl]-5-ethyl-1,3-oxazolidin-2-one was separated by SFC (Chiralpak AD, 3 um particle size; 60% [ethanol with 0.05% diethylamine] in CO$_2$) to afford:

Example 34.1

5-[4-(6-{[4-(difluoromethyl)pyridin-2-yl]amino}-4-methylpyridin-2-yl)-1H-pyrazol-1-yl]-5-ethyl-1,3-oxazolidin-2-one (Isomer 1, first eluting). MS ESI calc'd. for $C_{20}H_{21}F_2N_6O_2$ [M+H]$^+$ 415. found 415. $^1$H NMR (400 MHz, CD$_3$OD) δ 8.43 (s, 2H), 8.34-8.33 (m, 1H), 8.17 (s, 1H), 7.13 (s, 1H), 7.05 (s, 1H), 7.03-7.00 (m, 1H), 6.86 (t, J=54.4 Hz, 1H), 4.32 (d, J=10.4 Hz, 1H), 3.90 (d, J=10.4 Hz, 1H), 2.44-2.41 (m, 2H), 2.37 (s, 3H), 0.96 (t, J=7.2 Hz, 3H).

Example 34.2

5-[4-(6-{[4-(difluoromethyl)pyridin-2-yl]amino}-4-methylpyridin-2-yl)-1H-pyrazol-1-yl]-5-ethyl-1,3-oxazolidin-2-one (Isomer 2, second eluting): MS ESI calc'd. for $C_{20}H_{21}F_2N_6O_2$ [M+H]$^+$ 415. found 415. $^1$H NMR (400 MHz, CD$_3$OD) δ 8.43 (s, 2H), 8.34-8.33 (m, 1H), 8.17 (s, 1H), 7.14 (s, 1H), 7.05 (s, 1H), 7.03-7.02 (m, 2H), 6.86 (t, J=54.4 Hz, 1H), 4.32 (d, J=10.4 Hz, 1H), 3.90 (d, J=10.4 Hz, 1H), 2.44-2.41 (m, 2H), 2.37 (s, 3H), 0.96 (t, J=7.2 Hz, 3H).

Example 35

General Procedure for a Compound of Formula (A)

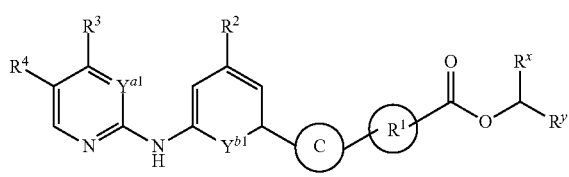

This general procedure describes the procedure for conversion of (A1) to (A) as shown in Scheme 16. To a mixture of compound of formula (A1) (1 mmol), 1° or 2° alcohol (5 mmol), and triphenylphosphine (resin-bound, 1.6 mmol/g loading, 2 mmol) in tetrahydrofuran is added di-tert-butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3×). The filtrate is concentrated under reduced pressure to afford the crude residue TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by column chromatography on silica gel (ethyl acetate/hexanes, linear gradient) to afford the product residue. The residue is lyophilized from acetonitrile and water to afford a compound of formula (A).

The following compounds could be prepared according to procedures which are analogous to those described in Example 35.

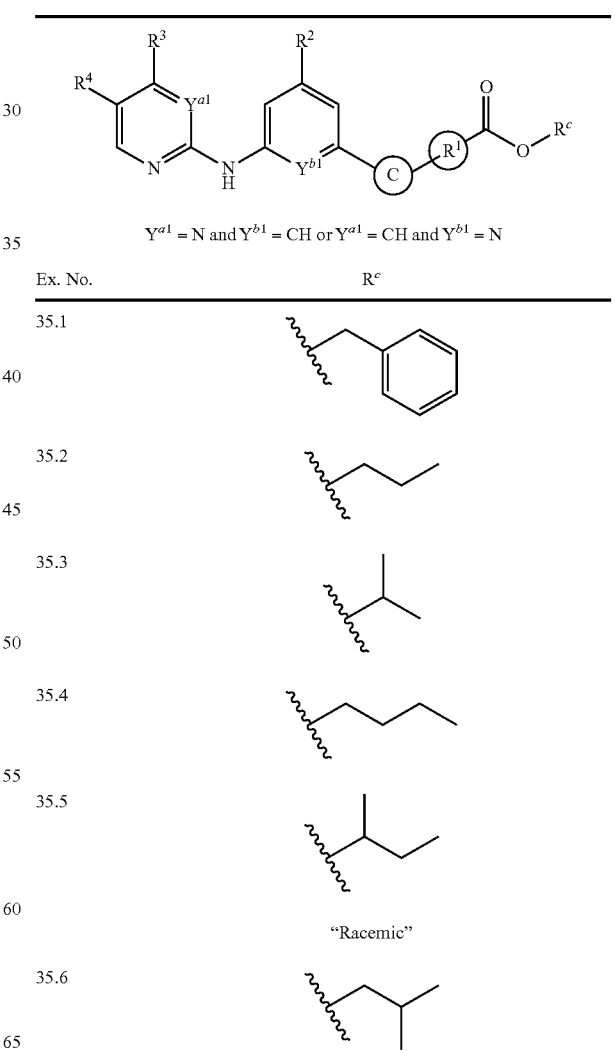

-continued

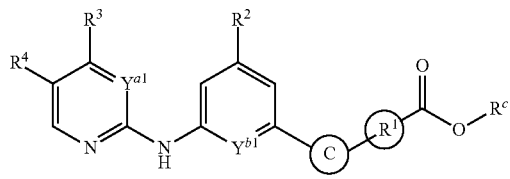

$Y^{a1}$ = N and $Y^{b1}$ = CH or $Y^{a1}$ = CH and $Y^{b1}$ = N

| Ex. No. | $R^c$ |
|---|---|
| 35.7 | 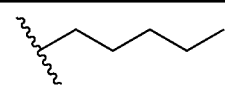 |
| 35.8 |  |
| 35.9 | 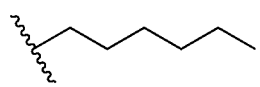 [SMILES: *CCCCCC] |
| 35.10 | 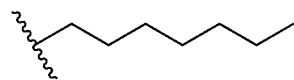 [SMILES: *CCCCCCC] |
| 35.11 | 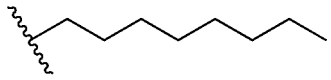 [SMILES: *CCCCCCCC] |
| 35.12 | 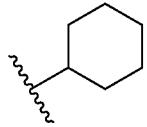 [SMILES: *C1CCCCC1] |
| 35.13 | 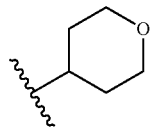 [SMILES: *C1CCOCC1] |
| 35.14 | 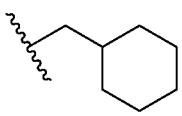 [SMILES: *CC1CCCCC1] |
| 35.15 | 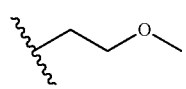 [SMILES: *CCOC] |
| 35.16 | 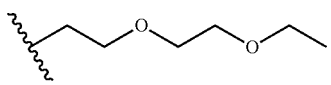 [SMILES: *CCOCCOCC] |
| 35.17 | 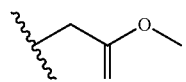 |
| 35.18 | 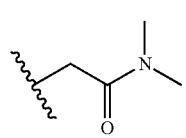 [SMILES: *CC(=O)N(C)C] |

-continued

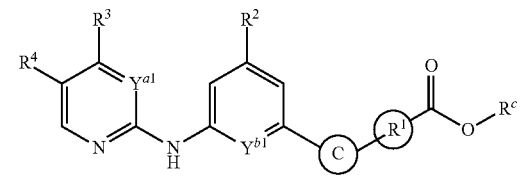

$Y^{a1}$ = N and $Y^{b1}$ = CH or $Y^{a1}$ = CH and $Y^{b1}$ = N

| Ex. No. | $R^c$ |
|---|---|
| 35.19 | 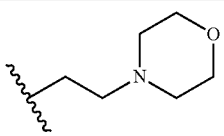 [SMILES: *CCN1CCOCC1] |
| 35.20 | 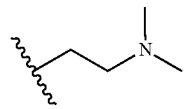 [SMILES: *CCN(C)C] |
| 35.21 | 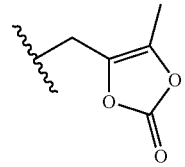 [SMILES: *Cc1oc(=O)oc1C] |

Example 36

General Procedure for the Preparation the Compound of Formula (C) as Shown in Scheme 16

$Y^{a1}$=N and $Y^{b1}$=CH or $Y^{a1}$=CH and $Y^{b1}$=N

This general procedure describes the procedure for conversion of (A1) to (C) as shown in Scheme 16. A mixture of compound of formula (A1) (1.0 mmol), potassium carbonate (2.0 mmol), and sodium iodide (0.50 mmol) in DMF is stirred at 20° C. After 30 minutes, alkyl halide of formula (C1) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography (ethyl acetate/hexanes, linear gradient) to afford the product residue. The residue is lyophilized from acetonitrile and water to afford a compound of formula (C).

The following compounds could be prepared according to procedures, which are analogous to those described in Example 36.

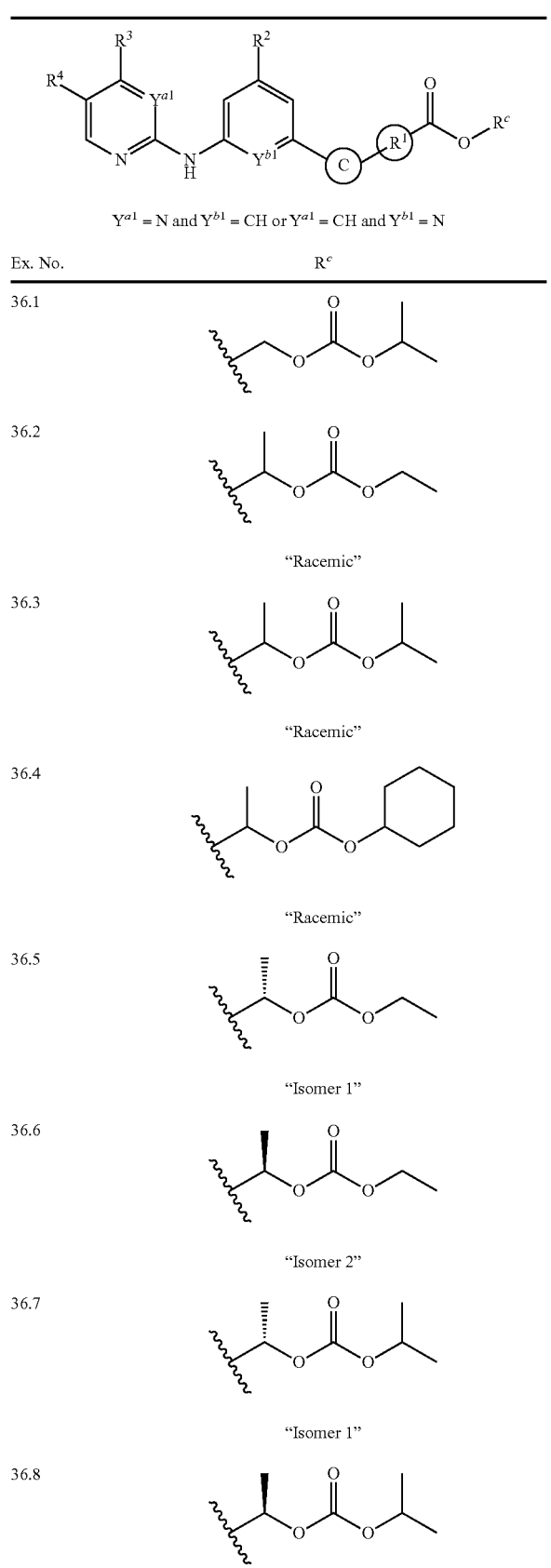

$Y^{a1}$ = N and $Y^{b1}$ = CH or $Y^{a1}$ = CH and $Y^{b1}$ = N

| Ex. No. | $R^c$ |
|---|---|
| 36.1 | |
| 36.2 | "Racemic" |
| 36.3 | "Racemic" |
| 36.4 | "Racemic" |
| 36.5 | "Isomer 1" |
| 36.6 | "Isomer 2" |
| 36.7 | "Isomer 1" |
| 36.8 | "Isomer 2" |

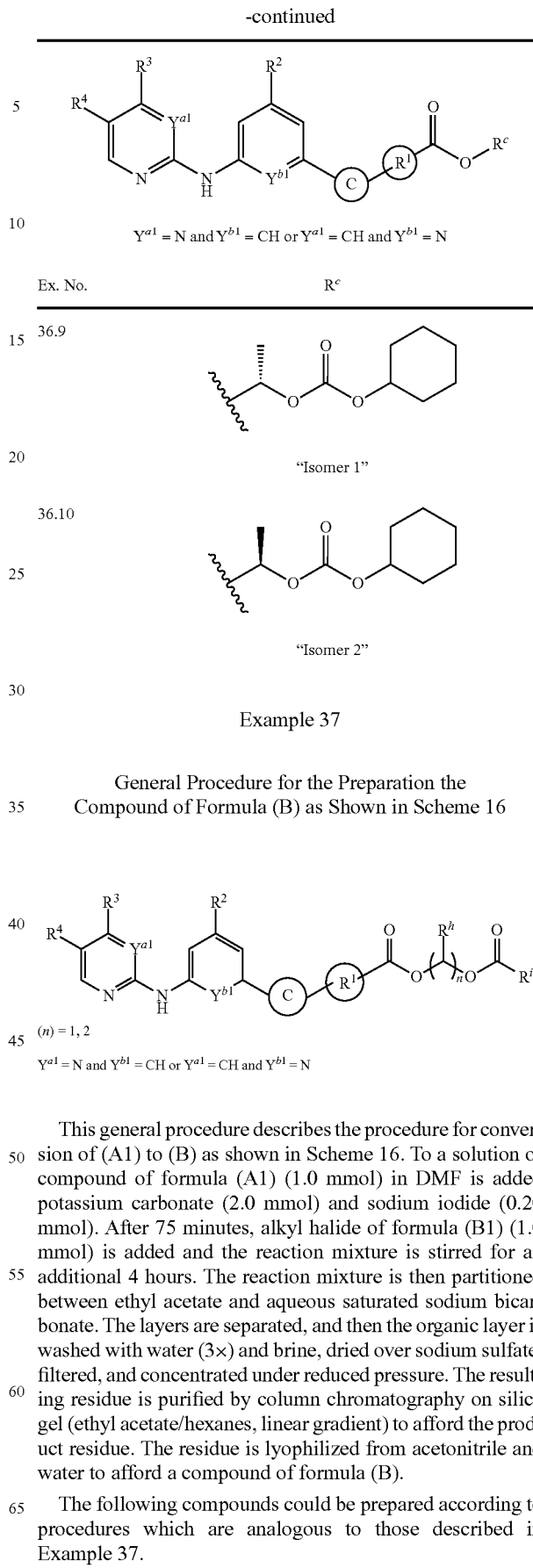

$Y^{a1}$ = N and $Y^{b1}$ = CH or $Y^{a1}$ = CH and $Y^{b1}$ = N

| Ex. No. | $R^c$ |
|---|---|
| 36.9 | "Isomer 1" |
| 36.10 | "Isomer 2" |

Example 37

General Procedure for the Preparation the Compound of Formula (B) as Shown in Scheme 16

(n) = 1, 2

$Y^{a1}$ = N and $Y^{b1}$ = CH or $Y^{a1}$ = CH and $Y^{b1}$ = N

This general procedure describes the procedure for conversion of (A1) to (B) as shown in Scheme 16. To a solution of compound of formula (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by column chromatography on silica gel (ethyl acetate/hexanes, linear gradient) to afford the product residue. The residue is lyophilized from acetonitrile and water to afford a compound of formula (B).

The following compounds could be prepared according to procedures which are analogous to those described in Example 37.

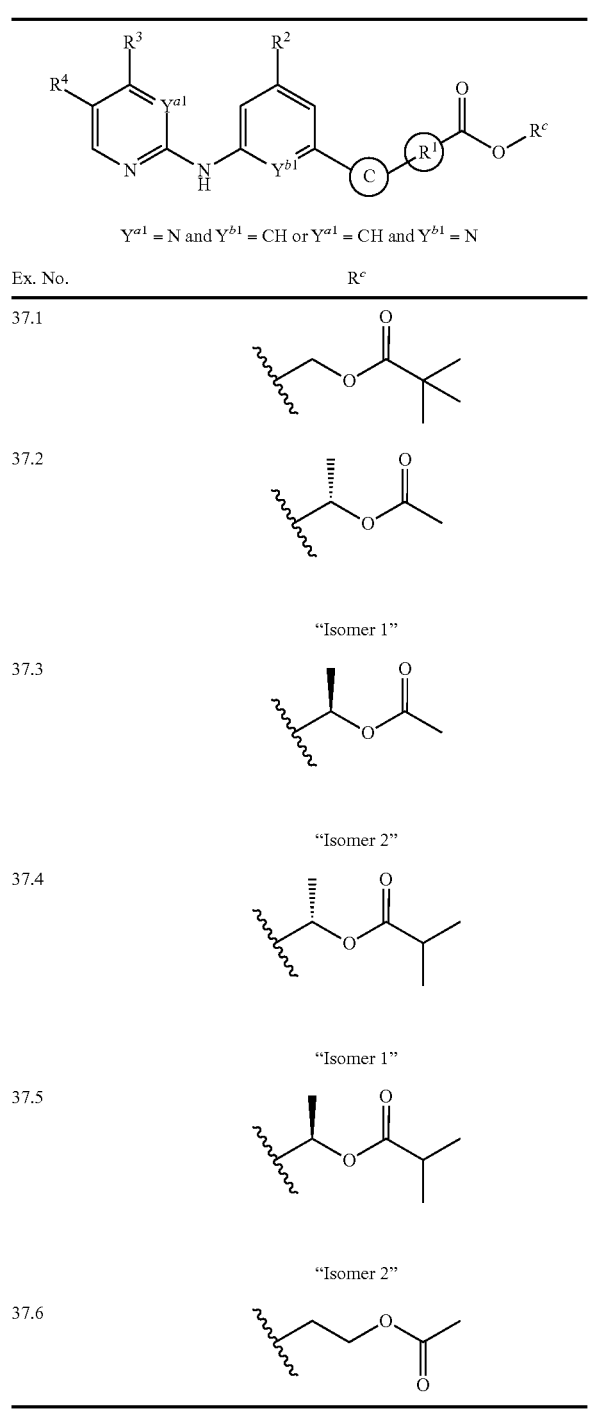

| Ex. No. | $R^c$ |
|---|---|
| 37.1 | |
| 37.2 | |
| 37.3 | "Isomer 1" |
| 37.4 | "Isomer 2" |
| 37.5 | "Isomer 1" |
| | "Isomer 2" |
| 37.6 | |

What is claimed is:
1. A compound of Formula I:

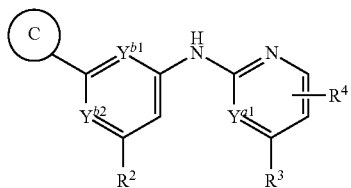

or a pharmaceutically acceptable salt thereof, wherein:

C is:

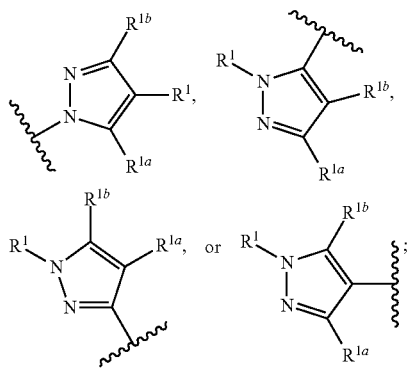

ring a is

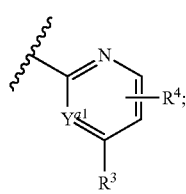

ring b is

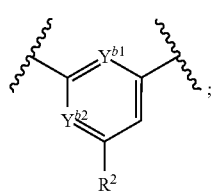

$Y^{a1}$ is independently CH or N;
$Y^{b1}$ and $Y^{b2}$ are independently CH or N, such that $Y^{a1}$ and $Y^{b1}$ are not both simultaneously C or N;
$R^{1a}$ and $R^{1b}$ are independently: H, halogen, $C_1$-$C_3$-alkyl, or $C_1$-$C_3$-fluoroalkyl;
$R^1$ is:
  H;
  halogen;
  $C_1$-$C_6$-alkyl, optionally with one to four substituents selected from: CN, OH, oxo, $NH_2$, $CF_3$, $C_1$-$C_3$-alkyl, and $C_1$-$C_3$-alkoxyl;
  $(CR^aR^b)_n CO_2R^c$;
  $(CR^aR^b)_n CONR^dR^e$;
  $(CHR^a)_n NHCONR^dR^e$;
  $(CHR^a)_n NHCO_2R^c$;
  $(CHR^a)_n NHCOR^c$;
  $(CHR^a)_n CONHSO_2R^d$;
  $(CHR^a)_n SO_2R^d$;
  $(CHR^a)_n SO_2NR^dR^e$;
  $(CHR^a)_n NHSO_2R^d$;
  $(CR^aR^b)_n$-heterocyclyl; wherein heterocyclyl is as defined below;
  $(CHR^a)_p$—C(O)-heterocyclyl; wherein heterocyclyl is as defined below;

$(CR^aR^b)_n$-carbocyclyl; wherein carbocyclyl is as defined below;
$CR^a(\text{carbocyclyl})_2$; wherein carbocyclyl is as defined below;
$(CR^aR^b)_n$-aryl; wherein aryl is as defined below;
$(CR^aR^b)_n$—O-carbocyclyl; wherein carbocyclyl is as defined below;
$(CR^aR^b)_n$—O-aryl; wherein aryl is as defined below;
or optionally, $R^1$ and $R^{1a}$, $R^1$ and $R^{1b}$, $R^{1a}$ and $R^{1b}$, when present on adjacent pyrazolyl ring atoms, taken together can form a 5- or 6-membered ring with the atoms to which they are attached; the ring may contain one or two heteroatoms selected from N, O, or S including the nitrogens of the pyrazole ring to which the ring is fused and the ring may be saturated, unsaturated or aromatic and may be optionally substituted with one to three substituents selected from: $C_1$-$C_3$-alkoxyl and $C_1$-$C_3$-alkyl;

Heterocyclyl is a 4-, 5-, 6-, or 7-membered monocyclic ring or 8-, 9-, 10-membered bicyclic ring, or 13- or 14-membered tricyclic ring; the monocyclic, bicyclic or tricyclic ring can be saturated, unsaturated or aromatic, containing one to four heteroatoms selected from O, N, or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, $C_{3-6}$cycloalkyl, $(CR^aR^b)_nCO_2R^c$, $(CR^aR^b)_nCONR^dR^e$, $(CHR^a)_n NHCONR^dR^e$, $(CHR^a)NHCO_2R^c$, and $(CHR^a)_p$ —C(O)-heterocyclyl; or alternatively 2 substituents geminally substituted on a common ring carbon atom of said heterocyclyl may together with the common ring carbon atom form a $C_{3-6}$ spirocyclic ring;

Carbocyclyl is a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated and that ring being isolated or fused to one or two such rings or to a benzene ring; the carbocyclyl may optionally be substituted with one to four substituents selected from hydroxyl, $C_1$-$C_3$-alkyl, $C_1$-$C_3$-alkoxyl, $(CR^aR^b)_nCO_2R^c$, $(CR^aR^b)_nCONR^dR^e$, and a spiro-linked —$OCH_2CH_2O$—;

Aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, $(CR^aR^b)_n CO_2R^c$; and $(CR^aR^b)_n CONR^dR^e$;

$R^2$ is H, halogen, $C_1$-$C_3$-alkyl, $C_1$-$C_3$-haloalkyl, $C_3$-$C_7$-cycloalkyl, heterocyclyl, $NR^dR^e$, $CONR^dR^e$, $NHCONR^dR^e$, or $NO_2$;

$R^3$ is H or $C_1$-$C_4$-alkyl, $C_1$-$C_3$-fluoroalkyl, $C_1$-$C_3$-alkoxyl, optionally substituted with one to three substituents selected from hydroxyl; —O—$(CH_2)_2$—O—$Si(CH_3)_3$; $C_3$-$C_6$-cycloalkyl and pyridyl;

$R^4$ is H, halogen, or $C_1$-$C_3$-alkyl;

$R^a$ and $R^b$ are independently: H, OH, CN, $NH_2$, cyclopropyl, $C_1$-$C_3$-fluoroalkyl, or $C_1$-$C_3$-alkyl optionally substituted with hydroxyl;

$R^c$ is: H, $C_{1-6}$alkyl, $C_{3-6}$cycloalkyl, -M-$R^{CH}$, —$(CH_2)_{1-2}$—$R^f$, —$(CH_2)_2$—O—$(CH_2)_2$—$R^f$, —$(CH_2)_2$—$R^g$, —$CHR^hOCO_2R^i$, or —$(CHR^h)_{1-2}OC(O)R^i$;

$R^d$ and $R^e$ are independently: H, $C_1$-$C_3$-alkoxyl or $C_1$-$C_6$-alkyl, optionally substituted with one to four substituents selected from: CN, OH, oxo, $NH_2$, halogen, $CO_2R^c$, $CONH_2$, $C_1$-$C_3$-alkoxyl, $CO_2R^c$; aryl, carbocyclyl, or heterocyclyl, as defined above;

$R^f$ is $CO_2R^{f1}$, CN, $C(O)N(R^{f2})_2$, —$OC(O)R^{f1}$, or $C_{1-2}$alkoxyl;

$R^{f1}$ is $C_{1-4}$alkyl; and $R^{f2}$ is H or $C_{1-4}$alkyl;

$R^g$ is OH, $C_{1-4}$alkoxyl, $NH_2$, $NH(C_{1-4}$alkyl) or $N(C_{1-4}$alkyl)$_2$;

$R^h$ is H or $C_{1-4}$alkyl;

$R^i$ is $C_{1-6}$alkyl, $C_{3-6}$cycloalkyl, or phenyl;

M is a bond or —$(CH_2)_{1-3}$—;

$R^{CH}$ is (a) aryl, aryl is phenyl or naphthalyl, optionally substituted with one to three groups independently selected from halo, $C_{1-4}$alkyl, or $C_{1-4}$alkoxy; (b) carbocyclyl, carbocyclyl is a 5-, 6- or 7-membered monocyclic carbon ring, that is saturated or partially unsaturated and the carbocyclyl is optionally substituted with one to three substituents independently selected from halo, $C_{1-4}$alkyl, or $C_{1-4}$alkoxy; or (c) a 5- to 6-membered monocyclic heterocyclyl containing one or two heteroatoms independently selected from the group consisting of N and O, and the heterocyclyl is optionally substituted with one or two substituents independently selected from the group consisting of: oxo and $C_{1-3}$ alkyl;

n is 0, 1, 2, 3 or 4; and p is 0 or 1.

2. The compound of claim 1 or a pharmaceutically acceptable salt thereof wherein:

$R^{1a}$ and $R^{1b}$ are independently: H, Cl, F, $CH_3$, or $CF_3$;

$R^2$ is H, or $CH_3$;

$R^3$ is H, Cl, F, $CH_3$, $CH(CH_3)_2$, cyclopropyl, $OCH(CH_3)_2$, $OCH_3$, $OCHFCH_3$, $OCH_2CH_2OH$, $CHF_2$, or $CF_3$;

$R^4$ is H, Cl or F; and all other substituents are as defined in claim 1.

3. The compound of claim 1 or a pharmaceutically acceptable salt thereof, wherein rings a and b are defined as follows:

a) $Y^{a1}$ is N; and $Y^{b1}$ and $Y^{b2}$ are CH;

b) $Y^{b1}$ is N; and $Y^{a1}$ and $Y^{b2}$ are CH;

c) $Y^{a1}$ and $Y^{b2}$ are N; and $Y^{b1}$ is CH; or d) $Y^{b1}$ and $Y^{b2}$ are N; and $Y^{a1}$ is CH;

and all other substituents are as defined in claim 1.

4. The compound of claim 2 having the Formula Ia

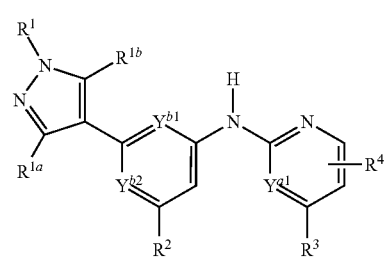

Ia wherein rings a and b are defined as follows:

a) $Y^{b1}$ and $Y^{b2}$ are N; and $Y^{a1}$ is CH; or b) $Y^{a1}$ and $Y^{b2}$ are N; and $Y^{b1}$ is CH;

or a pharmaceutically acceptable salt thereof.

5. The compound of claim 4, wherein $R^1$ is H; $C_1$-$C_6$-alkyl, optionally with one or more substituent selected from the group consisting of: CN, OH, oxo, $NH_2$, $CF_3$, $C_1$-$C_3$-alkyl, and $C_1$-$C_3$-alkoxyl; $(CR^aR^b)_nCO_2R^c$; $(CR^aR^b)_nCONR^dR^e$; $(CR^aR^b)_n$-heterocyclyl; or $(CR^aR^b)_n$-carbocyclyl; or a pharmaceutically acceptable salt thereof.

6. The compound of claim 1 having the Formula Ia(i)

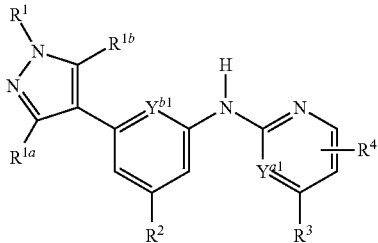

wherein rings a and b are defined as follows:
a) $Y^{a1}$ is N; and $Y^{b1}$ is CH; or
b) $Y^{b1}$ is N; and $Y^{a1}$ is CH;
or a pharmaceutically acceptable salt thereof.

7. The compound of claim 6 or a pharmaceutically acceptable salt thereof, wherein $R^1$ is H; $C_1$-$C_6$-alkyl, optionally with one or more substituent selected from the group consisting of: CN, OH, oxo, $NH_2$, $CF_3$, $C_1$-$C_3$-alkyl, and $C_1$-$C_3$-alkoxyl; $(CR^aR^b)_nCO_2R^c$; $(CR^aR^b)_nCONR^dR^e$; $(CR^aR^b)_n$-heterocyclyl; or $(CR^aR^b)_n$-carbocyclyl.

8. The compound of claim 7 or a pharmaceutically acceptable salt thereof, wherein $R^1$ is H; $C_1$-$C_6$-alkyl, optionally with one or more substituent selected from the group consisting of: CN, OH, oxo, $NH_2$, $CF_3$, $CH_3$ and $OCH_3$; $(CR^aR^b)_nCO_2R^c$; $(CR^aR^b)_nCONH_2$; $(CR^aR^b)_n$-heterocyclyl; or $(CR^aR^b)_n$-carbocyclyl; $R^a$ and $R^b$ are independently H, $CH_3$, or OH; and n is 0, 1, 2, 3 or 4.

9. The compound of claim 2 having the Formula Ib

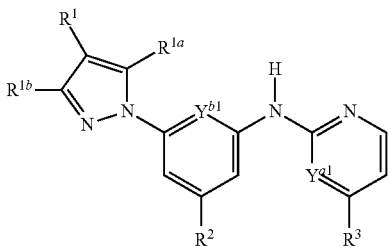

wherein rings a and b are defined as follows:
a) $Y^{a1}$ is N; and $Y^{b1}$ is CH; or
b) $Y^{b1}$ is N; and $Y^{a1}$ is CH;
or a pharmaceutically acceptable salt thereof.

10. The compound of claim 9 or a pharmaceutically salt thereof, wherein $R^1$ is H; $C_1$-$C_6$-alkyl, optionally with one or more substituent selected from the group consisting of: CN, OH, oxo, $NH_2$, $CF_3$, $C_1$-$C_3$-alkyl, and $C_1$-$C_3$-alkoxyl; $(CR^aR^b)_nCO_2R^c$; $(CR^aR^b)_nCONR^dR^e$; $(CR^aR^b)_n$-heterocyclyl; or $(CR^aR^b)_n$-carbocyclyl.

11. The compound of claim 2, wherein the compound of Formula I has the Formula Ic or Id

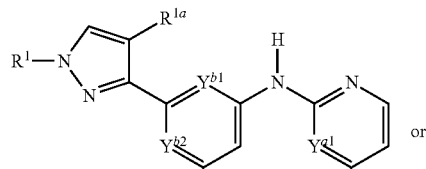

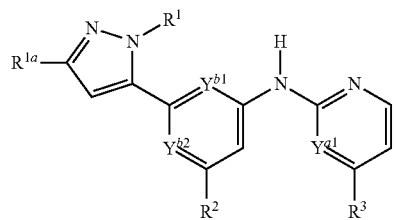

wherein rings a and b are defined as follows:
a) $Y^{a1}$ is N; and $Y^{b1}$ and $Y^{b2}$ is CH;
b) $Y^{b1}$ is N; and $Y^{a1}$ and $Y^{b2}$ are CH; or
c) $Y^{b1}$ and $Y^{b2}$ are N; and $Y^{a1}$ is CH;
or a pharmaceutically acceptable salt thereof.

12. The compound of claim 11 or a pharmaceutically acceptable salt thereof, wherein $R^1$ is H; $C_1$-$C_6$-alkyl, optionally with one or more substituent selected from the group consisting of: CN, OH, oxo, $NH_2$, $CF_3$, $C_1$-$C_3$-alkyl, or $C_1$-$C_3$-alkoxyl; $(CR^aR^b)_nCO_2R^c$; $(CR^aR^b)_nCONR^dR^e$; $(CR^aR^b)_n$-heterocyclyl; or $(CR^aR^b)_n$-carbocyclyl.

13. The compound of claim 1, or a pharmaceutically acceptable salt thereof, which is selected from the group consisting of:
N-(3-methyl-5-(pyrazolo[1,5-a]pyridin-3-yl)phenyl)-4-(trifluoromethyl)pyrimidin-2-amine;
3-[4-(3-methyl-5-{[4-(trifluoromethyl)-pyrimidin-2-yl]amino}-phenyl)-1H-pyrazol-1-yl]-propanoic acid;
N-[3-methyl-5-(1-methyl-1H-pyrazol-4-yl)phenyl]-4-(trifluoromethyl)-pyrimidin-2-amine;
tert-butyl 4-[4-(3-methyl-5-{[4-(trifluoromethyl)-pyrimidin-2-yl]amino}-phenyl)-1H-pyrazol-1-yl]-cyclohexanecarboxylate;
N-[3-(1-cyclohex-2-en-1-yl-1H-pyrazol-4-yl)-5-methylphenyl]-4-(trifluoromethyl)-pyrimidin-2-amine;
N-[3-methyl-5-(1H-pyrazol-4-yl)phenyl]-4-(trifluoromethyl)-pyrimidin-2-amine;
N-[3-methyl-5-(1H-pyrazol-3-yl)phenyl]-4-(trifluoromethyl) pyrimidin-2-amine;
N-{3-methyl-5-[1-(1-methylethyl)-1H-pyrazol-5-yl]phenyl}-4-(trifluoromethyl)pyrimidin-2-amine;
N-[3-methyl-5-(1-methyl-1H-pyrazol-5-yl)phenyl]-4-(trifluoromethyl) pyrimidin-2-amine;
N-{3-methyl-5-[1-methyl-3-(trifluoromethyl)-1H-pyrazol-5-yl]phenyl}-4-(trifluoromethyl) pyrimidin-2-amine;
tert-butyl 4-(4-methyl-6-{[4-(trifluoromethyl)pyridin-2-yl]amino}-pyridin-2-yl)-1H-pyrazole-1-carboxylate;
4-methyl-6-(1H-pyrazol-4-yl)-N-[4-(trifluoromethyl)pyridin-2-yl]pyridin-2-amine;
4-methyl-6-(1-methyl-1H-pyrazol-4-yl)-N-[4-(trifluoromethyl)pyridin-2-yl]pyridin-2-amine;
4-methyl-6-[1-(3-methylbutyl)-1H-pyrazol-4-yl]-N-[4-(trifluoromethyl)pyridin-2-yl]pyridin-2-amine;
6-(5,6-dihydro-4H-pyrrolo[1,2-b]pyrazol-3-yl)-4-methyl-N-[4-(trifluoromethyl)pyridin-2-yl]pyridin-2-amine;

ethyl 3-[4-(4-methyl-6-{[4-(trifluoromethyl)pyridin-2-yl] amino}pyridin-2-yl)-1H-pyrazol-1-yl]propanoate;
ethyl 3-(4-{6-[(4-cyclopropylpyridin-2-yl)amino]-4-methylpyridin-2-yl}-1H-pyrazol-1-yl)propanoate;
3-(4-{6-[(4-methylpyridin-2-yl)amino]pyridin-2-yl}-1H-pyrazol-1-yl)propanoic acid;
3-[4-(6-{[4-(trifluoromethyl)pyridin-2-yl]amino}pyridin-2-yl)-1H-pyrazol-1-yl]propanoic acid;
3-(4-{4-methyl-6-[(4-methylpyridin-2-yl)amino]pyridin-2-yl}-1H-pyrazol-1-yl)propanoic acid;
3-[4-(4-methyl-6-{[4-(trifluoromethyl)pyridin-2-yl] amino}pyridin-2-yl)-1H-pyrazol-1-yl]propanoic acid;
3-(4-{6-[(4-cyclopropylpyridin-2-yl)amino]-4-methylpyridin-2-yl}-1H-pyrazol-1-yl)propanoic acid;
ethyl 3-(4-{6-[(4-methylpyridin-2-yl)amino]pyridin-2-yl}-1H-pyrazol-1-yl)propanoate;
ethyl 3-[4-(6-{[4-(trifluoromethyl)pyridin-2-yl] amino}pyridin-2-yl)-1H-pyrazol-1-yl]propanoate;
ethyl 3-(4-{6-[(5-chloro-4-methylpyridin-2-yl)amino]-4-methylpyridin-2-yl}-1H-pyrazol-1-yl)propanoate;
ethyl 3-(4-{4-methyl-6-[(4-methylpyridin-2-yl)amino]pyridin-2-yl}-1H-pyrazol-1-yl)propanoate;
3-(4-{6-[(5-chloro-4-methylpyridin-2-yl)amino]-4-methylpyridin-2-yl}-1H-pyrazol-1-yl)propanoic acid;
5R-{[4-(4-methyl-6-{[4-(trifluoromethyl)pyridin-2-yl] amino}pyridin-2-yl)-1H-pyrazol-1-yl]methyl}-1,3-oxazolidin-2-one;
5S-{[4-(4-methyl-6-{[4-(trifluoromethyl)pyridin-2-yl] amino}pyridin-2-yl)-1H-pyrazol-1-yl]methyl}-1,3-oxazolidin-2-one;
tert-butyl [4-(4-methyl-6-{[4-(trifluoromethyl)pyridin-2-yl]amino}pyridin-2-yl)-1H-pyrazol-1-yl]acetate;
[4-(4-methyl-6-{[4-(trifluoromethyl)pyridin-2-yl] amino}pyridin-2-yl)-1H-pyrazol-1-yl]acetic acid;
4R-{1R-[4-(4-methyl-6-{[4-(trifluoromethyl)pyridin-2-yl]amino}pyridin-2-yl)-1H-pyrazol-1-yl] ethyl}pyrrolidin-2-one;
4R-{1 S-[4-(4-methyl-6-{[4-(trifluoromethyl)pyridin-2-yl]amino}pyridin-2-yl)-1H-pyrazol-1-yl] ethyl}pyrrolidin-2-one;
4S-{1R-[4-(4-methyl-6-{[4-(trifluoromethyl)pyridin-2-yl]amino}pyridin-2-yl)-1H-pyrazol-1-yl] ethyl}pyrrolidin-2-one;
4R-{[4-(6-{[4-(difluoromethyl)pyridin-2-yl]amino}-4-methylpyridin-2-yl)-1H-pyrazol-1-yl] methyl}pyrrolidin-2-one;
4S-{1S-[4-(4-methyl-6-{[4-(trifluoromethyl)pyridin-2-yl]amino}pyridin-2-yl)-1H-pyrazol-1-yl] ethyl}pyrrolidin-2-one;
4S-{[4-(6-{[4-(difluoromethyl)pyridin-2-yl]amino}-4-methylpyridin-2-yl)-1H-pyrazol-1-yl] methyl}pyrrolidin-2-one;
4-{[4-(4-methyl-6-{[4-(trifluoromethyl)pyridin-2-yl] amino}pyridin-2-yl)-1H-pyrazol-1-yl] methyl}pyrrolidin-2-one;
3-[4-(4-methyl-6-{[4-(trifluoromethyl)pyridin-2-yl] amino}pyrimidin-2-yl)-1H-pyrazol-1-yl]propanoic acid;
6-methyl-2-(1H-pyrazol-4-yl)-N-[4-(trifluoro-methyl)pyridin-2-yl]pyrimidin-4-amine;
6-methyl-2-pyrazolo[1,5-a]pyridin-3-yl-N-[4-(trifluoromethyl)pyridin-2-yl]pyrimidin-4-amine;
N-[2-methyl-6-(1-methyl-1H-pyrazol-4-yl)pyridin-4-yl]-4-(trifluoro-methyl)pyrimidin-2-amine;
N-[2-methyl-6-(1H-pyrazol-4-yl)pyridin-4-yl]-4-(trifluoro-methyl)pyrimidin-2-amine;
6-methyl-2-(1-methyl-1H-pyrazol-5-yl)-N-[4-(trifluoromethyl)pyridin-2-yl]pyrimidin-4-amine;
6-methyl-2-[1-methyl-3-(trifluoromethyl)-1H-pyrazol-5-yl]-N-[4-(trifluoromethyl)pyridin-2-yl]pyrimidin-4-amine;
3-(4-(3-((4-methoxypyrimidin-2-yl)amino)-5-methylphenyl)-1H-pyrazol-1-yl)propanoic acid;
ethyl 3-[4-(3-{[4-(trifluoromethyl)pyrimidin-2-yl] amino}phenyl)-1H-pyrazol-1-yl]propanoate;
ethyl 3-(4-{3-[(4-methoxypyrimidin-2-yl)amino]-5-methylphenyl}-1H-pyrazol-1-yl)propanoate;
5R-{[4-(3-methyl-5-{[4-(trifluoromethyl)pyrimidin-2-yl] amino}phenyl)-1H-pyrazol-1-yl]methyl}-1,3-oxazolidin-2-one;
3-[4-(3-{[4-(trifluoromethyl)pyrimidin-2-yl] amino}phenyl)-1H-pyrazol-1-yl]propanoic acid;
3-(4-{3-[(5-fluoro-4-methylpyrimidin-2-yl)amino]-5-methylphenyl}-1H-pyrazol-1-yl)propanamide;
3-(4-{3-[(5-chloro-4-methoxypyrimidin-2-yl)amino]-5-methylphenyl}-1H-pyrazol-1-yl)propanamide;
3-[4-(3-methyl-5-{[4-(1-methylethyl)pyrimidin-2-yl] amino}phenyl)-1H-pyrazol-1-yl]propanamide;
3-[4-(3-{[4-(difluoromethyl)pyrimidin-2-yl]amino}-5-methylphenyl)-1H-pyrazol-1-yl]propanamide;
3-(4-{3-[(4-methylpyrimidin-2-yl)amino]phenyl}-1H-pyrazol-1-yl)propanamide;
3-(4-{3-[(5-fluoro-4-methoxypyrimidin-2-yl)amino]-5-methylphenyl}-1H-pyrazol-1-yl)propanamide;
3-(4-{3-methyl-5-[(4-methylpyrimidin-2-yl)amino]phenyl}-1H-pyrazol-1-yl)propanamide;
3-(4-{3-[(5-chloro-4-methylpyrimidin-2-yl)amino]-5-methylphenyl}-1H-pyrazol-1-yl)propanamide;
3-(4-{3-[(4-cyclopropylpyrimidin-2-yl)amino]-5-methylphenyl}-1H-pyrazol-1-yl)propanamide;
3-[4-(3-{[4-(trifluoromethyl)pyrimidin-2-yl] amino}phenyl)-1H-pyrazol-1-yl]propanamide;
5R or 5S-[(4-{3-[(4-methylpyrimidin-2-yl)amino]phenyl}-1H-pyrazol-1-yl)methyl]-1,3-oxazolidin-2-one;
5-[(4-{3-[(4-methoxypyrimidin-2-yl)amino]-5-methylphenyl}-1H-pyrazol-1-yl)methyl]-1,3-oxazolidin-2-one;
5-[(4-{3-methyl-5-[(4-methylpyrimidin-2-yl)amino]phenyl}-1H-pyrazol-1-yl)methyl]-1,3-oxazolidin-2-one;
5-[(4-{3-[(4-cyclopropylpyrimidin-2-yl)amino]-5-methylphenyl}-1H-pyrazol-1-yl)methyl]-1,3-oxazolidin-2-one;
5-[(4-{3-[(4-methylpyrimidin-2-yl)amino]phenyl}-1H-pyrazol-1-yl)methyl]-1,3-oxazolidin-2-one;
5-[(4-{3-[(4-methoxypyrimidin-2-yl)amino]-5-methylphenyl}-1H-pyrazol-1-yl)methyl]-1,3-oxazolidin-2-one;
5R or 5S-[(4-{3-[(5-fluoro-4-methylpyrimidin-2-yl) amino]-5-methylphenyl}-1H-pyrazol-1-yl)methyl]-1, 3-oxazolidin-2-one;
5R-[(4-{3-[(5-chloro-4-methoxypyrimidin-2-yl)amino]-5-methylphenyl}-1H-pyrazol-1-yl)methyl]-1,3-oxazolidin-2-one;
5R-{[4-(3-methyl-5-{[4-(1-methylethyl)pyrimidin-2-yl] amino}phenyl)-1H-pyrazol-1-yl]methyl}-1,3-oxazolidin-2-one;
5R-[(4-{3-[(5-fluoro-4-methoxypyrimidin-2-yl)amino]-5-methylphenyl}-1H-pyrazol-1-yl)methyl]-1,3-oxazolidin-2-one;
5R-[(4-{3-[(5-chloro-4-methylpyrimidin-2-yl)amino]-5-methylphenyl}-1H-pyrazol-1-yl)methyl]-1,3-oxazolidin-2-one;

5R-{[4-(3-{[4-(trifluoromethyl)pyrimidin-2-yl]amino}phenyl)-1H-pyrazol-1-yl]methyl}-1,3-oxazolidin-2-one;

5S-[(4-{3-[(5-chloro-4-methoxypyrimidin-2-yl)amino]-5-methylphenyl}-1H-pyrazol-1-yl)methyl]-1,3-oxazolidin-2-one;

5S-{[4-(3-methyl-5-{[4-(1-methylethyl)pyrimidin-2-yl]amino}phenyl)-1H-pyrazol-1-yl]methyl}-1,3-oxazolidin-2-one;

5S-[(4-{3-[(5-fluoro-4-methoxypyrimidin-2-yl)amino]-5-methylphenyl}-1H-pyrazol-1-yl)methyl]-1,3-oxazolidin-2-one;

5R-[(4-{3-methyl-5-[(4-methylpyrimidin-2-yl)amino]phenyl}-1H-pyrazol-1-yl)methyl]-1,3-oxazolidin-2-one;

5S-[(4-{3-[(5-chloro-4-methylpyrimidin-2-yl)amino]-5-methylphenyl}-1H-pyrazol-1-yl)methyl]-1,3-oxazolidin-2-one;

5R or 5S-[(4-{3-[(4-cyclopropylpyrimidin-2-yl)amino]-5-methylphenyl}-1H-pyrazol-1-yl)methyl]-1,3-oxazolidin-2-one;

5S-{[4-(3-{[4-(trifluoromethyl)pyrimidin-2-yl]amino}phenyl)-1H-pyrazol-1-yl]methyl}-1,3-oxazolidin-2-one;

N-(3-methyl-5-pyrazolo[1,5-b]pyridazin-3-ylphenyl)-4-(trifluoromethyl)pyrimidin-2-amine;

N-[3-(6-methoxypyrazolo[1,5-b]pyridazin-3-yl)-5-methylphenyl]-4-(trifluoromethyl)pyrimidin-2-amine;

N-(3-methyl-5-pyrazolo[1,5-a]pyrimidin-3-ylphenyl)-4-(trifluoromethyl)pyrimidin-2-amine;

N-[3-(3,5-dimethyl-1H-pyrazol-4-yl)-5-methylphenyl]-4-(trifluoromethyl)pyrimidin-2-amine;

N-[3-methyl-5-(3-methyl-1H-pyrazol-4-yl)phenyl]-4-(trifluoromethyl)pyrimidin-2-amine;

3-(4-{3-[(4-cyclopropylpyrimidin-2-yl)amino]-5-methylphenyl}-H-pyrazol-1-yl)propanoic acid;

ethyl 3-(4-{3-[(4-cyclopropylpyrimidin-2-yl)amino]-5-methylphenyl}-1H-pyrazol-1-yl)propanoate;

ethyl 3-(4-{3-methyl-5-[(4-methylpyrimidin-2-yl)amino]phenyl}-1H-pyrazol-1-yl)propanoate;

ethyl 3-[4-(3-methyl-5-{[4-(trifluoromethyl)pyrimidin-2-yl]amino}phenyl)-1H-pyrazol-1-yl]propanoate;

3-(4-{3-methyl-5-[(4-methylpyrimidin-2-yl)amino]phenyl}-1H-pyrazol-1-yl)propanoic acid;

5S-{[4-(3-methyl-5-{[4-(trifluoromethyl)pyrimidin-2-yl]amino}phenyl)-1H-pyrazol-1-yl]methyl}-1,3-oxazolidin-2-one;

N-[3-methyl-5-(1-methyl-1H-pyrazol-3-yl)phenyl]-4-(trifluoromethyl)pyrimidin-2-amine;

N-[3-(1H-indazol-3-yl)-5-methylphenyl]-4-(trifluoromethyl)pyrimidin-2-amine;

N-[3-methyl-5-(1-methyl-1H-pyrazol-5-yl)phenyl]-4-(trifluoromethyl)pyrimidin-2-amine;

3-methyl-5-{[4-(3-methyl-5-{[4-(trifluoromethyl)pyrimidin-2-yl]amino}phenyl)-1H-pyrazol-1-yl]methyl}-1,3-oxazolidin-2-one;

(3R)-3-hydroxy-4-[4-(3-methyl-5-{[4-(trifluoromethyl)-pyrimidin-2-yl]amino}phenyl)-1H-pyrazol-1-yl]-butanenitrile;

3-[4-(3-methyl-5-{[4-(trifluoromethyl)-pyrimidin-2-yl]amino}-phenyl)-1H-pyrazol-1-yl]-propanamide;

(2R)-2-methyl-3-[4-(3-methyl-5-{[4-(trifluoromethyl)-pyrimidin-2-yl-amino}phenyl)-1H-pyrazol-1-yl]-propan-1-ol;

(2S)-2-methyl-3-[4-(3-methyl-5-{[4-(trifluoromethyl)-pyrimidin-2-yl]amino}-phenyl)-1H-pyrazol-1-yl]-propan-1-ol;

1-{3-[4-(3-methyl-5-{[4-(trifluoro-methyl)pyrimidin-2-yl]amino}-phenyl)-1H-pyrazol-1-yl]-propyl}imidazolidin-2-one;

N-(3-{1-[2-(4-acetylpiperazin-1-yl)-2-oxoethyl]-1H-pyrazol-4-yl}-5-methylphenyl)-4-(trifluoromethyl)pyrimidin-2-amine;

N-tert-butyl-2-[4-(3-methyl-5-{[4-(trifluoromethyl)pyrimidin-2-yl]amino}-phenyl)-1H-pyrazol-1-yl]acetamide;

N-{3-[1-(1,4-dioxan-2-ylmethyl)-1H-pyrazol-4-yl]-5-methyl-phenyl}-4-(trifluoro-methyl)pyrimidin-2-amine;

N-(3-methyl-5-{1-[(5-methyl-1,2,4-oxadiazol-3-yl)methyl]-1H-pyrazol-4-yl}phenyl)-4-(trifluoromethyl)pyrimidin-2-amine;

N-(3-{1-[2-(4,4-dimethyl-1,3-oxazolidin-3-yl)-2-oxoethyl]-1H-pyrazol-4-yl}-5-methylphenyl)-4-(trifluoromethyl)pyrimidin-2-amine;

N-(2-methoxy-1,1-dimethylethyl)-2-[4-(3-methyl-5-{[4-(trifluoromethyl)pyrimidin-2-yl]amino}phenyl)-1H-pyrazol-1-yl]acetamide;

N-(3-{1-[2-(3,3-dimethylmorpholin-4-yl)-2-oxoethyl]-1H-pyrazol-4-yl}-5-methylphenyl)-4-(trifluoromethyl)pyrimidin-2-amine;

N-[3-(1-{2-[(3R,5S)-3,5-dimethyl-morpholin-4-yl]-2-oxoethyl}-1H-pyrazol-4-yl)-5-methylphenyl]-4-(trifluoromethyl)-pyrimidin-2-amine;

N-[3-(1-{2-[(3R,5R)-3,5-dimethylmorpholin-4-yl]-2-oxoethyl}-1H-pyrazol-4-yl)-5-methylphenyl]-4-(trifluoromethyl)-pyrimidin-2-amine;

1-{2-[4-(3-methyl-5-{[4-(trifluoromethyl)-pyrimidin-2-yl]-amino}phenyl)-1H-pyrazol-1-yl]ethyl}urea;

3-[4-(3-methyl-5-{[4-(trifluoromethyl)pyrimidin-2-yl]amino}-phenyl)-1H-pyrazol-1-yl]dihydrofuran-2(3h)-one;

N-{3-methyl-5-[1-(oxetan-2-ylmethyl)-1H-pyrazol-4-yl]-phenyl}-4-(trifluoromethyl)-pyrimidin-2-amine;

2-{2-[4-(3-methyl-5-{[4-(trifluoromethyl)-pyrimidin-2-yl]-amino}phenyl)-1H-pyrazol-1-yl]ethoxy}ethanol;

N-{3-[1-(3-aminopropyl)-1H-pyrazol-4-yl]-5-methylphenyl}-4-(trifluoromethyl)pyrimidin-2-amine;

N-{3-[1-(cyclopropylmethyl)-1H-pyrazol-4-yl]-5-methylphenyl}-4-(trifluoromethyl)pyrimidin-2-amine;

1-[4-(3-methyl-5-{[4-(trifluoromethyl)pyrimidin-2-yl]amino}phenyl)-1H-pyrazol-1-yl]propan-2-one;

N-{3-[1-(2,2-diethoxyethyl)-1H-pyrazol-4-yl]-5-methylphenyl}-4-(trifluoromethyl)pyrimidin-2-amine;

N-(3-methyl-5-{1-[(5-methyl-1,3,4-oxadiazol-2-yl)methyl]-1H-pyrazol-4-yl}phenyl)-4-(trifluoromethyl)pyrimidin-2-amine;

N-(3-methyl-5-{1-[(3-methylisoxazol-5-yl)methyl]-1H-pyrazol-4-yl}phenyl)-4-(trifluoromethyl)pyrimidin-2-amine;

N-{3-[1-(2-azetidin-1-yl-2-oxoethyl)-1H-pyrazol-4-yl]-5-methylphenyl}-4-(trifluoromethyl)pyrimidin-2-amine;

N-{3-methyl-5-[1-(2-oxo-2-pyrrolidin-1-ylethyl)-1H-pyrazol-4-yl]phenyl}-4-(trifluoromethyl)pyrimidin-2-amine;

methyl 2-[4-(3-methyl-5-{[4-(trifluoromethyl)pyrimidin-2-yl]amino}phenyl)-1H-pyrazol-1-yl]butanoate;

methyl 2-[4-(3-methyl-5-{[4-(trifluoromethyl)pyrimidin-2-yl]amino}phenyl)-1H-pyrazol-1-yl]propanoate;

ethyl 2-[4-(3-methyl-5-{[4-(trifluoromethyl)pyrimidin-2-yl]amino}phenyl)-1H-pyrazol-1-yl]propanoate;

3-[4-(3-methyl-5-{[4-(trifluoromethyl)pyrimidin-2-yl]amino}phenyl)-1H-pyrazol-1-yl]propan-1-ol;

N-{3-methyl-5-[1-(pyridazin-4-ylmethyl)-1H-pyrazol-4-yl]phenyl}-4-(trifluoromethyl)pyrimidin-2-amine;
5-{[4-(3-methyl-5-{[4-(trifluoromethyl)pyrimidin-2-yl]amino}phenyl)-1H-pyrazol-1-yl]methyl}-1,3-oxazolidin-2-one;
2-[4-(3-methyl-5-{[4-(trifluoromethyl)pyrimidin-2-yl]amino}phenyl)-1H-pyrazol-1-yl]butanoic acid;
2-[4-(3-methyl-5-{[4-(trifluoromethyl)pyrimidin-2-yl]amino}phenyl)-1H-pyrazol-1-yl]propanoic acid;
2-[4-(3-methyl-5-{[4-(trifluoromethyl)pyrimidin-2-yl]amino}phenyl)-1H-pyrazol-1-yl]ethanol;
2-[4-(3-methyl-5-{[4-(trifluoromethyl)pyrimidin-2-yl]amino}phenyl)-1H-pyrazol-1-yl]acetamide;
3-[4-(3-{[4-(2-hydroxyethoxy)pyrimidin-2-yl]amino}-5-methylphenyl)-1H-pyrazol-1-yl]propanamide;
1-[4-(3-methyl-5-{[4-(trifluoromethyl)pyrimidin-2-yl]amino}phenyl)-1H-pyrazol-1-yl]methanesulfonamide;
3-(4-{3-[(4-methoxypyrimidin-2-yl)amino]-5-methylphenyl}-1H-pyrazol-1-yl)propanamide;
(2R)-3-[4-(3-methyl-5-{[4-(trifluoromethyl)pyrimidin-2-yl]amino}phenyl)-1H-pyrazol-1-yl]propane-1,2-diol;
(2S)-3-[4-(3-methyl-5-{[4-(trifluoromethyl)pyrimidin-2-yl]amino}phenyl)-1H-pyrazol-1-yl]propane-1,2-diol;
1,1,1-trifluoro-3-[4-(3-methyl-5-{[4-(trifluoromethyl)pyrimidin-2-yl]amino}phenyl)-1H-pyrazol-1-yl]propan-2R-ol;
1,1,1-trifluoro-3-[4-(3-methyl-5-{[4-(trifluoromethyl)pyrimidin-2-yl]amino}phenyl)-1H-pyrazol-1-yl]propan-2S-ol;
3-methyl-5R or 5S-{[4-(3-methyl-5-{[4-(trifluoromethyl)pyrimidin-2-yl]amino}phenyl)-1H-pyrazol-1-yl]methyl}-1,3-oxazolidin-2-one;
(3S)-3-hydroxy-4-[4-(3-methyl-5-{[4-(trifluoromethyl)pyrimidin-2-yl]amino}phenyl)-1H-pyrazol-1-yl]butanenitrile;
N-(3-methyl-5-{1-[2-(methylsulfonyl)ethyl]-1H-pyrazol-4-yl}phenyl)-4-(trifluoromethyl)pyrimidin-2-amine;
methyl 4-[4-(3-methyl-5-{[4-(trifluoromethyl)pyrimidin-2-yl]amino}phenyl)-1H-pyrazol-1-yl]butanoate;
4-[4-(3-methyl-5-{[4-(trifluoromethyl)pyrimidin-2-yl]amino}phenyl)-1H-pyrazol-1-yl]butanoic acid;
4-[4-(3-methyl-5-{[4-(trifluoromethyl)pyrimidin-2-yl]amino}phenyl)-1H-pyrazol-1-yl]-1,2,3,4-tetrahydronaphthalene-1-carboxylic acid;
methyl 4-[4-(3-methyl-5-{[4-(trifluoromethyl)pyrimidin-2-yl]amino}phenyl)-1H-pyrazol-1-yl]-1,2,3,4-tetrahydronaphthalene-1-carboxylate;
4-{1-hydroxy-2-[4-(3-methyl-5-{[4-(trifluoromethyl)pyrimidin-2-yl]amino}phenyl)-1H-pyrazol-1-yl]ethyl}benzoic acid;
methyl 4-{1-hydroxy-2-[4-(3-methyl-5-{[4-(trifluoromethyl)pyrimidin-2-yl]amino}phenyl)-1H-pyrazol-1-yl]ethyl}benzoate;
N-{3-[1-(1,4-dioxaspiro[4.5]dec-8-yl)-1H-pyrazol-4-yl]-5-methylphenyl}-4-(trifluoromethyl)pyrimidin-2-amine;
3-[4-(3-methyl-5-{[4-(trifluoromethyl)pyrimidin-2-yl]amino}phenyl)-1H-pyrazol-1-yl]butanamide;
tert-butyl 4-[4-(3-methyl-5-{[4-(trifluoromethyl)pyrimidin-2-yl]amino}phenyl)-1H-pyrazol-1-yl]piperidine-1-carboxylate;
4-hydroxy-2-[4-(3-methyl-5-{[4-(trifluoromethyl)pyrimidin-2-yl]amino}phenyl)-1H-pyrazol-1-yl]butanoic acid;
6-[1-(methoxyacetyl)-1H-pyrazol-4-yl]-4-methyl-N-[4-(trifluoromethyl)pyridin-2-yl]pyridin-2-amine;
3-[4-(4-methyl-6-{[4-(trifluoro-methyl)pyridin-2-yl]amino}pyridin-2-yl)-1H-pyrazol-1-yl]propan-1-ol;
3-[4-(4-methyl-6-{[4-(trifluoro-methyl)pyridin-2-yl]amino}pyridin-2-yl)-1H-pyrazol-1-yl]propanamide;
2-[4-(4-methyl-6-{[4-(trifluoro-methyl)pyridin-2-yl]amino}pyridin-2-yl)-1H-pyrazol-1-yl]acetamide;
1-{3-[4-(4-methyl-6-{[4-(trifluoro-methyl)pyridin-2-yl]amino}pyridin-2-yl)-1H-pyrazol-1-yl]propyl}imidazolidin-2-one;
6-[1-(1,4-dioxan-2-ylmethyl)-1H-pyrazol-4-yl]-4-methyl-N-[4-(trifluoromethyl)pyridin-2-yl]pyridin-2-amine;
N-(2-methoxy-1,1-dimethylethyl)-2-[4-(4-methyl-6-{[4-(trifluoromethyl)pyridin-2-yl]amino}-pyridin-2-yl)-1H-pyrazol-1-yl]-acetamide;
6-(1-{2-[(3R,5S)-3,5-dimethylmorpholin-4-yl]-2-oxoethyl}-1H-pyrazol-4-yl)-4-methyl-N-[4-(trifluoromethyl)pyridin-2-yl]pyridin-2-amine;
4-methyl-6-[1-(3-morpholin-4-ylpropyl)-1H-pyrazol-4-yl]-N-[4-(trifluoromethyl)pyridin-2-yl]pyridin-2-amine;
4-methyl-6-[1-(oxetan-2-ylmethyl)-1H-pyrazol-4-yl]-N-[4-(trifluoromethyl)-pyridin-2-yl]pyridin-2-amine;
2-{2-[4-(4-methyl-6-{[4-(trifluoromethyl)-pyridin-2-yl]amino}-pyridin-2-yl)-1H-pyrazol-1-yl]-ethoxy}ethanol;
6-[1-(3-aminopropyl)-1H-pyrazol-4-yl]-4-methyl-N-[4-(trifluoromethyl)pyridin-2-yl]pyridin-2-amine;
6-[1-(cyclopropyl-methyl)-1H-pyrazol-4-yl]-4-methyl-N-[4-(trifluoromethyl)pyridin-2-yl]pyridin-2-amine;
6-[1-(2,2-diethoxyethyl)-1H-pyrazol-4-yl]-4-methyl-N-[4-(trifluoromethyl)pyridin-2-yl]pyridin-2-amine;
4-methyl-6-[1-(1-methylethyl)-1H-pyrazol-4-yl]-N-[4-(trifluoromethyl)pyridin-2-yl]pyridin-2-amine;
2-[4-(4-methyl-6-{[4-(trifluoro-methyl)pyridin-2-yl]amino}pyridin-2-yl)-1H-pyrazol-1-yl]ethanol;
4-[4-(4-methyl-6-{[4-(trifluoro-methyl)pyridin-2-yl]amino}pyridin-2-yl)-1H-pyrazol-1-yl]-1,2,3,4-tetrahydro-naphthalene-1-carboxylic acid;
methyl 4-[4-(4-methyl-6-{[4-(trifluoromethyl)pyridin-2-yl]amino}pyridin-2-yl)-1H-pyrazol-1-yl]-1,2,3,4-tetrahydro-naphthalene-1-carboxylate;
4-{1-hydroxy-2-[4-(4-methyl-6-{[4-(trifluoromethyl)pyridin-2-yl]amino}pyridin-2-yl)-1H-pyrazol-1-yl]ethyl}-benzoic acid;
methyl 4-{1-hydroxy-2-[4-(4-methyl-6-{[4-(trifluoromethyl)pyridin-2-yl]amino}pyridin-2-yl)-1H-pyrazol-1-yl]ethyl}-benzoate;
tert-Butyl 4-[4-(4-methyl-6-{[4-(trifluoromethyl)pyridin-2-yl]amino}pyridin-2-yl)-1H-pyrazol-1-yl]piperidine-1-carboxylate;
[4-(4-methyl-6-{[4-(trifluoromethyl)pyridin-2-yl]amino}-pyridin-2-yl)-1H-pyrazol-1-yl]-acetonitrile;
(S) methyl 3-[4-(3-methyl-5-{[4-(trifluoromethyl)pyrimidin-2-yl]amino}phenyl)-1H-pyrazo(-1-yl]-L-alaninate;
2-(4-(3-methyl-5-((4-(trifluoromethyl)pyrimidin-2-yl)amino)phenyl)-1H-pyrazol-1-yl)-1-phenylethanol;
methyl (2S)-2-hydroxy-3-[4-(3-methyl-5-{[4-(trifluoromethyl)-pyrimidin-2-yl]amino}phenyl)-1H-pyrazol-1-yl]propanoate;
methyl (2R)-2-hydroxy-3-[4-(3-methyl-5-{[4-(trifluoromethyl)pyrimidin-2-yl]amino}phenyl)-1H-pyrazol-1-yl]propanoate;
methyl 2-hydroxy-2-methyl-3-[4-(3-methyl-5-{[4-(trifluoromethyl)pyrimidin-2-yl]amino}phenyl)-1H-pyrazol-1-yl]propanoate;

Cis-4-hydroxy-4-{[4-(3-methyl-5-{[4-(trifluoromethyl)pyrimidin-2-yl]amino}phenyl)-1H-pyrazol-1-yl]methyl}cyclohexanecarboxylic acid;

2-hydroxy-2-methyl-3-[4-(3-methyl-5-{[4-(trifluoromethyl)pyrimidin-2-yl]amino}phenyl)-1H-pyrazol-1-yl]propanoic acid;

1-(1-methylethoxy)-3-[4-(3-methyl-5-{[4-(trifluoromethyl)pyrimidin-2-yl]amino}-phenyl)-1H-pyrazol-1-yl]propan-2-ol;

1-[4-(3-methyl-5-{[4-(trifluoromethyl)pyrimidin-2-yl]amino}-phenyl)-1H-pyrazol-1-yl]-3-phenoxypropan-2-ol;

1-[4-(3-methyl-5-{[4-(trifluoromethyl)pyrimidin-2-yl]amino}-phenyl)-1H-pyrazol-1-yl]butan-2-ol;

1-[4-(3-methyl-5-{[4-(trifluoromethyl)pyrimidin-2-yl]amino}-phenyl)-1H-pyrazol-1-yl]-3-morpholin-4-yl-propan-2-ol;

1-(4-methoxy-phenoxy)-3-[4-(3-methyl-5-{[4-(trifluoromethyl)-pyrimidin-2-yl]amino}phenyl)-1H-pyrazol-1-yl]propan-2-ol;

2-methyl-1-[4-(3-methyl-5-{[4-(trifluoromethyl)pyrimidin-2-yl]amino}-phenyl)-1H-pyrazol-1-yl]propan-2-ol;

1-fluoro-3-({3-[1-(3-fluoro-2-hydroxy-propyl)-1H-pyrazol-4-yl]-5-methylphenyl}-[4-(trifluoromethyl)-pyrimidin-2-yl]amino)propan-2-ol;

2-hydroxy-3-[4-(3-methyl-5-{[4-(trifluoromethyl)pyrimidin-2-yl]amino}phenyl)-1H-pyrazol-1-yl]propanoic acid;

3-[4-(3-methyl-5-{[4-(trifluoromethyl)pyrimidin-2-yl]amino}phenyl)-1H-pyrazol-1-yl]propane-1,2-diol;

(2R)-2-hydroxy-3-[4-(3-methyl-5-{[4-(trifluoromethyl)pyrimidin-2-yl]amino}phenyl)-1H-pyrazol-1-yl]propanoic acid;

(2S)-2-hydroxy-3-[4-(3-methyl-5-{[4-(trifluoromethyl)pyrimidin-2-yl]amino}phenyl)-1H-pyrazol-1-yl]propanoic acid;

(2S)-2-hydroxy-N-(2-hydroxyethyl)-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-{[4-(2-hydroxyethoxy)pyrimidin-2-yl]amino}-5-methylphenyl)-1H-pyrazol-1-yl]propanamide;

(2S)-2-hydroxy-3-(4-{3-methyl-5-[(4-methylpyrimidin-2-yl)amino]phenyl}-1H-pyrazol-1-yl)propanamide;

(2S)-2-hydroxy-3-(4-{3-[(4-methoxypyrimidin-2-yl)amino]-5-methylphenyl}-1H-pyrazol-1-yl)propanamide;

(2S)-3-(4-{3-[(4-cyclopropylpyrimidin-2-yl)amino]-5-methylphenyl}-1H-pyrazol-1-yl)-2-hydroxypropanamide;

(2S)-2-hydroxy-3-[4-(3-methyl-5-{[4-(1-methylethoxy)pyrimidin-2-yl]amino}phenyl)-1H-pyrazol-1-yl]propanamide;

(2S)-3-(4-{3-[(4-tert-butylpyrimidin-2-yl)amino]-5-methylphenyl}-1H-pyrazol-1-yl)-2-hydroxypropanamide;

(2S)-3-[4-(3-{[4-(1-fluoroethyl)pyrimidin-2-yl]amino}-5-methylphenyl)-1H-pyrazol-1-yl]-2-hydroxypropanamide;

(2S)-2-hydroxy-3-[4-(3-methyl-5-{[4-(1-methylethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]-N-[3-(2-oxopyrrolidin-1-yl)propyl]propanamide;

(2S)-2-hydroxy-N-methyl-3-[4-(3-methyl-5-{[4-(trifluoromethyl)pyrimidin-2-yl]amino}phenyl)-1H-pyrazol-1-yl]propanamide;

(2S)-2-hydroxy-N-(3-methoxypropyl)-3-[4-(3-methyl-5-{[4-(trifluoromethyl)pyrimidin-2-yl]amino}phenyl)-1H-pyrazol-1-yl]propanamide;

(2S)-2-hydroxy-N-(2-methoxyethyl)-3-[4-(3-methyl-5-{[4-(trifluoromethyl)pyrimidin-2-yl]amino}phenyl)-1H-pyrazol-1-yl]propanamide;

4-[4-(4-methyl-6-{[4-(trifluoromethyl)pyridin-2-yl]amino}pyridin-2-yl)-1H-pyrazol-1-yl]-1,2,3,4-tetrahydronaphthalene-1-carboxamide;

(2S)-2-hydroxy-3-[4-(4-methyl-6-{[4-(trifluoromethyl)pyridin-2-yl]amino}pyridin-2-yl)-1H-pyrazol-1-yl]propanamide;

4-{1-hydroxy-2-[4-(4-methyl-6-{[4-(trifluoromethyl)pyridin-2-yl]amino}pyridin-2-yl)-1H-pyrazol-1-yl]ethyl}benzamide;

(R or S)-2-hydroxy-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]-1-alaninamide;

(2R)-2-hydroxy-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

2-hydroxy-3-[4-(3-methyl-5-{[4-(trifluoromethyl)pyrimidin-2-yl]amino}phenyl)-1H-pyrazol-1-yl]butanamide;

2-hydroxy-3-[4-(3-methyl-5-{[4-(trifluoromethyl)pyrimidin-2-yl]amino}phenyl)-1H-pyrazol-1-yl]butanamide;

(R)-2-hydroxy-2-methyl-3-[4-(3-methyl-5-{[4-(trifluoromethyl)pyrimidin-2-yl]amino}phenyl)-1H-pyrazol-1-yl]propanamide;

(2R)-2-hydroxy-3-[4-(3-methyl-5-{[4-(trifluoromethyl)pyrimidin-2-yl]amino}phenyl)-1H-pyrazol-1-yl]propanamide;

(S)-2-hydroxy-2-methyl-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

4-[4-(3-{[4-(2-hydroxyethoxy)pyrimidin-2-yl]amino}-5-methylphenyl)-1H-pyrazol-1-yl]cyclohexanecarboxamide;

4-[4-(3-methyl-5-{[4-(trifluoromethyl)pyrimidin-2-yl]amino}phenyl)-1H-pyrazol-1-yl]cyclohexanecarboxamide;

2,2-dimethyl-4-[4-(3-methyl-5-{[4-(trifluoromethyl)pyrimidin-2-yl]amino}phenyl)-1H-pyrazol-1-yl]cyclohexanecarboxamide;

2-[4-(3-methyl-5-{[4-(trifluoromethyl)pyrimidin-2-yl]amino}phenyl)-1H-pyrazol-1-yl]propanamide;

4-[4-(3-methyl-5-{[4-(trifluoromethyl)pyrimidin-2-yl]amino}phenyl)-1H-pyrazol-1-yl]butanamide;

2-methyl-2-(4-{3-methyl-5-[(4-methylpyrimidin-2-yl)amino]phenyl}-1H-pyrazol-1-yl)propanamide;

2-hydroxy-2-methyl-3-[4-(3-methyl-5-{[4-(trifluoromethyl)pyrimidin-2-yl]amino}phenyl)-1H-pyrazol-1-yl]propanamide;

4-{1-hydroxy-2-[4-(3-methyl-5-{[4-(trifluoromethyl)pyrimidin-2-yl]amino}phenyl)-1H-pyrazol-1-yl]ethyl}benzamide;

(2R)-2-hydroxy-3-[4-(3-methyl-5-{[4-(trifluoromethyl)pyrimidin-2-yl]amino}phenyl)-1H-pyrazol-1-yl]propanamide;
2-hydroxy-2-methyl-3-[4-(3-methyl-5-{[4-(trifluoromethyl)pyrimidin-2-yl]amino}phenyl)-1H-pyrazol-1-yl]propanamide;
2-hydroxy-2-methyl-3-[4-(3-methyl-5-{[4-(trifluoromethyl)pyrimidin-2-yl]amino}phenyl)-1H-pyrazol-1-yl]propanamide;
(2S)-2-hydroxy-3-[4-(3-methyl-5-{[4-(trifluoromethyl)pyrimidin-2-yl]amino}phenyl)-1H-pyrazol-1-yl]propanamide;
4-[4-(3-{[4-(2-hydroxyethoxy)pyrimidin-2-yl]amino}-5-methylphenyl)-1H-pyrazol-1-yl]cyclohexanecarboxamide;
4-[4-(3-methyl-5-{[4-(trifluoromethyl)pyrimidin-2-yl]amino}phenyl)-1H-pyrazol-1-yl]cyclohexanecarboxamide;
2,2-dimethyl-4-[4-(3-methyl-5-{[4-(trifluoromethyl)pyrimidin-2-yl]amino}phenyl)-1H-pyrazol-1-yl]cyclohexanecarboxamide;
2-[4-(3-methyl-5-{[4-(trifluoromethyl)pyrimidin-2-yl]amino}phenyl)-1H-pyrazol-1-yl]propanamide;
4-[4-(3-methyl-5-{[4-(trifluoromethyl)pyrimidin-2-yl]amino}phenyl)-1H-pyrazol-1-yl]butanamide;
2-methyl-2-(4-{3-methyl-5-[(4-methylpyrimidin-2-yl)amino]phenyl}-1H-pyrazol-1-yl)propanamide;
2-hydroxy-2-methyl-3-[4-(3-methyl-5-{[4-(trifluoromethyl)pyrimidin-2-yl]amino}phenyl)-1H-pyrazol-1-yl]propanamide;
4-{1-hydroxy-2-[4-(3-methyl-5-{[4-(trifluoromethyl)pyrimidin-2-yl]amino}phenyl)-1H-pyrazol-1-yl]ethyl}benzamide;
3-methyl-3-[4-(3-methyl-5-{[4-(trifluoromethyl)pyrimidin-2-yl]amino}phenyl)-1H-pyrazol-1-yl]butanenitrile;
2-[4-(3-methyl-5-{[4-(trifluoromethyl)pyrimidin-2-yl]amino}phenyl)-1H-pyrazol-1-yl]-ethanesulfonamide;
3-[4-(3-methyl-5-{[4-(trifluoromethyl)pyrimidin-2-yl]amino}phenyl)-1H-pyrazol-1-yl]cyclohexane-(1R,2S)-diol;
3-[4-(3-methyl-5-{[4-(trifluoromethyl)pyrimidin-2-yl]amino}phenyl)-1H-pyrazol-1-yl]cyclohexane-(1R,2R)-diol;
3-[4-(3-methyl-5-{[4-(trifluoromethyl)pyrimidin-2-yl]amino}phenyl)-1H-pyrazol-1-yl]cyclohexane-(1S,2R)-diol;
3-[4-(3-methyl-5-{[4-(trifluoromethyl)pyrimidin-2-yl]amino}phenyl)-1H-pyrazol-1-yl]cyclohexane-(1S,2S)-diol;
(2R)-3-(4-(3-(4-cyclopropylpyrimidin-2-ylamino)-5-methylphenyl)-1H-pyrazol-1-yl)-2-hydroxypropanoic acid;
(2S)-2-hydroxy-3-(4-{3-[(4-methoxy-pyrimidin-2-yl)amino]-5-methylphenyl}-1H-pyrazol-1-yl)-propanoic acid;
(2S)-2-hydroxy-3-(4-{3-methyl-5-[(4-methylpyrimidin-2-yl)amino]phenyl}-1H-pyrazol-1-yl)-propanoic acid;
(2S)-2-hydroxy-3-(4-{3-[(4-methoxy-pyrimidin-2-yl)amino]-5-methylphenyl}-1H-pyrazol-1-yl)-propanoic acid;
(2S)-3-(4-{3-[(4-cyclopropylpyrimidin-2-yl)amino]-5-methyl-phenyl}-1H-pyrazol-1-yl)-2-hydroxy-propanoic acid;
(2S)-3-(4-{3-[(5-chloro-4-methoxy-pyrimidin-2-yl)amino]-5-methyl-phenyl}-1H-pyrazol-1-yl)-2-hydroxy-propanoic acid;
(2R)-3-(4-{3-[(5-chloro-4-methyl-pyrimidin-2-yl)amino]-5-methyl-phenyl}-1H-pyrazol-1-yl)-2-hydroxy-propanoic acid;
(2R)-2-hydroxy-3-(4-{3-[(4-methoxy-pyrimidin-2-yl)amino]-5-methyl-phenyl}-1H-pyrazol-1-yl)propanoic acid;
(2R)-3-(4-{3-[(5-chloro-4-methoxy-pyrimidin-2-yl)amino]-5-methyl-phenyl}-1H-pyrazol-1-yl)-2-hydroxy-propanoic acid;
(2R)-2-hydroxy-3-(4-{3-methyl-5-[(4-methylpyrimidin-2-yl)amino]phenyl}-1H-pyrazol-1-yl)propanoic acid;
(2R)-2-hydroxy-3-(4-{3-[(4-methoxypyrimidin-2-yl)amino]phenyl}-1H-pyrazol-1-yl)propanoic acid;
(2R)-3-(4-{3-[(4-cyclopropylpyrimidin-2-yl)amino]-5-methylphenyl}-1H-pyrazol-1-yl)-2-hydroxypropanoic acid;
(2R)-3-(4-{3-[(5-fluoro-4-methylpyrimidin-2-yl)amino]-5-methylphenyl}-1H-pyrazol-1-yl)-2-hydroxypropanoic acid;
(2R)-2-hydroxy-3-[4-(3-methyl-5-{[4-(1-methylethoxy)pyrimidin-2-yl]amino}-phenyl)-1H-pyrazol-1-yl]propanoic acid;
(2R)-3-(4-{3-[(5-chloro-4-methoxy-pyrimidin-2-yl)amino]-5-methyl-phenyl}-1H-pyrazol-1-yl)-2-hydroxy-propanoic acid;
(2R)-2-hydroxy-3-[4-(3-methyl-5-{[4-(1-methylethyl)pyrimidin-2-yl]amino}phenyl)-1H-pyrazol-1-yl]propanoic acid;
(2S)-2-hydroxy-3-(4-{4-methyl-6-[(4-methyl-pyridin-2-yl)amino]-pyrimidin-2-yl}-1H-pyrazol-1-yl)propanoic acid;
(2S)-2-hydroxy-3-[4-(6-methyl-4-{[4-(trifluoro-methyl)pyrimidin-2-yl]amino}pyridin-2-yl)-1H-pyrazol-1-yl]propanoic acid;
(2R)-2-hydroxy-3-(4-{4-methyl-6-[(4-methyl-pyridin-2-yl)amino]-pyrimidin-2-yl}-1H-pyrazol-1-yl)propanoic acid;
(2R)-2-hydroxy-3-[4-(6-methyl-4-{[4-(trifluoro-methyl)pyrimidin-2-yl]amino}pyridin-2-yl)-1H-pyrazol-1-yl]propanoic acid;
4-((4-(3-methyl-5-((4-(trifluoromethyl)pyrimidin-2-yl)amino)phenyl)-1H-pyrazol-1-yl)methyl)piperidin-4-ol;
1-{[4-(3-methyl-5-{[4-(trifluoro-methyl)pyrimidin-2-yl]amino}-phenyl)-1H-pyrazol-1-yl]-methyl}-cyclobutanol;
3-methoxy-1-[(4-{3-methyl-5-[(4-methylpyrimidin-2-yl)amino]phenyl}-1H-pyrazol-1-yl)methyl]-cyclobutanol;
tert-Butyl (4-hydroxy-4-{[4-(3-methyl-5-{[4-(trifluoromethyl)pyrimidin-2-yl]amino}phenyl)-1H-pyrazol-1-yl]methyl}-piperidin-1-yl)acetate;
4-{[4-(3-methyl-5-{[4-(trifluoromethyl)pyrimidin-2-yl]amino}phenyl)-1H-pyrazol-1-yl]methyl}-tetrahydro-2H-pyran-4-ol;
(1R,4S and 1S,4R)-4-hydroxy-2,2-dimethyl-4-{[4-(3-methyl-5-{[4-(trifluoromethyl)pyrimidin-2-yl]amino}phenyl)-1H-pyrazol-1-yl]methyl}-cyclohexanecarboxylic acid;
3-{[4-(3-methyl-5-{[4-(trifluoromethyl)pyrimidin-2-yl]amino}phenyl)-1H-pyrazol-1-yl]methyl}tetrahydro-2H-pyran-3-ol;
Meso (2R,4s,6S)-2,6-dimethyl-4-{[4-(3-methyl-5-{[4-(trifluoro-methyl)pyrimidin-2-yl]amino}phenyl)-1H-pyrazol-1-yl]methyl}-tetrahydro-2H-pyran-4-ol;
2,2-dimethyl-4R-{[4-(3-methyl-5-{[4-(trifluoro-methyl)pyrimidin-2-yl]amino}phenyl)-1H-pyrazol-1-yl]methyl}tetrahydro-2H-pyran-4-ol;

2,2-dimethyl-4S-{[4-(3-methyl-5-{[4-(trifluoromethyl)pyrimidin-2-yl]amino}phenyl)-1H-pyrazol-1-yl]methyl}-tetrahydro-2H-pyran-4-ol;
3R-{[4-(3-methyl-5-{[4-(trifluoromethyl)pyrimidin-2-yl]amino}phenyl)-1H-pyrazol-1-yl]methyl}tetrahydro-2H-pyran-3-ol;
3S-{[4-(3-methyl-5-{[4-(trifluoromethyl)pyrimidin-2-yl]amino}phenyl)-1H-pyrazol-1-yl]methyl}tetrahydro-2H-pyran-3-ol;
4-[(4-{3-methyl-5-[(4-methylpyrimidin-2-yl)amino]phenyl}-1H-pyrazol-1-yl)methyl]-tetrahydro-2H-pyran-4-ol;
4-{1-[4-(3-methyl-5-{[4-(trifluoromethyl)pyrimidin-2-yl]amino}phenyl)-1H-pyrazol-1-yl]ethyl}-tetrahydro-2H-pyran-4-ol;
(4-hydroxy-4-{[4-(3-methyl-5-{[4-(trifluoromethyl)-pyrimidin-2-yl]amino}-phenyl)-1H-pyrazol-1-yl]methyl}piperidin-1-yl)acetic acid;
N-(3-(1-isopropyl-1H-pyrazol-4-yl)-5-methylphenyl)-4-(trifluoromethyl)-pyrimidin-2-amine;
N-{3-methyl-5-[1-(2-pyrrolidin-2-ylethyl)-1H-pyrazol-4-yl]phenyl}-4-(trifluoromethyl)-pyrimidin-2-amine;
N-{3-methyl-5-[1-(tetrahydrofuran-2-ylmethyl)-1H-pyrazol-4-yl]phenyl}-4-(trifluoromethyl)-pyrimidin-2-amine;
(5R)-[4-(3-methyl-5-{[4-(trifluoromethyl)pyrimidin-2-yl]amino}phenyl)-1H-pyrazol-1-yl]azepan-2-one;
(5S)-[4-(3-methyl-5-{[4-(trifluoromethyl)pyrimidin-2-yl]amino}phenyl)-1H-pyrazol-1-yl]azepan-2-one;
cis-4-[4-(3-methyl-5-{[4-(trifluoromethyl)pyrimidin-2-yl]amino}phenyl)-1H-pyrazol-1-yl]cyclohexanol;
(2S)-3-[4-(3-{[4-(difluoromethyl)pyrimidin-2-yl]amino}-5-methylphenyl)-1H-pyrazol-1-yl]-2-hydroxypropanamide;
4-hydroxy-4-((4-(3-methyl-5-((4-(trifluoromethyl)pyrimidin-2-yl)amino)phenyl)-1H-pyrazol-1-yl)methyl)piperidine-1-carboxamide;
3-(1-(6-((4-(trifluoromethyl)pyridin-2-yl)amino)pyridin-2-yl)-1H-pyrazol-4-yl)propanoic acid;
3-(1-{6-[(4-methylpyridin-2-yl)amino]pyridin-2-yl}-1H-pyrazol-4-yl)propanoic acid;
3-(1-{6-[(4-cyclopropylpyridin-2-yl)amino]-4-methylpyridin-2-yl}-1H-pyrazol-4-yl)propanoic acid;
3-(1-{6-[(5-chloro-4-methylpyridin-2-yl)amino]-4-methylpyridin-2-yl}-1H-pyrazol-4-yl)propanoic acid;
3-(1-(3-methyl-5-((4-(trifluoromethyl)pyrimidin-2-yl)amino)phenyl)-1H-pyrazol-4-yl)propanoic acid;
ethyl 3-[1-(3-methyl-5-{[4-(trifluoromethyl)pyrimidin-2-yl]amino}phenyl)-1H-pyrazol-4-yl]propanoate;
3-(1-{3-[(4-cyclopropylpyrimidin-2-yl)amino]-5-methylphenyl}-1H-pyrazol-4-yl)propanoic acid;
ethyl 3-(1-{3-[(4-cyclopropylpyrimidin-2-yl)amino]-5-methylphenyl}-1H-pyrazol-4-yl)propanoate;
ethyl 3-(1-{3-[(4-methoxypyrimidin-2-yl)amino]-5-methylphenyl}-1H-pyrazol-4-yl)propanoate;
ethyl 3-(1-{3-methyl-5-[(4-methylpyrimidin-2-yl)amino]phenyl}-1H-pyrazol-4-yl)propanoate;
4-[4-(3-methyl-5-{[4-(trifluoromethyl)pyrimidin-2-yl]amino}phenyl)-1H-pyrazol-1-yl]-cyclohexanecarboxylic acid;
2,2-dimethyl-4-[4-(3-methyl-5-{[4-(trifluoromethyl)pyrimidin-2-yl]amino}-phenyl)-1H-pyrazol-1-yl]-cyclohexanecarboxylic acid;
4-{1-[4-(3-methyl-5-{[4-(trifluoromethyl)pyrimidin-2-yl]amino}phenyl)-1H-pyrazol-1-yl]ethyl}benzoic acid;
5-[4-(3-methyl-5-{[4-(trifluoromethyl)pyrimidin-2-yl]amino}phenyl)-1H-pyrazol-1-yl]-5,6,7,8-tetrahydronaphthalene-2-carboxylic acid;
8-[4-(3-methyl-5-{[4-(trifluoromethyl)pyrimidin-2-yl]amino}phenyl)-1H-pyrazol-1-yl]-5,6,7,8-tetrahydronaphthalene-2-carboxylic acid;
4-hydroxy-4-[1-(3-methyl-5-{[4-(trifluoromethyl)-pyrimidin-2-yl]amino}-phenyl)-1H-pyrazol-4-yl]-cyclohexanecarboxylic acid;
4-hydroxy-2,2-dimethyl-4-[1-(3-methyl-5-{[4-(trifluoromethyl)pyrimidin-2-yl]amino}phenyl)-1H-pyrazol-4-yl]-cyclohexanecarboxylic acid;
4-{1-hydroxy-1-[1-(3-methyl-5-{[4-(trifluoromethyl)pyrimidin-2-yl]amino}phenyl)-1H-pyrazol-4-yl]ethyl}-cyclohexanecarboxylic acid;
5-hydroxy-5-[1-(3-methyl-5-{[4-(trifluoromethyl)-pyrimidin-2-yl]amino}-phenyl)-1H-pyrazol-4-yl]-5,6,7,8-tetrahydronaphthalene-2-carboxylic acid;
4-{1-hydroxy-1-[1-(3-methyl-5-{[4-(trifluoromethyl)pyrimidin-2-yl]amino}phenyl)-1H-pyrazol-4-yl]ethyl}benzoic acid;
N-[3-(5-chloro-1H-pyrazol-1-yl)-5-methylphenyl]-4-(trifluoromethyl)pyrimidin-2-amine;
N-[3-(5-fluoro-1H-pyrazol-1-yl)-5-methylphenyl]-4-(trifluoromethyl)pyrimidin-2-amine-methane (1:1);
4-[4-(4-chloro-6-{[4-(trifluoromethyl)pyridin-2-yl]amino}pyridin-2-yl)-1H-pyrazol-1-yl]-cyclohexanecarboxylic acid;
4-[4-(4-cyclopropyl-6-{[4-(trifluoromethyl)pyridin-2-yl]amino}pyridin-2-yl)-1H-pyrazol-1-yl]-cyclohexanecarboxylic acid;
4-[4-(4-amino-6-{[4-(trifluoromethyl)pyridin-2-yl]amino}pyridin-2-yl)-1H-pyrazol-1-yl]-cyclohexanecarboxylic acid;
4-{4-[4-(acetylamino)-6-{[4-(trifluoromethyl)pyridin-2-yl]amino}pyridin-2-yl]-1H-pyrazol-1-yl}-cyclohexanecarboxylic acid;
4-(1,1-difluoroethyl)-N-[3-methyl-5-(1H-pyrazol-4-yl)phenyl]pyrimidin-2-amine;
(1R)-4-{1-[4-(3-methyl-5-{[4-(trifluoromethyl)pyrimidin-2-yl]amino}phenyl)-1H-pyrazol-1-yl]ethyl}benzoic acid;
(1S)-4-{1-[4-(3-methyl-5-{[4-(trifluoromethyl)pyrimidin-2-yl]amino}phenyl)-1H-pyrazol-1-yl]ethyl}benzoic acid;
4-[4-(3-amino-5-{[4-(trifluoromethyl)pyrimidin-2-yl]amino}phenyl)-1H-pyrazol-1-yl]cyclohexanecarboxylic acid;
4-{4-[3-(acetylamino)-5-{[4-(trifluoromethyl)pyrimidin-2-yl]amino}phenyl]-1H-pyrazol-1-yl}cyclohexanecarboxylic acid;
4-[4-(4-chloro-6-{[4-(trifluoromethyl)pyridin-2-yl]amino}pyridin-2-yl)-1H-pyrazol-1-yl]cyclohexanecarboxylic acid;
4-[4-(3-methyl-5-{[4-(trifluoromethyl)pyrimidin-2-yl]amino}phenyl)-1H-pyrazol-1-yl]cyclohexanecarboxylic acid;
4-(4-{3-methyl-5-[(4-methylpyrimidin-2-yl)amino]phenyl}-1H-pyrazol-1-yl)cyclohexanecarboxylic acid;
4-[4-(3-chloro-5-{[4-(trifluoromethyl)pyrimidin-2-yl]amino}phenyl)-1H-pyrazol-1-yl]cyclohexanecarboxylic acid;
4-{1-[4-(6-{[4-(difluoromethyl)pyridin-2-yl]amino}-4-methylpyridin-2-yl)-1H-pyrazol-1-yl]ethyl}pyrrolidin-2-one;
4-(difluoromethyl)-N-[3-methyl-5-(1H-pyrazol-4-yl)phenyl]pyrimidin-2-amine 4-{1-[4-(6-{[4-(difluoromethyl)pyridin-2-yl]amino}-4-methylpyridin-2-yl)-1H-pyrazol-1-yl]ethyl}pyrrolidin-2-one;

3-[4-(3-{[4-(difluoromethyl)pyrimidin-2-yl]amino}-5-methylphenyl)-1H-pyrazol-1-yl]hexane-2,5-diol;

4-({4-[3-methyl-5-(pyrimidin-2-ylamino)phenyl]-1H-pyrazol-1-yl}methyl)benzamide;

4-({4-[3-methyl-5-(pyrimidin-2-ylamino)phenyl]-1H-pyrazol-1-yl}methyl)phenol;

2,2-dimethyl-4-[4-(3-methyl-5-{[4-(trifluoromethyl)pyrimidin-2-yl]amino}phenyl)-1H-pyrazol-1-yl]cyclohexanecarboxylic acid;

cis-4-[4-(3-{[4-(difluoromethyl)pyrimidin-2-yl]amino}-5-methylphenyl)-1H-pyrazol-1-yl]cyclohexanecarboxylic acid;

trans-4-[4-(3-{[4-(difluoromethyl)pyrimidin-2-yl]amino}-5-methylphenyl)-1H-pyrazol-1-yl]cyclohexanecarboxylic acid;

(R)-5-{[4-(3-{[4-(difluoromethyl)pyrimidin-2-yl]amino}-5-methylphenyl)-1H-pyrazol-1-yl]methyl}-1,3-oxazolidin-2-one;

(S)-5-{[4-(3-{[4-(difluoromethyl)pyrimidin-2-yl]amino}-5-methylphenyl)-1H-pyrazol-1-yl]methyl}-1,3-oxazolidin-2-one;

(R)-5-{[4-(3-{[4-(difluoromethyl)pyrimidin-2-yl]amino}phenyl)-1H-pyrazol-1-yl]methyl}-1,3-oxazolidin-2-one;

(S)-5-{[4-(3-{[4-(difluoromethyl)pyrimidin-2-yl]amino}phenyl)-1H-pyrazol-1-yl]methyl}-1,3-oxazolidin-2-one;

4-{1-[4-(3-{[4-(difluoromethyl)pyrimidin-2-yl]amino}-5-methylphenyl)-1H-pyrazol-1-yl]ethyl}pyrrolidin-2-one;

(R)-3-{[4-(3-{[4-(difluoromethyl)pyrimidin-2-yl]amino}-5-methylphenyl)-1H-pyrazol-1-yl]methyl}pyrrolidine-2,5-dione;

4-{[4-(3-{[4-(difluoromethyl)pyrimidin-2-yl]amino}-5-methylphenyl)-1H-pyrazol-1-yl]methyl}pyridin-2(1H)-one;

(S)-3-{[4-(3-{[4-(difluoromethyl)pyrimidin-2-yl]amino}-5-methylphenyl)-1H-pyrazol-1-yl]methyl}pyrrolidine-2,5-dione;

(R)-5-{[4-(3-{[4-(difluoromethyl)pyrimidin-2-yl]amino}-5-methylphenyl)-1H-pyrazol-1-yl]methyl}-1,3-oxazolidine-2,4-dione;

(S)-5-{[4-(3-{[4-(difluoromethyl)pyrimidin-2-yl]amino}-5-methylphenyl)-1H-pyrazol-1-yl]methyl}-1,3-oxazolidine-2,4-dione;

4-{[4-(3-{[4-(difluoromethyl)pyrimidin-2-yl]amino}-5-methylphenyl)-1H-pyrazol-1-yl]methyl}-5-methylpyrrolidin-2-one;

(R)-4-{[4-(3-{[4-(difluoromethyl)pyrimidin-2-yl]amino}-5-methylphenyl)-1H-pyrazol-1-yl]methyl}-4-methylpyrrolidin-2-one;

(R)-6-{[4-(3-{[4-(difluoromethyl)pyrimidin-2-yl]amino}-5-methylphenyl)-1H-pyrazol-1-yl]methyl}-1,3-oxazinan-2-one;

(S)-4-{[4-(3-{[4-(difluoromethyl)pyrimidin-2-yl]amino}-5-methylphenyl)-1H-pyrazol-1-yl]methyl}-4-methylpyrrolidin-2-one;

(S)-6-{[4-(3-{[4-(difluoromethyl)pyrimidin-2-yl]amino}-5-methylphenyl)-1H-pyrazol-1-yl]methyl}-1,3-oxazinan-2-one;

N-{3-[1-(2-aminoethyl)-1H-pyrazol-4-yl]-5-methylphenyl}-4-(difluoromethyl)pyrimidin-2-amine;

4-(difluoromethyl)-N-(3-methyl-5-{1-[(2S)-morpholin-2-ylmethyl]-1H-pyrazol-4-yl}phenyl)pyrimidin-2-amine;

4-(difluoromethyl)-N-(3-methyl-5-{1-[(2R)-morpholin-2-ylmethyl]-1H-pyrazol-4-yl}phenyl)pyrimidin-2-amine;

N-{3-[1-(2-amino-2-methylpropyl)-1H-pyrazol-4-yl]-5-methylphenyl}-4-(difluoromethyl)pyrimidin-2-amine;

(2S)-2-methyl-3-[4-(3-{[4-(trifluoromethyl)pyrimidin-2-yl]amino}phenyl)-1H-pyrazol-1-yl]propane-1,2-diol;

(2S)-3-[4-(3-{[4-(1-hydroxyethyl)pyrimidin-2-yl]amino}-5-methylphenyl)-1H-pyrazol-1-yl]-2-methylpropane-1,2-diol;

(2S)-3-(4-{3-[(4-methoxypyrimidin-2-yl)amino]-5-methylphenyl}-1H-pyrazol-1-yl)-2-methylpropane-1,2-diol;

(2S)-3-(4-{3-[(5-fluoro-4-methoxypyrimidin-2-yl)amino]-5-methylphenyl}-1H-pyrazol-1-yl)-2-methylpropane-1,2-diol;

(2S)-3-(4-{3-[(4-cyclopropylpyrimidin-2-yl)amino]-5-methylphenyl}-1H-pyrazol-1-yl)-2-methylpropane-1,2-diol;

(2S)-3-[4-(3-fluoro-5-{[4-(trifluoromethyl)pyrimidin-2-yl]amino}phenyl)-1H-pyrazol-1-yl]-2-methylpropane-1,2-diol;

(2S)-3-[4-(3-{[4-(difluoromethyl)pyrimidin-2-yl]amino}phenyl)-1H-pyrazol-1-yl]-2-methylpropane-1,2-diol;

(2S)-3-[4-(3-{[4-(1-hydroxyethyl)pyrimidin-2-yl]amino}phenyl)-1H-pyrazol-1-yl]-2-methylpropane-1,2-diol;

(2S)-3-(4-{3-[(5-fluoro-4-methylpyrimidin-2-yl)amino]-5-methylphenyl}-1H-pyrazol-1-yl)-2-methylpropane-1,2-diol;

(2S)-2-methyl-3-(4-{3-[(4-methylpyrimidin-2-yl)amino]phenyl}-1H-pyrazol-1-yl)propane-1,2-diol;

(2S)-2-methyl-3-[4-(3-methyl-5-{[4-(1-methylethoxy)pyrimidin-2-yl]amino}phenyl)-1H-pyrazol-1-yl]propane-1,2-diol;

(2S)-3-(4-{3-[(5-chloro-4-methylpyrimidin-2-yl)amino]-5-methylphenyl}-1H-pyrazol-1-yl)-2-methylpropane-1,2-diol;

(2S)-3-(4-{3-[(5-chloro-4-methoxypyrimidin-2-yl)amino]-5-methylphenyl}-1H-pyrazol-1-yl)-2-methylpropane-1,2-diol;

(R)-5-{[4-(6-{[4-(difluoromethyl)pyridin-2-yl]amino}-4-methylpyridin-2-yl)-1H-pyrazol-1-yl]methyl}-1,3-oxazolidin-2-one;

(R)-5-{[4-(6-{[4-(difluoromethyl)pyridin-2-yl]amino}pyridin-2-yl)-1H-pyrazol-1-yl]methyl}-1,3-oxazolidin-2-one;

(S)-5-{[4-(6-{[4-(difluoromethyl)pyridin-2-yl]amino}-4-methylpyridin-2-yl)-1H-pyrazol-1-yl]methyl}-1,3-oxazolidin-2-one;

(S)-5-{[4-(6-{[4-(difluoromethyl)pyridin-2-yl]amino}pyridin-2-yl)-1H-pyrazol-1-yl]methyl}-1,3-oxazolidin-2-one;

(R)-5-{[4-(6-{[4-(1,1-difluoroethyl)pyridin-2-yl]amino}-4-methylpyridin-2-yl)-1H-pyrazol-1-yl]methyl}-1,3-oxazolidin-2-one;

(S)-5-{[4-(6-{[4-(1,1-difluoroethyl)pyridin-2-yl]amino}-4-methylpyridin-2-yl)-1H-pyrazol-1-yl]methyl}-1,3-oxazolidin-2-one;

5-{1-[4-(6-{[4-(difluoromethyl)pyridin-2-yl]amino}-4-methylpyridin-2-yl)-1H-pyrazol-1-yl]ethyl}-1,3-oxazolidin-2-one;

(R)-7-{[4-(3-{[4-(difluoromethyl)pyrimidin-2-yl] amino}-5-methylphenyl)-1H-pyrazol-1-yl]methyl}-4-azaspiro[2.4]heptan-5-one;
(S)-7-{[4-(3-{[4-(difluoromethyl)pyrimidin-2-yl] amino}-5-methylphenyl)-1H-pyrazol-1-yl]methyl}-4-azaspiro[2.4]heptan-5-one;
5-{1-[4-(3-{[4-(difluoromethyl)pyrimidin-2-yl]amino}-5-methylphenyl)-1H-pyrazol-1-yl]ethyl}-1,3-oxazolidin-2-one;
(R)-7-{[4-(3-{[4-(difluoromethyl)pyrimidin-2-yl] amino}-5-methylphenyl)-1H-pyrazol-1-yl]methyl}-6-oxa-4-azaspiro[2.4]heptan-5-one;
5-{1-[4-(3-{[4-(difluoromethyl)pyrimidin-2-yl]amino}-5-methylphenyl)-1H-pyrazol-1-yl]ethyl}-1,3-oxazolidin-2-one;
(S)-7-{[4-(3-{[4-(difluoromethyl)pyrimidin-2-yl] amino}-5-methylphenyl)-1H-pyrazol-1-yl]methyl}-6-oxa-4-azaspiro[2.4]heptan-5-one;
5-{[4-(3-{[4-(difluoromethyl)pyrimidin-2-yl]amino}-5-methylphenyl)-1H-pyrazol-1-yl]methyl}pyridin-2 (1H)-one;
(4S)-4-{[4-(3-methyl-5-{[4-(trifluoromethyl)pyrimidin-2-yl]amino}phenyl)-1H-pyrazol-1-yl]methyl}-1,3-oxazolidin-2-one;
(4R)-4-{[4-(3-methyl-5-{[4-(trifluoromethyl)pyrimidin-2-yl]amino}phenyl)-1H-pyrazol-1-yl]methyl}-1,3-oxazolidin-2-one;
3-[4-(3-{[4-(difluoromethyl)pyrimidin-2-yl]amino}-5-methylphenyl)-1H-pyrazol-1-yl]butan-2-one;
(R)-4,4-dimethyl-5-{[4-(3-methyl-5-{[4-(trifluoromethyl)pyrimidin-2-yl]amino}phenyl)-1H-pyrazol-1-yl] methyl}-1,3-oxazolidin-2-one;
(S)-4,4-dimethyl-5-{[4-(3-methyl-5-{[4-(trifluoromethyl)pyrimidin-2-yl]amino}phenyl)-1H-pyrazol-1-yl] methyl}-1,3-oxazolidin-2-one;
(R)-5-{[4-(3-{[4-(1,1-difluoroethyl)pyrimidin-2-yl] amino}-5-methylphenyl)-1H-pyrazol-1-yl]methyl}-4,4-dimethyl-1,3-oxazolidin-2-one;
(R)-5-{[4-(3-{[4-(difluoromethyl)pyrimidin-2-yl] amino}-5-methylphenyl)-1H-pyrazol-1-yl]methyl}-4,4-dimethyl-1,3-oxazolidin-2-one;
(S)-5-{[4-(3-{[4-(difluoromethyl)pyrimidin-2-yl] amino}-5-methylphenyl)-1H-pyrazol-1-yl]methyl}-4,4-dimethyl-1,3-oxazolidin-2-one;
(S)-5-{[4-(3-{[4-(1,1-difluoroethyl)pyrimidin-2-yl] amino}-5-methylphenyl)-1H-pyrazol-1-yl]methyl}-4,4-dimethyl-1,3-oxazolidin-2-one;
(R)-4,4-dimethyl-5-[(4-{3-methyl-5-[(4-methylpyrimidin-2-yl)amino]phenyl}-1H-pyrazol-1-yl)methyl]-1,3-oxazolidin-2-one;
(S)-4,4-dimethyl-5-[(4-{3-methyl-5-[(4-methylpyrimidin-2-yl)amino]phenyl}-1H-pyrazol-1-yl)methyl]-1,3-oxazolidin-2-one;
5-methyl-4-{[4-(3-methyl-5-{[4-(trifluoromethyl)pyrimidin-2-yl]amino}phenyl)-1H-pyrazol-1-yl]methyl}-1,3-oxazolidin-2-one;
4-(difluoromethyl)-N-(3-methyl-5-{1-[(2-methyl-1H-imidazol-5-yl)methyl]-1H-pyrazol-4-yl}phenyl)pyrimidin-2-amine;
4-(difluoromethyl)-N-(3-methyl-5-{1-[(4-methyl-1H-imidazol-5-yl)methyl]-1H-pyrazol-4-yl}phenyl)pyrimidin-2-amine;
4-(difluoromethyl)-N-{3-[1-(1H-imidazol-4-ylmethyl)-1H-pyrazol-4-yl]-5-methylphenyl}pyrimidin-2-amine;
4-(difluoromethyl)-N-(3-methyl-5-{1-[2-(1H-pyrazol-4-yl)ethyl]-1H-pyrazol-4-yl}phenyl)pyrimidin-2-amine;
3-[4-(3-{[4-(difluoromethyl)pyrimidin-2-yl]amino}-5-methylphenyl)-1H-pyrazol-1-yl]propane-1,2-diol;
(R)-1-[4-(3-{[4-(difluoromethyl)pyrimidin-2-yl]amino}-5-methylphenyl)-1H-pyrazol-1-yl]-2-methylbutan-2-ol;
(S)-1-[4-(3-{[4-(difluoromethyl)pyrimidin-2-yl]amino}-5-methylphenyl)-1H-pyrazol-1-yl]-2-methylbutan-2-ol;
(5R)-5-({4-[3-methyl-5-(pyrimidin-2-ylamino)phenyl]-1H-pyrazol-1-yl}methyl)-1,3-oxazolidin-2-one;
(5S)-5-({4-[3-methyl-5-(pyrimidin-2-ylamino)phenyl]-1H-pyrazol-1-yl}methyl)-1,3-oxazolidin-2-one;
(5R)-5-methyl-5-{[4-(3-methyl-5-{[4-(trifluoromethyl) pyrimidin-2-yl]amino}phenyl)-1H-pyrazol-1-yl]methyl}-1,3-oxazolidin-2-one;
(5S)-5-methyl-5-{[4-(3-methyl-5-{[4-(trifluoromethyl) pyrimidin-2-yl]amino}phenyl)-1H-pyrazol-1-yl]methyl}-1,3-oxazolidin-2-one;
4-methyl-5-{[4-(3-methyl-5-{[4-(trifluoromethyl)pyrimidin-2-yl]amino}phenyl)-1H-pyrazol-1-yl]methyl}-1,3-oxazolidin-2-one;
(5R)-5-methyl-5-[(4-{3-methyl-5-[(4-methylpyrimidin-2-yl)amino]phenyl}-1H-pyrazol-1-yl)methyl]-1,3-oxazolidin-2-one;
(5S)-5-methyl-5-[(4-{3-methyl-5-[(4-methylpyrimidin-2-yl)amino]phenyl}-1H-pyrazol-1-yl)methyl]-1,3-oxazolidin-2-one;
(5R)-5-{[4-(3-{[4-(difluoromethyl)pyrimidin-2-yl] amino}-5-methylphenyl)-1H-pyrazol-1-yl]methyl}-5-methyl-1,3-oxazolidin-2-one;
(5S)-5-{[4-(3-{[4-(difluoromethyl)pyrimidin-2-yl] amino}-5-methylphenyl)-1H-pyrazol-1-yl]methyl}-5-methyl-1,3-oxazolidin-2-one;
(5R)-5-{[4-(3-{[4-(1,1-difluoroethyl)pyrimidin-2-yl] amino}-5-methylphenyl)-1H-pyrazol-1-yl]methyl}-1,3-oxazolidin-2-one;
(5S)-5-{[4-(3-{[4-(1,1-difluoroethyl)pyrimidin-2-yl] amino}-5-methylphenyl)-1H-pyrazol-1-yl]methyl}-1,3-oxazolidin-2-one;
3-[4-(3-methyl-5-{[4-(trifluoromethyl)pyrimidin-2-yl] amino}phenyl)-1H-pyrazol-1-yl]cyclohexane-1,2-diol;
(1S,2R,3S)-3-(4-(3-((4-(difluoromethyl)pyrimidin-2-yl) amino)-5-methylphenyl)-1H-pyrazol-1-yl)cyclohexane-1,2-diol;
(1R,2S,3S)-3-(4-(3-((4-(difluoromethyl)pyrimidin-2-yl) amino)-5-methylphenyl)-1H-pyrazol-1-yl)cyclohexane-1,2-diol;
(1S,2R,3R)-3-(4-(3-((4-(difluoromethyl)pyrimidin-2-yl) amino)-5-methylphenyl)-1H-pyrazol-1-yl)cyclohexane-1,2-diol;
(1R,2S,3R)-3-(4-(3-((4-(difluoromethyl)pyrimidin-2-yl) amino)-5-methylphenyl)-1H-pyrazol-1-yl)cyclohexane-1,2-diol;
3-(4-{3-methyl-5-[(4-methylpyrimidin-2-yl)amino]phenyl}-1H-pyrazol-1-yl)cyclohexane-1,2-diol;
3-[4-(3-{[4-(difluoromethyl)-5-fluoropyrimidin-2-yl] amino}-5-methylphenyl)-1H-pyrazol-1-yl]cyclohexane-1,2-diol;
(R)-4-{1-hydroxy-1-[1-(3-methyl-5-{[4-(trifluoromethyl) pyrimidin-2-yl]amino}phenyl)-1H-pyrazol-4-yl] ethyl}benzoic acid;
(S)-4-{1-hydroxy-1-[1-(3-methyl-5-{[4-(trifluoromethyl) pyrimidin-2-yl]amino}phenyl)-1H-pyrazol-4-yl] ethyl}benzoic acid;
N-[3-(3-chloro-1H-pyrazol-1-yl)-5-methylphenyl]-4-(trifluoromethyl)pyrimidin-2-amine 4-hydroxy-4-[1-(3-methyl-5-{[4-(trifluoromethyl)pyrimidin-2-yl]amino}phenyl)-1H-pyrazol-4-yl]cyclohexanecarboxylic acid;

(1R)-trans-4-{1-hydroxy-1-[1-(3-methyl-5-{[4-(trifluoromethyl)pyrimidin-2-yl]amino}phenyl)-1H-pyrazol-4-yl]ethyl}cyclohexanecarboxylic acid;

(1S)-trans-4-{1-hydroxy-1-[1-(3-methyl-5-{[4-(trifluoromethyl)pyrimidin-2-yl]amino}phenyl)-1H-pyrazol-4-yl]ethyl}cyclohexanecarboxylic acid;

4-hydroxy-2,2-dimethyl-4-[1-(3-methyl-5-{[4-(trifluoromethyl)pyrimidin-2-yl]amino}phenyl)-1H-pyrazol-4-yl]cyclohexanecarboxylic acid;

(R)-3-hydroxy-3-methyl-4-(4-(4-methyl-6-((4-(trifluoromethyl)pyridin-2-yl)amino)pyridin-2-yl)-1H-pyrazol-1-yl)butanenitrile;

(R)-3-hydroxy-3-methyl-4-[4-(3-methyl-5-{[4-(trifluoromethyl)pyrimidin-2-yl]amino}phenyl)-1H-pyrazol-1-yl]butanenitrile;

(S)-3-hydroxy-3-methyl-4-[4-(3-methyl-5-{[4-(trifluoromethyl)pyrimidin-2-yl]amino}phenyl)-1H-pyrazol-1-yl]butanenitrile;

(S)-3-hydroxy-3-methyl-4-[4-(4-methyl-6-{[4-(trifluoromethyl)pyridin-2-yl]amino}pyridin-2-yl)-1H-pyrazol-1-yl]butanenitrile;

(R)-4-[4-(3-{[4-(difluoromethyl)-5-fluoropyrimidin-2-yl]amino}-5-methylphenyl)-1H-pyrazol-1-yl]-3-hydroxy-3-methylbutanenitrile;

(S)-4-[4-(3-{[4-(difluoromethyl)-5-fluoropyrimidin-2-yl]amino}-5-methylphenyl)-1H-pyrazol-1-yl]-3-hydroxy-3-methylbutanenitrile;

(R)-4-[4-(3-{[4-(difluoromethyl)pyrimidin-2-yl]amino}-5-methylphenyl)-1H-pyrazol-1-yl]-3-hydroxy-3-methylbutanenitrile;

(S)-4-[4-(3-{[4-(difluoromethyl)pyrimidin-2-yl]amino}-5-methylphenyl)-1H-pyrazol-1-yl]-3-hydroxy-3-methylbutanenitrile;

(R)-4-[4-(3-{[4-(1,1-difluoroethyl)pyrimidin-2-yl]amino}-5-methylphenyl)-1H-pyrazol-1-yl]-3-hydroxy-3-methylbutanenitrile;

(S)-4-[4-(3-{[4-(1,1-difluoroethyl)pyrimidin-2-yl]amino}-5-methylphenyl)-1H-pyrazol-1-yl]-3-hydroxy-3-methylbutanenitrile;

(R)-2-methyl-3-(4-(3-methyl-5-((4-(trifluoromethyl)pyrimidin-2-yl)amino)phenyl)-1H-pyrazol-1-yl)propane-1,2-diol;

(S)-2-methyl-3-(4-(3-methyl-5-((4-(trifluoromethyl)pyrimidin-2-yl)amino)phenyl)-H-pyrazol-1-yl)propane-1,2-diol;

3-[4-(3-{[4-(difluoromethyl)pyrimidin-2-yl]amino}-5-methylphenyl)-1H-pyrazol-1-yl]butan-2-one;

(R)-2-methyl-3-[4-(4-methyl-6-{[4-(trifluoromethyl)pyridin-2-yl]amino}pyridin-2-yl)-1H-pyrazol-1-yl]propane-1,2-diol;

(S)-2-methyl-3-[4-(4-methyl-6-{[4-(trifluoromethyl)pyridin-2-yl]amino}pyridin-2-yl)-1H-pyrazol-1-yl]propane-1,2-diol;

(R)-1-[4-(3-{[4-(difluoromethyl)pyrimidin-2-yl]amino}-5-methylphenyl)-1H-pyrazol-1-yl]-2,3-dimethylbutane-2,3-diol;

(S)-1-[4-(3-{[4-(difluoromethyl)pyrimidin-2-yl]amino}-5-methylphenyl)-1H-pyrazol-1-yl]-2,3-dimethylbutane-2,3-diol;

(2R,3S)-2-methyl-3-[4-(3-methyl-5-{[4-(trifluoromethyl)pyrimidin-2-yl]amino}phenyl)-1H-pyrazol-1-yl]butane-1,2-diol;

(2S,3R)-2-methyl-3-[4-(3-methyl-5-{[4-(trifluoromethyl)pyrimidin-2-yl]amino}phenyl)-1H-pyrazol-1-yl]butane-1,2-diol;

(2R,3R)-2-methyl-3-[4-(3-methyl-5-{[4-(trifluoromethyl)pyrimidin-2-yl]amino}phenyl)-1H-pyrazol-1-yl]butane-1,2-diol;

(2S,3S)-2-methyl-3-[4-(3-methyl-5-{[4-(trifluoromethyl)pyrimidin-2-yl]amino}phenyl)-1H-pyrazol-1-yl]butane-1,2-diol;

3-(4-(3-((4-(difluoromethyl)pyrimidin-2-yl)amino)-5-methylphenyl)-1H-pyrazol-1-yl)-2-methylbutane-1,2-diol;

(R)-1-[4-(3-{[4-(1,1-difluoroethyl)pyrimidin-2-yl]amino}-5-methylphenyl)-1H-pyrazol-1-yl]-2,3-dimethylbutane-2,3-diol;

(S)-1-[4-(3-{[4-(1,1-difluoroethyl)pyrimidin-2-yl]amino}-5-methylphenyl)-1H-pyrazol-1-yl]-2,3-dimethylbutane-2,3-diol;

3-[4-(3-{[4-(difluoromethyl)pyrimidin-2-yl]amino}-5-methylphenyl)-1H-pyrazol-1-yl]-1-methylcyclohexane-1,2-diol;

6-[4-(3-{[4-(difluoromethyl)pyrimidin-2-yl]amino}-5-methylphenyl)-1H-pyrazol-1-yl]-3,3-dimethylcyclohexane-1,2-diol;

3-[4-(3-{[4-(difluoromethyl)pyrimidin-2-yl]amino}-5-methylphenyl)-1H-pyrazol-1-yl]-1,5,5-trimethylcyclohexane-1,2-diol;

3-[4-(3-{[4-(difluoromethyl)pyrimidin-2-yl]amino}-5-methylphenyl)-1H-pyrazol-1-yl]-1,2-dimethylcyclohexane-1,2-diol;

5-[4-(3-{[4-(difluoromethyl)pyrimidin-2-yl]amino}-5-methylphenyl)-1H-pyrazol-1-yl]-1-methylcyclopentane-1,2-diol;

3-[4-(3-{[4-(difluoromethyl)pyrimidin-2-yl]amino}-5-methylphenyl)-1H-pyrazol-1-yl]cycloheptane-1,2-diol;

(4S,5S)-4-methyl-5-((4-(3-methyl-5-((4-(trifluoromethyl)pyrimidin-2-yl)amino)phenyl)-1H-pyrazol-1-yl)methyl)oxazolidin-2-one;

4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one;

4-(1-methylethyl)-5-{[4-(3-methyl-5-{[4-(trifluoromethyl)pyrimidin-2-yl]amino}phenyl)-1H-pyrazol-1-yl]methyl}-1,3-oxazolidin-2-one;

4-methyl-5-[(4-{3-methyl-5-[(4-methylpyrimidin-2-yl)amino]phenyl}-1H-pyrazol-1-yl)methyl]-1,3-oxazolidin-2-one;

5-{[4-(3-{[4-(difluoromethyl)pyrimidin-2-yl]amino}-5-methylphenyl)-1H-pyrazol-1-yl]methyl}-4-methyl-1,3-oxazolidin-2-one;

5-{[4-(3-{[4-(1,1-difluoroethyl)pyrimidin-2-yl]amino}-5-methylphenyl)-1H-pyrazol-1-yl]methyl}-4-methyl-1,3-oxazolidin-2-one;

5-{[4-(3-{[4-(difluoromethyl)pyrimidin-2-yl]amino}-5-methylphenyl)-1H-pyrazol-1-yl]methyl}-4-methyl-1,3-oxazolidin-2-one;

4-(1-methylethyl)-5-[(4-{3-methyl-5-[(4-methylpyrimidin-2-yl)amino]phenyl}-1H-pyrazol-1-yl)methyl]-1,3-oxazolidin-2-one;

4-cyclopropyl-5-{[4-(3-{[4-(difluoromethyl)pyrimidin-2-yl]amino}-5-methylphenyl)-1H-pyrazol-1-yl]methyl}-1,3-oxazolidin-2-one;

5-{[4-(3-{[4-(difluoromethyl)-5-fluoropyrimidin-2-yl]amino}-5-methylphenyl)-1H-pyrazol-1-yl]methyl}-4-methyl-1,3-oxazolidin-2-one;

(R)-3-(4-(3-((4-(difluoromethyl)pyrimidin-2-yl)amino)-5-methylphenyl)-1H-pyrazol-1-yl)-1,1,1-trifluoro-2-methylpropan-2-ol;

(S)-3-(4-(3-((4-(difluoromethyl)pyrimidin-2-yl)amino)-5-methylphenyl)-1H-pyrazol-1-yl)-1,1,1-trifluoro-2-methylpropan-2-ol;

2-((4-(3-((4-(difluoromethyl)pyrimidin-2-yl)amino)-5-methylphenyl)-1H-pyrazol-1-yl)methyl)-3,3,3-trifluoropropane-1,2-diol;

(R)-2-methyl-3-(4-{3-methyl-5-[(4-methylpyrimidin-2-yl)amino]phenyl}-1H-pyrazol-1-yl)propane-1,2-diol;

(R)-3-[4-(3-{[4-(difluoromethyl)pyrimidin-2-yl]amino}-5-methylphenyl)-1H-pyrazol-1-yl]-2-methylpropane-1,2-diol;

(S)-2-methyl-3-(4-{3-methyl-5-[(4-methylpyrimidin-2-yl)amino]phenyl}-1H-pyrazol-1-yl)propane-1,2-diol;

(S)-3-[4-(3-{[4-(difluoromethyl)pyrimidin-2-yl]amino}-5-methylphenyl)-1H-pyrazol-1-yl]-2-methylpropane-1,2-diol;

3-{4-[3-({4-[(1R)-1-fluoroethyl]pyrimidin-2-yl}amino)-5-methylphenyl]-1H-pyrazol-1-yl}-2-methylpropane-1,2-diol;

3-{4-[3-({4-[(1S)-1-fluoroethyl]pyrimidin-2-yl}amino)-5-methylphenyl]-1H-pyrazol-1-yl}-2-methylpropane-1,2-diol;

3-[4-(3-{[4-(difluoromethyl)-5-fluoropyrimidin-2-yl]amino}-5-methylphenyl)-1H-pyrazol-1-yl]-2-methylpropane-1,2-diol;

3-[4-(3-{[4-(difluoromethyl)-5-fluoropyrimidin-2-yl]amino}-5-methylphenyl)-1H-pyrazol-1-yl]-2-methylpropane-1,2-diol;

N-(2-(4-(3-((4-(Difluoromethyl)pyrimidin-2-yl)amino)-5-methylphenyl)-1H-pyrazol-1-yl)ethyl)cyclopropanecarboxamide;

N-{2-[4-(3-{[4-(difluoromethyl)pyrimidin-2-yl]amino}-5-methylphenyl)-1H-pyrazol-1-yl]-1,1-dimethylethyl}cyclopropanecarboxamide;

N-{2-[4-(3-{[4-(difluoromethyl)pyrimidin-2-yl]amino}-5-methylphenyl)-1H-pyrazol-1-yl]-1,1-dimethylethyl}-2-methoxyacetamide;

2-cyano-N-{2-[4-(3-{[4-(difluoromethyl)pyrimidin-2-yl]amino}-5-methylphenyl)-1H-pyrazol-1-yl]ethyl}acetamide;

N-{2-[4-(3-{[4-(difluoromethyl)pyrimidin-2-yl]amino}-5-methylphenyl)-1H-pyrazol-1-yl]ethyl}-2-methoxyacetamide;

N-(2-(4-(3-((4-(difluoromethyl)pyrimidin-2-yl)amino)-5-methylphenyl)-1H-pyrazol-1-yl)ethyl)methanesulfonamide;

methyl {2-[4-(3-{[4-(difluoromethyl)pyrimidin-2-yl]amino}-5-methylphenyl)-1H-pyrazol-1-yl]ethyl}carbamate;

2-methoxyethyl {2-[4-(3-{[4-(difluoromethyl)pyrimidin-2-yl]amino}-5-methylphenyl)-1H-pyrazol-1-yl]ethyl}carbamate;

N-{2-[4-(3-{[4-(difluoromethyl)pyrimidin-2-yl]amino}-5-methylphenyl)-1H-pyrazol-1-yl]-1,1-dimethylethyl}methanesulfonamide;

N-{2-[4-(3-{[4-(difluoromethyl)pyrimidin-2-yl]amino}-5-methylphenyl)-1H-pyrazol-1-yl]-1,1-dimethylethyl}cyclopropanesulfonamide;

N-{2-[4-(3-{[4-(difluoromethyl)pyrimidin-2-yl]amino}-5-methylphenyl)-1H-pyrazol-1-yl]-1,1-dimethylethyl}morpholine-4-sulfonamide;

1-tert-butyl-3-{2-[4-(3-{[4-(difluoromethyl)pyrimidin-2-yl]amino}-5-methylphenyl)-1H-pyrazol-1-yl]-1,1-dimethylethyl}urea;

1-{2-[4-(3-{[4-(difluoromethyl)pyrimidin-2-yl]amino}-5-methylphenyl)-1H-pyrazol-1-yl]-1,1-dimethylethyl}-3-ethylurea;

1-{2-[4-(3-{[4-(difluoromethyl)pyrimidin-2-yl]amino}-5-methylphenyl)-1H-pyrazol-1-yl]-1,1-dimethylethyl}-3-(tetrahydro-2H-pyran-4-ylmethyl)urea;

2-fluoroethyl {2-[4-(3-{[4-(difluoromethyl)pyrimidin-2-yl]amino}-5-methylphenyl)-1H-pyrazol-1-yl]-1,1-dimethylethyl}carbamate;

methyl {2-[4-(3-{[4-(difluoromethyl)pyrimidin-2-yl]amino}-5-methylphenyl)-1H-pyrazol-1-yl]-1,1-dimethylethyl}carbamate;

2-methoxyethyl {2-[4-(3-{[4-(difluoromethyl)pyrimidin-2-yl]amino}-5-methylphenyl)-1H-pyrazol-1-yl]-1,1-dimethylethyl}carbamate;

N-{2-[4-(3-{[4-(difluoromethyl)pyrimidin-2-yl]amino}-5-methylphenyl)-1H-pyrazol-1-yl]ethyl}cyclopropanesulfonamide;

N-{2-[4-(3-{[4-(difluoromethyl)pyrimidin-2-yl]amino}-5-methylphenyl)-1H-pyrazol-1-yl]ethyl}morpholine-4-sulfonamide;

1-tert-butyl-3-{2-[4-(3-{[4-(difluoromethyl)pyrimidin-2-yl]amino}-5-methylphenyl)-1H-pyrazol-1-yl]ethyl}urea;

1-{2-[4-(3-{[4-(difluoromethyl)pyrimidin-2-yl]amino}-5-methylphenyl)-1H-pyrazol-1-yl]ethyl}-3-ethylurea;

1-{2-[4-(3-{[4-(difluoromethyl)pyrimidin-2-yl]amino}-5-methylphenyl)-1H-pyrazol-1-yl]ethyl}-3-(tetrahydro-2H-pyran-4-ylmethyl)urea;

2-fluoroethyl {2-[4-(3-{[4-(difluoromethyl)pyrimidin-2-yl]amino}-5-methylphenyl)-1H-pyrazol-1-yl]ethyl}carbamate;

(R)-4-(1-(4-(3-Methyl-5-(pyrimidin-2-ylamino)phenyl)-1H-pyrazol-1-yl)ethyl)benzamide;

(S)-4-(1-(4-(3-Methyl-5-(pyrimidin-2-ylamino)phenyl)-1H-pyrazol-1-yl)ethyl)benzamide;

1-((4-(3-((4-(Difluoromethyl)pyrimidin-2-yl)amino)-5-methylphenyl)-1H-pyrazol-1-yl)methyl)cyclobutanol;

1-{[4-(6-{[4-(difluoromethyl)pyridin-2-yl]amino}-4-methylpyridin-2-yl)-1H-pyrazol-1-yl]methyl}cyclobutanol;

1-[(4-{4-methyl-6-[(4-methylpyridin-2-yl)amino]pyridin-2-yl}-1H-pyrazol-1-yl)methyl]cyclobutanol;

1-{[4-(3-{[4-(difluoromethyl)pyrimidin-2-yl]amino}phenyl)-1H-pyrazol-1-yl]methyl}cyclobutanol;

1-[(4-{3-methyl-5-[(4-methylpyrimidin-2-yl)amino]phenyl}-1H-pyrazol-1-yl)methyl]cyclobutanol;

1-{[4-(3-{[4-(difluoromethyl)-5-fluoropyrimidin-2-yl]amino}-5-methylphenyl)-1H-pyrazol-1-yl]methyl}cyclobutanol;

1-[(4-{6-[(4-cyclopropylpyridin-2-yl)amino]-4-methylpyridin-2-yl}-1H-pyrazol-1-yl)methyl]cyclobutanol;

3-(4-(3-methyl-5-(pyrimidin-2-ylamino)phenyl)-1H-pyrazol-1-yl)cyclobutanecarboxamide;

3-(4-(3-Methyl-5-(pyrimidin-2-ylamino)phenyl)-1H-pyrazol-1-yl)cyclobutanecarboxamide;

(R)-2-((4-(3-((4-(difluoromethyl)pyrimidin-2-yl)amino)-5-methylphenyl)-1H-pyrazol-1-yl)methyl)-3,3,3-trifluoropropane-1,2-diol;

(S)-2-((4-(3-((4-(difluoromethyl)pyrimidin-2-yl)amino)-5-methylphenyl)-1H-pyrazol-1-yl)methyl)-3,3,3-trifluoropropane-1,2-diol;

5-{[4-(3-{[4-(difluoromethyl)pyrimidin-2-yl]amino}-5-methylphenyl)-1H-pyrazol-1-yl]methyl}-4-(hydroxymethyl)-1,3-oxazolidin-2-one;

(R)-5-[4-(6-{[4-(difluoromethyl)pyridin-2-yl]amino}-4-methylpyridin-2-yl)-1H-pyrazol-1-yl]-5-ethyl-1,3-oxazolidin-2-one; and (S)-5-[4-(6-{[4-(difluoromethyl)pyridin-2-yl]amino}-4-methylpyridin-2-yl)-1H-pyrazol-1-yl]-5-ethyl-1,3-oxazolidin-2-one.

14. The compound of claim 1, or a pharmaceutically acceptable salt thereof, which is selected from the group consisting of:

(5R)-5-{[4-(4-methyl-6-{[4-(trifluoromethyl)pyridin-2-yl]amino}pyridin-2-yl)-1H-pyrazol-1-yl]methyl}-1,3-oxazolidin-2-one;

4-methyl-6-(1-piperidin-4-yl-1H-pyrazol-4-yl)-N-[4-(trifluoromethyl)pyridin-2-yl]pyridin-2-amine;

2-[4-(4-methyl-6-{[4-(trifluoromethyl)pyridin-2-yl]amino}pyridin-2-yl)-1H-pyrazol-1-yl]ethanol;

6-[1-(methoxyacetyl)-1H-pyrazol-4-yl]-4-methyl-N-[4-(trifluoromethyl)pyridin-2-yl]pyridin-2-amine;

(5S)-5-{[4-(4-methyl-6-{[4-(trifluoromethyl)pyridin-2-yl]amino}pyridin-2-yl)-1H-pyrazol-1-yl]methyl}-1,3-oxazolidin-2-one;

[4-(4-methyl-6-{[4-(trifluoromethyl)pyridin-2-yl]amino}pyridin-2-yl)-1H-pyrazol-1-yl]acetonitrile;

4-methyl-6-(1H-pyrazol-4-yl)-N-[4-(trifluoromethyl)pyridin-2-yl]pyridin-2-amine;

3-[4-(4-methyl-6-{[4-(trifluoromethyl)pyridin-2-yl]amino}pyridin-2-yl)-1H-pyrazol-1-yl]propanamide;

(2S)-3-[4-(3-{[4-(1-fluoroethyl)pyrimidin-2-yl]amino}-5-methylphenyl)-1H-pyrazol-1-yl]-2-hydroxypropanamide;

2-hydroxy-2-methyl-3-[4-(3-methyl-5-{[4-(trifluoromethyl)pyrimidin-2-yl]amino}phenyl)-1H-pyrazol-1-yl]propanamide;

(5S)-5-{[4-(3-methyl-5-{[4-(trifluoromethyl)pyrimidin-2-yl]amino}phenyl)-1H-pyrazol-1-yl]methyl}-1,3-oxazolidin-2-one;

3-[4-(3-methyl-5-{[4-(trifluoromethyl)pyrimidin-2-yl]amino}phenyl)-1H-pyrazol-1-yl]butanamide (2R)-2-hydroxy-3-[4-(3-methyl-5-{[4-(trifluoromethyl)pyrimidin-2-yl]amino}phenyl)-1H-pyrazol-1-yl]propanamide;

(2S)-2-hydroxy-3-[4-(3-methyl-5-{[4-(trifluoromethyl)pyrimidin-2-yl]amino}phenyl)-1H-pyrazol-1-yl]propanamide;

(2R)-3-[4-(3-methyl-5-{[4-(trifluoromethyl)pyrimidin-2-yl]amino}phenyl)-1H-pyrazol-1-yl]propane-1,2-diol;

3-[4-(3-methyl-5-{[4-(trifluoromethyl)pyrimidin-2-yl]amino}phenyl)-1H-pyrazol-1-yl]propane-1,2-diol;

(3S)-3-hydroxy-4-[4-(3-methyl-5-{[4-(trifluoromethyl)pyrimidin-2-yl]amino}phenyl)-1H-pyrazol-1-yl]butanenitrile;

(2R)-2-hydroxy-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]propanamide;

5-[(4-{3-methyl-5-[(4-methylpyrimidin-2-yl)amino]phenyl}-1H-pyrazol-1-yl)methyl]-1,3-oxazolidin-2-one;

(3R)-3-hydroxy-4-[4-(3-methyl-5-{[4-(trifluoromethyl)pyrimidin-2-yl]amino}phenyl)-1H-pyrazol-1-yl]butanenitrile;

(2S)-3-[4-(3-methyl-5-{[4-(trifluoromethyl)pyrimidin-2-yl]amino}phenyl)-1H-pyrazol-1-yl]propane-1,2-diol;

2-hydroxy-3-[4-(3-methyl-5-{[4-(trifluoromethyl)pyrimidin-2-yl]amino}phenyl)-1H-pyrazol-1-yl]butanamide;

2-hydroxy-2-methyl-3-[4-(3-methyl-5-{[4-(trifluoromethyl)pyrimidin-2-yl]amino}phenyl)-1H-pyrazol-1-yl]propanamide;

3-[4-(3-methyl-5-{[4-(trifluoromethyl)pyrimidin-2-yl]amino}phenyl)-1H-pyrazol-1-yl]cyclohexane-1,2-diol;

2-[4-(3-methyl-5-{[4-(trifluoromethyl)pyrimidin-2-yl]amino}phenyl)-1H-pyrazol-1-yl]propanamide; and (5R)-5-{[4-(3-methyl-5-{[4-(trifluoromethyl)pyrimidin-2-yl]amino}phenyl)-1H-pyrazol-1-yl]methyl}-1,3-oxazolidin-2-one.

15. A pharmaceutical composition comprising a therapeutically effective amount of the compound of claim 1 or a pharmaceutically acceptable salt thereof, and a pharmaceutically acceptable carrier.

16. A method for the treatment of a Syk-mediated disease which comprises administering to a patient in need thereof a therapeutically effective amount of the compound of claim 1 or a pharmaceutically acceptable salt thereof, wherein the disease is selected from asthma, COPD, rheumatoid arthritis, and cancer.

17. The method of claim 16 wherein said disease is asthma or COPD.

18. The method of claim 16 wherein said disease is rheumatoid arthritis.

19. The method of claim 16 wherein said disease is cancer.

20. The compound of claim 1 having the Formula Ie

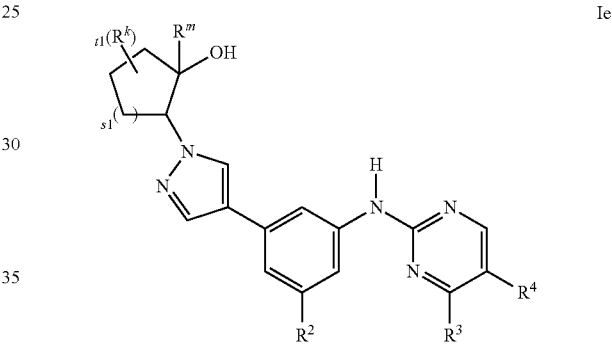

wherein
each $R^k$ is independently $C_{1-3}$alkyl or OH;
$R^m$ is H or $C_1$-$C_3$-alkyl;
$R^2$ is H or methyl;
$R^3$ is H, methyl, isopropyl, $C_1$-$C_3$-fluoroalkyl, cyclopropyl, or methoxy;
$R^4$ is H or fluoro;
s1 is 1, 2, or 3; and
t1 is 0, 1, 2, or 3;
or a pharmaceutically acceptable salt thereof.

21. The compound of claim 20, or a pharmaceutically acceptable salt thereof, wherein the group is

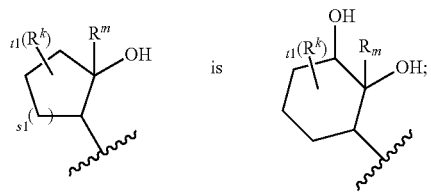

$R^2$ is methyl; and
t1 is 0, 1, or 2.

* * * * *